US011419869B2

(12) United States Patent
Decaris et al.

(10) Patent No.: US 11,419,869 B2
(45) Date of Patent: Aug. 23, 2022

(54) DOSAGE FORMS AND REGIMENS FOR AMINO ACID COMPOUNDS

(71) Applicant: Pliant Therapeutics, Inc., South San Francisco, CA (US)

(72) Inventors: Martin Decaris, Oakland, CA (US); Scott Turner, Oakland, CA (US); Eric Lefebvre, San Francisco, CA (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/843,824

(22) Filed: Apr. 8, 2020

(65) Prior Publication Data

US 2020/0352942 A1 Nov. 12, 2020

Related U.S. Application Data

(60) Provisional application No. 62/899,071, filed on Sep. 11, 2019, provisional application No. 62/850,530, filed on May 20, 2019, provisional application No. 62/831,060, filed on Apr. 8, 2019.

(51) Int. Cl.
*A61K 31/5025* (2006.01)
*A61K 31/502* (2006.01)
*A61P 11/00* (2006.01)
*A61K 9/00* (2006.01)
*A61K 31/4375* (2006.01)

(52) U.S. Cl.
CPC ........ *A61K 31/5025* (2013.01); *A61K 9/0053* (2013.01); *A61K 31/4375* (2013.01); *A61K 31/502* (2013.01); *A61P 11/00* (2018.01)

(58) Field of Classification Search
CPC .......................... C07D 471/04; A61K 31/5025
See application file for complete search history.

(56) References Cited

U.S. PATENT DOCUMENTS

| 10,131,658 | B2 | 11/2018 | Degrado |
| 10,214,522 | B2 | 2/2019 | Degrado |
| 10,604,520 | B2 | 3/2020 | Jiang |
| 10,696,672 | B2 | 6/2020 | Morgans, Jr. |
| 10,793,564 | B2 * | 10/2020 | Cha ..................... C07D 471/04 |
| 11,180,494 | B2 | 11/2021 | Cha et al. |
| 2002/0010176 | A1 | 1/2002 | Askew |
| 2016/0264566 | A1 | 9/2016 | Degrado |
| 2016/0376266 | A1 | 12/2016 | Degrado |
| 2018/0093984 | A1 | 4/2018 | Jiang |
| 2019/0276449 | A1 * | 9/2019 | Cha ........................ A61P 43/00 |
| 2019/0322663 | A1 | 10/2019 | Morgans, Jr. et al. |
| 2020/0109141 | A1 | 4/2020 | Cha |
| 2020/0123151 | A1 | 4/2020 | Leftheris |
| 2020/0352942 | A1 | 11/2020 | Cha et al. |
| 2021/0017171 | A1 | 1/2021 | Cha et al. |
| 2021/0024516 | A1 | 1/2021 | Jiang |
| 2021/0122747 | A1 | 4/2021 | Morgans, Jr. et al. |

FOREIGN PATENT DOCUMENTS

| JP | 2002508355 A | 3/2002 |
| JP | 2019524702 A | 9/2019 |
| WO | 199931061 A1 | 6/1999 |
| WO | 2002098849 A2 | 12/2002 |
| WO | 2002098849 A3 | 11/2003 |
| WO | 2004024675 A1 | 3/2004 |
| WO | 2015048819 A1 | 4/2015 |
| WO | 2016145258 A1 | 9/2016 |
| WO | 2017181062 A1 | 10/2017 |
| WO | 2018009501 A1 | 1/2018 |
| WO | 2018049068 A1 | 3/2018 |
| WO | 2018119087 A1 | 6/2018 |
| WO | 2019173653 A1 | 9/2019 |
| WO | 2020006315 A1 | 1/2020 |
| WO | 2020076862 A1 | 4/2020 |
| WO | 2021225912 A1 | 11/2021 |

OTHER PUBLICATIONS

Cannon, J.G et al. (1995), Chapter 19 in Burger's Medicinal Chemistry and Drug Discovery, 5th vol. 1: Principles and Practice, Wiley-Interscience, pp. 783-802.
Dorwald, F.A. (2005). Side Reactions in Organic Synthesis, Wiley: VCH , Weinheim, p. IX of Preface pp. 1-15.
International Preliminary Report on Patentability, dated Sep. 8, 2020, for PCT Application No. PCT/US2019/021243 filed on Mar. 7, 2019, 6 pages.
International Search Report and Written Opinion, dated Aug. 19, 2020, for PCT Application No. PCT/US2020/27335, filed on Apr. 8, 2020, 9 pages.

(Continued)

*Primary Examiner* — Rei Tsang Shiao
(74) *Attorney, Agent, or Firm* — Morrison & Foerster LLP; Kraig Anderson; Johannes Hull

(57) ABSTRACT

The invention relates to dosage forms for daily administration of compounds of formula (A) and formula (I):

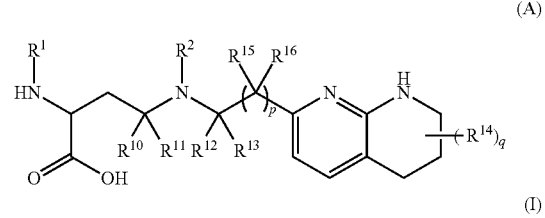

or a salt thereof, wherein $R^1$, $R^2$, $R^{10}$, $R^{11}$, $R^{12}$, $R^{13}$, $R^{14}$, $R^{15}$, $R^{16}$, q and p are as described herein. Compounds of formula (A), formula (I), and pharmaceutical compositions thereof are αvβ6 integrin inhibitors that are useful for treating fibrosis such as idiopathic pulmonary fibrosis (IPF) and nonspecific interstitial pneumonia (NSIP).

72 Claims, 62 Drawing Sheets

(56) References Cited

OTHER PUBLICATIONS

International Search Report dated Jul. 5, 2019, for PCT Application No. PCT/US2019/021243 filed on Mar. 7, 2019, 6 pages.
Invitation to Pay Additional Fees and, Where Applicable, Protest Fee dated Jun. 22, 2020, for PCT Application No. PCT/US2020/027335 filed on Apr. 8, 2020, 2 pages.
Invitation to Pay Additional Fees and, Where Applicable, Protest Fee dated May 9, 2019, for PCT Application No. PCT/US2019/021243 filed on Mar. 7, 2019, 2 pages.
Kim, D.S et al. (2006). "Classification and Natural History of the Idiopathic Interstitial Pneumonias," Proc. Am. Thorac. Soc. 3:285-292.
Kinder, B.W et al. (Jun. 2007). "Idiopathic Nonspecific Interstitial Pneumonia. Lung Manifestation of Undifferentiated Connective Tissue Disease?," Am. J. Respir. Crit. Care Med. 176:691-697.
PubMed Compound Record (Dec. 16, 2018). "CID 135390719,", 9 pages.
Ullman, E.F. et al. (Jun. 7, 1994). "Luminescent Oxygen Channeling Immunoassay: Measurement of Particle Binding Kinetics by Chemiluminescence," Proc. Natl. Acad. Sci. USA 91(12):5426-5430.
Vernkatesh, S. (2002). "Role of the Development of Scientist in Compound Lead Selection and Optimization," J. Pharm. Sci. 89:145-154.
Written Opinion dated Jul. 5, 2019, for PCT Application No. PCT/US2019/021243 filed on Mar. 7, 2019, 5 pages.
International Preliminary Report on Patentability, dated Sep. 28, 2021, for PCT Application No. PCT/US2020/027335, filed on Apr. 8, 2020, 6 pages.

\* cited by examiner

FIG. 2
Table B-3

| # | Solid phase assay | | Proximity-based assay | | # | Solid phase assay | | Proximity-based assay | |
|---|---|---|---|---|---|---|---|---|---|
| | $\alpha v \beta_1$ | $\alpha v \beta_6$ | $\alpha v \beta_1$ | $\alpha v \beta_6$ | | $\alpha v \beta_1$ | $\alpha v \beta_6$ | $\alpha v \beta_1$ | $\alpha v \beta_6$ |
| 1 | >1000 | 250-1000 | | 50-250 | 41 | | <50 | | <50 |
| 2 | >1000 | 250-1000 | | >1000 | 42 | <50 | <50 | | <50 |
| 3 | >1000 | 50-250 | | 250-1000 | 43 | | <50 | | |
| 4 | >1000 | 50-250 | >1000 | 50-250 | 44 | <50 | <50 | | |
| 5 | <50 | <50 | | | 45 | 50-250 | <50 | | |
| 6 | | 50-250 | | <50 | 46 | | <50 | <50 | <50 |
| 7 | | <50 | | <50 | 47 | | <50 | | <50 |
| 8 | | 50-250 | | <50 | 48 | | <50 | | <50 |
| 9 | | >1000 | | 50-250 | 49 | | <50 | | <50 |
| 10 | <50 | <50 | | | 50 | | <50 | | <50 |
| 11 | <50 | <50 | | <50 | 51 | | <50 | | <50 |
| 12 | <50 | <50 | | <50 | 52 | | <50 | | <50 |
| 13 | | 50-250 | | <50 | 53 | | <50 | 50-250 | <50 |
| 14 | | <50 | | <50 | 54 | | <50 | | <50 |
| 15 | | <50 | | <50 | 55 | | <50 | | <50 |
| 16 | <50 | <50 | | <50 | 56 | | <50 | | <50 |
| 17 | | <50 | | <50 | 57 | | <50 | | <50 |
| 18 | | <50 | | <50 | 58 | | <50 | | <50 |
| 19 | | <50 | | <50 | 59 | | <50 | | <50 |
| 20 | | <50 | | <50 | 60 | | <50 | | <50 |
| 21 | | <50 | | <50 | 61 | | <50 | | <50 |
| 22 | <50 | <50 | | <50 | 62 | <50 | <50 | | <50 |
| 23 | <50 | <50 | | <50 | 63 | | <50 | 50-250 | <50 |
| 24 | 250-1000 | <50 | | <50 | 64 | | <50 | | <50 |
| 25 | 250-1000 | <50 | 50-250 | <50 | 65 | <50 | <50 | <50 | <50 |
| 26 | | <50 | | <50 | 66 | <50 | <50 | <50 | <50 |
| 27 | | <50 | | <50 | 67 | <50 | <50 | | |
| 28 | <50 | <50 | | <50 | 68 | | <50 | | <50 |
| 29 | | <50 | | <50 | 69 | | <50 | | <50 |
| 30 | 50-250 | <50 | | <50 | 70 | | <50 | | <50 |
| 31 | 50-250 | <50 | | <50 | 71 | | <50 | | <50 |
| 32 | 50-250 | <50 | | <50 | 72 | | <50 | | <50 |
| 33 | | <50 | | <50 | 73 | | <50 | | 50-250 |
| 34 | | >1000 | | >1000 | 74 | | <50 | <50 | <50 |
| 35 | <50 | <50 | | <50 | 75 | | <50 | | <50 |
| 36 | | >1000 | | >1000 | 76 | | <50 | | <50 |
| 37 | | 50-250 | | <50 | 77 | | <50 | | <50 |
| 38 | <50 | <50 | | <50 | 78 | | <50 | | <50 |
| 39 | <50 | <50 | | <50 | 79 | | <50 | <50 | <50 |
| 40 | <50 | <50 | | <50 | 80 | | <50 | | <50 |

FIG. 2 (cont.)

| # | Solid phase assay | | Proximity-based assay | | # | Solid phase assay | | Proximity-based assay | |
|---|---|---|---|---|---|---|---|---|---|
| | $\alpha v\beta_1$ | $\alpha v\beta_6$ | $\alpha v\beta_1$ | $\alpha v\beta_6$ | | $\alpha v\beta_1$ | $\alpha v\beta_6$ | $\alpha v\beta_1$ | $\alpha v\beta_6$ |
| 81 | | <50 | | <50 | 121 | | >1000 | | >1000 |
| 82 | | <50 | | <50 | 122 | | 250-1000 | | 250-1000 |
| 83 | | <50 | | <50 | 123 | | <50 | | <50 |
| 84 | | 250-1000 | | 50-250 | 124 | | <50 | | <50 |
| 85 | | 250-1000 | | <50 | 125 | | 50-250 | | <50 |
| 86 | | 50-250 | | 50-250 | 126 | | >1000 | | 250-1000 |
| 87 | | 250-1000 | | 50-250 | 127 | | 250-1000 | | 50-250 |
| 88 | | >1000 | | >1000 | 128 | | >1000 | | 50-250 |
| 89 | | <50 | | <50 | 129 | | <50 | <50 | <50 |
| 90 | | <50 | | <50 | 130 | | <50 | | <50 |
| 91 | | <50 | | <50 | 131 | | 50-250 | | 50-250 |
| 92 | | <50 | | | 132 | | 50-250 | | 50-250 |
| 93 | | <50 | | | 133 | | 50-250 | | <50 |
| 94 | | <50 | | | 134 | | 50-250 | | 250-1000 |
| 95 | | >1000 | | >1000 | 135 | | 50-250 | | 50-250 |
| 96 | | >1000 | | >1000 | 136 | | <50 | | <50 |
| 97 | | >1000 | | >1000 | 137 | | <50 | | 50-250 |
| 98 | | >1000 | | >1000 | 138 | | <50 | | <50 |
| 99 | | 250-1000 | | 250-1000 | 139 | | <50 | | <50 |
| 100 | | <50 | | <50 | 140 | | <50 | | <50 |
| 101 | | 50-250 | | 50-250 | 141 | | 50-250 | | 50-250 |
| 102 | | >1000 | | 250-1000 | 142 | | >1000 | | |
| 103 | | >1000 | | 250-1000 | 143 | | 50-250 | | |
| 104 | | >1000 | | 250-1000 | 144 | | 50-250 | | |
| 105 | | <50 | | <50 | 145 | | <50 | | 50-250 |
| 106 | | <50 | | <50 | 146 | | >1000 | | >1000 |
| 107 | | 250-1000 | | <50 | 147 | | 50-250 | | <50 |
| 108 | | >1000 | | 250-1000 | 149 | | 50-250 | | 250-1000 |
| 109 | | <50 | | <50 | 152 | | >1000 | | 250-1000 |
| 110 | | <50 | | <50 | 154 | | >1000 | | 250-1000 |
| 111 | | <50 | | <50 | 156 | | 50-250 | | 250-1000 |
| 112 | | 250-1000 | | 250-1000 | 158 | | >1000 | | 250-1000 |
| 113 | | 250-1000 | | 50-250 | 159 | | >1000 | | 50-250 |
| 114 | | <50 | | 250-1000 | 162 | | <50 | | <50 |
| 115 | | 50-250 | | 250-1000 | 163 | | >1000 | | 50-250 |
| 116 | | 50-250 | | 50-250 | 172 | | >1000 | | 250-1000 |
| 117 | | <50 | | <50 | 178 | | >1000 | | 250-1000 |
| 118 | | >1000 | | >1000 | 181 | >1000 | >1000 | | >1000 |
| 119 | | >1000 | | | 182 | >1000 | >1000 | | >1000 |
| 120 | >1000 | >1000 | | >1000 | 183 | >1000 | >1000 | | >1000 |

FIG. 2 (cont.)

| # | Solid phase assay | | Proximity-based assay | | # | Solid phase assay | | Proximity-based assay | |
|---|---|---|---|---|---|---|---|---|---|
|  | $\alpha v\beta_1$ | $\alpha v\beta_6$ | $\alpha v\beta_1$ | $\alpha v\beta_6$ |  | $\alpha v\beta_1$ | $\alpha v\beta_6$ | $\alpha v\beta_1$ | $\alpha v\beta_6$ |
| 185 | >1000 | >1000 |  | >1000 | 264 | 250-1000 | >1000 |  | 50-250 |
| 186 | >1000 | >1000 |  | >1000 | 266 | >1000 | 50-250 |  | 50-250 |
| 187 | >1000 | >1000 |  | >1000 | 267 |  | <50 |  |  |
| 188 | >1000 | >1000 |  | >1000 | 268 |  | 50-250 |  | <50 |
| 190 | >1000 | >1000 |  | >1000 | 269 | <50 | 50-250 |  | <50 |
| 191 | >1000 | >1000 |  | >1000 | 270 |  | <50 |  |  |
| 192 | >1000 | >1000 |  | 50-250 | 272 |  | 250-1000 |  |  |
| 193 | >1000 | >1000 |  | >1000 | 273 |  | 50-250 |  |  |
| 194 | >1000 | >1000 |  | >1000 | 278 |  | <50 |  | <50 |
| 195 |  | <50 |  | <50 | 282 |  | >1000 |  |  |
| 196 |  | >1000 |  | 50-250 | 284 |  | <50 |  | 50-250 |
| 200 |  | <50 |  | <50 | 287 | 250-1000 | 250-1000 |  | 50-250 |
| 204 | <50 | <50 |  | <50 | 288 | 50-250 | <50 |  | 50-250 |
| 205 |  | <50 |  | <50 | 302 |  | <50 |  | <50 |
| 209 |  | 50-250 |  | 50-250 | 309 |  | 50-250 |  | <50 |
| 210 |  | <50 |  |  | 310 |  | <50 |  | <50 |
| 213 |  | >1000 |  | 50-250 | 311 |  | <50 |  | <50 |
| 215 |  | <50 |  | <50 | 312 | <50 | 50-250 |  | <50 |
| 220 |  | <50 |  | <50 | 313 | <50 | <50 |  | <50 |
| 222 |  | 50-250 |  | <50 | 314 |  | 50-250 |  | <50 |
| 224 |  | >1000 |  | 50-250 | 315 |  | <50 |  | <50 |
| 228 | <50 | <50 |  | <50 | 316 |  | <50 |  | <50 |
| 229 |  | <50 |  | <50 | 317 | <50 | <50 |  | <50 |
| 230 |  | <50 |  | <50 | 318 |  | <50 |  | <50 |
| 231 |  | <50 |  | <50 | 319 |  | <50 |  | <50 |
| 232 |  | <50 |  | <50 | 320 |  | <50 |  | <50 |
| 233 | >1000 | >1000 |  | >1000 | 321 | <50 | 50-250 |  | <50 |
| 236 |  | <50 |  |  | 322 | >1000 | 50-250 |  | <50 |
| 243 | 250-1000 | >1000 |  | 250-1000 | 323 | <50 | <50 |  | <50 |
| 246 | >1000 | 250-1000 |  | 50-250 | 324 | <50 | <50 |  | <50 |
| 248 |  | <50 |  | <50 | 325 | <50 | <50 |  | <50 |
| 250 | >1000 | 50-250 |  | 50-250 | 326 | <50 | <50 |  | <50 |
| 253 |  | 50-250 |  | <50 | 327 | <50 | <50 |  | <50 |
| 254 | <50 | <50 |  | 50-250 | 328 | 250-1000 | 50-250 |  | <50 |
| 255 |  | <50 |  | <50 | 329 | <50 | <50 |  | <50 |
| 256 | >1000 | 50-250 |  | <50 | 330 | >1000 | 50-250 |  | <50 |
| 257 |  | 50-250 |  | 50-250 | 332 |  | 50-250 |  | <50 |
| 258 |  | >1000 |  | 50-250 | 334 |  | 50-250 |  | <50 |
| 261 | >1000 | >1000 |  | 50-250 | 335 |  | <50 |  | <50 |
| 263 |  | <50 |  | <50 | 336 |  | 50-250 |  | <50 |

FIG. 2 (cont.)

| #   | Solid phase assay $\alpha v \beta_1$ | $\alpha v \beta_6$ | Proximity-based assay $\alpha v \beta_1$ | $\alpha v \beta_6$ | #   | Solid phase assay $\alpha v \beta_1$ | $\alpha v \beta_6$ | Proximity-based assay $\alpha v \beta_1$ | $\alpha v \beta_6$ |
| --- | --- | --- | --- | --- | --- | --- | --- | --- | --- |
| 340 | >1000 | 50-250 |  | <50 | 677 |  | >1000 |  | 250-1000 |
| 341 | >1000 | >1000 |  | <50 | 678 |  | <50 |  | <50 |
| 342 |  | 50-250 |  | 250-1000 | 679 |  | <50 |  | <50 |
| 343 |  | 50-250 |  | <50 | 680 |  |  | >1000 | <50 |
| 344 | 250-1000 | <50 |  | <50 | 681 |  |  | <50 | <50 |
| 345 | 50-250 | 50-250 |  | <50 | 682 | <50 | <50 | <50 | <50 |
| 346 |  | 250-1000 |  | <50 | 683 | 50-250 | <50 |  |  |
| 347 | 50-250 | >1000 |  | <50 | 684 | 250-1000 | <50 |  | <50 |
| 348 | >1000 | 250-1000 |  | 50-250 | 685 | 250-1000 | >1000 |  | 250-1000 |
| 349 | 250-1000 | 50-250 |  | <50 | 686 | <50 | <50 |  | <50 |
| 350 | >1000 | >1000 |  | 250-1000 | 687 | >1000 | >1000 |  | <50 |
| 352 | >1000 | >1000 |  | <50 | 688 | <50 | <50 |  | <50 |
| 353 | >1000 | >1000 |  | 50-250 | 689 | <50 | <50 |  | <50 |
| 354 |  | <50 | <50 | <50 | 690 | <50 | 50-250 |  | <50 |
| 357 | >1000 | >1000 |  | 50-250 | 691 | <50 | <50 |  | <50 |
| 360 | >1000 | <50 |  | <50 | 692 | >1000 | 50-250 |  | <50 |
| 362 | >1000 | >1000 |  | 50-250 | 693 | 50-250 | 50-250 |  | <50 |
| 364 |  | <50 |  | <50 | 694 | <50 | <50 |  | <50 |
| 365 |  | 50-250 |  | 50-250 | 695 | 250-1000 | 50-250 |  | 50-250 |
| 369 |  | 50-250 |  | <50 | 696 | 50-250 | 50-250 |  | 50-250 |
| 371 |  | 50-250 |  | 50-250 | 697 | 50-250 | 50-250 |  | <50 |
| 372 |  | 50-250 |  | <50 | 698 | 250-1000 | >1000 |  | 50-250 |
| 375 |  | <50 |  | <50 | 699 | >1000 | >1000 |  | 50-250 |
| 377 |  | <50 |  | <50 | 700 | >1000 | 250-1000 |  | 50-250 |
| 379 | <50 | <50 |  | <50 | 701 | <50 | <50 |  | <50 |
| 381 | <50 | <50 | <50 | <50 | 702 | 50-250 | <50 |  | <50 |
| 382 | <50 | <50 |  | <50 | 703 | <50 | <50 |  | <50 |
| 383 | <50 | <50 |  | <50 | 704 | <50 | <50 |  | <50 |
| 384 | >1000 | 250-1000 |  | 50-250 | 705 | >1000 | 50-250 |  | 250-1000 |
| 666 | 50-250 | <50 |  |  | 706 | <50 | <50 |  | <50 |
| 667 | 50-250 | <50 |  |  | 707 | <50 | <50 |  |  |
| 668 | <50 | <50 |  | <50 | 708 | >1000 | <50 |  |  |
| 669 | <50 | <50 | <50 | <50 | 709 | <50 | <50 |  |  |
| 670 | >1000 | 50-250 |  | <50 | 710 | <50 | <50 | <50 | <50 |
| 671 | 250-1000 | 50-250 |  | <50 | 711 | <50 | <50 | 50-250 | <50 |
| 672 |  | <50 |  |  | 712 | 50-250 | <50 | 50-250 | <50 |
| 673 |  | <50 |  | <50 | 713 | 250-1000 | <50 | 250-1000 | 50-250 |
| 674 |  | <50 |  |  | 714 | <50 | <50 | <50 | <50 |
| 675 | >1000 | >1000 |  | >1000 | 715 | <50 | <50 | <50 | <50 |
| 676 |  | <50 |  | <50 | 716 | <50 | 50-250 | 50-250 | <50 |

FIG. 2 (cont.)

| # | Solid phase assay | | Proximity-based assay | | # | Solid phase assay | | Proximity-based assay | |
|---|---|---|---|---|---|---|---|---|---|
| | $\alpha v \beta_1$ | $\alpha v \beta_6$ | $\alpha v \beta_1$ | $\alpha v \beta_6$ | | $\alpha v \beta_1$ | $\alpha v \beta_6$ | $\alpha v \beta_1$ | $\alpha v \beta_6$ |
| 717 | <50 | <50 | 50-250 | <50 | 757 | | | <50 | <50 |
| 718 | <50 | <50 | <50 | <50 | 758 | | | <50 | <50 |
| 719 | >1000 | <50 | 250-1000 | 50-250 | 759 | | | <50 | <50 |
| 720 | 250-1000 | <50 | 250-1000 | <50 | 760 | | | <50 | <50 |
| 721 | 250-1000 | <50 | 50-250 | 50-250 | 761 | | | <50 | <50 |
| 722 | >1000 | 50-250 | >1000 | 250-1000 | 762 | | | <50 | <50 |
| 723 | >1000 | 50-250 | >1000 | <50 | 763 | | | <50 | <50 |
| 724 | >1000 | 250-1000 | >1000 | 250-1000 | 764 | | | <50 | <50 |
| 725 | >1000 | 250-1000 | 250-1000 | 50-250 | 765 | | | <50 | <50 |
| 726 | 50-250 | <50 | 50-250 | <50 | 766 | | | <50 | <50 |
| 727 | <50 | <50 | | <50 | 767 | | | <50 | <50 |
| 728 | | | >1000 | 50-250 | 768 | | | <50 | <50 |
| 729 | | | <50 | <50 | 769 | | | 50-250 | <50 |
| 730 | | | 250-1000 | 50-250 | 770 | | | <50 | <50 |
| 731 | | | 250-1000 | <50 | 771 | | | <50 | <50 |
| 732 | | | 250-1000 | <50 | 772 | | | <50 | <50 |
| 733 | | | <50 | <50 | 773 | | | <50 | <50 |
| 734 | | | <50 | <50 | 774 | | | <50 | <50 |
| 735 | | | <50 | <50 | 775 | | | <50 | <50 |
| 736 | | | <50 | <50 | 776 | | | <50 | <50 |
| 737 | | | >1000 | 50-250 | 777 | | | <50 | <50 |
| 738 | | | 50-250 | <50 | 778 | | | <50 | <50 |
| 739 | | | <50 | <50 | 779 | | | <50 | <50 |
| 740 | | | 250-1000 | <50 | 780 | | | <50 | <50 |
| 741 | | | 250-1000 | <50 | | | | | |
| 742 | | | 50-250 | <50 | | | | | |
| 743 | | | | | | | | | |
| 744 | | | | | | | | | |
| 745 | | | 50-250 | 50-250 | | | | | |
| 746 | | | 50-250 | <50 | | | | | |
| 747 | | | 50-250 | <50 | | | | | |
| 748 | | | <50 | <50 | | | | | |
| 749 | | | 50-250 | <50 | | | | | |
| 750 | | | 250-1000 | <50 | | | | | |
| 751 | | | 50-250 | <50 | | | | | |
| 752 | | | 50-250 | <50 | | | | | |
| 753 | | | <50 | <50 | | | | | |
| 754 | | | <50 | <50 | | | | | |
| 755 | | | <50 | <50 | | | | | |
| 756 | | | | | | | | | |

| Parameter | 75 mg |
|---|---|
| Tmax (h) | 2.9 ± 1.0 (34%) |
| Cmax (ng/mL) | 1869 ± 1241 (66%) |
| AUC0-24 (ng.h/mL) | 19653 ± 10860 (55%) |
| AUC0-48 (ng.h/mL) | 22464 ± 15679 (59%) |
| Thalf (h) | 20.0 ± 3.6 (18 %) |

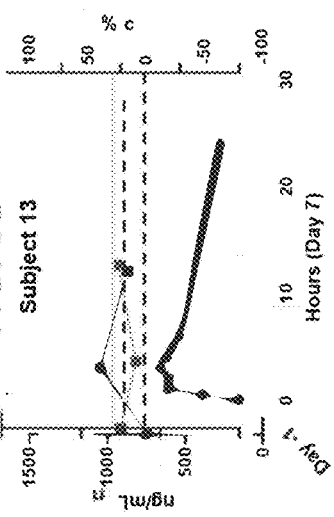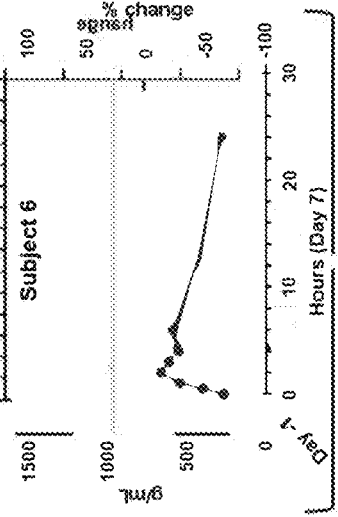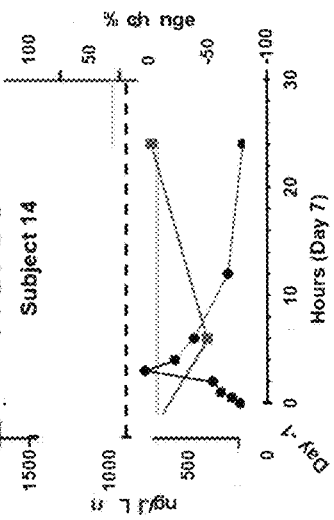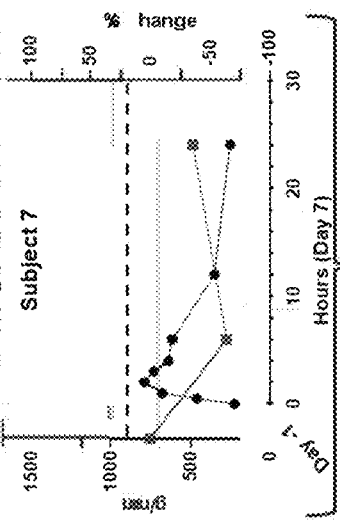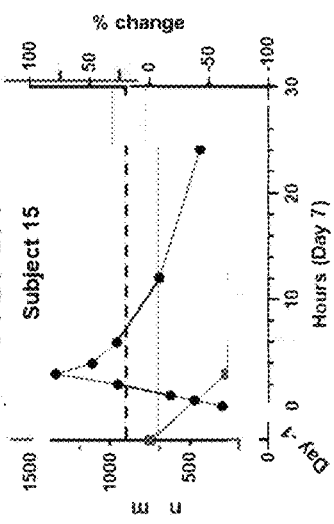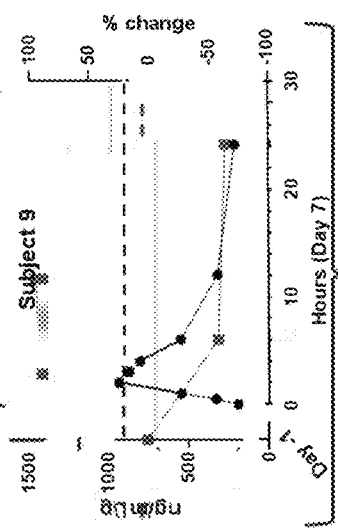

DOSAGE FORMS AND REGIMENS FOR AMINO ACID COMPOUNDS

CROSS-REFERENCE TO RELATED APPLICATIONS

This application claims priority benefit of U.S. Provisional Patent Appl. No. 62/831,060 filed Apr. 8, 2019, of U.S. Provisional Patent Appl. No. 62/850,530 filed May 20, 2019, and of U.S. Provisional Patent Appl. No. 62/899,071 filed Sep. 11, 2019. The entire contents of those patent applications are hereby incorporated by reference herein.

BACKGROUND OF THE INVENTION

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Primary biliary cholangitis (PBC), also known as primary biliary cirrhosis, is a chronic disease of the liver that causes damage and fibrosis in the liver. It results from a slow, progressive destruction of the small bile ducts of the liver, causing bile and other toxins to build up in the liver, a condition called cholestasis. Over time, this leads to scarring and fibrosis in both the liver and biliary tract.

Nonspecific interstitial pneumonia (NSIP) is a rare disorder that affects the tissue that surrounds and separates the tiny air sacs of the lungs. These air sacs, called the alveoli, are where the exchange of oxygen and carbon dioxide takes place between the lungs and the bloodstream. Interstitial pneumonia is a disease in which the mesh-like walls of the alveoli become inflamed. The pleura (a thin covering that protects and cushions the lungs and the individual lobes of the lungs) might become inflamed as well. There are two primary forms of NSIP—cellular and fibrotic. The cellular form is defined mainly by inflammation of the cells of the interstitium. The fibrotic form is defined by thickening and scarring of lung tissue. This scarring is known as fibrosis and is irreversible. When the lung tissue thickens or becomes scarred, it does not function as effectively. Breathing becomes less efficient, and there are lower levels of oxygen in the blood. (Kim et al., Proc. Am. Thorac. Soc. (2006) 3:285-292; Lynch, D., Radiology (2001) 221:583-584; Kinder et al., Am. J. Respir. Crit. Care Med. (2007) 176: 691-697)

Available courses of treatment are scarce, as there are currently no options on the market proven to have an effect on long-term patient survival or symptomatology. For example, agents such as pirfenidone and nintedanib have been studied for treatment of fibrosis. In the treatment of IPF, pirfenidone and nintedanib have been used, but have shown less therapeutic efficacy than desired while also exhibiting numerous side effects. There remains a need for treatment of fibrotic diseases.

The αvβ6 integrin is expressed in epithelial cells, and binds to the latency-associated peptide of transforming growth factor-β1 (TGFβ1) and mediates TGFβ1 activation. Its expression level is significantly increased after injury to lung and cholangiocytes, and plays a critical in vivo role in tissue fibrosis. Increased levels are also associated with increased mortality in IPF and NSIP patients.

Primary sclerosing cholangitis (PSC) involves bile duct inflammation, and fibrosis that obliterates the bile ducts. The resulting impediment to the flow of bile to the intestines can lead to cirrhosis of the liver and subsequent complications such as liver failure and liver cancer. Expression of αvβ6 is elevated in liver and bile duct of PSC patients.

The present disclosure provides for αvβ6 integrin inhibitors that may be useful for treatment of fibrosis.

BRIEF SUMMARY OF THE INVENTION

Disclosed are amino acid compounds that are αvβ6 integrin inhibitors, compositions containing these compounds and methods for treating diseases mediated by αvβ6 integrin such as a fibrotic disease.

In one aspect, provided is a compound of formula (A), or any variation thereof, or a salt thereof (e.g., a pharmaceutically acceptable salt thereof), as detailed herein.

Further provided is a pharmaceutical composition comprising a compound of formula (A), or any variation thereof detailed herein, or a salt thereof (e.g., a pharmaceutically acceptable salt thereof), and a pharmaceutically acceptable carrier or excipient.

In another aspect, provided is a method of treating a fibrotic disease in an individual (such as a human) in need thereof comprising administering to the individual a therapeutically effective amount of a compound of formula (A), or any variation thereof detailed herein, or a pharmaceutically acceptable salt thereof. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC). In some embodiments, the fibrotic disease is pulmonary fibrosis (such as IPF), liver fibrosis, skin fibrosis, psoriasis, scleroderma, cardiac fibrosis, renal fibrosis, gastrointestinal fibrosis, primary sclerosing cholangitis, or biliary fibrosis (such as PBC). In some embodiments, the fibrotic disease is pulmonary fibrosis (such as IPF). In some embodiments, the fibrotic disease is liver fibrosis. In some embodiments, the fibrotic disease is skin fibrosis. In some embodiments, the fibrotic disease is psoriasis. In some embodiments, the fibrotic disease is scleroderma. In some embodiments, the fibrotic disease is cardiac fibrosis. In some embodiments, the fibrotic disease is renal fibrosis. In some embodiments, the fibrotic disease is gastrointestinal fibrosis. In some embodiments, the fibrotic disease is primary sclerosing cholangitis. In some embodiments, the fibrotic disease is biliary fibrosis (such as PBC).

In another aspect, provided is a method of delaying the onset and/or development of a fibrotic disease in an individual (such as a human) who is at risk for developing a fibrotic disease comprising administering to the individual a therapeutically effective amount of a compound of formula (A), or any variation thereof detailed herein, or a pharmaceutically acceptable salt thereof. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or PBC. In some embodiments, the fibrotic disease is pulmonary fibrosis (such as IPF), liver fibrosis, skin fibrosis, psoriasis, scleroderma, cardiac fibrosis, renal fibrosis, gastrointestinal fibrosis, primary sclerosing cholangitis, or biliary fibrosis (such as PBC). In some embodiments, the fibrotic disease is psoriasis. In some embodiments, the individual at risk of developing a fibrotic disease has or is suspected of having NAFLD, NASH, CKD, scleroderma, Crohn's Disease, NSIP, PSC, PBC, or is an individual who has had or is suspected of having had a myocardial infarction. In some embodiments, the individual at risk of developing a fibrotic disease has or is suspected of having psoriasis.

Also provided is a compound of formula (A), or any variation thereof detailed herein, or a pharmaceutical composition thereof, for the treatment of a fibrotic disease.

Also provided is use of a compound of formula (A), or any variation thereof detailed herein, or a pharmaceutically acceptable salt thereof, or a pharmaceutical composition comprising any of the foregoing, in the manufacture of a medicament for the treatment of a fibrotic disease.

Further provided is a kit comprising a compound of formula (A), or any variation thereof detailed herein, or a pharmaceutically acceptable salt thereof. In some embodiments, the kit comprises instructions for use according to a method described herein, such as a method of treating a fibrotic disease in an individual.

In another aspect, provided is a method of making a compound of formula (A) or any variation thereof, or a pharmaceutically acceptable salt thereof. Also provided are compound intermediates useful in synthesis of a compound of formula (A), or any variation thereof.

In one aspect, provided is a compound of formula (I), or any variation thereof, or a salt thereof (e.g., a pharmaceutically acceptable salt thereof), as detailed herein.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient.

In another aspect, provided is a method of treating a fibrotic disease in an individual (such as a human) in need thereof comprising administering to the individual a therapeutically effective amount of a compound of formula (I), or any variation thereof detailed herein, or a pharmaceutically acceptable salt thereof. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC). In some embodiments, the fibrotic disease is pulmonary fibrosis (such as IPF), liver fibrosis, skin fibrosis, psoriasis, scleroderma, cardiac fibrosis, renal fibrosis, gastrointestinal fibrosis, primary sclerosing cholangitis, or biliary fibrosis (such as PBC). In some embodiments, the fibrotic disease is psoriasis.

In another aspect, provided is a method of delaying the onset and/or development of a fibrotic disease in an individual (such as a human) who is at risk for developing a fibrotic disease comprising administering to the individual a therapeutically effective amount of a compound of formula (I), or any variation thereof detailed herein, or a pharmaceutically acceptable salt thereof. In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or PBC. In some embodiments, the fibrotic disease is pulmonary fibrosis (such as IPF), liver fibrosis, skin fibrosis, psoriasis, scleroderma, cardiac fibrosis, renal fibrosis, gastrointestinal fibrosis, primary sclerosing cholangitis, or biliary fibrosis (such as PBC). In some embodiments, the fibrotic disease is psoriasis. In some embodiments, the individual at risk of developing a fibrotic disease has or is suspected of having NAFLD, NASH, CKD, scleroderma, Crohn's Disease, NSIP, PSC, PBC, or is an individual who has had or is suspected of having had a myocardial infarction. In some embodiments, the individual at risk of developing a fibrotic disease has or is suspected of having psoriasis.

Also provided is a compound of formula (I), or any variation thereof detailed herein, or a pharmaceutical composition thereof, for the treatment of a fibrotic disease.

Also provided is use of a compound of formula (I), or any variation thereof detailed herein, or a pharmaceutically acceptable salt thereof, or a pharmaceutical composition comprising any of the foregoing, in the manufacture of a medicament for the treatment of a fibrotic disease.

Further provided is a kit comprising a compound of formula (I), or any variation thereof detailed herein, or a pharmaceutically acceptable salt thereof. In some embodiments, the kit comprises instructions for use according to a method described herein, such as a method of treating a fibrotic disease in an individual.

In another aspect, provided is a method of making a compound of formula (I) or any variation thereof, or a pharmaceutically acceptable salt thereof. Also provided are compound intermediates useful in synthesis of a compound of formula (I), or any variation thereof.

BRIEF DESCRIPTION OF THE FIGURES

FIG. 2 shows Table B-3, with biological data for various compounds disclosed herein.

FIGS. 8A-8F are a series of graphs showing data for subjects administered 40 mg/day of the selected integrin inhibitor (compound 5). The data in FIGS. 8A-8F include the blood plasma concentration ("PK", round dots) of the administered integrin inhibitor and the relative change in pSMAD2:SMAD2 ratio from baseline (Day −1) in BAL (bronchoalveolar lavage) samples ("pSMAD", square dots) through the displayed time course (hours) subsequent to the dose of inhibitor administered on Day 7. The peak of the blood plasma concentration ("PK" curve) is recorded as $C_{max}$.

DETAILED DESCRIPTION OF THE INVENTION

Figure 1:
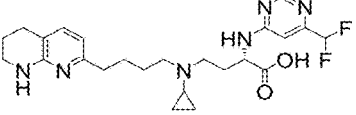
FIG. 1 shows compounds 1-780 as disclosed herein.
Figure 1:
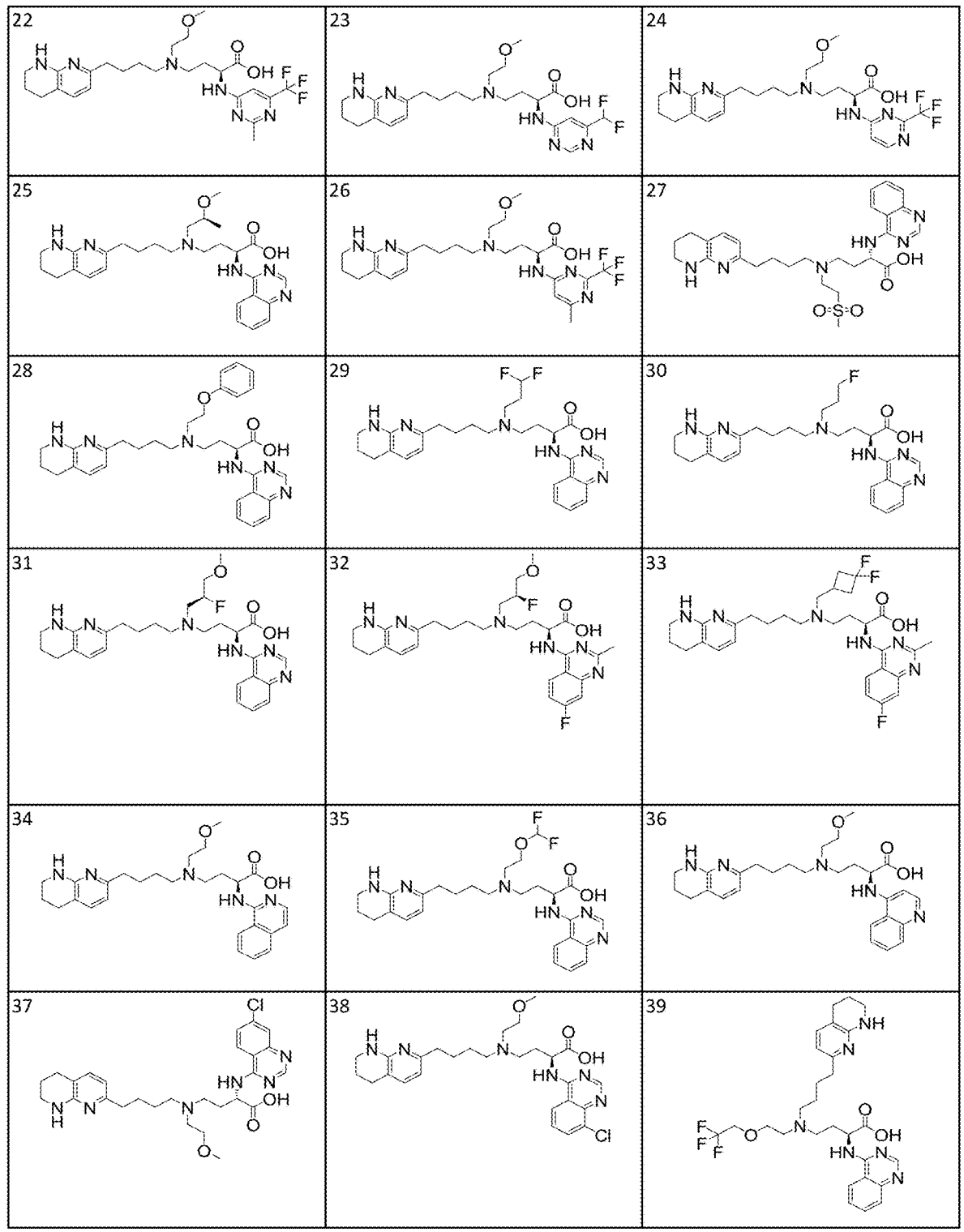
Figure 1:
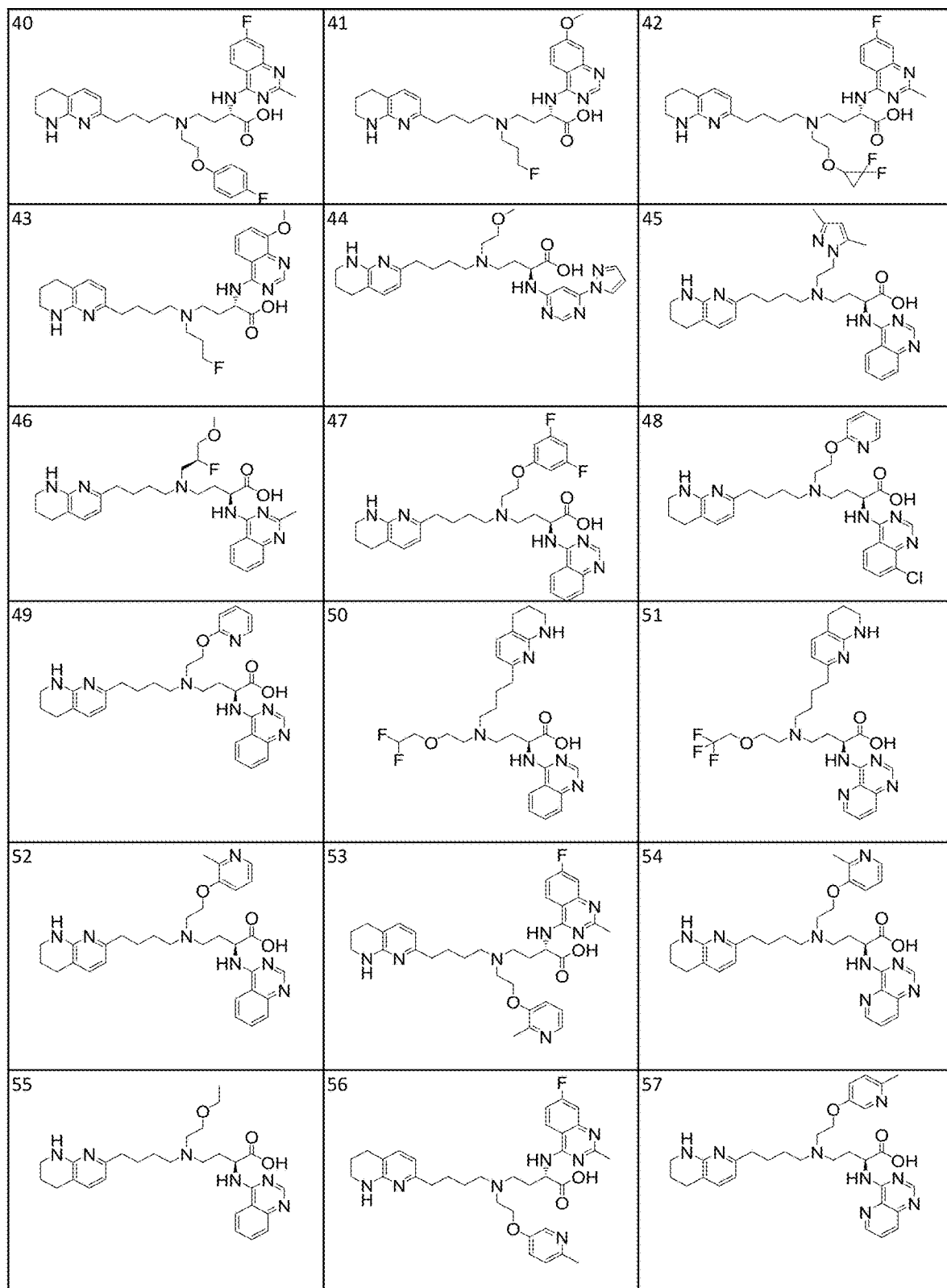
Figure 1:
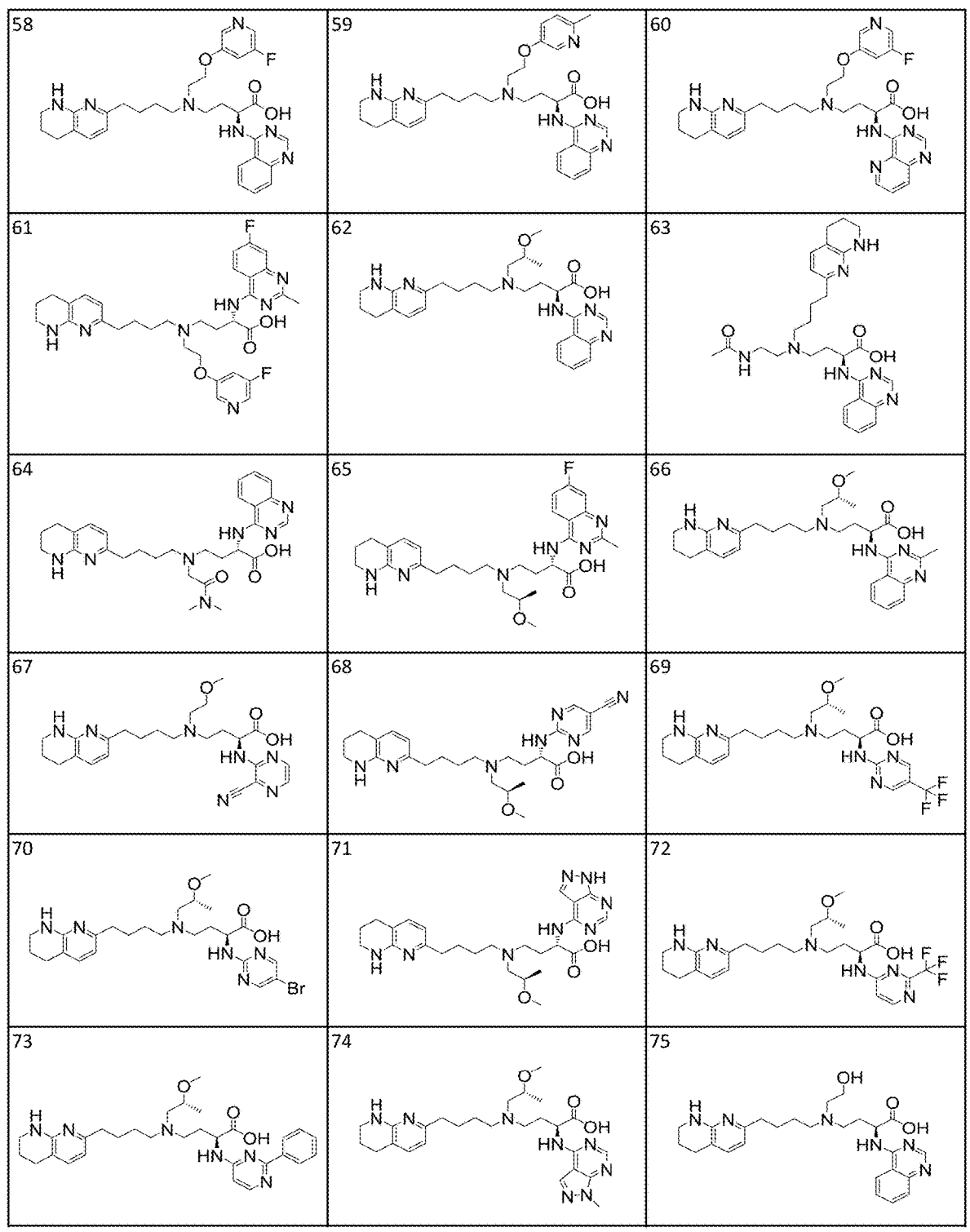
Figure 1:
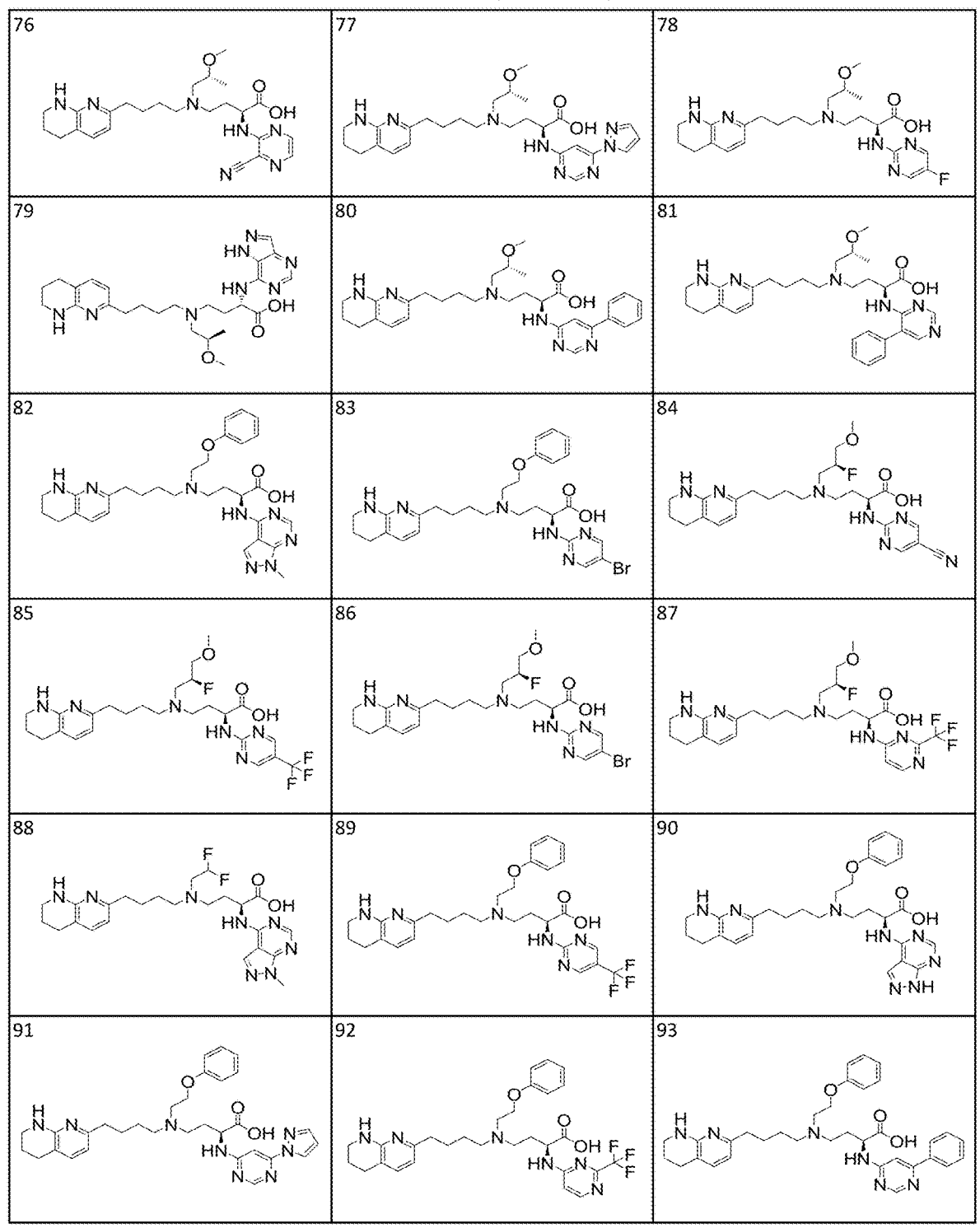
Figure 1:
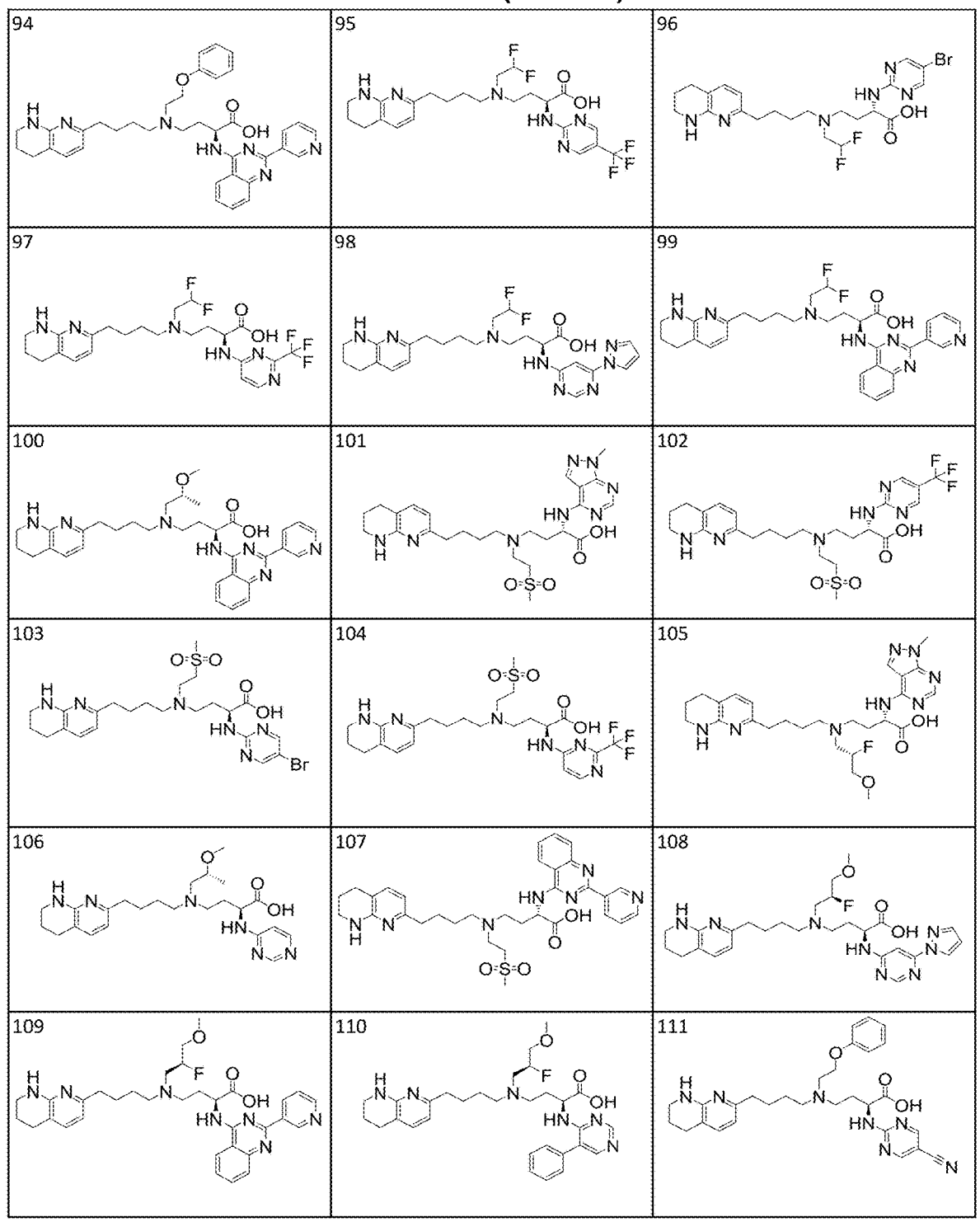
Figure 1:
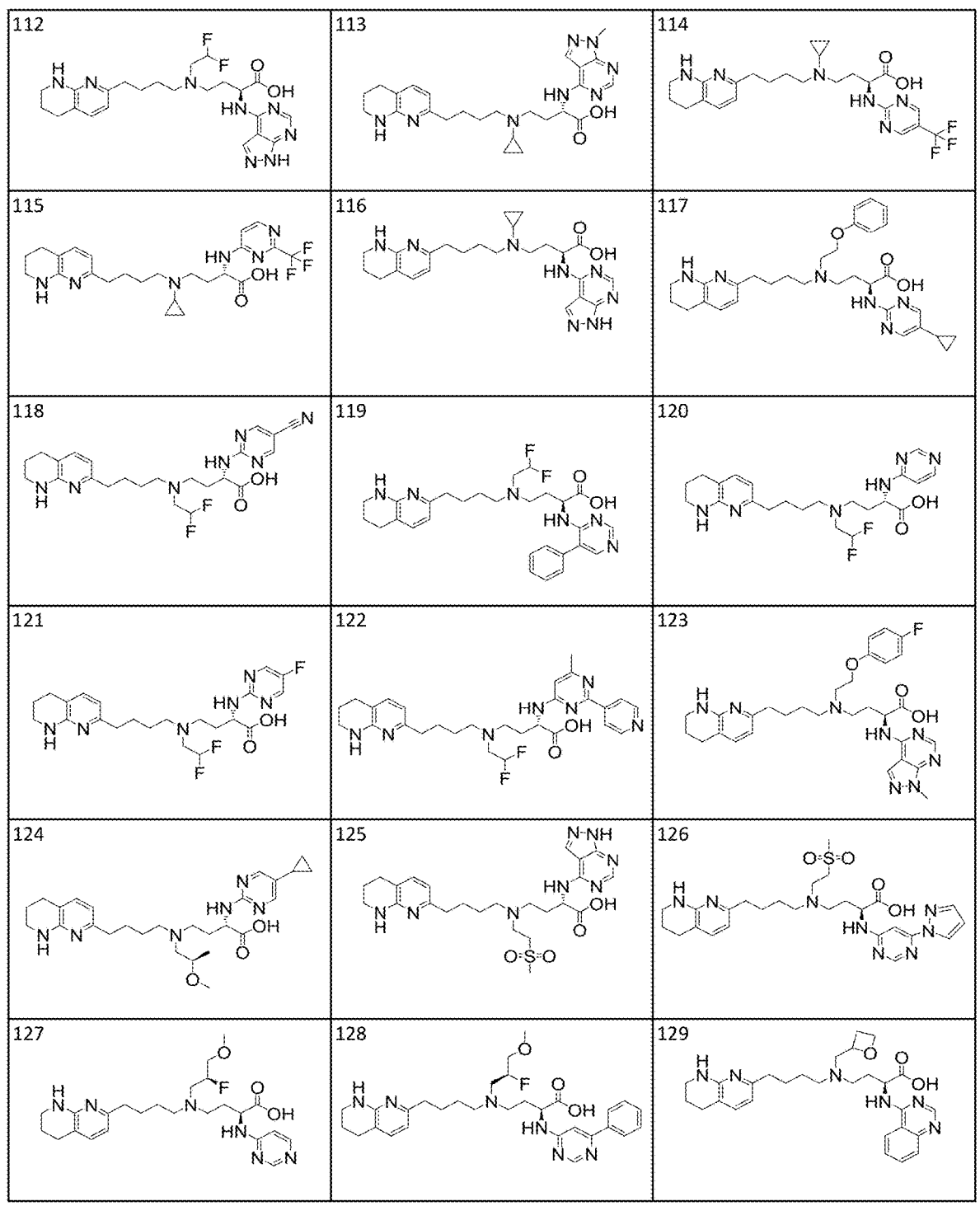
Figure 1:
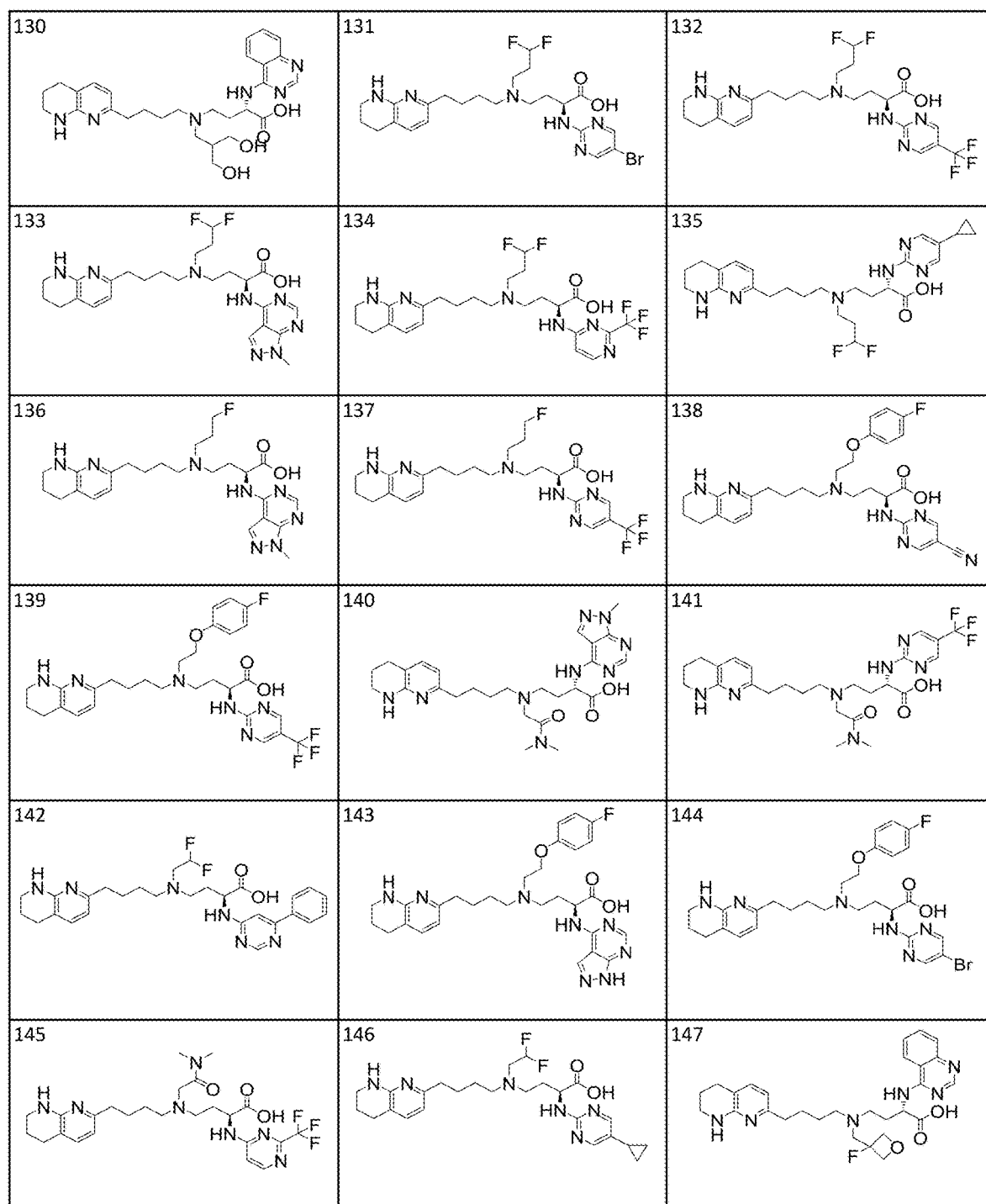
Figure 1:
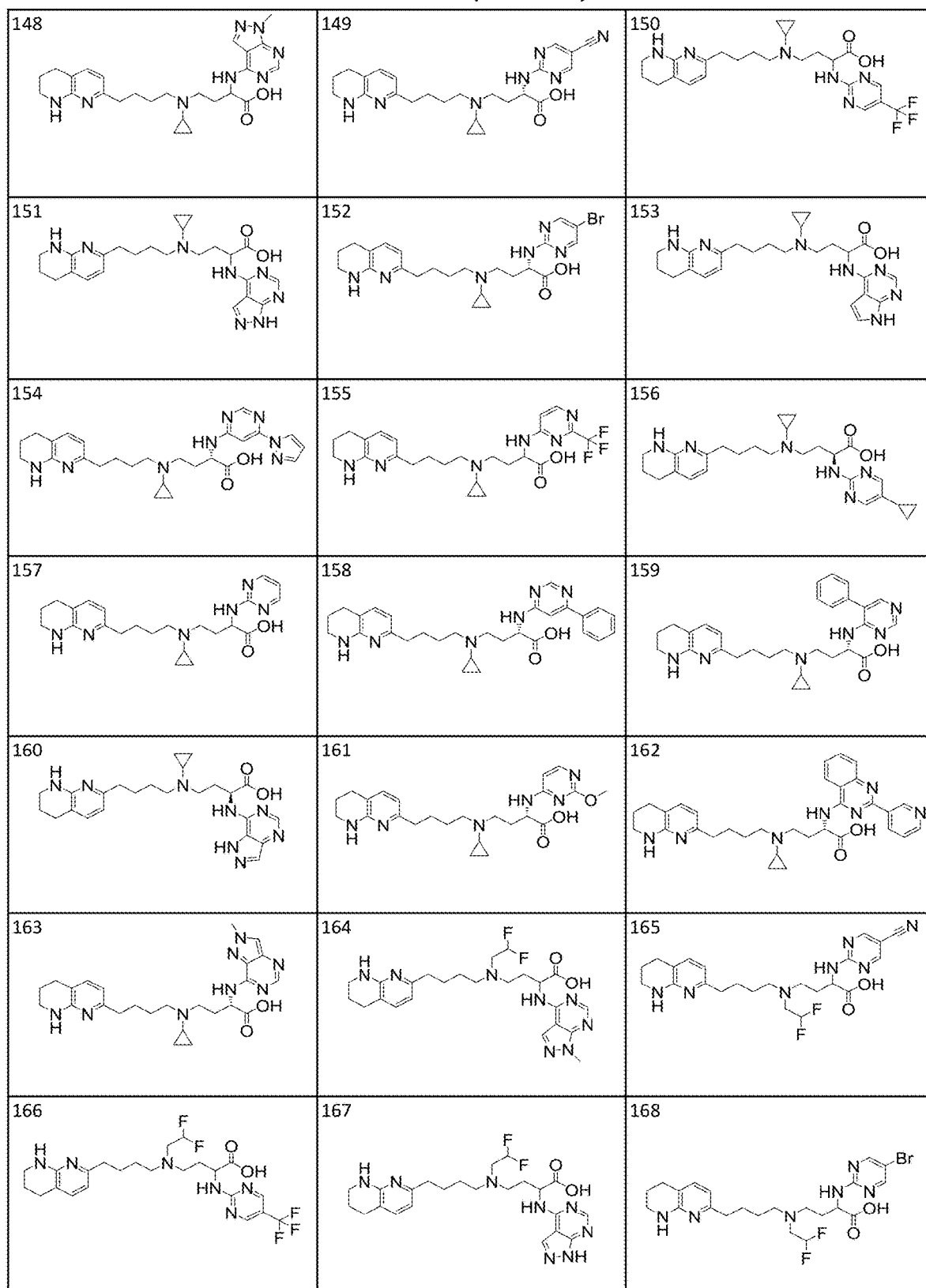
Figure 1:
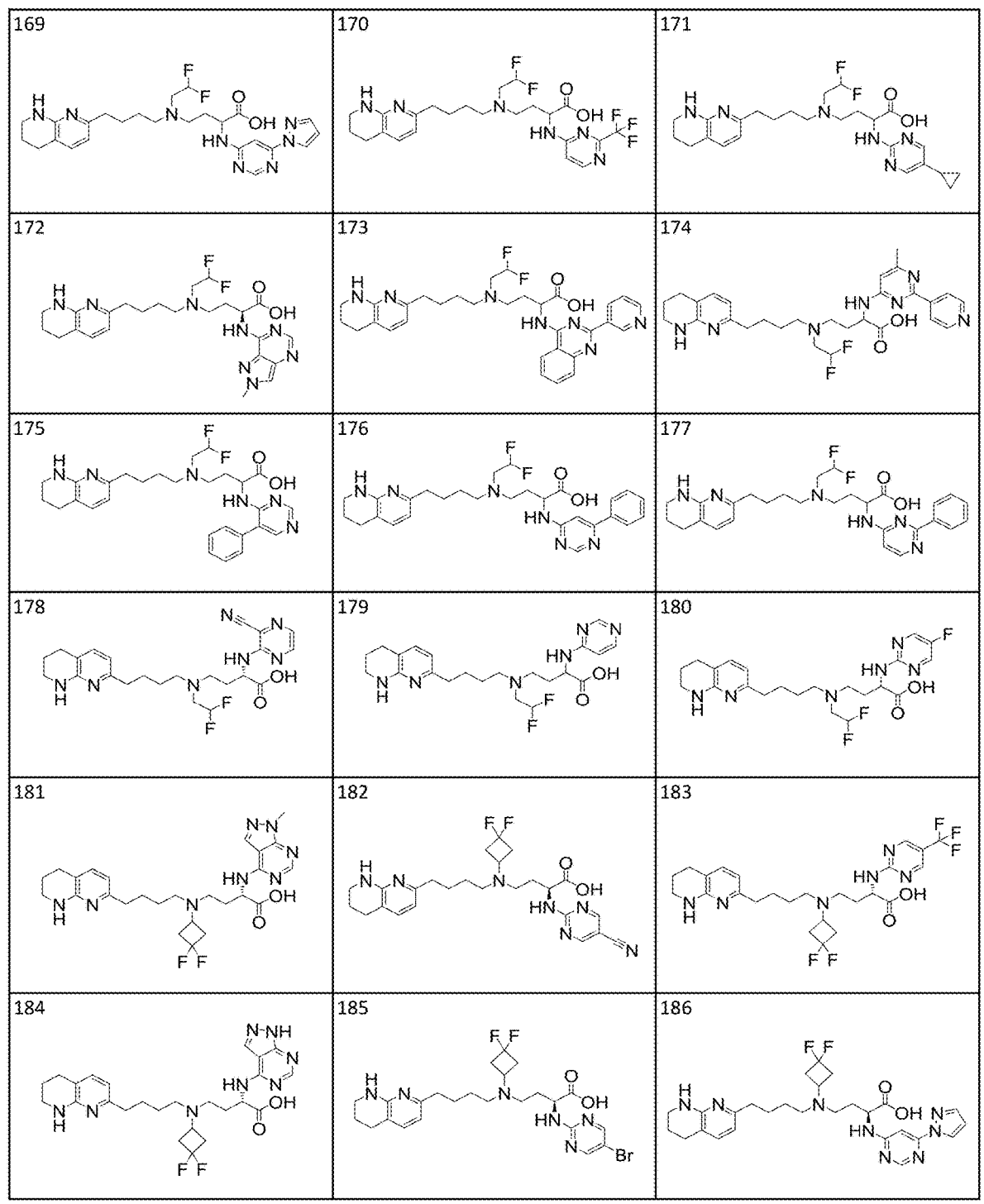
Figure 1:
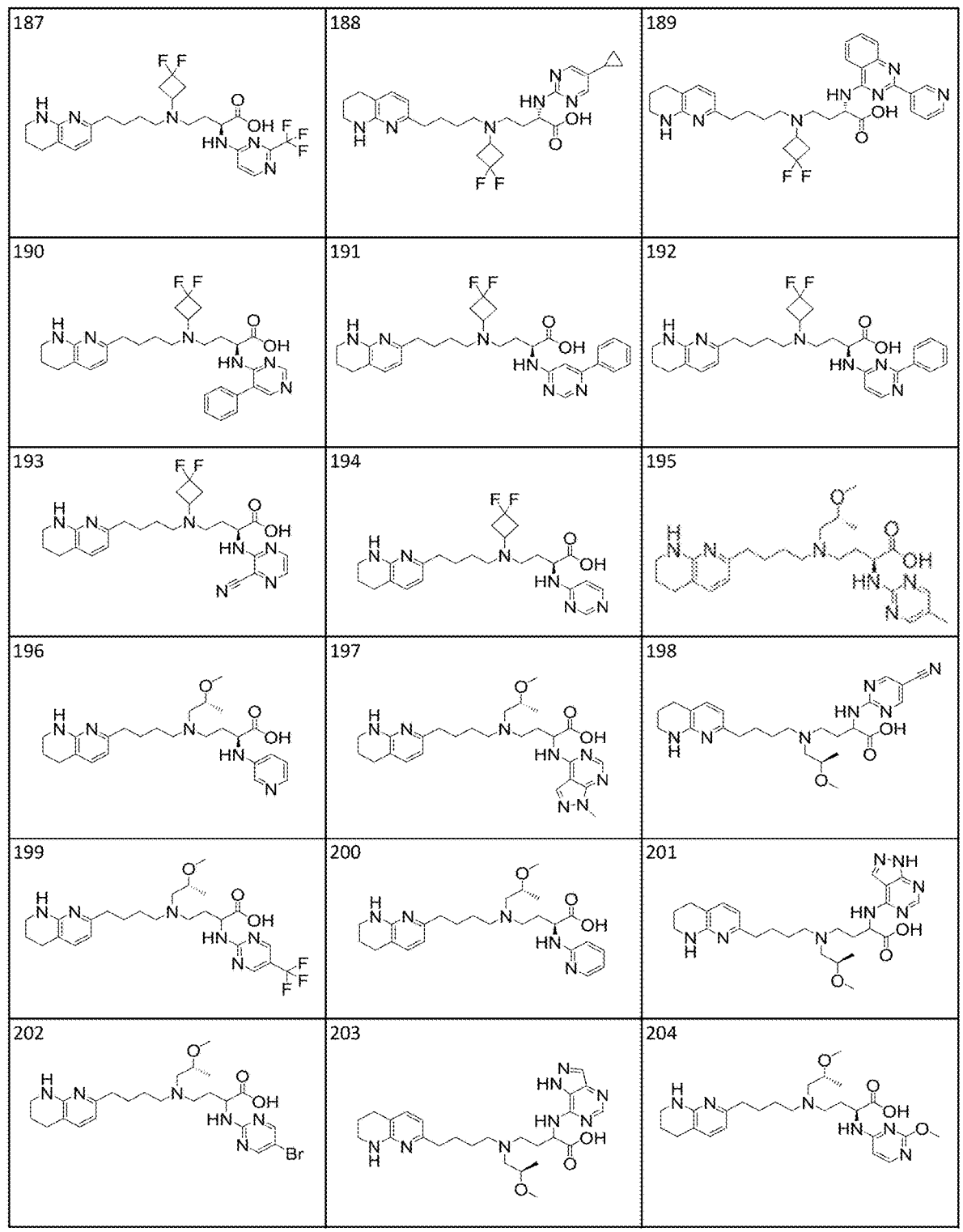
Figure 1:
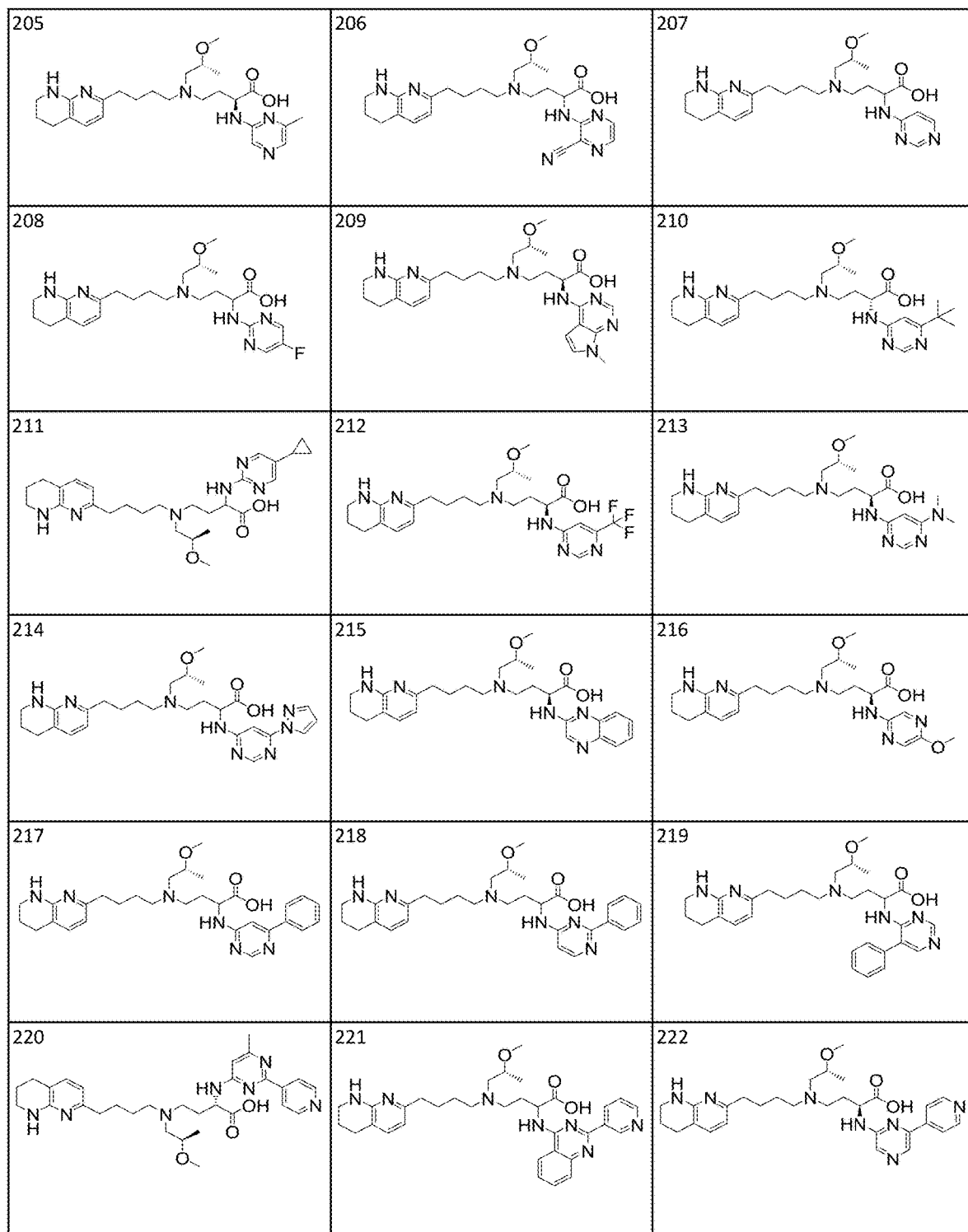
Figure 1:
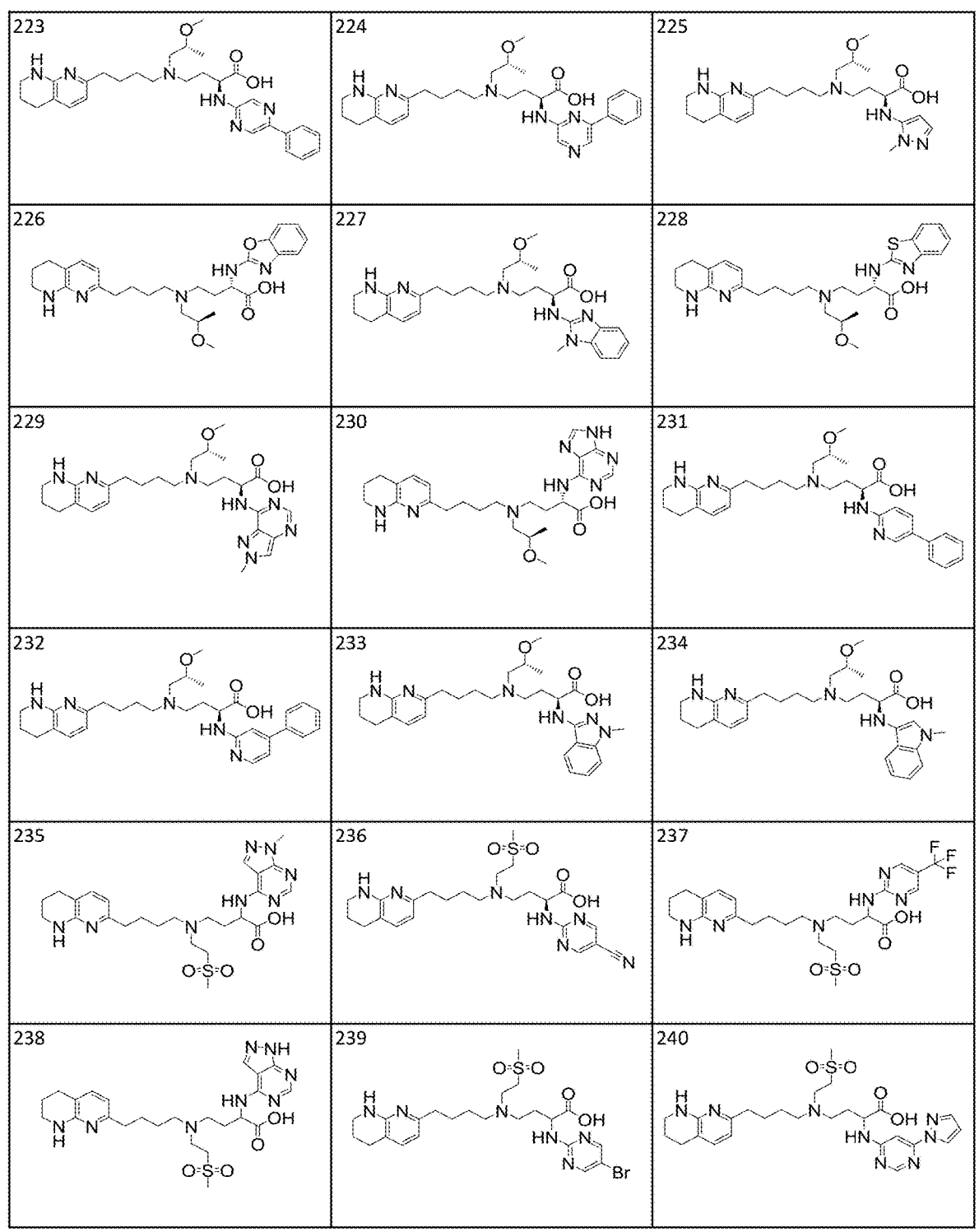
Figure 1:
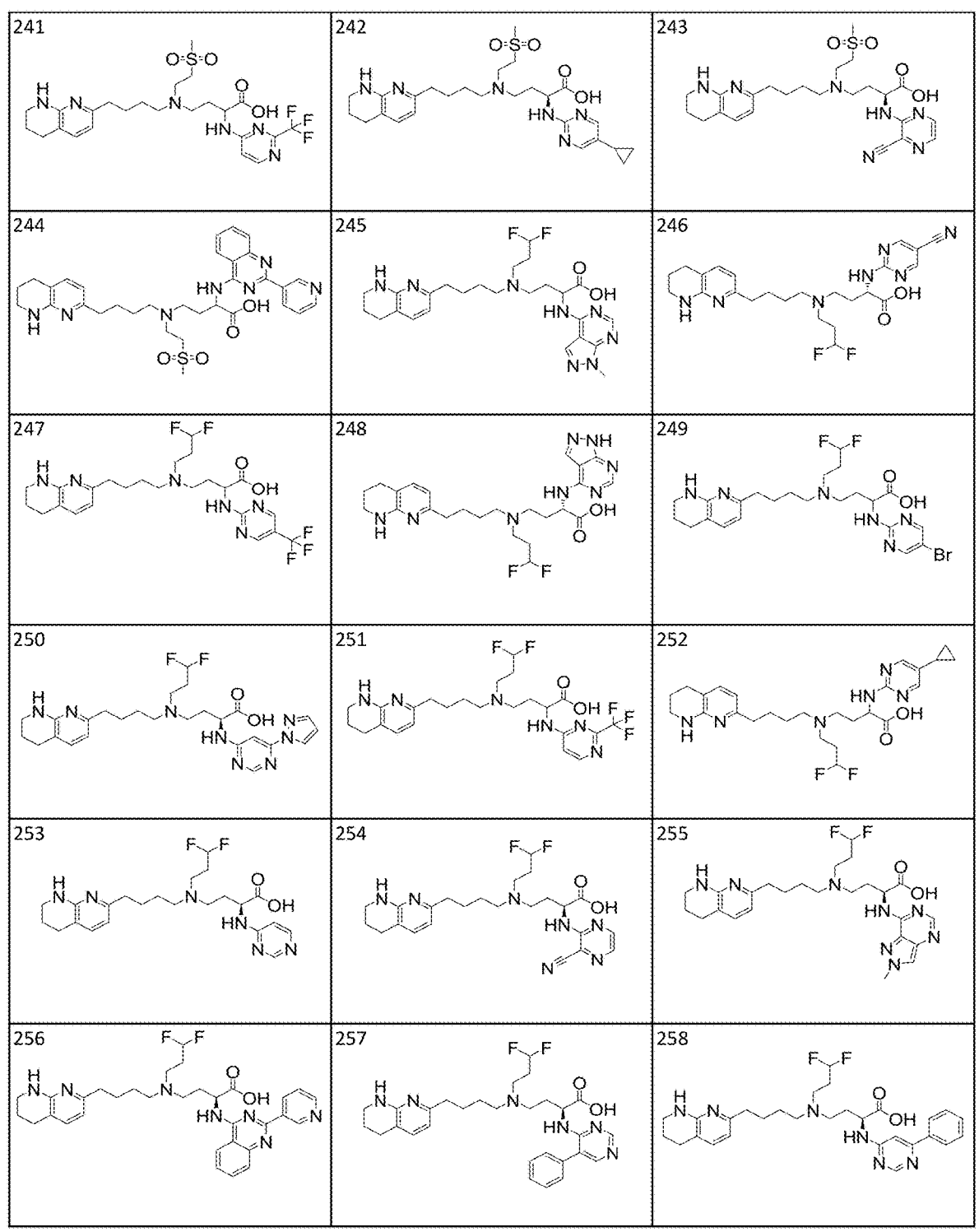
Figure 1:
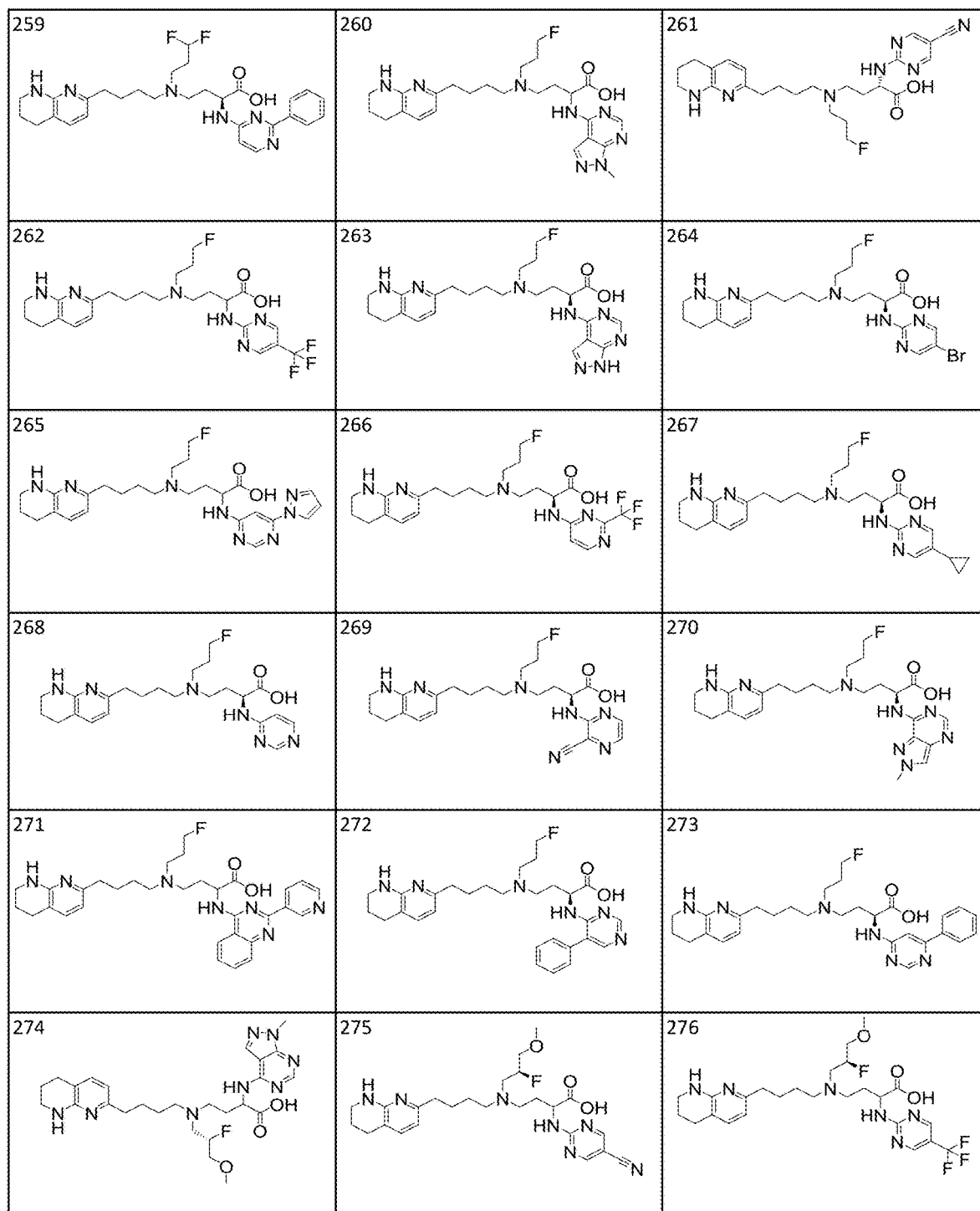
Figure 1:
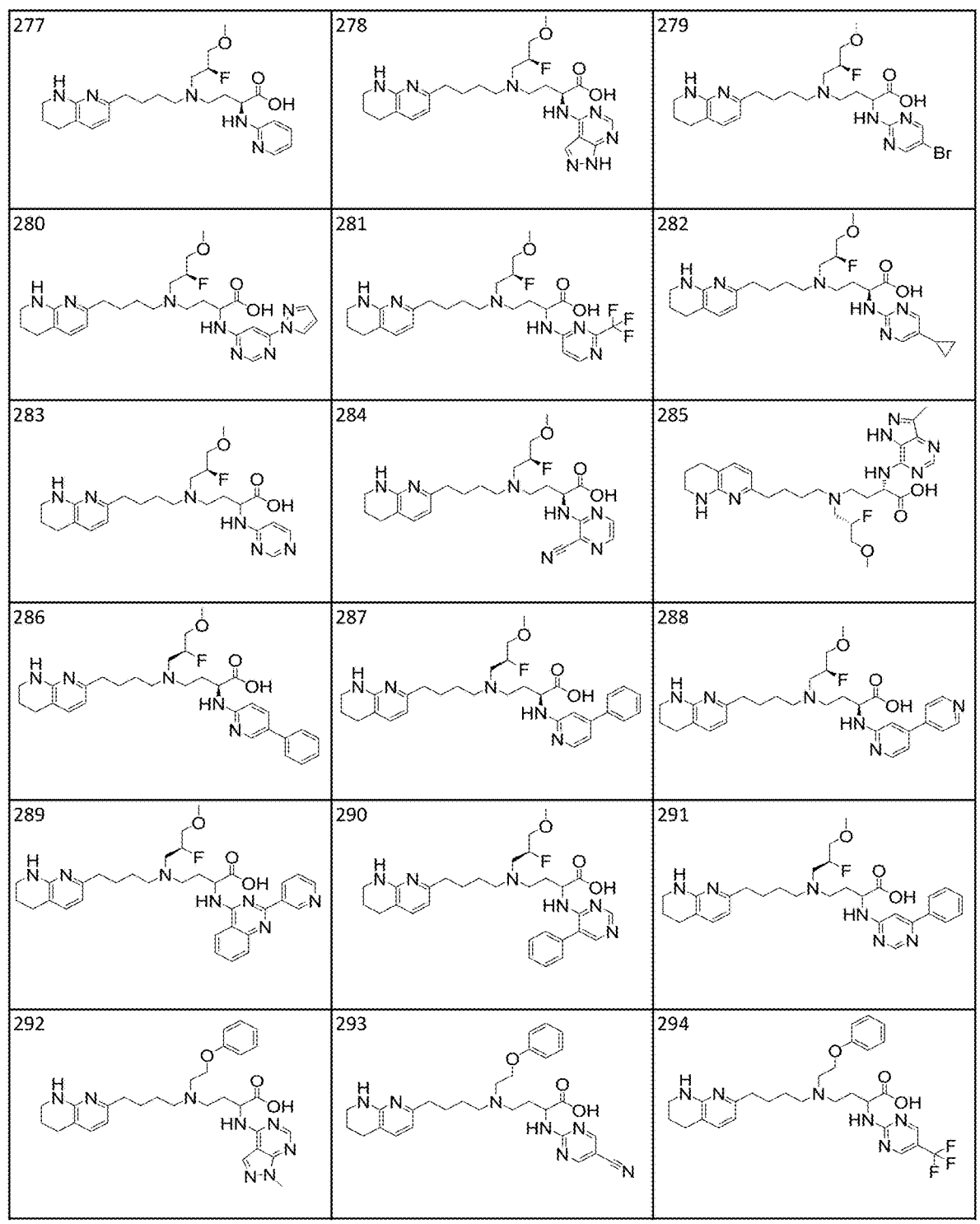
Figure 1:
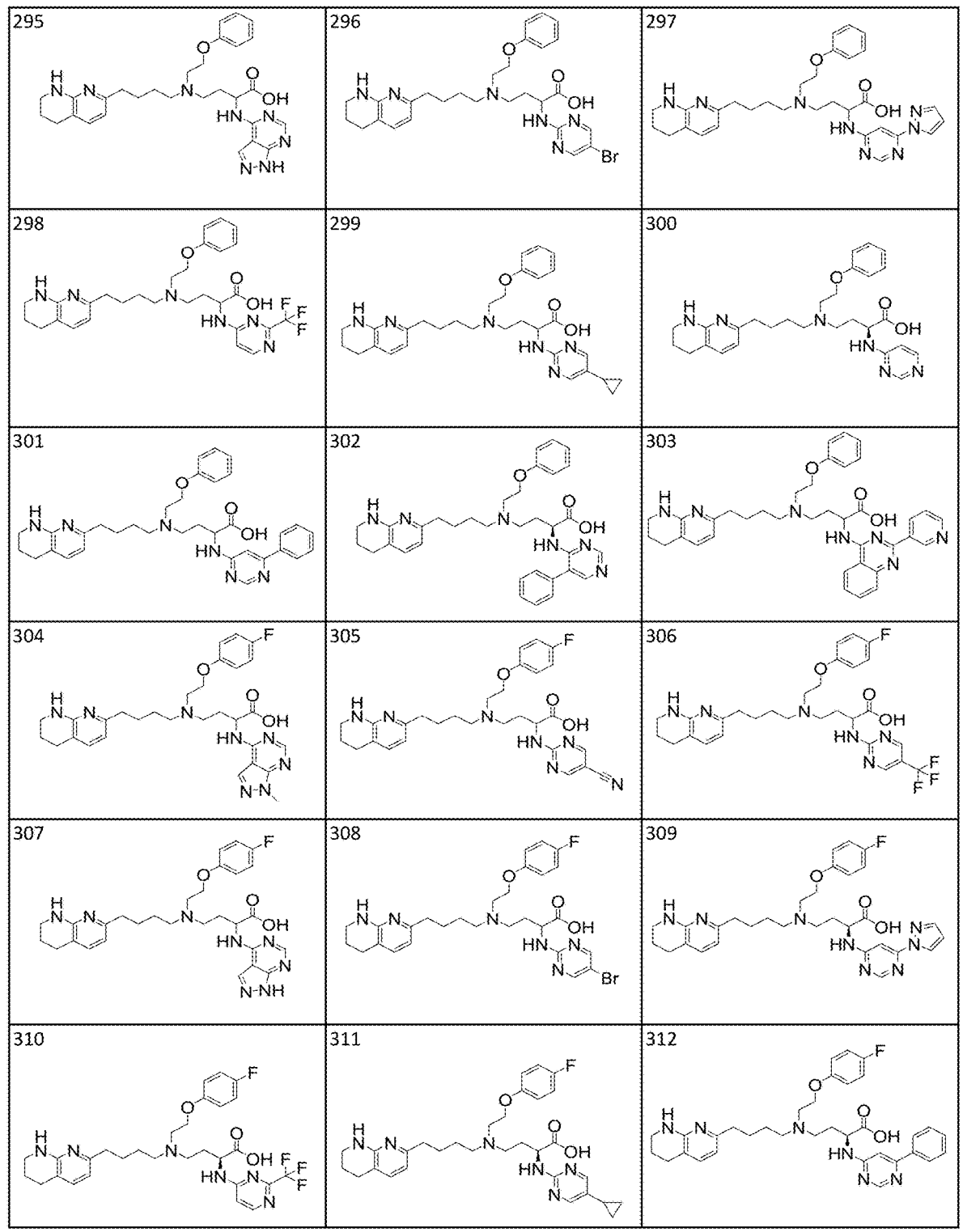
Figure 1:
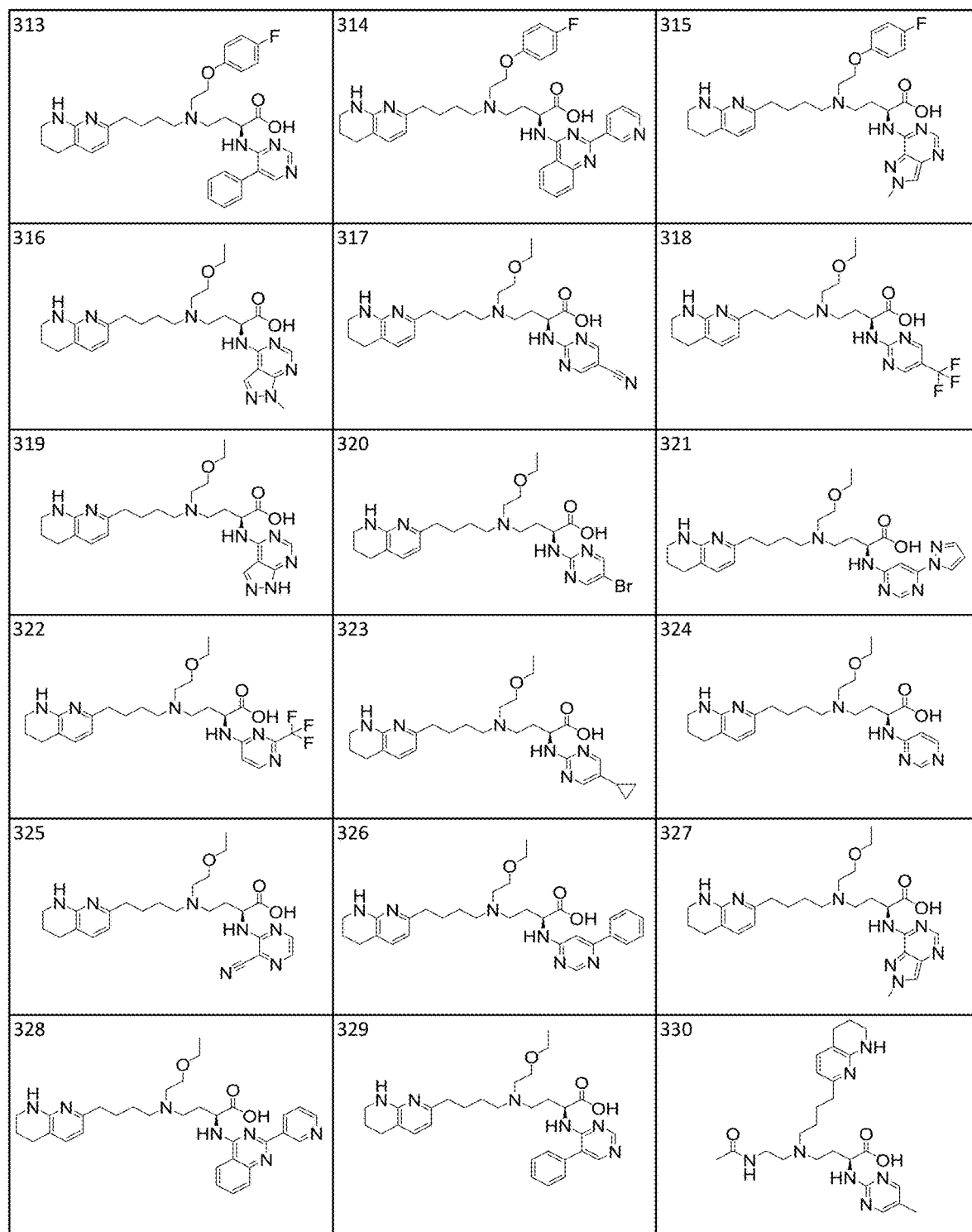
Figure 1:
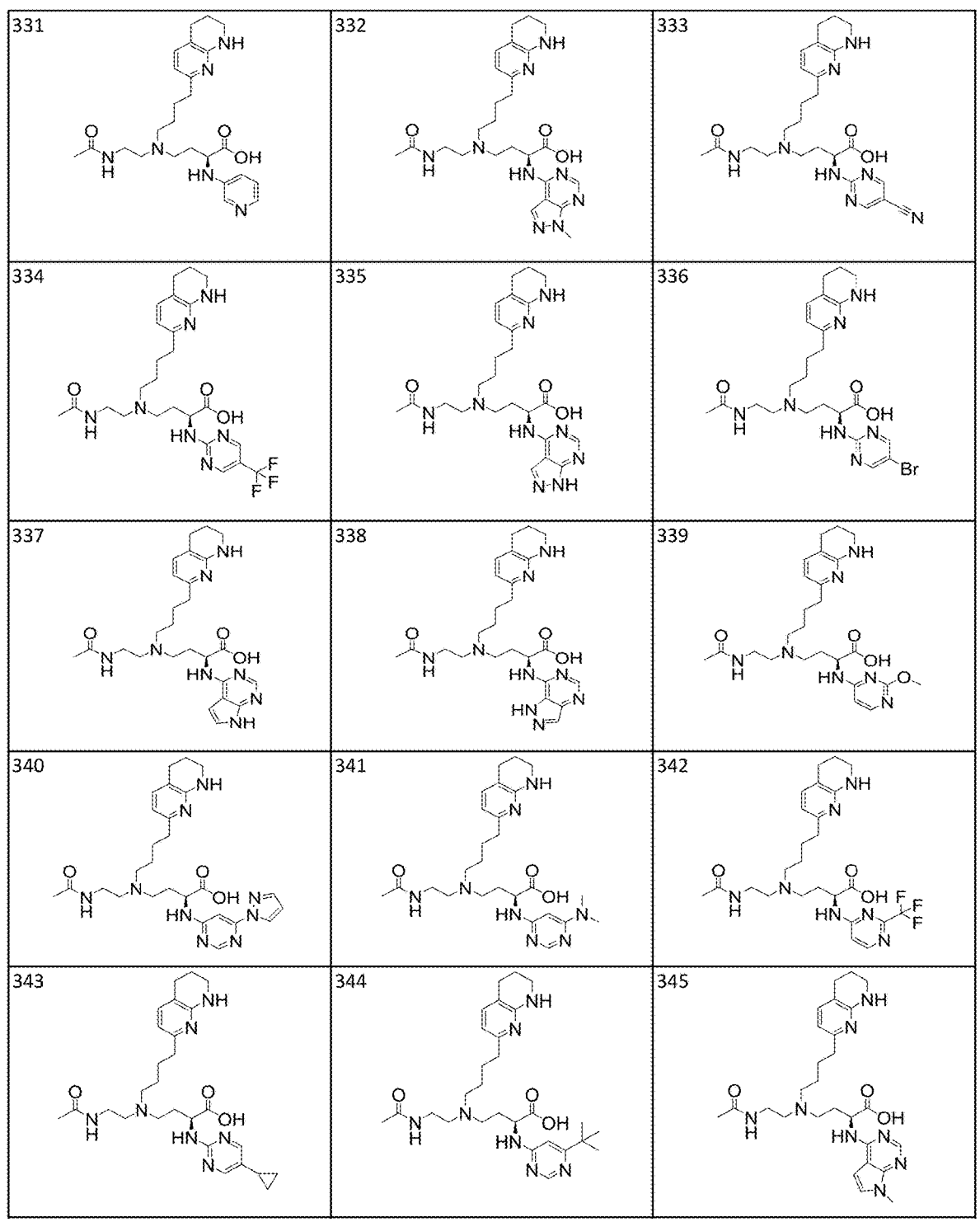
Figure 1:
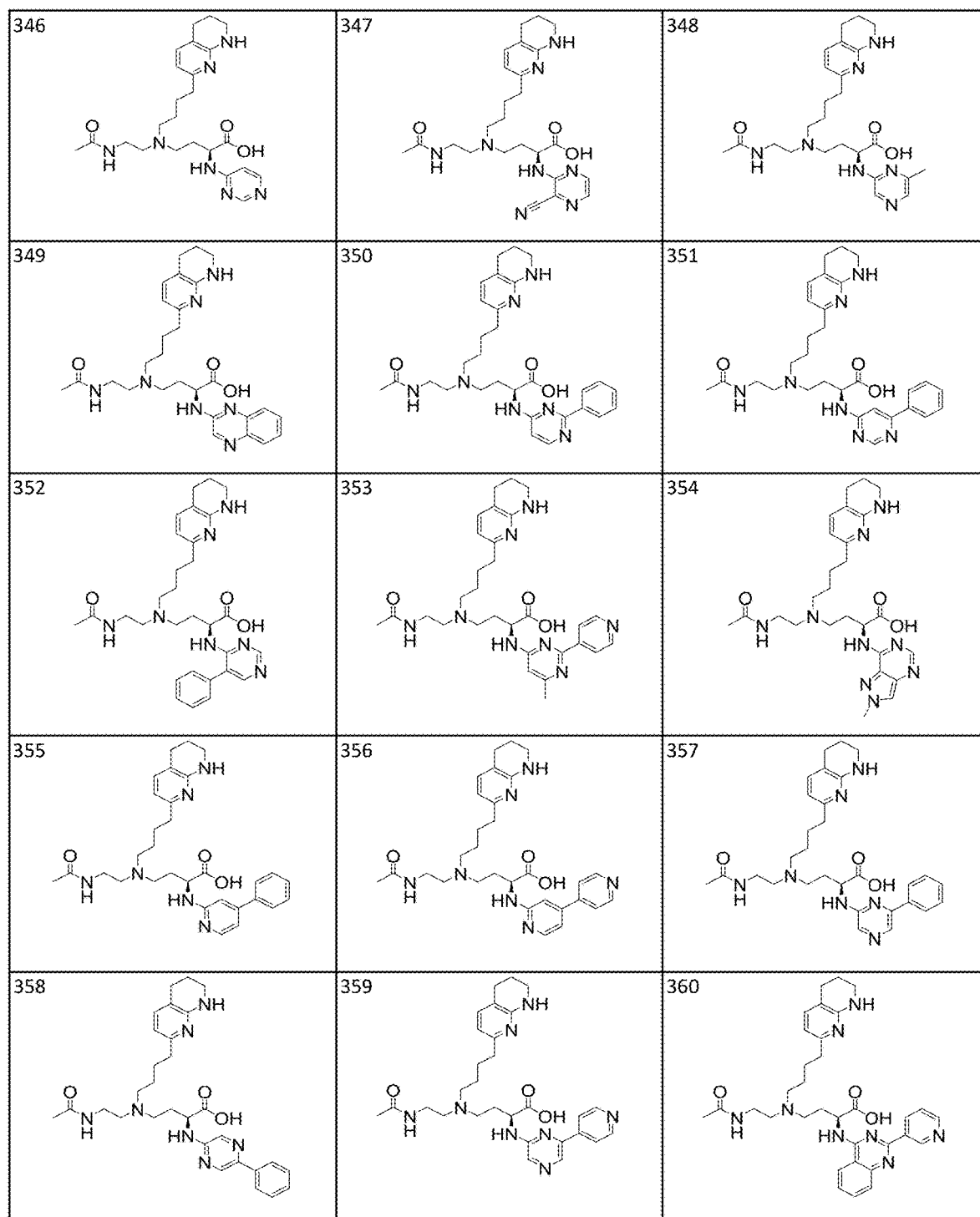
Figure 1:
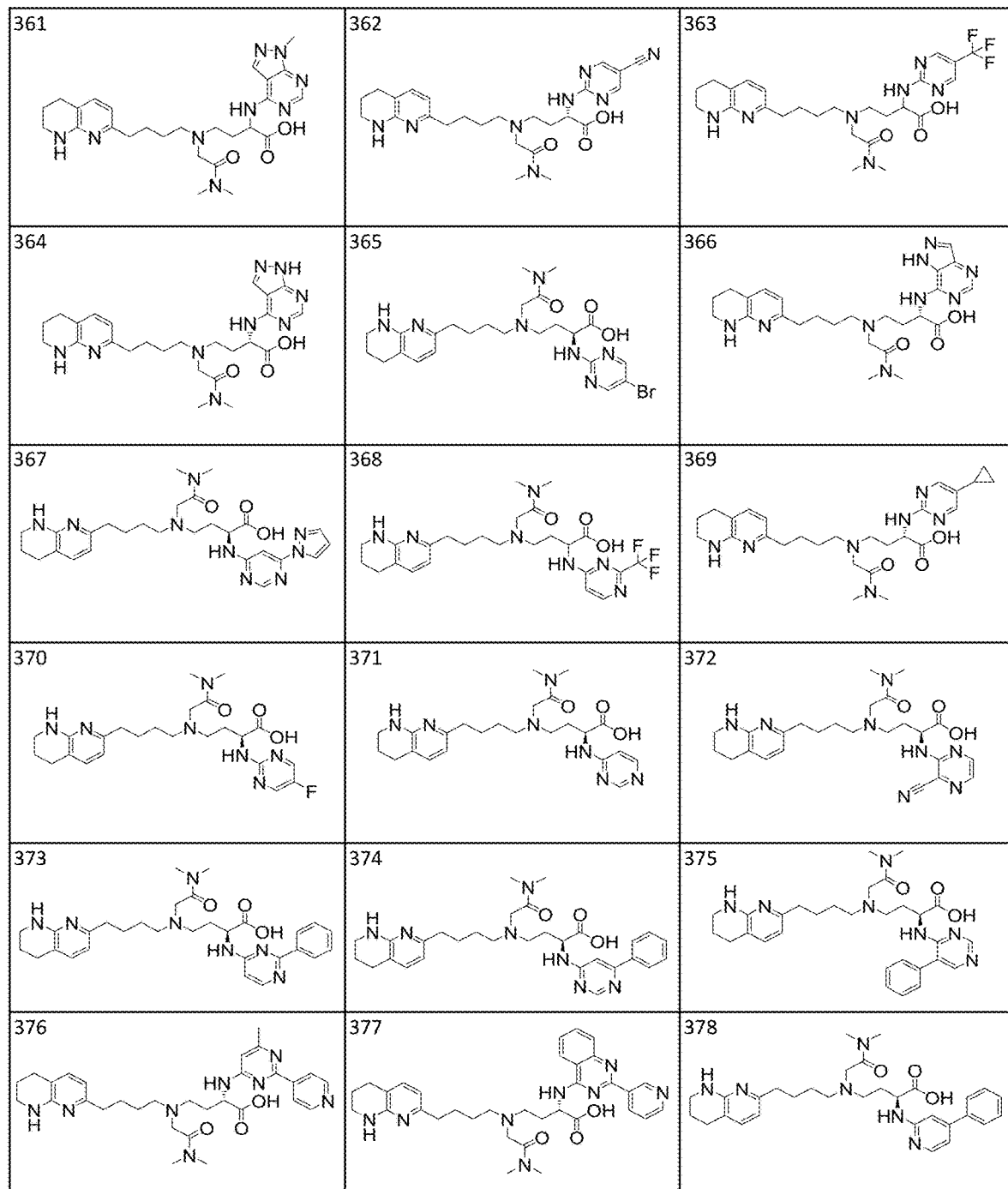
Figure 1:
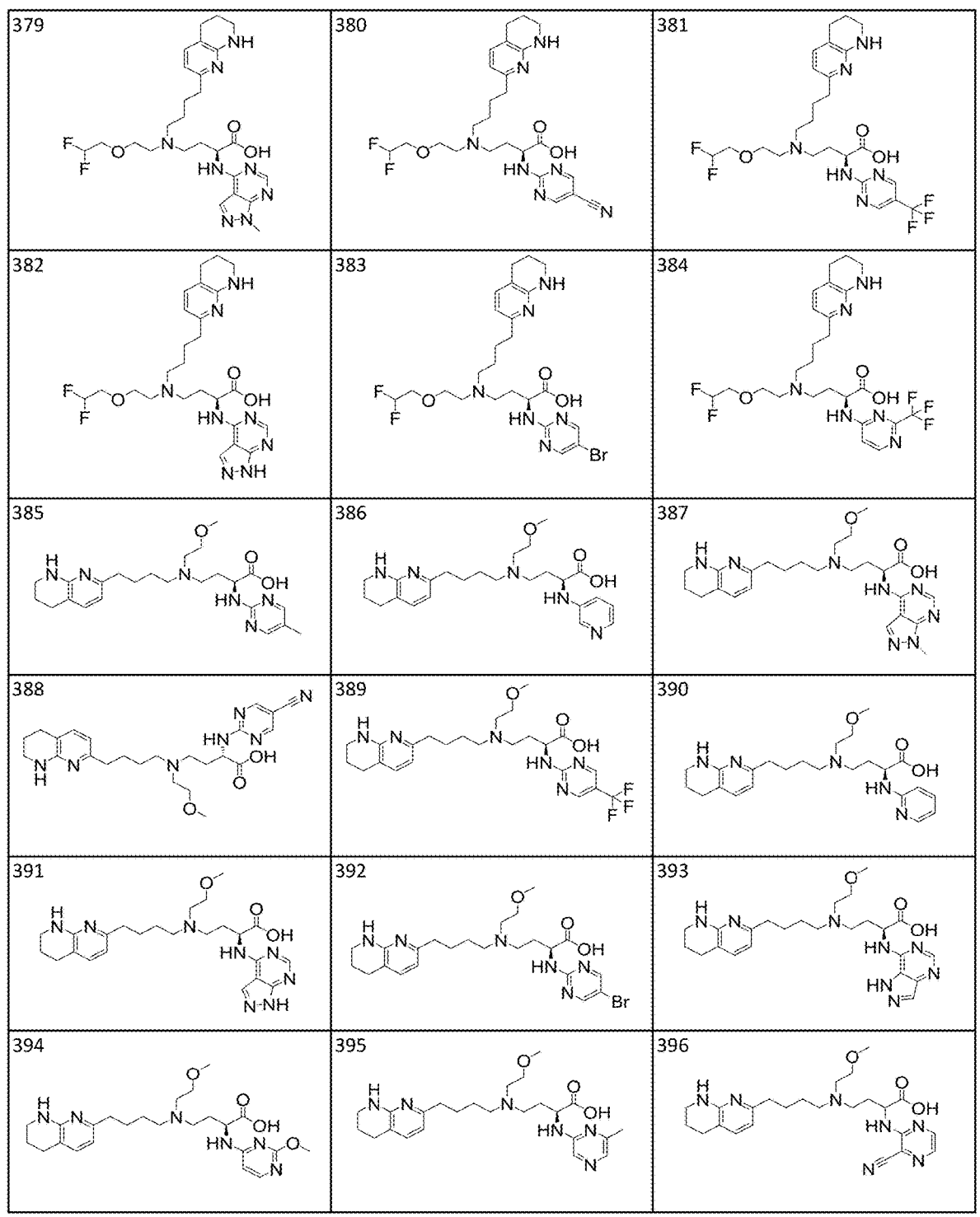
Figure 1:
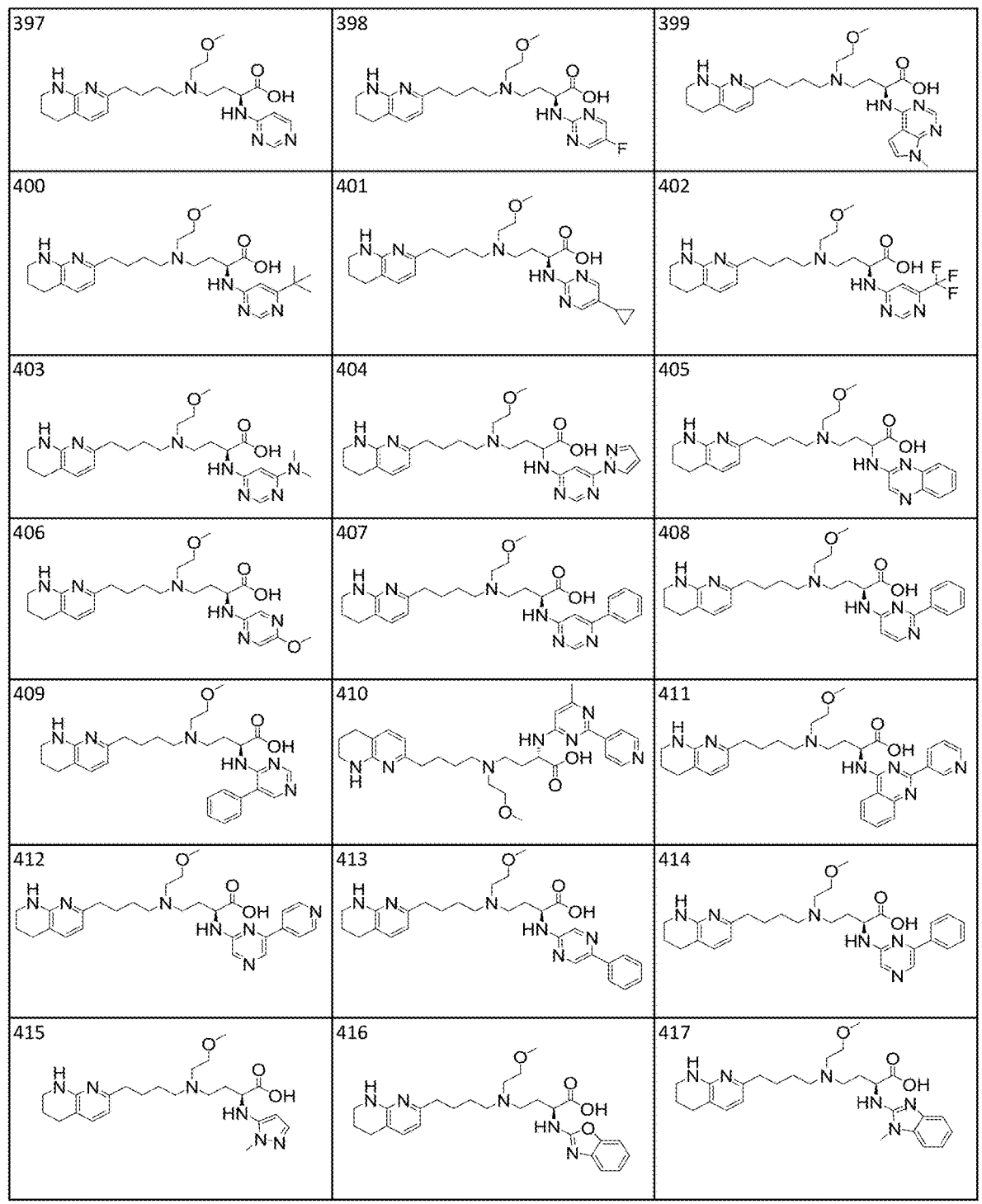
Figure 1:
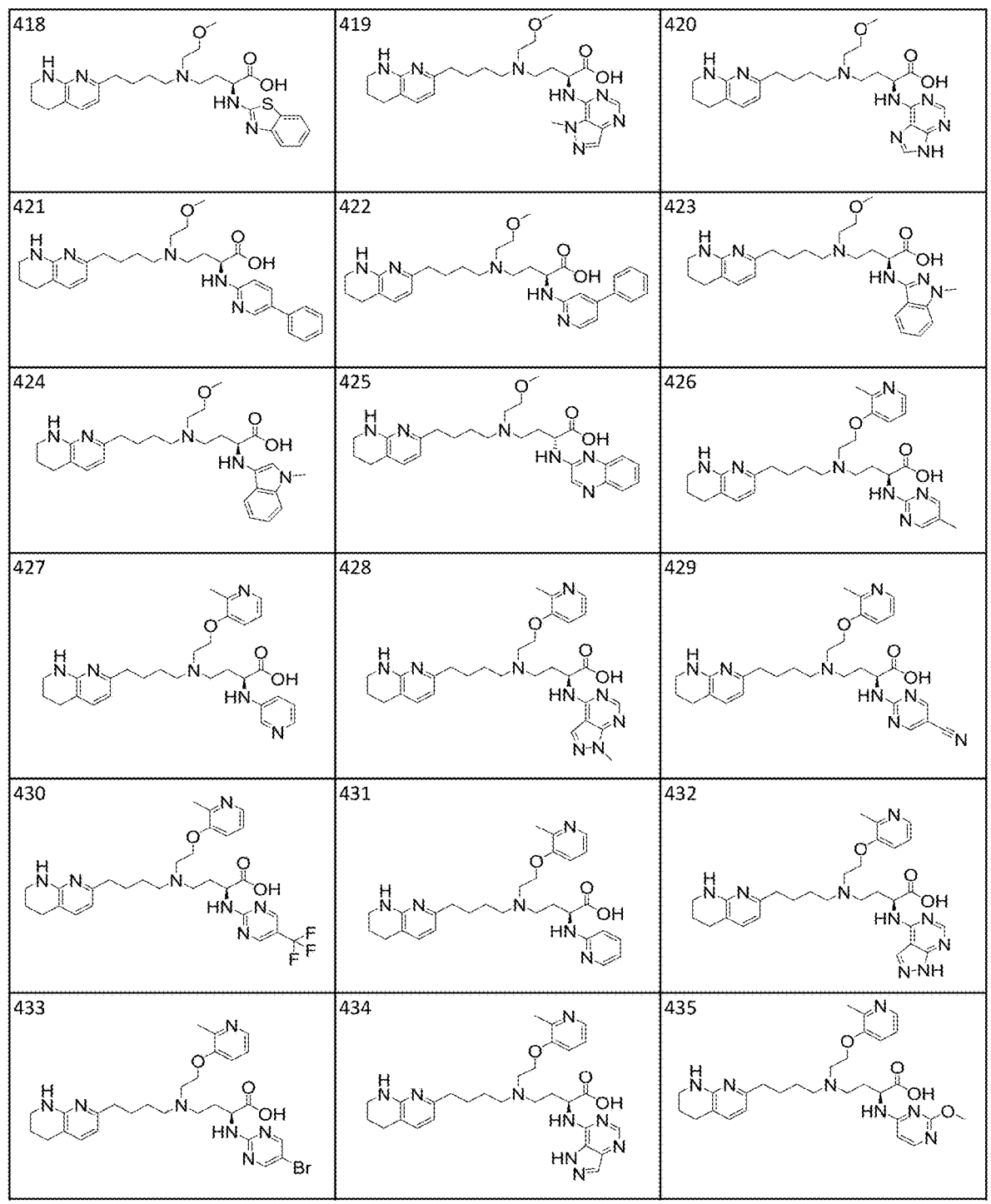
Figure 1:
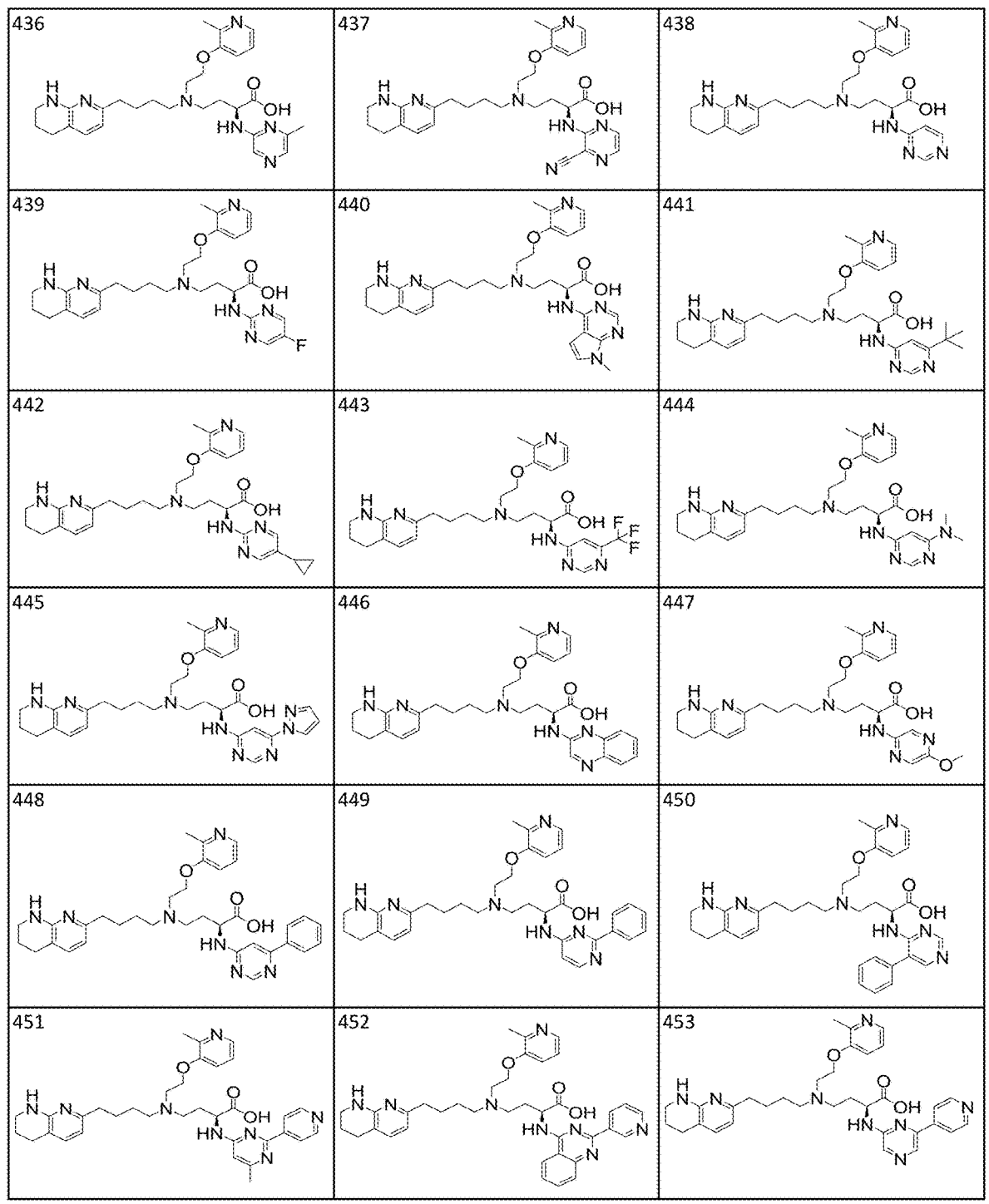
Figure 1:
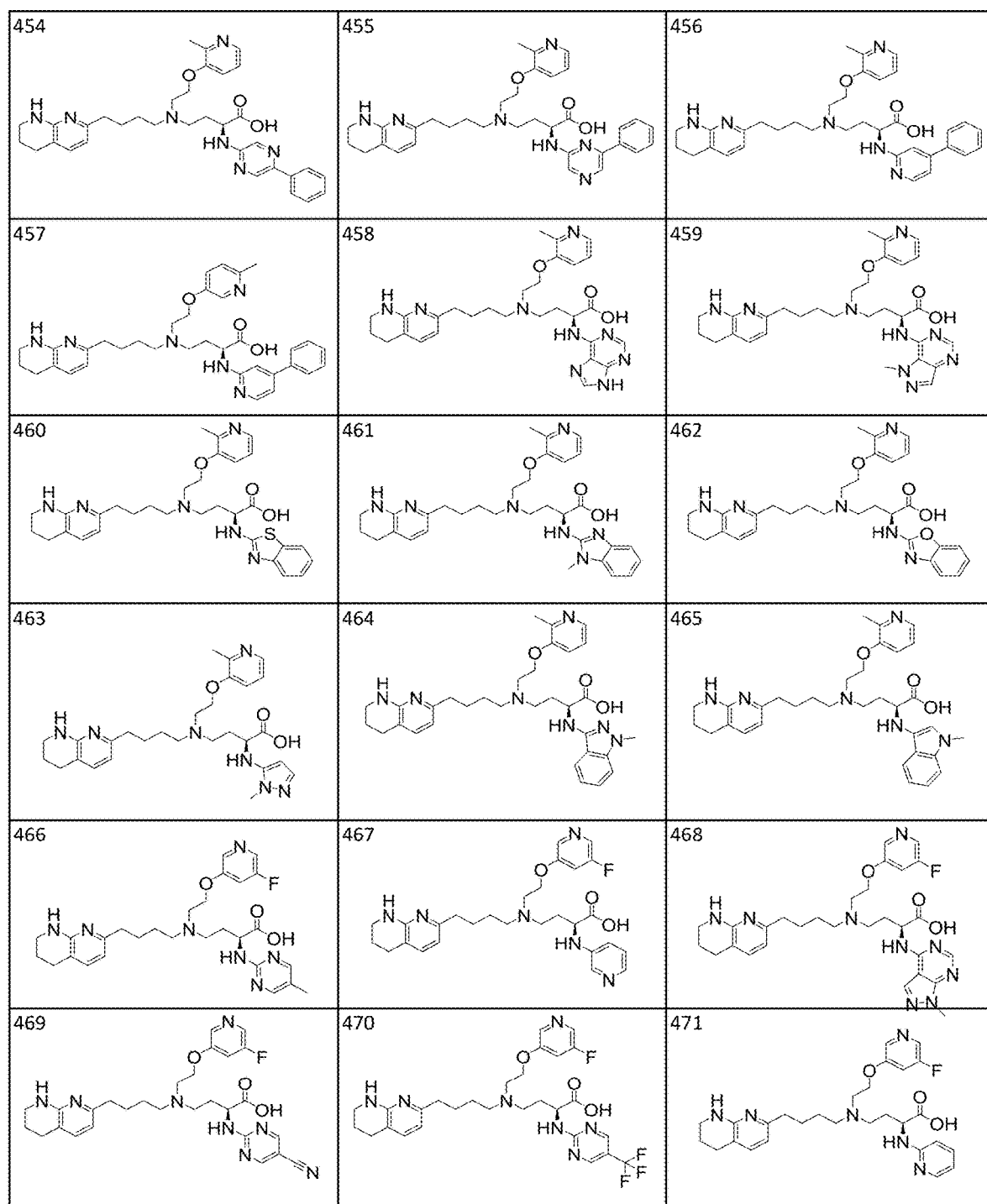
Figure 1:
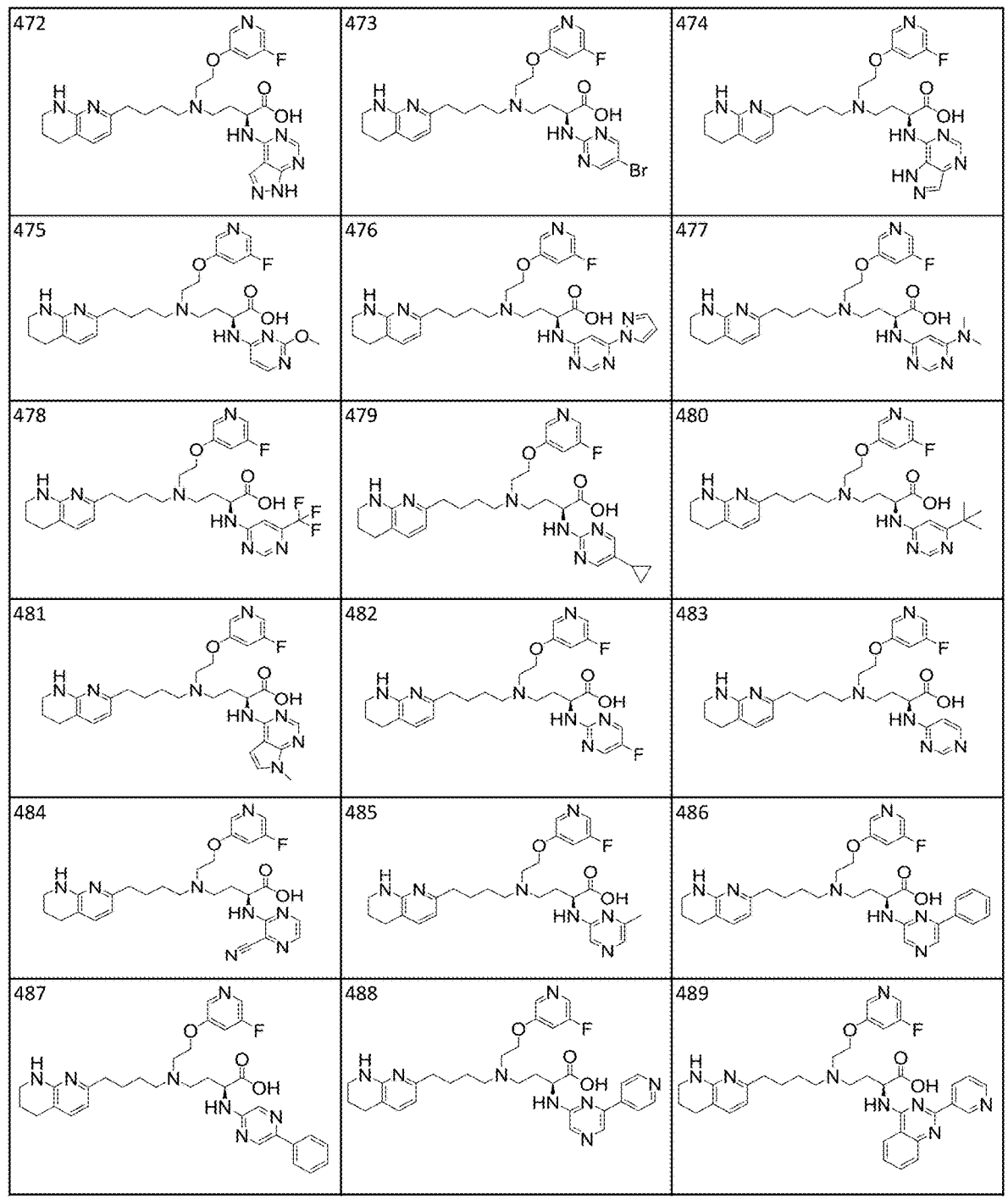
Figure 1:
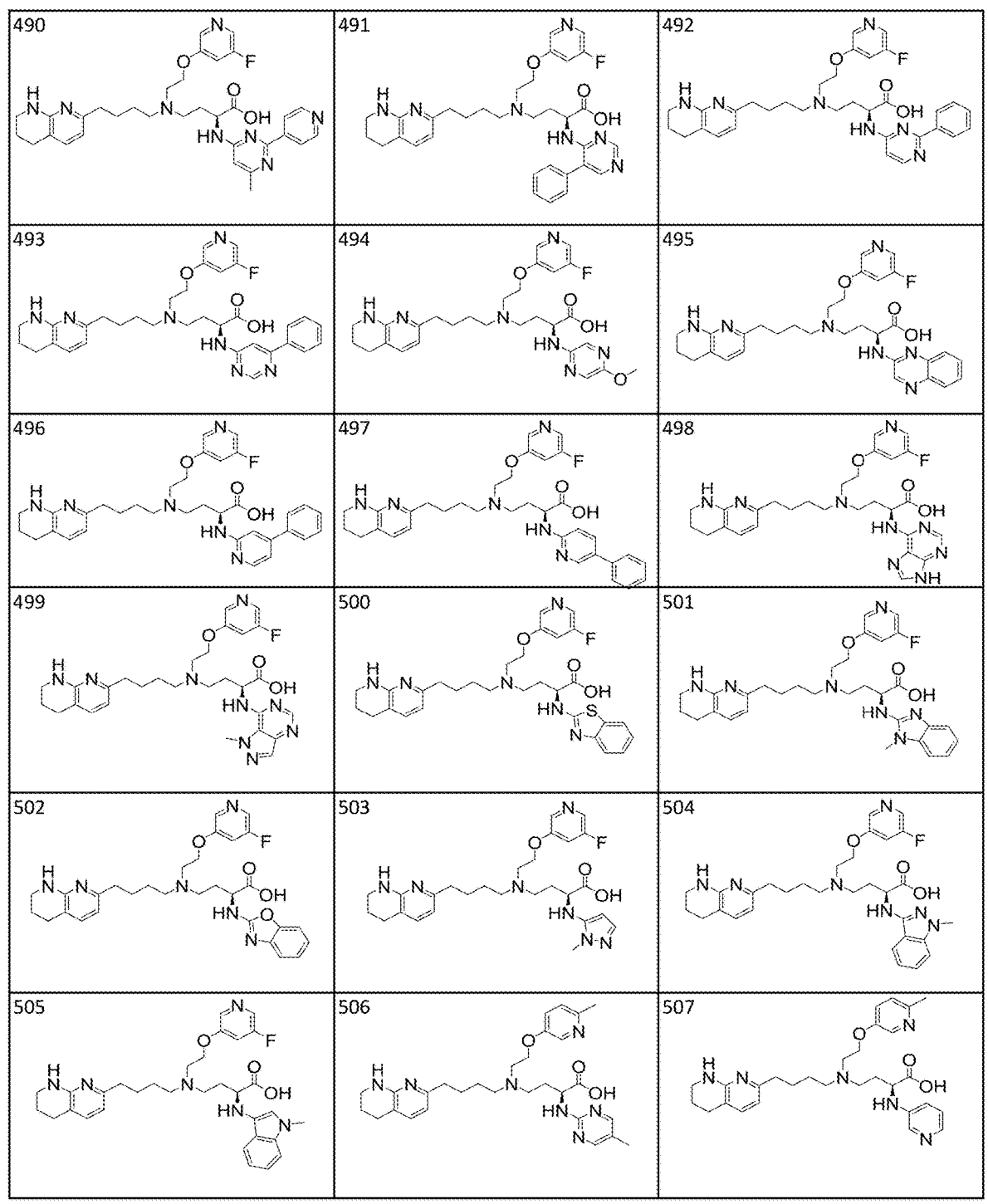
Figure 1:
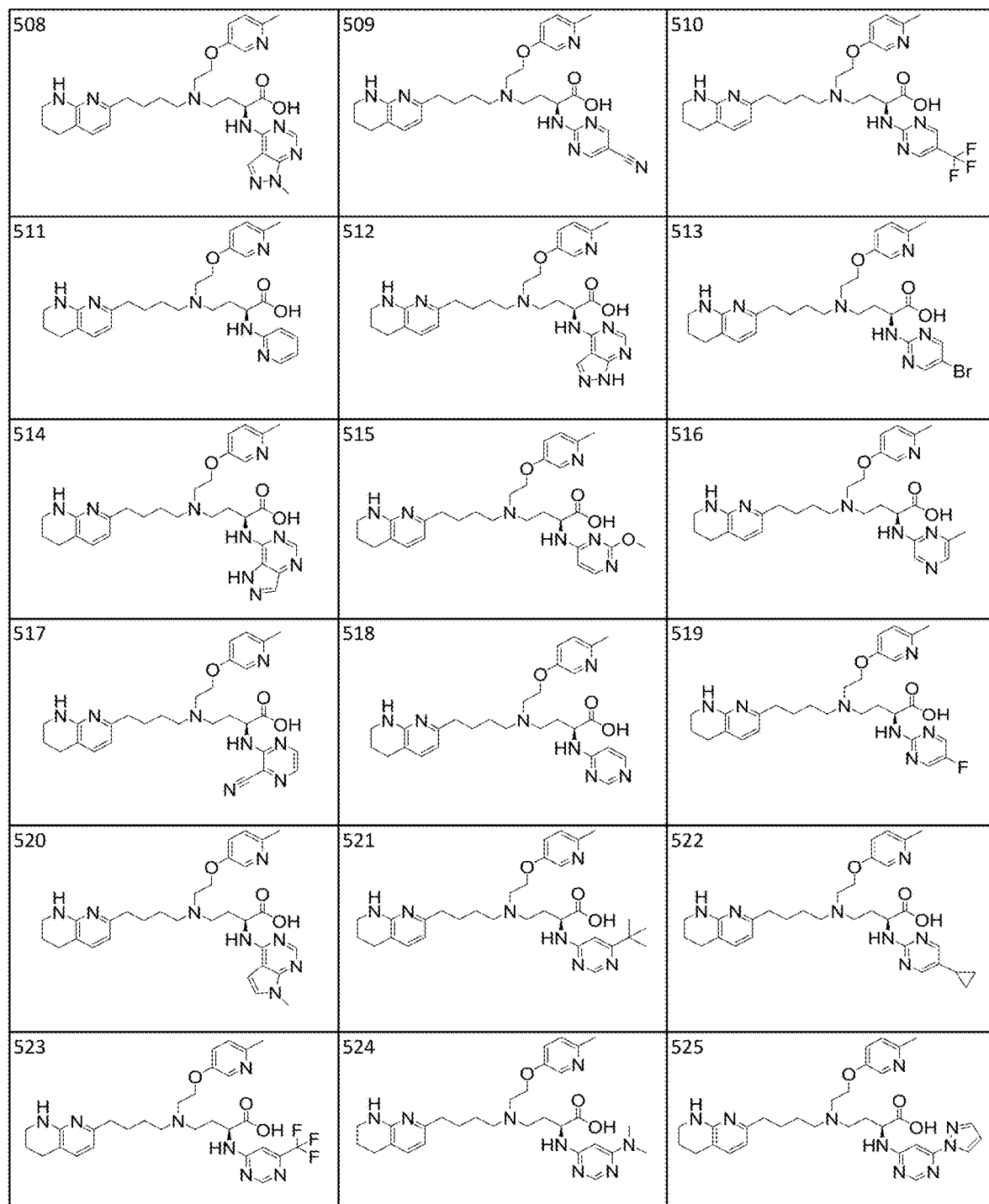
Figure 1:
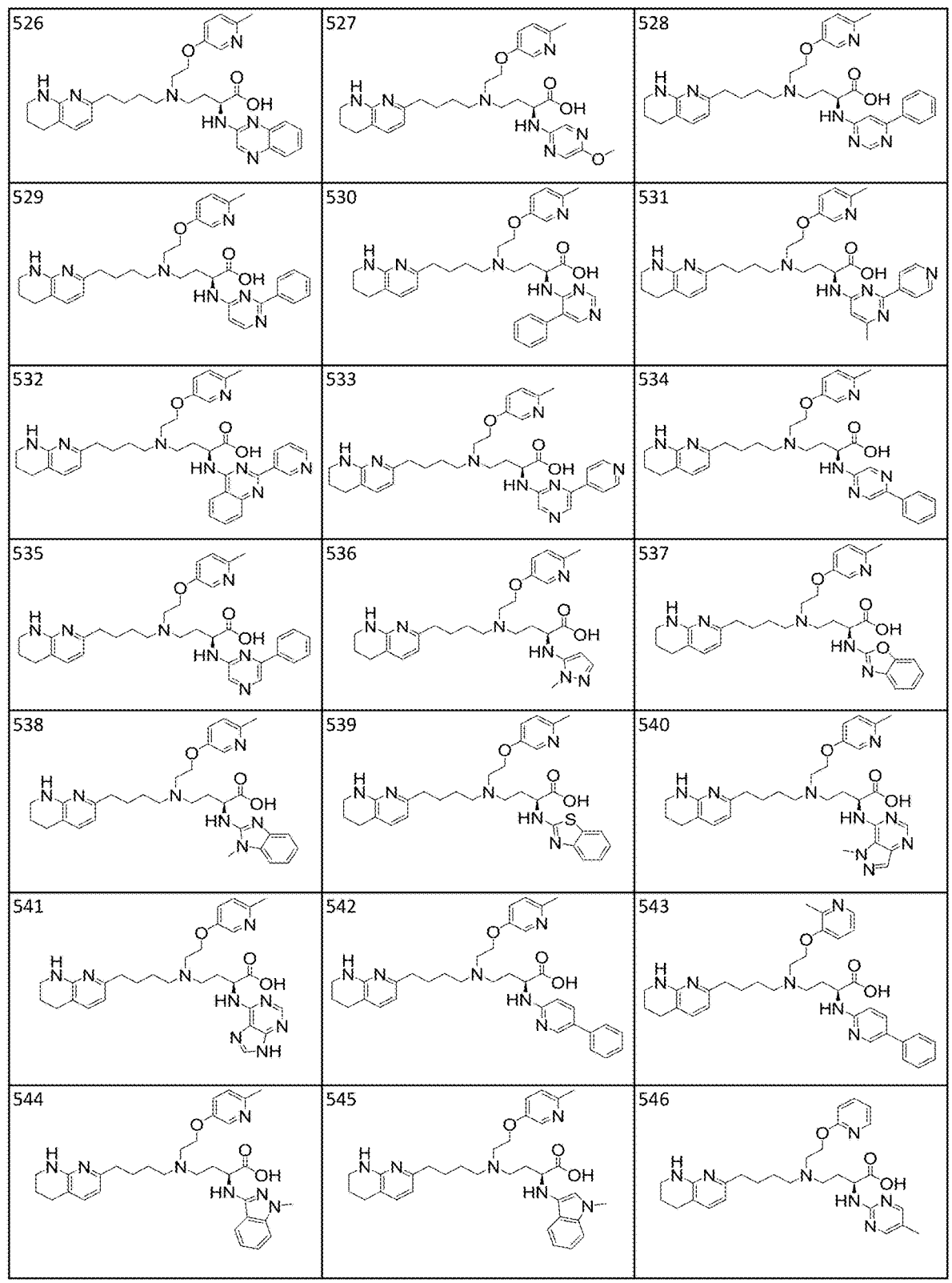
Figure 1:
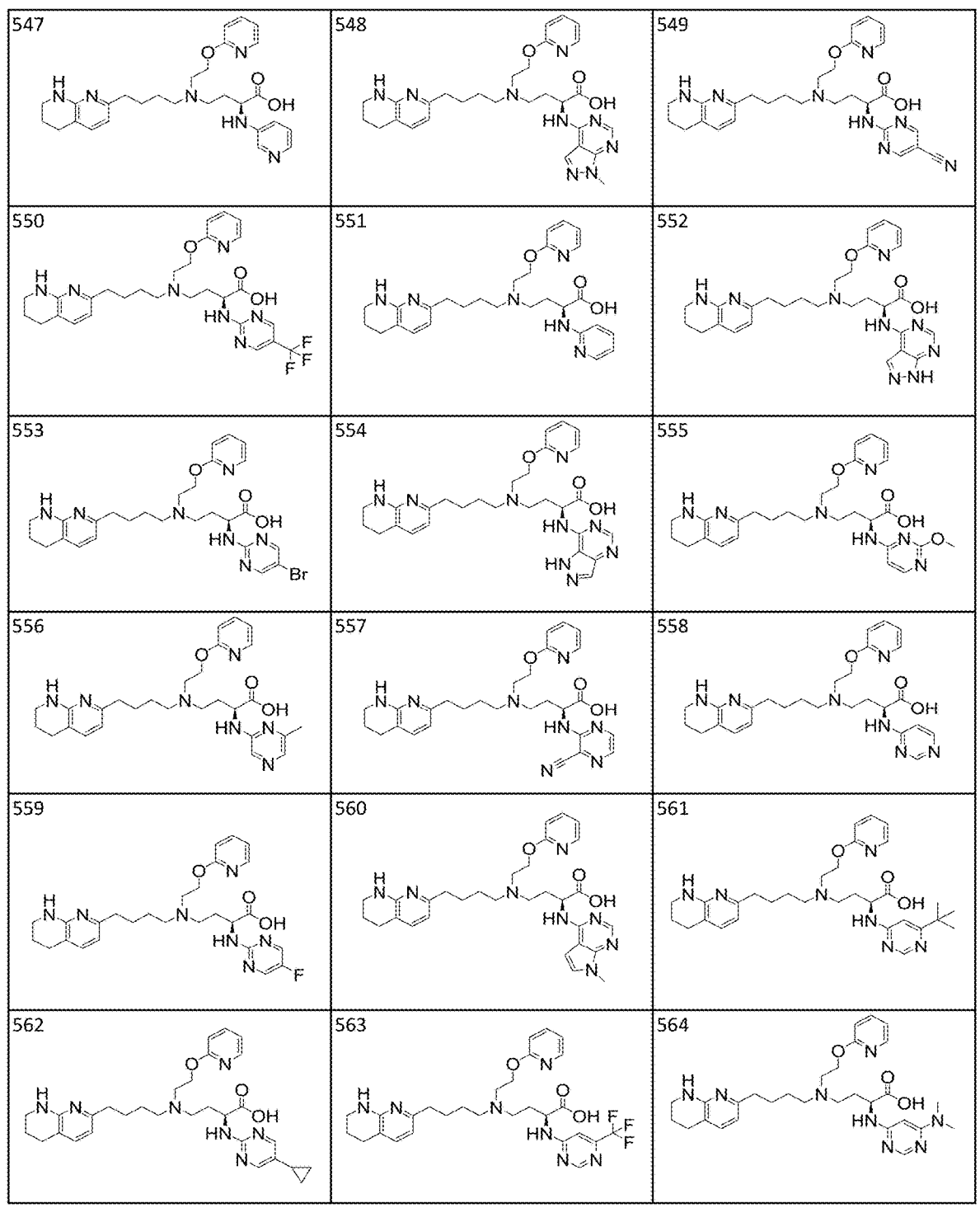
Figure 1:
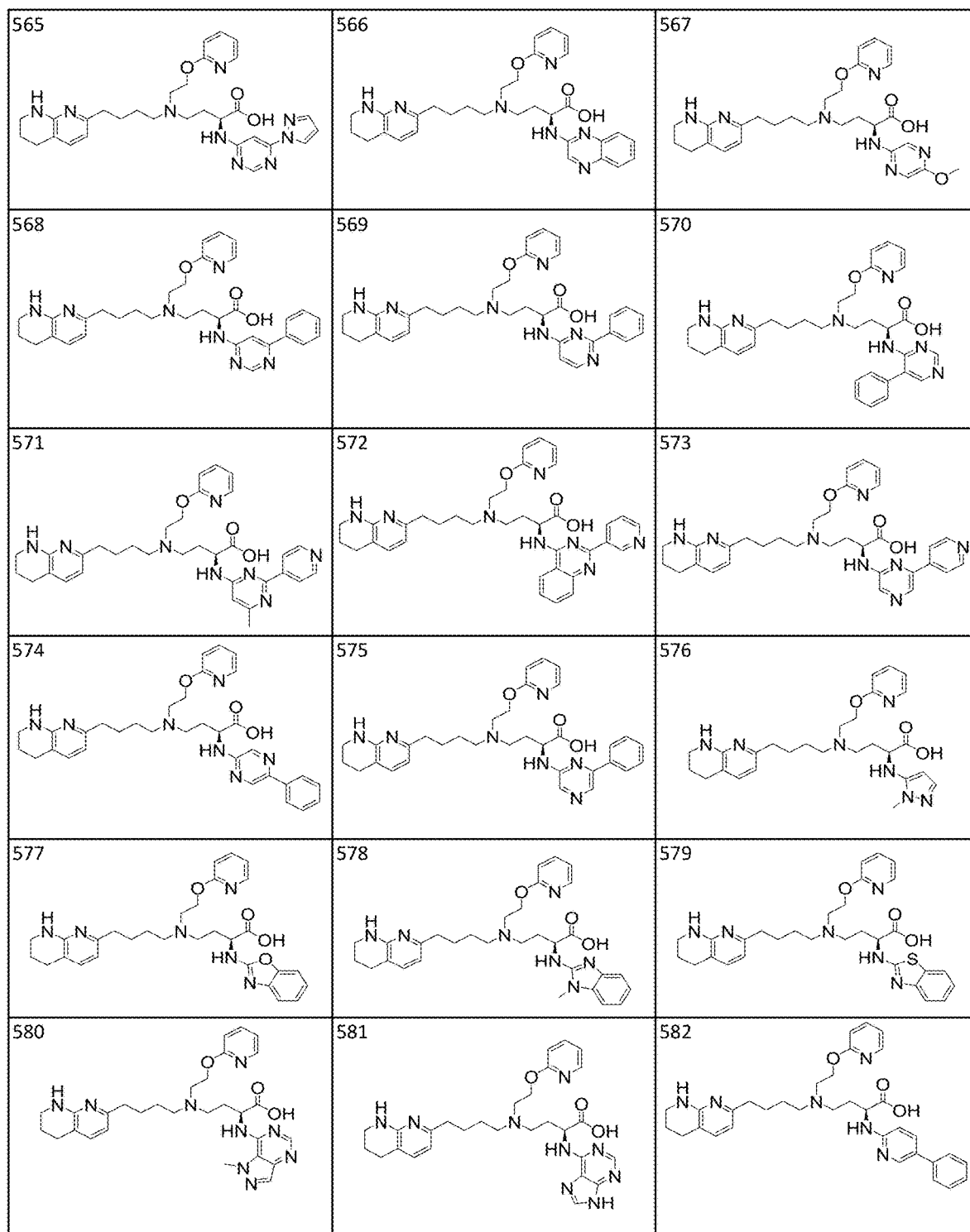
Figure 1:
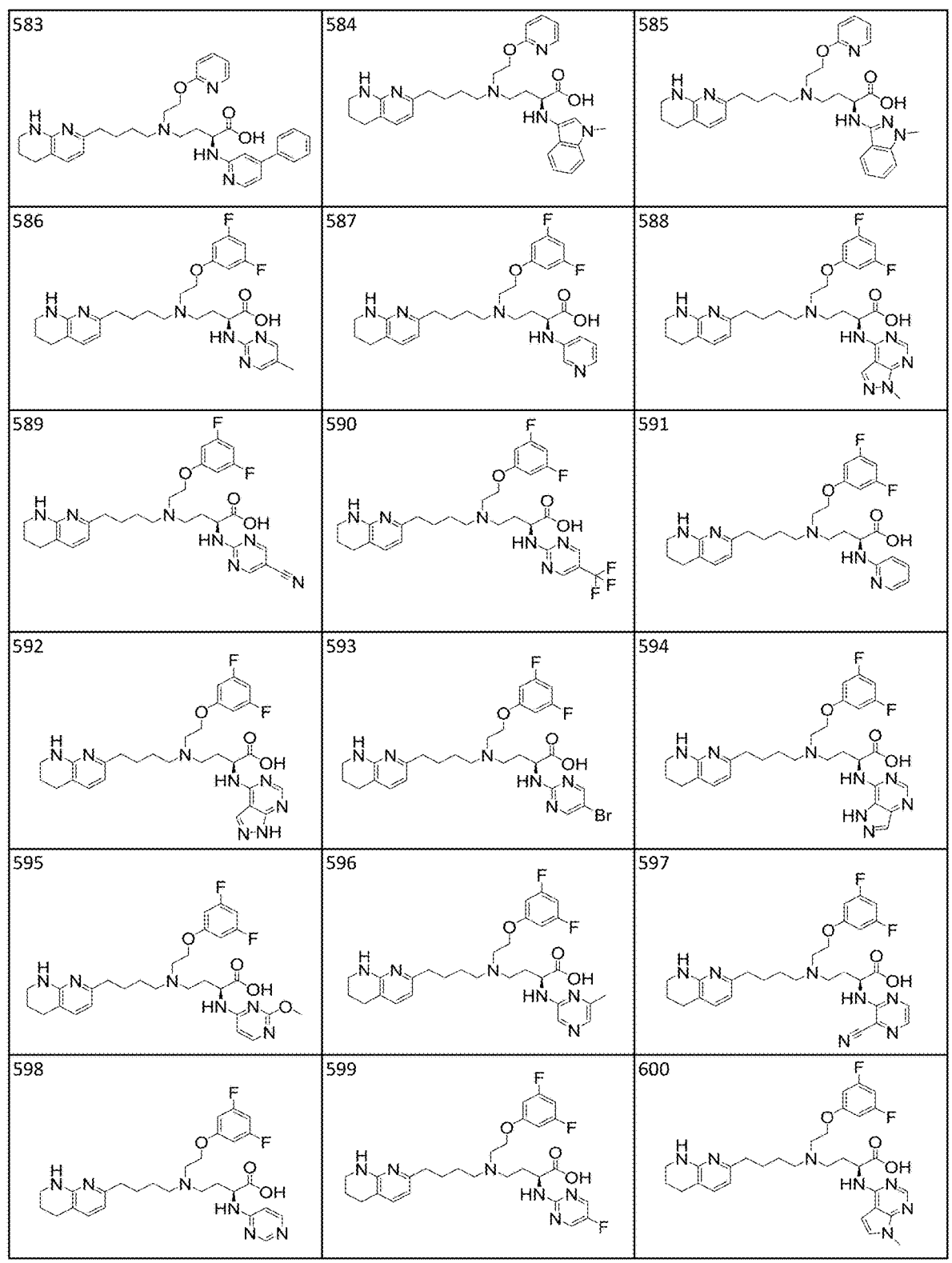
Figure 1:
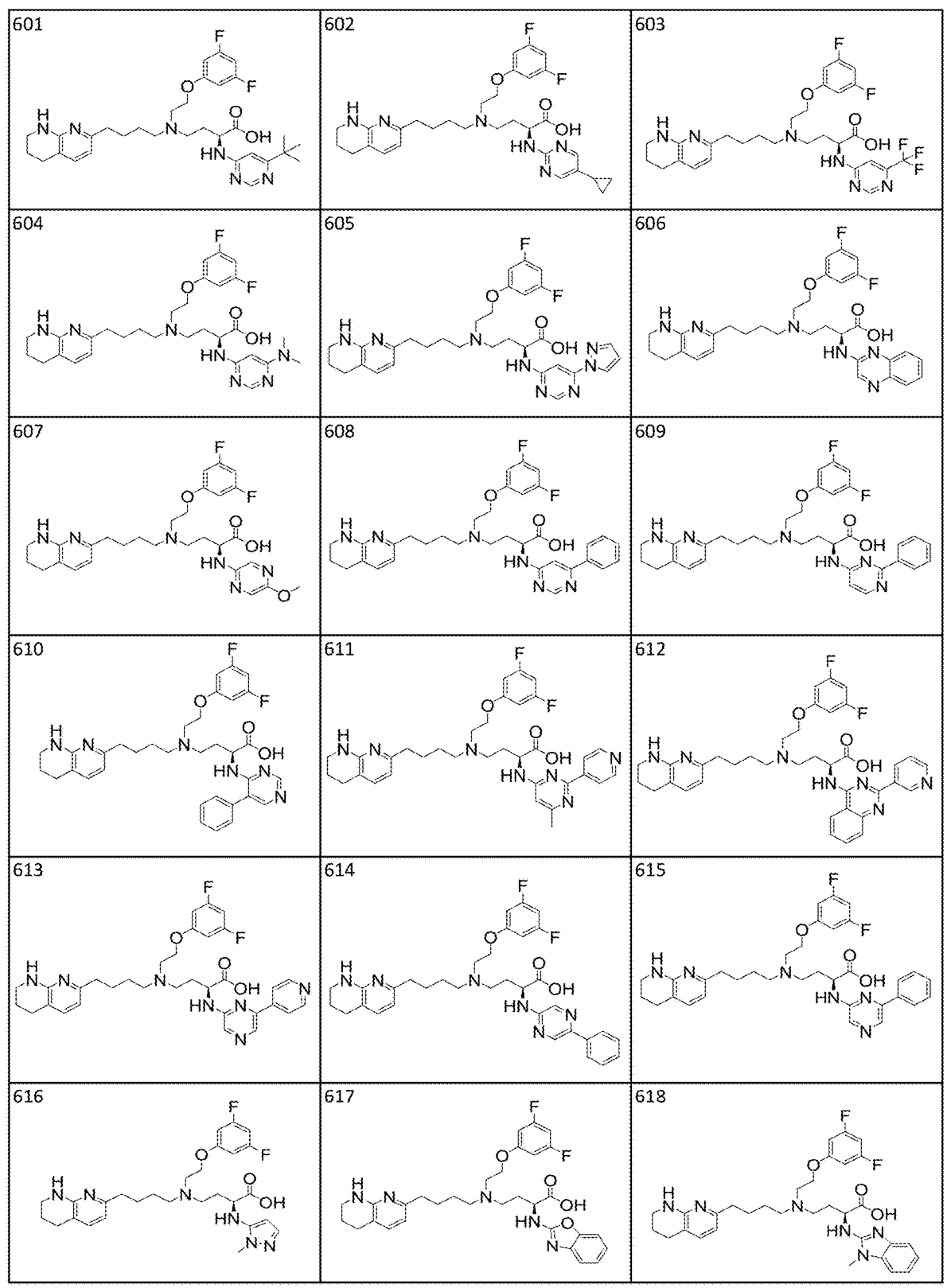
Figure 1:
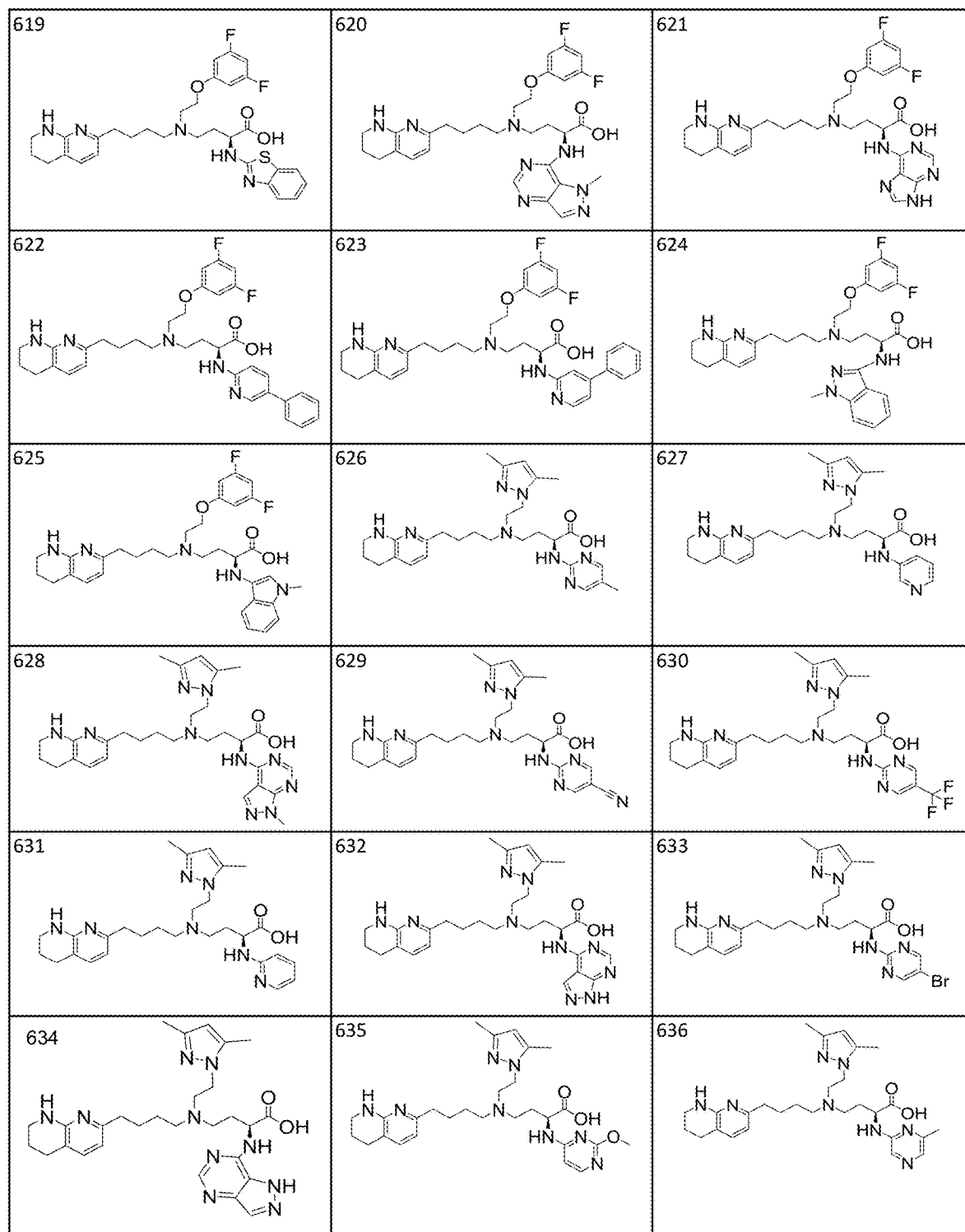
Figure 1:
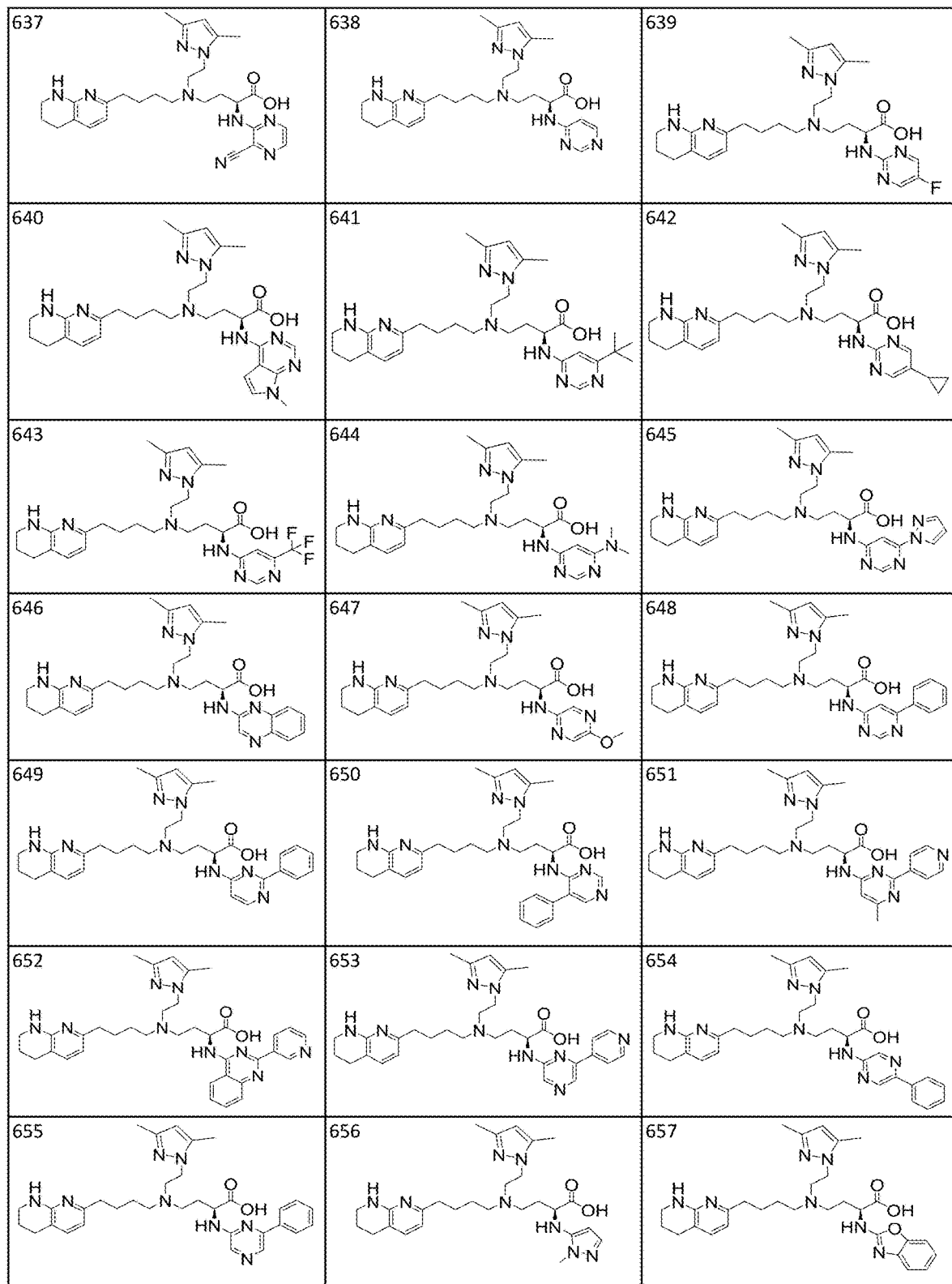
Figure 1:
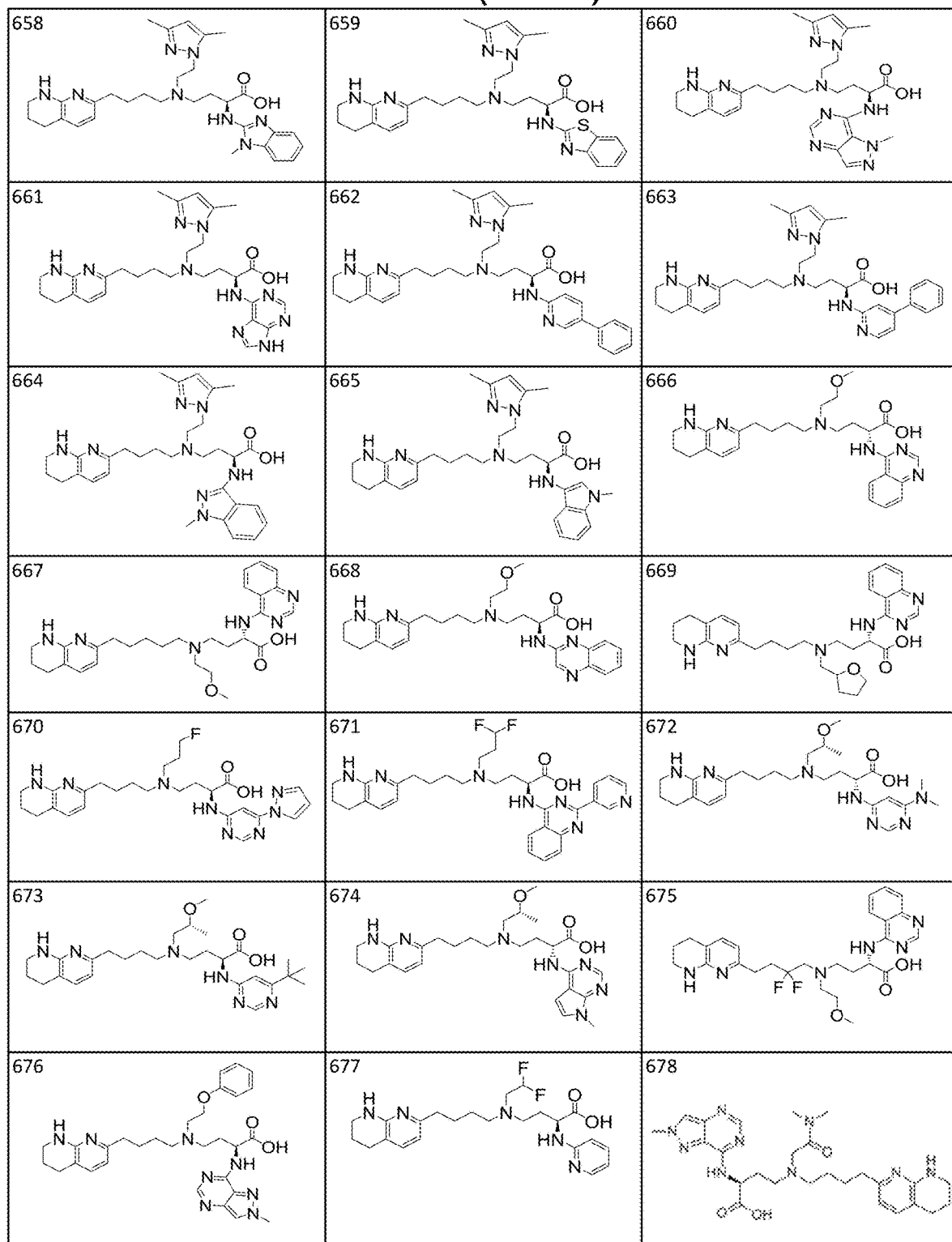
Figure 1:
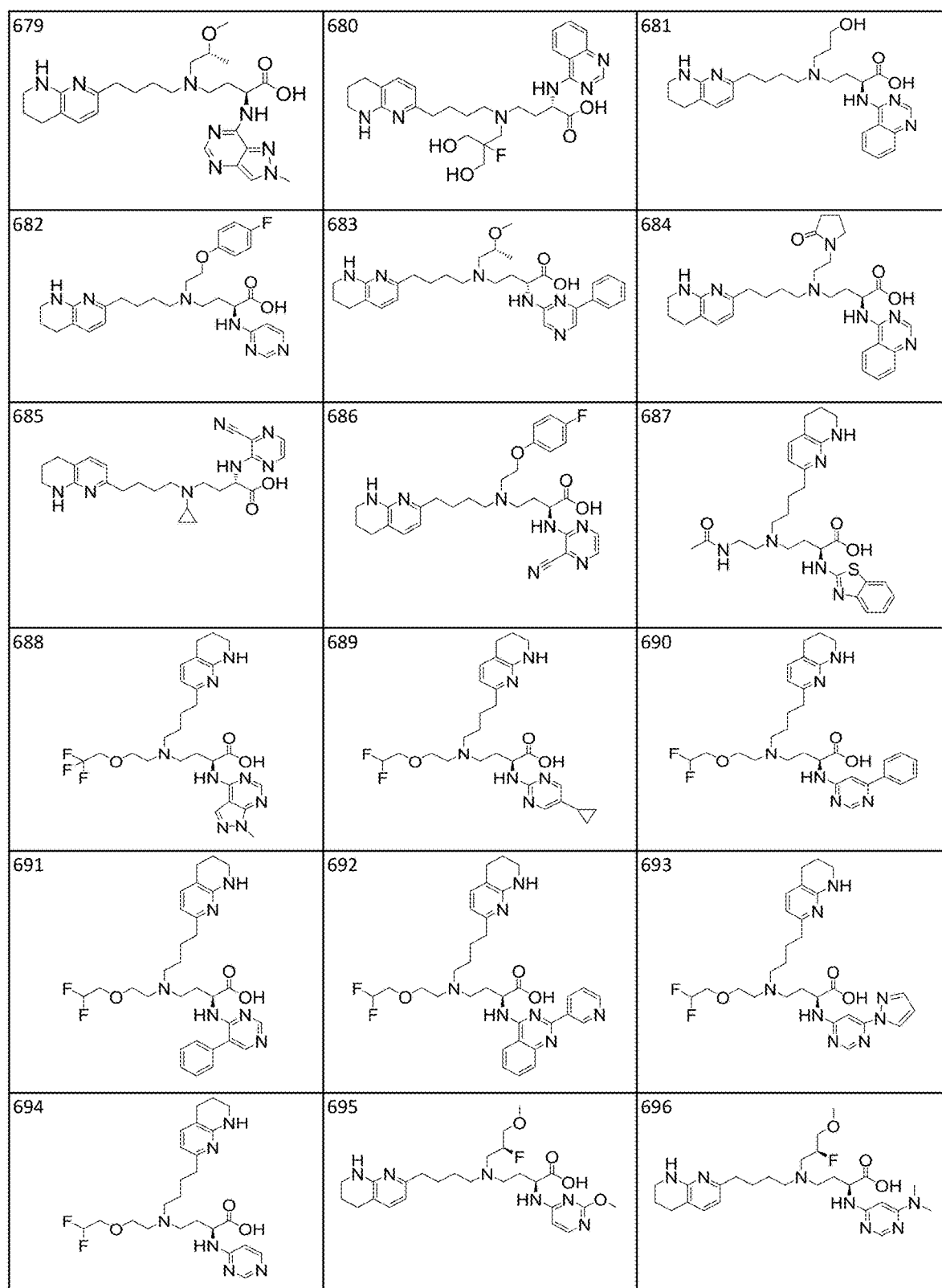
Figure 1:
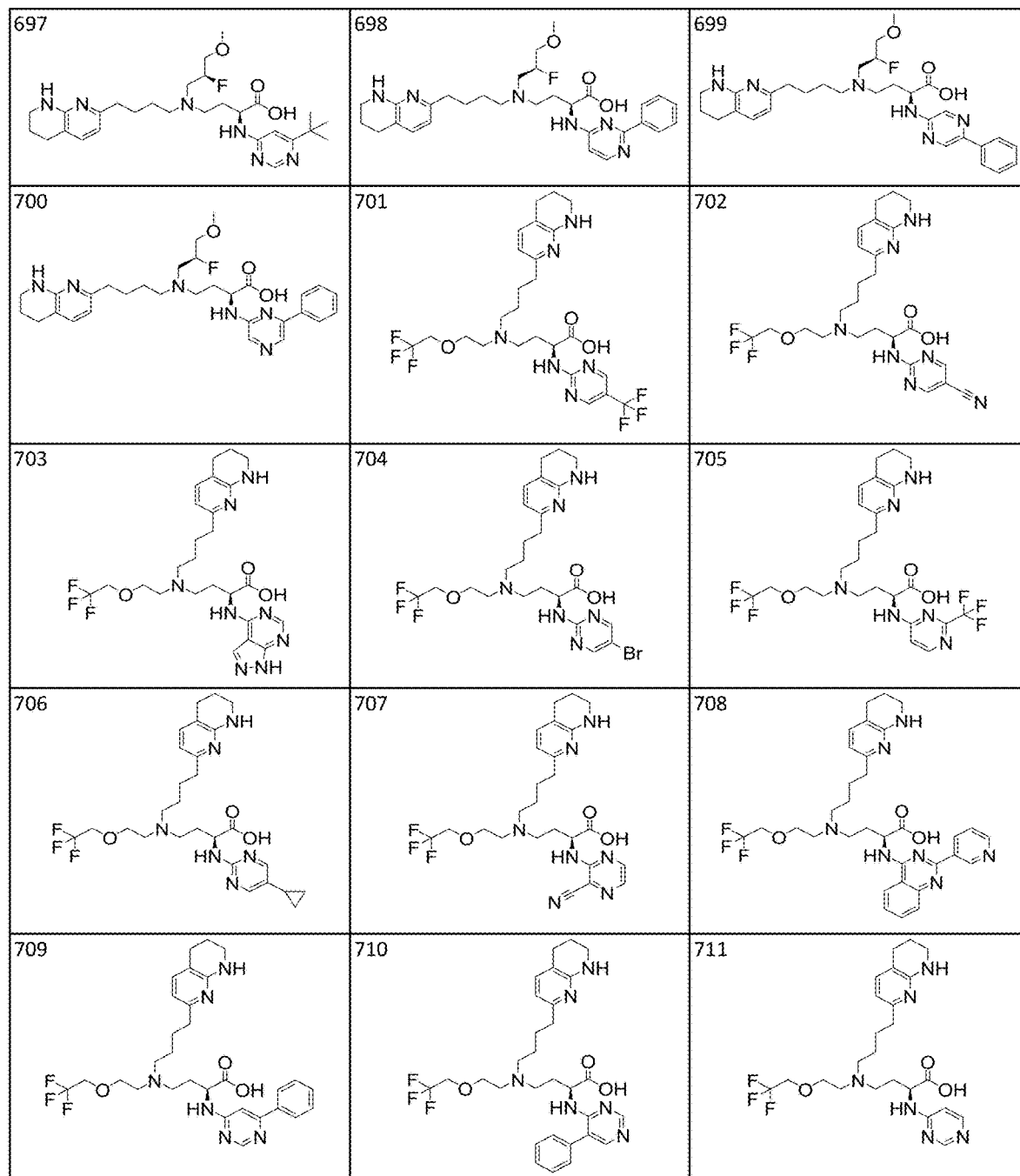
Figure 1:
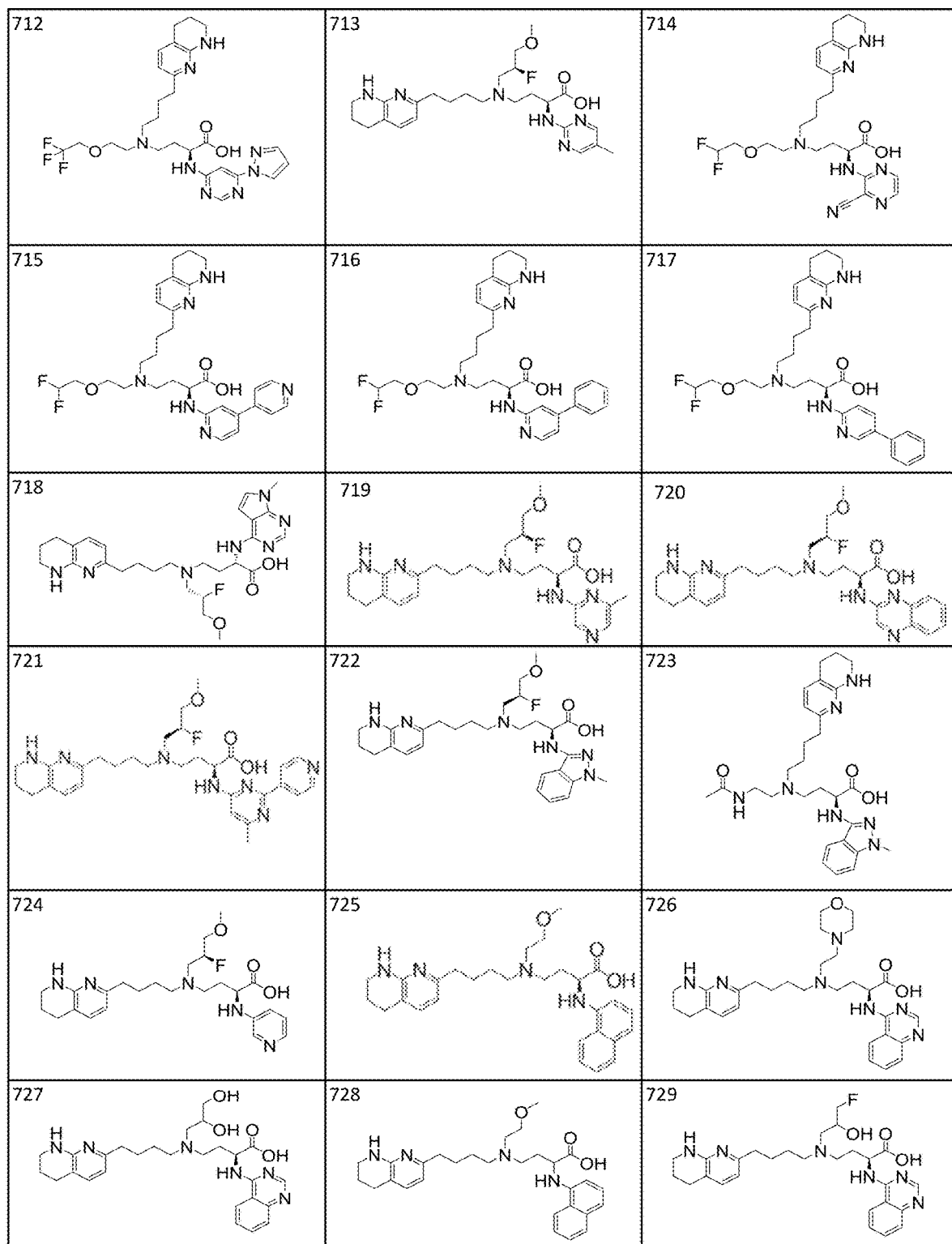
Figure 1:
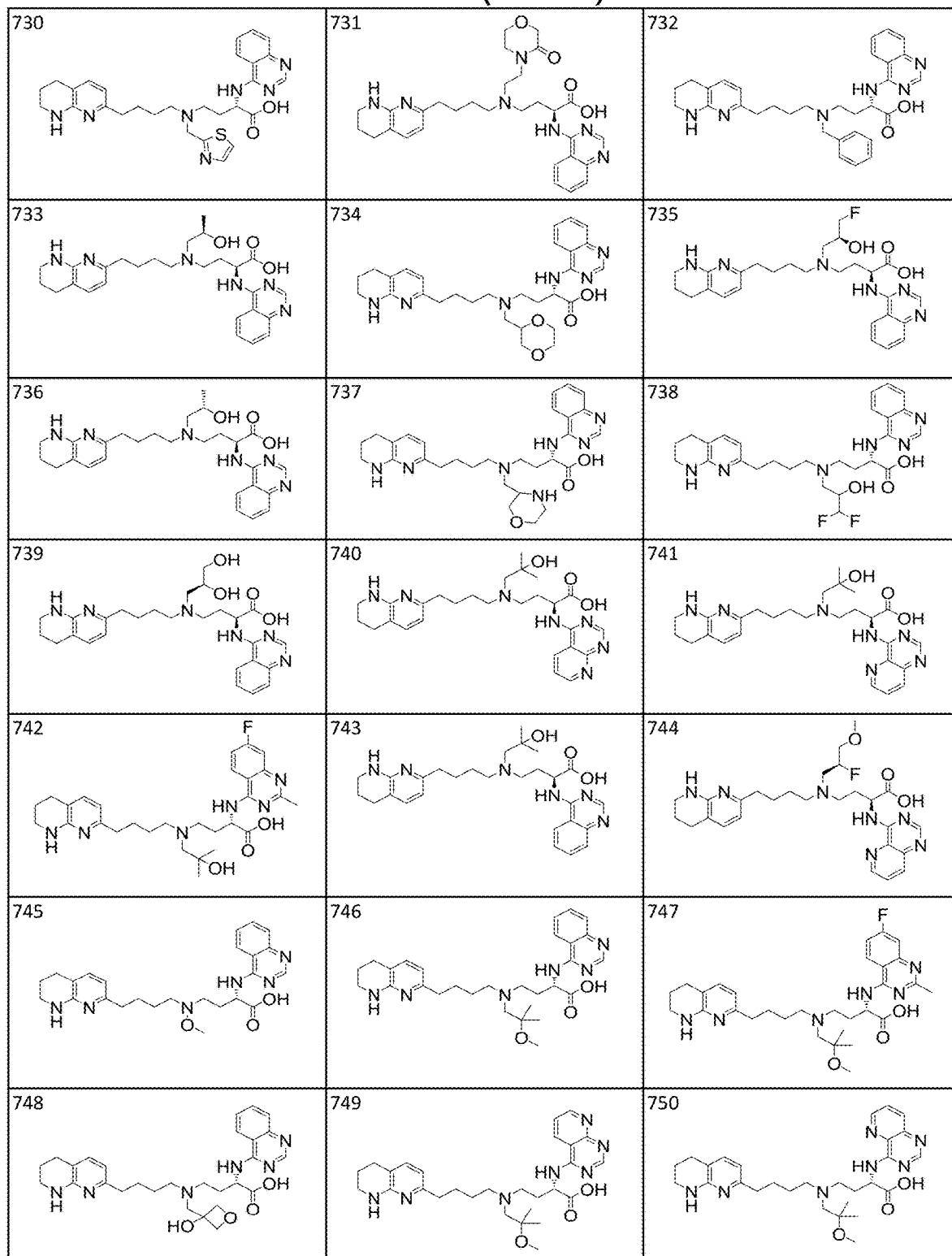
Figure 1:
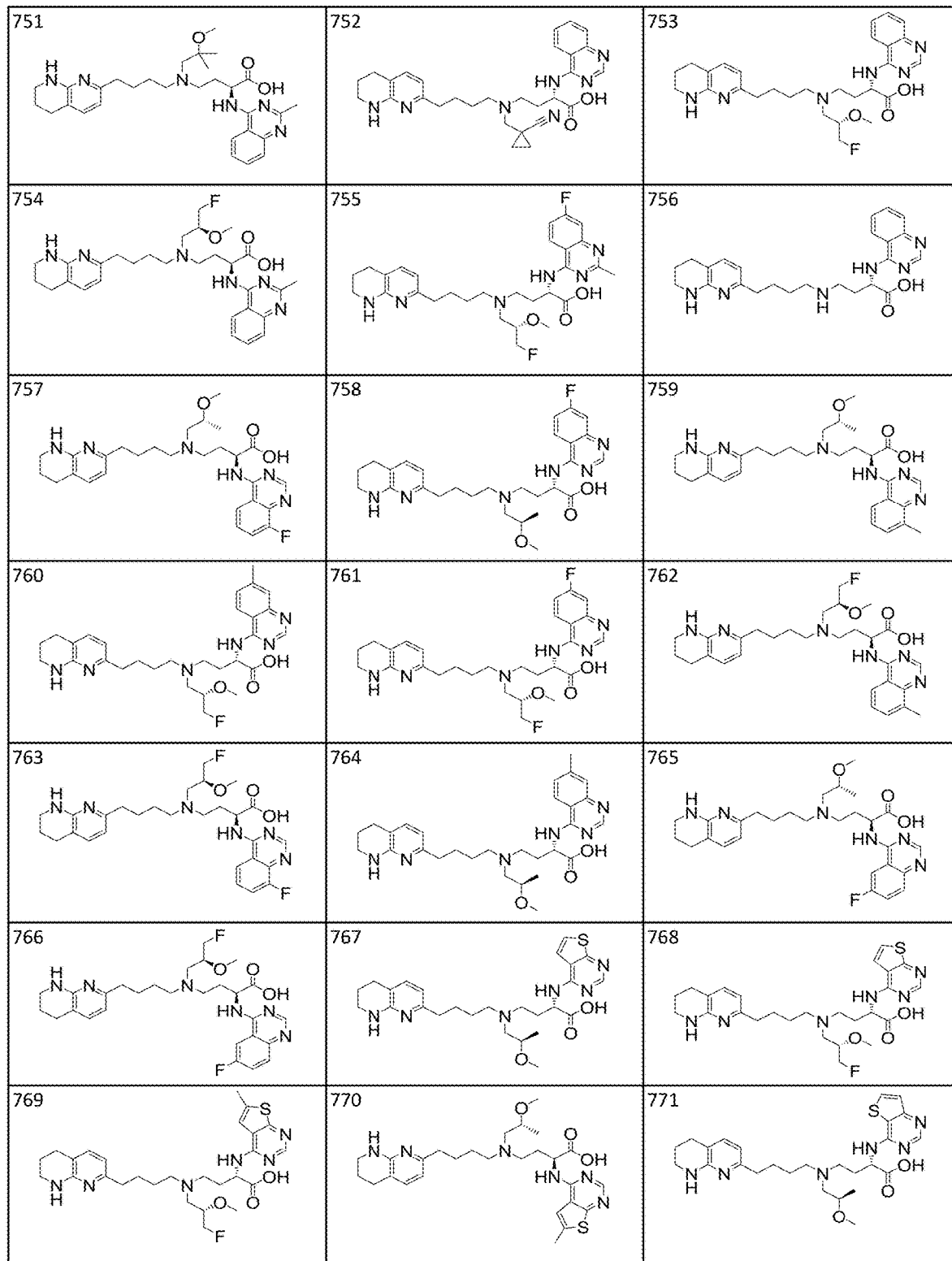
Figure 1:
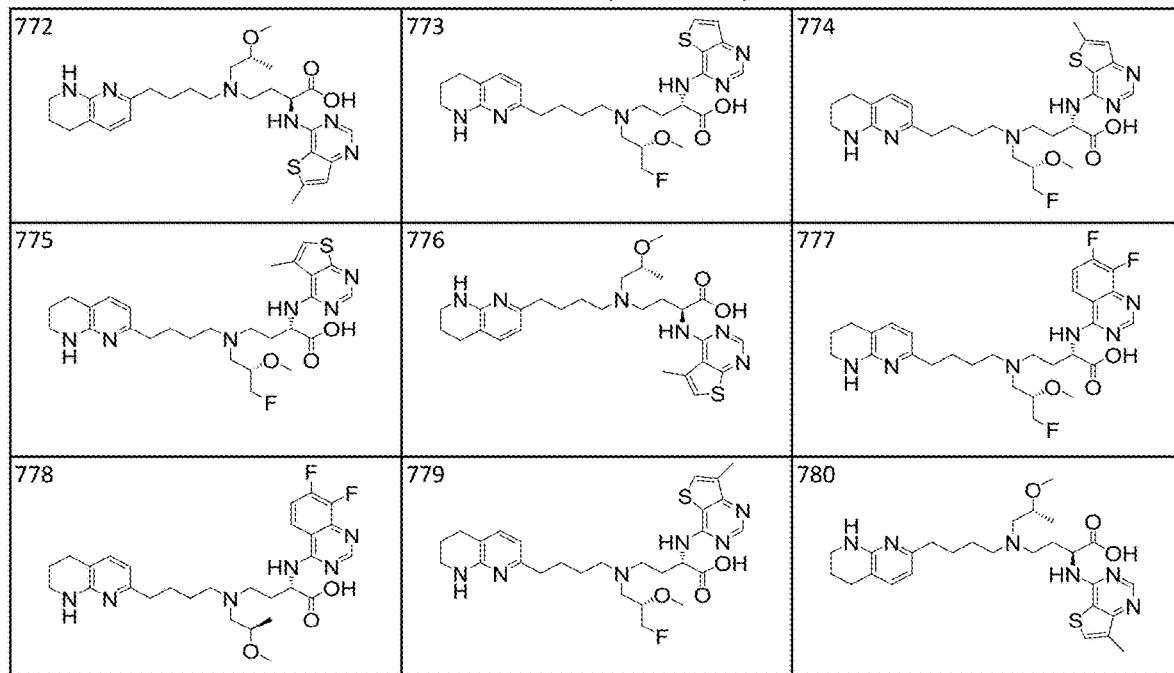

The present disclosure provides, inter alia, compounds of formula (A), and variations thereof, or a salt thereof, pharmaceutical compositions comprising compounds of formula (A) or a salt thereof, and methods of using such compounds and compositions in treating fibrotic diseases.

The present disclosure provides, inter alia, compounds of formula (I), and variations thereof, or a salt thereof, pharmaceutical compositions comprising compounds of formula (I) or a salt thereof, and methods of using such compounds and compositions in treating fibrotic diseases.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

As used herein, a "small molecule" is an organic molecule characterized by a mass of less than 900 daltons. Nonlimiting examples of small molecules include the compounds depicted in FIG. 1 or a salt thereof.

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_2$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH_2—), 1,4-but-1-enylene (—CH=CH—$CH_2CH_2$—), 1,4-but-2-enylene (—$CH_2$CH=CHCH_2—), 1,6-hex-1-enylene (—CH=CH—$(CH_2)_3CH_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH_2—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 annular carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_3$-$C_{10}$ means three to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

"D" refers to deuterium ($^2H$).

"T" refers to tritium ($^3H$).

An alkyl group in which each hydrogen is replaced with deuterium is referred to as "perdeuterated." An alkyl group in which each hydrogen is replaced with tritium is referred to as "pertritiated."

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

It is understood that an optionally substituted moiety can be substituted with more than five substituents, if permitted by the number of valences available for substitution on the moiety. For example, a propyl group can be substituted with seven halogen atoms to provide a perhalopropyl group. The substituents may be the same or different.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. Beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods of the invention contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Unless otherwise stated, "substantially pure" intends a composition that contains no more than 10% impurity, such as a composition comprising less than 9%, 7%, 5%, 3%, 1%, 0.5% impurity.

It is understood that aspects and embodiments described herein as "comprising" include "consisting of" and "consisting essentially of" embodiments.

Compounds

In one aspect, provided is a compound of formula (A):

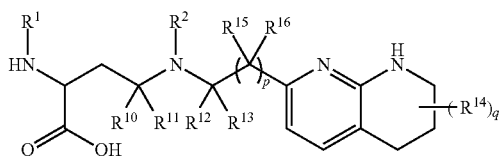

(A)

or a salt thereof, wherein:

$R^1$ is $C_6$-$C_{14}$ aryl or 5- to 10-membered heteroaryl wherein the $C_6$-$C_{14}$ aryl and 5- to 10-membered heteroaryl are optionally substituted by $R^{1a}$;

$R^2$ is hydrogen; deuterium; $C_1$-$C_6$ alkyl optionally substituted by $R^{2a}$; —OH; —O—$C_1$-$C_6$ alkyl optionally substituted by $R^{2a}$; $C_3$-$C_6$ cycloalkyl optionally substituted by $R^{2b}$; —O—$C_3$-$C_6$ cycloalkyl optionally substituted by $R^{2b}$; 3- to 12-membered heterocyclyl optionally substituted by $R^{2c}$; or —S(O)$_2R^{2d}$; with the proviso that any carbon atom bonded directly to a nitrogen atom is optionally substituted with an $R^{2a}$ moiety other than halogen;

each $R^{1a}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, deuterium, halogen, —CN, —OR$^3$, —SR$^3$, —NR$^4R^5$, —NO$_2$, —C=NH(OR$^3$), —C(O)R$^3$, —OC(O)R$^3$, —C(O)OR$^3$, —C(O)NR$^4R^5$, —NR$^3$C(O)R$^4$, —NR$^3$C(O)OR$^4$, —NR$^3$C(O)NR$^4R^5$, —S(O)R$^3$, —S(O)$_2$R$^3$, —NR$^3$S(O)R$^4$, —NR$^3$S(O)$_2$R$^4$, —S(O)NR$^4R^5$, —S(O)$_2$NR$^4R^5$, or —P(O)(OR$^4$)(OR$^5$), wherein each $R^{1a}$ is, where possible, independently optionally substituted by deuterium, halogen, oxo, —OR$^6$, —NR$^6R^7$, —C(O)R$^6$, —CN, —S(O)R$^6$, —S(O)$_2$R$^6$, —P(O)(OR$^6$)(OR$^7$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by deuterium, oxo, —OH or halogen;

each $R^{2a}$, $R^{2b}$, $R^{2c}$, $R^{2e}$, and $R^{2f}$ is independently oxo or $R^{1a}$;

$R^{2d}$ is $C_1$-$C_6$ alkyl optionally substituted by $R^{2e}$ or $C_3$-$C_5$ cycloalkyl optionally substituted by $R^{2f}$;

$R^3$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^3$ are independently optionally substituted by halogen, deuterium, oxo, —CN, —OR$^8$, —NR$^8R^9$, —P(O)(OR$^8$)(OR$^9$), or $C_1$-$C_6$ alkyl optionally substituted by deuterium, halogen, —OH or oxo;

$R^4$ and $R^5$ are each independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^4$ and $R^5$ are independently optionally substituted by deuterium, halogen, oxo, —CN, —OR$^8$, —NR$^8R^9$ or $C_1$-$C_6$ alkyl optionally substituted by deuterium, halogen, —OH or oxo;

or $R^4$ and $R^5$ are taken together with the atom to which they attached to form a 3- to 6-membered heterocyclyl optionally substituted by deuterium, halogen, oxo, —OR$^8$, —NR$^8R^9$ or $C_1$-$C_6$ alkyl optionally substituted by deuterium, halogen, oxo or —OH;

$R^6$ and $R^7$ are each independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;

or $R^6$ and $R^7$ are taken together with the atom to which they attached to form a 3- to 6-membered heterocyclyl optionally substituted by deuterium, halogen, oxo or $C_1$-$C_6$ alkyl optionally substituted by deuterium, halogen, or oxo;

$R^8$ and $R^9$ are each independently hydrogen, deuterium, $C_1$-$C_6$ alkyl optionally substituted by deuterium, halogen, or oxo, $C_2$-$C_6$ alkenyl optionally substituted by deuterium, halogen or oxo, or $C_2$-$C_6$ alkynyl optionally substituted by deuterium, halogen, or oxo;

or $R^8$ and $R^9$ are taken together with the atom to which they attached to form a 3-6 membered heterocyclyl optionally substituted by deuterium, halogen, oxo or $C_1$-$C_6$ alkyl optionally substituted by deuterium, oxo, or halogen;

each $R^{10}$, $R^{11}$, $R^{12}$ and $R^{13}$ are independently hydrogen or deuterium;

$R^{14}$ is deuterium;

q is 0, 1, 2, 3, 4, 5, 6, 7, or 8;

each $R^{15}$ is independently selected from hydrogen, deuterium, or halogen;

each $R^{16}$ is independently selected from hydrogen, deuterium, or halogen; and p is 3, 4, 5, 6, 7, 8, or 9.

In one variation is provided that the compound of Formula A excludes the free base of (2S)-4-[2-methoxyethyl-[4-(5,6,7,8-tetrahydro-1,8-naphthyridin-2-yl)butyl]amino]-2-(quinazolin-4-ylamino)butanoic acid:

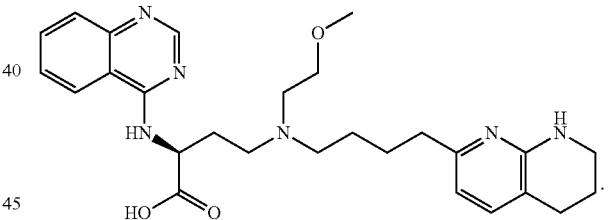

In various embodiments, the claimed compound excludes a free base of a compound represented by formula A wherein: R is unsubstituted quinazolin-4-yl; $R^2$ is —CH$_2$CH$_2$OCH$_3$; $R^{10}$, $R^{11}$, $R^{12}$, $R^{13}$, $R^{15}$, and $R^{16}$ are each H; p is 3; q is 0; and the carbon to which R$_1$NH— is bonded is in the S configuration, e.g., in some embodiments, the compound of formula A excludes the free base of (2S)-4-[2-methoxyethyl-[4-(5,6,7,8-tetrahydro-1,8-naphthyridin-2-yl)butyl]amino]-2-(quinazolin-4-ylamino)butanoic acid:

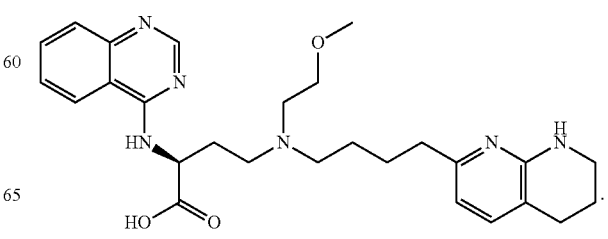

In some embodiments, the claimed compound excludes a free base of a compound represented by formula A wherein $R^2$ is —$CH_2CH_2OCH_3$; $R^{10}$, $R^{11}$, $R^{12}$, $R^{13}$, $R^{15}$, and $R^{16}$ are each H; p is 3; q is 0; the carbon to which $R^1NH$— is bonded is in the S configuration, and $R^1$ is one or more of the following separate lettered embodiments (a)-(k). (a) $R^1$ is unsubstituted quinazolin-4-yl. (b) $R^1$ is quinazolin-4-yl substituted by $R^{1a}$ wherein $R^{1a}$ is methyl. (c) $R^1$ is quinazolin-4-yl substituted by $R^{1a}$ wherein $R^{1a}$ is methyl or ethyl. (d) $R^1$ is quinazolin-4-yl substituted by $R^{1a}$ wherein $R^{1a}$ is $C_1$-$C_6$ alkyl. (e) $R^1$ is quinazolin-4-yl substituted by $R^{1a}$ (f) $R^1$ is a 10 membered fused bicyclic heterocycle containing two ring nitrogen atoms, and $R^1$ is unsubstituted or substituted by $R^{1a}$. (g) $R^1$ is unsubstituted quinazolinyl. (h) $R^1$ is quinazolinyl substituted by $R^{1a}$ wherein $R^{1a}$ is methyl. (i) $R^1$ is quinazolinyl substituted by $R^{1a}$ wherein $R^{1a}$ is methyl or ethyl. (j) $R^1$ is quinazolinyl substituted by $R^{1a}$ wherein $R^{1a}$ is $C_1$-$C_6$ alkyl. (k) $R^1$ is quinazolinyl substituted by $R^{1a}$.

In some embodiments, the claimed compound excludes a free base of a compound represented by formula A wherein $R^1$ is unsubstituted quinazolin-4-yl; $R^{10}$, $R^{11}$, $R^{12}$, $R^{13}$, $R^{15}$, and $R^{16}$ are each H; p is 3; q is 0; the carbon to which $R^1NH$— is bonded is in the S configuration, and $R^2$ is one or more of the following separate lettered embodiments (l)-(p). (l) $R^2$ is ethylene 2-substituted by $R^{2a}$ and $R^{2a}$ is methoxy. (m) $R^2$ is methylene, ethylene, or propylene substituted by $R^{2a}$, and $R^{2a}$ is methoxy. (n) $R^2$ is ethylene substituted by $R^{2a}$ and $R^{2a}$ is methoxy or ethoxy. (o) $R^2$ is ethylene substituted by $R^{2a}$ and $R^{2a}$ is hydroxy. (p) $R^2$ is methylene, ethylene, or propylene substituted by $R^{2a}$ and $R^{2a}$ is hydroxy, methoxy, or ethoxy.

In some embodiments, the claimed compound excludes a free base of a compound represented by formula A wherein $R^1$ is unsubstituted quinazolin-4-yl; $R^2$ is —$CH_2CH_2OCH_3$; $R^{15}$ and $R^{16}$ are each H; p is 3; q is 0; the carbon to which $R^1NH$— is bonded is in the S configuration, and $R^{10}$, $R^{11}$, $R^{12}$, and $R^{13}$ together represent one or more of the following separate lettered embodiments (q)-(u). (q) Each of $R^{10}$, $R^{11}$, $R^{12}$, and $R^{13}$ is hydrogen. (r) One of $R^{10}$, $R^{11}$, $R^{12}$, and $R^{13}$ is deuterium and the rest are hydrogen. (s) Two of $R^{10}$, $R^{11}$, $R^{12}$, and $R^{13}$ are deuterium and the rest are hydrogen. (t) Three of $R^{10}$, $R^{11}$, $R^{12}$, and $R^{13}$ are deuterium and the remaining is hydrogen. (u) Each of $R^{10}$, $R^{11}$, $R^{12}$, and $R^{13}$ is deuterium.

In some embodiments, the claimed compound excludes a free base of a compound represented by formula A wherein $R^1$ is unsubstituted quinazolin-4-yl; $R^2$ is —$CH_2CH_2OCH_3$; $R^{10}$, $R^{11}$, $R^{12}$, and $R^{13}$ are each H; p is 3; q is 0; the carbon to which $R^1NH$— is bonded is in the S configuration, and $R^{15}$ and $R^{16}$ together represent one or more of the following separate lettered embodiments (v)-(aa). (v) Each of $R^{15}$ and $R^{16}$ is hydrogen. (w) $R^{15}$ is hydrogen and $R^{16}$ is deuterium, or $R^{15}$ is deuterium and $R^{16}$ is hydrogen. (x) $R^{15}$ and $R^{16}$ are deuterium. (y) $R^{15}$ is hydrogen and $R^{16}$ is halogen, e.g., fluorine, or $R^{15}$ is halogen, e.g., fluorine, and $R^{16}$ is hydrogen. (z) $R^{15}$ is deuterium and $R^{16}$ is halogen, e.g., fluorine, or $R^{15}$ is halogen, e.g., fluorine, and $R^{16}$ is deuterium. (aa) $R^{15}$ and $R^{16}$ are each halogen, e.g., fluorine.

In some embodiments, the claimed compound excludes a free base of a compound represented by formula A wherein $R^1$ is unsubstituted quinazolin-4-yl; $R^2$ is —$CH_2CH_2OCH_3$; $R^{10}$, $R^{11}$, $R^{12}$, $R^{13}$, $R^{15}$, and $R^{16}$ are each H; q is 0; the carbon to which $R^1NH$— is bonded is in the S configuration; and p is one of the following separate lettered embodiments (ab)-(ad). (ab) p is 3. (ac) p is 4. (ad) p is 5.

In some embodiments, the claimed compound excludes a free base of a compound represented by formula A wherein $R^1$ is unsubstituted quinazolin-4-yl; $R^2$ is —$CH_2CH_2OCH_3$; $R^{10}$, $R^{11}$, $R^{12}$, $R^{13}$, $R^{15}$, and $R^{16}$ are each H; p is 3; the carbon to which $R^1NH$— is bonded is in the S configuration; and q is one of the following separate lettered embodiments (ae)-(ah). (ae) q is 0. (af) q is 1. (ag) q is 2. (ah) q is 3.

In some embodiments, excluded is a free base of a compound of any combination of the lettered embodiments selected for each of $R^1$; $R^2$; $R^{10}$, $R^{11}$, $R^{12}$, and $R^{13}$ together; $R^{15}$ and $R^{16}$ together; variable p; and variable q. For example, selected may be a combination of: $R^1$ from one of (a)-(k); $R^2$ from one of (l)-(p); $R^{10}$, $R^{11}$, $R^{12}$, and $R^{13}$ together from one of (q)-(u); $R^{15}$ and $R^{16}$ together from one of (v)-(aa); variable p from among one of (ab)-(ad); and variable q from among one of (ae)-(ah). Exemplary combinations of lettered embodiments may include, for example: (a), (l), (q), (v), (ab), and (ae); (b), (l), (q), (v), (ab), and (ae); (c), (l), (q), (v), (ab), and (ae); (d), (l), (q), (v), (ab), and (ae); (e), (l), (q), (v), (ab), and (ae); (f), (l), (q), (v), (ab), and (ae); (g), (l), (q), (v), (ab), and (ae); (h), (l), (q), (v), (ab), and (ae); (i), (l), (q), (v), (ab), and (ae); (j), (l), (q), (v), (ab), and (ae); (k), (l), (q), (v), (ab), and (ae); (a), (m), (q), (v), (ab), and (ae); (b), (m), (q), (v), (ab), and (ae); (c), (m), (q), (v), (ab), and (ae); (d), (m), (q), (v), (ab), and (ae); (e), (m), (q), (v), (ab), and (ae); (f), (m), (q), (v), (ab), and (ae); (g), (m), (q), (v), (ab), and (ae); (h), (m), (q), (v), (ab), and (ae); (i), (m), (q), (v), (ab), and (ae); (j), (m), (q), (v), (ab), and (ae); (k), (m), (q), (v), (ab), and (ae); (a), (n), (q), (v), (ab), and (ae); (b), (n), (q), (v), (ab), and (ae); (c), (n), (q), (v), (ab), and (ae); (d), (n), (q), (v), (ab), and (ae); (e), (n), (q), (v), (ab), and (ae); (f), (n), (q), (v), (ab), and (ae); (g), (n), (q), (v), (ab), and (ae); (h), (n), (q), (v), (ab), and (ae); (i), (n), (q), (v), (ab), and (ae); (j), (n), (q), (v), (ab), and (ae); (k), (n), (q), (v), (ab), and (ae); (a), (o), (q), (v), (ab), and (ae); (b), (o), (q), (v), (ab), and (ae); (c), (o), (q), (v), (ab), and (ae); (d), (o), (q), (v), (ab), and (ae); (e), (o), (q), (v), (ab), and (ae); (f), (o), (q), (v), (ab), and (ae); (g), (o), (q), (v), (ab), and (ae); (h), (o), (q), (v), (ab), and (ae); (i), (o), (q), (v), (ab), and (ae); (j), (o), (q), (v), (ab), and (ae); (k), (o), (q), (v), (ab), and (ae); (a), (p), (q), (v), (ab), and (ae); (b), (p), (q), (v), (ab), and (ae); (c), (p), (q), (v), (ab), and (ae); (d), (p), (q), (v), (ab), and (ae); (e), (p), (q), (v), (ab), and (ae); (f), (p), (q), (v), (ab), and (ae); (g), (p), (q), (v), (ab), and (ae); (h), (p), (q), (v), (ab), and (ae); (i), (p), (q), (v), (ab), and (ae); (j), (p), (q), (v), (ab), and (ae); (k), (p), (q), (v), (ab), and (ae); any one of the preceding combinations in which (v) is replaced by (y); any one of the preceding combinations in which (v) is replaced by (aa); any one of the preceding combinations in which (ab) is replaced by (ad); or any one of the preceding combinations in which (ab) is replaced by (ae);

In some embodiments, excluded are salts of the compound of any one of, or any combination of, the lettered embodiments (a)-(ah) as described above. In some embodiments, excluded are pharmaceutical compositions that include the compound of any one of, or any combination of, the lettered embodiments (a)-(ah) as described above, or salts thereof. In some embodiments, excluded are kits that include the compound of any one of, or any combination of, the lettered embodiments (a)-(ah) as described above, or salts thereof. In some embodiments, excluded are dosage forms that include the compound of any one of, or any combination of, the lettered embodiments (a)-(ah) as described above. In some embodiments, excluded are methods that include the compound of any one of, or any combination of, the lettered embodiments (a)-(ah) as described above, or salts thereof.

In one variation is provided a compound of the formula (A), or a salt thereof, wherein the carbon bearing the $CO_2H$ and NHR$^1$ moieties is in the "S" configuration. In another variation is provided a compound of the formula (A), or a salt thereof, wherein the carbon bearing the CO$_2$H and NHR$^1$ moieties is in the "R" configuration. Mixtures of a compound of the formula (A) are also embraced, including racemic or non-racemic mixtures of a given compound, and mixtures of two or more compounds of different chemical formulae.

In one variation of formula (A), R$^2$ has the proviso that any carbon atom bonded directly to a nitrogen atom is either unsubstituted or is substituted with deuterium.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to R$^1$ of formula (A) may be combined with every description, variation, embodiment or aspect of R$^2$ the same as if each and every combination were specifically and individually listed.

In one aspect, provided is a compound of formula (I)

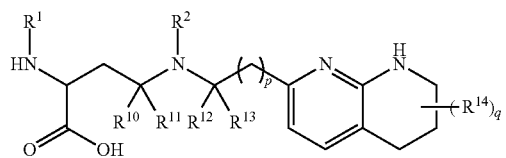

(I)

or a salt thereof, wherein:

R$^1$ is C$_6$-C$_{14}$ aryl or 5- to 10-membered heteroaryl wherein the C$_6$-C$_{14}$ aryl and 5- to 10-membered heteroaryl are optionally substituted by R$^{1a}$;

R$^2$ is C$_1$-C$_6$ alkyl optionally substituted by R$^{2a}$; C$_3$-C$_6$ cycloalkyl optionally substituted by R$^{2b}$; 3- to 12-membered heterocyclyl optionally substituted by R$^{2c}$; or —S(O)$_2$R$^{2d}$;

each R$^{1a}$ is independently C$_1$-C$_6$ alkyl, C$_2$-C$_6$ alkenyl, C$_2$-C$_6$ alkynyl, C$_3$-C$_8$ cycloalkyl, C$_4$-C$_8$ cycloalkenyl, 3- to 12-membered heterocyclyl, 5- to 10-membered heteroaryl, C$_6$-C$_{14}$ aryl, deuterium, halogen, —CN, —OR$^3$, —SR$^3$, —NR$^4$R$^5$, —NO$_2$, —C═NH(OR$^3$), —C(O)R$^3$, —OC(O)R$^3$, —C(O)OR$^3$, —C(O)NR$^4$R$^5$, —NR$^3$C(O)R$^4$, —NR$^3$C(O)OR$^4$, —NR$^3$C(O)NR$^4$R$^5$, —S(O)R$^3$, —S(O)$_2$R$^3$, —NR$^3$S(O)R$^4$, —NR$^3$S(O)$_2$R$^4$, —S(O)NR$^4$R$^5$, —S(O)$_2$NR$^4$R$^5$, or —P(O)(OR$^4$)(OR$^5$), wherein each R$^{1a}$ is, where possible, independently optionally substituted by deuterium, halogen, oxo, —OR$^6$, —NR$^6$R$^7$, —C(O)R$^6$, —CN, —S(O)R$^6$, —S(O)$_2$R$^6$, —P(O)(OR$^6$)(OR$^7$), C$_3$-C$_8$ cycloalkyl, 3- to 12-membered heterocyclyl, 5- to 10-membered heteroaryl, C$_6$-C$_{14}$ aryl, or C$_1$-C$_6$ alkyl optionally substituted by deuterium, oxo, —OH or halogen;

each R$^{2a}$, R$^{2b}$, R$^{2c}$, R$^{2e}$, and R$^{2f}$ is independently oxo or R$^{1a}$;

R$^{2d}$ is C$_1$-C$_6$ alkyl optionally substituted by R$^{2e}$ or C$_3$-C$_5$ cycloalkyl optionally substituted by R$^{2f}$;

R$^3$ is independently hydrogen, deuterium, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl of R$^3$ are independently optionally substituted by halogen, deuterium, oxo, —CN, —OR$^8$, —NR$^8$R$^9$, —P(O)(OR$^8$)(OR$^9$), or C$_1$-C$_6$ alkyl optionally substituted by deuterium, halogen, —OH or oxo;

R$^4$ and R$^5$ are each independently hydrogen, deuterium, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl of R$^4$ and R$^5$ are independently optionally substituted by deuterium, halogen, oxo, —CN, —OR$^8$, —NR$^8$R$^9$ or C$_1$-C$_6$ alkyl optionally substituted by deuterium, halogen, —OH or oxo;

or R$^4$ and R$^5$ are taken together with the atom to which they attached to form a 3- to 6-membered heterocyclyl optionally substituted by deuterium, halogen, oxo, —OR$^8$, —NR$^8$R$^9$ or C$_1$-C$_6$ alkyl optionally substituted by deuterium, halogen, oxo or —OH;

R$^6$ and R$^7$ are each independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

or R$^6$ and R$^7$ are taken together with the atom to which they attached to form a 3- to 6-membered heterocyclyl optionally substituted by deuterium, halogen, oxo or C$_1$-C$_6$ alkyl optionally substituted by deuterium, halogen, or oxo;

R$^8$ and R$^9$ are each independently hydrogen, deuterium, C$_1$-C$_6$ alkyl optionally substituted by deuterium, halogen, or oxo, C$_2$-C$_6$ alkenyl optionally substituted by deuterium, halogen or oxo, or C$_2$-C$_6$ alkynyl optionally substituted by deuterium, halogen, or oxo;

or R$^8$ and R$^9$ are taken together with the atom to which they attached to form a 3-6 membered heterocyclyl optionally substituted by deuterium, halogen, oxo or C$_1$-C$_6$ alkyl optionally substituted by deuterium, oxo, or halogen;

each R$^{10}$, R$^{11}$, R$^{12}$, and R$^{13}$ are independently hydrogen or deuterium;

R$^{14}$ is deuterium;

q is 0, 1, 2, 3, 4, 5, 6, 7, or 8; and p is 3, 4, 5, 6, 7, 8, or 9.

In one variation is provided a compound of the formula (I), or a salt thereof, wherein the carbon bearing the CO$_2$H and NHR$^1$ moieties is in the "S" configuration. In another variation is provided a compound of the formula (I), or a salt thereof, wherein the carbon bearing the CO$_2$H and NHR$^1$ moieties is in the "R" configuration. Mixtures of a compound of the formula (I) are also embraced, including racemic or non-racemic mixtures of a given compound, and mixtures of two or more compounds of different chemical formulae.

In one variation of formula (I), R$^2$ includes the proviso that any carbon atom bonded directly to a nitrogen atom is optionally substituted with an R$^{2a}$ moiety other than halogen. In one variation of formula (I), R$^2$ includes the proviso that any carbon atom bonded directly to a nitrogen atom is either unsubstituted or is substituted with deuterium.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to R$^1$ of formula (I) may be combined with every description, variation, embodiment or aspect of R$^2$ the same as if each and every combination were specifically and individually listed.

In some embodiments of the compound of formula (I), or a salt thereof, at least one of $R^{1a}$, $R^{2a}$, $R^{2b}$, $R^{2e}$, $R^{2f}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, or $R^{16}$ is deuterium.

In some embodiments of the compound of formula (I), or a salt thereof, $R^1$ is 5- to 10-membered heteroaryl optionally substituted by $R^{1a}$. In some embodiments, $R^1$ is pyrimidin-4-yl optionally substituted by $R^{1a}$. In some embodiments, $R^1$ is pyrimidin-4-yl optionally substituted by $R^{1a}$ wherein $R^{1a}$ is 5- to 10-membered heteroaryl (e.g., pyrazolyl) or $C_1$-$C_6$ alkyl optionally substituted by halogen (e.g., methyl, difluoromethyl, and trifluoromethyl). In some embodiments, $R^1$ is pyrimidin-4-yl optionally substituted by $R^{1a}$ wherein $R^{1a}$ is 5- to 10-membered heteroaryl (e.g., pyrazolyl or pyridinyl) or $C_1$-$C_6$ alkyl optionally substituted by halogen (e.g., methyl, difluoromethyl, and trifluoromethyl). In some embodiments, $R^1$ is pyrimidin-4-yl substituted by both methyl and trifluoromethyl. In some embodiments, $R^1$ is pyrimidin-4-yl substituted by both methyl and pyridinyl. In some embodiments, $R^1$ is pyrimidin-4-yl optionally substituted by $R^{1a}$ wherein $R^{1a}$ is $C_6$-$C_{14}$ aryl (e.g., phenyl). In some embodiments, $R^1$ is pyrimidin-4-yl optionally substituted by $R^{1a}$ wherein $R^{1a}$ is —CN. In some embodiments, $R^1$ is pyrimidin-2-yl optionally substituted by $R^{1a}$. In some embodiments, $R^1$ is pyrimidin-2-yl optionally substituted by $R^{1a}$ wherein $R^{1a}$ is halogen, $C_1$-$C_6$ alkyl optionally substituted by halogen (e.g., methyl or trifluoromethyl), —CN, or $C_3$-$C_8$ cycloalkyl (e.g., cyclopropyl). In some embodiments of the compound of formula (I), or a salt thereof, $R^1$ is quinazolin-4-yl optionally substituted by $R^{1a}$. In some embodiments, $R^1$ is quinazolin-4-yl optionally substituted by $R^{1a}$ wherein $R^{1a}$ is halogen (e.g., fluoro and chloro), $C_1$-$C_6$ alkyl optionally substituted by halogen (e.g., methyl or trifluoromethyl), or $C_1$-$C_6$ alkoxy (e.g., methoxy). In some embodiments, $R^1$ is quinazolin-4-yl optionally substituted by $R^{1a}$ wherein $R^{1a}$ is 5- to 10-membered heteroaryl (e.g., pyridinyl). In some embodiments, $R^1$ is pyrazolopyrimidinyl optionally substituted by $R^{1a}$. In some embodiments, $R^1$ is pyrazolopyrimidinyl optionally substituted by $R^{1a}$, wherein $R^{1a}$ is $C_1$-$C_6$ alkyl (e.g., methyl). In some embodiments where $R^1$ is indicated as optionally substituted by $R^{1a}$, the $R^1$ moiety is unsubstituted. In some embodiments where $R^1$ is indicated as optionally substituted by $R^{1a}$, the $R^1$ moiety is substituted by one $R^{1a}$. In some embodiments where $R^1$ is indicated as optionally substituted by $R^{1a}$, the $R^1$ moiety is substituted by 2 to 6 or 2 to 5 or 2 to 4 or 2 to 3 $R^{1a}$ moieties, which may be the same or different.

In some embodiments of formula (I), including the embodiments that describe the $R^1$ variable, each of $R^{10}$, $R^{11}$, $R^{12}$ and $R^{13}$ are hydrogen. In some embodiments of formula (I), including the embodiments that describe the R variable, and/or the $R^{10}$, $R^{11}$, $R^{12}$ and $R^{13}$ variables, q is 0. In some embodiments, including the embodiments that describe the R variable, and/or the $R^{10}$, $R^{11}$, $R^{12}$ and $R^{13}$ variables and/or the q variable, p is 3, 4 or 5.

In some embodiments of formula (I), $R^{10}$, $R^{11}$, $R^{12}$ and $R^{13}$ are hydrogen, p is 3, q is 0 and the compound is of the formula (II):

(II)

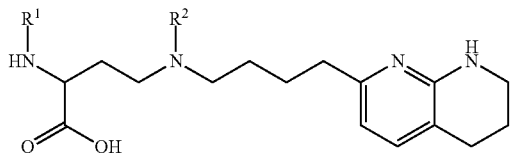

or a salt thereof, wherein $R^1$ and $R^2$ are as defined for formula (I).

In some embodiments of the compound of formula (I), wherein $R^1$ is 5- to 10-membered heteroaryl optionally substituted by $R^{1a}$, the compound is of the formula (I-A):

(I-A)

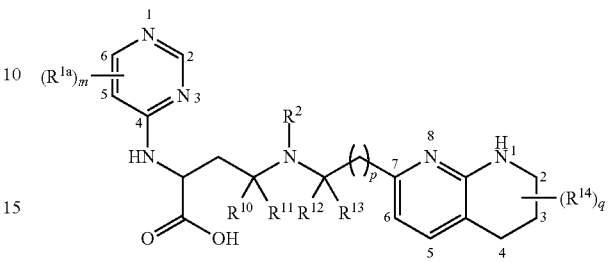

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, or 3, and the positions on the pyrimidine ring and tetrahydronaphthyridine ring are as indicated.

In one embodiment is provided a compound of the formula (I-A), or a salt thereof, wherein the carbon bearing the $CO_2H$ and NH moieties is in the "S" configuration. In another embodiment is provided a compound of the formula (I-A), or a salt thereof, wherein the carbon bearing the $CO_2H$ and NH moieties is in the "R" configuration. Mixtures of a compound of the formula (I-A) are also embraced, including racemic or non-racemic mixtures of a given compound, and mixtures of two or more compounds of different chemical formulae.

In some embodiments of the compound of formula (I-A), m is 0, 1, 2, or 3, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-A), m is 0, 1, 2, or 3, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of formula (I-A), m is 1, 2 or 3.

In some embodiments of the compound of formula (I-A), m is 0. In some embodiments of the compound of formula (I-A), m is 1, and $R^{1a}$ is at the 2-position. In some embodiments of the compound of formula (I-A), m is 1, and $R^{1a}$ is at the 5-position. In some embodiments of the compound of formula (I-A), m is 1, and $R^{1a}$ is at the 6-position. In some embodiments of the compound of formula (I-A), m is 2, and the $R^{1a}$ groups are at the 2-position and 5-position. In some embodiments of the compound of formula (I-A), m is 2, and the $R^{1a}$ groups are at the 2-position and 6-position. In some embodiments of the compound of formula (I-A), m is 2, and the $R^{1a}$ groups are at the 5-position and 6-position. In some embodiments of the compound of formula (I-A), m is 3, and the $R^{1a}$ groups are at the 2-position, 5-position, and 6-position. Whenever more than one $R^{1a}$ group is present, the $R^{1a}$ groups can be chosen independently. In any of these embodiments of the compound of formula (I-A), or a salt thereof, the carbon bearing the $CO_2H$ and NH moieties may be in the "S" configuration or the "R" configuration.

In some embodiments of formula (I-A), including the embodiments that describe the $R^{1a}$ and m variables, each of $R^{10}$, $R^{11}$, $R^{12}$ and $R^{13}$ are hydrogen. In some embodiments of formula (I-A), including the embodiments that describe the $R^{1a}$ and m variables, and/or the $R^{10}$, $R^{11}$, $R^{12}$ and $R^{13}$ variables, q is 0. In some embodiments of formula (I-A), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-A), $R^{10}$, $R^{11}$, $R^{12}$ and $R^{13}$ are hydrogen, p is 3, q is 0 and the compound is of the formula (II-A):

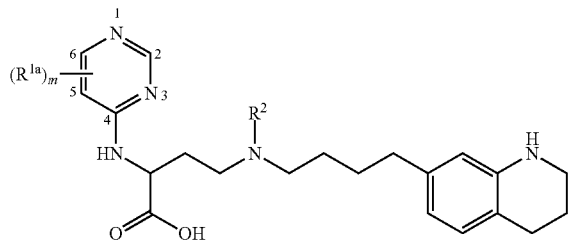

(II-A)

or a salt thereof, wherein $R^{1a}$ and $R^2$ are as defined for formula (I), m is 0, 1, 2, or 3, and the positions on the pyrimidine ring are as indicated. All descriptions of $R^{1a}$, $R^2$ and m with reference to formula (I) apply equally to formulae (I-A) and (II-A).

In some embodiments of the compound of formula (I), wherein $R^1$ is 5- to 10-membered heteroaryl optionally substituted by $R^{1a}$, the compound is of the formula (I-B):

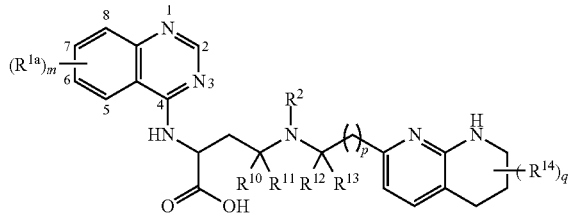

(I-B)

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, 3, 4, or 5, and the positions on the quinazoline ring are as indicated.

In one embodiment is provided a compound of the formula (I-B), or a salt thereof, wherein the carbon bearing the $CO_2H$ and NH moieties is in the "S" configuration. In another embodiment is provided a compound of the formula (I-B), or a salt thereof, wherein the carbon bearing the $CO_2H$ and NH moieties is in the "R" configuration. Mixtures of a compound of the formula (I-B) are also embraced, including racemic or non-racemic mixtures of a given compound, and mixtures of two or more compounds of different chemical formulae.

In some embodiments of the compound of formula (I-B), m is 0, 1, 2, 3, 4, or 5, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-B), m is 0, 1, 2, 3, 4, or 5, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-B), m is 1, 2, 3, 4, or 5.

In some embodiments of the compound of formula (I-B), m is 0. In some embodiments of the compound of formula (I-B), m is 1, and $R^{1a}$ is at the 2-position. In some embodiments of the compound of formula (I-B), m is 1, and $R^{1a}$ is at the 5-position. In some embodiments of the compound of formula (I-B), m is 1, and $R^{1a}$ is at the 6-position. In some embodiments of the compound of formula (I-B), m is 1, and $R^{1a}$ is at the 7-position. In some embodiments of the compound of formula (I-B), m is 1, and $R^{1a}$ is at the 8-position. In some embodiments of the compound of formula (I-B), m is 2, and the $R^{1a}$ groups are at the 2-position and 5-position. In some embodiments of the compound of formula (I-B), m is 2, and the $R^{1a}$ groups are at the 2-position and 6-position. In some embodiments of the compound of formula (I-B), m is 2, and the $R^{1a}$ groups are at the 2-position and 7-position. In some embodiments of the compound of formula (I-B), m is 2, and the $R^{1a}$ groups are at the 2-position and 8-position. In some embodiments of the compound of formula (I-B), m is 2, and the $R^{1a}$ groups are at the 5-position and 6-position. In some embodiments of the compound of formula (I-B), m is 2, and the $R^{1a}$ groups are at the 5-position and 7-position. In some embodiments of the compound of formula (I-B), m is 2, and the $R^{1a}$ groups are at the 5-position and 8-position. In some embodiments of the compound of formula (I-B), m is 2, and the $R^{1a}$ groups are at the 6-position and 7-position. In some embodiments of the compound of formula (I-B), m is 2, and the $R^{1a}$ groups are at the 6-position and 8-position. In some embodiments of the compound of formula (I-B), m is 2, and the $R^{1a}$ groups are at the 7-position and 8-position. In some embodiments of the compound of formula (I-B), m is 3, and the $R^{1a}$ groups are at the 2-position, 5-position, and 6-position. In some embodiments of the compound of formula (I-B), m is 3, and the $R^{1a}$ groups are at the 2-position, 5-position, and 7-position. In some embodiments of the compound of formula (I-B), m is 3, and the $R^{1a}$ groups are at the 2-position, 5-position, and 8-position. In some embodiments of the compound of formula (I-B), m is 3, and the $R^{1a}$ groups are at the 2-position, 6-position, and 7-position. In some embodiments of the compound of formula (I-B), m is 3, and the $R^{1a}$ groups are at the 2-position, 6-position, and 8-position. In some embodiments of the compound of formula (I-B), m is 3, and the $R^{1a}$ groups are at the 2-position, 7-position, and 8-position. In some embodiments of the compound of formula (I-B), m is 3, and the $R^{1a}$ groups are at the 5-position, 6-position, and 7-position. In some embodiments of the compound of formula (I-B), m is 3, and the $R^{1a}$ groups are at the 5-position, 6-position, and 8-position. In some embodiments of the compound of formula (I-B), m is 3, and the $R^{1a}$ groups are at the 5-position, 7-position, and 8-position. In some embodiments of the compound of formula (I-B), m is 3, and the $R^{1a}$ groups are at the 6-position, 7-position, and 8-position. In some embodiments of the compound of formula (I-B), m is 4, and the $R^{1a}$ groups are at the 2-position, 5-position, 6-position, and 7-position. In some embodiments of the compound of formula (I-B), m is 4, and the $R^{1a}$ groups are at the 2-position, 5-position, 6-position, and 8-position. In some embodiments of the compound of formula (I-B), m is 4, and the $R^{1a}$ groups are at the 2-position, 5-position, 7-position, and 8-position. In some embodiments of the compound of formula (I-B), m is 4, and the $R^{1a}$ groups are at the 2-position, 6-position, 7-position, and 8-position. In some embodiments of the compound of formula (I-B), m is 4, and the $R^{1a}$ groups are at the 5-position, 6-position, 7-position, and 8-position. In some embodiments of the compound of formula (I-B), m is 5, and the $R^{1a}$ groups are at the 2-position, 5-position, 6-position, 7-position, and 8-position. Whenever more than one $R^{1a}$ group is present, the $R^{1a}$ groups can be chosen independently. In any of these embodiments of the compound of formula (I-B), or a salt thereof, the carbon bearing the $CO_2H$ and NH moieties may be in the "S" configuration or the "R" configuration.

In some embodiments of formula (I-B), including the embodiments that describe the $R^{1a}$ and m variables, each of $R^{10}$, $R^{11}$, $R^{12}$ and $R^{13}$ are hydrogen. In some embodiments of formula (I-B), including the embodiments that describe the $R^{1a}$ and m variables, and/or the $R^{10}$, $R^{11}$, $R^{12}$ and $R^{13}$ variables, q is 0. In some embodiments of formula (I-B), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-B), $R^{10}$, $R^{11}$, $R^{12}$ and $R^{13}$ are hydrogen, p is 3, q is 0 and the compound is of the formula (II-B):

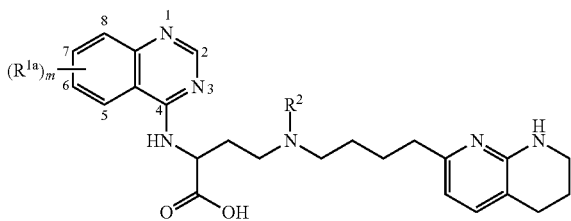

(II-B)

or a salt thereof, wherein $R^{1a}$ and $R^2$ are as defined for formula (I), m is 0, 1, 2, 3, 4, or 5, and the positions on the quinazoline ring are as indicated. All descriptions of $R^{1a}$, $R^2$ and m with reference to formula (I) apply equally to formulae (I-B) and (II-B).

In some embodiments of the compound of formula (I), wherein $R^1$ is 5- to 10-membered heteroaryl optionally substituted by $R^{1a}$, the compound is of the formula (I-C):

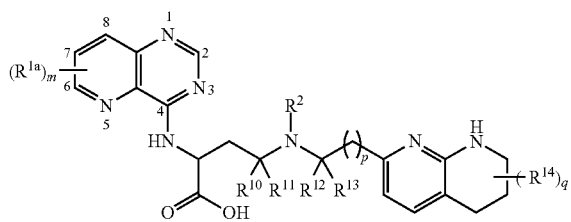

(I-C)

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, 3, or 4, and the positions on the pyrido[3,2-d]pyrimidine ring are as indicated. In one embodiment is provided a compound of the formula (I-C), or a salt thereof, wherein the carbon bearing the $CO_2H$ and NH moieties is in the "S" configuration. In another embodiment is provided a compound of the formula (I-C), or a salt thereof, wherein the carbon bearing the $CO_2H$ and NH moieties is in the "R" configuration. Mixtures of a compound of the formula (I-C) are also embraced, including racemic or non-racemic mixtures of a given compound, and mixtures of two or more compounds of different chemical formulae.

In some embodiments of the compound of formula (I-C), m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-C), m is 0, 1, 2, 3, or 4, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-C), m is 1, 2, 3, or 4

In some embodiments of the compound of formula (I-C), m is 0. In some embodiments of the compound of formula (I-C), m is 1, and $R^{1a}$ is at the 2-position. In some embodiments of the compound of formula (I-C), m is 1, and $R^{1a}$ is at the 6-position. In some embodiments of the compound of formula (I-C), m is 1, and $R^{1a}$ is at the 7-position. In some embodiments of the compound of formula (I-C), m is 1, and $R^{1a}$ is at the 8-position. In some embodiments of the compound of formula (I-C), m is 2, and the $R^{1a}$ groups are at the 2-position and 6-position. In some embodiments of the compound of formula (I-C), m is 2, and the $R^{1a}$ groups are at the 2-position and 7-position. In some embodiments of the compound of formula (I-C), m is 2, and the $R^{1a}$ groups are at the 2-position and 8-position. In some embodiments of the compound of formula (I-C), m is 2, and the $R^{1a}$ groups are at the 6-position and 7-position. In some embodiments of the compound of formula (I-C), m is 2, and the $R^{1a}$ groups are at the 6-position and 8-position. In some embodiments of the compound of formula (I-C), m is 2, and the $R^{1a}$ groups are at the 7-position and 8-position. In some embodiments of the compound of formula (I-C), m is 3, and the $R^{1a}$ groups are at the 2-position, 6-position, and 7-position. In some embodiments of the compound of formula (I-C), m is 3, and the $R^{1a}$ groups are at the 2-position, 6-position, and 8-position. In some embodiments of the compound of formula (I-C), m is 3, and the $R^{1a}$ groups are at the 2-position, 7-position, and 8-position. In some embodiments of the compound of formula (I-C), m is 3, and the $R^{1a}$ groups are at the 6-position, 7-position, and 8-position. In some embodiments of the compound of formula (I-C), m is 4, and the $R^{1a}$ groups are at the 2-position, 6-position, 7-position, and 8-position. Whenever more than one $R^{1a}$ group is present, the $R^{1a}$ groups can be chosen independently. In any of these embodiments of the compound of formula (I-C), or a salt thereof, the carbon bearing the $CO_2H$ and NH moieties may be in the "S" configuration or the "R" configuration.

In some embodiments of formula (I-C), including the embodiments that describe the $R^{1a}$ and m variables, each of $R^{10}$, $R^{11}$, $R^{12}$ and $R^{13}$ are hydrogen. In some embodiments of formula (I-C), including the embodiments that describe the $R^{1a}$ and m variables, and/or the $R^{10}$, $R^{11}$, $R^{12}$ and $R^{13}$ variables, q is 0. In some embodiments of formula (I-C), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-C), $R^{10}$, $R^{11}$, $R^{12}$ and $R^{13}$ are hydrogen, p is 3, q is 0 and the compound is of the formula (II-C):

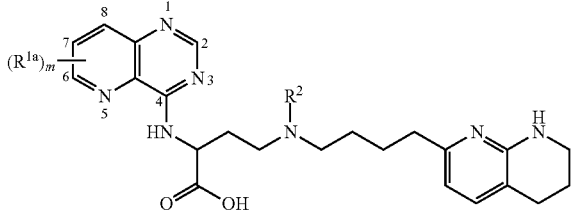

(II-C)

or a salt thereof, wherein $R^{1a}$ and $R^2$ are as defined for formula (I), m is 0, 1, 2, 3, or 4, and the positions on the pyrido[3,2-d]pyrimidine ring are as indicated. All descriptions of $R^{1a}$, $R^2$ and m with reference to formula (I) apply equally to formulae (I-C) and (II-C).

In some embodiments of the compound of formula (I), wherein $R^1$ is 5- to 10-membered heteroaryl optionally substituted by $R^{1a}$, the compound is of the formula (I-D):

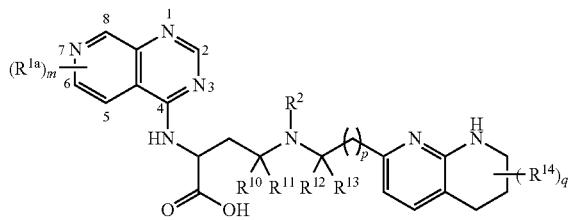

(I-D)

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, 3, or 4, and the positions on the pyrido[3,4-d]pyrimidine ring are as indicated.

In one embodiment is provided a compound of the formula (I-D), or a salt thereof, wherein the carbon bearing the $CO_2H$ and NH moieties is in the "S" configuration. In another embodiment is provided a compound of the formula (I-D), or a salt thereof, wherein the carbon bearing the $CO_2H$ and NH moieties is in the "R" configuration. Mixtures of a compound of the formula (I-D) are also embraced, including racemic or non-racemic mixtures of a given compound, and mixtures of two or more compounds of different chemical formulae.

In some embodiments of the compound of formula (I-D), m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-D), m is 0, 1, 2, 3, or 4, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-D), m is 1, 2, 3, or 4.

In some embodiments of the compound of formula (I-D), m is 0. In some embodiments of the compound of formula (I-D), m is 1, and $R^{1a}$ is at the 2-position. In some embodiments of the compound of formula (I-D), m is 1, and $R^{1a}$ is at the 5-position. In some embodiments of the compound of formula (I-D), m is 1, and $R^{1a}$ is at the 6-position. In some embodiments of the compound of formula (I-D), m is 1, and $R^{1a}$ is at the 8-position. In some embodiments of the compound of formula (I-D), m is 2, and the $R^{1a}$ groups are at the 2-position and 5-position. In some embodiments of the compound of formula (I-D), m is 2, and the $R^{1a}$ groups are at the 2-position and 6-position. In some embodiments of the compound of formula (I-D), m is 2, and the $R^{1a}$ groups are at the 2-position and 8-position. In some embodiments of the compound of formula (I-D), m is 2, and the $R^{1a}$ groups are at the 5-position and 6-position. In some embodiments of the compound of formula (I-D), m is 2, and the $R^{1a}$ groups are at the 5-position and 8-position. In some embodiments of the compound of formula (I-D), m is 2, and the $R^{1a}$ groups are at the 6-position and 8-position. In some embodiments of the compound of formula (I-D), m is 3, and the $R^{1a}$ groups are at the 2-position, 5-position, and 6-position. In some embodiments of the compound of formula (I-D), m is 3, and the $R^{1a}$ groups are at the 2-position, 5-position, and 8-position. In some embodiments of the compound of formula (I-D), m is 3, and the $R^{1a}$ groups are at the 2-position, 6-position, and 8-position. In some embodiments of the compound of formula (I-D), m is 3, and the $R^{1a}$ groups are at the 5-position, 6-position, and 8-position. In some embodiments of the compound of formula (I-D), m is 4, and the $R^{1a}$ groups are at the 2-position, 5-position, 6-position, and 8-position. Whenever more than one $R^{1a}$ group is present, the $R^{1a}$ groups can be chosen independently. In any of these embodiments of the compound of formula (I-D), or a salt thereof, the carbon bearing the $CO_2H$ and NH moieties may be in the "S" configuration or the "R" configuration.

In some embodiments of formula (I-D), including the embodiments that describe the $R^{1a}$ and m variables, each of $R^{10}$, $R^{11}$, $R^{12}$ and $R^{13}$ are hydrogen. In some embodiments of formula (I-D), including the embodiments that describe the $R^{1a}$ and m variables, and/or the $R^{10}$, $R^{11}$, $R^{12}$ and $R^{13}$ variables, q is 0. In some embodiments of formula (I-D), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-D), $R^{10}$, $R^{11}$, $R^{12}$ and $R^{13}$ are hydrogen, p is 3, q is 0 and the compound is of the formula (II-D):

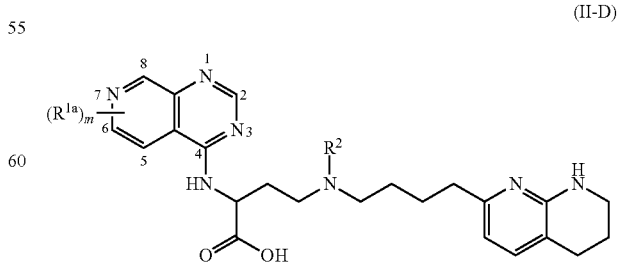

(II-D)

or a salt thereof, wherein $R^{1a}$ and $R^2$ are as defined for formula (I), m is 0, 1, 2, 3, or 4, and the positions on the pyrido[3,4-d]pyrimidine ring are as indicated. All descriptions of $R^{1a}$, $R^2$ and m with reference to formula (I) apply equally to formulae (I-D) and (II-D).

In some embodiments of the compound of formula (I), wherein $R^1$ is 5- to 10-membered heteroaryl optionally substituted by $R^{1a}$, the compound is of the formula (I-E):

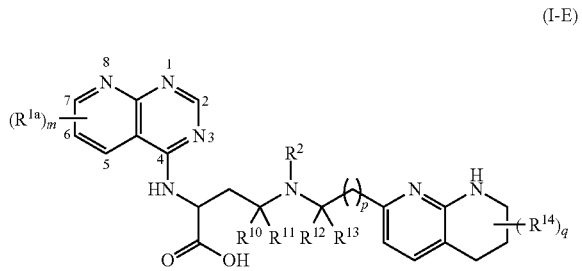

(I-E)

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, 3, or 4, and the positions on the pyrido[2,3-d]pyrimidine ring are as indicated.

In one embodiment is provided a compound of the formula (I-E), or a salt thereof, wherein the carbon bearing the $CO_2H$ and NH moieties is in the "S" configuration. In another embodiment is provided a compound of the formula (I-E), or a salt thereof, wherein the carbon bearing the $CO_2H$ and NH moieties is in the "R" configuration. Mixtures of a compound of the formula (I-E) are also embraced, including racemic or non-racemic mixtures of a given compound, and mixtures of two or more compounds of different chemical formulae.

In some embodiments of the compound of formula (I-E), m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-E), m is 0, 1, 2, 3, or 4, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-E), m is 1, 2, 3, or 4.

In some embodiments of the compound of formula (I-E), m is 0. In some embodiments of the compound of formula (I-E), m is 1, and $R^{1a}$ is at the 2-position. In some embodiments of the compound of formula (I-E), m is 1, and $R^{1a}$ is at the 5-position. In some embodiments of the compound of formula (I-E), m is 1, and $R^{1a}$ is at the 6-position. In some embodiments of the compound of formula (I-E), m is 1, and $R^{1a}$ is at the 7-position. In some embodiments of the compound of formula (I-E), m is 2, and the $R^{1a}$ groups are at the 2-position and 5-position. In some embodiments of the compound of formula (I-E), m is 2, and the $R^{1a}$ groups are at the 2-position and 6-position. In some embodiments of the compound of formula (I-E), m is 2, and the $R^{1a}$ groups are at the 2-position and 7-position. In some embodiments of the compound of formula (I-E), m is 2, and the $R^{1a}$ groups are at the 5-position and 6-position. In some embodiments of the compound of formula (I-E), m is 2, and the $R^{1a}$ groups are at the 5-position and 7-position. In some embodiments of the compound of formula (I-E), m is 2, and the $R^{1a}$ groups are at the 6-position and 7-position. In some embodiments of the compound of formula (I-E), m is 3, and the $R^{1a}$ groups are at the 2-position, 5-position, and 6-position. In some embodiments of the compound of formula (I-E), m is 3, and the $R^{1a}$ groups are at the 2-position, 5-position, and 7-position. In some embodiments of the compound of formula (I-E), m is 3, and the $R^{1a}$ groups are at the 2-position, 6-position, and 7-position. In some embodiments of the compound of formula (I-E), m is 3, and the $R^{1a}$ groups are at the 5-position, 6-position, and 7-position. In some embodiments of the compound of formula (I-E), m is 4, and the $R^{1a}$ groups are at the 2-position, 5-position, 6-position, and 7-position. Whenever more than one $R^{1a}$ group is present, the $R^{1a}$ groups can be chosen independently. In any of these embodiments of the compound of formula (I-E), or a salt thereof, the carbon bearing the $CO_2H$ and NH moieties may be in the "S" configuration or the "R" configuration.

In some embodiments of formula (I-E), including the embodiments that describe the $R^{1a}$ and m variables, each of $R^{10}$, $R^{11}$, $R^{12}$ and $R^{13}$ are hydrogen. In some embodiments of formula (I-E), including the embodiments that describe the $R^{1a}$ and m variables, and/or the $R^{10}$, $R^{11}$, $R^{12}$ and $R^{13}$ variables, q is 0. In some embodiments of formula (I-E), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-E), $R^{10}$, $R^{11}$, $R^{12}$ and $R^{13}$ are hydrogen, p is 3, q is 0 and the compound is of the formula (II-E):

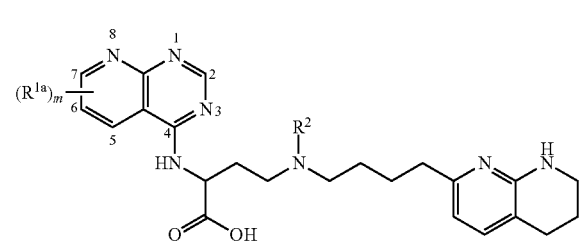

(II-E)

or a salt thereof, wherein $R^{1a}$ and $R^2$ are as defined for formula (I), m is 0, 1, 2, 3, or 4, and the positions on the pyrido[2,3-d]pyrimidine ring are as indicated. All descriptions of $R^{1a}$, $R^2$ and m with reference to formula (I) apply equally to formulae (I-E) and (II-E).

In some embodiments of the compound of formula (I), wherein $R^1$ is 5- to 10-membered heteroaryl optionally substituted by $R^{1a}$, the compound is of the formula (I-F):

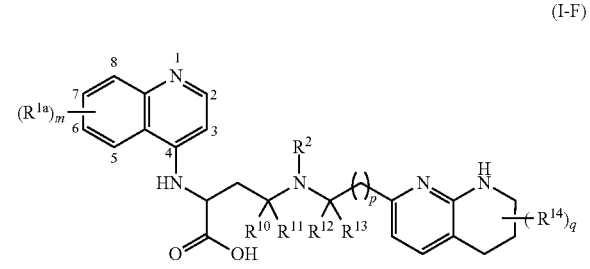

(I-F)

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, 3, 4, 5, or 6 and the positions on the quinoline ring are as indicated.

In one embodiment is provided a compound of the formula (I-F), or a salt thereof, wherein the carbon bearing the $CO_2H$ and NH moieties is in the "S" configuration. In another embodiment is provided a compound of the formula (I-F), or a salt thereof, wherein the carbon bearing the $CO_2H$ and NH moieties is in the "R" configuration. Mixtures of a compound of the formula (I-F) are also embraced, including racemic or non-racemic mixtures of a given compound, and mixtures of two or more compounds of different chemical formulae.

In some embodiments of the compound of formula (I-F), m is 0, 1, 2, 3, 4, 5, or 6 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-F), m is 0, 1, 2, 3, 4, 5, or 6, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-F), m is 1, 2, 3, 4, 5, or 6.

In some embodiments of the compound of formula (I-F), m is 0. In some embodiments of the compound of formula (I-F), m is 1, and $R^{1a}$ is at the 2-position. In some embodiments of the compound of formula (I-F), m is 1, and $R^{1a}$ is at the 3-position. In some embodiments of the compound of formula (I-F), m is 1, and $R^{1a}$ is at the 5-position. In some embodiments of the compound of formula (I-F), m is 1, and $R^{1a}$ is at the 6-position. In some embodiments of the compound of formula (I-F), m is 1, and $R^{1a}$ is at the 7-position. In some embodiments of the compound of formula (I-F), m is 1, and $R^{1a}$ is at the 8-position. In some embodiments of the compound of formula (I-F), m is 2, and the $R^{1a}$ groups are at the 2-position and 3-position. In some embodiments of the compound of formula (I-F), m is 2, and the $R^{1a}$ groups are at the 2-position and 5-position. In some embodiments of the compound of formula (I-F), m is 2, and the $R^{1a}$ groups are at the 2-position and 6-position. In some embodiments of the compound of formula (I-F), m is 2, and the $R^{1a}$ groups are at the 2-position and 7-position. In some embodiments of the compound of formula (I-F), m is 2, and the $R^{1a}$ groups are at the 2-position and 8-position. In some embodiments of the compound of formula (I-F), m is 2, and the $R^{1a}$ groups are at the 3-position and 5-position. In some embodiments of the compound of formula (I-F), m is 2, and the $R^{1a}$ groups are at the 3-position and 6-position. In some embodiments of the compound of formula (I-F), m is 2, and the $R^{1a}$ groups are at the 3-position and 7-position. In some embodiments of the compound of formula (I-F), m is 2, and the $R^{1a}$ groups are at the 3-position and 8-position. In some embodiments of the compound of formula (I-F), m is 2, and the $R^{1a}$ groups are at the 5-position and 6-position. In some embodiments of the compound of formula (I-F), m is 2, and the $R^{1a}$ groups are at the 5-position and 7-position. In some embodiments of the compound of formula (I-F), m is 2, and the $R^{1a}$ groups are at the 5-position and 8-position. In some embodiments of the compound of formula (I-F), m is 2, and the $R^{1a}$ groups are at the 6-position and 7-position. In some embodiments of the compound of formula (I-F), m is 2, and the $R^{1a}$ groups are at the 6-position and 8-position. In some embodiments of the compound of formula (I-F), m is 2, and the $R^{1a}$ groups are at the 7-position and 8-position. In some embodiments of the compound of formula (I-F), m is 3, and the $R^{1a}$ groups are at the 2-position, 3-position, and 5-position. In some embodiments of the compound of formula (I-F), m is 3, and the $R^{1a}$ groups are at the 2-position, 3-position, and 6-position. In some embodiments of the compound of formula (I-F), m is 3, and the $R^{1a}$ groups are at the 2-position, 3-position, and 7-position. In some embodiments of the compound of formula (I-F), m is 3, and the $R^{1a}$ groups are at the 2-position, 3-position, and 8-position. In some embodiments of the compound of formula (I-F), m is 3, and the $R^{1a}$ groups are at the 2-position, 5-position, and 6-position. In some embodiments of the compound of formula (I-F), m is 3, and the $R^{1a}$ groups are at the 2-position, 5-position, and 7-position. In some embodiments of the compound of formula (I-F), m is 3, and the $R^{1a}$ groups are at the 2-position, 5-position, and 8-position. In some embodiments of the compound of formula (I-F), m is 3, and the $R^{1a}$ groups are at the 2-position, 6-position, and 7-position. In some embodiments of the compound of formula (I-F), m is 3, and the $R^{1a}$ groups are at the 2-position, 6-position, and 8-position. In some embodiments of the compound of formula (I-F), m is 3, and the $R^{1a}$ groups are at the 2-position, 7-position, and 8-position. In some embodiments of the compound of formula (I-F), m is 3, and the $R^{1a}$ groups are at the 3-position, 5-position, and 6-position. In some embodiments of the compound of formula (I-F), m is 3, and the $R^{1a}$ groups are at the 3-position, 5-position, and 7-position. In some embodiments of the compound of formula (I-F), m is 3, and the $R^{1a}$ groups are at the 3-position, 5-position, and 8-position. In some embodiments of the compound of formula (I-F), m is 3, and the $R^{1a}$ groups are at the 3-position, 6-position, and 7-position. In some embodiments of the compound of formula (I-F), m is 3, and the $R^{1a}$ groups are at the 3-position, 6-position, and 8-position. In some embodiments of the compound of formula (I-F), m is 3, and the $R^{1a}$ groups are at the 3-position, 7-position, and 8-position. In some embodiments of the compound of formula (I-F), m is 3, and the $R^{1a}$ groups are at the 5-position, 6-position, and 7-position. In some embodiments of the compound of formula (I-F), m is 3, and the $R^{1a}$ groups are at the 5-position, 6-position, and 8-position. In some embodiments of the compound of formula (I-F), m is 3, and the $R^{1a}$ groups are at the 5-position, 7-position, and 8-position. In some embodiments of the compound of formula (I-F), m is 3, and the $R^{1a}$ groups are at the 6-position, 7-position, and 8-position. In some embodiments of the compound of formula (I-F), m is 4, and the $R^{1a}$ groups are at the 2-position, 3-position, 5-position, and 6-position. In some embodiments of the compound of formula (I-F), m is 4, and the $R^{1a}$ groups are at the 2-position, 3-position, 5-position, and 7-position. In some embodiments of the compound of formula (I-F), m is 4, and the $R^{1a}$ groups are at the 2-position, 3-position, 5-position, and 8-position. In some embodiments of the compound of formula (I-F), m is 4, and the $R^{1a}$ groups are at the 2-position, 3-position, 6-position, and 7-position. In some embodiments of the compound of formula (I-F), m is 4, and the $R^{1a}$ groups are at the 2-position, 3-position, 6-position, and 8-position. In some embodiments of the compound of formula (I-F), m is 4, and the $R^{1a}$ groups are at the 2-position, 3-position, 7-position, and 8-position. In some embodiments of the compound of formula (I-F), m is 4, and the $R^{1a}$ groups are at the 2-position, 5-position, 6-position, and 7-position. In some embodiments of the compound of formula (I-F), m is 4, and the $R^{1a}$ groups are at the 2-position, 5-position, 6-position, and 8-position. In some embodiments of the compound of formula (I-F), m is 4, and the $R^{1a}$ groups are at the 2-position, 5-position, 7-position, and 8-position. In some embodiments of the compound of formula (I-F), m is 4, and the $R^{1a}$ groups are at the 2-position, 6-position, 7-position, and 8-position. In some embodiments of the compound of formula (I-F), m is 4, and the $R^{1a}$ groups are at the 3-position, 5-position, 6-position, and 7-position. In some embodiments of the compound of formula (I-F), m is 4, and the $R^{1a}$ groups are at the 3-position, 5-position, 6-position, and 8-position. In some embodiments of the compound of formula (I-F), m is 4, and the $R^{1a}$ groups are at the 3-position, 5-position, 7-position, and 8-position. In some embodiments of the compound of formula (I-F), m is 4, and the $R^{1a}$ groups are at the 3-position, 6-position, 7-position, and 8-position. In some embodiments of the compound of formula (I-F), m is 4, and the $R^{1a}$ groups are at the 5-position, 6-position, 7-position, and 8-position. In some embodiments of the compound of formula (I-F), m is 5, and the $R^{1a}$ groups are at the 2-position, 3-position, 5-position, 6-position, and 7-position. In some embodiments of the compound of formula (I-F), m is 5, and the $R^{1a}$ groups are at the 2-position, 3-position, 5-position, 6-position, and 8-position. In some embodiments of the compound of formula (I-F), m is 5, and the $R^{1a}$ groups are at the 2-position, 3-position, 5-position, 7-position, and 8-position. In some embodiments of the compound of formula (I-F), m is 5, and the $R^{1a}$ groups are at the 2-position, 3-position, 6-position, 7-position, and 8-position. In some embodiments of the compound of formula (I-F), m is 5, and the $R^{1a}$ groups are at the 2-position, 5-position, 6-position, 7-position, and 8-position. In some embodiments of the compound of formula (I-F), m is 5, and the $R^{1a}$ groups are at the 3-position, 5-position, 6-position, 7-position, and 8-position. In some embodiments of the compound of formula (I-F), m is 6, and the $R^{1a}$ groups are at the 2-position, 3-position, 5-position, 6-position, 7-position, and 8-position. Whenever more than one $R^{1a}$ group is present, the $R^{1a}$ groups can be chosen independently. In any of these embodiments of the compound of formula (I-F), or a salt thereof, the carbon bearing the $CO_2H$ and NH moieties may be in the "S" configuration or the "R" configuration.

In some embodiments of formula (I-F), including the embodiments that describe the $R^{1a}$ and m variables, each of $R^{10}$, $R^{11}$, $R^{12}$ and $R^{13}$ are hydrogen. In some embodiments of formula (I-F), including the embodiments that describe the $R^{1a}$ and m variables, and/or the $R^{10}$, $R^{11}$, $R^{12}$ and $R^{13}$ variables, q is 0. In some embodiments of formula (I-F), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-F), $R^{10}$, $R^{11}$, $R^{12}$ and $R^{13}$ are hydrogen, p is 3, q is 0 and the compound is of the formula (II-F):

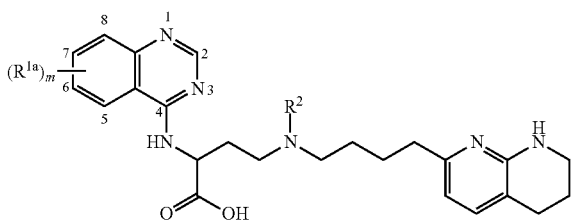

(II-F)

or a salt thereof, wherein $R^{1a}$ and $R^2$ are as defined for formula (I), m is 0, 1, 2, 3, 4, 5, or 6 and the positions on the quinoline ring are as indicated. All descriptions of $R^{1a}$, $R^2$ and m with reference to formula (I) apply equally to formulae (I-F) and (II-F).

In some embodiments of the compound of formula (I), wherein $R^1$ is 5- to 10-membered heteroaryl optionally substituted by $R^{1a}$, the compound is of the formula (I-G):

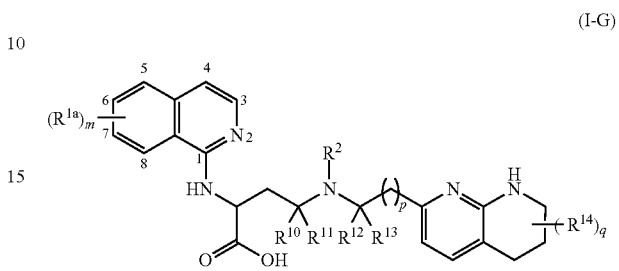

(I-G)

or a salt thereof, wherein $R^{1a}$, $R^2$, $R^{10}$, $R^{11}$, $R^{12}$, $R^{13}$, $R^{14}$, q and p are as defined for formula (I), m is 0, 1, 2, 3, 4, 5, or 6 and the positions on the isoquinoline ring are as indicated.

In one embodiment is provided a compound of the formula (I-G), or a salt thereof, wherein the carbon bearing the $CO_2H$ and NH moieties is in the "S" configuration. In another embodiment is provided a compound of the formula (I-G), or a salt thereof, wherein the carbon bearing the $CO_2H$ and NH moieties is in the "R" configuration. Mixtures of a compound of the formula (I-G) are also embraced, including racemic or non-racemic mixtures of a given compound, and mixtures of two or more compounds of different chemical formulae.

In some embodiments of the compound of formula (I-G), m is 0, 1, 2, 3, 4, 5, or 6 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-G), m is 0, 1, 2, 3, 4, 5, or 6, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-G), m is 1, 2, 3, 4, 5, or 6.

In some embodiments of the compound of formula (I-G), m is 0. In some embodiments of the compound of formula (I-G), m is 1, and $R^{1a}$ is at the 3-position. In some embodiments of the compound of formula (I-G), m is 1, and $R^{1a}$ is at the 4-position. In some embodiments of the compound of formula (I-G), m is 1, and $R^{1a}$ is at the 5-position. In some embodiments of the compound of formula (I-G), m is 1, and $R^{1a}$ is at the 6-position. In some embodiments of the compound of formula (I-G), m is 1, and $R^{1a}$ is at the 7-position. In some embodiments of the compound of formula (I-G), m is 1, and $R^{1a}$ is at the 8-position. In some embodiments of the compound of formula (I-G), m is 2, and the $R^{1a}$ groups are at the 3-position and 4-position. In some embodiments of the compound of formula (I-G), m is 2, and the $R^{1a}$ groups are at the 4-position and 5-position. In some embodiments of the compound of formula (I-G), m is 2, and the $R^{1a}$ groups are at the 4-position and 6-position. In some embodiments of the compound of formula (I-G), m is 2, and the $R^{1a}$ groups are at the 4-position and 7-position. In some embodiments of the compound of formula (I-G), m is 2, and the $R^{1a}$ groups are at the 4-position and 8-position. In some embodiments of the compound of formula (I-G), m is 2, and the $R^{1a}$ groups are at the 3-position and 5-position. In some embodiments of the compound of formula (I-G), m is 2, and the $R^{1a}$ groups are at the 3-position and 6-position. In some embodiments of the compound of formula (I-G), m is 2, and the $R^{1a}$ groups are at the 3-position and 7-position. In some embodiments of the compound of formula (I-G), m is 2, and the $R^{1a}$ groups are at the 3-position and 8-position. In some embodiments of the compound of formula (I-G), m is 2, and the $R^{1a}$ groups are at the 5-position and 6-position. In some embodiments of the compound of formula (I-G), m is 2, and the $R^{1a}$ groups are at the 5-position and 7-position. In some embodiments of the compound of formula (I-G), m is 2, and the $R^{1a}$ groups are at the 5-position and 8-position. In some embodiments of the compound of formula (I-G), m is 2, and the $R^{1a}$ groups are at the 6-position and 7-position. In some embodiments of the compound of formula (I-G), m is 2, and the $R^{1a}$ groups are at the 6-position and 8-position. In some embodiments of the compound of formula (I-G), m is 2, and the $R^{1a}$ groups are at the 7-position and 8-position. In some embodiments of the compound of formula (I-G), m is 3, and the $R^{1a}$ groups are at the 3-position, 4-position, and 5-position. In some embodiments of the compound of formula (I-G), m is 3, and the $R^{1a}$ groups are at the 3-position, 4-position, and 6-position. In some embodiments of the compound of formula (I-G), m is 3, and the $R^{1a}$ groups are at the 3-position, 4-position, and 7-position. In some embodiments of the compound of formula (I-G), m is 3, and the $R^{1a}$ groups are at the 3-position, 4-position, and 8-position. In some embodiments of the compound of formula (I-G), m is 3, and the $R^{1a}$ groups are at the 4-position, 5-position, and 6-position. In some embodiments of the compound of formula (I-G), m is 3, and the $R^{1a}$ groups are at the 4-position, 5-position, and 7-position. In some embodiments of the compound of formula (I-G), m is 3, and the $R^{1a}$ groups are at the 4-position, 5-position, and 8-position. In some embodiments of the compound of formula (I-G), m is 3, and the $R^{1a}$ groups are at the 4-position, 6-position, and 7-position. In some embodiments of the compound of formula (I-G), m is 3, and the $R^{1a}$ groups are at the 4-position, 6-position, and 8-position. In some embodiments of the compound of formula (I-G), m is 3, and the $R^{1a}$ groups are at the 4-position, 7-position, and 8-position. In some embodiments of the compound of formula (I-G), m is 3, and the $R^{1a}$ groups are at the 3-position, 5-position, and 6-position. In some embodiments of the compound of formula (I-G), m is 3, and the $R^{1a}$ groups are at the 3-position, 5-position, and 7-position. In some embodiments of the compound of formula (I-G), m is 3, and the $R^{1a}$ groups are at the 3-position, 5-position, and 8-position. In some embodiments of the compound of formula (I-G), m is 3, and the $R^{1a}$ groups are at the 3-position, 6-position, and 7-position. In some embodiments of the compound of formula (I-G), m is 3, and the $R^{1a}$ groups are at the 3-position, 6-position, and 8-position. In some embodiments of the compound of formula (I-G), m is 3, and the $R^{1a}$ groups are at the 3-position, 7-position, and 8-position. In some embodiments of the compound of formula (I-G), m is 3, and the $R^{1a}$ groups are at the 5-position, 6-position, and 7-position. In some embodiments of the compound of formula (I-G), m is 3, and the $R^{1a}$ groups are at the 5-position, 6-position, and 8-position. In some embodiments of the compound of formula (I-G), m is 3, and the $R^{1a}$ groups are at the 5-position, 7-position, and 8-position. In some embodiments of the compound of formula (I-G), m is 3, and the $R^{1a}$ groups are at the 6-position, 7-position, and 8-position. In some embodiments of the compound of formula (I-G), m is 4, and the $R^{1a}$ groups are at the 3-position, 4-position, 5-position, and 6-position. In some embodiments of the compound of formula (I-G), m is 4, and the $R^{1a}$ groups are at the 3-position, 4-position, 5-position, and 7-position. In some embodiments of the compound of formula (I-G), m is 4, and the $R^{1a}$ groups are at the 3-position, 4-position, 5-position, and 8-position. In some embodiments of the compound of formula (I-G), m is 4, and the $R^{1a}$ groups are at the 3-position, 4-position, 6-position, and 7-position. In some embodiments of the compound of formula (I-G), m is 4, and the $R^{1a}$ groups are at the 4-position, 3-position, 6-position, and 8-position. In some embodiments of the compound of formula (I-G), m is 4, and the $R^{1a}$ groups are at the 3-position, 4-position, 7-position, and 8-position. In some embodiments of the compound of formula (I-G), m is 4, and the $R^{1a}$ groups are at the 4-position, 5-position, 6-position, and 7-position. In some embodiments of the compound of formula (I-G), m is 4, and the $R^{1a}$ groups are at the 4-position, 5-position, 6-position, and 8-position. In some embodiments of the compound of formula (I-G), m is 4, and the $R^{1a}$ groups are at the 4-position, 5-position, 7-position, and 8-position. In some embodiments of the compound of formula (I-G), m is 4, and the $R^{1a}$ groups are at the 4-position, 6-position, 7-position, and 8-position. In some embodiments of the compound of formula (I-G), m is 4, and the $R^{1a}$ groups are at the 3-position, 5-position, 6-position, and 7-position. In some embodiments of the compound of formula (I-G), m is 4, and the $R^{1a}$ groups are at the 3-position, 5-position, 6-position, and 8-position. In some embodiments of the compound of formula (I-G), m is 4, and the $R^{1a}$ groups are at the 3-position, 5-position, 7-position, and 8-position. In some embodiments of the compound of formula (I-G), m is 4, and the $R^{1a}$ groups are at the 3-position, 6-position, 7-position, and 8-position. In some embodiments of the compound of formula (I-G), m is 4, and the $R^{1a}$ groups are at the 5-position, 6-position, 7-position, and 8-position. In some embodiments of the compound of formula (I-G), m is 5, and the $R^{1a}$ groups are at the 3-position, 4-position, 5-position, 6-position, and 7-position. In some embodiments of the compound of formula (I-G), m is 5, and the $R^{1a}$ groups are at the 3-position, 4-position, 5-position, 6-position, and 8-position. In some embodiments of the compound of formula (I-G), m is 5, and the $R^{1a}$ groups are at the 3-position, 4-position, 5-position, 7-position, and 8-position. In some embodiments of the compound of formula (I-G), m is 5, and the $R^{1a}$ groups are at the 3-position, 4-position, 6-position, 7-position, and 8-position. In some embodiments of the compound of formula (I-G), m is 5, and the $R^{1a}$ groups are at the 4-position, 5-position, 6-position, 7-position, and 8-position. In some embodiments of the compound of formula (I-G), m is 5, and the $R^{1a}$ groups are at the 3-position, 5-position, 6-position, 7-position, and 8-position. In some embodiments of the compound of formula (I-G), m is 6, and the $R^{1a}$ groups are at the 3-position, 4-position, 5-position, 6-position, 7-position, and 8-position. Whenever more than one $R^{1a}$ group is present, the $R^{1a}$ groups can be chosen independently. In any of these embodiments of the compound of formula (I-G), or a salt thereof, the carbon bearing the $CO_2H$ and NH moieties may be in the "S" configuration or the "R" configuration.

In some embodiments of formula (I-G), including the embodiments that describe the $R^{1a}$ and m variables, each of $R^{10}$, $R^{11}$, $R^{12}$ and $R^{13}$ are hydrogen. In some embodiments of formula (I-G), including the embodiments that describe the $R^{1a}$ and m variables, and/or the $R^{10}$, $R^{11}$, $R^{12}$ and $R^{13}$ variables, q is 0. In some embodiments of formula (I-G), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-G), $R^{10}$, $R^{11}$, $R^{12}$ and $R^{13}$ are hydrogen, p is 3, q is 0 and the compound is of the formula (II-G):

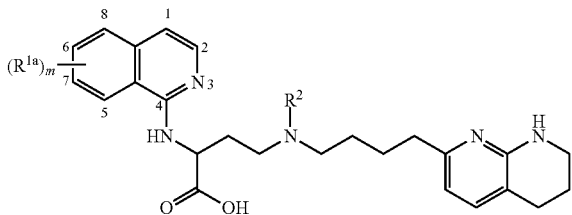

(II-F)

or a salt thereof, wherein $R^{1a}$ and $R^2$ are as defined for formula (I), m is 0, 1, 2, 3, 4, 5, or 6 and the positions on the isoquinoline ring are as indicated. All descriptions of $R^{1a}$, $R^2$ and m with reference to formula (I) apply equally to formulae (I-G) and (II-G).

In some embodiments of the compound of formula (I), wherein $R^1$ is 5- to 10-membered heteroaryl optionally substituted by $R^{1a}$, the compound is of the formula (I-H):

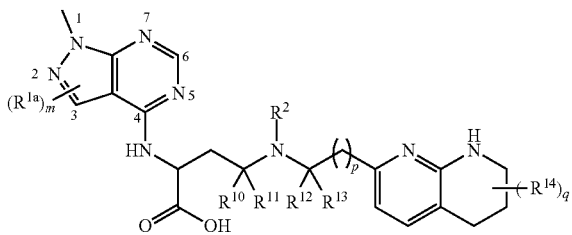

(I-H)

or a salt thereof, wherein $R^{1a}$, $R^2$, $R^{10}$, $R^{11}$, $R^{12}$, $R^{13}$, $R^{14}$, q and p are as defined for formula (I), m is 0, 1, or 2, and the positions on the 1-methyl-H-pyrazolo[3,4-d]pyrimidine ring are as indicated.

In one embodiment is provided a compound of the formula (I-H), or a salt thereof, wherein the carbon bearing the $CO_2H$ and NH moieties is in the "S" configuration. In another embodiment is provided a compound of the formula (I-H), or a salt thereof, wherein the carbon bearing the $CO_2H$ and NH moieties is in the "R" configuration. Mixtures of a compound of the formula (I-H) are also embraced, including racemic or non-racemic mixtures of a given compound, and mixtures of two or more compounds of different chemical formulae.

In some embodiments of the compound of formula (I-H), m is 0, 1, or 2, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I-H), m is 0, 1, or 2, and each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium. In some embodiments of the compound of formula (I-H), m is 1 or 2.

In some embodiments of the compound of formula (I-H), m is 0. In some embodiments of the compound of formula (I-H), m is 1, and $R^{1a}$ is at the 3-position. In some embodiments of the compound of formula (I-H), m is 1, and $R^{1a}$ is at the 6-position. In some embodiments of the compound of formula (I-H), m is 2, and the $R^{1a}$ groups are at the 3-position and 6-position. Whenever more than one $R^{1a}$ group is present, the $R^{1a}$ groups can be chosen independently. In any of these embodiments of the compound of formula (I-H), or a salt thereof, the carbon bearing the $CO_2H$ and NH moieties may be in the "S" configuration or the "R" configuration.

In some embodiments of formula (I-H), including the embodiments that describe the $R^{1a}$ and m variables, each of $R^{10}$, $R^{11}$, $R^{12}$ and $R^{13}$ are hydrogen. In some embodiments of formula (I-H), including the embodiments that describe the $R^{1a}$ and m variables, and/or the $R^{10}$, $R^{11}$, $R^{12}$ and $R^{13}$ variables, q is 0. In some embodiments of formula (I-H), including the embodiments that describe the $R^{1a}$ and m variables, and/or the $R^{10}$, $R^{11}$, $R^{12}$ and $R^{13}$ variables and/or the q variable, p is 3, 4 or 5.

In some embodiments of formula (I-H), $R^{10}$, $R^{11}$, $R^{12}$ and $R^{13}$ are hydrogen, p is 3, q is 0 and the compound is of the formula (II-H):

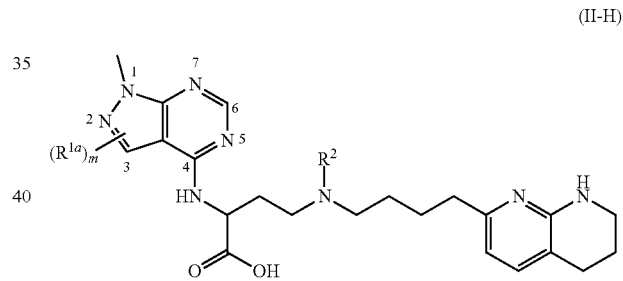

(II-H)

or a salt thereof, wherein $R^{1a}$ and $R^2$ are as defined for formula (I), m is 0, 1, or 2, and the positions on the 1-methyl-1H-pyrazolo[3,4-d]pyrimidine ring are as indicated. All descriptions of $R^{1a}$, $R^2$ and m with reference to formula (I) apply equally to formulae (I-H) and (II-H).

Also provided is a compound of formula (I) or (II), or a salt thereof, wherein $R^1$ is 5- to 10-membered heteroaryl optionally substituted by $R^{1a}$. In some embodiments, $R^1$ is unsubstituted 5- to 10-membered heteroaryl (e.g., pyridinyl, pyrimidinyl, quinoxalinyl, quinazolinyl, pyrazolopyrimidinyl, quinolinyl, pyridopyrimidinyl, thienopyrimidinyl, pyridinyl, pyrrolopyrimidinyl, benzothiazolyl, isoquinolinyl, purinyl, or benzooxazolyl). In some embodiments, $R^1$ is 5- to 10-membered heteroaryl substituted by 1, 2, 3, 4, or 5 $R^{1a}$ groups which may be the same or different, wherein each $R^{1a}$ is independently selected from halogen (e.g., fluoro, chloro, or bromo), $C_1$-$C_6$ alkyl optionally substituted by halogen (e.g., —$CH_3$, —$CHF_2$, —$CF_3$, or $C(CH_3)_3$), $C_3$-$C_6$ cycloalkyl (e.g., cyclopropyl), 5- to 10-membered heteroaryl (e.g., pyridinyl or pyrazolyl), $C_6$-$C_{14}$ aryl (e.g., phenyl), —CN, —$OR^3$ (e.g., —$OCH_3$), and —$NR^4R^5$ (e.g., —$N(CH_3)_2$). In some embodiments, $R^1$ is 5-membered heteroaryl (e.g., pyrazolyl) substituted by 1, 2, 3, or 4 $R^{1a}$ groups which may be the same or different and is selected from —CH₃, —CH₂F, —CHF₂, and —CF₃. In some embodiments, R¹ is 6-membered heteroaryl (e.g., pyridinyl, pyrimidinyl, or pyrazinyl) substituted by 1, 2, 3, 4, or 5 R¹ᵃ groups which may be the same or different and is selected from halogen (e.g., fluoro, chloro, or bromo), C₃-C₆ cycloalkyl (e.g., cyclopropyl), 5- to 6-membered heteroaryl (e.g., pyridinyl or pyrazolyl), C₆-C₁₀ aryl (e.g., phenyl), C₁-C₄ alkyl optionally substituted by halogen (e.g., —CH₃, —CF₃ or C(CH₃)₃), —CN, —OR³ (e.g., —OCH₃), and —NR⁴R⁵ (e.g., —N(CH₃)₂). In some embodiments, R¹ is 9-membered heteroaryl (e.g., pyrazolopyrimidinyl, pyrrolopyrimidinyl, thienopyrimidinyl, indazolyl, indolyl, or benzoimidazolyl) substituted by 1, 2, 3, 4, or 5 R¹ᵃ groups which may be the same or different and is selected from —CH₃, —CH₂F, —CHF₂, and —CF₃. In some embodiments, R¹ is 10-membered heteroaryl (e.g., quinazolinyl) substituted by 1, 2, 3, 4, or 5 R¹ᵃ groups which may be the same or different and is selected from halogen (e.g., fluoro or chloro), 5- to 6-membered heteroaryl (e.g., pyridinyl), C₁ alkyl optionally substituted by halogen (e.g., —CH₃ or —CF₃), and —OR³ (e.g., —OCH₃).

Also provided is a compound of formula (I) or (II), or a salt thereof, wherein R¹ is selected from the group consisting of

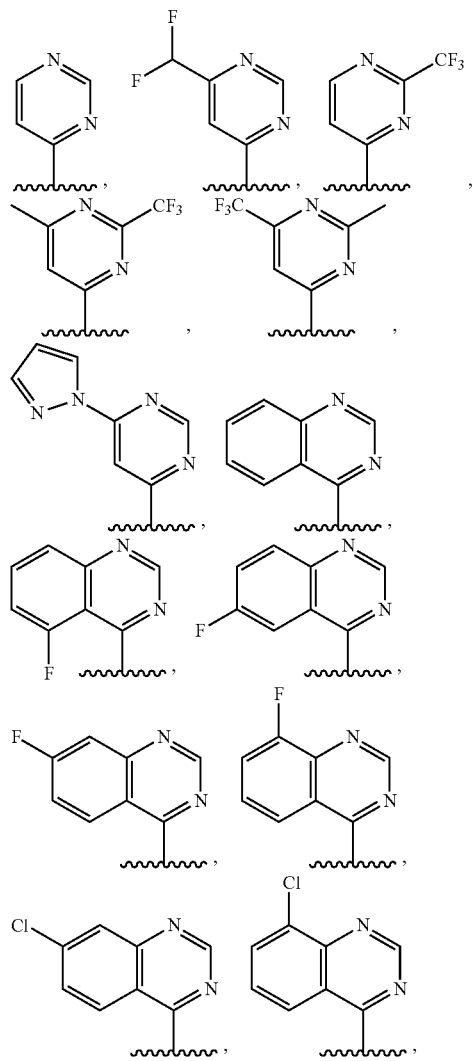

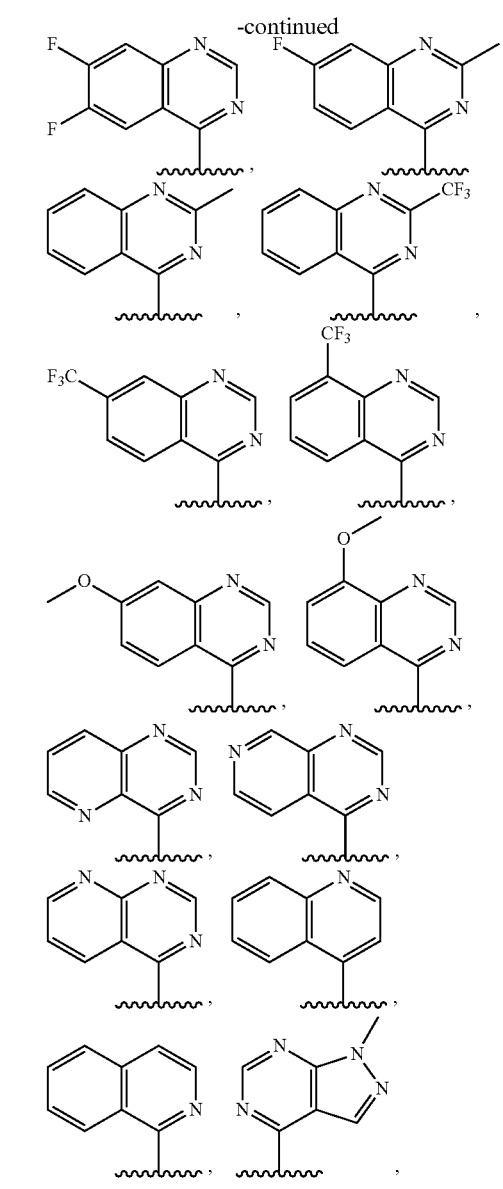

and any of the foregoing groups wherein any one or more hydrogen atom(s) are replaced with deuterium atom(s). Also provided is a compound of formula (I) or (II), or a salt thereof, wherein R¹ is selected from any of the foregoing groups wherein any one or more hydrogen atom(s) are replaced with tritium atom(s). For example, in some embodiments, each hydrogen bonded to a ring carbon in the foregoing groups may be replaced with a corresponding isotope, e.g., deuterium or tritium. Each hydrogen bonded to an acyclic carbon in the foregoing groups, e.g., methyl or methoxy carbons, may be replaced with a corresponding isotope, e.g., deuterium or tritium. Further, for example, the foregoing groups may be perdeuterated, in which every hydrogen is replaced with deuterium, or pertritiated, in which every hydrogen is replaced with tritium. In some embodiments, one or more ring carbons in the foregoing groups may be replaced with ¹³C. For example, in polycyclic rings among the foregoing groups, one or more ring carbons in the ring directly bonded to the rest of the compound may be replaced with ¹³C. In polycyclic rings among the foregoing groups, one or more ring carbons may be replaced with $^{13}C$ in the ring that substitutes or is fused to the ring bonded to the rest of the compound. Further, for example, every ring carbon in the foregoing groups may be replaced with $^{13}C$.
Also provided is a compound of formula (I) or (II), or a salt thereof, wherein $R^1$ is selected from the group consisting of
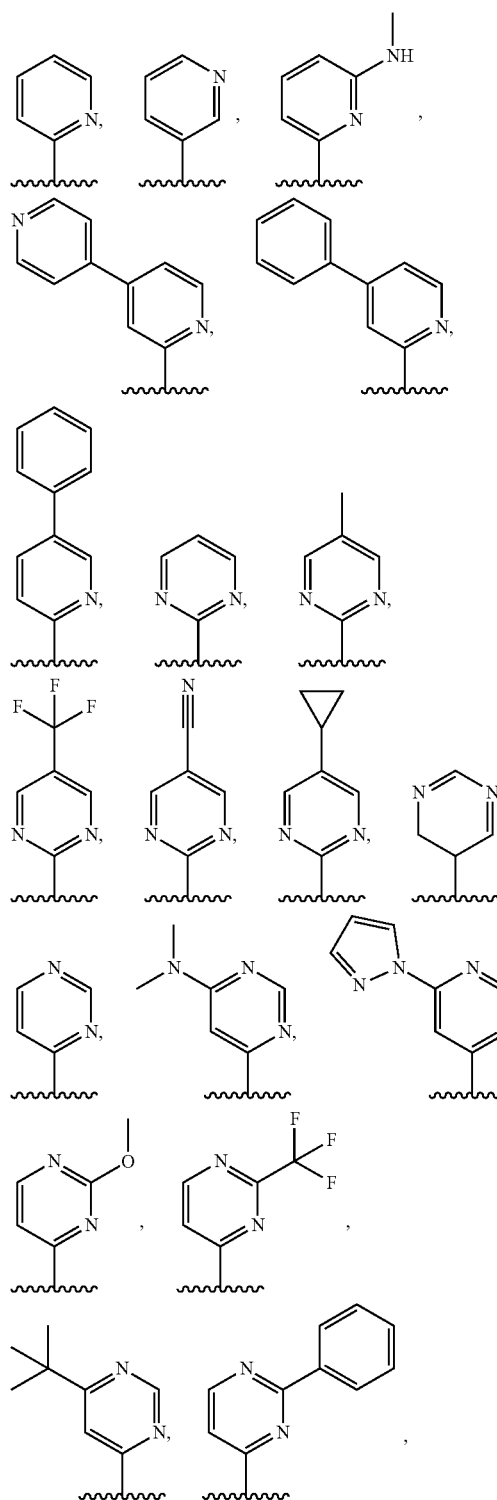
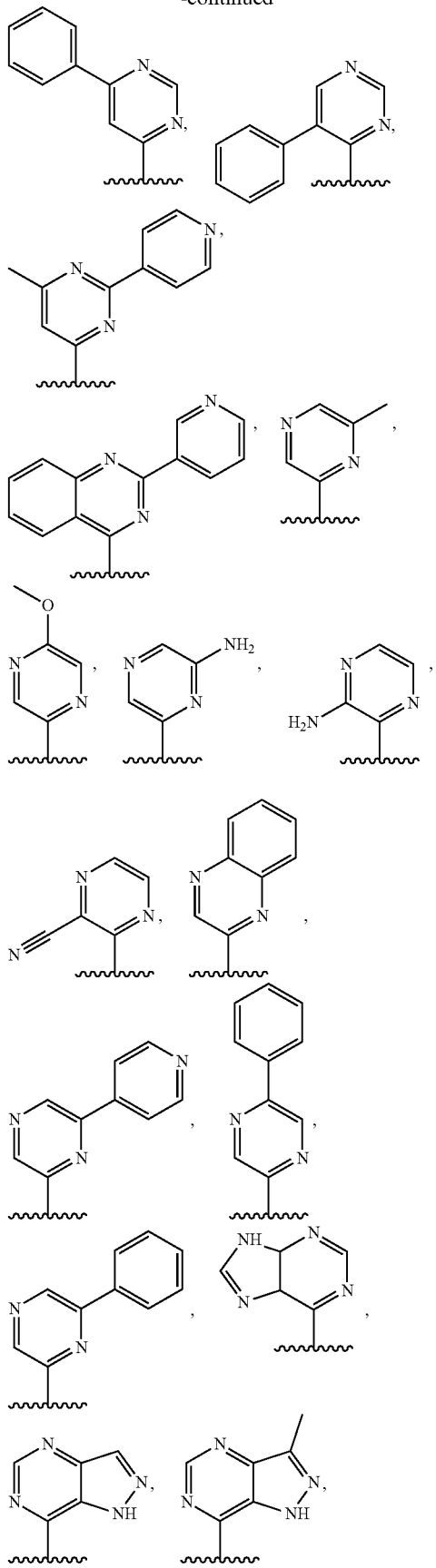

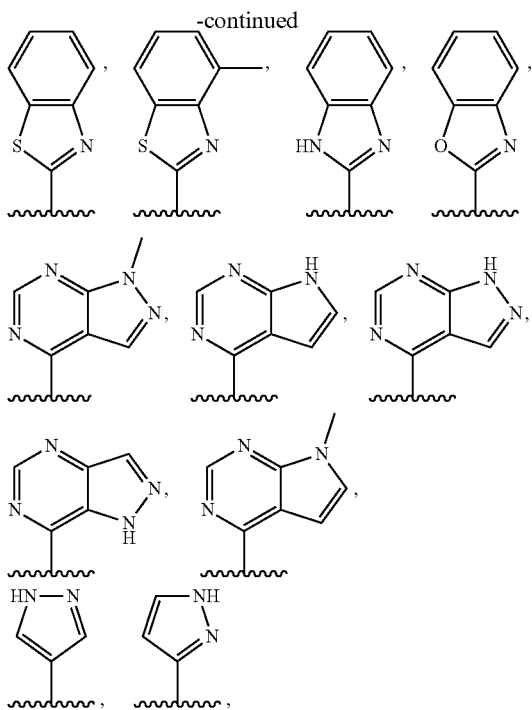

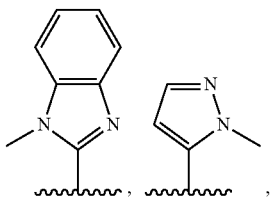

and any of the foregoing groups wherein any one or more hydrogen atom(s) are replaced with deuterium atom(s). Also provided is a compound of formula (I) or (II), or a salt thereof, wherein $R^1$ is selected from any of the foregoing groups wherein any one or more hydrogen atom(s) are replaced with tritium atom(s). For example, in some embodiments, each hydrogen bonded to a ring carbon in the forgoing groups may be replaced with a corresponding isotope, e.g., deuterium or tritium. Each hydrogen bonded to an acyclic carbon in the forgoing groups, e.g., methyl or methoxy carbons, may be replaced with a corresponding isotope, e.g., deuterium or tritium. Further, for example, the forgoing groups may be perdeuterated, in which every hydrogen is replaced with deuterium, or pertritiated, in which every hydrogen is replaced with tritium. In some embodiments, one or more ring carbons in the forgoing groups may be replaced with $^{13}C$. For example, in polycyclic rings among the forgoing groups, one or more ring carbons in the ring directly bonded to the rest of the compound may be replaced with $^{13}C$. In polycyclic rings among the forgoing groups, one or more ring carbons may be replaced with $^{13}C$ in the ring that substitutes or is fused to the ring bonded to the rest of the compound. Further, for example, every ring carbon in the forgoing groups may be replaced with $^{13}C$.

Also provided is a compound of formula (I) or (II), or a salt thereof, wherein $R^1$ is selected from the group consisting of

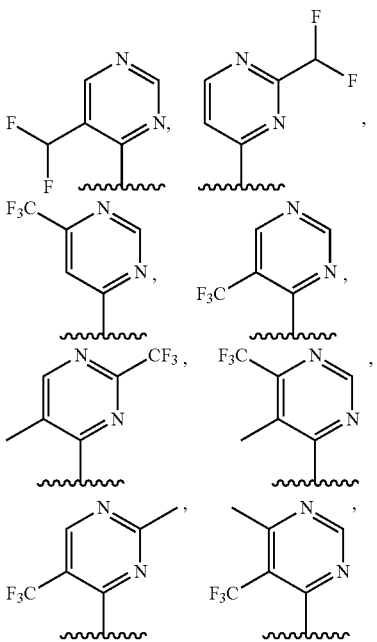

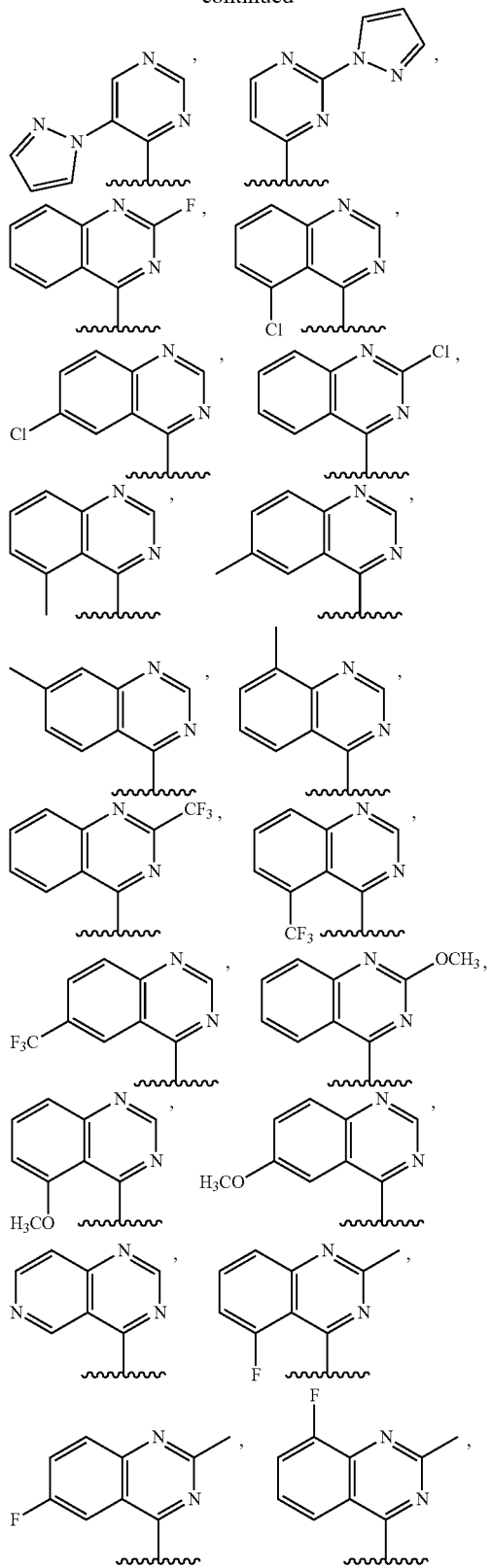

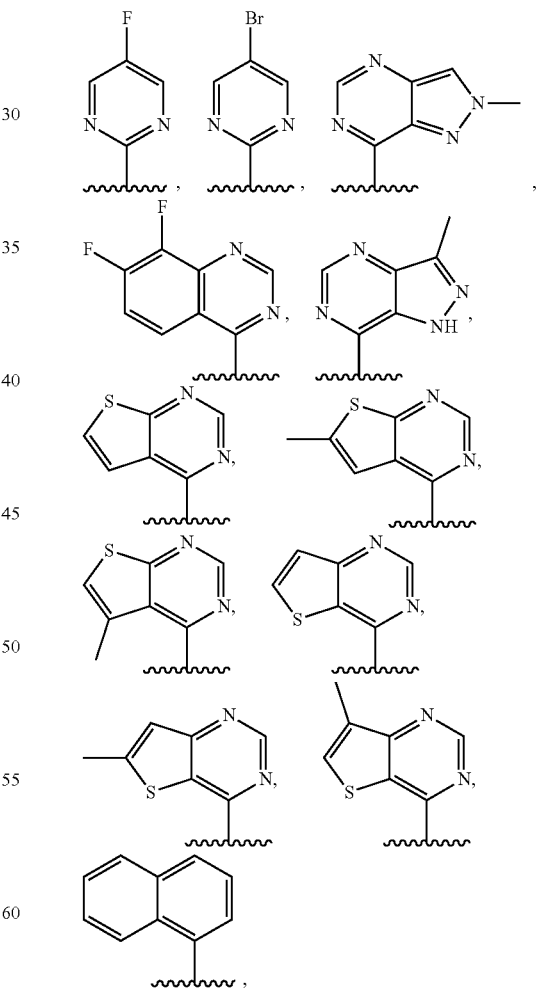

groups wherein any one or more hydrogen atom(s) are replaced with tritium atom(s). For example, in some embodiments, each hydrogen bonded to a ring carbon in the forgoing groups may be replaced with a corresponding isotope, e.g., deuterium or tritium. Each hydrogen bonded to an acyclic carbon in the forgoing groups, e.g., methyl or methoxy carbons, may be replaced with a corresponding isotope, e.g., deuterium or tritium. Further, for example, the forgoing groups may be perdeuterated, in which every hydrogen is replaced with deuterium, or pertritiated, in which every hydrogen is replaced with tritium. In some embodiments, one or more ring carbons in the forgoing groups may be replaced with $^{13}C$. For example, in polycyclic rings among the forgoing groups, one or more ring carbons in the ring directly bonded to the rest of the compound may be replaced with $^{13}C$. In polycyclic rings among the forgoing groups, one or more ring carbons may be replaced with $^{13}C$ in the ring that substitutes or is fused to the ring bonded to the rest of the compound. Further, for example, every ring carbon in the forgoing groups may be replaced with $^{13}C$.

Also provided is a compound of formula (I) or (II), or a salt thereof, wherein $R^1$ is selected from the group consisting of and any of the foregoing groups wherein any one or more hydrogen atom(s) are replaced with deuterium atom(s). Also provided is a compound of formula (I) or (II), or a salt thereof, wherein $R^1$ is selected from any of the foregoing and any of the foregoing groups wherein any one or more hydrogen atom(s) are replaced with deuterium atom(s). Also provided is a compound of formula (I) or (II), or a salt thereof, wherein $R^1$ is selected from any of the foregoing groups wherein any one or more hydrogen atom(s) are replaced with tritium atom(s). For example, in some embodiments, each hydrogen bonded to a ring carbon in the forgoing groups may be replaced with a corresponding isotope, e.g., deuterium or tritium. Each hydrogen bonded to an acyclic carbon in the forgoing groups, e.g., methyl or methoxy carbons, may be replaced with a corresponding isotope, e.g., deuterium or tritium. Further, for example, the forgoing groups may be perdeuterated, in which every hydrogen is replaced with deuterium, or pertritiated, in which every hydrogen is replaced with tritium. In some embodiments, one or more ring carbons in the forgoing groups may be replaced with $^{13}C$. For example, in polycyclic rings among the forgoing groups, one or more ring carbons in the ring directly bonded to the rest of the compound may be replaced with $^{13}C$. In polycyclic rings among the forgoing groups, one or more ring carbons may be replaced with $^{13}C$ in the ring that substitutes or is fused to the ring bonded to the rest of the compound. Further, for example, every ring carbon in the forgoing groups may be replaced with $^{13}C$.

The $R^1$ groups described herein as moieties (shown with a ∿∿∿ symbol) are shown as attached at specific positions (e.g., pyrimid-4-yl, quinazolin-4-yl, isoquinolin-1-yl) but they can also be attached via any other available valence (e.g., pyrimid-2-yl). In some embodiments of the compound of formula (I) or (II), or a salt thereof, $R^1$ is

wherein m is 0, 1, 2, or 3 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I) or (II), or a salt thereof, $R^1$ is

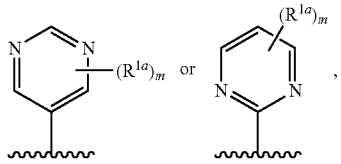

wherein m is 1, 2, or 3 and each $R^{1a}$ is independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In another embodiment, $R^1$ is

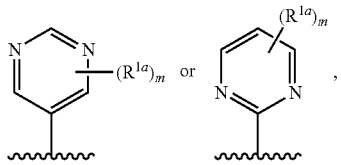

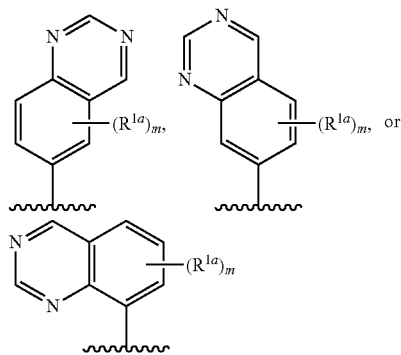

wherein m is 0, 1, 2, 3, 4, or 5 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further embodiment of the compound of formula (I) or (II), or a salt thereof, $R^1$ is

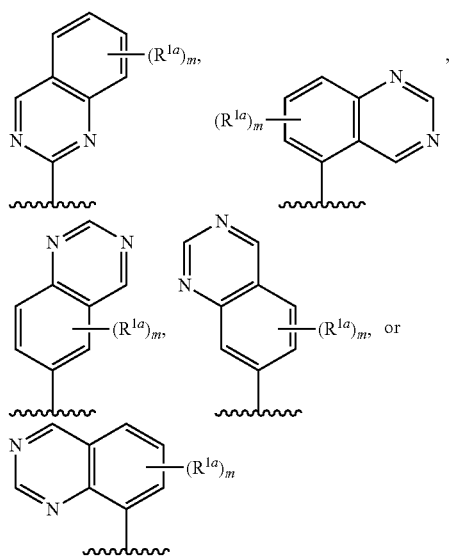

wherein m is 1, 2, 3, 4, or 5 and each $R^{1a}$ is independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium. In a further variation of such embodiments, each $R^{1a}$ is, where applicable, independently deuterium, halogen, $C_1$-$C_6$ alkyl, $C_1$-$C_6$ haloalkyl (which in one variation may be $C_1$-$C_6$ perhaloalky), $C_1$-$C_6$ alkoxy, hydroxy, —CN, or 5- to 10-membered heteroaryl, wherein the $C_1$-$C_6$ alkyl, $C_1$-$C_6$ haloalkyl, $C_1$-$C_6$ alkoxy, hydroxy, and 5- to 10-membered heteroaryl of $R^{1a}$ are independently optionally substituted by deuterium.

In some embodiments of the compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, $R^2$ is $C_1$-$C_6$ alkyl optionally substituted by $R^{2a}$. In some embodiments, $R^2$ is $C_1$-$C_6$ alkyl optionally substituted by $R^{2a}$ where $R^{2a}$ is: halogen (e.g., fluoro); $C_3$—C cycloalkyl optionally substituted by halogen (e.g., cyclobutyl optionally substituted by fluoro); 5- to 10-membered heteroaryl optionally substituted by $C_1$-$C_6$ alkyl (e.g., pyrazolyl optionally substituted by methyl); —S(O)$_2$R$^3$; —NR$^4$R$^5$; —NR$^3$C(O)R$^4$; oxo; or —OR$^3$. In some embodiments, R$^2$ is $C_1$-$C_6$ alkyl optionally substituted by R$^{2a}$ where R$^{2a}$ is: halogen (e.g., fluoro); $C_3$-$C_8$ cycloalkyl optionally substituted by halogen (e.g., cyclobutyl optionally substituted by fluoro); 5- to 10-membered heteroaryl optionally substituted by $C_1$-$C_6$ alkyl (e.g., pyrazolyl optionally substituted by methyl); 3- to 12-membered heterocyclyl optionally substituted by halogen (e.g., oxetanyl optionally substituted by fluoro), —S(O)$_2$R$^3$; —NR$^4$R$^5$; —NR$^3$C(O)R$^4$; oxo; or —OR$^3$. In some embodiments, R$^2$ is $C_1$-$C_6$ alkyl optionally substituted by —OR$^3$ wherein R$^3$ is: hydrogen; $C_1$-$C_6$ alkyl optionally substituted by halogen (e.g., methyl, ethyl, difluoromethyl, —CH$_2$CHF$_2$, and —CH$_2$CF$_3$); $C_3$-$C_6$ cycloalkyl optionally substituted by halogen (e.g., cyclopropyl substituted by fluoro); $C_6$-$C_{14}$ aryl optionally substituted by halogen (e.g., phenyl optionally substituted by fluoro); or 5- to 6-membered heteroaryl optionally substituted by halogen or $C_1$-$C_6$ alkyl (e.g., pyridinyl optionally substituted by fluoro or methyl). In some embodiments, R$^2$ is —CH$_2$CH$_2$OCH$_3$. In some embodiments, R$^2$ is $C_1$-$C_6$ alkyl substituted by both halogen and OR$^3$. In some embodiments, R$^2$ is n-propyl substituted by both halogen and alkoxy (e.g., —CH$_2$CH(F)CH$_2$OCH$_3$). In some embodiments where R$^2$ is indicated as optionally substituted by R$^{2a}$, the R$^2$ moiety is unsubstituted. In some embodiments where R$^2$ is indicated as optionally substituted by R$^{2a}$, the R$^2$ moiety is substituted by one R$^{2a}$. In some embodiments where R$^2$ is indicated as optionally substituted by R$^{2a}$, the R$^2$ moiety is substituted by 2 to 6 or 2 to 5 or 2 to 4 or 2 to 3 R$^{2a}$ moieties, which may be the same or different.

In some embodiments of the compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, R$^2$ is $C_1$-$C_6$ alkyl optionally substituted by R$^{2a}$. In some embodiments, R$^2$ is $C_1$-$C_6$ alkyl optionally substituted by R$^{2a}$ where R$^{2a}$ is: halogen (e.g., fluoro); $C_3$-$C_8$ cycloalkyl optionally substituted by halogen (e.g., cyclobutyl optionally substituted by fluoro); 5- to 10-membered heteroaryl optionally substituted by $C_1$-$C_6$ alkyl (e.g., pyrazolyl optionally substituted by methyl); —S(O)$_2$R$^3$; —NR$^4$R$^5$; —NR$^3$C(O)R$^4$; oxo; or —OR$^3$. In some embodiments, R$^2$ is $C_1$-$C_6$ alkyl optionally substituted by R$^{2a}$ where R$^{2a}$ is: halogen (e.g., fluoro); $C_3$-$C_8$ cycloalkyl optionally substituted by halogen (e.g., cyclobutyl optionally substituted by fluoro); 5- to 10-membered heteroaryl optionally substituted by $C_1$-$C_6$ alkyl (e.g., pyrazolyl optionally substituted by methyl); 3- to 12-membered heterocyclyl optionally substituted by halogen (e.g., oxetanyl optionally substituted by fluoro); —S(O)$_2$R$^3$; —NR$^4$R$^5$; —NR$^3$C(O)R$^4$; oxo; or —OR$^3$. In some embodiments, R$^2$ is $C_1$-$C_6$ alkyl optionally substituted by R$^{2a}$ where R$^{2a}$ is: halogen (e.g., fluoro); $C_3$-$C_8$ cycloalkyl optionally substituted by halogen (e.g., cyclobutyl optionally substituted by fluoro); $C_6$-$C_{14}$ aryl (e.g., phenyl); 5- to 10-membered heteroaryl optionally substituted by $C_1$-$C_6$ alkyl (e.g., thiazolyl or pyrazolyl optionally substituted by methyl); 3- to 12-membered heterocyclyl optionally substituted by halogen or oxo (e.g., R$^{2a}$ is: oxetanyl optionally substituted by fluoro; tetrahydrofuranyl; pyrrolidinyl optionally substituted by oxo; morpholinyl optionally substituted by oxo; or dioxanyl); —S(O)$_2$R$^3$; —NR$^4$R$^5$; —NR$^3$C(O)R$^4$; oxo; —OR$^3$; or —CN. In some embodiments, R$^2$ is $C_1$-$C_6$ alkyl optionally substituted by —OR$^3$ wherein R$^3$ is: hydrogen; $C_1$-$C_6$ alkyl optionally substituted by halogen (e.g., methyl, ethyl, difluoromethyl, —CH$_2$CHF$_2$, and —CH$_2$CF$_3$); $C_3$-$C_6$ cycloalkyl optionally substituted by halogen (e.g., cyclopropyl substituted by fluoro); $C_6$-$C_{14}$ aryl optionally substituted by halogen (e.g., phenyl optionally substituted by fluoro); or 5- to 6-membered heteroaryl optionally substituted by halogen or $C_1$-$C_6$ alkyl (e.g., pyridinyl optionally substituted by fluoro or methyl). In some embodiments, R$^2$ is —CH$_2$CH$_2$OCH$_3$. In some embodiments, R$^2$ is $C_1$-$C_6$ alkyl substituted by both halogen and OR$^3$. In some embodiments, R$^2$ is n-propyl substituted by both halogen and alkoxy (e.g., —CH$_2$CH(F)CH$_2$OCH$_3$). In some embodiments where R$^2$ is indicated as optionally substituted by R$^{2a}$, the R$^2$ moiety is unsubstituted. In some embodiments where R$^2$ is indicated as optionally substituted by R$^{2a}$, the R$^2$ moiety is substituted by one R$^{2a}$. In some embodiments where R$^2$ is indicated as optionally substituted by R$^{2a}$, the R$^2$ moiety is substituted by 2 to 6 or 2 to 5 or 2 to 4 or 2 to 3 R$^{2a}$ moieties, which may be the same or different. In some embodiments, R$^2$ is $C_1$-$C_6$ alkyl substituted by two halogen groups, which may be the same or different (e.g., two fluoro groups). In some embodiments, R$^2$ is $C_1$-$C_6$ alkyl substituted by two —OR$^3$ groups, which may be the same or different (e.g., two —OH groups, one —OH group and one —OCH$_3$ group, or two —OCH$_3$ groups). In some embodiments, R$^2$ is $C_1$-$C_6$ alkyl substituted by one halogen group (e.g., fluoro) and one —OR$^3$ group (e.g., —OH or —OCH$_3$). In some embodiments, R$^2$ is $C_1$-$C_6$ alkyl substituted by two halogen groups, which may be the same or different (e.g., two fluoro groups), and one —OR$^3$ group (e.g., —OH or —OCH$_3$). In some embodiments, R$^2$ is $C_1$-$C_6$ alkyl substituted by one halogen group (e.g., fluoro) and two —OR$^3$ groups, which may be the same or different (e.g., two —OH groups, one —OH group and one —OCH$_3$ group, or two —OCH$_3$ groups).

In some embodiments of the compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, R$^2$ is $C_3$-$C_6$ cycloalkyl optionally substituted by R$^{2b}$. In some embodiments, R$^2$ is $C_3$-$C_6$ cycloalkyl substituted by 1 or 2 R$^{2b}$ moieties which may be the same or different. In some embodiments, R$^2$ is $C_3$-$C_4$ cycloalkyl optionally substituted by halogen (e.g., unsubstituted cyclopropyl or cyclobutyl optionally substituted by fluoro). In some embodiments, R$^2$ is $C_3$-$C_4$ cycloalkyl optionally substituted by deuterium, or tritium atom(s). For example, in some embodiments, each hydrogen bonded to a ring carbon in the forgoing groups may be replaced with a corresponding isotope, e.g., deuterium or tritium. Each hydrogen bonded to an acyclic carbon in the forgoing groups, e.g., methyl or methoxy carbons, may be replaced with a corresponding isotope, e.g., deuterium or tritium. Further, for example, the forgoing groups may be perdeuterated, in which every hydrogen is replaced with deuterium, or pertritiated, in which every hydrogen is replaced with tritium. In some embodiments, one or more ring carbons in the forgoing groups may be replaced with $^{13}$C. For example, in polycyclic rings among the forgoing groups, one or more ring carbons in the ring directly bonded to the rest of the compound may be replaced with $^{13}$C. In polycyclic rings among the forgoing groups, one or more ring carbons may be replaced with $^{13}$C in the ring that substitutes or is fused to the ring bonded to the rest of the compound. Further, for example, every ring carbon in the forgoing groups may be replaced with $^{13}$C.

In some embodiments of the compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, R$^2$ is hydrogen.

In some embodiments of the compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, $R^2$ is —O—$C_1$-$C_6$ alkyl optionally substituted by $R^{2a}$. In some embodiments, $R^2$ is —OCH$_3$.

Also provided is a compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, wherein $R^2$ is selected from the group consisting of

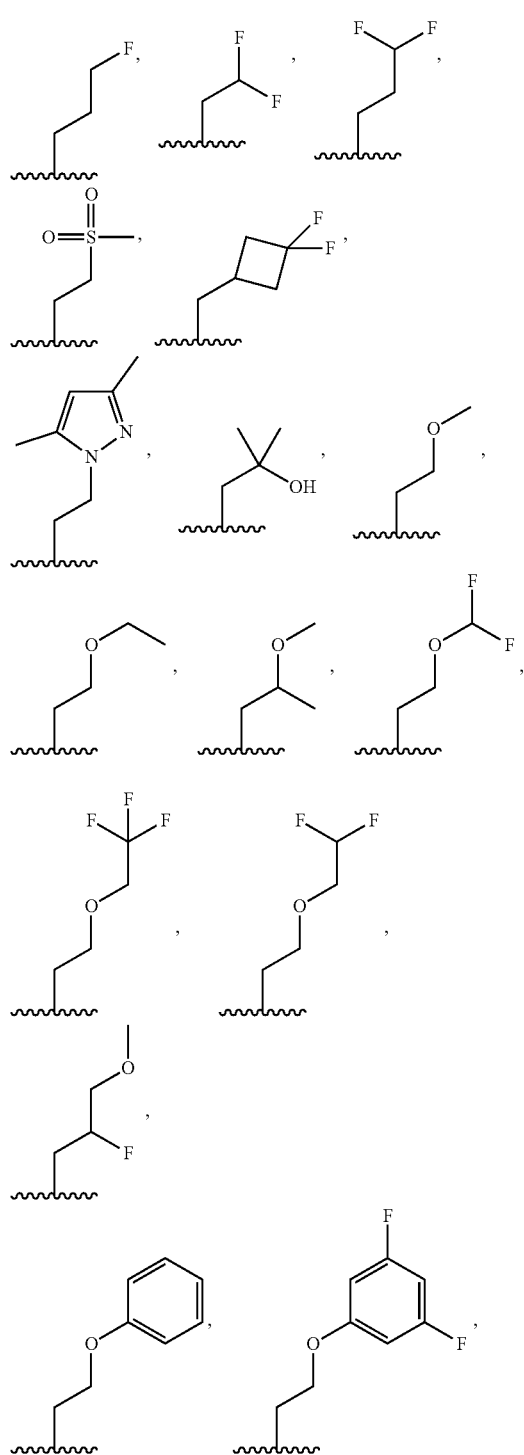

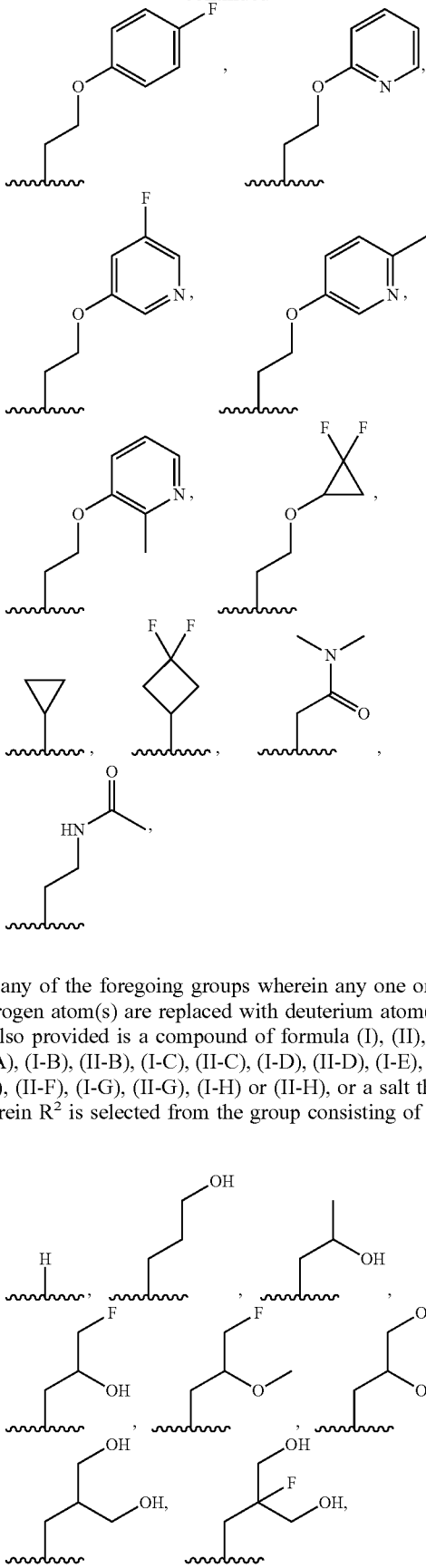

and any of the foregoing groups wherein any one or more hydrogen atom(s) are replaced with deuterium atom(s).

Also provided is a compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, wherein $R^2$ is selected from the group consisting of -continued and any of the foregoing groups wherein any one or more hydrogen atom(s) are replaced with deuterium atom(s).

Also provided is a compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, wherein $R^2$ is wherein $R^3$ and each $R^{2a}$ are as defined for formula (I).

Also provided is a compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, wherein $R^2$ is wherein each $R^{2a}$ are as defined for formula (I).

Also provided is a compound of formula (I), (II), (I-A), (II-A), (I-B), (II-B), (I-C), (II-C), (I-D), (II-D), (I-E), (II-E), (I-F), (II-F), (I-G), (II-G), (I-H) or (II-H), or a salt thereof, wherein $R^2$ is wherein $R^3$ is as defined for formula (I).

In one embodiment of formula (I), the tetrahydronaphthyridine group is disubstituted with deuterium at the 2-position.

In one aspect, provided is a compound of formula (I), or a salt thereof (including a pharmaceutically acceptable salt thereof), wherein the compound or salt thereof has any one or more of the following structural features ("SF"):
(SFI) p is 3;
(SFII) each $R^{10}$, $R^{11}$, $R^{12}$, $R^{13}$ is hydrogen;
(SFIII) $R^1$ is:
(A) unsubstituted 5- to 10-membered heteroaryl;
(B) 5- to 10-membered heteroaryl substituted by 1, 2, 3, 4 or 5 $R^{1a}$ groups which may be the same or different;
wherein the 5- to 10-membered heteroaryl of (III)(A) and (III)(B) is:
(i) pyridinyl;
(ii) pyrimidinyl;
(iii) quinoxalinyl;
(iv) quinazolinyl;
(v) pyrazolopyrimidinyl;
(vi) quinolinyl;
(vii) pyridopyrimidinyl;
(viii) thienopyrimidinyl;
(ix) purinyl;
(x) pyrrolopyrimidinyl;
(xi) benzooxazolyl;
(xii) benzothiazolyl;
(xiii) isoquinolinyl;
(xiv) indolyl;
(xv) benzoimidazolyl;
(xvi) pyrazinyl;
(xvii) indazolyl; or
(xviii) pyrazolyl;
(C) unsubstituted naphthalenyl; or
(D) naphthalenyl substituted by 1, 2, 3, 4 or 5 $R^{1a}$ groups which may be the same or different;
(SFIV) each $R^{1a}$ is:
(A) halogen, such as fluoro, chloro, or bromo;
(B) $C_1$-$C_6$ alkyl optionally substituted by halogen, such as —$CH_3$, —$CHF_2$, —$CF_3$, or $C(CH_3)_3$;
(C) $C_3$-$C_6$ cycloalkyl, such as cyclopropyl;
(D) 5- to 10-membered heteroaryl, such as pyridinyl or pyrazolyl;
(E) $C_6$-$C_{14}$ aryl, such as phenyl;
(F) —CN;
(G) —$OR^3$, such as —$OCH_3$; or
(H) —$NR^4R^5$, such as —$N(CH_3)_2$;
(SFV) $R^2$ is:
(A) unsubstituted $C_1$-$C_6$ alkyl, such as $C_1$-$C_2$ alkyl;
(B) $C_1$-$C_6$ alkyl, such as $C_1$-$C_2$ alkyl, each of which is substituted by 1, 2, 3, 4 or 5 $R^{2a}$ groups which may be the same or different;

(C) unsubstituted —O—$C_1$-$C_6$ alkyl, such as —O—$C_1$-$C_2$ alkyl;
(D) —O—$C_1$-$C_6$ alkyl, such as —O—$C_1$-$C_2$ alkyl, each of which is substituted by 1, 2, 3, 4 or 5 $R^{2a}$ groups which may be the same or different;
(E) unsubstituted $C_3$-$C_6$ cycloalkyl, such as cyclopropyl or cyclobutyl; or
(F) $C_3$-$C_6$ cycloalkyl, such as cyclopropyl or cyclobutyl, each of which is substituted by 1, 2, 3, 4 or 5 $R^{2b}$ groups which may be the same or different; and (SFVI) $R^{2a}$ is:
(A) halogen, such as fluoro;
(B) $C_3$-$C_8$ cycloalkyl, such as cyclopropyl or cyclobutyl, each of which is optionally substituted by halogen;
(C) 5- to 10-membered heteroaryl optionally substituted by $C_1$-$C_6$ alkyl, such as pyrazolyl substituted by methyl;
(D) 3- to 12-membered heterocyclyl optionally substituted by halogen or oxo, such as oxetanyl optionally substituted by fluoro, unsubstituted tetrahydrofuranyl, pyrrolidinyl substituted by oxo, unsubstituted morpholinyl, morpholinyl substituted by oxo, or dioxanyl;
(E) —$S(O)_2R^3$, such as —$S(O)_2CH_3$;
(F) —$C(O)NR^4R^5$, such as —$C(O)N(CH_3)_2$;
(G) —$NR^3C(O)R^4$, such as —$NHC(O)CH_3$; or
(H) —$OR^3$, wherein $R^3$ is:
  (i) hydrogen;
  (ii) —$CH_3$;
  (iii) —$CH_2CH_3$;
  (iv) —$CH_2CHF_2$;
  (v) —$CH_2CF_3$;
  (vi) phenyl substituted by 0-2 fluoro groups; or
  (vii) pyridinyl substituted by 0-1 methyl group.

It is understood that compounds of formula (I) or any variation thereof described herein, or a salt thereof, can in one embodiment have any one or more of the structural features as noted above. For example, compounds of formula (I) or any variation thereof described herein, or a salt thereof, can in one embodiment have the following structural features: one or two or three or all of (SFI), (SFII), (SFIII) and (SFV). In one such example, a compound of formula (I) or any variation thereof described herein, or a salt thereof, can in one embodiment have the following structural features: (SFI) and any one or two or all of (SFII), (SFIII) and (SFV) or any sub-embodiment thereof. In one such example, a compound of formula (I) or any variation thereof described herein, or a salt thereof, can in one embodiment have the following structural features: (SFII) and any one or two or all of (SFI), (SFIII) and (SFV) or any sub-embodiment thereof. In one such example, a compound of formula (I) or any variation thereof described herein, or a salt thereof, can in one embodiment have the following structural features: (SFIII) and any one or two or all of (SFI), (SFII) and (SFV) or any sub-embodiment thereof. In one such example, a compound of formula (I) or any variation thereof described herein, or a salt thereof, can in one embodiment have the following structural features: (SFV) and any one or two or all of (SFI), (SFII) and (SFIII) or any sub-embodiment thereof. It is understood that the sub-embodiments of structural features can likewise be combined in any manner. Although specific combinations of structural features are specifically noted below, it is understood that each and every combination of features is embraced. In one aspect of this variation, (SFI) and (SFII) apply. In another variation, (SFI) and (SFIII) apply. In another variation, (SFI) and (SFV) apply. In another variation, (SFII) and (SFIII) apply. In another variation, (SFII) and (SFV) apply. In another variation, (SFIII) and (SFV) apply. In another variation, (SFI), (SFII), and (SFIII) apply. In another variation, (SFI), (SFII), and (SFV) apply. In another variation, (SFI), (SFIII), and (SFV) apply. In another variation, (SFII), (SFIII), and (SFV) apply. It is understood that each sub-embodiment of the structural features apply. For example, (SFIII) is (SFIII)(A)(i), (SFIII)(A)(ii), (SFIII)(A)(iii), (SFIII)(A)(iv), (SFIII)(A)(v), (SFIII)(A)(vi), (SFIII)(A)(vii), (SFIII)(A)(viii), (SFIII)(A)(ix), (SFIII)(A)(x), (SFIII)(A)(xi), (SFIII)(A)(xii), (SFIII)(A)(xiii), (SFIII)(A)(xiv), (SFIII)(A)(xv), (SFIII)(A)(xvi), (SFIII)(A)(xvii), (SFIII)(A)(xviii), (SFIII)(B)(i), (SFIII)(B)(ii), (SFIII)(B)(iii), (SFIII)(B)(iv), (SFIII)(B)(v), (SFIII)(B)(vi), (SFIII)(B)(vii), (SFIII)(B)(viii), (SFIII)(B)(ix), (SFIII)(B)(x), (SFIII)(B)(xi), (SFIII)(B)(xii), (SFIII)(B)(xiii), (SFIII)(B)(xiv), (SFIII)(B)(xv), (SFIII)(B)(xvi), (SFIII)(B)(xvii), (SFIII)(B)(xviii), (SFIII)(C), or (SFIII)(D). In one aspect of this variation, (SFV) is (SFV)(A), (SFV)(B), (SFV)(C), (SFV)(D), (SFV)(E), or (SFV)(F).

In another variation, (SFI), (SFII), (SFIII)(A)(i), (SFV)(B), and (SFVI)(A) apply. In another variation, (SFI), (SFII), (SFIII)(A)(ii), (SFV)(B), and (SFVI)(A) apply. In another variation, (SFI), (SFII), (SFIII)(A)(iii), (SFV)(B), and (SFVI)(A) apply. In another variation, (SFI), (SFII), (SFIII)(A)(iv), (SFV)(B), and (SFVI)(A) apply. In another variation, (SFI), (SFII), (SFIII)(A)(v), (SFV)(B), and (SFVI)(A) apply. In another variation, (SFI), (SFII), (SFIII)(A)(vi), (SFV)(B), and (SFVI)(A) apply. In another variation, (SFI), (SFII), (SFIII)(A)(vii), (SFV)(B), and (SFVI)(A) apply. In another variation, (SFI), (SFII), (SFIII)(A)(viii), (SFV)(B), and (SFVI)(A) apply. In another variation, (SFI), (SFII), (SFIII)(A)(ix), (SFV)(B), and (SFVI)(A) apply. In another variation, (SFI), (SFII), (SFIII)(A)(x), (SFV)(B), and (SFVI)(A) apply. In another variation, (SFI), (SFII), (SFIII)(A)(xi), (SFV)(B), and (SFVI)(A) apply. In another variation, (SFI), (SFII), (SFIII)(A)(xii), (SFV)(B), and (SFVI)(A) apply. In another variation, (SFI), (SFII), (SFIII)(A)(xiii), (SFV)(B), and (SFVI)(A) apply. In another variation, (SFI), (SFII), (SFIII)(B)(ii), (SFIV)(A), (SFV)(B), and (SFVI)(A) apply. In another variation, (SFI), (SFII), (SFIII)(B)(ii), (SFIV)(B), (SFV)(B), and (SFVI)(A) apply. In another variation, (SFI), (SFII), (SFIII)(B)(ii), (SFIV)(C), (SFV)(B), and (SFVI)(A) apply. In another variation, (SFI), (SFII), (SFIII)(B)(ii), (SFIV)(D), (SFV)(B), and (SFVI)(A) apply. In another variation, (SFI), (SFII), (SFIII)(B)(ii), (SFIV)(E), (SFV)(B), and (SFVI)(A) apply. In another variation, (SFI), (SFII), (SFIII)(B)(ii), (SFIV)(F), (SFV)(B), and (SFVI)(A) apply. In another variation, (SFI), (SFII), (SFIII)(B)(ii), (SFIV)(G), (SFV)(B), and (SFVI)(A) apply. In another variation, (SFI), (SFII), (SFIII)(B)(ii), (SFIV)(H), (SFV)(B), and (SFVI)(A) apply. In another variation, (SFI), (SFII), (SFIII)(B)(iv), (SFIV)(A), (SFV)(B), and (SFVI)(A) apply. In another variation, (SFI), (SFII), (SFIII)(B)(iv), (SFIV)(B), (SFV)(B), and (SFVI)(A) apply. In another variation, (SFI), (SFII), (SFIII)(B)(iv), (SFIV)(C), (SFV)(B), and (SFVI)(A) apply. In another variation, (SFI), (SFII), (SFIII)(B)(iv), (SFIV)(D), (SFV)(B), and (SFVI)(A) apply. In another variation, (SFI), (SFII), (SFIII)(B)(iv), (SFIV)(E), (SFV)(B), and (SFVI)(A) apply. In another variation, (SFI), (SFII), (SFIII)(B)(iv), (SFIV)(F), (SFV)(B), and (SFVI)(A) apply. In another variation, (SFI), (SFII), (SFIII)(B)(iv), (SFIV)(G), (SFV)(B), and (SFVI)(A) apply. In another variation, (SFI), (SFII), (SFIII)(B)(iv), (SFIV)(H), (SFV)(B), and (SFVI)(A) apply. In another variation, (SFI), (SFII), (SFIII)(B)(vii), (SFIV)(A), (SFV)(B), and (SFVI)(A) apply. In another variation, (SFI), (SFII), (SFIII)(B)(vii), (SFIV)(B), (SFV)(B), and (SFVI)(A) apply. In another variation, (SFI), (SFII), (SFIII)(B)(vii), (SFIV)(C), (SFV)(B), and (SFVI)(A) apply. In another variation, (SFI), (SFII), (SFIII)(B)(vii), (SFIV)(D), (SFV)(B), and (SFVI)(A) apply. In another variation, (SFI), (SFII), (SFIII)(B)(vii), (SFIV)(E), (SFV)(B), and (SFVI)(A) apply. In another variation, (SFI), (SFII), (SFIII)(B)(vii), (SFIV)(F), (SFV)(B), and (SFVI)(A) apply. In another variation, (SFI), (SFII), (SFIII)(B)(vii), (SFIV)(G), (SFV)(B), and (SFVI)(A) apply. In another variation, (SFI), (SFII), (SFIII)(B)(vii), (SFIV)(H), (SFV)(B), and (SFVI)(A) apply. In another variation, (SFI), (SFII), (SFIII)(B)(xvi), (SFIV)(A), (SFV)(B), and (SFVI)(A) apply. In another variation, (SFI), (SFII), (SFIII)(B)(xvi), (SFIV)(B), (SFV)(B), and (SFVI)(A) apply. In another variation, (SFI), (SFII), (SFIII)(B)(xvi), (SFIV)(C), (SFV)(B), and (SFVI)(A) apply. In another variation, (SFI), (SFII), (SFIII)(B)(xvi), (SFIV)(D), (SFV)(B), and (SFVI)(A) apply. In another variation, (SFI), (SFII), (SFIII)(B)(xvi), (SFIV)(E), (SFV)(B), and (SFVI)(A) apply. In another variation, (SFI), (SFII), (SFIII)(B)(xvi), (SFIV)(F), (SFV)(B), and (SFVI)(A) apply. In another variation, (SFI), (SFII), (SFIII)(B)(xvi), (SFIV)(G), (SFV)(B), and (SFVI)(A) apply. In another variation, (SFI), (SFII), (SFIII)(B)(xvi), (SFIV)(H), (SFV)(B), and (SFVI)(A) apply. In another variation, (SFI), (SFII), (SFIII)(B)(v), (SFIV)(B), (SFV)(B), and (SFVI)(A) apply. In another variation, (SFI), (SFII), (SFIII)(B)(viii), (SFIV)(B), (SFV)(B), and (SFVI)(A) apply. In another variation, (SFI), (SFII), (SFIII)(B)(x), (SFIV)(B), (SFV)(B), and (SFVI)(A) apply. In another variation, (SFI), (SFII), (SFIII)(B)(xii), (SFIV)(B), (SFV)(B), and (SFVI)(A) apply. In another variation, (SFI), (SFII), (SFIII)(B)(xiv), (SFIV)(B), (SFV)(B), and (SFVI)(A) apply. In another variation, (SFI), (SFII), (SFIII)(B)(xv), (SFIV)(B), (SFV)(B), and (SFVI)(A) apply. In another variation, (SFI), (SFII), (SFIII)(B)(xvii), (SFIV)(B), (SFV)(B), and (SFVI)(A) apply. In another variation, (SFI), (SFII), (SFIII)(B)(xviii), (SFIV)(B), (SFV)(B), and (SFVI)(A) apply.

In another variation, (SFI), (SFII), (SFIII)(A)(i), (SFV)(B), and (SFVI)(H)(ii) apply. In another variation, (SFI), (SFII), (SFIII)(A)(ii), (SFV)(B), and (SFVI)(H)(ii) apply. In another variation, (SFI), (SFII), (SFIII)(A)(iii), (SFV)(B), and (SFVI)(H)(ii) apply. In another variation, (SFI), (SFII), (SFIII)(A)(iv), (SFV)(B), and (SFVI)(H)(ii) apply. In another variation, (SFI), (SFII), (SFIII)(A)(v), (SFV)(B), and (SFVI)(H)(ii) apply. In another variation, (SFI), (SFII), (SFIII)(A)(vi), (SFV)(B), and (SFVI)(H)(ii) apply. In another variation, (SFI), (SFII), (SFIII)(A)(vii), (SFV)(B), and (SFVI)(H)(ii) apply. In another variation, (SFI), (SFII), (SFIII)(A)(viii), (SFV)(B), and (SFVI)(H)(ii) apply. In another variation, (SFI), (SFII), (SFIII)(A)(ix), (SFV)(B), and (SFVI)(H)(ii) apply. In another variation, (SFI), (SFII), (SFIII)(A)(x), (SFV)(B), and (SFVI)(H)(ii) apply. In another variation, (SFI), (SFII), (SFIII)(A)(xi), (SFV)(B), and (SFVI)(H)(ii) apply. In another variation, (SFI), (SFII), (SFIII)(A)(xii), (SFV)(B), and (SFVI)(H)(ii) apply. In another variation, (SFI), (SFII), (SFIII)(A)(xiii), (SFV)(B), and (SFVI)(H)(ii) apply. In another variation, (SFI), (SFII), (SFIII)(B)(ii), (SFIV)(A), (SFV)(B), and (SFVI)(H)(ii) apply. In another variation, (SFI), (SFII), (SFIII)(B)(ii), (SFIV)(B), (SFV)(B), and (SFVI)(H)(ii) apply. In another variation, (SFI), (SFII), (SFIII)(B)(ii), (SFIV)(C), (SFV)(B), and (SFVI)(H)(ii) apply. In another variation, (SFI), (SFII), (SFIII)(B)(ii), (SFIV)(D), (SFV)(B), and (SFVI)(H)(ii) apply. In another variation, (SFI), (SFII), (SFIII)(B)(ii), (SFIV)(E), (SFV)(B), and (SFVI)(H)(ii) apply. In another variation, (SFI), (SFII), (SFIII)(B)(ii), (SFIV)(F), (SFV)(B), and (SFVI)(H)(ii) apply. In another variation, (SFI), (SFII), (SFIII)(B)(ii), (SFIV)(G), (SFV)(B), and (SFVI)(H)(ii) apply. In another variation, (SFI), (SFII), (SFIII)(B)(ii), (SFIV)(H), (SFV)(B), and (SFVI)(H)(ii) apply. In another variation, (SFI), (SFII), (SFIII)(B)(iv), (SFIV)(A), (SFV)(B), and (SFVI)(H)(ii) apply. In another variation, (SFI), (SFIII)(B)(iv), (SFIV)(B), (SFV)(B), and (SFVI)(H)(ii) apply. In another variation, (SFI), (SFII), (SFIII)(B)(iv), (SFIV)(C), (SFV)(B), and (SFVI)(H)(ii) apply. In another variation, (SFI), (SFII), (SFIII)(B)(iv), (SFIV)(D), (SFV)(B), and (SFVI)(H)(ii) apply. In another variation, (SFI), (SFII), (SFIII)(B)(iv), (SFIV)(E), (SFV)(B), and (SFVI)(H)(ii) apply. In another variation, (SFI), (SFII), (SFIII)(B)(iv), (SFIV)(F), (SFV)(B), and (SFVI)(H)(ii) apply. In another variation, (SFI), (SFII), (SFIII)(B)(iv), (SFIV)(G), (SFV)(B), and (SFVI)(H)(ii) apply. In another variation, (SFI), (SFII), (SFIII)(B)(iv), (SFIV)(H), (SFV)(B), and (SFVI)(H)(ii) apply. In another variation, (SFI), (SFII), (SFIII)(B)(vii), (SFIV)(A), (SFV)(B), and (SFVI)(H)(ii) apply. In another variation, (SFI), (SFII), (SFIII)(B)(vii), (SFIV)(B), (SFV)(B), and (SFVI)(H)(ii) apply. In another variation, (SFI), (SFII), (SFIII)(B)(vii), (SFIV)(C), (SFV)(B), and (SFVI)(H)(ii) apply. In another variation, (SFI), (SFII), (SFIII)(B)(vii), (SFIV)(D), (SFV)(B), and (SFVI)(H)(ii) apply. In another variation, (SFI), (SFII), (SFIII)(B)(vii), (SFIV)(E), (SFV)(B), and (SFVI)(H)(ii) apply. In another variation, (SFI), (SFII), (SFIII)(B)(vii), (SFIV)(F), (SFV)(B), and (SFVI)(H)(ii) apply. In another variation, (SFI), (SFII), (SFIII)(B)(vii), (SFIV)(G), (SFV)(B), and (SFVI)(H)(ii) apply. In another variation, (SFI), (SFII), (SFIII)(B)(vii), (SFIV)(H), (SFV)(B), and (SFVI)(H)(ii) apply. In another variation, (SFI), (SFII), (SFIII)(B)(xvi), (SFIV)(A), (SFV)(B), and (SFVI)(H)(ii) apply. In another variation, (SFI), (SFII), (SFIII)(B)(xvi), (SFIV)(B), (SFV)(B), and (SFVI)(H)(ii) apply. In another variation, (SFI), (SFII), (SFIII)(B)(xvi), (SFIV)(C), (SFV)(B), and (SFVI)(H)(ii) apply. In another variation, (SFI), (SFII), (SFIII)(B)(xvi), (SFIV)(D), (SFV)(B), and (SFVI)(H)(ii) apply. In another variation, (SFI), (SFII), (SFIII)(B)(xvi), (SFIV)(E), (SFV)(B), and (SFVI)(H)(ii) apply. In another variation, (SFI), (SFII), (SFIII)(B)(xvi), (SFIV)(F), (SFV)(B), and (SFVI)(H)(ii) apply. In another variation, (SFI), (SFII), (SFIII)(B)(xvi), (SFIV)(G), (SFV)(B), and (SFVI)(H)(ii) apply. In another variation, (SFI), (SFII), (SFIII)(B)(xvi), (SFIV)(H), (SFV)(B), and (SFVI)(H)(ii) apply. In another variation, (SFI), (SFII), (SFIII)(B)(v), (SFIV)(B), (SFV)(B), and (SFVI)(H)(ii) apply. In another variation, (SFI), (SFII), (SFIII)(B)(viii), (SFIV)(B), (SFV)(B), and (SFVI)(H)(ii) apply. In another variation, (SFI), (SFII), (SFIII)(B)(x), (SFIV)(B), (SFV)(B), and (SFVI)(H)(ii) apply. In another variation, (SFI), (SFII), (SFIII)(B)(xii), (SFIV)(B), (SFV)(B), and (SFVI)(H)(ii) apply. In another variation, (SFI), (SFII), (SFIII)(B)(xiv), (SFIV)(B), (SFV)(B), and (SFVI)(H)(ii) apply. In another variation, (SFI), (SFII), (SFIII)(B)(xv), (SFIV)(B), (SFV)(B), and (SFVI)(H)(ii) apply. In another variation, (SFI), (SFII), (SFIII)(B)(xvii), (SFIV)(B), (SFV)(B), and (SFVI)(H)(ii) apply. In another variation, (SFI), (SFII), (SFIII)(B)(xviii), (SFIV)(B), (SFV)(B), and (SFVI)(H)(ii) apply.

In another variation, (SFI), (SFII), (SFIII)(A)(i), (SFV)(B), and (SFVI)(H)(v) apply. In another variation, (SFI), (SFII), (SFIII)(A)(ii), (SFV)(B), and (SFVI)(H)(v) apply. In another variation, (SFI), (SFII), (SFIII)(A)(iii), (SFV)(B), and (SFVI)(H)(v) apply. In another variation, (SFI), (SFII), (SFIII)(A)(iv), (SFV)(B), and (SFVI)(H)(v) apply. In another variation, (SFI), (SFII), (SFIII)(A)(v), (SFV)(B), and (SFVI)(H)(v) apply. In another variation, (SFI), (SFII), (SFIII)(A)(vi), (SFV)(B), and (SFVI)(H)(v) apply. In another variation, (SFI), (SFII), (SFIII)(A)(vii), (SFV)(B), and (SFVI)(H)(v) apply. In another variation, (SFI), (SFII), (SFIII)(A)(viii), (SFV)(B), and (SFVI)(H)(v) apply. In another variation, (SFI), (SFII), (SFIII)(A)(ix), (SFV)(B), and (SFVI)(H)(v) apply. In another variation, (SFI), (SFII), (SFIII)(A)(x), (SFV)(B), and (SFVI)(H)(v) apply. In another variation, (SFI), (SFII), (SFIII)(A)(xi), (SFV)(B), and (SFVI)(H)(v) apply. In another variation, (SFI), (SFII), (SFIII)(A)(xii), (SFV)(B), and (SFVI)(H)(v) apply. In another variation, (SFI), (SFII), (SFIII)(A)(xiii), (SFV)(B), and (SFVI)(H)(v) apply. In another variation, (SFI), (SFII), (SFIII)(B)(ii), (SFIV)(A), (SFV)(B), and (SFVI)(H)(v) apply. In another variation, (SFI), (SFII), (SFIII)(B)(ii), (SFIV)(B), (SFV)(B), and (SFVI)(H)(v) apply. In another variation, (SFI), (SFII), (SFIII)(B)(ii), (SFIV)(C), (SFV)(B), and (SFVI)(H)(v) apply. In another variation, (SFI), (SFII), (SFIII)(B)(ii), (SFIV)(D), (SFV)(B), and (SFVI)(H)(v) apply. In another variation, (SFI), (SFII), (SFIII)(B)(ii), (SFIV)(E), (SFV)(B), and (SFVI)(H)(v) apply. In another variation, (SFI), (SFII), (SFIII)(B)(ii), (SFIV)(F), (SFV)(B), and (SFVI)(H)(v) apply. In another variation, (SFI), (SFII), (SFIII)(B)(ii), (SFIV)(G), (SFV)(B), and (SFVI)(H)(v) apply. In another variation, (SFI), (SFII), (SFIII)(B)(ii), (SFIV)(H), (SFV)(B), and (SFVI)(H)(v) apply. In another variation, (SFI), (SFII), (SFIII)(B)(iv), (SFIV)(A), (SFV)(B), and (SFVI)(H)(v) apply. In another variation, (SFI), (SFII), (SFIII)(B)(iv), (SFIV)(B), (SFV)(B), and (SFVI)(H)(v) apply. In another variation, (SFI), (SFII), (SFIII)(B)(iv), (SFIV)(C), (SFV)(B), and (SFVI)(H)(v) apply. In another variation, (SFI), (SFII), (SFIII)(B)(iv), (SFIV)(D), (SFV)(B), and (SFVI)(H)(v) apply. In another variation, (SFI), (SFII), (SFIII)(B)(iv), (SFIV)(E), (SFV)(B), and (SFVI)(H)(v) apply. In another variation, (SFI), (SFII), (SFIII)(B)(iv), (SFIV)(F), (SFV)(B), and (SFVI)(H)(v) apply. In another variation, (SFI), (SFII), (SFIII)(B)(iv), (SFIV)(G), (SFV)(B), and (SFVI)(H)(v) apply. In another variation, (SFI), (SFII), (SFIII)(B)(iv), (SFIV)(H), (SFV)(B), and (SFVI)(H)(v) apply. In another variation, (SFI), (SFII), (SFIII)(B)(vii), (SFIV)(A), (SFV)(B), and (SFVI)(H)(v) apply. In another variation, (SFI), (SFII), (SFIII)(B)(vii), (SFIV)(B), (SFV)(B), and (SFVI)(H)(v) apply. In another variation, (SFI), (SFII), (SFIII)(B)(vii), (SFIV)(C), (SFV)(B), and (SFVI)(H)(v) apply. In another variation, (SFI), (SFII), (SFIII)(B)(vii), (SFIV)(D), (SFV)(B), and (SFVI)(H)(v) apply. In another variation, (SFI), (SFII), (SFIII)(B)(vii), (SFIV)(E), (SFV)(B), and (SFVI)(H)(v) apply. In another variation, (SFI), (SFII), (SFIII)(B)(vii), (SFIV)(F), (SFV)(B), and (SFVI)(H)(v) apply. In another variation, (SFI), (SFII), (SFIII)(B)(vii), (SFIV)(G), (SFV)(B), and (SFVI)(H)(v) apply. In another variation, (SFI), (SFII), (SFIII)(B)(vii), (SFIV)(H), (SFV)(B), and (SFVI)(H)(v) apply. In another variation, (SFI), (SFII), (SFIII)(B)(xvi), (SFIV)(A), (SFV)(B), and (SFVI)(H)(v) apply. In another variation, (SFI), (SFII), (SFIII)(B)(xvi), (SFIV)(B), (SFV)(B), and (SFVI)(H)(v) apply. In another variation, (SFI), (SFII), (SFIII)(B)(xvi), (SFIV)(C), (SFV)(B), and (SFVI)(H)(v) apply. In another variation, (SFI), (SFII), (SFIII)(B)(xvi), (SFIV)(D), (SFV)(B), and (SFVI)(H)(v) apply. In another variation, (SFI), (SFII), (SFIII)(B)(xvi), (SFIV)(E), (SFV)(B), and (SFVI)(H)(v) apply. In another variation, (SFI), (SFII), (SFIII)(B)(xvi), (SFIV)(F), (SFV)(B), and (SFVI)(H)(v) apply. In another variation, (SFI), (SFII), (SFIII)(B)(xvi), (SFIV)(G), (SFV)(B), and (SFVI)(H)(v) apply. In another variation, (SFI), (SFII), (SFIII)(B)(xvi), (SFIV)(H), (SFV)(B), and (SFVI)(H)(v) apply. In another variation, (SFI), (SFII), (SFIII)(B)(v), (SFIV)(B), (SFV)(B), and (SFVI)(H)(v) apply. In another variation, (SFI), (SFII), (SFIII)(B)(viii), (SFIV)(B), (SFV)(B), and (SFVI)(H)(v) apply. In another variation, (SFI), (SFII), (SFIII)(B)(x), (SFIV)(B), (SFV)(B), and (SFVI)(H)(v) apply. In another variation, (SFI), (SFII), (SFIII)(B)(xii), (SFIV)(B), (SFV)(B), and (SFVI)(H)(v) apply. In another variation, (SFI), (SFII), (SFIII)(B)(xiv), (SFIV)(B), (SFV)(B), and (SFVI)(H)(v) apply. In another variation, (SFI), (SFII), (SFIII)(B)(xv), (SFIV)(B), (SFV)(B), and (SFVI)(H)(v) apply. In another variation, (SFI), (SFII), (SFIII)(B)(xvii), (SFIV)(B), (SFV)(B), and (SFVI)(H)(v) apply. In another variation, (SFI), (SFII), (SFIII)(B)(xviii), (SFIV)(B), (SFV)(B), and (SFVI)(H)(v) apply.

In another variation, (SFI), (SFII), (SFIII)(A)(i), (SFV)(B), and (SFVI)(H)(vi) apply. In another variation, (SFI), (SFII), (SFIII)(A)(ii), (SFV)(B), and (SFVI)(H)(vi) apply. In another variation, (SFI), (SFII), (SFIII)(A)(iii), (SFV)(B), and (SFVI)(H)(vi) apply. In another variation, (SFI), (SFII), (SFIII)(A)(iv), (SFV)(B), and (SFVI)(H)(vi) apply. In another variation, (SFI), (SFII), (SFIII)(A)(v), (SFV)(B), and (SFVI)(H)(vi) apply. In another variation, (SFI), (SFII), (SFIII)(A)(vi), (SFV)(B), and (SFVI)(H)(vi) apply. In another variation, (SFI), (SFII), (SFIII)(A)(vii), (SFV)(B), and (SFVI)(H)(vi) apply. In another variation, (SFI), (SFII), (SFIII)(A)(viii), (SFV)(B), and (SFVI)(H)(vi) apply. In another variation, (SFI), (SFII), (SFIII)(A)(ix), (SFV)(B), and (SFVI)(H)(vi) apply. In another variation, (SFI), (SFII), (SFIII)(A)(x), (SFV)(B), and (SFVI)(H)(vi) apply. In another variation, (SFI), (SFII), (SFIII)(A)(xi), (SFV)(B), and (SFVI)(H)(vi) apply. In another variation, (SFI), (SFII), (SFIII)(A)(xii), (SFV)(B), and (SFVI)(H)(vi) apply. In another variation, (SFI), (SFII), (SFIII)(A)(xiii), (SFV)(B), and (SFVI)(H)(vi) apply. In another variation, (SFI), (SFII), (SFIII)(B)(ii), (SFIV)(A), (SFV)(B), and (SFVI)(H)(vi) apply. In another variation, (SFI), (SFII), (SFIII)(B)(ii), (SFIV)(B), (SFV)(B), and (SFVI)(H)(vi) apply. In another variation, (SFI), (SFII), (SFIII)(B)(ii), (SFIV)(C), (SFV)(B), and (SFVI)(H)(vi) apply. In another variation, (SFI), (SFII), (SFIII)(B)(ii), (SFIV)(D), (SFV)(B), and (SFVI)(H)(vi) apply. In another variation, (SFI), (SFII), (SFIII)(B)(ii), (SFIV)(E), (SFV)(B), and (SFVI)(H)(vi) apply. In another variation, (SFI), (SFII), (SFIII)(B)(ii), (SFIV)(F), (SFV)(B), and (SFVI)(H)(vi) apply. In another variation, (SFI), (SFII), (SFIII)(B)(ii), (SFIV)(G), (SFV)(B), and (SFVI)(H)(vi) apply. In another variation, (SFI), (SFII), (SFIII)(B)(ii), (SFIV)(H), (SFV)(B), and (SFVI)(H)(vi) apply. In another variation, (SFI), (SFII), (SFIII)(B)(iv), (SFIV)(A), (SFV)(B), and (SFVI)(H)(vi) apply. In another variation, (SFI), (SFII), (SFIII)(B)(iv), (SFIV)(B), (SFV)(B), and (SFVI)(H)(vi) apply. In another variation, (SFI), (SFII), (SFIII)(B)(iv), (SFIV)(C), (SFV)(B), and (SFVI)(H)(vi) apply. In another variation, (SFI), (SFII), (SFIII)(B)(iv), (SFIV)(D), (SFV)(B), and (SFVI)(H)(vi) apply. In another variation, (SFI), (SFII), (SFIII)(B)(iv), (SFIV)(E), (SFV)(B), and (SFVI)(H)(vi) apply. In another variation, (SFI), (SFII), (SFIII)(B)(iv), (SFIV)(F), (SFV)(B), and (SFVI)(H)(vi) apply. In another variation, (SFI), (SFII), (SFIII)(B)(iv), (SFIV)(G), (SFV)(B), and (SFVI)(H)(vi) apply. In another variation, (SFI), (SFII), (SFIII)(B)(iv), (SFIV)(H), (SFV)(B), and (SFVI)(H)(vi) apply. In another variation, (SFI), (SFII), (SFIII)(B)(vii), (SFIV)(A), (SFV)(B), and (SFVI)(H)(vi) apply. In another variation, (SFI), (SFII), (SFIII)(B)(vii), (SFIV)(B), (SFV)(B), and (SFVI)(H)(vi) apply. In another variation, (SFI), (SFII), (SFIII)(B)(vii), (SFIV)(C), (SFV)(B), and (SFVI)(H)(vi) apply. In another variation, (SFI), (SFII), (SFIII)(B)(vii), (SFIV)(D), (SFV)(B), and (SFVI)(H)(vi) apply. In another variation, (SFI), (SFII), (SFIII)(B)(vii), (SFIV)(E), (SFV)(B), and (SFVI)(H)(vi) apply. In another variation, (SFI), (SFII), (SFIII)(B)(vii), (SFIV)(F), (SFV)(B), and (SFVI)(H)(vi) apply. In another variation, (SFI), (SFII), (SFIII)(B)(vii), (SFIV)(G), (SFV)(B), and (SFVI)(H)

(vi) apply. In another variation, (SFI), (SFII), (SFIII)(B) (vii), (SFIV)(H), (SFV)(B), and (SFVI)(H)(vi) apply. In another variation, (SFI), (SFII), (SFIII)(B)(xvi), (SFIV)(A), (SFV)(B), and (SFVI)(H)(vi) apply. In another variation, (SFI), (SFII), (SFIII)(B)(xvi), (SFIV)(B), (SFV)(B), and (SFVI)(H)(vi) apply. In another variation, (SFI), (SFII), (SFIII)(B)(xvi), (SFIV)(C), (SFV)(B), and (SFVI)(H)(vi) apply. In another variation, (SFI), (SFII), (SFIII)(B)(xvi), (SFIV)(D), (SFV)(B), and (SFVI)(H)(vi) apply. In another variation, (SFI), (SFII), (SFIII)(B)(xvi), (SFIV)(E), (SFV) (B), and (SFVI)(H)(vi) apply. In another variation, (SFI), (SFII), (SFIII)(B)(xvi), (SFIV)(F), (SFV)(B), and (SFVI) (H)(vi) apply. In another variation, (SFI), (SFII), (SFIII)(B) (xvi), (SFIV)(G), (SFV)(B), and (SFVI)(H)(vi) apply. In another variation, (SFI), (SFII), (SFIII)(B)(xvi), (SFIV)(H), (SFV)(B), and (SFVI)(H)(vi) apply. In another variation, (SFI), (SFII), (SFIII)(B)(v), (SFIV)(B), (SFV)(B), and (SFVI)(H)(vi) apply. In another variation, (SFI), (SFII), (SFIII)(B)(viii), (SFIV)(B), (SFV)(B), and (SFVI)(H)(vi) apply. In another variation, (SFI), (SFII), (SFIII)(B)(x), (SFIV)(B), (SFV)(B), and (SFVI)(H)(vi) apply. In another variation, (SFI), (SFII), (SFIII)(B)(xii), (SFIV)(B), (SFV) (B), and (SFVI)(H)(vi) apply. In another variation, (SFI), (SFII), (SFIII)(B)(xiv), (SFIV)(B), (SFV)(B), and (SFVI) (H)(vi) apply. In another variation, (SFI), (SFII), (SFIII)(B) (xv), (SFIV)(B), (SFV)(B), and (SFVI)(H)(vi) apply. In another variation, (SFI), (SFII), (SFIII)(B)(xvii), (SFIV)(B), (SFV)(B), and (SFVI)(H)(vi) apply. In another variation, (SFI), (SFII), (SFIII)(B)(xviii), (SFIV)(B), (SFV)(B), and (SFVI)(H)(vi) apply.

In another variation, (SFI), (SFII), (SFIII)(A)(i), (SFV) (B), and (SFVI)(H)(vii) apply. In another variation, (SFI), (SFII), (SFIII)(A)(ii), (SFV)(B), and (SFVI)(H)(vii) apply. In another variation, (SFI), (SFII), (SFIII)(A)(iii), (SFV)(B), and (SFVI)(H)(vii) apply. In another variation, (SFI), (SFII), (SFIII)(A)(iv), (SFV)(B), and (SFVI)(H)(vii) apply. In another variation, (SFI), (SFII), (SFIII)(A)(v), (SFV)(B), and (SFVI)(H)(vii) apply. In another variation, (SFI), (SFII), (SFIII)(A)(vi), (SFV)(B), and (SFVI)(H)(vii) apply. In another variation, (SFI), (SFII), (SFIII)(A)(vii), (SFV)(B), and (SFVI)(H)(vii) apply. In another variation, (SFI), (SFII), (SFIII)(A)(viii), (SFV)(B), and (SFVI)(H)(vii) apply. In another variation, (SFI), (SFII), (SFIII)(A)(ix), (SFV)(B), and (SFVI)(H)(vii) apply. In another variation, (SFI), (SFII), (SFIII)(A)(x), (SFV)(B), and (SFVI)(H)(vii) apply. In another variation, (SFI), (SFII), (SFIII)(A)(xi), (SFV)(B), and (SFVI)(H)(vii) apply. In another variation, (SFI), (SFII), (SFIII)(A)(xii), (SFV)(B), and (SFVI)(H)(vii) apply. In another variation, (SFI), (SFII), (SFIII)(A)(xiii), (SFV)(B), and (SFVI)(H)(vii) apply. In another variation, (SFI), (SFII), (SFIII)(B)(ii), (SFIV)(A), (SFV)(B), and (SFVI)(H)(vii) apply. In another variation, (SFI), (SFII), (SFIII)(B)(ii), (SFIV)(B), (SFV)(B), and (SFVI)(H)(vii) apply. In another variation, (SFI), (SFII), (SFIII)(B)(ii), (SFIV)(C), (SFV)(B), and (SFVI)(H)(vii) apply. In another variation, (SFI), (SFII), (SFIII)(B)(ii), (SFIV)(D), (SFV)(B), and (SFVI)(H)(vii) apply. In another variation, (SFI), (SFII), (SFIII)(B)(ii), (SFIV)(E), (SFV)(B), and (SFVI)(H)(vii) apply. In another variation, (SFI), (SFII), (SFIII)(B)(ii), (SFIV)(F), (SFV)(B), and (SFVI)(H)(vii) apply. In another variation, (SFI), (SFII), (SFIII)(B)(ii), (SFIV)(G), (SFV)(B), and (SFVI)(H)(vii) apply. In another variation, (SFI), (SFII), (SFIII)(B)(ii), (SFIV)(H), (SFV)(B), and (SFVI)(H)(vii) apply. In another variation, (SFI), (SFII), (SFIII)(B)(iv), (SFIV)(A), (SFV) (B), and (SFVI)(H)(vii) apply. In another variation, (SFI), (SFII), (SFIII)(B)(iv), (SFIV)(B), (SFV)(B), and (SFVI)(H) (vii) apply. In another variation, (SFI), (SFII), (SFIII)(B) (iv), (SFIV)(C), (SFV)(B), and (SFVI)(H)(vii) apply. In another variation, (SFI), (SFII), (SFIII)(B)(iv), (SFIV)(D), (SFV)(B), and (SFVI)(H)(vii) apply. In another variation, (SFI), (SFII), (SFIII)(B)(iv), (SFIV)(E), (SFV)(B), and (SFVI)(H)(vii) apply. In another variation, (SFI), (SFII), (SFIII)(B)(iv), (SFIV)(F), (SFV)(B), and (SFVI)(H)(vii) apply. In another variation, (SFI), (SFII), (SFIII)(B)(iv), (SFIV)(G), (SFV)(B), and (SFVI)(H)(vii) apply. In another variation, (SFI), (SFII), (SFIII)(B)(iv), (SFIV)(H), (SFV) (B), and (SFVI)(H)(vii) apply. In another variation, (SFI), (SFII), (SFIII)(B)(vii), (SFIV)(A), (SFV)(B), and (SFVI)(H) (vii) apply. In another variation, (SFI), (SFII), (SFIII)(B) (vii), (SFIV)(B), (SFV)(B), and (SFVI)(H)(vii) apply. In another variation, (SFI), (SFII), (SFIII)(B)(vii), (SFIV)(C), (SFV)(B), and (SFVI)(H)(vii) apply. In another variation, (SFI), (SFII), (SFIII)(B)(vii), (SFIV)(D), (SFV)(B), and (SFVI)(H)(vii) apply. In another variation, (SFI), (SFII), (SFIII)(B)(vii), (SFIV)(E), (SFV)(B), and (SFVI)(H)(vii) apply. In another variation, (SFI), (SFII), (SFIII)(B)(vii), (SFIV)(F), (SFV)(B), and (SFVI)(H)(vii) apply. In another variation, (SFI), (SFII), (SFIII)(B)(vii), (SFIV)(G), (SFV) (B), and (SFVI)(H)(vii) apply. In another variation, (SFI), (SFII), (SFIII)(B)(vii), (SFIV)(H), (SFV)(B), and (SFVI)(H) (vii) apply. In another variation, (SFI), (SFII), (SFIII)(B) (xvi), (SFIV)(A), (SFV)(B), and (SFVI)(H)(vii) apply. In another variation, (SFI), (SFII), (SFIII)(B)(xvi), (SFIV)(B), (SFV)(B), and (SFVI)(H)(vii) apply. In another variation, (SFI), (SFII), (SFIII)(B)(xvi), (SFIV)(C), (SFV)(B), and (SFVI)(H)(vii) apply. In another variation, (SFI), (SFII), (SFIII)(B)(xvi), (SFIV)(D), (SFV)(B), and (SFVI)(H)(vii) apply. In another variation, (SFI), (SFII), (SFIII)(B)(xvi), (SFIV)(E), (SFV)(B), and (SFVI)(H)(vii) apply. In another variation, (SFI), (SFII), (SFIII)(B)(xvi), (SFIV)(F), (SFV) (B), and (SFVI)(H)(vii) apply. In another variation, (SFI), (SFII), (SFIII)(B)(xvi), (SFIV)(G), (SFV)(B), and (SFVI) (H)(vii) apply. In another variation, (SFI), (SFII), (SFIII)(B) (xvi), (SFIV)(H), (SFV)(B), and (SFVI)(H)(vii) apply. In another variation, (SFI), (SFII), (SFIII)(B)(v), (SFIV)(B), (SFV)(B), and (SFVI)(H)(vii) apply. In another variation, (SFI), (SFII), (SFIII)(B)(viii), (SFIV)(B), (SFV)(B), and (SFVI)(H)(vii) apply. In another variation, (SFI), (SFII), (SFIII)(B)(x), (SFIV)(B), (SFV)(B), and (SFVI)(H)(vii) apply. In another variation, (SFI), (SFII), (SFIII)(B)(xii), (SFIV)(B), (SFV)(B), and (SFVI)(H)(vii) apply. In another variation, (SFI), (SFII), (SFIII)(B)(xiv), (SFIV)(B), (SFV) (B), and (SFVI)(H)(vii) apply. In another variation, (SFI), (SFII), (SFIII)(B)(xv), (SFIV)(B), (SFV)(B), and (SFVI)(H) (vii) apply. In another variation, (SFI), (SFII), (SFIII)(B) (xvii), (SFIV)(B), (SFV)(B), and (SFVI)(H)(vii) apply. In another variation, (SFI), (SFII), (SFIII)(B)(xviii), (SFIV) (B), (SFV)(B), and (SFVI)(H)(vii) apply.

Any variations or combinations recited herein for compounds of formula (I) also apply to formula (A), with the addition of any possible combinations of $R^{15}$ and $R^{16}$.

Representative compounds are listed in FIG. 1.

In some embodiments, provided is a compound selected from Compound Nos. 1-66 in FIG. 1, or a stereoisomer thereof (including a mixture of two or more stereoisomers thereof), or a salt thereof. In some embodiments, the compound is a salt of a compound selected from Compound Nos. 1-66 in FIG. 1, or a stereoisomer thereof.

In some embodiments, provided is a compound selected from Compound Nos. 1-147, or a stereoisomer thereof (including a mixture of two or more stereoisomers thereof), or a salt thereof. In some embodiments, the compound is a salt of a compound selected from Compound Nos. 1-147, or a stereoisomer thereof.

In some embodiments, provided is a compound selected from Compound Nos. 1-665, or a stereoisomer thereof (including a mixture of two or more stereoisomers thereof), or a salt thereof. In some embodiments, the compound is a salt of a compound selected from Compound Nos. 1-665, or a stereoisomer thereof.

In some embodiments, provided is a compound selected from Compound Nos. 1-780, or a stereoisomer thereof (including a mixture of two or more stereoisomers thereof), or a salt thereof. In some embodiments, the compound is a salt of a compound selected from Compound Nos. 1-780, or a stereoisomer thereof.

In one variation, the compound detailed herein is selected from the group consisting of:

4-(cyclopropyl(4-(5,6,7,8-tetrahydro-1,8-naphthyridin-2-yl)butyl)amino)-2-((6-(difluoromethyl)pyrimidin-4-yl)amino)butanoic acid;

4-(cyclopropyl(4-(5,6,7,8-tetrahydro-1,8-naphthyridin-2-yl)butyl)amino)-2-(pyrimidin-4-ylamino)butanoic acid;

4-(cyclopropyl(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((2-hydroxy-2-methylpropyl)(4-(5,6,7,8-tetrahydro-1,8-naphthyridin-2-yl)butyl)amino)-2-(pyrimidin-4-ylamino)butanoic acid;

4-((2-methoxyethyl)(4-(5,6,7,8-tetrahydro-1,8-naphthyridin-2-yl)butyl)amino)-2-(quinazolin-4-ylamino)butanoic acid;

4-(cyclopropyl(4-(5,6,7,8-tetrahydro-1,8-naphthyridin-2-yl)butyl)amino)-2-(quinazolin-4-ylamino)butanoic acid;

2-((7-fluoroquinazolin-4-yl)amino)-4-((2-methoxyethyl)(4-(5,6,7,8-tetrahydro-1,8-naphthyridin-2-yl)butyl)amino)butanoic acid;

4-((2,2-difluoroethyl)(4-(5,6,7,8-tetrahydro-1,8-naphthyridin-2-yl)butyl)amino)-2-(quinazolin-4-ylamino)butanoic acid;

4-((3,3-difluorocyclobutyl)(4-(5,6,7,8-tetrahydro-1,8-naphthyridin-2-yl)butyl)amino)-2-(quinazolin-4-ylamino)butanoic acid;

4-((2-methoxyethyl)(4-(5,6,7,8-tetrahydro-1,8-naphthyridin-2-yl)butyl)amino)-2-((2-methylquinazolin-4-yl)amino)butanoic acid;

4-((2-methoxyethyl)(4-(5,6,7,8-tetrahydro-1,8-naphthyridin-2-yl)butyl)amino)-2-(pyrido[2,3-d]pyrimidin-4-ylamino)butanoic acid;

2-((7-fluoro-2-methylquinazolin-4-yl)amino)-4-((2-methoxyethyl)(4-(5,6,7,8-tetrahydro-1,8-naphthyridin-2-yl)butyl)amino)butanoic acid;

4-((2-methoxyethyl)(4-(5,6,7,8-tetrahydro-1,8-naphthyridin-2-yl)butyl)amino)-2-((7-(trifluoromethyl)quinazolin-4-yl)amino)butanoic acid;

4-((2-methoxyethyl)(4-(5,6,7,8-tetrahydro-1,8-naphthyridin-2-yl)butyl)amino)-2-((2-(trifluoromethyl)quinazolin-4-yl)amino)butanoic acid;

4-((2-methoxyethyl)(4-(5,6,7,8-tetrahydro-1,8-naphthyridin-2-yl)butyl)amino)-2-((8-(trifluoromethyl)quinazolin-4-yl)amino)butanoic acid;

4-((2-methoxyethyl)(4-(5,6,7,8-tetrahydro-1,8-naphthyridin-2-yl)butyl)amino)-2-(pyrido[3,2-d]pyrimidin-4-ylamino)butanoic acid;

4-((2-methoxyethyl)(4-(5,6,7,8-tetrahydro-1,8-naphthyridin-2-yl)butyl)amino)-2-(pyrido[3,4-d]pyrimidin-4-ylamino)butanoic acid;

2-((5-fluoroquinazolin-4-yl)amino)-4-((2-methoxyethyl)(4-(5,6,7,8-tetrahydro-1,8-naphthyridin-2-yl)butyl)amino)butanoic acid;

2-((6-fluoroquinazolin-4-yl)amino)-4-((2-methoxyethyl)(4-(5,6,7,8-tetrahydro-1,8-naphthyridin-2-yl)butyl)amino)butanoic acid;

2-((8-fluoroquinazolin-4-yl)amino)-4-((2-methoxyethyl)(4-(5,6,7,8-tetrahydro-1,8-naphthyridin-2-yl)butyl)amino)butanoic acid;

2-((6,7-difluoroquinazolin-4-yl)amino)-4-((2-methoxyethyl)(4-(5,6,7,8-tetrahydro-1,8-naphthyridin-2-yl)butyl)amino)butanoic acid;

4-((2-methoxyethyl)(4-(5,6,7,8-tetrahydro-1,8-naphthyridin-2-yl)butyl)amino)-2-((2-methyl-6-(trifluoromethyl)pyrimidin-4-yl)amino)butanoic acid;

2-((6-(difluoromethyl)pyrimidin-4-yl)amino)-4-((2-methoxyethyl)(4-(5,6,7,8-tetrahydro-1,8-naphthyridin-2-yl)butyl)amino)butanoic acid;

4-((2-methoxyethyl)(4-(5,6,7,8-tetrahydro-1,8-naphthyridin-2-yl)butyl)amino)-2-((2-(trifluoromethyl)pyrimidin-4-yl)amino)butanoic acid;

4-((2-methoxypropyl)(4-(5,6,7,8-tetrahydro-1,8-naphthyridin-2-yl)butyl)amino)-2-(quinazolin-4-ylamino)butanoic acid;

4-((2-methoxyethyl)(4-(5,6,7,8-tetrahydro-1,8-naphthyridin-2-yl)butyl)amino)-2-((6-methyl-2-(trifluoromethyl)pyrimidin-4-yl)amino)butanoic acid;

4-((2-(methylsulfonyl)ethyl)(4-(5,6,7,8-tetrahydro-1,8-naphthyridin-2-yl)butyl)amino)-2-(quinazolin-4-ylamino)butanoic acid;

4-((2-phenoxyethyl)(4-(5,6,7,8-tetrahydro-1,8-naphthyridin-2-yl)butyl)amino)-2-(quinazolin-4-ylamino)butanoic acid;

4-((3,3-difluoropropyl)(4-(5,6,7,8-tetrahydro-1,8-naphthyridin-2-yl)butyl)amino)-2-(quinazolin-4-ylamino)butanoic acid;

4-((3-fluoropropyl)(4-(5,6,7,8-tetrahydro-1,8-naphthyridin-2-yl)butyl)amino)-2-(quinazolin-4-ylamino)butanoic acid;

4-((2-fluoro-3-methoxypropyl)(4-(5,6,7,8-tetrahydro-1,8-naphthyridin-2-yl)butyl)amino)-2-(quinazolin-4-ylamino)butanoic acid;

2-((7-fluoro-2-methylquinazolin-4-yl)amino)-4-((2-fluoro-3-methoxypropyl)(4-(5,6,7,8-tetrahydro-1,8-naphthyridin-2-yl)butyl)amino)butanoic acid;

4-(((3,3-difluorocyclobutyl)methyl)(4-(5,6,7,8-tetrahydro-1,8-naphthyridin-2-yl)butyl)amino)-2-((7-fluoro-2-methylquinazolin-4-yl)amino)butanoic acid;

2-(isoquinolin-1-ylamino)-4-((2-methoxyethyl)(4-(5,6,7,8-tetrahydro-1,8-naphthyridin-2-yl)butyl)amino)butanoic acid;

4-((2-(difluoromethoxy)ethyl)(4-(5,6,7,8-tetrahydro-1,8-naphthyridin-2-yl)butyl)amino)-2-(quinazolin-4-ylamino)butanoic acid;

4-((2-methoxyethyl)(4-(5,6,7,8-tetrahydro-1,8-naphthyridin-2-yl)butyl)amino)-2-(quinolin-4-ylamino)butanoic acid;

2-((7-chloroquinazolin-4-yl)amino)-4-((2-methoxyethyl)(4-(5,6,7,8-tetrahydro-1,8-naphthyridin-2-yl)butyl)amino)butanoic acid;

2-((8-chloroquinazolin-4-yl)amino)-4-((2-methoxyethyl)(4-(5,6,7,8-tetrahydro-1,8-naphthyridin-2-yl)butyl)amino)butanoic acid;

2-(quinazolin-4-ylamino)-4-((4-(5,6,7,8-tetrahydro-1,8-naphthyridin-2-yl)butyl)(2-(2,2,2-trifluoroethoxy)ethyl)amino)butanoic acid;

2-((7-fluoro-2-methylquinazolin-4-yl)amino)-4-((2-(4-fluorophenoxy)ethyl)(4-(5,6,7,8-tetrahydro-1,8-naphthyridin-2-yl)butyl)amino)butanoic acid;

4-((3-fluoropropyl)(4-(5,6,7,8-tetrahydro-1,8-naphthyridin-2-yl)butyl)amino)-2-((7-methoxyquinazolin-4-yl)amino)butanoic acid;

4-((2-(2,2-difluorocyclopropoxy)ethyl)(4-(5,6,7,8-tetrahydro-1,8-naphthyridin-2-yl)butyl)amino)-2-((7-fluoro-2-methylquinazolin-4-yl)amino)butanoic acid;

4-((3-fluoropropyl)(4-(5,6,7,8-tetrahydro-1,8-naphthyridin-2-yl)butyl)amino)-2-((8-methoxyquinazolin-4-yl)amino)butanoic acid;

2-((6-(1H-pyrazol-1-yl)pyrimidin-4-yl)amino)-4-((2-methoxyethyl)(4-(5,6,7,8-tetrahydro-1,8-naphthyridin-2-yl)butyl)amino)butanoic acid;

4-((2-(3,5-dimethyl-1H-pyrazol-1-yl)ethyl)(4-(5,6,7,8-tetrahydro-1,8-naphthyridin-2-yl)butyl)amino)-2-(quinazolin-4-ylamino)butanoic acid;

4-(((S)-2-fluoro-3-methoxypropyl)(4-(5,6,7,8-tetrahydro-1,8-naphthyridin-2-yl)butyl)amino)-2-((2-methylquinazolin-4-yl)amino)butanoic acid;

4-((2-(3,5-difluorophenoxy)ethyl)(4-(5,6,7,8-tetrahydro-1,8-naphthyridin-2-yl)butyl)amino)-2-(quinazolin-4-ylamino)butanoic acid;

2-((8-chloroquinazolin-4-yl)amino)-4-((2-(pyridin-2-yloxy)ethyl)(4-(5,6,7,8-tetrahydro-1,8-naphthyridin-2-yl)butyl)amino)butanoic acid;

4-((2-(pyridin-2-yloxy)ethyl)(4-(5,6,7,8-tetrahydro-1,8-naphthyridin-2-yl)butyl)amino)-2-(quinazolin-4-ylamino)butanoic acid;

4-((2-(2,2-difluoroethoxy)ethyl)(4-(5,6,7,8-tetrahydro-1,8-naphthyridin-2-yl)butyl)amino)-2-(quinazolin-4-ylamino)butanoic acid;

2-(pyrido[3,2-d]pyrimidin-4-ylamino)-4-((4-(5,6,7,8-tetrahydro-1,8-naphthyridin-2-yl)butyl)(2-(2,2,2-trifluoroethoxy)ethyl)amino)butanoic acid;

4-((2-((2-methylpyridin-3-yl)oxy)ethyl)(4-(5,6,7,8-tetrahydro-1,8-naphthyridin-2-yl)butyl)amino)-2-(quinazolin-4-ylamino)butanoic acid;

2-((7-fluoro-2-methylquinazolin-4-yl)amino)-4-((2-((2-methylpyridin-3-yl)oxy)ethyl)(4-(5,6,7,8-tetrahydro-1,8-naphthyridin-2-yl)butyl)amino)butanoic acid;

4-((2-((2-methylpyridin-3-yl)oxy)ethyl)(4-(5,6,7,8-tetrahydro-1,8-naphthyridin-2-yl)butyl)amino)-2-(pyrido[3,2-d]pyrimidin-4-ylamino)butanoic acid;

4-((2-ethoxyethyl)(4-(5,6,7,8-tetrahydro-1,8-naphthyridin-2-yl)butyl)amino)-2-(quinazolin-4-ylamino)butanoic acid;

2-((7-fluoro-2-methylquinazolin-4-yl)amino)-4-((2-((6-methylpyridin-3-yl)oxy)ethyl)(4-(5,6,7,8-tetrahydro-1,8-naphthyridin-2-yl)butyl)amino)butanoic acid;

4-((2-((6-methylpyridin-3-yl)oxy)ethyl)(4-(5,6,7,8-tetrahydro-1,8-naphthyridin-2-yl)butyl)amino)-2-(pyrido[3,2-d]pyrimidin-4-ylamino)butanoic acid;

4-((2-((5-fluoropyridin-3-yl)oxy)ethyl)(4-(5,6,7,8-tetrahydro-1,8-naphthyridin-2-yl)butyl)amino)-2-(quinazolin-4-ylamino)butanoic acid;

4-((2-((6-methylpyridin-3-yl)oxy)ethyl)(4-(5,6,7,8-tetrahydro-1,8-naphthyridin-2-yl)butyl)amino)-2-(quinazolin-4-ylamino)butanoic acid;

4-((2-((5-fluoropyridin-3-yl)oxy)ethyl)(4-(5,6,7,8-tetrahydro-1,8-naphthyridin-2-yl)butyl)amino)-2-(pyrido[3,2-d]pyrimidin-4-ylamino)butanoic acid;

2-((7-fluoro-2-methylquinazolin-4-yl)amino)-4-((2-((5-fluoropyridin-3-yl)oxy)ethyl)(4-(5,6,7,8-tetrahydro-1,8-naphthyridin-2-yl)butyl)amino)butanoic acid;

4-(((R)-2-methoxypropyl)(4-(5,6,7,8-tetrahydro-1,8-naphthyridin-2-yl)butyl)amino)-2-(quinazolin-4-ylamino)butanoic acid;

4-((2-acetamidoethyl)(4-(5,6,7,8-tetrahydro-1,8-naphthyridin-2-yl)butyl)amino)-2-(quinazolin-4-ylamino)butanoic acid;

4-((2-(dimethylamino)-2-oxoethyl)(4-(5,6,7,8-tetrahydro-1,8-naphthyridin-2-yl)butyl)amino)-2-(quinazolin-4-ylamino)butanoic acid;

2-((7-fluoro-2-methylquinazolin-4-yl)amino)-4-((2-methoxypropyl)(4-(5,6,7,8-tetrahydro-1,8-naphthyridin-2-yl)butyl)amino)butanoic acid; and 4-((2-methoxypropyl)(4-(5,6,7,8-tetrahydro-1,8-naphthyridin-2-yl)butyl)amino)-2-((2-methylquinazolin-4-yl)amino)butanoic acid.

In another variation, the compound detailed herein is selected from the group consisting of 2-((3-cyanopyrazin-2-yl)amino)-4-((2-methoxyethyl)(4-(5,6,7,8-tetrahydro-1,8-naphthyridin-2-yl)butyl)amino)butanoic acid;

2-((5-cyanopyrimidin-2-yl)amino)-4-((2-methoxypropyl)(4-(5,6,7,8-tetrahydro-1,8-naphthyridin-2-yl)butyl)amino)butanoic acid;

4-((2-methoxypropyl)(4-(5,6,7,8-tetrahydro-1,8-naphthyridin-2-yl)butyl)amino)-2-((5-(trifluoromethyl)pyrimidin-2-yl)amino)butanoic acid;

2-((5-bromopyrimidin-2-yl)amino)-4-((2-methoxypropyl)(4-(5,6,7,8-tetrahydro-1,8-naphthyridin-2-yl)butyl)amino)butanoic acid;

2-((1H-pyrazolo[3,4-d]pyrimidin-4-yl)amino)-4-((2-methoxypropyl)(4-(5,6,7,8-tetrahydro-1,8-naphthyridin-2-yl)butyl)amino)butanoic acid;

4-((2-methoxypropyl)(4-(5,6,7,8-tetrahydro-1,8-naphthyridin-2-yl)butyl)amino)-2-((2-(trifluoromethyl)pyrimidin-4-yl)amino)butanoic acid;

4-((2-methoxypropyl)(4-(5,6,7,8-tetrahydro-1,8-naphthyridin-2-yl)butyl)amino)-2-((2-phenylpyrimidin-4-yl)amino)butanoic acid;

4-((2-methoxypropyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((2-hydroxyethyl)(4-(5,6,7,8-tetrahydro-1,8-naphthyridin-2-yl)butyl)amino)-2-(quinazolin-4-ylamino)butanoic acid;

2-((3-cyanopyrazin-2-yl)amino)-4-((2-methoxypropyl)(4-(5,6,7,8-tetrahydro-1,8-naphthyridin-2-yl)butyl)amino)butanoic acid;

2-((6-(1H-pyrazol-1-yl)pyrimidin-4-yl)amino)-4-((2-methoxypropyl)(4-(5,6,7,8-tetrahydro-1,8-naphthyridin-2-yl)butyl)amino)butanoic acid;

2-((5-fluoropyrimidin-2-yl)amino)-4-((2-methoxypropyl)(4-(5,6,7,8-tetrahydro-1,8-naphthyridin-2-yl)butyl)amino)butanoic acid;

2-((1H-pyrazolo[4,3-d]pyrimidin-7-yl)amino)-4-((2-methoxypropyl)(4-(5,6,7,8-tetrahydro-1,8-naphthyridin-2-yl)butyl)amino)butanoic acid;

4-((2-methoxypropyl)(4-(5,6,7,8-tetrahydro-1,8-naphthyridin-2-yl)butyl)amino)-2-((6-phenylpyrimidin-4-yl)amino)butanoic acid;

4-((2-methoxypropyl)(4-(5,6,7,8-tetrahydro-1,8-naphthyridin-2-yl)butyl)amino)-2-((5-phenylpyrimidin-4-yl)amino)butanoic acid;

2-((1-methyl-1H-pyrazolo[3,4-d]pyrimidin-4-yl)amino)-4-((2-phenoxyethyl)(4-(5,6,7,8-tetrahydro-1,8-naphthyridin-2-yl)butyl)amino)butanoic acid;

2-((5-bromopyrimidin-2-yl)amino)-4-((2-phenoxyethyl)(4-(5,6,7,8-tetrahydro-1,8-naphthyridin-2-yl)butyl)amino)butanoic acid;

2-((5-cyanopyrimidin-2-yl)amino)-4-((2-fluoro-3-methoxypropyl)(4-(5,6,7,8-tetrahydro-1,8-naphthyridin-2-yl)butyl)amino)butanoic acid;

4-((2-fluoro-3-methoxypropyl)(4-(5,6,7,8-tetrahydro-1,8-naphthyridin-2-yl)butyl)amino)-2-((5-(trifluoromethyl)pyrimidin-2-yl)amino)butanoic acid;

2-((5-bromopyrimidin-2-yl)amino)-4-((2-fluoro-3-methoxypropyl)(4-(5,6,7,8-tetrahydro-1,8-naphthyridin-2-yl)butyl)amino)butanoic acid;

4-((2-fluoro-3-methoxypropyl)(4-(5,6,7,8-tetrahydro-1,8-naphthyridin-2-yl)butyl)amino)-2-((2-(trifluoromethyl)pyrimidin-4-yl)amino)butanoic acid;

4-((2,2-difluoroethyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((2-phenoxyethyl)(4-(5,6,7,8-tetrahydro-1,8-naphthyridin-2-yl)butyl)amino)-2-((5-(trifluoromethyl)pyrimidin-2-yl)amino)butanoic acid;

2-((1H-pyrazolo[3,4-d]pyrimidin-4-yl)amino)-4-((2-phenoxyethyl)(4-(5,6,7,8-tetrahydro-1,8-naphthyridin-2-yl)butyl)amino)butanoic acid;

2-((6-(1H-pyrazol-1-yl)pyrimidin-4-yl)amino)-4-((2-phenoxyethyl)(4-(5,6,7,8-tetrahydro-1,8-naphthyridin-2-yl)butyl)amino)butanoic acid;

4-((2-phenoxyethyl)(4-(5,6,7,8-tetrahydro-1,8-naphthyridin-2-yl)butyl)amino)-2-((2-(trifluoromethyl)pyrimidin-4-yl)amino)butanoic acid;

4-((2-phenoxyethyl)(4-(5,6,7,8-tetrahydro-1,8-naphthyridin-2-yl)butyl)amino)-2-((6-phenylpyrimidin-4-yl)amino)butanoic acid;

4-((2-phenoxyethyl)(4-(5,6,7,8-tetrahydro-1,8-naphthyridin-2-yl)butyl)amino)-2-((2-(pyridin-3-yl)quinazolin-4-yl)amino)butanoic acid;

4-((2,2-difluoroethyl)(4-(5,6,7,8-tetrahydro-1,8-naphthyridin-2-yl)butyl)amino)-2-((5-(trifluoromethyl)pyrimidin-2-yl)amino)butanoic acid;

2-((5-bromopyrimidin-2-yl)amino)-4-((2,2-difluoroethyl)(4-(5,6,7,8-tetrahydro-1,8-naphthyridin-2-yl)butyl)amino)butanoic acid;

4-((2,2-difluoroethyl)(4-(5,6,7,8-tetrahydro-1,8-naphthyridin-2-yl)butyl)amino)-2-((2-(trifluoromethyl)pyrimidin-4-yl)amino)butanoic acid;

2-((6-(1H-pyrazol-1-yl)pyrimidin-4-yl)amino)-4-((2,2-difluoroethyl)(4-(5,6,7,8-tetrahydro-1,8-naphthyridin-2-yl)butyl)amino)butanoic acid;

4-((2,2-difluoroethyl)(4-(5,6,7,8-tetrahydro-1,8-naphthyridin-2-yl)butyl)amino)-2-((2-(pyridin-3-yl)quinazolin-4-yl)amino)butanoic acid;

4-((2-methoxypropyl)(4-(5,6,7,8-tetrahydro-1,8-naphthyridin-2-yl)butyl)amino)-2-((2-(pyridin-3-yl)quinazolin-4-yl)amino)butanoic acid;

2-((1-methyl-1H-pyrazolo[3,4-d]pyrimidin-4-yl)amino)-4-((2-(methylsulfonyl)ethyl)(4-(5,6,7,8-tetrahydro-1,8-naphthyridin-2-yl)butyl)amino)butanoic acid;

4-((2-(methylsulfonyl)ethyl)(4-(5,6,7,8-tetrahydro-1,8-naphthyridin-2-yl)butyl)amino)-2-((5-(trifluoromethyl)pyrimidin-2-yl)amino)butanoic acid;

2-((5-bromopyrimidin-2-yl)amino)-4-((2-(methylsulfonyl)ethyl)(4-(5,6,7,8-tetrahydro-1,8-naphthyridin-2-yl)butyl)amino)butanoic acid;

4-((2-(methylsulfonyl)ethyl)(4-(5,6,7,8-tetrahydro-1,8-naphthyridin-2-yl)butyl)amino)-2-((2-(trifluoromethyl)pyrimidin-4-yl)amino)butanoic acid;

4-((2-fluoro-3-methoxypropyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((2-methoxypropyl)(4-(5,6,7,8-tetrahydro-1,8-naphthyridin-2-yl)butyl)amino)-2-(pyrimidin-4-ylamino)butanoic acid;

4-((2-(methylsulfonyl)ethyl)(4-(5,6,7,8-tetrahydro-1,8-naphthyridin-2-yl)butyl)amino)-2-((2-(pyridin-3-yl)quinazolin-4-yl)amino)butanoic acid;

2-((6-(1H-pyrazol-1-yl)pyrimidin-4-yl)amino)-4-((2-fluoro-3-methoxypropyl)(4-(5,6,7,8-tetrahydro-1,8-naphthyridin-2-yl)butyl)amino)butanoic acid;

4-((2-fluoro-3-methoxypropyl)(4-(5,6,7,8-tetrahydro-1,8-naphthyridin-2-yl)butyl)amino)-2-((2-(pyridin-3-yl)quinazolin-4-yl)amino)butanoic acid;

4-((2-fluoro-3-methoxypropyl)(4-(5,6,7,8-tetrahydro-1,8-naphthyridin-2-yl)butyl)amino)-2-((5-phenylpyrimidin-4-yl)amino)butanoic acid;

2-((5-cyanopyrimidin-2-yl)amino)-4-((2-phenoxyethyl)(4-(5,6,7,8-tetrahydro-1,8-naphthyridin-2-yl)butyl)amino)butanoic acid;

2-((1H-pyrazolo[3,4-d]pyrimidin-4-yl)amino)-4-((2,2-difluoroethyl)(4-(5,6,7,8-tetrahydro-1,8-naphthyridin-2-yl)butyl)amino)butanoic acid;

4-cyclopropyl(4-(5,6,7,8-tetrahydro-1,8-naphthyridin-2-yl)butyl)amino)-2-((5-(trifluoromethyl)pyrimidin-2-yl)amino)butanoic acid;

4-cyclopropyl(4-(5,6,7,8-tetrahydro-1,8-naphthyridin-2-yl)butyl)amino)-2-((2-(trifluoromethyl)pyrimidin-4-yl)amino)butanoic acid;

2-((1H-pyrazolo[3,4-d]pyrimidin-4-yl)amino)-4-(cyclopropyl(4-(5,6,7,8-tetrahydro-1,8-naphthyridin-2-yl)butyl)amino)butanoic acid;

2-((5-cyclopropylpyrimidin-2-yl)amino)-4-((2-phenoxyethyl)(4-(5,6,7,8-tetrahydro-1,8-naphthyridin-2-yl)butyl)amino)butanoic acid;

2-((5-cyanopyrimidin-2-yl)amino)-4-((2,2-difluoroethyl)(4-(5,6,7,8-tetrahydro-1,8-naphthyridin-2-yl)butyl)amino)butanoic acid;

4-((2,2-difluoroethyl)(4-(5,6,7,8-tetrahydro-1,8-naphthyridin-2-yl)butyl)amino)-2-((5-phenylpyrimidin-4-yl)amino)butanoic acid;

4-((2,2-difluoroethyl)(4-(5,6,7,8-tetrahydro-1,8-naphthyridin-2-yl)butyl)amino)-2-(pyrimidin-4-ylamino)butanoic acid;

4-((2,2-difluoroethyl)(4-(5,6,7,8-tetrahydro-1,8-naphthyridin-2-yl)butyl)amino)-2-((5-fluoropyrimidin-2-yl)amino)butanoic acid;

4-((2,2-difluoroethyl)(4-(5,6,7,8-tetrahydro-1,8-naphthyridin-2-yl)butyl)amino)-2-((6-methyl-2-(pyridin-4-yl)pyrimidin-4-yl)amino)butanoic acid;

4-((2-(4-fluorophenoxy)ethyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

2-((5-cyclopropylpyrimidin-2-yl)amino)-4-((2-methoxypropyl)(4-(5,6,7,8-tetrahydro-1,8-naphthyridin-2-yl)butyl)amino)butanoic acid;

2-((1H-pyrazolo[3,4-d]pyrimidin-4-yl)amino)-4-((2-(methylsulfonyl)ethyl)(4-(5,6,7,8-tetrahydro-1,8-naphthyridin-2-yl)butyl)amino)butanoic acid;

2-((6-(1H-pyrazol-1-yl)pyrimidin-4-yl)amino)-4-((2-(methylsulfonyl)ethyl)(4-(5,6,7,8-tetrahydro-1,8-naphthyridin-2-yl)butyl)amino)butanoic acid;

4-((2-fluoro-3-methoxypropyl)(4-(5,6,7,8-tetrahydro-1,8-naphthyridin-2-yl)butyl)amino)-2-(pyrimidin-4-ylamino)butanoic acid;

4-((2-fluoro-3-methoxypropyl)(4-(5,6,7,8-tetrahydro-1,8-naphthyridin-2-yl)butyl)amino)-2-((6-phenylpyrimidin-4-yl)amino)butanoic acid;

4-((oxetan-2-ylmethyl)(4-(5,6,7,8-tetrahydro-1,8-naphthyridin-2-yl)butyl)amino)-2-(quinazolin-4-ylamino)butanoic acid;

4-((3-hydroxy-2-(hydroxymethyl)propyl)(4-(5,6,7,8-tetrahydro-1,8-naphthyridin-2-yl)butyl)amino)-2-(quinazolin-4-ylamino)butanoic acid;

2-((5-bromopyrimidin-2-yl)amino)-4-((3,3-difluoropropyl)(4-(5,6,7,8-tetrahydro-1,8-naphthyridin-2-yl)butyl)amino)butanoic acid;

4-((3,3-difluoropropyl)(4-(5,6,7,8-tetrahydro-1,8-naphthyridin-2-yl)butyl)amino)-2-((5-(trifluoromethyl)pyrimidin-2-yl)amino)butanoic acid;

4-((3,3-difluoropropyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((3,3-difluoropropyl)(4-(5,6,7,8-tetrahydro-1,8-naphthyridin-2-yl)butyl)amino)-2-((2-(trifluoromethyl)pyrimidin-4-yl)amino)butanoic acid;

2-((5-cyclopropylpyrimidin-2-yl)amino)-4-((3,3-difluoropropyl)(4-(5,6,7,8-tetrahydro-1,8-naphthyridin-2-yl)butyl)amino)butanoic acid;

4-((3-fluoropropyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((3-fluoropropyl)(4-(5,6,7,8-tetrahydro-1,8-naphthyridin-2-yl)butyl)amino)-2-((5-(trifluoromethyl)pyrimidin-2-yl)amino)butanoic acid;

2-((5-cyanopyrimidin-2-yl)amino)-4-((2-(4-fluorophenoxy)ethyl)(4-(5,6,7,8-tetrahydro-1,8-naphthyridin-2-yl)butyl)amino)butanoic acid;

4-((2-(4-fluorophenoxy)ethyl)(4-(5,6,7,8-tetrahydro-1,8-naphthyridin-2-yl)butyl)amino)-2-((5-(trifluoromethyl)pyrimidin-2-yl)amino)butanoic acid;

4-((2-(dimethylamino)-2-oxoethyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;

4-((2-(dimethylamino)-2-oxoethyl)(4-(5,6,7,8-tetrahydro-1,8-naphthyridin-2-yl)butyl)amino)-2-((5-(trifluoromethyl)pyrimidin-2-yl)amino)butanoic acid;

4-((2,2-difluoroethyl)(4-(5,6,7,8-tetrahydro-1,8-naphthyridin-2-yl)butyl)amino)-2-((6-phenylpyrimidin-4-yl)amino)butanoic acid;

2-((1H-pyrazolo[3,4-d]pyrimidin-4-yl)amino)-4-((2-(4-fluorophenoxy)ethyl)(4-(5,6,7,8-tetrahydro-1,8-naphthyridin-2-yl)butyl)amino)butanoic acid;

2-((5-bromopyrimidin-2-yl)amino)-4-((2-(4-fluorophenoxy)ethyl)(4-(5,6,7,8-tetrahydro-1,8-naphthyridin-2-yl)butyl)amino)butanoic acid;

4-((2-(dimethylamino)-2-oxoethyl)(4-(5,6,7,8-tetrahydro-1,8-naphthyridin-2-yl)butyl)amino)-2-((2-(trifluoromethyl)pyrimidin-4-yl)amino)butanoic acid;

2-((5-cyclopropylpyrimidin-2-yl)amino)-4-((2,2-difluoroethyl)(4-(5,6,7,8-tetrahydro-1,8-naphthyridin-2-yl)butyl)amino)butanoic acid; and 4-(((3-fluorooxetan-3-yl)methyl)(4-(5,6,7,8-tetrahydro-1,8-naphthyridin-2-yl)butyl)amino)-2-(quinazolin-4-ylamino)butanoic acid.

In some embodiments, a composition, such as a pharmaceutical composition, is provided wherein the composition comprises a compound selected from the group consisting of one or more of Compound Nos. 1-66 in FIG. 1, or a stereoisomer thereof (including a mixture of two or more stereoisomers thereof), or a salt thereof. In some embodiments, the composition comprises a compound selected from the group consisting of a salt of one or more of Compound Nos. 1-66. In one aspect, the composition is a pharmaceutical composition that further comprises a pharmaceutically acceptable carrier.

In some embodiments, a composition, such as a pharmaceutical composition, is provided wherein the composition comprises a compound selected from the group consisting of one or more of Compound Nos. 1-147, or a stereoisomer thereof (including a mixture of two or more stereoisomers thereof), or a salt thereof. In some embodiments, the composition comprises a compound selected from the group consisting of a salt of one or more of Compound Nos. 1-147. In one aspect, the composition is a pharmaceutical composition that further comprises a pharmaceutically acceptable carrier.

In some embodiments, a composition, such as a pharmaceutical composition, is provided wherein the composition comprises a compound selected from the group consisting of one or more of Compound Nos. 1-665, or a stereoisomer thereof (including a mixture of two or more stereoisomers thereof), or a salt thereof. In some embodiments, the composition comprises a compound selected from the group consisting of a salt of one or more of Compound Nos. 1-665. In one aspect, the composition is a pharmaceutical composition that further comprises a pharmaceutically acceptable carrier.

In some embodiments, a composition, such as a pharmaceutical composition, is provided wherein the composition comprises a compound selected from the group consisting of one or more of Compound Nos. 1-780, or a stereoisomer thereof (including a mixture of two or more stereoisomers thereof), or a salt thereof. In some embodiments, the composition comprises a compound selected from the group consisting of a salt of one or more of Compound Nos. 1-780. In one aspect, the composition is a pharmaceutical composition that further comprises a pharmaceutically acceptable carrier.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also described and embraced by the invention. All forms of the compounds are also embraced by the invention, such as crystalline or non-crystalline forms of the compounds. It is also understood that prodrugs, solvates and metabolites of the compounds are embraced by this disclosure. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced. Where one or more tertiary amine moiety is present in the compound, the N-oxides are also provided and described.

Compounds described herein are αvβ6 integrin inhibitors. In some instances, it is desirable for the compound to inhibit other integrins in addition to αvβ6 integrin. In some embodiments, the compound inhibits αvβ6 integrin and one or more of αvβ1, αvβ3, αvβ5, α2β1, α3β1, α6β1, α7β1 and α11β1 integrin. In some embodiments, the compound inhibits αvβ6 integrin and αvβ1 integrin. In some embodiments, the compound inhibits αvβ6 integrin, αvβ3 integrin and αvβ5 integrin. In some embodiments, the compound inhibits αvβ6 integrin and α2β1 integrin. In some embodiments, the compound inhibits αvβ6 integrin, α2β1 integrin and α3β1 integrin. In some embodiments, the compound inhibits αvβ6 integrin and α6β1 integrin. In some embodiments, the compound inhibits αvβ6 integrin and α7β1 integrin. In some embodiments, the compound inhibits αvβ6 integrin and α11β1 integrin.

In some instances, it is desirable to avoid inhibition of other integrins. In some embodiments, the compound is a selective αvβ6 integrin inhibitor. In some embodiments, the compound does not inhibit substantially α4β1, αvβ8 and/or α2β3 integrin. In some embodiments, the compound inhibits αvβ6 integrin but does not inhibit substantially α4β1 integrin. In some embodiments, the compound inhibits αvβ6 integrin but does not inhibit substantially αvβ8 integrin. In some embodiments, the compound inhibits αvβ6 integrin but does not inhibit substantially α2β3 integrin. In some embodiments, the compound inhibits αvβ6 integrin but does not inhibit substantially the αvβ8 integrin and the α4β1 integrin.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{32}P$, $^{35}S$, $^{18}F$, $^{36}Cl$. Incorporation of heavier isotopes such as deuterium ($^{2}H$ or D) can afford certain therapeutic advantages resulting from greater metabolic stability, for example, increased in vivo half-life, or reduced dosage requirements and, hence may be preferred in some instances. As used herein, each instance of replacement of a hydrogen by deuterium is also a disclosure of replacing that hydrogen with tritium. As used herein, each instance of enrichment, substitution, or replacement of an atom with corresponding isotope of that atom encompasses isotopic enrichment levels of one of about: 50%, 60%, 70%, 80%, 90%, 95%, 96%, 97%, 98%, 99%, 99.5%, 99.6%, 99.7%, 99.8%, 99.9%, or 100%, or a range between any two of the preceding percentages.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

In various embodiments, for each of the compounds named or depicted herein, specifically disclosed are corresponding isotopically substituted compounds according to the following description. For example, disclosed are corresponding isotopically substituted compounds in which the groups corresponding to structural variables $R^1$ and $R^{1a}$ may be independently deuterated, e.g., structural variables $R^1$ and $R^{1a}$ may be perdeuterated such that every hydrogen therein may be independently replaced with deuterium. Further disclosed are corresponding isotopically substituted compounds in which one or more hydrogens in the group corresponding to structural variable RI, but not in optional substituent $R^{1a}$, may be independently replaced with deuterium. For example, disclosed are corresponding isotopically substituted compounds in which every hydrogen bonded to a ring in the group corresponding to $R^1$, but not in optional substituent $R^{1a}$, may be replaced with deuterium. Also disclosed are corresponding isotopically substituted compounds in which one or more hydrogens in $R^{1a}$ may be independently replaced with deuterium, e.g., every hydrogen in the group corresponding to $R^{1a}$ may be replaced with deuterium.

Further disclosed, for example, are corresponding isotopically substituted compounds in which the groups corresponding to structural variables $R^2$ and $R^{2a}$ may be independently deuterated, e.g., structural variables $R^2$ and $R^{2a}$ may be perdeuterated such that every hydrogen therein may be independently replaced with deuterium. Also disclosed are corresponding isotopically substituted compounds in which one or more hydrogens in the group corresponding to $R^2$, but not in optional substituent $R^{2a}$, may be independently replaced with deuterium. Additionally disclosed are corresponding isotopically substituted compounds in which each hydrogen at the 1-position of $R^2$, the carbon bonding $R^2$ to the rest of the compound, may be independently replaced with deuterium. For example, for named compounds having —$CH_2CH_2CH_2F$ corresponding to $R^2$, also disclosed are corresponding isotopically substituted compounds in which $R^2$ is —$CD_2CH_2CH_2F$; for named compounds having —$CH_2$-cyclopropyl corresponding to $R^2$, also disclosed are corresponding isotopically substituted compounds in which $R^2$ is —$CD_2$-cyclopropyl; and the like. Disclosed are corresponding isotopically substituted compounds in which each hydrogen in the group corresponding to $R^{2a}$ may be independently replaced with deuterium. For example, for each compound in which $R^{2a}$ is —$OCH_3$, also disclosed are corresponding isotopically substituted compounds in which $R^{2a}$ may be —$OCD_3$; for each compound in which $R^{2a}$ is —$N(CH_3)_2$, also disclosed are corresponding isotopically substituted compounds in which $R^{2a}$ may be —$N(CD_3)_2$; and the like. Further disclosed are compounds in which the 1-position of $R^2$ may be di-deuterated and each hydrogen in the group corresponding to $R^{2a}$ may be replaced with deuterium.

Also disclosed are corresponding isotopically substituted compounds in which $R^{10}$, $R^{11}$, $R^{12}$, $R^{13}$, and each $R^{14}$ are independently deuterated. For example, disclosed are corresponding isotopically substituted compounds in which $R^{10}$, $R^{11}$ are deuterium, or $R^{12}$, $R^{13}$ are deuterium, or $R^{10}$, $R^{11}$, $R^{12}$, and $R^{13}$ are all deuterium. Further disclosed are compounds in which $R^{14}$ is deuterium and $R^{14}$ substitutes the tetrahydronaphthyridine-2-yl group at the 3-position, the 4-position, or the 3- and 4-positions. Also disclosed are compounds in which $R^{14}$ is deuterium and each $R^{14}$ independently replaces each hydrogen in the tetrahydronaphthyridine-2-yl group at the 5-position, the 6-position, the 7-position, the 5- and 6-positions, the 5- and 7-positions, the 6- and 7-positions, or the 5-, 6-, and 7-positions, e.g., the 7-position may be substituted with two deuterium atoms.

In some embodiments, disclosed are corresponding isotopically substituted compounds in which: every ring hydrogen in $R^1$ may be replaced with deuterium; the 1-position of $R^2$ may be di-deuterated; and $R^{2a}$ may be perdeuterated. Disclosed are corresponding isotopically substituted compounds in which every ring hydrogen in $R^1$ may be replaced with deuterium. Disclosed are corresponding isotopically substituted compounds in which: every ring hydrogen in $R^1$ may be replaced with deuterium; the 1-position of $R^2$ may be di-deuterated; $R^{2a}$ may be perdeuterated; $R^{12}$ and $R^{13}$ may be deuterium; and the 7-position of the tetrahydronaphthyridine-2-yl group may be di-deuterated. Disclosed are corresponding isotopically substituted compounds in which: every ring hydrogen in $R^1$ may be replaced with deuterium; and each hydrogen in $R^{2a}$ may be independently replaced with deuterium. Disclosed are corresponding isotopically substituted compounds in which: every ring hydrogen in $R^1$ may be replaced with deuterium; the 1-position of $R^2$ may be di-deuterated; $R^{2a}$ may be perdeuterated; and $R^{12}$ and $R^{13}$ may be deuterium. Disclosed are corresponding isotopically substituted compounds in which: $R^1$ and $R^{1a}$ may be perdeuterated; the 1-position of $R^2$ may be di-deuterated; $R^{2a}$ may be perdeuterated; $R^{12}$ and $R^{13}$ may be deuterium; and the 7-position of the tetrahydronaphthyridine-2-yl group may be di-deuterated. Disclosed are corresponding isotopically substituted compounds in which: every ring hydrogen in $R^1$ may be replaced with deuterium; the 1-position of $R^2$ may be di-deuterated; $R^{2a}$ may be perdeuterated; and $R^{12}$ and $R^{13}$ may be deuterium.

In some embodiments of the named compounds, each hydrogen represented in $R^1, R^{1a}, R^2, R^{2a}, R^{10}, R^{11}, R^{12}, R^{13}$, and $R^{14}$ may independently be tritium. For example, disclosed are corresponding isotopically substituted compounds in which one or more hydrogens in $R^1$, $R^{1a}$, or $R^1$ and $R^{1a}$ may be independently be replaced by tritium. Disclosed are corresponding isotopically substituted compounds in which one or more ring hydrogens in $R^1$, $R^{1a}$, or $R^1$ and $R^{1a}$ may be independently be replaced by tritium. Disclosed are corresponding isotopically substituted compounds in which one or more hydrogens in $R^2$, $R^{2a}$, or $R^2$ and $R^{2a}$ may be independently be replaced by tritium. Disclosed are corresponding isotopically substituted compounds in which one or more hydrogens in $R^2$, $R^{2a}$, or $R^2$ and $R^{2a}$ may be independently be replaced by tritium. Disclosed are corresponding isotopically substituted compounds in which one of the 3- or 4-positions of the tetrahydronaphthyridine-2-yl group may be tritiated, e.g., the 3-position. Disclosed are corresponding isotopically substituted compounds in which one of the 5-, 6-, or 7-positions of the tetrahydronaphthyridine-2-yl group may be mono- or di-tritiated, e.g., the 7-position may be di-tritiated.

In some embodiments of the named compounds, disclosed are corresponding isotopically substituted compounds in which one or more carbons may be replaced with $^{13}C$. For example, disclosed are corresponding isotopically substituted compounds in which one or more carbons may be replaced with $^{13}C$, such as carbons in $R^1$, $R^{1a}$, $R^2$, $R^{2a}$, the tetrahydronaphthyridine-2-yl ring depicted in the structural formulas herein, and the like. For example, in rings represented by $R^1$, $R^{1a}$, $R^{2a}$, and/or the tetrahydronaphthyridine-2-yl group, one or more ring carbons may be replaced with $^{13}C$. For example, polycyclic rings represented by $R^1$, $R^{1a}$, $R^{2a}$, and/or the tetrahydronaphthyridine-2-yl group, one or more ring carbons in the ring directly bonded to the rest of the compound may be replaced with $^{13}C$; e.g., in the tetrahydronaphthyridine-2-yl group, the ring directly bonded to the rest of the compound is a heteroaromatic ring bonded at the 2-position. In polycyclic rings in the groups corresponding to $R^1$, $R^{1a}$, $R^2$, $R^{2a}$, and/or the tetrahydronaphthyridine-2-yl group, one or more ring carbons may be replaced with $^{13}C$ in a ring that substitutes or is fused to the ring bonded to the rest of the compound. For example, in the tetrahydronaphthyridine-2-yl ring, the nonaromatic heterocyclyl ring is fused to the ring bonded to the rest of the compound. Further, for example, every ring carbon, or every carbon in the group corresponding to $R^1$, $R^{1a}$, $R^2$, $R^{2a}$, and/or the tetrahydronaphthyridine-2-yl ring may be replaced with $^{13}C$.

The invention also includes any or all metabolites of any of the compounds described. The metabolites may include any chemical species generated by a biotransformation of any of the compounds described, such as intermediates and products of metabolism of the compound.

Articles of manufacture comprising a compound of the invention, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms.

General Synthetic Methods

The compounds of the invention may be prepared by a number of processes as generally described below and more specifically in the Examples hereinafter (such as the schemes provides in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds provided herein may be prepared according to General Schemes A, B, C, and D, General Procedures A, B, C, D, E, F, G, H, and P, and the examples herein.

Compounds provided herein may be prepared according to General Schemes A, B, C, and D, General Procedures A, B, C, D, E, F, G, H, P, Q, R, S, T, and U, and the examples herein.

Compounds of formula 11A can be prepared according to General Scheme A, wherein $R^1$ and $R^2$ are as defined for formula (I), or any applicable variations detailed herein.

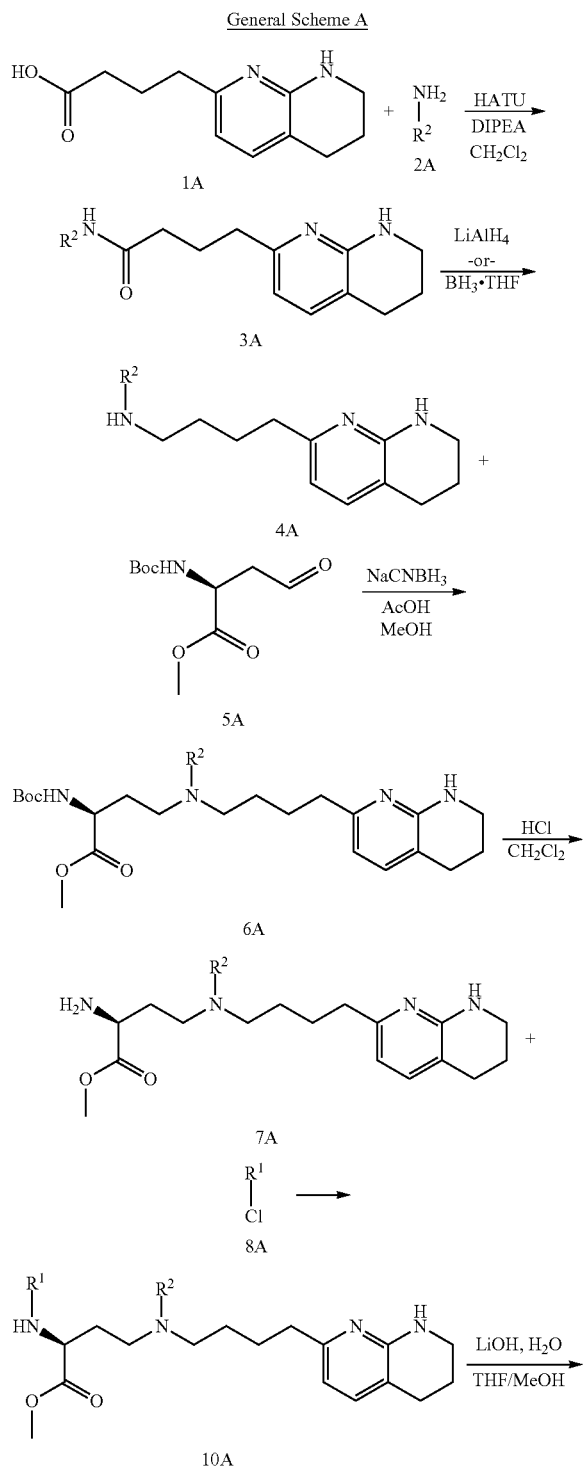

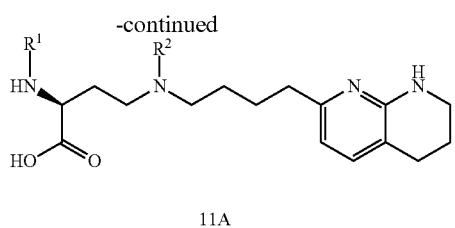

11A

Coupling of 1A with a compound of formula 2A in the presence of a suitable coupling agent yields a compound of formula 3A, which is reduced to yield a compound of formula 4A. Reductive amination of a compound of formula 4A with compound 5A gives a compound of formula 6A. Removal of the N-Boc protecting group with a compound of formula 6A by exposure to an appropriate acid gives a compound of formula 7A, which can be coupled with a compound of formula 8A to give a compound of formula 10A. Hydrolysis of a compound of formula 10A in the presence of a suitable hydroxide source gives compounds of formula 11A.

Reaction conditions for the transformations of General Scheme A are provided in the General Procedures that follow, in particular General Procedures A, D, E, F, G, H, and P.

General Scheme A can be modified to prepare variants of compounds of formula 11A by beginning with variants of 1A with 5 and 6 carbon linkers between the nitrogen bearing the $R^2$ group and the tetrahydronaphthyridine group. These variants of compounds of formula 11A can be synthesized by using the route described in General Scheme A substituting 1A with either 5,6,7,8-tetrahydro-1,8-naphthyridine-2-pentanoic acid or 5,6,7,8-tetrahydro-1,8-naphthyridine-2-hexanoic acid. 6-oxoheptanoic acid and 7-oxooctanoic acid can be converted to 5,6,7,8-tetrahydro-1,8-naphthyridine-2-pentanoic acid and 5,6,7,8-tetrahydro-1,8-naphthyridine-2-hexanoic acid, respectively, by condensation with 2-aminonicotinaldehyde in the presence of an appropriate catalyst followed by hydrogenation of the resulting naphthyridine ring to the 5,6,7,8-tetrahydronaphthyridine ring using procedures known in the chemical literature.

Compounds of formula 11A can alternatively be prepared according to General Scheme B, wherein $R^1$ and $R^2$ are as defined for formula (I), or any applicable variations detailed herein.

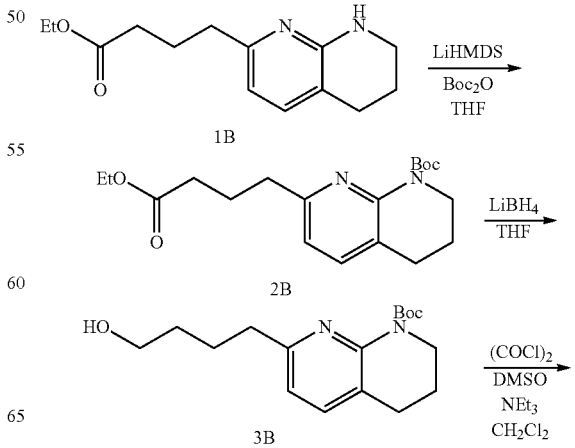

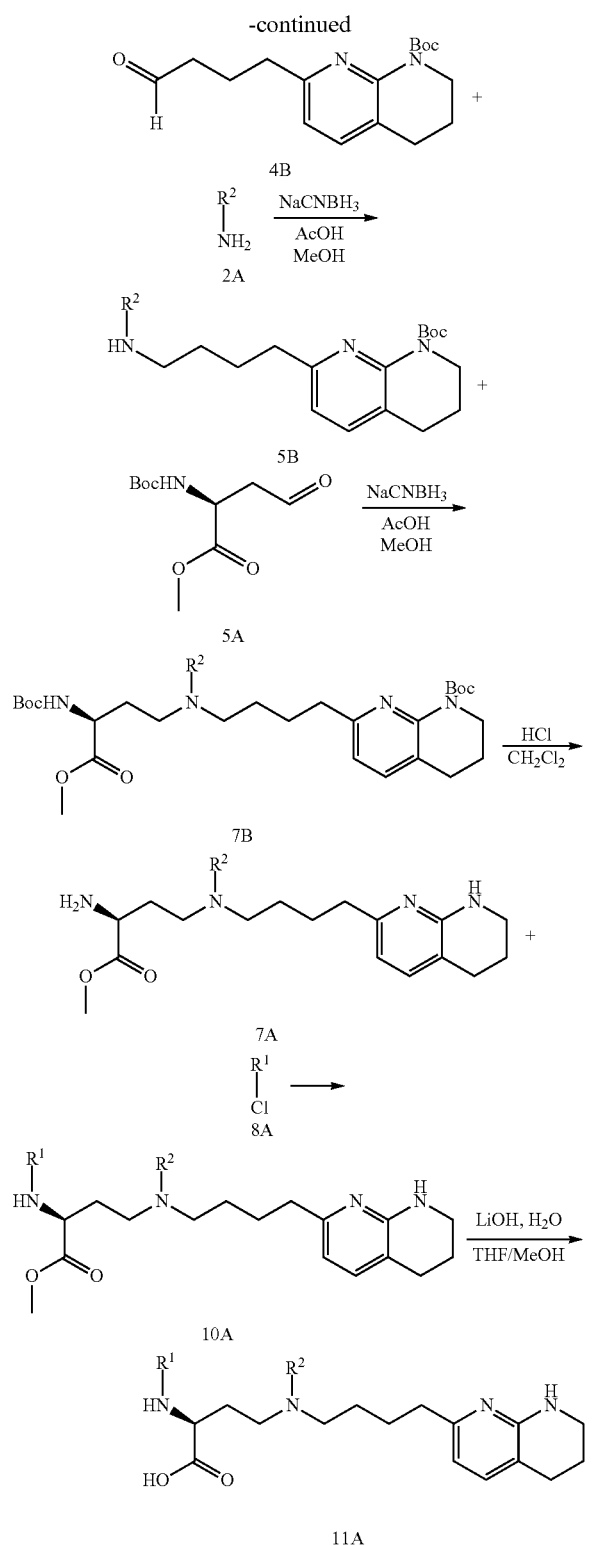

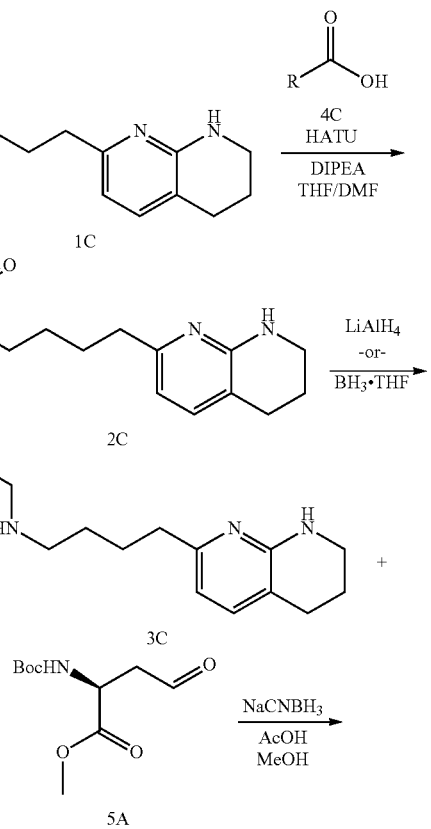

amination of a compound of formula 5B with compound 5A gives a compound of formula 7B. Removal of the N-Boc protecting group with a compound of formula 7B by exposure to an appropriate acid gives a compound of formula 7A, which can be coupled with a compound of formula 8A to give a compound of formula 10A. Hydrolysis of a compound of formula 10A in the presence of a suitable hydroxide source gives compounds of formula 11A.

Reaction conditions for the transformations of General Scheme B are provided in the General Procedures that follow, in particular General Procedures B, D, F, G, H, and P.

General Scheme B can be modified to prepare variants of compounds of formula 11A by beginning with variants of 1B with 5 and 6 carbon linkers between the nitrogen bearing the $R^2$ group and the tetrahydronaphthyridine group. These variants of compounds of formula 11A can be synthesized by using the route described in General Scheme B substituting 1B with either ethyl 5-(5,6,7,8-tetrahydro-1,8-naphthyridin-2-yl)pentanoate or ethyl 6-(5,6,7,8-tetrahydro-1,8-naphthyridin-2-yl)hexanoate. Ethyl 6-oxoheptanoate and ethyl 7-oxooctanoate can be converted to ethyl 5-(5,6,7,8-tetrahydro-1,8-naphthyridin-2-yl)pentanoate and ethyl 6-(5,6,7,8-tetrahydro-1,8-naphthyridin-2-yl)hexanoate, respectively, by condensation with 2-aminonicotinaldehyde in the presence of an appropriate catalyst followed by hydrogenation of the resulting naphthyridine ring to the 5,6,7,8-tetrahydronaphthyridine ring using procedures known in the chemical literature.

Compounds of formula 10C can be prepared according to General Scheme C, wherein R is $C_1$-$C_5$ alkyl optionally substituted by $R^{2a}$, and $R^1$ and $R^{2a}$ are as defined for formula (I), or any applicable variations detailed herein.

General Scheme C

Installation of a N-Boc group of 1B in the presence of a suitable base and di-tert-butyl decarbonate yields a compound of formula 2B, which is reduced to yield a compound of formula 3B. Oxidation of a compound of formula 3B with a suitable oxidizing agent gives a compound of formula 4B. Reductive amination of a compound of formula 4B with compound 2A gives a compound of formula 5B. Reductive

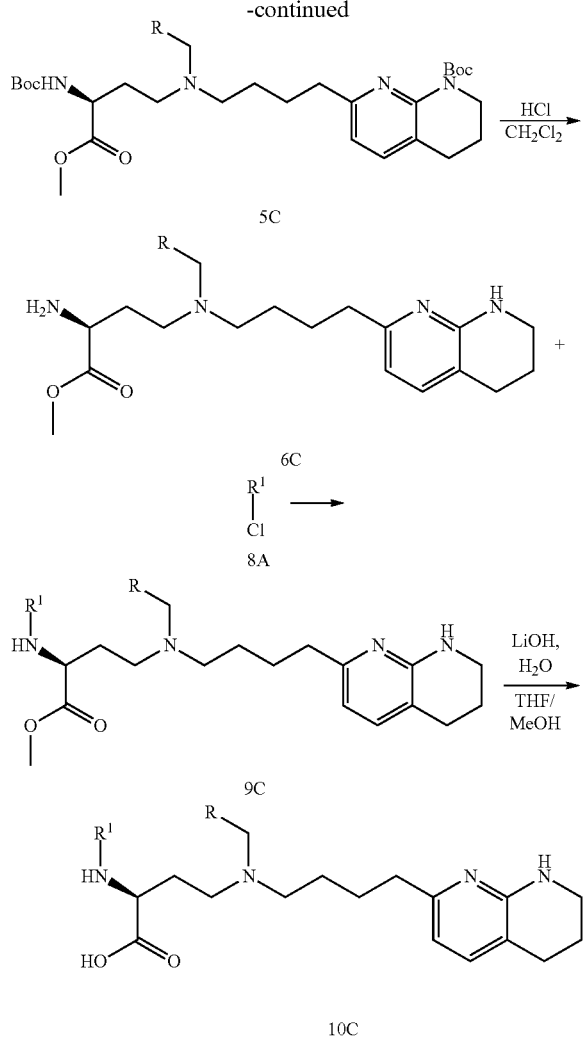

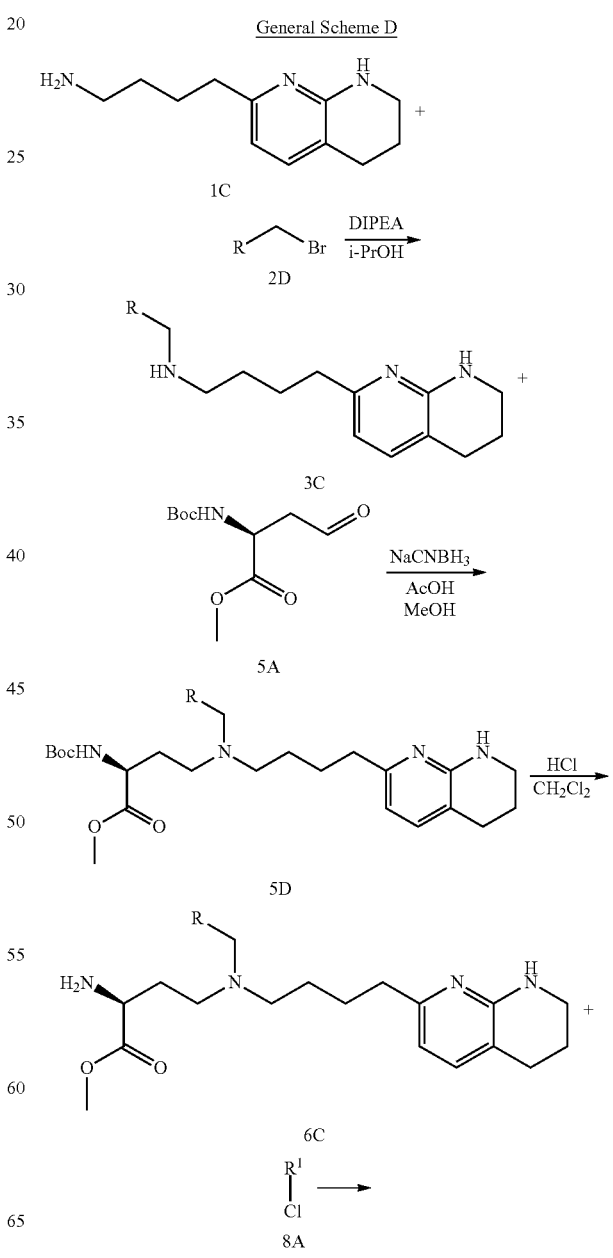

Coupling of 1C with a compound of formula 4C in the presence of a suitable coupling agent yields a compound of formula 2C, which is reduced to yield a compound of formula 3C. Reductive amination of a compound of formula 3C with compound 5A gives a compound of formula 5C. Global removal of the N-Boc protecting groups with a compound of formula 5C by exposure to an appropriate acid gives a compound of formula 6C, which can be coupled with a compound of formula 8A to give a compound of formula 9C. Hydrolysis of a compound of formula 9C in the presence of a suitable hydroxide source gives compounds of formula 10C.

Reaction conditions for the transformations of General Scheme C are provided in the General Procedures that follow, in particular General Procedures B, D, F, G, H, and P.

General Scheme C can be modified to prepare variants of compounds of formula 10C by beginning with variants of 1C with 5 and 6 carbon linkers between the nitrogen bearing the —CH$_2$R group and the tetrahydronaphthyridine group. These variants of compounds of formula 10C can be synthesized by using the route described in General Scheme C substituting 1C with either 5-(5,6,7,8-tetrahydro-1,8-naphthyridin-2-yl)pentan-1-amine or 6-(5,6,7,8-tetrahydro-1,8-naphthyridin-2-yl)hexan-1-amine. 6-oxoheptanoic acid and 7-oxooctanoic acid can be converted to 5,6,7,8-tetrahydro-1,8-naphthyridine-2-pentanoic acid and 5,6,7,8-tetrahydro-1,8-naphthyridine-2-hexanoic acid, respectively, by condensation with 2-aminonicotinaldehyde in the presence of an appropriate catalyst followed by hydrogenation of the resulting naphthyridine ring to the 5,6,7,8-tetrahydronaphthyridine ring using procedures known in the chemical literature. The resulting carboxylic acids can be converted to a primary amine by a two-step procedure that includes coupling of the carboxylic acid with an appropriate ammonia source in the presence of suitable coupling reagents followed by reduction.

Compounds of formula 10C can alternatively be prepared according to General Scheme D, wherein R is $C_1$-$C_5$ alkyl optionally substituted by $R^{2a}$, and $R^1$ and $R^{2a}$ are as defined for formula (I), or any applicable variations detailed herein.

-continued

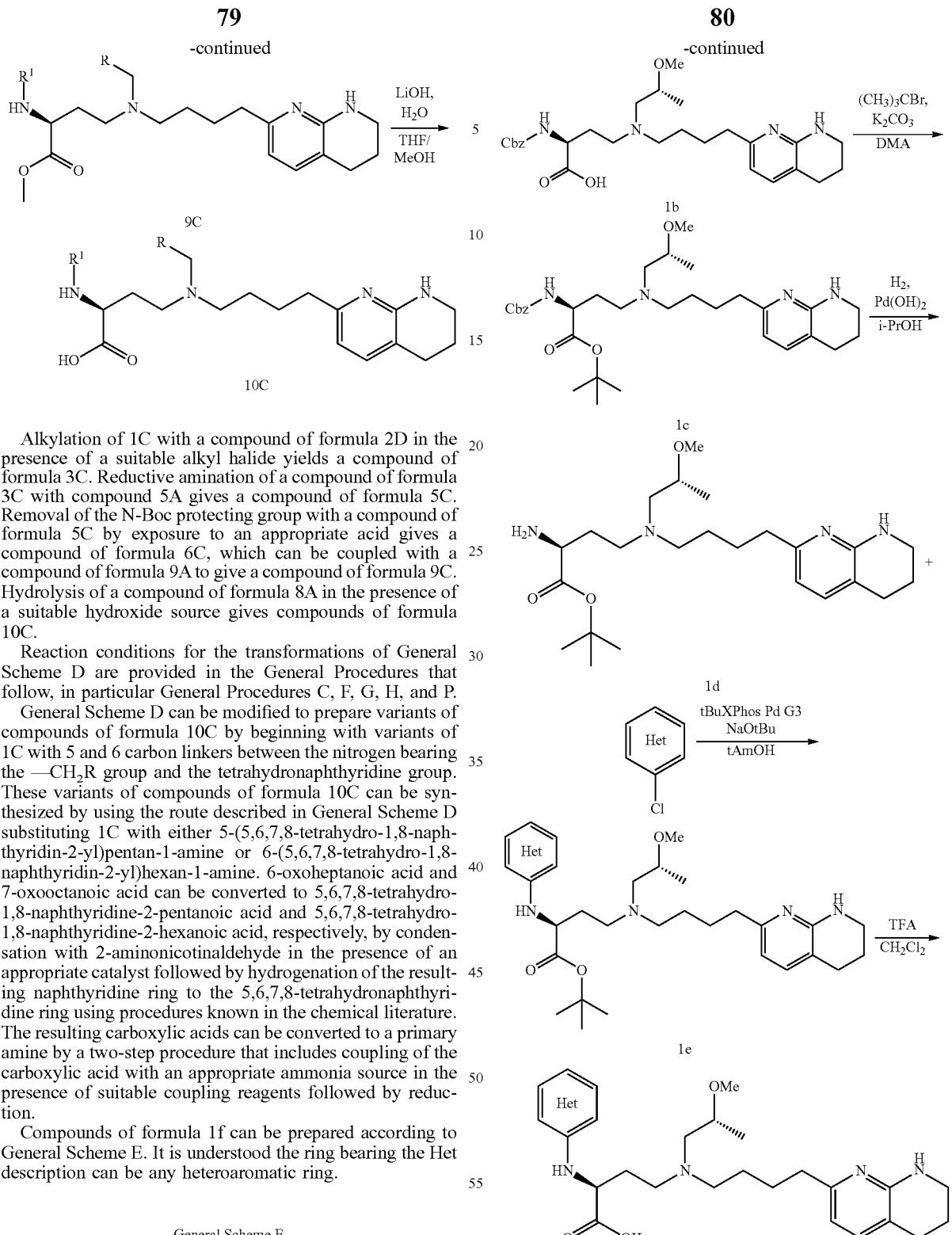

Alkylation of 1C with a compound of formula 2D in the presence of a suitable alkyl halide yields a compound of formula 3C. Reductive amination of a compound of formula 3C with compound 5A gives a compound of formula 5C. Removal of the N-Boc protecting group with a compound of formula 5C by exposure to an appropriate acid gives a compound of formula 6C, which can be coupled with a compound of formula 9A to give a compound of formula 9C. Hydrolysis of a compound of formula 8A in the presence of a suitable hydroxide source gives compounds of formula 10C.

Reaction conditions for the transformations of General Scheme D are provided in the General Procedures that follow, in particular General Procedures C, F, G, H, and P.

General Scheme D can be modified to prepare variants of compounds of formula 10C by beginning with variants of 1C with 5 and 6 carbon linkers between the nitrogen bearing the —CH₂R group and the tetrahydronaphthyridine group. These variants of compounds of formula 10C can be synthesized by using the route described in General Scheme D substituting 1C with either 5-(5,6,7,8-tetrahydro-1,8-naphthyridin-2-yl)pentan-1-amine or 6-(5,6,7,8-tetrahydro-1,8-naphthyridin-2-yl)hexan-1-amine. 6-oxoheptanoic acid and 7-oxooctanoic acid can be converted to 5,6,7,8-tetrahydro-1,8-naphthyridine-2-pentanoic acid and 5,6,7,8-tetrahydro-1,8-naphthyridine-2-hexanoic acid, respectively, by condensation with 2-aminonicotinaldehyde in the presence of an appropriate catalyst followed by hydrogenation of the resulting naphthyridine ring to the 5,6,7,8-tetrahydronaphthyridine ring using procedures known in the chemical literature. The resulting carboxylic acids can be converted to a primary amine by a two-step procedure that includes coupling of the carboxylic acid with an appropriate ammonia source in the presence of suitable coupling reagents followed by reduction.

Compounds of formula 1f can be prepared according to General Scheme E. It is understood the ring bearing the Het description can be any heteroaromatic ring.

General Scheme E

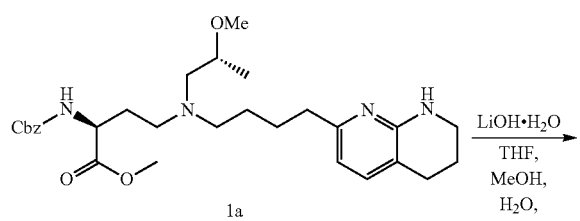

Hydrolysis of a compound of formula 1a gives a compound of formula 1b which can be alkylated with a suitable electrophile to give a compound of formula 1c. Deprotection under reductive conditions of a compound of formula 1e gives a compound of formula 1d. Metal catalyzed cross coupling of a halogenated arene with a compound of formula 1d gives a compound of formula 1e, which can be hydrolyzed under acidic conditions to give compound of formula 1f.

Reaction conditions for the transformations of General Scheme E are provided in the General Procedures that follow, in particular General Procedures Q, R, S, T, and U.

It is understood that the schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4$^{th}$ edition, Wiley-Interscience, New York, 2006.

Additional methods of preparing compounds according to Formula (I), and salts thereof, are provided in the Examples. As a skilled artisan would recognize, the methods of preparation taught herein may be adapted to provide additional compounds within the scope of Formula (I), for example, by selecting starting materials which would provide a desired compound.

Pharmaceutical Compositions and Formulations

Pharmaceutical compositions of any of the compounds detailed herein, including compounds of the formula (I), (I-A), (I-B), (I-C), (I-D), (I-E), (I-F), (I-G), (I-H), (II), (II-A), (II-B), (II-C), (II-D), (II-E), (II-F), (II-G), or (II-H), or a salt thereof, or any of compounds of FIG. 1, or a salt thereof, or mixtures thereof, are embraced by this invention. Pharmaceutical compositions of any of the compounds detailed herein, including compounds of the formula (I), (I-A), (I-B), (I-C), (I-D), (I-E), (I-F), (I-G), (I-H), (II), (II-A), (II-B), (II-C), (II-D), (II-E), (II-F), (II-G), or (II-H), or a salt thereof, or any of compounds of FIG. 1, or a salt thereof, or mixtures thereof, are embraced by this invention. Pharmaceutical compositions of compounds of the formula (A), or a salt thereof, or mixtures thereof, are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation. In one embodiment, the pharmaceutical composition is a composition for controlled release of any of the compounds detailed herein.

A compound as detailed herein may in one aspect be in a purified form and compositions comprising a compound in purified forms are detailed herein. In one embodiment, compositions may have no more than 35% impurity, wherein the impurity denotes a compound other than the compound comprising the majority of the composition or a salt thereof, for example, a composition of a compound selected from a compound of FIG. 1 may contains no more than 35% impurity, wherein the impurity denotes a compound other than the compound of FIG. 1 or a salt thereof. In one embodiment, compositions may have no more than 35% impurity, wherein the impurity denotes a compound other than the compound comprising the majority of the composition or a salt thereof, for example, a composition of a compound selected from a compound of FIG. 1 may contain no more than 35% impurity, wherein the impurity denotes a compound other than the compound of FIG. 1, or a salt thereof. In one embodiment, compositions may contain no more than 25% impurity. In one embodiment, compositions may contains no more than 20% impurity. In still further embodiments, compositions comprising a compound as detailed herein or a salt thereof are provided as compositions of substantially pure compounds. "Substantially pure" compositions comprise no more than 10% impurity, such as a composition comprising less than 9%, 7%, 5%, 3%, 1%, or 0.5% impurity. In some embodiments, a composition containing a compound as detailed herein or a salt thereof is in substantially pure form. In still another variation, a composition of substantially pure compound or a salt thereof is provided wherein the composition contains or no more than 10% impurity. In a further variation, a composition of substantially pure compound or a salt thereof is provided wherein the composition contains or no more than 9% impurity. In a further variation, a composition of substantially pure compound or a salt thereof is provided wherein the composition contains or no more than 7% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 10% or preferably no more than 5% or more preferably no more than 3% or even more preferably no more than 1% impurity or most preferably no more than 0.5% impurity, which impurity may be the compound in a different stereochemical form. For instance, a composition of substantially pure (S) compound means that the composition contains no more than 10% or no more than 5% or no more than 3% or no more than 1% or no more than 0.5% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21$^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

In one embodiment, the compounds can be administered in the liquid vehicle ORA-SWEET® from PERRIGO®, Allegan, Mich., which is a syrup vehicle having ingredients of purified water, glycerin, sorbitol, sodium saccharin, xanthan gum, and flavoring, buffered with citric acid and sodium citrate, preserved with methylparaben (0.03%), potassium sorbate (0.1%), and propylparaben (0.008%); or in a mixture of ORA-SWEET® and water of any proportion, such as a 50:50 mixture of ORA-SWEET® to water. The water used should be a pharmaceutically acceptable grade of water, for example, sterile water.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use

Compounds and compositions of the invention, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided is a method of treating a fibrotic disease in an individual in need thereof comprising administering to the individual a therapeutically effective amount of a compound of formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof. In one aspect, provided is a method of treating a fibrotic disease in an individual in need thereof comprising administering to the individual a therapeutically effective amount of a compound of formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-147, or a stereoisomer thereof, or a pharmaceutically acceptable salt thereof. In one aspect, provided is a method of treating a fibrotic disease in an individual in need thereof comprising administering to the individual a therapeutically effective amount of a compound of formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-665, or a stereoisomer thereof, or a pharmaceutically acceptable salt thereof. In one aspect, provided is a method of treating a fibrotic disease in an individual in need thereof comprising administering to the individual a therapeutically effective amount of a compound of formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof. In one aspect, provided is a method of treating a fibrotic disease in an individual in need thereof comprising administering to the individual a therapeutically effective amount of a compound of formula (A), or any variation thereof, or a stereoisomer thereof, or a pharmaceutically acceptable salt thereof. In one aspect, the individual is a human. The individual, such as human, may be in need of treatment, such as a human who has or is suspected of having a fibrotic disease.

In another aspect, provided is a method of delaying the onset and/or development of a fibrotic disease in an individual (such as a human) who is at risk for developing a fibrotic disease. It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease. In some embodiments, the individual at risk for developing a fibrotic disease is an individual who has or is suspected of having NAFLD, NASH, CKD, scleroderma, Crohn's Disease, NSIP, PSC, PBC, or is an individual who has had or is suspected of having had a myocardial infarction. In some embodiments, the individual at risk for developing a fibrotic disease has or is suspected of having psoriasis.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC). In some embodiments, the fibrotic disease is pulmonary fibrosis (such as IPF), liver fibrosis, skin fibrosis, psoriasis, scleroderma, cardiac fibrosis, renal fibrosis, gastrointestinal fibrosis, primary sclerosing cholangitis, or biliary fibrosis (such as PBC). In some embodiments, the fibrotic disease is psoriasis.

In some embodiments, the fibrotic disease is a pulmonary fibrosis, e.g., idiopathic pulmonary fibrosis (IPF). In some embodiments, the pulmonary fibrosis is, e.g., interstitial lung disease, radiation-induced pulmonary fibrosis, or systemic sclerosis associated interstitial lung disease.

In some embodiments, the fibrotic disease is a primary sclerosing cholangitis, or biliary fibrosis. In some embodiments, the fibrotic disease is primary biliary cholangitis (also known as primary biliary cirrhosis) or biliary atresia.

In some embodiments, the fibrotic disease is fibrotic nonspecific interstitial pneumonia (NSIP).

In some embodiments, the fibrotic disease is a liver fibrosis, e.g., infectious liver fibrosis (from pathogens such as HCV, HBV or parasites such as schistosomiasis), NASH, alcoholic steatosis induced liver fibrosis, and cirrhosis. In some embodiments, the liver fibrosis is nonalcoholic fatty liver disease (NAFLD). In some embodiments, the liver fibrosis is NASH.

In some embodiments, the fibrotic disease is biliary tract fibrosis.

In some embodiments, the fibrotic disease is renal fibrosis, e.g., diabetic nephrosclerosis, hypertensive nephrosclerosis, focal segmental glomerulosclerosis ("FSGS"), and acute kidney injury from contrast induced nephropathy. In several embodiments, the fibrotic disease is diabetic nephropathy, diabetic kidney disease, or chronic kidney disease.

In some embodiments, the fibrotic disease is characterized by one or more of glomerulonephritis, end-stage kidney disease, hearing loss, changes to the lens of the eye, hematuria, or proteinuria. In some embodiments, the fibrotic disease is Alport syndrome.

In some embodiments, the fibrotic disease is systemic and local sclerosis or scleroderma, keloids and hypertrophic scars, or post surgical adhesions. In some embodiments, the fibrotic disease is scleroderma or systemic sclerosis.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In some embodiments, the fibrotic disease is psoriasis.

In some embodiments, methods may include modulating the activity of at least one integrin in a subject in need thereof. For example, the method may include modulating the activity of $\alpha v \beta_6$. The method may include modulating the activity of $\alpha v \beta_1$. The method may include modulating the activity of $\alpha v \beta_1$ and $\alpha v \beta_6$. Modulating the activity of the at least one integrin may include, e.g., inhibiting the at least one integrin. The method may include administering to the subject an amount of the compound or a pharmaceutically acceptable salt thereof effective to modulate the activity of the at least one integrin in the subject, e.g., at least one of $\alpha v \beta_1$ and $\alpha v \beta_6$. The subject in need of modulating the activity of at least one integrin may have any of the fibrotic disease or conditions described herein. For example, the fibrotic disease or condition may include idiopathic pulmonary fibrosis, interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis, primary biliary cholangitis (also known as primary biliary cirrhosis), biliary atresia, systemic sclerosis associated interstitial lung disease, scleroderma (also known as systemic sclerosis), diabetic nephropathy, diabetic kidney disease, focal segmental glomerulosclerosis, chronic kidney disease, or Crohn's Disease. The fibrotic disease or condition may include psoriasis. The method may include administering to the subject an amount of the compound or a pharmaceutically acceptable salt thereof effective to modulate the activity of the at least one integrin in the subject, e.g., at least one of $\alpha v \beta_1$ and $\alpha v \beta_6$, the subject being in need of treatment for NASH. The method may include administering to the subject an amount of the compound or a pharmaceutically acceptable salt thereof effective to modulate the activity of the at least one integrin in the subject, e.g., at least one of $\alpha v \beta_1$ and $\alpha v \beta_6$, the subject being in need of treatment for IPF.

The fibrotic disease may be mediated primarily by $\alpha v \beta_6$, for example, the fibrotic disease may include idiopathic pulmonary fibrosis or renal fibrosis. Accordingly, the method may include modulating the activity of $\alpha v \beta_6$ to treat conditions primarily mediated by $\alpha v \beta_6$ such as IPF. The fibrotic disease may be mediated primarily by $\alpha v \beta_1$, for example, the fibrotic disease may include NASH. Accordingly, the method may include modulating the activity of $\alpha v \beta_1$ to treat conditions primarily mediated by $\alpha v \beta_1$, e.g., NASH. The fibrotic disease may be mediated by $\alpha v \beta_1$ and $\alpha v \beta_6$, for example, the fibrotic disease may include PSC or biliary atresia. Accordingly, the method may include modulating the activity of $\alpha v \beta_1$ and $\alpha v \beta_6$ to treat conditions mediated by both $\alpha v \beta_1$ and $\alpha v \beta_6$.

The compound may be a modulator, e.g., an inhibitor, of $\alpha v \beta_1$. The compound may be a modulator, e.g., an inhibitor, of $\alpha v \beta_6$. The compound may be a dual modulator, such as a dual inhibitor, e.g., dual selective inhibitor, of $\alpha v \beta_1$ and $\alpha v \beta_6$. For example, Table B-3 demonstrates that some exemplary compounds primarily inhibit $\alpha v \beta_1$ over $\alpha v \beta_6$; some exemplary compounds primarily inhibit $\alpha v \beta_6$ over $\alpha v \beta_1$; and some exemplary compounds inhibit $\alpha v \beta_1$ and $\alpha v \beta_6$, comparably, and may be considered, e.g., "dual $\alpha v \beta_1$/$\alpha v \beta_6$ inhibitors."

Modulating or inhibiting the activity of one or both of $\alpha v \beta_1$ integrin and $\alpha v \beta_6$ integrin, thereby treating a subject with a fibrotic disease, indicates that $\alpha v \beta_1$ integrin, $\alpha v \beta_6$ integrin, or $\alpha v \beta_1$ integrin and $\alpha v \beta_6$ integrin are modulated or inhibited to a degree sufficient to treat the fibrotic disease in the subject.

In one aspect, provided is a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof, for use in the treatment of a fibrotic disease.

In one aspect, provided is a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-147, or a stereoisomer thereof, or a pharmaceutically acceptable salt thereof, for use in the treatment of a fibrotic disease.

In one aspect, provided is a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-665, or a stereoisomer thereof, or a pharmaceutically acceptable salt thereof, for use in the treatment of a fibrotic disease.

In one aspect, provided is a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof, for use in the treatment of a fibrotic disease.

Also provided is use of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof, in the manufacture of a medicament for the treatment of a fibrotic disease.

Also provided is use of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-147, or a stereoisomer thereof, or a pharmaceutically acceptable salt thereof, in the manufacture of a medicament for the treatment of a fibrotic disease.

Also provided is use of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-665, or a stereoisomer thereof, or a pharmaceutically acceptable salt thereof, in the manufacture of a medicament for the treatment of a fibrotic disease.

Also provided is use of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof, in the manufacture of a medicament for the treatment of a fibrotic disease.

In another aspect, provided herein is a method of treating a subject in need thereof, comprising administering to the subject a therapeutically effective amount of a compound of formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof, or a dosage form disclosed herein, wherein the subject has at least one tissue in need of therapy and the tissue has at least one elevated level of: αVβ1 integrin activity and/or expression; αVβ6 integrin activity and/or expression; a pSMAD/SMAD value; new collagen formation or accumulation; total collagen; and Type I Collagen gene Col1a1 expression; and wherein the level is elevated compared to a healthy state of the tissue. In some embodiments, the at least one tissue in the subject comprises one or more of: lung tissue, liver tissue, skin tissue, cardiac tissue, kidney tissue, gastrointestinal tissue, gall bladder tissue, and bile duct tissue. In some embodiments, the tissue has an elevated pSMAD2/SMAD2 value or an elevated pSMAD3/SMAD3 value compared to the healthy state of the tissue.

Methods of determine the values of αVβ1 integrin activity and/or expression; αVβ6 integrin activity and/or expression; a pSMAD/SMAD value; new collagen formation or accumulation; total collagen; and Type I Collagen gene Col1a1 expression are known in the art and exemplary methods are disclosed in the Examples, such as antibody assays of tissue samples, such as a biopsy sample.

In some embodiments, the method selectively reduces αVβ1 integrin activity and/or expression compared to αVβ6 integrin activity and/or expression in the subject. In some embodiments, the method selectively reduces $\alpha v \beta_6$ integrin activity and/or expression compared to $\alpha v \beta_1$ integrin activity and/or expression in the subject. In some embodiments, the method reduces both $\alpha v \beta_1$ integrin and $\alpha v \beta_6$ integrin activity and/or expression compared to at least one other αv-containing integrin in the subject. In some embodiments, the activity of αVβ1 integrin in one or more fibroblasts is reduced in the subject. In some embodiments, the activity of αVβ6 integrin in one or more epithelial cells is reduced in the subject.

In another aspect, provided herein is a method of treating a subject in need thereof, comprising administering to the subject a therapeutically effective amount of a compound of formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof, or a dosage form disclosed herein, wherein the subject has at least one tissue in need of therapy and the tissue has at least one elevated level of: αVβ1 integrin activity and/or expression; αVβ6 integrin activity and/or expression; a pSMAD/SMAD value; new collagen formation or accumulation; total collagen; and Type I Collagen gene Col1a1 expression; and wherein the level is elevated compared to a healthy state of the tissue. In some embodiments, the at least one tissue in the subject comprises one or more of: lung tissue, liver tissue, skin tissue, cardiac tissue, kidney tissue, gastrointestinal tissue, gall bladder tissue, and bile duct tissue. In some embodiments, the tissue has an elevated pSMAD2/SMAD2 value or an elevated pSMAD3/SMAD3 value compared to the healthy state of the tissue.

Methods of determine the values of αVβ1 integrin activity and/or expression; αVβ6 integrin activity and/or expression; a pSMAD/SMAD value; new collagen formation or accumulation; total collagen; and Type I Collagen gene Col1a1 expression are known in the art and exemplary methods are disclosed in the Examples, such as antibody assays of tissue samples, such as a biopsy sample.

In some embodiments, the method selectively reduces αVβ1 integrin activity and/or expression compared to αVβ6 integrin activity and/or expression in the subject. In some embodiments, the method selectively reduces $\alpha v \beta_6$ integrin activity and/or expression compared to $\alpha v \beta_1$ integrin activity and/or expression in the subject. In some embodiments, the method reduces both $\alpha v \beta_1$ integrin and $\alpha v \beta_6$ integrin activity and/or expression compared to at least one other αv-containing integrin in the subject. In some embodiments, the activity of αVβ1 integrin in one or more fibroblasts is reduced in the subject. In some embodiments, the activity of αVβ6 integrin in one or more epithelial cells is reduced in the subject.

Also provided herein is a method of characterizing the antifibrotic activity of a small molecule in a subject, comprising: providing a first live cell sample from the subject, the first live cell sample characterized by the presence of at least one integrin capable of activating transforming growth factor β (TGF-β) from latency associated peptide-TGF-β; determining a first pSMAD/SMAD value in the first live cell sample; administering the small molecule to the subject; providing a second live cell sample from the subject, the second live cell sample being drawn from the same tissue in the subject as the first live cell sample; determining a second pSMAD/SMAD value in the second live cell sample; and characterizing the antifibrotic activity of the small molecule in the subject by comparing the second pSMAD/SMAD value to the first pSMAD/SMAD value. In some embodiments, the small molecule is a compound disclosed herein, optionally in a dosage form disclosed herein.

In some embodiments, each live cell sample is a plurality of cells derived from a tissue of the subject, or a plurality of macrophages associated with the tissue of the subject. In some embodiments, the tissue comprises one of: lung tissue, liver tissue, skin tissue, cardiac tissue, kidney tissue, gastrointestinal tissue, gall bladder tissue, and bile duct tissue. In some embodiments, each live cell sample comprises a plurality of alveolar macrophages derived from a bronchoalveolar lavage fluid of the subject.

In some embodiments, the method further comprising conducting a bronchoalveolar lavage on a lung of the subject effective to produce a bronchoalveolar lavage fluid that comprises the plurality of macrophages as a plurality of alveolar macrophages.

In some embodiments, the subject has a fibrotic disease selected from the group consisting of: idiopathic pulmonary fibrosis (IPF), interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis (PSC), primary biliary cholangitis, biliary atresia, systemic sclerosis associated interstitial lung disease, scleroderma, diabetic nephropathy, diabetic kidney disease, focal segmental glomerulosclerosis, chronic kidney disease, and Crohn's Disease. In some embodiments, the subject has the fibrotic disease psoriasis.

In some embodiments, the at least one integrin comprises αv. In some embodiments, the at least one integrin comprises $\alpha v \beta_1$. In some embodiments, the at least one integrin comprises $\alpha v \beta_6$.

In some embodiments, determining the first pSMAD/SMAD value in the at least one live cell comprises determining a pSMAD2/SMAD2 value or a pSMAD3/SMAD3 value; and determining the second pSMAD/SMAD value in the at least one live cell after contacting the at least one live cell with the small molecule comprises determining a pSMAD2/SMAD2 value or a pSMAD3/SMAD3 value.

Also provided herein is a method of treating a fibrotic disease in a subject in need thereof, comprising: providing a first live cell sample from the subject, the first live cell sample having at least one integrin capable of activating transforming growth factor β (TGF-β) from latency associated peptide-TGF-β; determining a first pSMAD/SMAD value in the first live cell sample; administering a small molecule to the subject; providing a second live cell sample from the subject, the second live cell sample being drawn from the same tissue in the subject as the first live cell sample; determining a second pSMAD/SMAD value in the second live cell sample; comparing the second pSMAD/SMAD value to the first pSMAD/SMAD value; and administering the small molecule to the subject if the second pSMAD/SMAD value is lower than the first pSMAD/SMAD value. In some embodiments, the small molecule is a compound disclosed herein or a salt thereof, optionally in a dosage form disclosed herein. In some embodiments, the first live cell sample is obtained from the subject prior to treatment with a small molecule.

In some embodiments, each live cell sample is a plurality of cells derived from a tissue of the subject, or a plurality of macrophages associated with the tissue of the subject. In some embodiments, the tissue comprises one of: lung tissue, liver tissue, skin tissue, cardiac tissue, kidney tissue, gastrointestinal tissue, gall bladder tissue, and bile duct tissue. In some embodiments, each live cell sample comprises a plurality of alveolar macrophages derived from a bronchoalveolar lavage fluid of the subject. In some embodiments, the method further comprising conducting a bronchoalveolar lavage on a lung of the subject effective to produce a bronchoalveolar lavage fluid that comprises the plurality of macrophages as a plurality of alveolar macrophages.

In some embodiments, the subject is characterized by having a fibrotic disease selected from the group consisting of: idiopathic pulmonary fibrosis (IPF), interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis (PSC), primary biliary cholangitis, biliary atresia, systemic sclerosis associated interstitial lung disease, scleroderma, diabetic nephropathy, diabetic kidney disease, focal segmental glomerulosclerosis, chronic kidney disease, and Crohn's Disease. In some embodiments, the subject is characterized by having psoriasis.

In some embodiments, the at least one integrin comprises αv. In some embodiments, the at least one integrin comprises $\alpha v \beta_1$. In some embodiments, the at least one integrin comprises $\alpha v \beta_6$.

In some embodiments, determining the first pSMAD/SMAD value in the first live cell sample comprises determining a pSMAD2/SMAD2 value or a pSMAD3/SMAD3 value; and determining the second pSMAD/SMAD value in the at least one live cell after contacting the first live cell sample with the small molecule comprises determining a pSMAD2/SMAD2 value or a pSMAD3/SMAD3 value.

In another aspect, provided is a method of inhibiting αvβ6 integrin in an individual comprising administering a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a stereoisomer thereof, or a compound selected from Compound Nos. 1-66 in FIG. 1, or a pharmaceutically acceptable salt thereof.

In another aspect, provided is a method of inhibiting αvβ6 integrin in an individual comprising administering a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a stereoisomer thereof, or a compound selected from Compound Nos. 1-147, or a pharmaceutically acceptable salt thereof.

In another aspect, provided is a method of inhibiting αvβ6 integrin in an individual comprising administering a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a stereoisomer thereof, or a compound selected from Compound Nos. 1-665, or a pharmaceutically acceptable salt thereof.

In another aspect, provided is a method of inhibiting αvβ6 integrin in an individual comprising administering a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a stereoisomer thereof, or a compound selected from Compound Nos. 1-780, or a pharmaceutically acceptable salt thereof.

Also provided is a method of inhibiting TGFβ activation in a cell comprising administering to the cell a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof.

Also provided is a method of inhibiting TGFβ activation in a cell comprising administering to the cell a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-147, or a stereoisomer thereof, or a pharmaceutically acceptable salt thereof.

Also provided is a method of inhibiting TGFβ activation in a cell comprising administering to the cell a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-665, or a stereoisomer thereof, or a pharmaceutically acceptable salt thereof.

Also provided is a method of inhibiting TGFβ activation in a cell comprising administering to the cell a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof.

Also provided is a method of inhibiting αvβ6 integrin in an individual in need thereof, comprising administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof. Also provided is a method of inhibiting αvβ$_6$ integrin in an individual in need thereof, comprising administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-147, or a stereoisomer thereof, or a pharmaceutically acceptable salt thereof. Also provided is a method of inhibiting αvβ6 integrin in an individual in need thereof, comprising administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-665, or a stereoisomer thereof, or a pharmaceutically acceptable salt thereof. Also provided is a method of inhibiting αvβ6 integrin in an individual in need thereof, comprising administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof. In one such method, the compound is a selective αvβ6 integrin inhibitor. In another such method, the compound does not inhibit substantially α4β1, αvβ8 and/or α2β3 integrin. In yet another such method, the compound inhibits αvβ6 integrin but does not inhibit substantially α4β1 integrin. In still another such method, the compound inhibits αvβ6 integrin but does not inhibit substantially αvβ8 integrin. In a further such method, the compound inhibits αvβ6 integrin but does not inhibit substantially α2β3 integrin. In one embodiment is provided a method of inhibiting αvβ6 integrin and one or more of αvβ1, αvβ3, αvβ5, α2β1, α3β1, α6β1, α7β1 and α11β1 integrin in an individual in need thereof. In another embodiment is provided a method of inhibiting αvβ6 integrin and αvβ1 integrin. In another embodiment is provided a method of inhibiting αvβ6 integrin, αvβ3 integrin and αvβ5 integrin. In another embodiment is provided a method of inhibiting αvβ6 integrin and α2β1 integrin. In another embodiment is provided a method of inhibiting αvβ6 integrin, α2β1 integrin and α3β1 integrin. In another embodiment is provided a method of inhibiting αvβ6 integrin and α6β1 integrin. In another embodiment is provided a method of inhibiting αvβ6 integrin and α7β1 integrin. In another embodiment is provided a method of inhibiting αvβ6 integrin and α11β1 integrin. In all such embodiments, in one aspect the method of inhibition is for an individual in need thereof, such as an individual who has or is suspected of having a fibrotic disease, and wherein the method comprises administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-66 in FIG. 1, or a stereoisomer thereof, or a pharmaceutically acceptable salt thereof. In all such embodiments, in one aspect the method of inhibition is for an individual in need thereof, such as an individual who has or is suspected of having a fibrotic disease, and wherein the method comprises administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-147, or a stereoisomer thereof, or a pharmaceutically acceptable salt thereof. In all such embodiments, in one aspect the method of inhibition is for an individual in need thereof, such as an individual who has or is suspected of having a fibrotic disease, and wherein the method comprises administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-665, or a stereoisomer thereof, or a pharmaceutically acceptable salt thereof. In all such embodiments, in one aspect the method of inhibition is for an individual in need thereof, such as an individual who has or is suspected of having a fibrotic disease, and wherein the method comprises administering to the individual a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof.

Compounds of formula (A) can be used in any of the compositions, methods, and uses recited herein for formula (I) and variations of formula (I).

In any of the described methods, in one aspect the individual is a human, such as a human in need of the method. The individual may be a human who has been diagnosed with or is suspected of having a fibrotic disease. The individual may be a human who does not have detectable disease but who has one or more risk factors for developing a fibrotic disease.

Also provided herein are dosage forms configured for daily administration, comprising a pharmaceutically acceptable carrier or excipient; and a unit dose of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof.

A unit dose, such as a unit dose for daily administration, can comprise about 1, 2.5, 5, 7.5, 10, 15, 20, 25, 30, 35, 40, 50, 75, 80, 85, 90, 95, 100, 105, 110, 115, 120, or 125 mg of the compound, or a range between any two of the preceding values, such as about 1-125, 1-5, 2.5-7.5, 5-15, 10-15, 10-20, 10-25, 10-30, 10-35, 10-40, 10-50, 10-75, 15-20, 15-25, 15-30, 15-35, 15-40, 15-50, 15-75, 20-25, 20-30, 20-35, 20-40, 20-50, 20-75, 25-30, 25-35, 25-40, 25-50, 25-75, 30-35, 30-40, 30-50, 30-75, 35-40, 35-50, 35-75, 40-50, 40-75, 50-75, 50-100, 60-85, 70-90, 70-100, 80-125, 90-125, or 100-125 mg.

A unit dose, such as a unit dose for daily administration, can comprise about 1, 2.5, 5, 7.5, 10, 15, 20, 25, 30, 35, 40, 50, 75, 80, 85, 90, 95, 100, 105, 110, 115, 120, 125, 150, 175, 200, 225, or 250 mg of the compound, or a range between any two of the preceding values, such as about 1-125, 1-250, 1-5, 2.5-7.5, 5-15, 10-15, 10-20, 10-25, 10-30, 10-35, 10-40, 10-50, 10-75, 15-20, 15-25, 15-30, 15-35, 15-40, 15-50, 15-75, 20-25, 20-30, 20-35, 20-40, 20-50, 20-75, 25-30, 25-35, 25-40, 25-50, 25-75, 30-35, 30-40, 30-50, 30-75, 35-40, 35-50, 35-75, 40-50, 40-75, 50-75, 50-100, 50-150, 50-250, 60-85, 70-90, 70-100, 80-125, 90-125, 100-125, 100-150, 100-200, 125-175, 100-225, 100-250, and 150-250 mg. For example, the unit dose may be 10 mg. The unit dose may be 15 mg. The unit dose may be 20 mg. The unit dose may be 30 mg. The unit dose may be 40 mg. The unit dose may be 50 mg. The unit dose may be 60 mg. The unit dose may be 70 mg. The unit dose may be 75 mg. The unit dose may be 80 mg. The unit dose may be 90 mg. The unit dose may be 100 mg. The unit dose may be 110 mg. The unit dose may be 120 mg. The unit dose may be 125 mg. The unit dose may be 150 mg. The unit dose may be 175 mg. The unit dose may be 200 mg. The unit dose may be 225 mg. The unit dose may be 250 mg.

A unit dose, such as a unit dose for daily administration, can comprise the compound in an amount effective on administration to an individual to produce a $C_{max}$ in plasma of the individual in ng/mL of at least about, or greater than about, one of 700, 750, 800, 850, 900, 950, 1000, 1050, 1100, 1150, 1200, 1250, 1300, 1350, 1400, 1450, or 1500; or a range between any two of the preceding concentrations, such as 700-1500, 700-900, 800-1300, 750-950, 800-1000, 850-950, 850-1050, 900-1400, 900-1300, 900-1200, 900-1100, 950-1050, 950-1400, 950-1150, 1000-1400, 1000-1300, 1000-1200, and the like. For example, $C_{max}$ can be about 700 ng/mL or greater. $C_{max}$ can be about 750 ng/mL or greater. $C_{max}$ can be about 800 ng/mL or greater. $C_{max}$ can be about about 850 ng/mL or greater. $C_{max}$ can be 900 ng/mL or greater. $C_{max}$ can be about 950 ng/mL or greater. $C_{max}$ can be about 1000 ng/mL or greater. $C_{max}$ can be about 1050 ng/mL or greater. $C_{max}$ can be about 1100 ng/mL or greater. $C_{max}$ can be about 1200 ng/mL or greater. $C_{max}$ can be about 1300 ng/mL or greater. $C_{max}$ can be about 1400 ng/mL or greater. $C_{max}$ can be about 1500 ng/mL or greater.

A unit dose, such as a unit dose for daily administration, can comprise the compound in an amount effective on administration to an individual to produce a $C_{max}$ in ng/mL in plasma of the individual, the $C_{max}$ corresponding to a plasma-adjusted concentration effective to inhibit a percentage of $\alpha v \beta_6$ or $\alpha v \beta_1$ in the individual of at least about one of 50, 55, 60, 65, 70, 75, 80, 85, 90, 95, or 100, or a range between any two of the preceding percentages, for example, 50-100, 60-90, 70-90, 75-95, and the like. In some embodiments, the compound may be a dual $\alpha v \beta_6$ and $\alpha v \beta_1$ inhibitor, and the $C_{max}$ can correspond to a plasma-adjusted concentration effective to inhibit a percentage of each of $\alpha v \beta_6$ and $\alpha v \beta_1$ in the individual, each percentage independently selected from the preceding percentages, or a range between any two of the preceding percentages. For example, the plasma-adjusted concentration can be effective to inhibit $\alpha v \beta_6$ by at least about 50%. The plasma-adjusted concentration can be effective to inhibit $\alpha v \beta_6$ by at least about 60%. The plasma-adjusted concentration can be effective to inhibit $\alpha v \beta_6$ by at least about 70%. The plasma-adjusted concentration can be effective to inhibit $\alpha v \beta_6$ by at least about 80%. The plasma-adjusted concentration can be effective to inhibit $\alpha v \beta_6$ by at least about 90%. Further, for example, the plasma-adjusted concentration can be effective to inhibit $\alpha v \beta_1$ by at least about 50%. The plasma-adjusted concentration can be effective to inhibit $\alpha v \beta_1$ by at least about 60%. The plasma-adjusted concentration can be effective to inhibit $\alpha v \beta_1$ by at least about 70%. The plasma-adjusted concentration can be effective to inhibit $\alpha v \beta_1$ by at least about 80%. The plasma-adjusted concentration can be effective to inhibit $\alpha v \beta_1$ by at least about 90%. The recitation "percentage of each of $\alpha v \beta_6$ and/or $\alpha v \beta_1$ in the subject, each percentage independently selected" means, in the alternative, a single $\alpha v \beta_6$ inhibitor and corresponding percentage, a single $\alpha v \beta_1$ inhibitor and corresponding percentage, or a dual $\alpha v \beta_6/\alpha v \beta_6$ inhibitor and corresponding independently selected percentages.

The dosage form for daily administration can be administered to an individual in need thereof once daily. That is, the total amount of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof, which is to be administered each day, can be administered all together at one time daily. Alternatively, if it is desirable that the total amount of a compound of formula (A), formula (I), or any variation thereof, e.g., a compound of formula (I-A), (I-B), (I-C), (I-D), (I-E), (I-F), (I-G), (I-H), (II), (II-A), (II-B), (II-C), (II-D), (II-E), (II-F), (II-G), or (II-H), a compound selected from Compound Nos. 1-780, or a stereoisomer thereof, or a pharmaceutically acceptable salt thereof, is to be administered in two or more portions daily, the dosage form containing the appropriate amount of compound can be administered two times or more daily, such as twice a day, three times a day, or four times a day.

Kits

The invention further provides kits for carrying out the methods of the invention, which comprises one or more compounds described herein, or a salt thereof, or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a fibrotic disease.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The kits may optionally further comprise instructions for daily administration of the dosage form to an individual in need thereof, such as instructions for administration of the dosage form to an individual in need thereof one, two, three, or four times daily, for example, instructions for administration of the dosage form to an individual in need thereof once daily.

General Procedures

Compounds provided herein may be prepared according to General Schemes, as exemplified by the General Procedures and Examples. Minor variations in temperatures, concentrations, reaction times, and other parameters can be made when following the General Procedures, which do not substantially affect the results of the procedures.

When a specific stereoisomer, or an unspecified stereoisomer, or a mixture of stereoisomers is shown in the following general procedures, it is understood that similar chemical transformations can be performed on other specific stereoisomers, or an unspecified stereoisomer, or mixtures thereof. For example, a hydrolysis reaction of a methyl (S)-4-amino-butanoate to an (S)-4-amino-butanoic acid can also be performed on a methyl (R)-4-amino-butanoate to prepare an (R)-4-amino-butanoic acid, or on a mixture of a methyl (S)-4-amino-butanoat and a methyl (R)-4-amino-butanoate to prepare a mixture of an (S)-4-amino-butanoic acid and an (R)-4-amino-butanoic acid.

Some of the following general procedures use specific compounds to illustrate a general reaction (e.g., deprotection of a compound having a Boc-protected amine to a compound having a deprotected amine using acid). The general reaction can be carried out on other specific compounds having the same functional group (e.g., a different compound having a protected amine where the Boc-protecting group can be removed using acid in the same manner) as long as such other specific compounds do not contain additional functional groups affected by the general reaction (i.e., such other specific compounds do not contain acid-sensitive functional groups), or if the effect of the general reaction on those additional functional groups is desired (e.g., such other specific compounds have another group that is affected by acid, and the effect of the acid on that other group is a desirable reaction).

Where specific reagents or solvents are specified for reactions in the general procedures, the skilled artisan will recognize that other reagents or solvents can be substituted as desired. For example, where hydrochloric acid is used to remove a Boc group, trifluoroacetic acid can be used instead. As another example, where HATU (1-[bis(dimethylamino)methylene]-1H-1,2,3-triazolo[4,5-b]pyridinium 3-oxide hexafluorophosphate) is used as a coupling reagent, BOP (benzotriazol-1-yloxytris(dimethylamino)phosphonium hexafluorophosphate) or PyBOP (benzotriazol-1-yloxytripyrrolidinophosphonium hexafluorophosphate) can be used instead.

General Procedure A

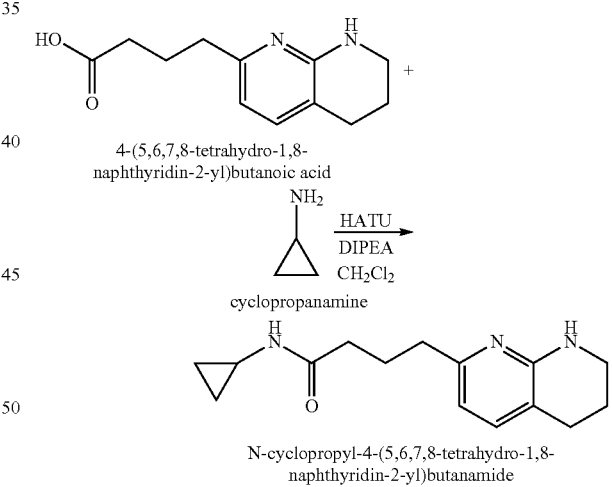

N-cyclopropyl-4-(5,6,7,8-tetrahydro-1,8-naphthyridin-2-yl)butanamide

To a mixture of 4-(5,6,7,8-tetrahydro-1,8-naphthyridin-2-yl)butanoic acid hydrochloride (5.0 g, 19.48 mmol) and cyclopropanamine (1.51 mL, 21.42 mmol) in $CH_2Cl_2$ (80 mL) at rt was added DIPEA (13.57 mL, 77.9 mmol). To this was then added HATU (8.1 g, 21.42 mmol) and the resulting mixture was stirred at rt for 2 hrs. The reaction mixture was concentrated in vacuo and purified by normal phase silica gel chromatography to give N-cyclopropyl-4-(5,6,7,8-tetrahydro-1,8-naphthyridin-2-yl)butanamide.

General Procedure B

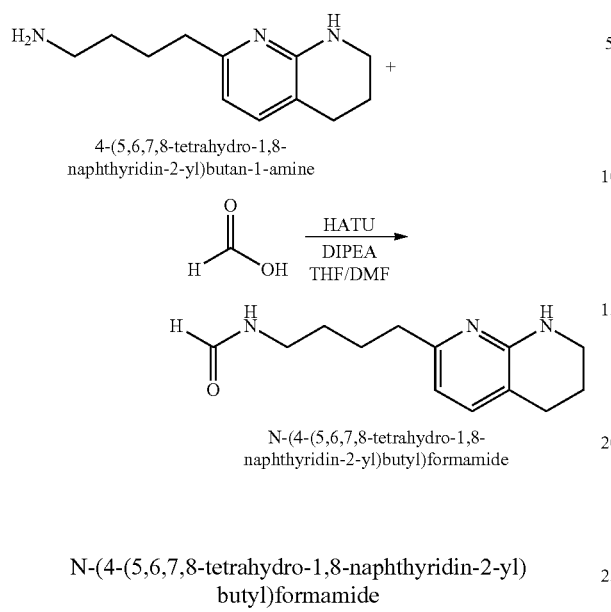

N-(4-(5,6,7,8-tetrahydro-1,8-naphthyridin-2-yl)butyl)formamide

To a mixture of 4-(5,6,7,8-tetrahydro-1,8-naphthyridin-2-yl)butan-1-amine (351 mg, 1.71 mmol) and formic acid (0.09 mL, 2.22 mmol) in 4:1 THF/DMF (5 mL) was added HATU (844 mg, 2.22 mmol) followed by DIPEA (0.89 mL, 5.13 mmol) and the reaction was allowed to stir at rt for 1 hr. The reaction mixture was concentrated in vacuo and purified by normal phase silica gel chromatography to give N-(4-(5,6,7,8-tetrahydro-1,8-naphthyridin-2-yl)butyl)formamide.

General Procedure C

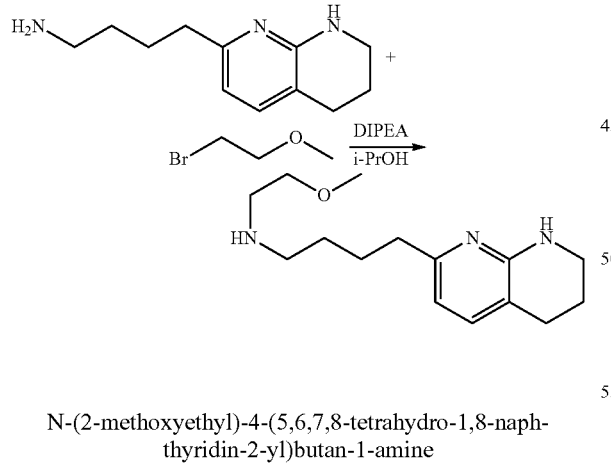

N-(2-methoxyethyl)-4-(5,6,7,8-tetrahydro-1,8-naphthyridin-2-yl)butan-1-amine

A mixture of 4-(5,6,7,8-tetrahydro-1,8-naphthyridin-2-yl)butan-1-amine (300 mg, 1.46 mmol), 1-bromo-2-methoxyethane (0.11 mL, 1.17 mmol) and DIPEA (0.25 mL, 1.46 mmol) in i-PrOH (3 mL) was heated to 70° C. for 18 hr. The reaction mixture was allowed to cool to rt and then concentrated in vacuo and purified by normal phase silica gel chromatography to give N-(2-methoxyethyl)-4-(5,6,7,8-tetrahydro-1,8-naphthyridin-2-yl)butan-1-amine.

General Procedure D

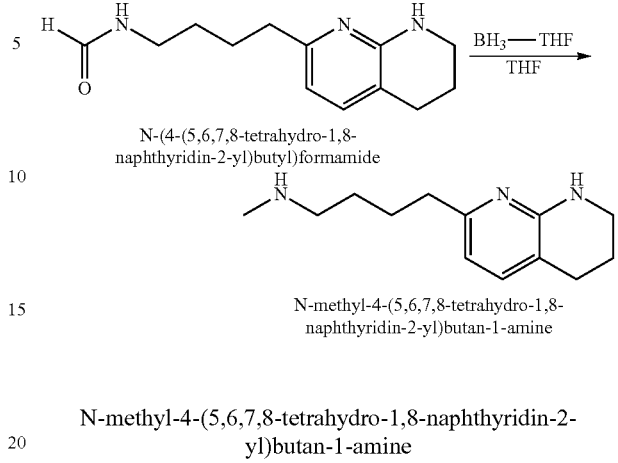

N-methyl-4-(5,6,7,8-tetrahydro-1,8-naphthyridin-2-yl)butan-1-amine

To a solution of N-(4-(5,6,7,8-tetrahydro-1,8-naphthyridin-2-yl)butyl)formamide (200 mg, 0.86 mmol) in THF (2 mL) at rt was added borane tetrahydrofuran complex solution (1.0M in THF, 4.0 mL, 4.0 mmol) dropwise. The resulting mixture was then heated to 60° C. for 2 hr and then allowed to cool to rt. The reaction mixture was diluted with MeOH and concentrated in vacuo. The crude residue was purified by normal phase silica gel chromatography to give N-methyl-4-(5,6,7,8-tetrahydro-1,8-naphthyridin-2-yl)butan-1-amine.

General Procedure E

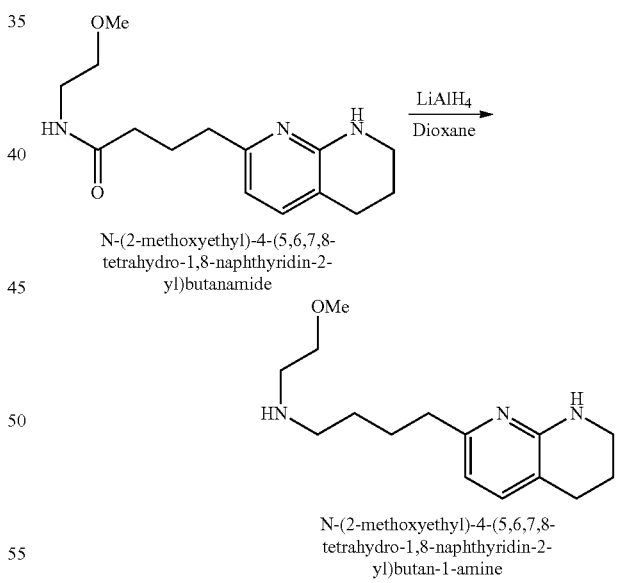

N-(2-methoxyethyl)-4-(5,6,7,8-tetrahydro-1,8-naphthyridin-2-yl)butan-1-amine (5)

To a solution of N-(2-methoxyethyl)-4-(5,6,7,8-tetrahydro-1,8-naphthyridin-2-yl)butanamide (15.5 g, 1.0 equiv) in 1,4-dioxane (124 mL) at rt was slowly added LiAlH$_4$ (1.0 M in THF, 123 mL, 2.2 equiv) and the resulting mixture was heated to reflux for 20 hours and then cooled to 0° C. To this solution was added H$_2$O (4.7 mL), then 1M NaOH (4.7 mL)

then H₂O (4.7 mL) and warmed to room temperature and stirred for 30 minutes, at which time, solid MgSO₄ was added and stirred for an additional 30 minutes. The resulting mixture was filtered and the filter cake was washed with THF. The filtrate were concentrated in vacuo to give N-(2-methoxyethyl)-4-(5,6,7,8-tetrahydro-1,8-naphthyridin-2-yl)butan-1-amine.

General Procedure F

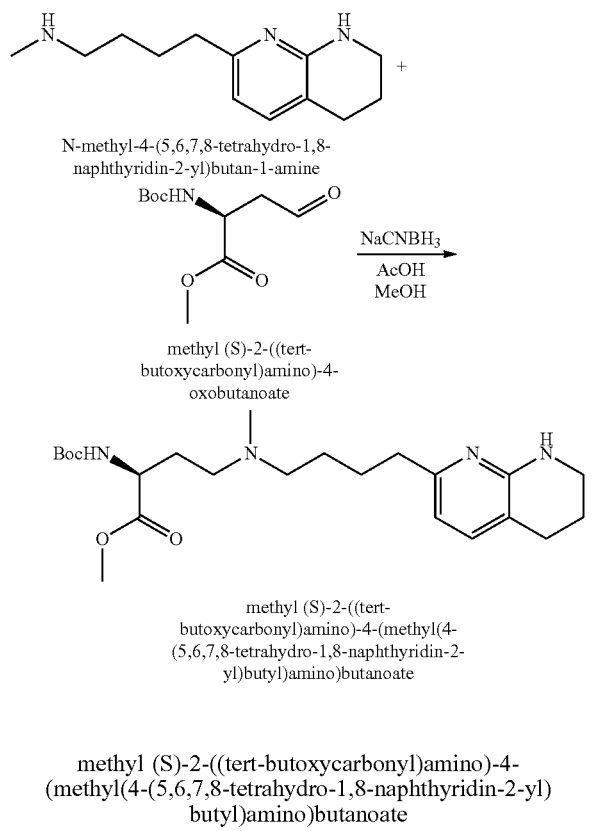

methyl (S)-2-((tert-butoxycarbonyl)amino)-4-(methyl(4-(5,6,7,8-tetrahydro-1,8-naphthyridin-2-yl)butyl)amino)butanoate To a mixture of N-methyl-4-(5,6,7,8-tetrahydro-1,8-naphthyridin-2-yl)butan-1-amine (5) (187 mg, 0.85 mmol) in MeOH (5 mL) at rt was added acetic acid (0.12 mL, 2.05 mmol) followed by methyl (S)-2-((tert-butoxycarbonyl)amino)-4-oxobutanoate (217 mg, 0.94 mmol). The resulting mixture was allowed to stir at rt for 15 min, at which time, sodium cyanoborohydride (80 mg, 1.28 mmol) was added to the reaction mixture and stirred for 30 min and then concentrated in vacuo. The crude residue was purified by normal phase silica gel chromatography to give methyl (S)-2-((tert-butoxycarbonyl)amino)-4-(methyl(4-(5,6,7,8-tetrahydro-1,8-naphthyridin-2-yl)butyl)amino)butanoate.

General Procedure G

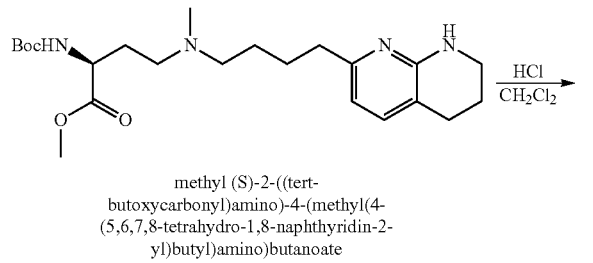

methyl (S)-2-((tert-butoxycarbonyl)amino)-4-(methyl(4-(5,6,7,8-tetrahydro-1,8-naphthyridin-2-yl)butyl)amino)butanoate

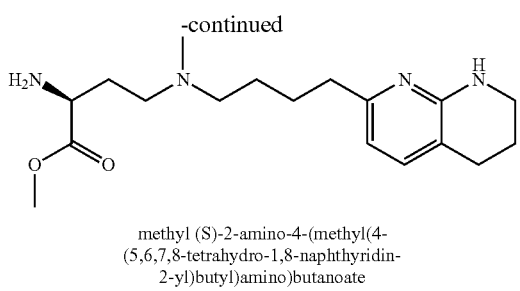

methyl (S)-2-amino-4-(methyl(4-(5,6,7,8-tetrahydro-1,8-naphthyridin-2-yl)butyl)amino)butanoate methyl (S)-2-amino-4-(methyl(4-(5,6,7,8-tetrahydro-1,8-naphthyridin-2-yl)butyl)amino)butanoate To a solution of methyl (S)-2-((tert-butoxycarbonyl)amino)-4-(methyl(4-(5,6,7,8-tetrahydro-1,8-naphthyridin-2-yl)butyl)amino)butanoate (152 mg, 0.35 mmol) in CH₂Cl₂ (2 mL) at rt was added 4N HCl in 1,4-dioxane (1 mL, 4 mmol) and the resulting mixture was allowed to stir for 2 hr. The reaction mixture was concentrated in vacuo to give methyl (S)-2-amino-4-(methyl(4-(5,6,7,8-tetrahydro-1,8-naphthyridin-2-yl)butyl)amino)butanoate as the trihydrochloride salt.

General Procedure H

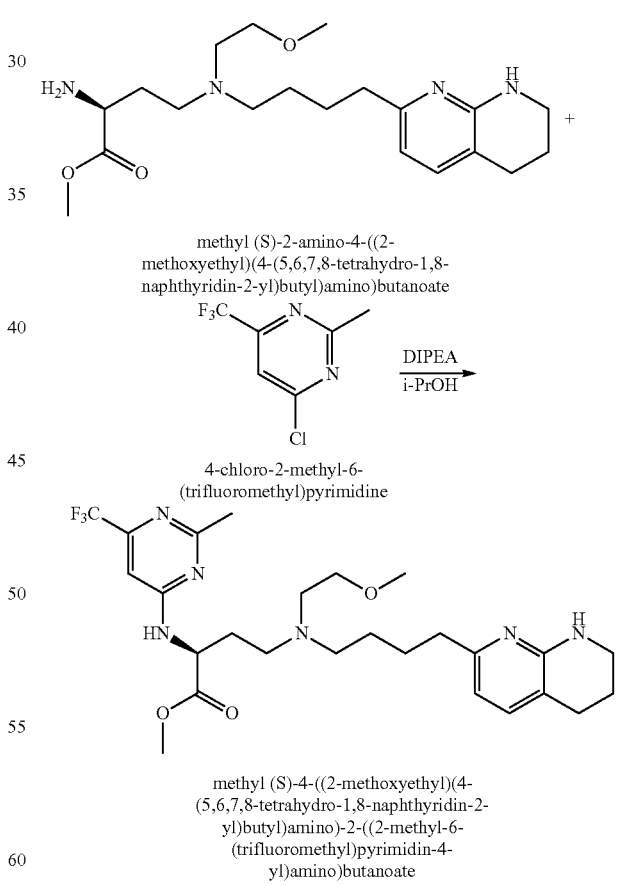

A solution of methyl (S)-2-amino-4-((2-methoxyethyl)(4-(5,6,7,8-tetrahydro-1,8-naphthyridin-2-yl)butyl)amino)butanoate trihydrochloride (80 mg, 0.16 mmol), 4-chloro-2-methyl-6-(trifluoromethyl)pyrimidine (64 mg, 0.33 mmol) and DIPEA (0.23 mL, 1.31 mmol) in i-PrOH (1 mL) was heated at 60° C. overnight. The reaction was allowed to cool to rt and then concentrated in vacuo. The resulting crude residue was purified by normal phase silica gel chromatography to give methyl (S)-4-((2-methoxyethyl)(4-(5,6,7,8-tetrahydro-1,8-naphthyridin-2-yl)butyl)amino)-2-((2-methyl-6-(trifluoromethyl)pyrimidin-4-yl)amino)butanoate.

General Procedure P

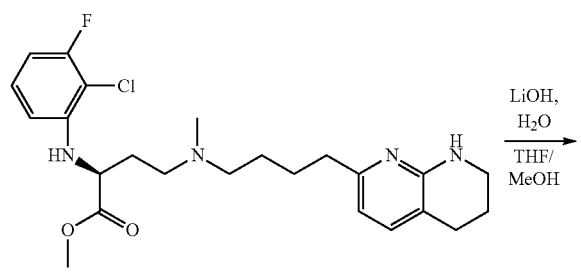

methyl (S)-2-((2-chloro-3-fluorophenyl)amino)-4-(methyl(4-(5,6,7,8-tetrahydro-1,8-naphthyridin-2-yl)butyl)amino)butanoate

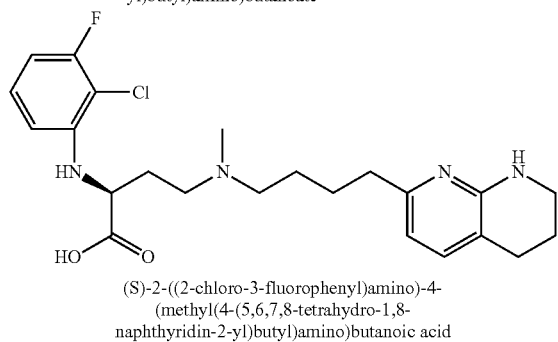

(S)-2-((2-chloro-3-fluorophenyl)amino)-4-(methyl(4-(5,6,7,8-tetrahydro-1,8-naphthyridin-2-yl)butyl)amino)butanoic acid

(S)-2-((2-chloro-3-fluorophenyl)amino)-4-(methyl(4-(5,6,7,8-tetrahydro-1,8-naphthyridin-2-yl)butyl)amino)butanoic acid To a solution of methyl (S)-2-((2-chloro-3-fluorophenyl)amino)-4-(methyl(4-(5,6,7,8-tetrahydro-1,8-naphthyridin-2-yl)butyl)amino)butanoate in 4:1:1 THF/MeOH/H₂O at rt was added lithium hydroxide (approximately four equivalents) and the resulting mixture was stirred for 30 min. The reaction mixture was concentrated in vacuo and the resulting crude residue purified by reverse phase HPLC to give (S)-2-((2-chloro-3-fluorophenyl)amino)-4-(methyl(4-(5,6,7,8-tetrahydro-1,8-naphthyridin-2-yl)butyl)amino)butanoic acid, as the trifluoroacetate salt.

General Procedure Q

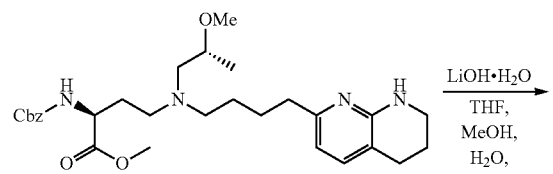

methyl (S)-2-(((benzyloxy)carbonyl)amino-4-(((R)-2-methoxypropyl)(4-(5,6,7,8-tetrahydro-1,8-naphthyridin-2-yl)butyl)amino)butanoate

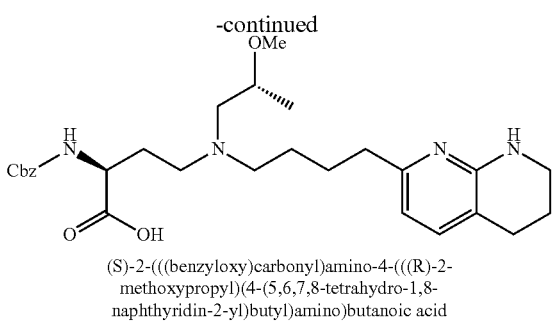

(S)-2-(((benzyloxy)carbonyl)amino-4-(((R)-2-methoxypropyl)(4-(5,6,7,8-tetrahydro-1,8-naphthyridin-2-yl)butyl)amino)butanoic acid (S)-2-(((benzyloxy)carbonyl)amino)-4-(((R)-2-methoxypropyl)(4-(5,6,7,8-tetrahydro-1,8-naphthyridin-2-yl)butyl)amino)butanoic acid. A mixture of methyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate (1 g, 1.90 mmol) in H₂O (3 mL) and THF (3 mL) and MeOH (3 mL) was added LiOH.H₂O (159.36 mg, 3.80 mmol) and then the mixture was stirred at room temperature for 1 h and the resulting mixture was concentrated in vacuo. The mixture was adjusted to pH=6 by AcOH (2 mL) and the residue was concentrated in vacuo to give a residue to yield compound (S)-2-(((benzyloxy)carbonyl)amino)-4-(((R)-2-methoxypropyl)(4-(5,6,7,8-tetrahydro-1,8-naphthyridin-2-yl)butyl)amino)butanoic acid.

LCMS (ESI+): m/z=513.5 (M+H)⁺. ¹H NMR (400 MHz, DMSO-d): δ ppm 7.25-7.37 (m, 5H) 7.00 (d, J=7.28 Hz, 1H) 6.81 (br d, J=7.50 Hz, 1H) 6.22 (d, J=7.28 Hz, 1H₆) 4.93-5.05 (m, 2H) 3.68-3.77 (m, 1H) 3.25-3.34 (m, 1H) 3.15-3.24 (m, 5H) 2.58 (br t, J=6.06 Hz, 2H) 2.29-2.49 (m, 8H) 2.16 (br dd, J=12.90, 6.06 Hz, 1H) 1.69-1.78 (m, 2H) 1.58-1.68 (m, 1H) 1.53 (quin, J=7.39 Hz, 2H) 1.28-1.40 (m, 2H) 1.00 (d, J=5.95 Hz, 3H).

General Procedure R

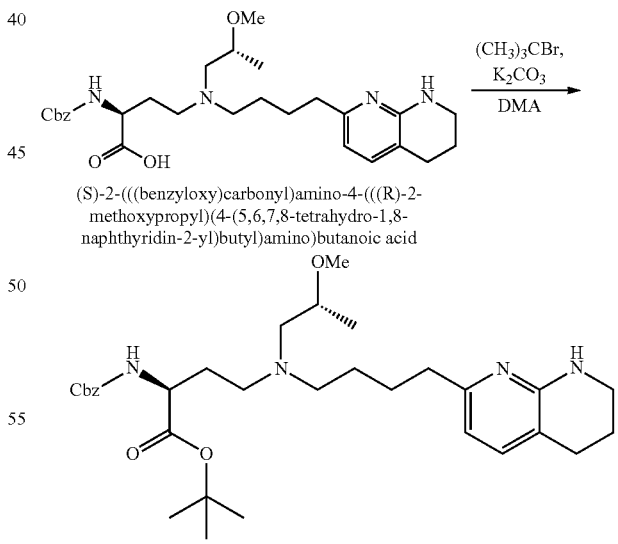

tert-butyl (S)-2-(((benzyloxy)carbonyl)amino-4-(((R)-2-methoxypropyl)(4-(5,6,7,8-tetrahydro-1,8-naphthyridin-2-yl)butyl)amino)butanoate tert-butyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate: A solution of (S)-2-(((benzyloxy)

carbonyl)amino)-4-(((R)-2-methoxypropyl)(4-(5,6,7,8-tetrahydro-1,8-naphthyridin-2-yl)butyl)amino)butanoic acid (300 mg, 523.84 umol, HOAc salt) in DMA (4 mL) was added N-benzyl-N,N-diethylethanaminium chloride (119.32 mg 523.84 umol), K₂CO₃ (1.88 g, 13.62 mmol), 2-bromo-2-methylpropane (3.45 g, 25.14 mmol). The mixture was stirred for 18 h at the 55° C. and then allowed to cool to room temperature. The reaction mixture was concentrated in vacuo and the aqueous phase was extracted with ethyl acetate. The combined organic extracts were washed with brine, dried over Na₂SO₄, filtered, and concentrated in vacuo. The crude residue was purified by prep-TLC to give tert-butyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate. LCMS (ESI+): m/z=569.3 (M+H)⁺.

General Procedure S

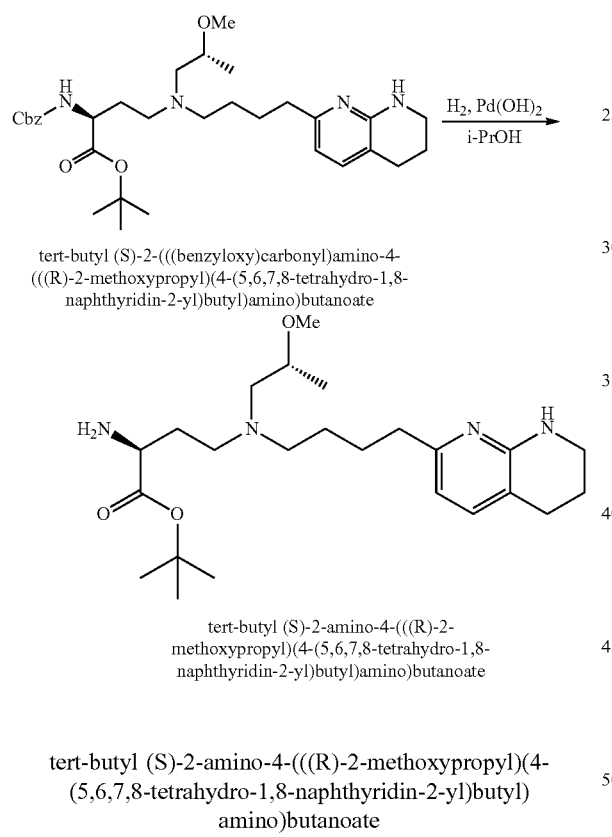

tert-butyl (S)-2-(((benzyloxy)carbonyl)amino-4-(((R)-2-methoxypropyl)(4-(5,6,7,8-tetrahydro-1,8-naphthyridin-2-yl)butyl)amino)butanoate tert-butyl (S)-2-amino-4-(((R)-2-methoxypropyl)(4-(5,6,7,8-tetrahydro-1,8-naphthyridin-2-yl)butyl)amino)butanoate To a solution of tert-butyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate (107 mg, 188.13 umol) in i-PrOH (2 mL) was added Pd(OH)₂ (26 mg) under an N₂ atmosphere. The suspension was degassed under vacuum and purged with H₂ several times. The mixture was stirred under H₂ (15 psi) at room temperature for 15 h. The mixture was filtered and concentrated in vacuo to give tert-butyl (S)-2-amino-4-(((R)-2-methoxypropyl)(4-(5,6,7,8-tetrahydro-1,8-naphthyridin-2-yl)butyl)amino)butanoate. LCMS (ESI+): m/z=435.5 (M+H)⁺. ¹H NMR (400 MHz, CDCl₃): δ ppm 7.06 (d, J=7.34 Hz, 1H) 6.34 (d, J=7.34 Hz, 1H) 4.98 (br s, 1H) 3.38-3.44 (m, 4H) 3.34 (s, 3H) 2.69 (t, J=6.30 Hz, 2H) 2.51-2.59 (m, 5H) 2.31 (dd, J=13.39, 5.56 Hz, 1H) 1.86-1.94 (m, 5H) 1.49-1.69 (m, 6H) 1.47 (s, 9H) 1.13 (d, J=6.11 Hz, 3H).

General Procedure T

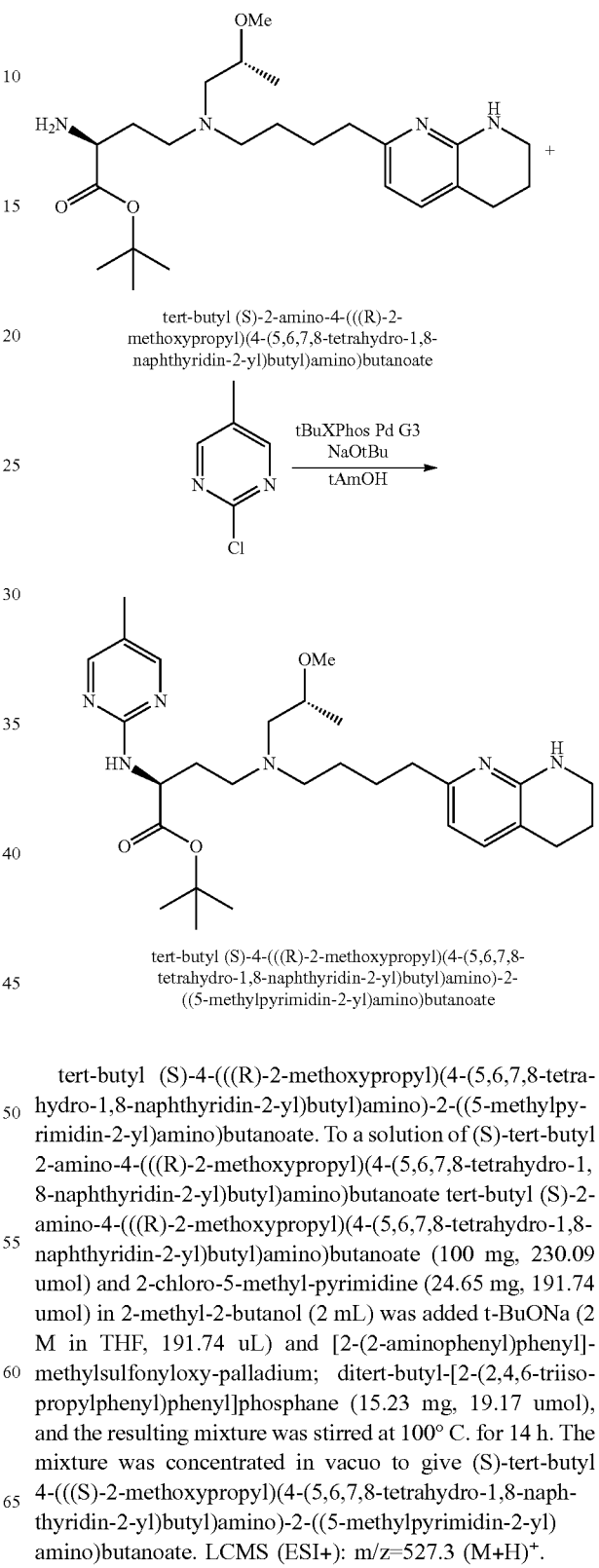

tert-butyl (S)-2-amino-4-(((R)-2-methoxypropyl)(4-(5,6,7,8-tetrahydro-1,8-naphthyridin-2-yl)butyl)amino)butanoate tert-butyl (S)-4-(((R)-2-methoxypropyl)(4-(5,6,7,8-tetrahydro-1,8-naphthyridin-2-yl)butyl)amino)-2-((5-methylpyrimidin-2-yl)amino)butanoate tert-butyl (S)-4-(((R)-2-methoxypropyl)(4-(5,6,7,8-tetrahydro-1,8-naphthyridin-2-yl)butyl)amino)-2-((5-methylpyrimidin-2-yl)amino)butanoate. To a solution of (S)-tert-butyl 2-amino-4-(((R)-2-methoxypropyl)(4-(5,6,7,8-tetrahydro-1,8-naphthyridin-2-yl)butyl)amino)butanoate tert-butyl (S)-2-amino-4-(((R)-2-methoxypropyl)(4-(5,6,7,8-tetrahydro-1,8-naphthyridin-2-yl)butyl)amino)butanoate (100 mg, 230.09 umol) and 2-chloro-5-methyl-pyrimidine (24.65 mg, 191.74 umol) in 2-methyl-2-butanol (2 mL) was added t-BuONa (2 M in THF, 191.74 uL) and [2-(2-aminophenyl)phenyl]-methylsulfonyloxy-palladium; ditert-butyl-[2-(2,4,6-triisopropylphenyl)phenyl]phosphane (15.23 mg, 19.17 umol), and the resulting mixture was stirred at 100° C. for 14 h. The mixture was concentrated in vacuo to give (S)-tert-butyl 4-(((S)-2-methoxypropyl)(4-(5,6,7,8-tetrahydro-1,8-naphthyridin-2-yl)butyl)amino)-2-((5-methylpyrimidin-2-yl)amino)butanoate. LCMS (ESI+): m/z=527.3 (M+H)⁺.

General Procedure U

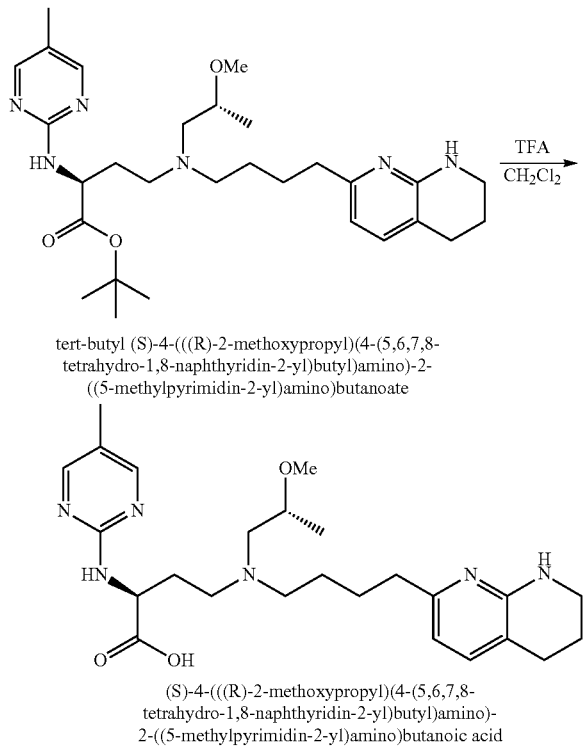

tert-butyl (S)-4-(((R)-2-methoxypropyl)(4-(5,6,7,8-tetrahydro-1,8-naphthyridin-2-yl)butyl)amino)-2-((5-methylpyrimidin-2-yl)amino)butanoate (S)-4-(((R)-2-methoxypropyl)(4-(5,6,7,8-tetrahydro-1,8-naphthyridin-2-yl)butyl)amino)-2-((5-methylpyrimidin-2-yl)amino)butanoic acid (S)-4-(((R)-2-methoxypropyl)(4-(5,6,7,8-tetrahydro-1,8-naphthyridin-2-yl)butyl)amino)-2-((5-methylpyrimidin-2-yl)amino)butanoic acid. To a solution of tert-butyl (S)-4-(((R)-2-methoxypropyl)(4-(5,6,7,8-tetrahydro-1,8-naphthyridin-2-yl)butyl)amino)-2-((5-methylpyrimidin-2-yl)amino)butanoate (80 mg, 151.89 umol) in DCM (2 mL) was added TFA (254.14 mg, 2.23 mmol) at 0° C. The mixture was stirred at room temperature for 6 h. The mixture was concentrated in vacuo and the resulting crude residue was purified by prep-HPLC to give compound (S)-4-(((R)-2-methoxypropyl)(4-(5,6,7,8-tetrahydro-1,8-naphthyridin-2-yl)butyl)amino)-2-((5-methylpyrimidin-2-yl)amino)butanoic acid. LCMS (ESI+): m/z=471.2 (M+H)+. $^1$H NMR (400 MHz, Methanol-$d_4$) δ ppm 8.57 (br s, 2H) 7.60 (d, J=7.28 Hz, 1H) 6.67 (d, J=7.28 Hz, 1H) 4.81-4.86 (m, 1H) 3.86 (br s, 1H) 3.41-3.59 (m, 4H) 3.39 (s, 3H) 3.33-3.38 (m, 1H) 3.12-3.30 (m, 3H) 2.76-2.86 (m, 4H) 2.54 (br s, 1H) 2.39 (br d, J=8.82 Hz, 1H) 2.30 (s, 3H) 1.76-1.99 (m, 6H) 1.22 (d, J=5.95 Hz, 3H).

ENUMERATED EMBODIMENTS

The following enumerated embodiments are representative of some aspects of the invention.

Embodiment 1

A compound of formula (I)

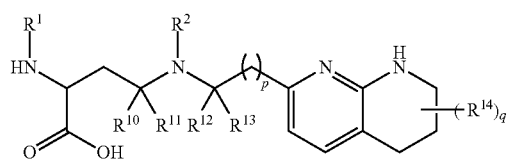

(I)

or a salt thereof, wherein:
$R^1$ is $C_6$-$C_{14}$ aryl or 5- to 10-membered heteroaryl wherein the $C_6$-$C_{14}$ aryl and 5- to 10-membered heteroaryl are optionally substituted by $R^{1a}$;
$R^2$ is $C_1$-$C_6$ alkyl optionally substituted by $R^{2a}$; $C_3$-$C_6$ cycloalkyl optionally substituted by $R^{2b}$; 3- to 12-membered heterocyclyl optionally substituted by $R^{2c}$; or —$S(O)_2R^{2d}$;
each $R^{1a}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, deuterium, halogen, —CN, —$OR^3$, —$SR^3$, —$NR^4R^5$, —$NO_2$, —C=NH($OR^3$), —C(O)$R^3$, —OC(O)$R^3$, —C(O)$OR^3$, —C(O)$NR^4R^5$, —$NR^3$C(O)$R^4$, —$NR^3$C(O)$OR^4$, —$NR^3$C(O)$NR^4R^5$, —S(O)$R^3$, —$S(O)_2R^3$, —$NR^3$S(O)$R^4$, —$NR^3$S(O)$_2R^4$, —$S(O)NR^4R^5$, —$S(O)_2NR^4R^5$, or —P(O)($OR^4$)($OR^5$), wherein each $R^{1a}$ is, where possible, independently optionally substituted by deuterium, halogen, oxo, —$OR^6$, —$NR^6R^7$, —C(O)$R^6$, —CN, —S(O)$R^6$, —$S(O)_2R^6$, —P(O)($OR^6$)($OR^7$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by deuterium, oxo, —OH or halogen;
each $R^{2a}$, $R^{2b}$, $R^{2c}$, $R^{2e}$, and $R^{2f}$ is independently oxo or $R^{1a}$;
$R^{2d}$ is $C_1$-$C_6$ alkyl optionally substituted by $R^{2e}$ or $C_3$-$C_5$ cycloalkyl optionally substituted by $R^{2f}$;
$R^3$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^3$ are independently optionally substituted by halogen, deuterium, oxo, —CN, —$OR^8$, —$NR^8R^9$, —P(O)($OR^8$)($OR^9$), or $C_1$-$C_6$ alkyl optionally substituted by deuterium, halogen, —OH or oxo;
$R^4$ and $R^5$ are each independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^4$ and $R^5$ are independently optionally substituted by deuterium, halogen, oxo, —CN, —$OR^8$, —$NR^8R^9$ or $C_1$-$C_6$ alkyl optionally substituted by deuterium, halogen, —OH or oxo;
or $R^4$ and $R^5$ are taken together with the atom to which they attached to form a 3- to 6-membered heterocyclyl optionally substituted by deuterium, halogen, oxo, —$OR^8$, —$NR^8R^9$ or $C_1$-$C_6$ alkyl optionally substituted by deuterium, halogen, oxo or —OH;
$R^6$ and $R^7$ are each independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;
or $R^6$ and $R^7$ are taken together with the atom to which they attached to form a 3- to 6-membered heterocyclyl optionally substituted by deuterium, halogen, oxo or $C_1$-$C_6$ alkyl optionally substituted by deuterium, halogen, or oxo;
$R^8$ and $R^9$ are each independently hydrogen, deuterium, $C_1$-$C_6$ alkyl optionally substituted by deuterium, halogen, or oxo, $C_2$-$C_6$ alkenyl optionally substituted by deuterium, halogen or oxo, or $C_2$-$C_6$ alkynyl optionally substituted by deuterium, halogen, or oxo;

or $R^8$ and $R^9$ are taken together with the atom to which they attached to form a 3-6 membered heterocyclyl optionally substituted by deuterium, halogen, oxo or $C_1$-$C_6$ alkyl optionally substituted by deuterium, oxo, or halogen;

each $R^{10}$, $R^{11}$, $R^{12}$ and $R^{13}$ are independently hydrogen or deuterium;

$R^{14}$ is deuterium;

q is 0, 1, 2, 3, 4, 5, 6, 7, or 8 and p is 3, 4, 5, 6, 7, 8, or 9.

Embodiment 2

The compound of embodiment 1, or a salt thereof, wherein at least one of $R^{1a}$, $R^{2a}$, $R^{2b}$, $R^{2c}$, $R^{2e}$, $R^{2f}$, $R^3$, $R^4$, $R^5$, $R^6$, $R^7$, $R^8$, $R^9$, $R^{10}$, $R^{11}$, $R^{12}$, $R^{13}$, or $R^{14}$ is deuterium.

Embodiment 3

The compound of embodiment 1 or a salt thereof, wherein $R^{10}$, $R^{11}$, $R^{12}$, $R^{13}$, and $R^{14}$ are hydrogen; p is 3; and is represented by the compound of formula (II):

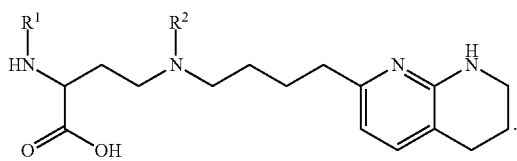

(II)

Embodiment 4

The compound of embodiment 1, 2, or 3, or a salt thereof, wherein $R^1$ is 5- to 10-membered heteroaryl optionally substituted by $R^{1a}$.

Embodiment 5

The compound of embodiment 1, 2, or 3, or a salt thereof, wherein $R^1$ is pyrimidin-4-yl optionally substituted by $R^{1a}$.

Embodiment 6

The compound of embodiment 1, 2, or 3, or a salt thereof, wherein $R^1$ is pyrimidin-4-yl optionally substituted by $R^{1a}$ wherein $R^{1a}$ is 5- to 10-membered heteroaryl or $C_1$-$C_6$ alkyl optionally substituted by halogen.

Embodiment 7

The compound of embodiment 1, 2, or 3, or a salt thereof, wherein $R^1$ is pyrimidin-4-yl optionally substituted by pyrazolyl, methyl, difluoromethyl, or trifluoromethyl.

Embodiment 8

The compound of embodiment 1, 2, or 3, or a salt thereof, wherein $R^1$ is pyrimidin-4-yl substituted by both methyl and trifluoromethyl.

Embodiment 9

The compound of embodiment 1, 2, or 3, or a salt thereof, wherein R is quinazolin-4-yl optionally substituted by $R^{1a}$.

Embodiment 10

The compound of embodiment 1, 2, or 3, or a salt thereof, wherein $R^1$ is quinazolin-4-yl optionally substituted by halogen, $C_1$-$C_6$ alkyl optionally substituted by halogen, or $C_1$-$C_6$ alkoxy.

Embodiment 11

The compound of embodiment 1, 2, or 3, or a salt thereof, wherein $R^1$ is quinazolin-4-yl optionally substituted by fluoro, chloro, methyl, trifluoromethyl or methoxy.

Embodiment 12

The compound of any one of embodiments 1 to 11, or a salt thereof, wherein $R^2$ is $C_1$-$C_6$ alkyl optionally substituted by $R^{2a}$.

Embodiment 13

The compound of any one of embodiments 1 to 11, or a salt thereof, wherein $R^2$ is $C_1$-$C_6$ alkyl optionally substituted by $R^{2a}$ wherein $R^{2a}$ is: halogen; $C_3$-$C_8$ cycloalkyl optionally substituted by halogen; 5- to 10-membered heteroaryl optionally substituted by $C_1$-$C_6$ alkyl; —$NR^4R^5$; —$NR^3C(O)R^4$; —$S(O)_2R^3$; or oxo.

Embodiment 14

The compound of any one of embodiments 1 to 11, or a salt thereof, wherein $R^2$ is $C_1$-$C_6$ alkyl optionally substituted by $R^{2a}$ wherein $R^{2a}$ is: fluoro; cyclobutyl substituted by fluoro; pyrazolyl substituted by methyl; or —$S(O)_2CH_3$.

Embodiment 15

The compound of any one of embodiments 1 to 11, or a salt thereof, wherein $R^2$ is $C_1$-$C_6$ alkyl optionally substituted by —$OR^3$.

Embodiment 16

The compound of any one of embodiments 1 to 11, or a salt thereof, wherein $R^2$ is $C_1$-$C_6$ alkyl optionally substituted by —$OR^3$, and $R^3$ is: hydrogen; $C_1$-$C_6$ alkyl optionally substituted by halogen; $C_3$-$C_6$ cycloalkyl optionally substituted by halogen; $C_6$-$C_{14}$ aryl optionally substituted by halogen; or 5- to 6-membered heteroaryl optionally substituted by halogen or $C_1$-$C_6$ alkyl.

Embodiment 17

The compound of any one of embodiments 1 to 11, or a salt thereof, wherein $R^2$ is $C_1$-$C_6$ alkyl optionally substituted by —$OR^3$, and $R^3$ is: hydrogen; methyl; ethyl; difluoromethyl; —$CH_2CHF_2$; —$CH_2CF_3$; cyclopropyl substituted by fluoro; phenyl optionally substituted by fluoro; or pyridinyl optionally substituted by fluoro or methyl.

Embodiment 18

The compound of any one of embodiments 1 to 11, wherein $R^2$ is —$CH_2CH_2OCH_3$.

Embodiment 19

The compound of any one of embodiments 1 to 11, or a salt thereof, wherein $R^2$ is $C_1$-$C_6$ alkyl substituted by both halogen and $OR^3$, wherein $R^3$ is $C_1$-$C_6$ alkyl.

Embodiment 20

The compound of any one of embodiments 1 to 11, or a salt thereof, wherein $R^2$ is $C_3$-$C_6$ cycloalkyl optionally substituted by $R^{2b}$.

Embodiment 21

The compound of any one of embodiments 1 to 11, or a salt thereof, wherein $R^2$ is cyclopropyl.

Embodiment 22

The compound of embodiment 1, 2, or 3, or a salt thereof, wherein $R^1$

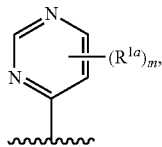

wherein m is 0, 1, 2, or 3 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 23

The compound of embodiment 22, or a salt thereof, wherein $R^1$ is

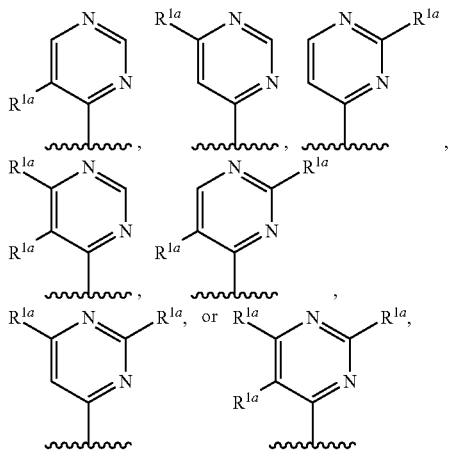

wherein each $R^{1a}$ is independently deuterium, alkyl, haloalkyl, or heteroaryl.

Embodiment 24

The compound of embodiment 1, 2, or 3, or a salt thereof, wherein $R^1$ is

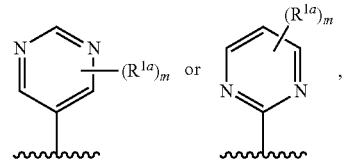

wherein m is 0, 1, 2, or 3 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 25

The compound of embodiment 1, 2, or 3, or a salt thereof, wherein $R^1$ is

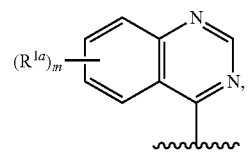

wherein m is 0, 1, 2, 3, 4, or 5 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 26

The compound of embodiment 25, or a salt thereof, wherein $R^1$ is

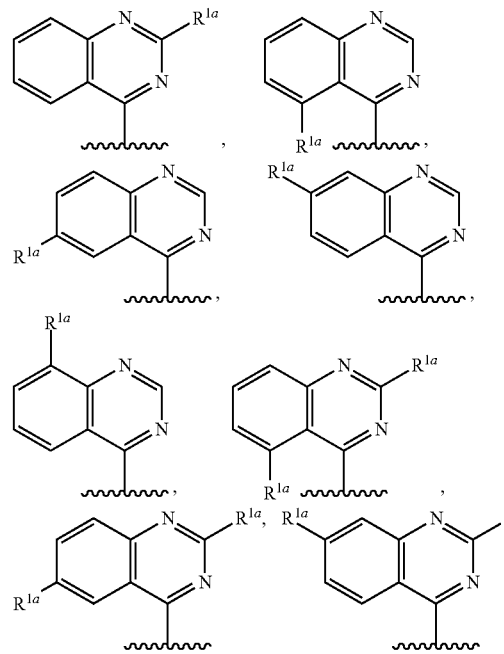

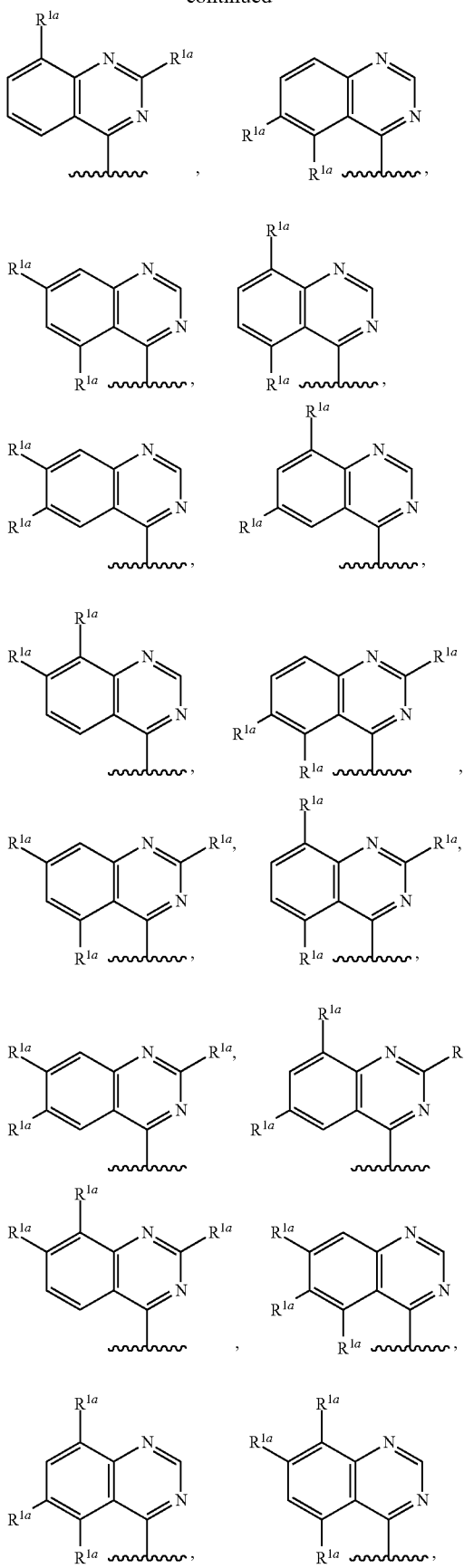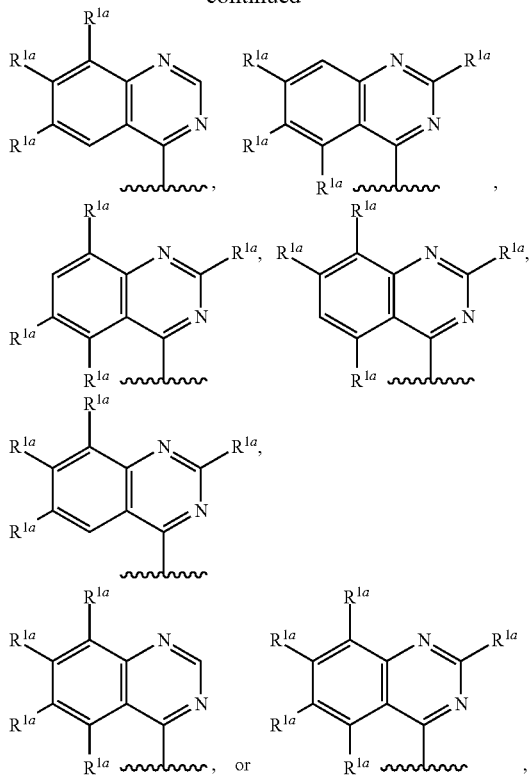
wherein each $R^{1a}$ is independently deuterium, halogen, alkyl, haloalkyl, or alkoxy.
Embodiment 27
The compound of embodiment 1, 2, or 3, or a salt thereof, wherein $R^1$ is
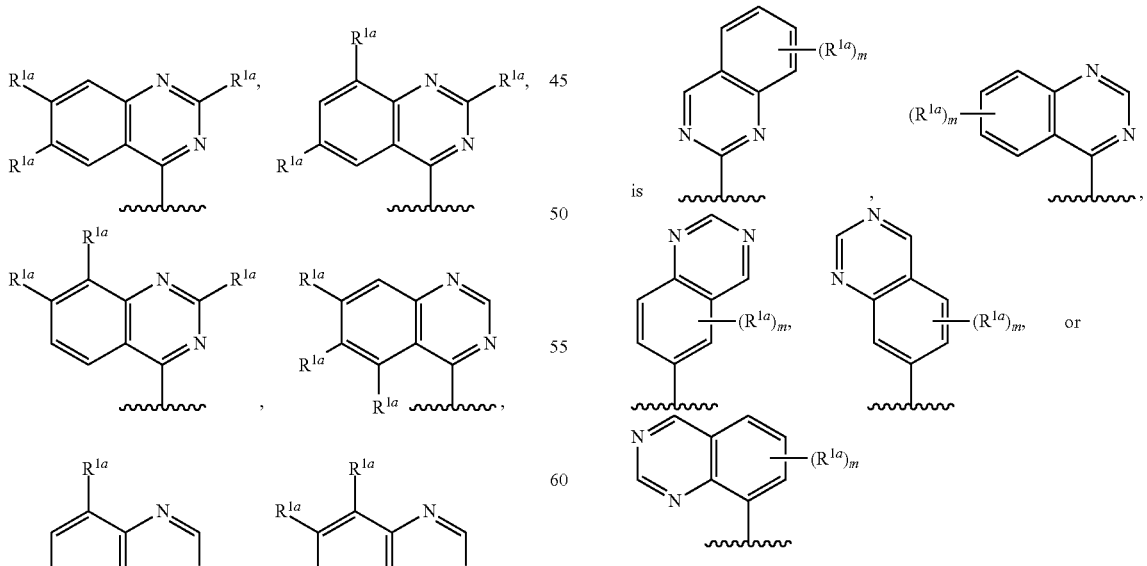
wherein m is 0, 1, 2, 3, 4, or 5 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 28

The compound of embodiment 1, 2, or 3, or a salt thereof, wherein $R^1$ is

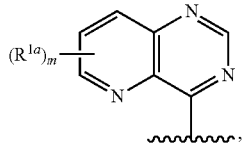

wherein m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 29

The compound of embodiment 28, or a salt thereof, wherein $R^1$ is selected from the group consisting of

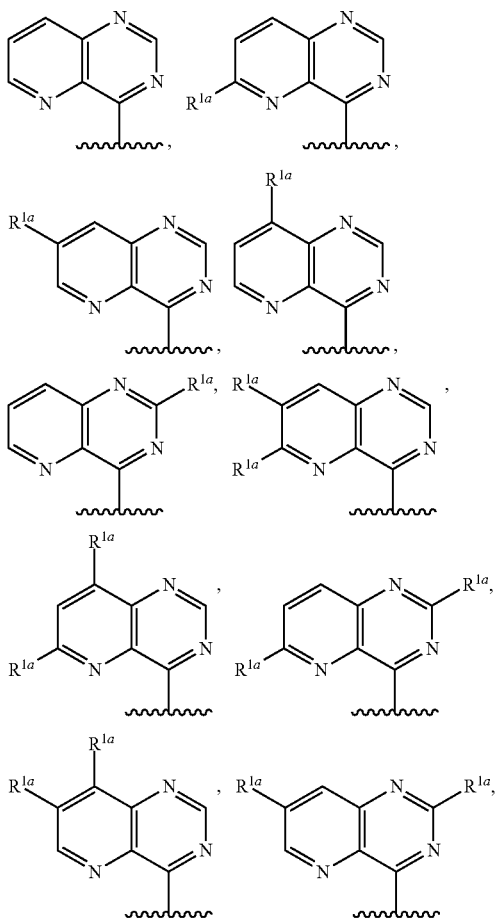

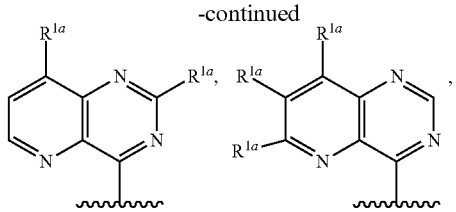

-continued

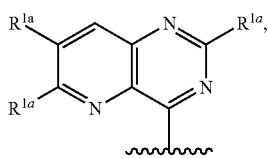

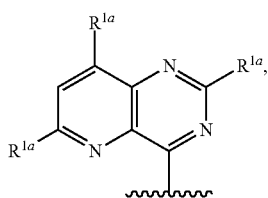

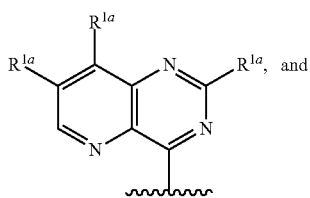

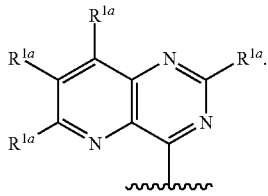

Embodiment 30

The compound of embodiment 1, 2, or 3, or a salt thereof, wherein $R^1$ is

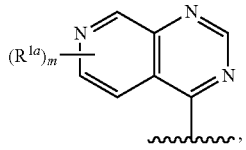

wherein m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 31

The compound of embodiment 30, or a salt thereof, wherein $R^1$ is selected from the group consisting of

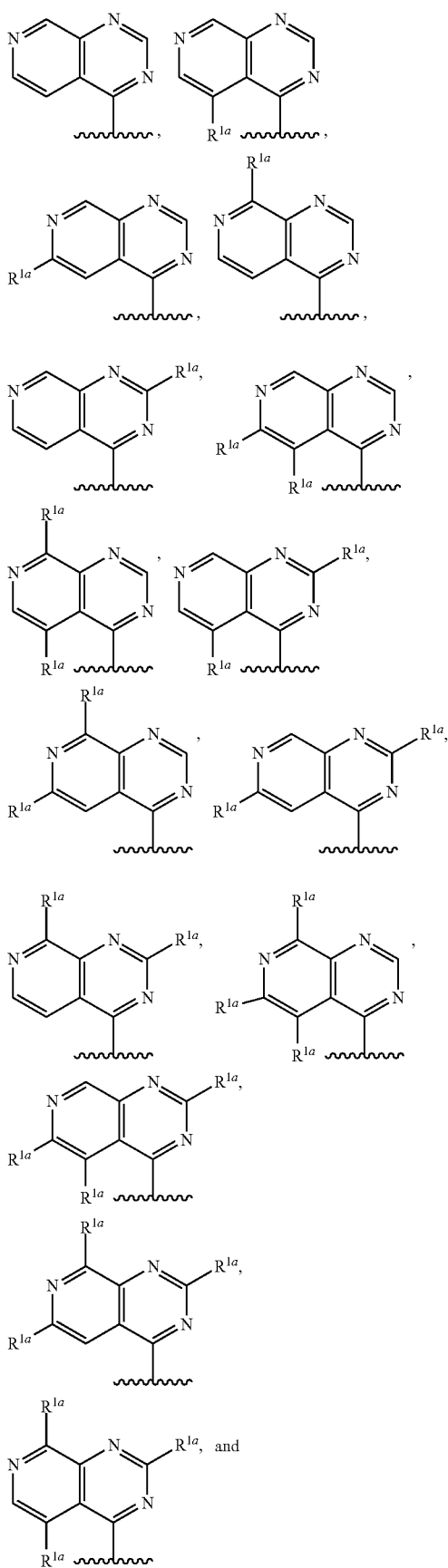

-continued

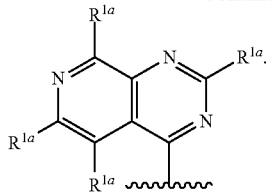

Embodiment 32

The compound of embodiment 1, 2, or 3, or a salt thereof, wherein $R^1$ is

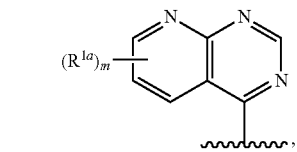

wherein m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 33

The compound of embodiment 32, or a salt thereof, wherein $R^1$ is selected from the group consisting of

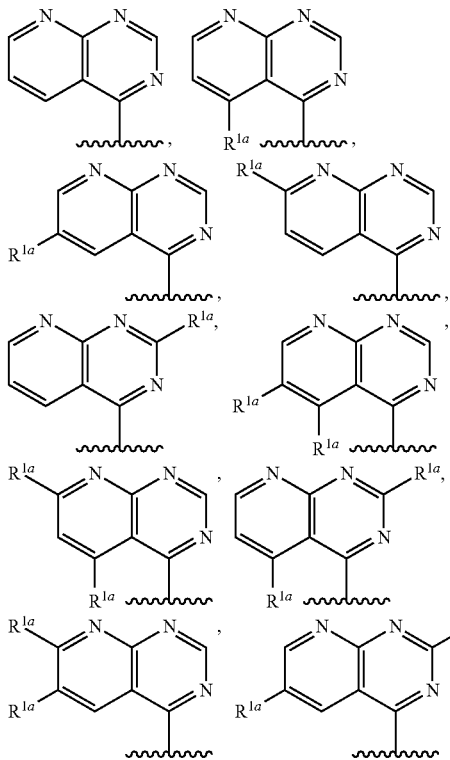

-continued

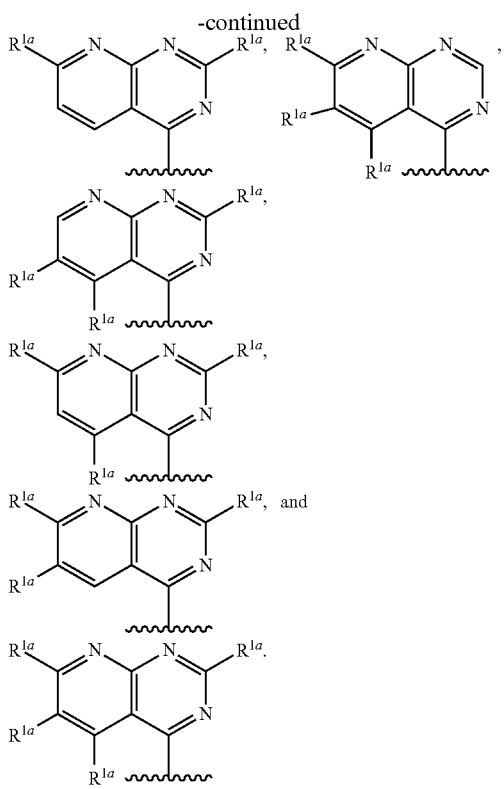

Embodiment 34

The compound of embodiment 1, 2, or 3, or a salt thereof, wherein $R^1$ is

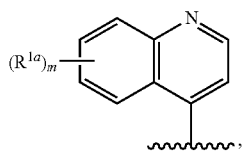

wherein m is 0, 1, 2, 3, 4, 5, or 6 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 35

The compound of embodiment 1, 2, or 3, or a salt thereof, wherein $R^1$ is

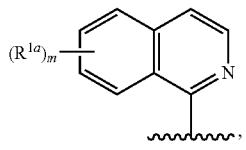

wherein m is 0, 1, 2, 3, 4, 5, or 6 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 36

The compound of embodiment 1, 2, or 3, or a salt thereof, wherein $R^1$ is

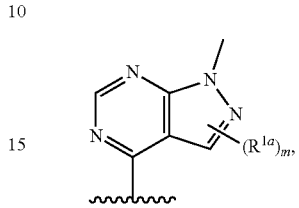

wherein m is 0, 1, or 2 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

Embodiment 37

The compound of embodiment 1, 2, or 3, or a salt thereof, wherein $R^1$ is selected from the group consisting of

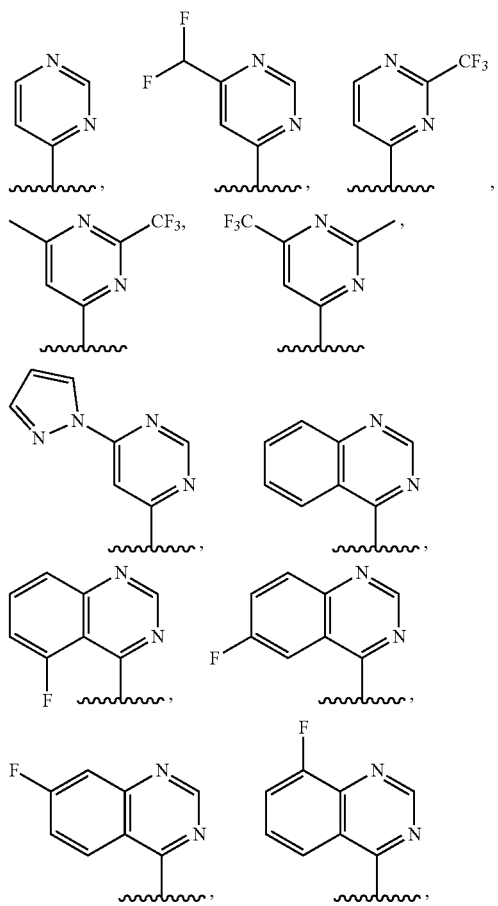

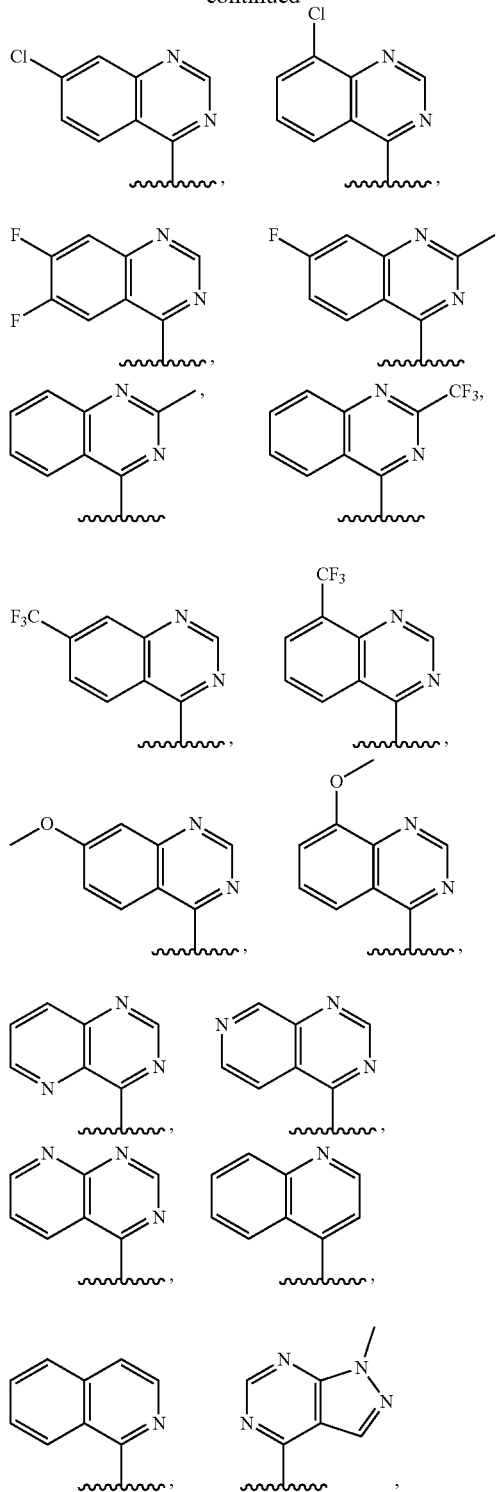
and any of the foregoing groups wherein any one or more hydrogen atom(s) are replaced with deuterium atom(s).
Embodiment 38
The compound of embodiment 1, 2, or 3, or a salt thereof, wherein R¹ is selected from the group consisting of
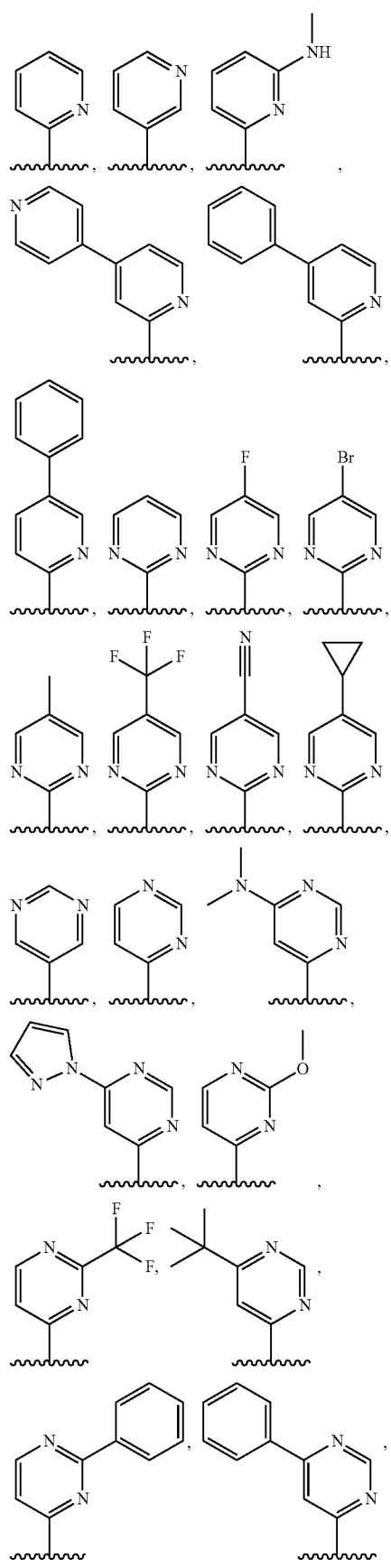

-continued
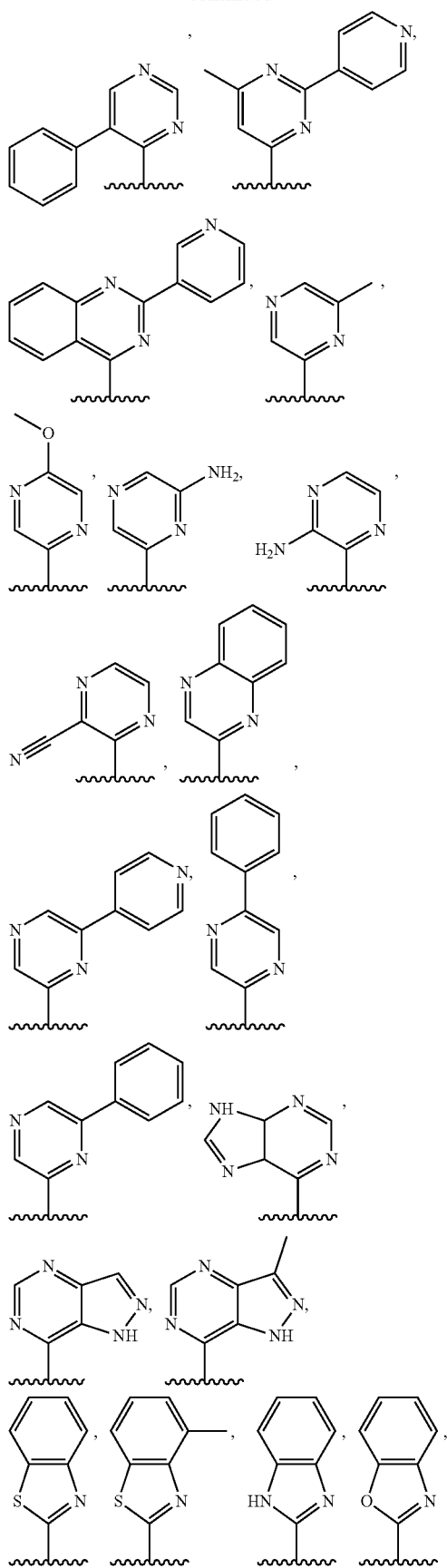
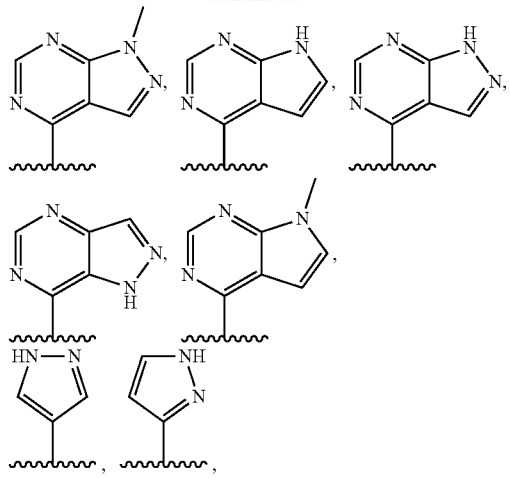
and any of the foregoing groups wherein any one or more hydrogen atom(s) are replaced with deuterium atom(s).
Embodiment 39
The compound of embodiment 1, 2, or 3, or a salt thereof, wherein $R^1$ is selected from the group consisting of
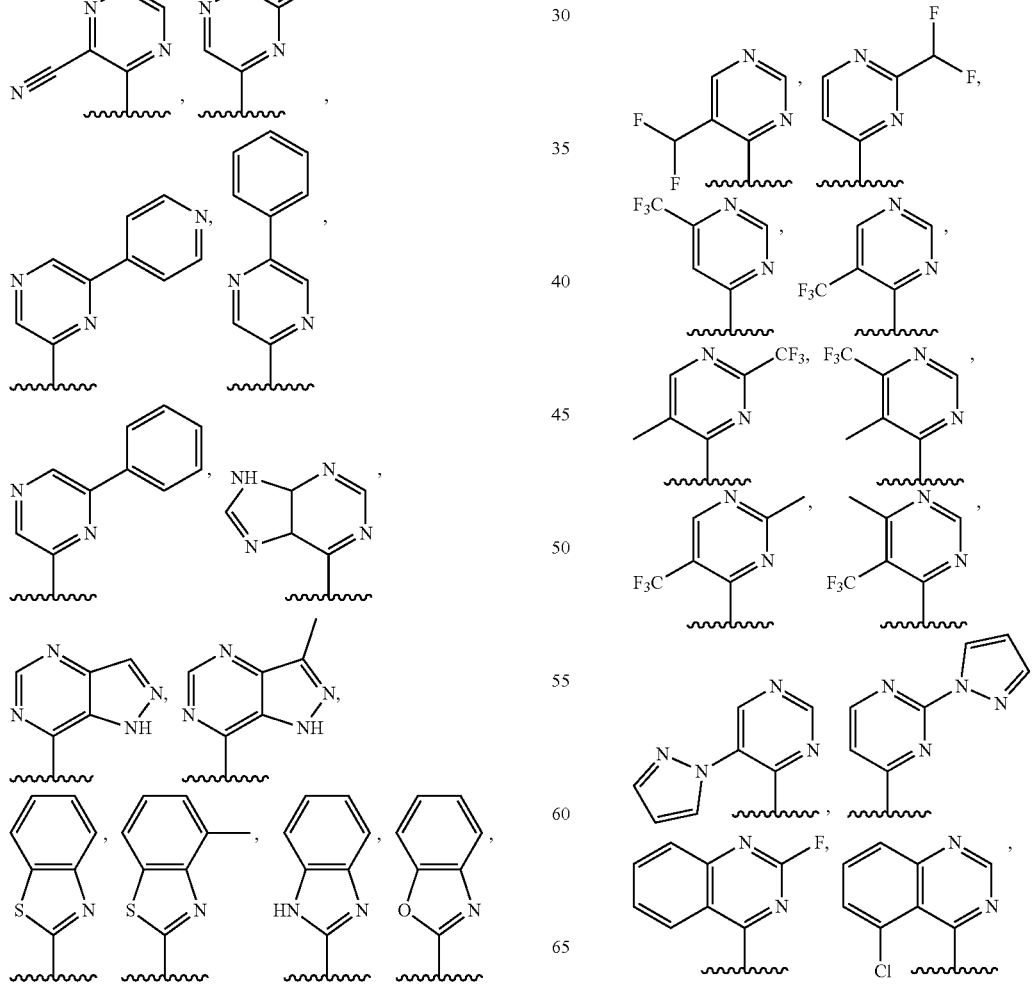

-continued

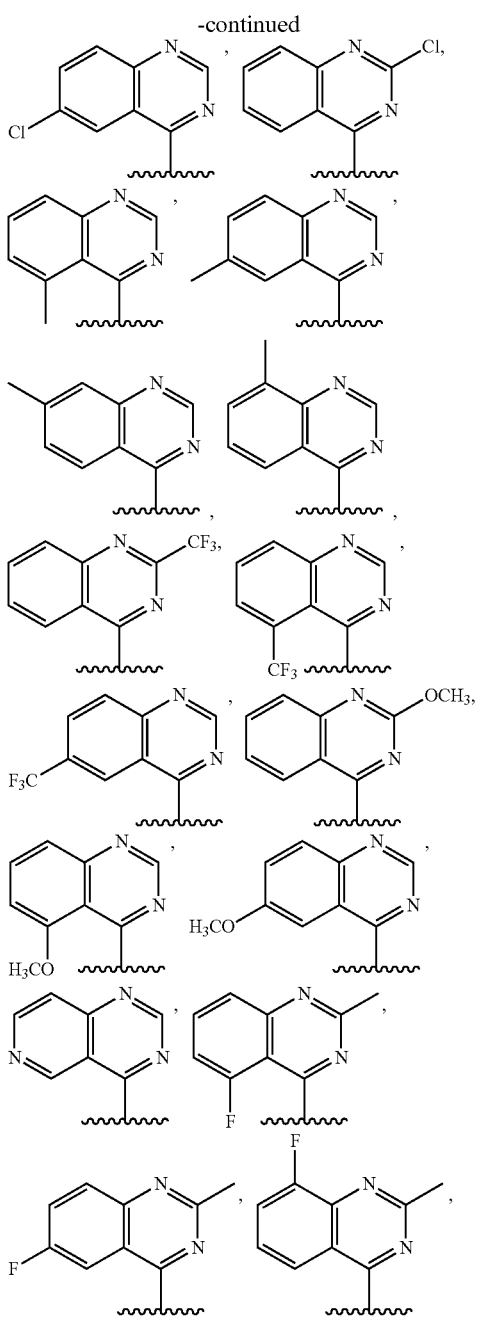

and any of the foregoing groups wherein any one or more hydrogen atom(s) are replaced with deuterium atom(s).

Embodiment 40

The compound of any one of embodiments 1 to 11, or a salt thereof, wherein $R^2$ is

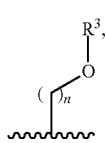

wherein n is 1, 2, 3, 4, 5, or 6, and $R^3$ is $C_1$-$C_2$ alkyl optionally substituted by fluoro; phenyl optionally substi-tuted by fluoro; pyridinyl optionally substituted by fluoro or methyl; or cyclopropyl optionally substituted by fluoro.

Embodiment 41

The compound of embodiment 1, 2, or 3, or a salt thereof, wherein $R^2$ is selected from the group consisting of

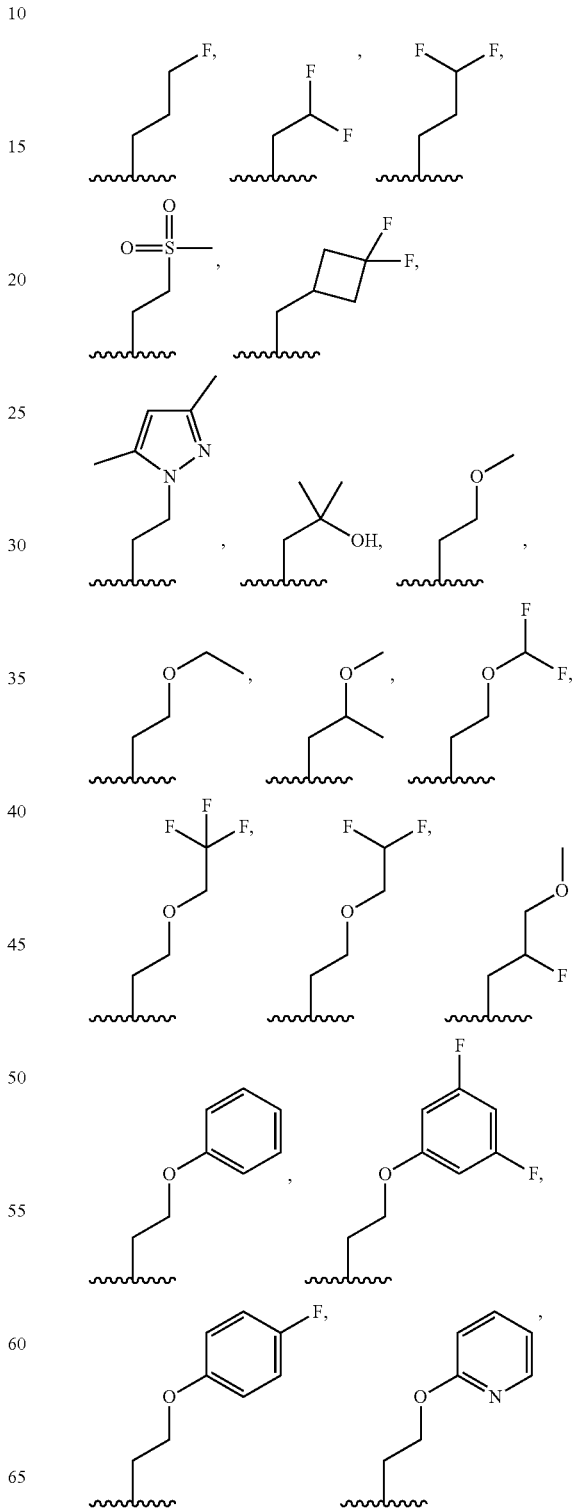

-continued and any of the foregoing groups wherein any one or more hydrogen atom(s) are replaced with deuterium atom(s).

Embodiment 42

A compound, or a salt thereof, selected from Compound Nos. 1-66 in FIG. 1.

Embodiment 43

A compound, or a salt thereof, selected from Compound Nos. 1-147.

Embodiment 44

A compound, or a salt thereof, selected from Compound Nos. 1-665.

Embodiment 45

A pharmaceutical composition comprising a compound of any one of embodiments 1 to 44, or a salt thereof, and a pharmaceutically acceptable carrier or excipient.

Embodiment 46

A method of treating a fibrotic disease in an individual in need thereof comprising administering a compound of any one of embodiments 1 to 44 or a pharmaceutically acceptable salt thereof.

Embodiment 47

The method of embodiment 46, wherein the fibrotic disease is pulmonary fibrosis, liver fibrosis, skin fibrosis, cardiac fibrosis, kidney fibrosis, gastrointestinal fibrosis, primary sclerosing cholangitis, or biliary fibrosis.

Embodiment 48

A kit comprising a compound of any one of embodiments 1 to 44, or a pharmaceutically acceptable salt thereof.

Embodiment 49

The kit of embodiment 48, further comprising instructions for the treatment of a fibrotic disease.

Embodiment 50

A method of inhibiting αvβ6 integrin in an individual comprising administering a compound of any one of embodiments 1 to 44 or a pharmaceutically acceptable salt thereof.

Embodiment 51

A method of inhibiting TGFβ activation in a cell comprising administering to the cell a compound of any one of embodiments 1 to 44 or a pharmaceutically acceptable salt thereof.

Embodiment 52

Use of a compound of any one of embodiments 1 to 44 or a pharmaceutically acceptable salt thereof in the manufacture of a medicament for the treatment of a fibrotic disease.

Embodiment 53

The compound of any one of embodiments 1 to 11, or a salt thereof, wherein $R^2$ is $C_3$-$C_5$ alkyl substituted by both fluorine and —$OCH_3$.

Embodiment 54

The compound of any one of embodiments 1 to 11, or a salt thereof, wherein $R^2$ is $C_1$-$C_6$ alkyl optionally substituted by —$OR^3$, and $R^3$ is phenyl optionally substituted by fluorine.

Embodiment 55

The compound of any one of embodiments 1 to 11, or a salt thereof, wherein $R^2$ is $C_1$-$C_6$ alkyl optionally substituted by —$OR^3$, and $R^3$ is pyridinyl optionally substituted by fluorine or methyl.

Embodiment 56

The compound of any one of embodiments 1 to 11, or a salt thereof, wherein $R^2$ is $C_1$-$C_6$ alkyl substituted by $R^{2a}$ wherein $R^{2a}$ is halogen.

Embodiment 57

The compound of any one of embodiments 1 to 11, or a salt thereof, wherein $R^2$ is $C_1$-$C_6$ alkyl substituted by $R^{2a}$ wherein $R^{2a}$ is deuterium.

Embodiment 58

The compound of any one of embodiments 1 to 11, or a salt thereof, wherein $R^2$ is $C_1$-$C_6$ alkyl substituted by $R^{2a}$ wherein $R^{2a}$ is 3- to 12-membered heterocyclyl optionally substituted by oxo.

Embodiment 59

The compound of any one of embodiments 1 to 11, or a salt thereof, wherein $R^2$ is $C_1$-$C_6$ alkyl substituted by $R^{2a}$ wherein $R^{2a}$ is 4- to 5-membered heterocyclyl optionally substituted by oxo.

Embodiment 60

The compound of any one of embodiments 1 to 11, or a salt thereof, wherein $R^2$ is $C_1$-$C_6$ alkyl substituted by $R^{2a}$ wherein $R^{2a}$ is $C_6$-$C_{14}$ aryl optionally substituted by halogen or —$OR^6$.

Embodiment 61

The compound of any one of embodiments 1 to 11, or a salt thereof, wherein $R^2$ is $C_1$-$C_6$ alkyl substituted by $R^{2a}$ wherein $R^{2a}$ is phenyl optionally substituted by halogen or —$OR^6$.

Embodiment 62

The compound of any one of embodiments 1 to 11, or a salt thereof, wherein $R^2$ is $C_1$-$C_6$ alkyl substituted by $R^{2a}$ wherein $R^{2a}$ is 5- to 10-membered heteroaryl optionally substituted by $C_1$-$C_6$ alkyl.

Embodiment 63

The compound of any one of embodiments 1 to 11, or a salt thereof, wherein $R^2$ is $C_1$-$C_6$ alkyl substituted by $R^{2a}$ wherein $R^{2a}$ is pyrazolyl optionally substituted by methyl.

Embodiment 64

The compound of any one of embodiments 1 to 11, or a salt thereof, wherein $R^2$ is $C_1$-$C_6$ alkyl substituted by $R^{2a}$ wherein $R^{2a}$ is $C_3$-$C_8$ cycloalkyl optionally substituted by —CN, halogen, or —$OR^6$.

Embodiment 65

The compound of any one of embodiments 1 to 11, or a salt thereof, wherein $R^2$ is $C_1$-$C_6$ alkyl substituted by $R^{2a}$ wherein $R^{2a}$ is —$S(O)_2R^3$.

Embodiment 66

The compound of embodiment 1, 2, or 3, or a salt thereof, wherein $R^1$ is pyridyl optionally substituted by $R^{1a}$.

Embodiment 67

The compound of embodiment 1, 2, or 3, or a salt thereof, wherein $R^1$ is indazolyl optionally substituted by $R^{1a}$.

Embodiment 68

The compound of embodiment 1, 2, or 3, or a salt thereof, wherein $R^1$ is 1H-pyrrolopyridyl optionally substituted by $R^{1a}$.

Embodiment 69

The compound of embodiment 1, 2, or 3, or a salt thereof, wherein $R^1$ is quinolinyl optionally substituted by $R^{1a}$.

Embodiment 70

The compound of embodiment 1, 2, or 3, or a salt thereof, wherein $R^1$ is phenyl optionally substituted by $R^{1a}$.

Embodiment 71

The compound of embodiment 1, 2, or 3, or a salt thereof, wherein $R^1$ is indanyl optionally substituted by $R^{1a}$.

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

For the examples described herein, reference to a General Procedure indicates that the reaction was prepared using similar reaction conditions and parameters as the General Procedures stated above.

Procedures

Compounds provided herein may be prepared according to Schemes, as exemplified by the Procedures and Examples. Minor variations in temperatures, concentrations, reaction times, and other parameters can be made when following the Procedures, which do not substantially affect the results of the procedures.

Procedure A

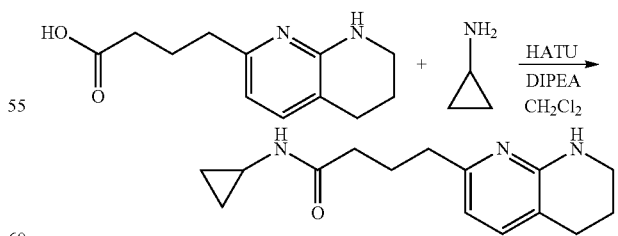

N-cyclopropyl-4-(5,6,7,8-tetrahydro-1,8-naphthyridin-2-yl)butanamide. To a mixture of 4-(5,6,7,8-tetrahydro-1,8-naphthyridin-2-yl)butanoic acid hydrochloride (5.0 g, 19.48 mmol) and cyclopropanamine (1.51 mL, 21.42 mmol) in $CH_2Cl_2$ (80 mL) at rt was added DIPEA (13.57 mL, 77.9 mmol). To this was then added HATU (8.1 g, 21.42 mmol)

and the resulting mixture was stirred at rt for 2 h. The reaction mixture was concentrated in vacuo and purified by normal phase silica gel chromatography to give N-cyclopropyl-4-(5,6,7,8-tetrahydro-1,8-naphthyridin-2-yl)butanamide.
Procedure B

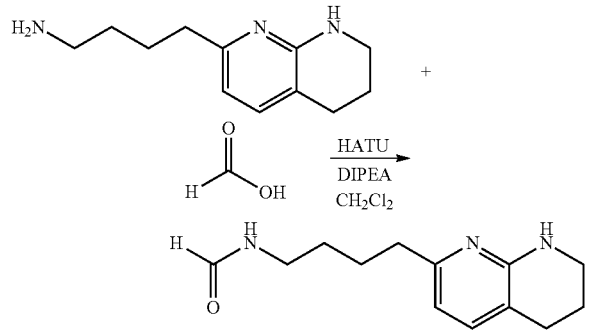

N-(4-(5,6,7,8-tetrahydro-1,8-naphthyridin-2-yl)butyl)formamide. To a mixture of 4-(5,6,7,8-tetrahydro-1,8-naphthyridin-2-yl)butan-1-amine (351 mg, 1.71 mmol) and formic acid (0.09 mL, 2.22 mmol) in 4:1 THF/DMF (5 mL) was added HATU (844 mg, 2.22 mmol) followed by DIPEA (0.89 mL, 5.13 mmol) and the reaction was allowed to stir at rt for 1 h. The reaction mixture was concentrated in vacuo and purified by normal phase silica gel chromatography to give N-(4-(5,6,7,8-tetrahydro-1,8-naphthyridin-2-yl)butyl) formamide.
Procedure C

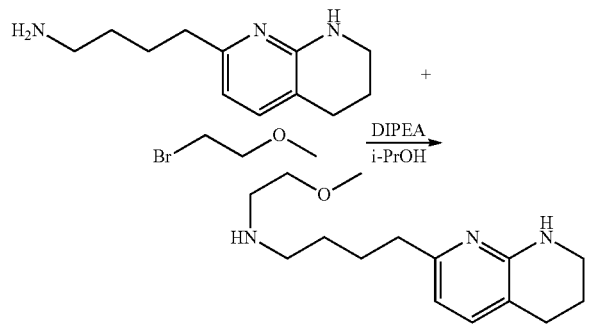

N-(2-methoxyethyl)-4-(5,6,7,8-tetrahydro-1,8-naphthyridin-2-yl)butan-1-amine. A mixture of 4-(5,6,7,8-tetrahydro-1,8-naphthyridin-2-yl)butan-1-amine (300 mg, 1.46 mmol), 1-bromo-2-methoxyethane (0.11 mL, 1.17 mmol) and DIPEA (0.25 mL, 1.46 mmol) in i-PrOH (3 mL) was heated to 70° C. for 18 h. The reaction mixture was allowed to cool to rt and then concentrated in vacuo and purified by normal phase silica gel chromatography to give N-(2-methoxyethyl)-4-(5,6,7,8-tetrahydro-1,8-naphthyridin-2-yl)butan-1-amine.
Procedure D

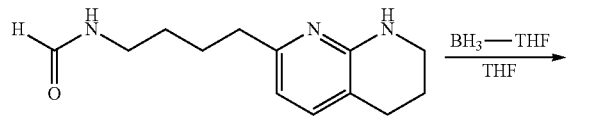

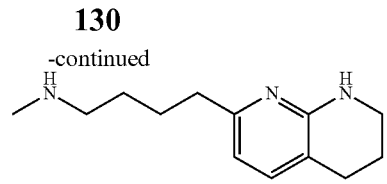

N-methyl-4-(5,6,7,8-tetrahydro-1,8-naphthyridin-2-yl)butan-1-amine. To a solution of N-(4-(5,6,7,8-tetrahydro-1,8-naphthyridin-2-yl)butyl)formamide (200 mg, 0.86 mmol) in THF (2 mL) at rt was added borane tetrahydrofuran complex solution (1.0M in THF, 4.0 mL, 4.0 mmol) dropwise. The resulting mixture was then heated to 60° C. for 2 h and then allowed to cool to rt. The reaction mixture was diluted with MeOH and concentrated in vacuo. The crude residue was purified by normal phase silica gel chromatography to give N-methyl-4-(5,6,7,8-tetrahydro-1,8-naphthyridin-2-yl)butan-1-amine.
Procedure E

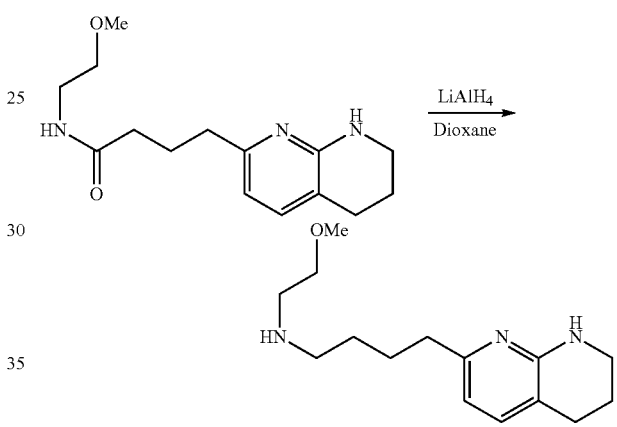

N-(2-methoxyethyl)-4-(5,6,7,8-tetrahydro-1,8-naphthyridin-2-yl)butan-1-amine (5). To a solution of N-(2-methoxyethyl)-4-(5,6,7,8-tetrahydro-1,8-naphthyridin-2-yl)butanamide (15.5 g, 1.0 equiv) in 1,4-dioxane (124 mL) at rt was slowly added LiAlH$_4$ (1.0 M in THF, 123 mL, 2.2 equiv) and the resulting mixture was heated to reflux for 20 hours and then cooled to 0° C. To this solution was added H$_2$O (4.7 mL), then 1M NaOH (4.7 mL) then H$_2$O (4.7 mL) and warmed to room temperature and stirred for 30 minutes, at which time, solid MgSO$_4$ was added and stirred for an additional 30 minutes. The resulting mixture was filtered and the filter cake was washed with THF. The filtrate were concentrated in vacuo to give N-(2-methoxyethyl)-4-(5,6,7,8-tetrahydro-1,8-naphthyridin-2-yl)butan-1-amine.
Procedure F

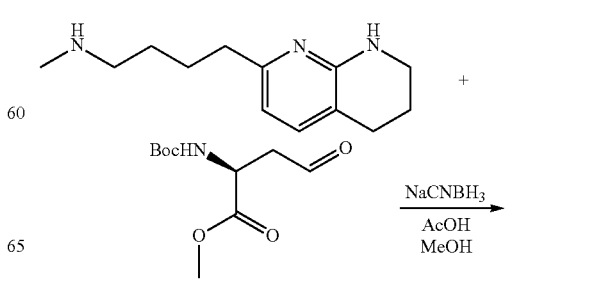

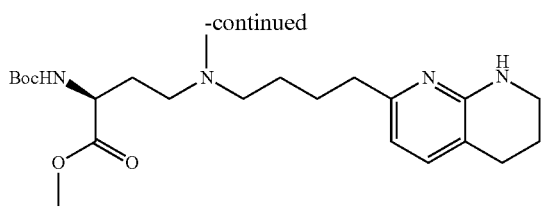

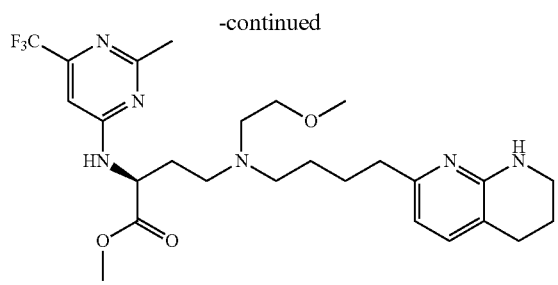

methyl (S)-2-((tert-butoxycarbonyl)amino)-4-(methyl(4-(5,6,7,8-tetrahydro-1,8-naphthyridin-2-yl)butyl)amino)butanoate. To a mixture of N-methyl-4-(5,6,7,8-tetrahydro-1,8-naphthyridin-2-yl)butan-1-amine (5) (187 mg, 0.85 mmol) in MeOH (5 mL) at rt was added acetic acid (0.12 mL, 2.05 mmol) followed by methyl (S)-2-((tert-butoxycarbonyl)amino)-4-oxobutanoate (217 mg, 0.94 mmol). The resulting mixture was allowed to stir at rt for 15 min, at which time, sodium cyanoborohydride (80 mg, 1.28 mmol) was added to the reaction mixture and stirred for 30 min and then concentrated in vacuo. The crude residue was purified by normal phase silica gel chromatography to give methyl (S)-2-((tert-butoxycarbonyl)amino)-4-(methyl(4-(5,6,7,8-tetrahydro-1,8-naphthyridin-2-yl)butyl)amino)butanoate. Procedure G A solution of methyl (S)-2-amino-4-((2-methoxyethyl)(4-(5,6,7,8-tetrahydro-1,8-naphthyridin-2-yl)butyl)amino)butanoate trihydrochloride (80 mg, 0.16 mmol), 4-chloro-2-methyl-6-(trifluoromethyl)pyrimidine (64 mg, 0.33 mmol) and DIPEA (0.23 mL, 1.31 mmol) in i-PrOH (1 mL) was heated at 60° C. overnight. The reaction was allowed to cool to rt and then concentrated in vacuo. The resulting crude residue was purified by normal phase silica gel chromatography to give methyl (S)-4-((2-methoxyethyl)(4-(5,6,7,8-tetrahydro-1,8-naphthyridin-2-yl)butyl)amino)-2-((2-methyl-6-(trifluoromethyl)pyrimidin-4-yl)amino)butanoate. Procedure P

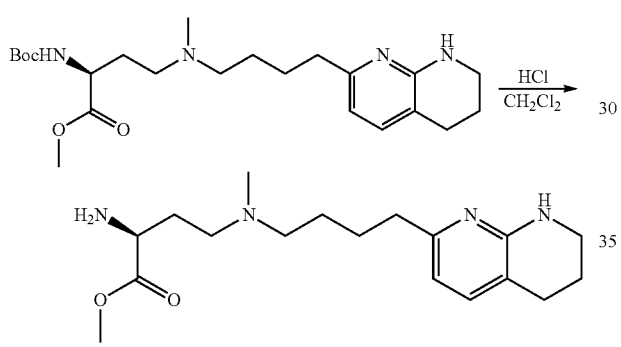

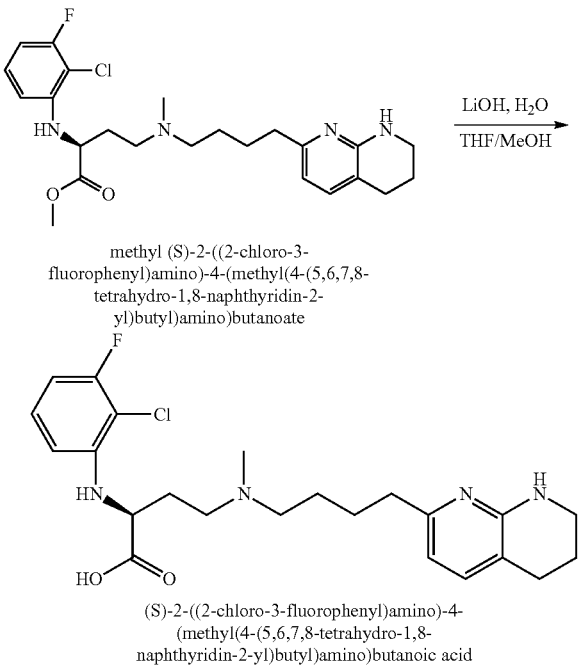

methyl (S)-2-((2-chloro-3-fluorophenyl)amino)-4-(methyl(4-(5,6,7,8-tetrahydro-1,8-naphthyridin-2-yl)butyl)amino)butanoate (S)-2-((2-chloro-3-fluorophenyl)amino)-4-(methyl(4-(5,6,7,8-tetrahydro-1,8-naphthyridin-2-yl)butyl)amino)butanoic acid methyl (S)-2-amino-4-(methyl(4-(5,6,7,8-tetrahydro-1,8-naphthyridin-2-yl)butyl)amino)butanoate. To a solution of methyl (S)-2-((tert-butoxycarbonyl)amino)-4-(methyl(4-(5,6,7,8-tetrahydro-1,8-naphthyridin-2-yl)butyl)amino)butanoate (152 mg, 0.35 mmol) in CH$_2$Cl$_2$ (2 mL) at rt was added 4N HCl in 1,4-dioxane (1 mL, 4 mmol) and the resulting mixture was allowed to stir for 2 h. The reaction mixture was concentrated in vacuo to give methyl (S)-2-amino-4-(methyl(4-(5,6,7,8-tetrahydro-1,8-naphthyridin-2-yl)butyl)amino)butanoate as the trihydrochloride salt. Procedure H

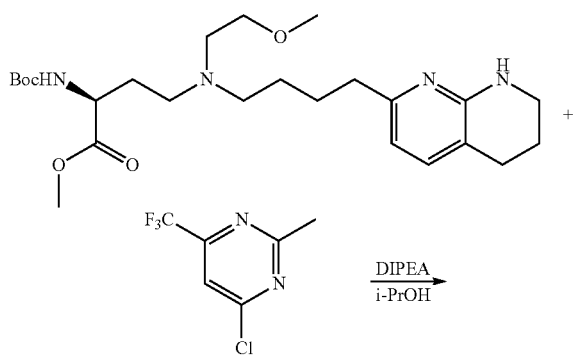

(S)-2-((2-chloro-3-fluorophenyl)amino)-4-(methyl (4-(5,6,7,8-tetrahydro-1,8-naphthyridin-2-yl)butyl) amino)butanoic acid To a solution of methyl (S)-2-((2-chloro-3-fluorophenyl)amino)-4-(methyl(4-(5,6,7,8-tetrahydro-1,8-naphthyridin-2-yl)butyl)amino)butanoate in 4:1:1 THF/MeOH/H$_2$O at rt was added lithium hydroxide (approximately four equivalents) and the resulting mixture was stirred for 30 min. The reaction mixture was concentrated in vacuo and the resulting crude residue purified by reverse phase HPLC to give (S)-2-((2-chloro-3-fluorophenyl)amino)-4-(methyl(4-(5,6,7,8-tetrahydro-1,8-naphthyridin-2-yl)butyl)amino)butanoic acid.

Procedure Q

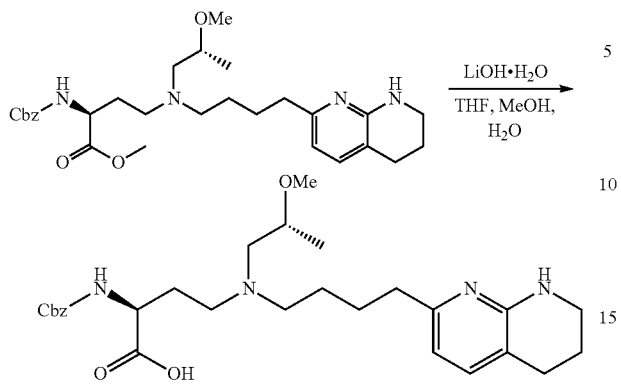

(S)-2-(((benzyloxy)carbonyl)amino)-4-(((R)-2-methoxypropyl)(4-(5,6,7,8-tetrahydro-1,8-naphthyridin-2-yl)butyl)amino)butanoic acid. A mixture of methyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate (1 g, 1.90 mmol) in H₂O (3 mL) and THF (3 mL) and MeOH (3 mL) was added LiOH.H₂O (159.36 mg, 3.80 mmol) and then the mixture was stirred at room temperature for 1 h and the resulting mixture was concentrated in vacuo. The mixture was adjusted to pH=6 by AcOH (2 mL) and the residue was concentrated in vacuo to give a residue to yield compound (S)-2-(((benzyloxy)carbonyl)amino)-4-(((R)-2-methoxypropyl)(4-(5,6,7,8-tetrahydro-1,8-naphthyridin-2-yl)butyl)amino)butanoic acid. LCMS (ESI+): m/z=513.5 (M+H)⁺. ¹H NMR (400 MHz, DMSO-d): δ ppm 7.25-7.37 (m, 5H) 7.00 (d, J=7.28 Hz, 1H) 6.81 (br d, J=7.50 Hz, 1H) 6.22 (d, J=7.28 Hz, 1H₆) 4.93-5.05 (m, 2H) 3.68-3.77 (m, 1H) 3.25-3.34 (m, 1H) 3.15-3.24 (m, 5H) 2.58 (b rt, J=6.06 Hz, 2H) 2.29-2.49 (m, 8H) 2.16 (br dd, J=12.90, 6.06 Hz, 1H) 1.69-1.78 (m, 2H) 1.58-1.68 (m, 1H) 1.53 (quin, J=7.39 Hz, 2H) 1.28-1.40 (m, 2H) 1.00 (d, J=5.95 Hz, 3H).

Procedure R

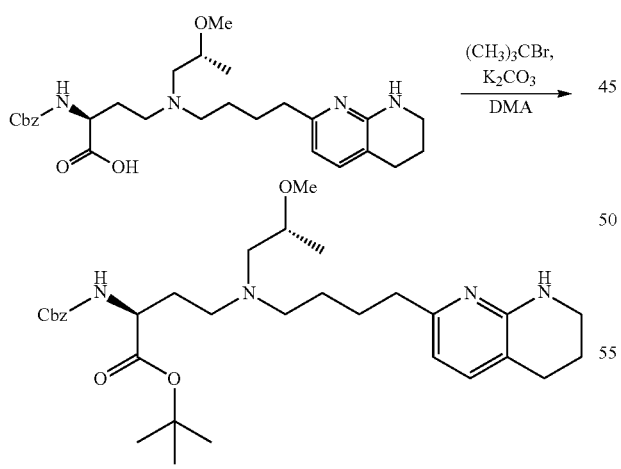

tert-butyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate: A solution of (S)-2-(((benzyloxy)carbonyl)amino)-4-(((R)-2-methoxypropyl)(4-(5,6,7,8-tetrahydro-1,8-naphthyridin-2-yl)butyl)amino)butanoic acid (300 mg, 523.84 μmol, HOAc salt) in DMA (4 mL) was added N-benzyl-N,N-diethylethanaminium chloride (119.32 mg, 523.84 μmol), K₂CO₃ (1.88 g, 13.62 mmol), 2-bromo-2-methylpropane (3.45 g, 25.14 mmol). The mixture was stirred for 18 h at the 55° C. and then allowed to cool to room temperature. The reaction mixture was concentrated in vacuo and the aqueous phase was extracted with ethyl acetate. The combined organic extracts were washed with brine, dried over Na₂SO₄, filtered, and concentrated in vacuo. The crude residue was purified by prep-TLC to give tert-butyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate. LCMS (ESI+): m/z=569.3 (M+H)⁺.

Procedure S

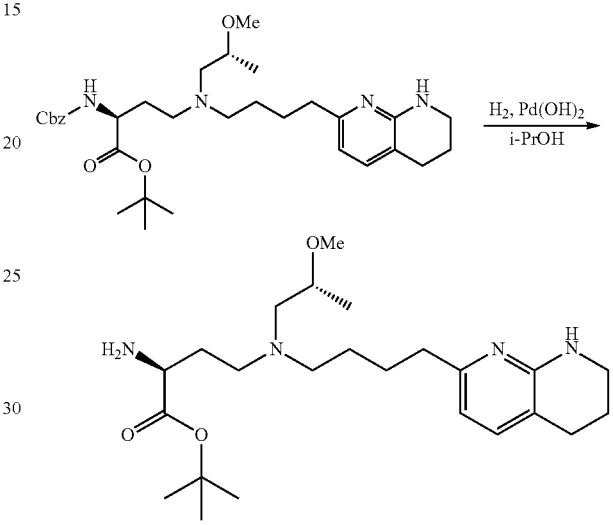

tert-butyl (S)-2-amino-4-(((R)-2-methoxypropyl)(4-(5,6,7,8-tetrahydro-1,8-naphthyridin-2-yl)butyl)amino)butanoate. To a solution of tert-butyl (S)-2-(((benzyloxy)carbonyl)amino)-4-(((R)-2-methoxypropyl)(4-(5,6,7,8-tetrahydro-1,8-naphthyridin-2-yl)butyl)amino)butanoate (107 mg, 188.13 μmol) in i-PrOH (2 mL) was added Pd(OH)₂ (26 mg) under an N₂ atmosphere. The suspension was degassed under vacuum and purged with H₂ several times. The mixture was stirred under H₂ (15 psi) at room temperature for 15 h. The mixture was filtered and concentrated in vacuo to give tert-butyl (S)-2-amino-4-(((R)-2-methoxypropyl)(4-(5,6,7,8-tetrahydro-1,8-naphthyridin-2-yl)butyl)amino)butanoate. LCMS (ESI+): m/z=435.5 (M+H)⁺. ¹H NMR (400 MHz, CDCl₃): δ ppm 7.06 (d, J=7.34 Hz, 1H) 6.34 (d, J=7.34 Hz, 1H) 4.98 (br s, 1H) 3.38-3.44 (m, 4H) 3.34 (s, 3H) 2.69 (t, J=6.30 Hz, 2H) 2.51-2.59 (m, 5H) 2.31 (dd, J=13.39, 5.56 Hz, 1H) 1.86-1.94 (m, 5H) 1.49-1.69 (m, 6H) 1.47 (s, 9H) 1.13 (d, J=6.11 Hz, 3H).

Procedure T

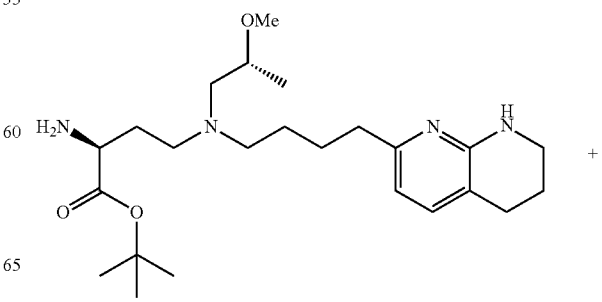

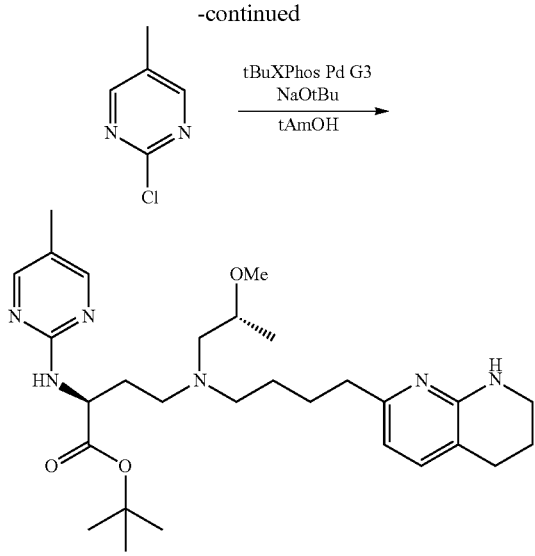

tert-butyl (S)-4-(((R)-2-methoxypropyl)(4-(5,6,7,8-tetrahydro-1,8-naphthyridin-2-yl)butyl)amino)-2-((5-methylpyrimidin-2-yl)amino)butanoate. To a solution of (S)-tert-butyl 2-amino-4-(((R)-2-methoxypropyl)(4-(5,6,7,8-tetrahydro-1,8-naphthyridin-2-yl)butyl)amino)butanoate tert-butyl (S)-2-amino-4-(((R)-2-methoxypropyl)(4-(5,6,7,8-tetrahydro-1,8-naphthyridin-2-yl)butyl)amino)butanoate (100 mg, 230.09 μmol) and 2-chloro-5-methyl-pyrimidine (24.65 mg, 191.74 μmol) in 2-methyl-2-butanol (2 mL) was added t-BuONa (2 M in THF, 191.74 uL) and [2-(2-aminophenyl)phenyl]-methylsulfonyloxy-palladium; ditert-butyl-[2-(2,4,6-triisopropylphenyl)phenyl]phosphane (15.23 mg, 19.17 μmol), and the resulting mixture was stirred at 100° C. for 14 h. The mixture was concentrated in vacuo to give (S)-tert-butyl 4-(((S)-2-methoxypropyl)(4-(5,6,7,8-tetrahydro-1,8-naphthyridin-2-yl)butyl)amino)-2-((5-methylpyrimidin-2-yl)amino)butanoate. LCMS (ESI+): m/z=527.3 (M+H)+.

Procedure U

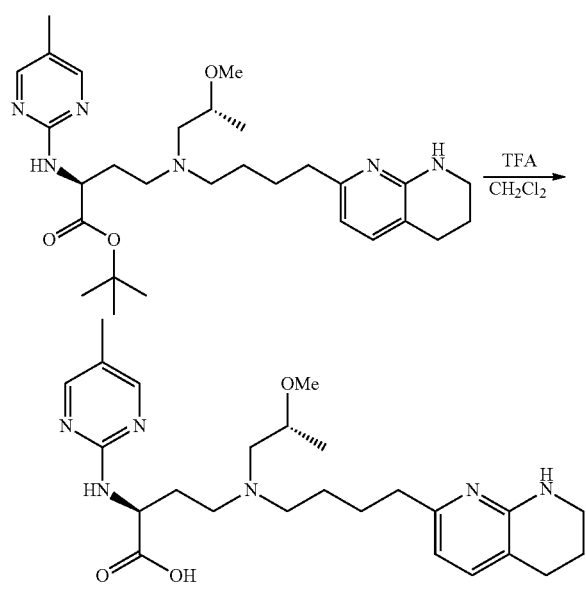

(S)-4-(((R)-2-methoxypropyl)(4-(5,6,7,8-tetrahydro-1,8-naphthyridin-2-yl)butyl)amino)-2-((5-methylpyrimidin-2-yl)amino)butanoic acid. To a solution of tert-butyl (S)-4-(((R)-2-methoxypropyl)(4-(5,6,7,8-tetrahydro-1,8-naphthyridin-2-yl)butyl)amino)-2-((5-methyl pyrimidin-2-yl)amino)butanoate (80 mg, 151.89 μmol) in DCM (2 mL) was added TFA (254.14 mg, 2.23 mmol) at 0° C. The mixture was stirred at room temperature for 6 h. The mixture was concentrated in vacuo and the resulting crude residue was purified by prep-HPLC to give compound (S)-4-(((R)-2-methoxypropyl)(4-(5,6,7,8-tetrahydro-1,8-naphthyridin-2-yl)butyl)amino)-2-((5-methylpyrimidin-2-yl)amino)butanoic acid. LCMS (ESI+): m/z=471.2 (M+H)+. $^1$H NMR (400 MHz, Methanol-$d_4$) δ ppm 8.57 (br s, 2H) 7.60 (d, J=7.28 Hz, 1H) 6.67 (d, J=7.28 Hz, 1H) 4.81-4.86 (m, 1H) 3.86 (br s, 1H) 3.41-3.59 (m, 4H) 3.39 (s, 3H) 3.33-3.38 (m, 1H) 3.12-3.30 (m, 3H) 2.76-2.86 (m, 4H) 2.54 (br s, 1H) 2.39 (br d, J=8.82 Hz, 1H) 2.30 (s, 3H) 1.76-1.99 (m, 6H) 1.22 (d, J=5.95 Hz, 3H).

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

For the examples described herein, reference to a Procedure indicates that the reaction was prepared using similar reaction conditions and parameters as the Procedures stated above.

Example A1

Synthesis of (S)-2-fluoro-3-methoxypropan-1-amine

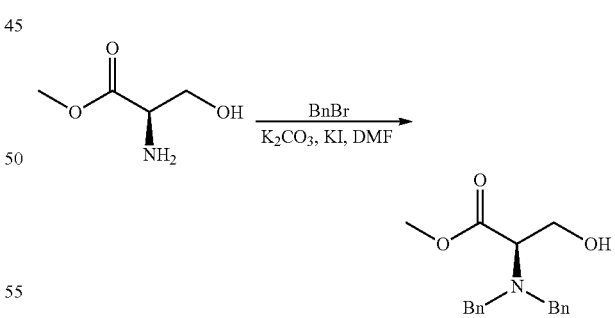

Methyl dibenzyl-D-serinate. To a mixture of methyl D-serinate hydrochloride (100 g, 642.76 mmol) and K$_2$CO$_3$ (177.67 g, 1.29 mol) and KI (53.35 g, 321.38 mmol) in DMF (1.5 L) was added benzyl bromide (241.85 g, 1.41 mol) at 0° C. The mixture was stirred at 25° C. for 12 h. The mixture was quenched with H$_2$O (3000 mL) and EtOAc (1 L×3). The organic layer was washed with brine (1 L), dried over Na$_2$SO$_4$, and concentracted in vacuo. The crude product was purified by normal phase silica gel chromatography to give methyl dibenzyl-D-serinate.

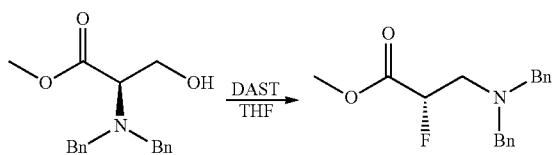

Methyl (S)-3-(dibenzylamino)-2-fluoropropanoate. To a solution of methyl dibenzyl-D-serinate (155 g, 517.77 mmol) in THF (1.2 L) was added DAST (102.65 g, 636.85 mmol, 84.14 mL) dropwise at 0° C. and the reaction mixture was stirred for 14 h at rt. The reaction mixture was quenched with saturated aq. NaHCO₃ (1 L) at 0° C. and extracted with EtOAc (500 mL×3). The organic phase was dried over Na₂SO₄, filtered, and concentrated in vacuo. The crude product was purified by normal phase silica gel chromatography to give methyl (S)-3-(dibenzylamino)-2-fluoropropanoate.

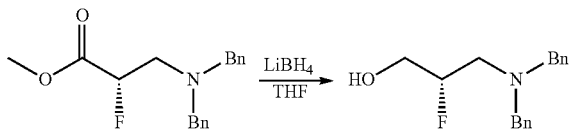

(S)-3-(dibenzylamino)-2-fluoropropan-1-ol. To a solution of methyl (S)-3-(dibenzylamino)-2-fluoropropanoate (103 g, 341.79 mmol) in THF (1 L) was added LiBH₄ (14.89 g, 683.58 mmol) at 0° C. The mixture was stirred at 40° C. for 12 h. The mixture was poured into aq. NH₄Cl (500 mL) at 0° C. The aqueous phase was extracted with ethyl acetate (300 mL×3). The combined organic extracts were dried over Na₂SO₄, filtered, and concentrated in vacuo to give (S)-3-(dibenzylamino)-2-fluoropropan-1-ol that was used without further purification.

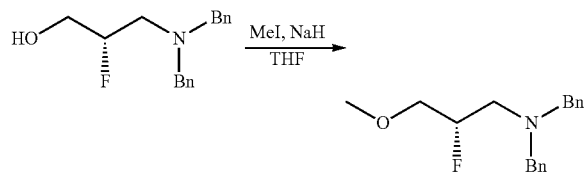

(S)—N,N-dibenzyl-2-fluoro-3-methoxypropan-1-amine. To a solution of (S)-3-(dibenzylamino)-2-fluoropropan-1-ol (51 g, 186.58 mmol) in THF (400 mL) was added NaH (60% dispersion in mineral oil, 11.19 g, 279.87 mmol) at 0° C. and the resulting mixture was stirred at 0° C. for 30 min. To this was then added iodomethane (18.58 mL, 298.52 mmol) and the mixture was stirred at rt for 12 h. The mixture was quenched with aq. NH₄Cl (500 mL) at 0° C. The aqueous phase was extracted with EtOAc (500 mL×3). The combined organic extracts were dried over Na₂SO₄, filtered, and concentrated in vacuo. The resulting crude residue was purified by normal phase silica gel chromatography to give (S)—N,N-dibenzyl-2-fluoro-3-methoxypropan-1-amine.

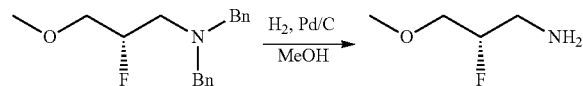

(S)-2-fluoro-3-methoxypropan-1-amine. To a solution of (S)—N,N-dibenzyl-2-fluoro-3-methoxypropan-1-amine (15 g, 52.20 mmol) in MeOH (200 mL) was added Pd/C (3 g). The suspension was degassed under vacuum and purged with H₂ three times. The mixture was stirred under H₂ (50 psi) at 50° C. for 12 h. The reaction mixture was filtered through a pad of Celite and the filtrate was treated with HCl/EtOAc (50 mL) and then concentrated in vacuo to give (S)-2-fluoro-3-methoxypropan-1-amine hydrochloride that was used without further purification.

Example A2

Synthesis of tert-butyl 7-(4-oxobutyl)-3,4-dihydro-1,8-naphthyridine-1(2H)-carboxylate

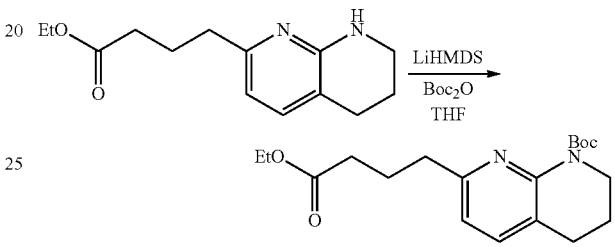

tert-Butyl 7-(4-ethoxy-4-oxobutyl)-3,4-dihydro-1,8-naphthyridine-1(2H)-carboxylate. To a solution of ethyl 4-(5,6,7,8-tetrahydro-1,8-naphthyridin-2-yl)butanoate (5.25 g, 21.1 mmol) and di-tert-butyl dicarbonate (5.89 mL, 25.4 mmol in THF (70 mL) was added lithium bis(trimethylsilyl) amide (25.4 mL, 25.4 mmol) was added at 0° C. After 2 h, the reaction was diluted with EtOAc (50 mL) and was quenched with sat NH₄Cl (50 mL). After 30 min of stirring, the layers were separated and the organic layer was washed with brine (20 mL), dried over Na₂SO₄, and concentrated in vacuo. The resulting crude residue was purified by normal phase silica gel chromatography to give tert-butyl 7-(4-ethoxy-4-oxobutyl)-3,4-dihydro-1,8-naphthyridine-1(2H)-carboxylate.

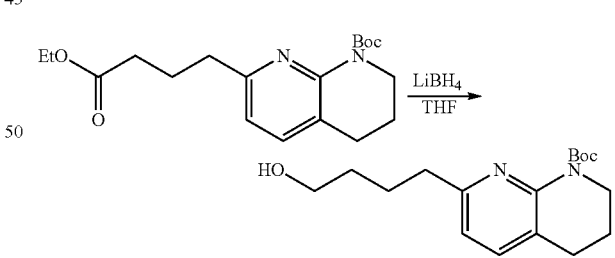

tert-Butyl 7-(4-hydroxybutyl)-3,4-dihydro-1,8-naphthyridine-1(2H)-carboxylate. To a solution of tert-butyl 7-(4-ethoxy-4-oxobutyl)-3,4-dihydro-1,8-naphthyridine-1(2H)-carboxylate (6.81 g, 19.5 mmol) in THF (50 mL) was added LiBH₄ (1.0M in THF, 19.5 mL, 19.5 mmol) at rt. The mixture was stirred overnight and then quenched with sat. NH₄Cl and diluted with EtOAc. The layers were separated and the aqueous layer was extracted with EtOAc. The combined organic extracts were washed with H₂O, dried over Na₂SO₄, filtered, and concentrated in vacuo. The resulting crude residue was purified by normal phase silica gel chromatography to give tert-butyl 7-(4-hydroxybutyl)-3,4-dihydro-1,8-naphthyridine-1(2H)-carboxylate.

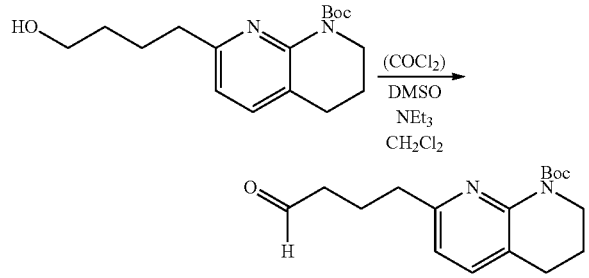

tert-Butyl 7-(4-oxobutyl)-3,4-dihydro-1,8-naphthyridine-1(2H)-carboxylate. A solution of oxalyl chloride (2.57 mL, 29.3 mmol) in CH$_2$Cl$_2$ (69 mL) was cooled to −78° C. for 5 minutes, at which time, dimethyl sulfoxide (4.2 mL, 58.6 mmol) was added and the mixture was stirred for 30 min. A solution of tert-butyl 7-(4-hydroxybutyl)-3,4-dihydro-2H-1,8-naphthyridine-1-carboxylate (6.9 g, 22.6 mmol) in CH$_2$Cl$_2$ (10.5 mL) was added and stirred at −78° C. for 1 h. Triethylamine (10.5 mL, 75.1 mmol) was then added to the reaction mixture and stirred for 30 mins. The reaction was quenched with water and extracted with CH$_2$C$_2$. The organic layer was collected and dried over sodium sulfate. The organic layer was concentrate to give tert-butyl 7-(4-oxobutyl)-3,4-dihydro-1,8-naphthyridine-1(2H)-carboxylate that was used without further purification.

Example A3

Synthesis of methyl (S)-4-((2-methoxyethyl)(4-(5,6,7,8-tetrahydro-1,8-naphthyridin-2-yl)butyl)amino)-2-(quinolin-4-ylamino)butanoate

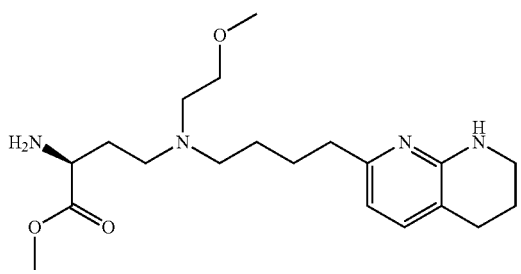 [SMILES: COCCN(CCCCc1ccc2c(n1)NCCC2)CC[C@H](N)C(=O)OC]

Methyl (S)-2-amino-4-((2-methoxyethyl)(4-(5,6,7,8-tetrahydro-1,8-naphthyridin-2-yl) butyl)amino)butanoate. Prepared according to Scheme A using Procedure A with 2-methoxyethylamine, then Procedure E, Procedure F, and Procedure G to give methyl (S)-2-amino-4-((2-methoxyethyl)(4-(5,6,7,8-tetrahydro-1,8-naphthyridin-2-yl)butyl)amino)butanoate.

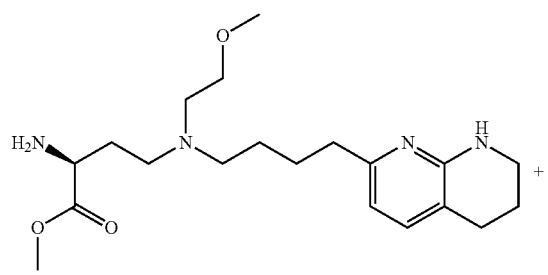

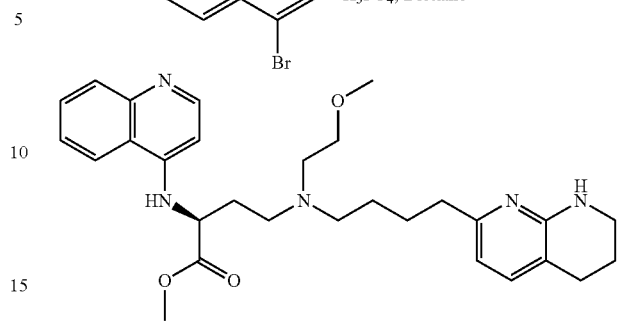

Methyl (S)-4-((2-methoxyethyl)(4-(5,6,7,8-tetrahydro-1,8-naphthyridin-2-yl)butyl) amino)-2-(quinolin-4-ylamino)butanoate. A microwave vial containing methyl (S)-2-amino-4-((2-methoxyethyl)(4-(5,6,7,8-tetrahydro-1,8-naphthyridin-2-yl)butyl)amino)butanoate (125 mg, 0.3 mmol) was charged with 4-bromoquinoline (65 mg, 0.3 mmol), Pd(OAc)$_2$ (6.3 mg, 0.03 mmol), rac-BINAP (35 mg, 0.6 mmol), and K$_3$PO$_4$ (210 mg, 1.0 mmol) and then diluted with Dioxane (2 mL). The mixture was degassed and then sealed and heated to 100° C. for 1 h. The reaction mixture was allowed to cool to rt and then filtered and concentrated in vacuo. The crude residue was purified by normal phase silica gel chromatography to give methyl (S)-4-((2-methoxyethyl)(4-(5,6,7,8-tetrahydro-1,8-naphthyridin-2-yl)butyl)amino)-2-(quinolin-4-ylamino)butanoate.

Example A4

Synthesis of methyl (S)-2-(isoquinolin-1-ylamino)-4-((2-methoxyethyl)(4-(5,6,7,8-tetrahydro-1,8-naphthyridin-2-yl)butyl)amino)butanoate

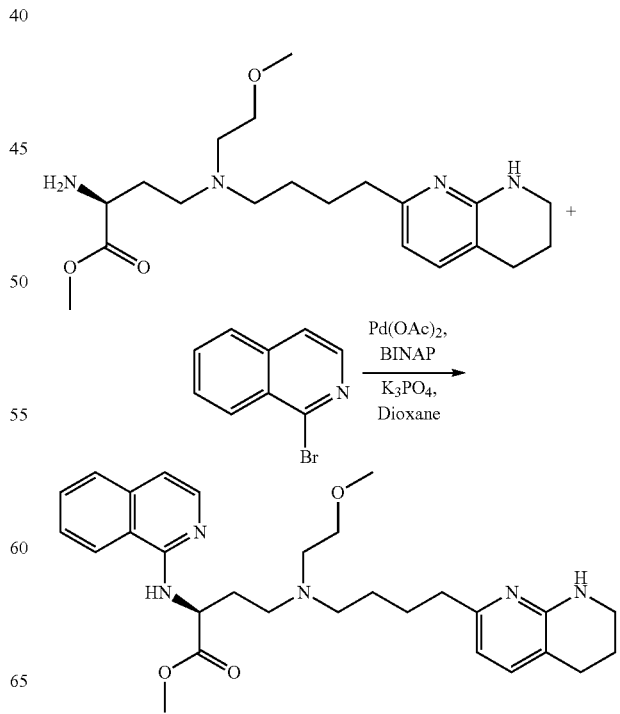

Methyl (S)-2-(isoquinolin-1-ylamino)-4-((2-methoxyethyl)(4-(5,6,7,8-tetrahydro-1,8-naphthyridin-2-yl)butyl)amino)butanoate. A microwave vial containing methyl (S)-2-amino-4-((2-methoxyethyl)(4-(5,6,7,8-tetrahydro-1,8-naphthyridin-2-yl)butyl)amino)butanoate (125 mg, 0.3 mmol) was charged with 1-bromoisoquinoline (65 mg, 0.3 mmol), Pd(OAc)$_2$ (6.3 mg, 0.03 mmol), rac-BINAP (35 mg, 0.6 mmol), and K$_3$PO$_4$ (210 mg, 1.0 mmol) and then diluted with Dioxane (2 mL). The mixture was degassed and then sealed and heated to 100° C. for 1 h. The reaction mixture was allowed to cool to rt and then filtered and concentrated in vacuo. The crude residue was purified by normal phase silica gel chromatography to give methyl (S)-2-(isoquinolin-1-ylamino)-4-((2-methoxyethyl)(4-(5,6,7,8-tetrahydro-1,8-naphthyridin-2-yl)butyl)amino) butanoate.

In the following examples, compounds without specific synthetic descriptions may be synthesized by procedures described herein, for example, analogous to that for compound 2, Scheme 1; compound 81, Scheme 5; and Compound 213, Scheme 24.

For example, (S)-2-((3-cyanopyrazin-2-yl)amino)-4-((2-(3,5-difluorophenoxy)ethyl)(4-(5,6,7,8-tetrahydro-1,8-naphthyridin-2-yl)butyl)amino)butanoic acid (compound 597) may be prepared by slight modification of the procedures from Scheme 1. In step 1, 2-(3,5-difluorophenoxy)ethan-1-amine may be substituted for cyclopropylamine which may afford the analogous amine product. The amine product may then undergo a Boc deprotection as in step 2 followed by a reductive amination as in step 3 to afford an analogous tertiary amine product. This tertiary amine may then undergo a base mediated hydrolysis as in step 4 followed by deprotection of the benzyl carbamate under reductive conditions as in step 5 to afford an analogous amino acid product. This amino acid may then be reacted with a suitably activated heterocycle in an S$_N$Ar reaction, such as 3-chloropyrazine-2-carbonitrile to give the described compound. Similarly, the analogous free amino acid product from step 5 may be reacted with an analogous activated heterocycle as depicted in step 6 and then subjected to either reducing conditions as shown in step 7 of Scheme 1 or cross-coupling conditions as shown in step 2 of Scheme 5 to afford further prophetic compounds described.

The tertiary amine products arising from step 3 in Scheme 1, if alternative amines were substituted for cyclopropylamine, may alternatively be hydrolyzed as depicted in step 1 of Scheme 24 followed by t-butylation of the acid product with t-butyl bromide under basic conditions as shown in step 2 of Scheme 24. The resulting t-butyl ester product may be deprotected under reductive conditions as in step 3 of Scheme 24 to afford an amino ester product, which may then undergo palladium catalyzed cross-coupling with an appropriate aryl or heteroaryl halide as in step 4 of Scheme 24 to give an ester product that may be exposed to acid to generate a final compound as in step 5 of Scheme 24.

For example, (S)-4-((2-(3,5-difluorophenoxy)ethyl)(4-(5,6,7,8-tetrahydro-1,8-naphthyridin-2-yl)butyl)amino)-2-((1-methyl-1H-indazol-3-yl)amino)butanoic acid (compound 624) may be prepared by slight modification of the procedures from Scheme 1. In step 1, 2-(3,5-difluorophenoxy)ethan-1-amine may be substituted for cyclopropylamine which would afford the analogous amine product. This amine product may then undergo a Boc deprotection as in step 2 followed by a reductive amination as in step 3 to afford an analogous tertiary amine product. The tertiary amine product may be hydrolyzed as depicted in step 1 of Scheme 24 followed by t-butylation of the acid product with t-butyl bromide under basic conditions as shown in step 2 of Scheme 24. The resulting t-butyl ester product may be deprotected under reductive conditions as in step 3 of Scheme 24 to afford an amino ester product, which may then undergo palladium catalyzed cross-coupling substituting 3-bromo-1-methyl-1H-indazole for 6-chloro-N,N-dimethylpyrimidin-4-amine in step 4 of Scheme 24 to give an ester product that may be exposed to acid to generate the described compound.

Compound 1: (S)-4-(cyclopropyl(4-(5,6,7,8-tetrahydro-1,8-naphthyridin-2-yl) butyl)amino)-2-((6-(difluoromethyl)pyrimidin-4-yl) amino) butanoic acid. Prepared according to Scheme A using Procedure A with cyclopropylamine, and Procedure H with 4-chloro-6-(difluoromethyl)pyrimidine. LCMS theoretical m/z=475.3. [M+H]+, found 475.2.

Compound 1: (S)-4-(cyclopropyl(4-(5,6,7,8-tetrahydro-1,8-naphthyridin-2-yl) butyl)amino)-2-((6-(difluoromethyl)pyrimidin-4-yl) amino) butanoic acid. Prepared according to Scheme A using Procedure A with cyclopropylamine, and Procedure H with 4-chloro-6-(difluoromethyl)pyrimidine. LCMS theoretical m/z=475.3. [M+H]+, found 475.2.

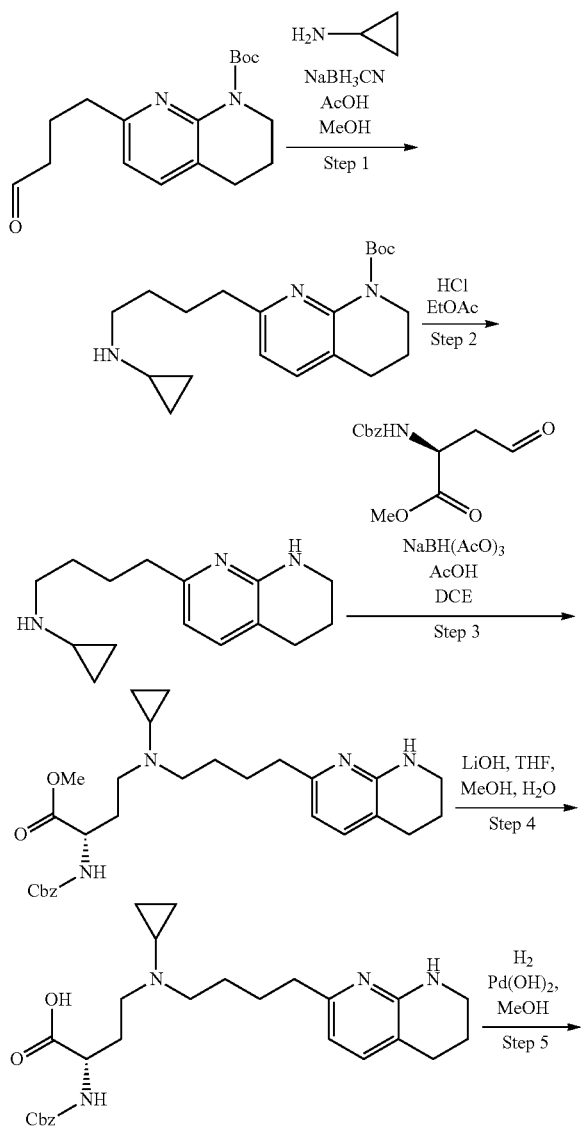

Scheme 1, Compound 2

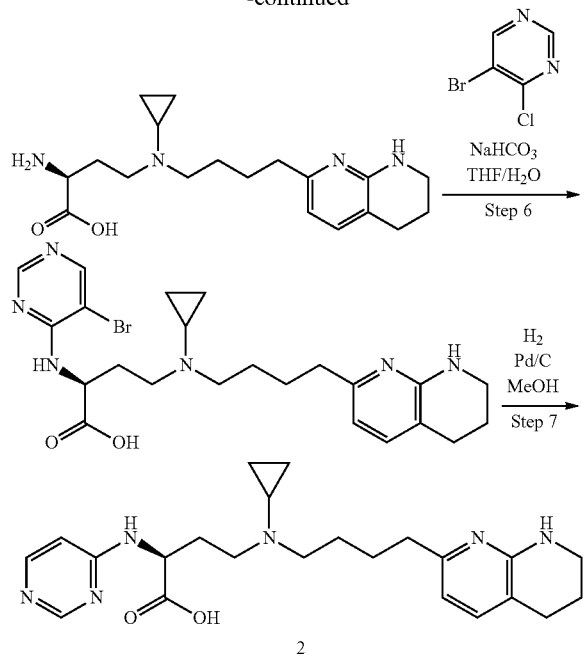

Step 1: tert-butyl 7-(4-(cyclopropylamino) butyl)-3,4-dihydro-1,8-naphthyridine-1(2H)-carboxylate To a solution of cyclopropanamine (22.8 mL, 328.5 mmol), AcOH (18.8 mL, 328.5 mmol), and NaBH₃CN (4.13 g, 65.7 mmol) in MeOH (100 mL) at 0° C. was added a solution of tert-butyl 7-(4-oxobutyl)-3,4-dihydro-1,8-naphthyridine-1(2H)-carboxylate (10.0 g, 32.9 mmol) in MeOH (100 mL) and the resulting mixture was stirred at rt for 16 h. The mixture was diluted with sat. NaHCO₃ and stirred until gas evolution ceased and then concentrated in vacuo to remove the volatiles. The aqueous layer was extracted with EtOAc and the combined organic extracts were dried over Na₂SO₄, filtered, and concentrated in vacuo. The crude residue was purified by prep-HPLC to give the title compound. LCMS theoretical m/z=346.3. [M+H]+, found 346.5.

Step 2: N-(4-(5,6,7,8-tetrahydro-1,8-naphthyridin-2-yl) butyl)cyclopropanamine To a solution of tert-butyl 7-(4-(cyclopropylamino)butyl)-3,4-dihydro-1,8-naphthyridine-1(2H)-carboxylate (2.5 g, 7.24 mmol) in EtOAc (10 mL) was added 4 M HCl in EtOAc (1.8 mL) and the resulting mixture was stirred at rt for 12 h and then concentrated in vacuo. The crude residue was used without further purification. LCMS theoretical m/z=246.2. [M+H]+, found 246.0.

Step 3: methyl (S)-2-(((benzyloxy)carbonyl)amino)-4-(cyclopropyl(4-(5,6,7,8-tetrahydro-1,8-naphthyridin-2-yl) butyl)amino) butanoate To a mixture of methyl (S)-2-(((benzyloxy)carbonyl)amino)-4-oxobutanoate (2.59 g, 9.8 mmol) and N-(4-(5,6,7,8-tetrahydro-1,8-naphthyridin-2-yl) butyl)cyclopropanamine hydrochloride (2.5 g, 8.9 mmol) in DCE (40 mL) was added AcOH (761 µL, 13.3 mmol) at 0° C. was added NaBH(OAc)₃ (2.82 g, 13.3 mmol) and the resulting mixture was stirred for 1 h at rt. The mixture was diluted with sat. aq. NaHCO₃ and stirred until gas evolution ceased and then was extracted with CH₂Cl₂. The combined organic extracts were washed with brine and then dried over Na₂SO₄, filtered, and concentrated in vacuo. The crude residue was purified by normal phase silica gel chromatography to give the title compound. LCMS theoretical m/z=495.3. [M+H]+, found 495.4.

Step 4: (S)-2-(((benzyloxy)carbonyl)amino)-4-(cyclopropyl(4-(5,6,7,8-tetrahydro-1,8-naphthyridin-2-yl) butyl)amino) butanoic acid To a solution of methyl (S)-2-(((benzyloxy)carbonyl)amino)-4-(cyclopropyl(4-(5,6,7,8-tetrahydro-1,8-naphthyridin-2-yl) butyl)amino) butanoate (4 g, 7.9 mmol) in 1:1:1 THF/MeOH/H₂O (36 mL) was added LiOH.H₂O (664 mg, 15.8 mmol) at 0° C. and the resulting mixture was stirred at rt for 1 h. The mixture was then adjusted to pH=6 by the careful addition of 1 N HCl and then concentrated in vacuo to give the title compound. LCMS theoretical m/z=480.3 [M]+, found 480.1.

Step 5: (S)-2-amino-4-(cyclopropyl(4-(5,6,7,8-tetrahydro-1,8-naphthyridin-2-yl) butyl)amino) butanoic acid A flask containing (S)-2-(((benzyloxy)carbonyl)amino)-4-(cyclopropyl(4-(5,6,7,8-tetrahydro-1,8-naphthyridin-2-yl) butyl)amino) butanoic acid (4.5 g, 9.4 mmol) was charged with 20 wt % Pd(OH)₂/C (4.5 g) and then diluted with i-PrOH (300 mL) and stirred under an H₂ atmosphere at 50 psi for 48 h at rt. The reaction mixture was filtered through a pad of CELITE® and rinsed with MeOH and then concentrated in vacuo. The crude residue was purified by reverse phase prep-HPLC to give the title compound. LCMS theoretical m/z=347.2. [M+H]+, found 347.2.

Step 6: (S)-2-((5-bromopyrimidin-4-yl) amino)-4-(cyclopropyl(4-(5,6,7,8-tetrahydro-1,8-naphthyridin-2-yl) butyl)amino) butanoic acid To a solution of (S)-2-amino-4-(cyclopropyl(4-(5,6,7,8-tetrahydro-1,8-naphthyridin-2-yl) butyl)amino) butanoic acid trifluoroacetate (150 mg, 0.3 mmol) in 4:1 THF/H₂O (3 mL) was added 5-bromo-4-chloro-pyrimidine (69 mg, 0.4 mmol) and NaHCO₃ (137 mg, 1.63 mmol) and then was stirred at 70° C. for 2 h and then cooled to rt and concentrated in vacuo. The crude residue was used without further purification.

Step 7: (S)-4-(cyclopropyl(4-(5,6,7,8-tetrahydro-1,8-naphthyridin-2-yl) butyl)amino)-2-(pyrimidin-4-ylamino) butanoic acid A flask containing (S)-2-((5-bromopyrimidin-4-yl) amino)-4-(cyclopropyl(4-(5,6,7,8-tetrahydro-1,8-naphthyridin-2-yl) butyl)amino) butanoic acid (157 mg, 0.3 mmol) was charged with 20 wt % Pd/C (200 mg) and then diluted with MeOH (20 mL) and the resulting mixture was stirred at rt under an H₂ atmosphere for 4 h and then filtered and concentrated in vacuo. The crude residue was purified by reverse phase prep-HPLC to give the title compound. LCMS (ESI+): m/z=425.2 (M+H)+. ¹H NMR (400 MHz, Methanol-d₄): δ ppm 8.34 (s, 1H) 7.96 (br s, 1H) 7.18 (d, J=7.21 Hz, 1H) 6.52 (m, 1H) 6.39 (d, J=7.21 Hz, 1H) 3.87-4.65 (m, 1H) 3.34-3.42 (m, 2H) 2.76-2.96 (m, 2H) 2.70 (br t, J=6.11 Hz, 4H) 2.54 (br t, J=7.03 Hz, 2H) 2.14-2.26 (m, 1H)

1.96-2.08 (m, 1H) 1.87 (q, J=5.87 Hz, 3H) 1.62 (br d, J=4.40 Hz, 4H) 0.37-0.59 (m, 4H). LCMS theoretical m/z=425.3. [M+H]+, found 425.2.

Compound 3: (S)-4-(cyclopropyl(4-(5,6,7,8-tetrahydro-1,8-naphthyridin-2-yl) butyl)amino)-2-((1-methyl-1H-pyrazolo[3,4-d]pyrimidin-4-yl) amino) butanoic acid. To a mixture of (S)-2-amino-4-(cyclopropyl(4-(5,6,7,8-tetrahydro-1,8-naphthyridin-2-yl) butyl)amino) butanoic acid hydrochloride (170 mg, 0.4 mmol) in 4:1 THF/H$_2$O (2.5 mL) was added 4-chloro-1-methyl-1H-pyrazolo[3,4-d]pyrimidine (75 mg, 0.4 mmol) and NaHCO$_3$ (112 mg, 1.33 mmol) and the resulting mixture was stirred at 70° C. for 1 h. The reaction mixture was cooled to rt and concentrated in vacuo. The resulting crude residue was purified by reverse phase prep-HPLC to give the title compound as the trifluoroacetate salt. $^1$H NMR (400 MHz, D$_2$O): δ ppm 8.32-8.47 (m, 2H) 7.51 (br d, J=6.60 Hz, 1H) 6.56 (br s, 1H) 4.85 (br s, 1H) 4.03 (br s, 3H) 3.29-3.63 (m, 6H) 2.38-2.91 (m, 7H) 1.64-1.95 (m, 6H) 0.90-1.09 (m, 4H). LCMS theoretical m/z=479.3. [M+H]+, found 479.2.

Compound 4: (S)-4-((2-hydroxy-2-methylpropyl) (4-(5,6,7,8-tetrahydro-1,8-naphthyridin-2-yl) butyl)amino)-2-(pyrimidin-4-ylamino) butanoic acid. Prepared according to Scheme A using Procedure A with 1-amino-2-methylpropan-2-ol, Procedure H with 4-chloropyrimidine, and Procedure P. LCMS theoretical m/z=457.3. [M+H]+, found 457.2.

Compound 5: (S)-4-((2-methoxyethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-methoxyethan-1-amine, Procedure H with 4-chloroquinazoline, and Procedure P. LCMS theoretical m/z=493.1. [M+H]+, found 493.1.

Compound 6: (S)-4-(cyclopropyl(4-(5,6,7,8-tetrahydro-1,8-naphthyridin-2-yl) butyl)amino)-2-(quinazolin-4-ylamino) butanoic acid. Prepared according to Scheme A using Procedure A with cyclopropylamine, Procedure H with 4-chloroquinazoline, and Procedure P. LCMS theoretical m/z=475.3. [M+H]+, found 475.3.

Compound 7: (S)-2-((7-fluoroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-7-fluoroquinazoline, and Procedure P. LCMS theoretical m/z=511.3. [M+H]+, found 511.3.

Compound 8: (S)-4-((2,2-difluoroethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2,2-difluoroethan-1-amine, Procedure H with 4-chloroquinazoline, and Procedure P. LCMS theoretical m/z=499.3. [M+H]+, found 499.3.

Compound 9: (S)-4-((3,3-difluorocyclobutyl) (4-(5,6,7,8-tetrahydro-1,8-naphthyridin-2-yl) butyl)amino)-2-(quinazolin-4-ylamino) butanoic acid. Prepared according to Scheme A using Procedure A with 3,3-difluorocyclobutan-1-amine, Procedure H with 4-chloroquinazoline, and Procedure P. LCMS theoretical m/z=523.3. [M+H]+, found 525.3.

Compound 10: (S)-4-((2-methoxyethyl) (4-(5,6,7,8-tetrahydro-1,8-naphthyridin-2-yl) butyl)amino)-2-((2-methylquinazolin-4-yl) amino) butanoic acid. Prepared according to Scheme A using Procedure A with 2-methoxyethan-1-amine, Procedure H with 4-chloro-2-methylquinazoline, and Procedure P. LCMS theoretical m/z=507.3. [M+H]+, found 507.3.

Compound 11: (S)-4-((2-methoxyethyl) (4-(5,6,7,8-tetrahydro-1,8-naphthyridin-2-yl) butyl)amino)-2-(pyrido[2,3-d]pyrimidin-4-ylamino) butanoic acid. Prepared according to Scheme A using Procedure A with 2-methoxyethan-1-amine, Procedure H with 4-chloropyrido[2,3-d]pyrimidine, and Procedure P. LCMS theoretical m/z=494.3. [M+H]+, found 494.3.

Compound 12: (S)-2-((7-fluoro-2-methylquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-7-fluoro-2-methylquinazoline, and Procedure P. LCMS theoretical m/z=525.3. [M+H]+, found 525.3.

Compound 13: (S)-4-((2-methoxyethyl) (4-(5,6,7,8-tetrahydro-1,8-naphthyridin-2-yl) butyl)amino)-2-((7-(trifluoromethyl)quinazolin-4-yl) amino) butanoic acid. Prepared according to Scheme A using Procedure A with 2-methoxyethan-1-amine, Procedure H with 4-chloro-7-(trifluoromethyl)quinazoline, and Procedure P. LCMS theoretical m/z=561.3. [M+H]+, found 561.3.

Compound 14: (S)-4-((2-methoxyethyl) (4-(5,6,7,8-tetrahydro-1,8-naphthyridin-2-yl) butyl)amino)-2-((2-(trifluoromethyl)quinazolin-4-yl) amino) butanoic acid. Prepared according to Scheme A using Procedure A with 2-methoxyethan-1-amine, Procedure H with 4-chloro-2-(trifluoromethyl)quinazoline, and Procedure P. LCMS theoretical m/z=561.3. [M+H]+, found 561.3.

Compound 15: (S)-4-((2-methoxyethyl) (4-(5,6,7,8-tetrahydro-1,8-naphthyridin-2-yl) butyl)amino)-2-((8-(trifluoromethyl)quinazolin-4-yl) amino) butanoic acid. Prepared according to Scheme A using Procedure A with 2-methoxyethan-1-amine, Procedure H with 4-chloro-8-(trifluoromethyl)quinazoline, and Procedure P. LCMS theoretical m/z=561.3. [M+H]+, found 561.3.

Compound 16: (S)-4-((2-methoxyethyl) (4-(5,6,7,8-tetrahydro-1,8-naphthyridin-2-yl) butyl)amino)-2-(pyrido[3,2-d]pyrimidin-4-ylamino) butanoic acid. Prepared according to Scheme A using Procedure A with 2-methoxyethan-1-amine, Procedure H with 4-chloropyrido[3,2-d]pyrimidine, and Procedure P. LCMS theoretical m/z=494.3. [M+H]+, found 494.3.

Compound 17: (S)-4-((2-methoxyethyl) (4-(5,6,7,8-tetrahydro-1,8-naphthyridin-2-yl) butyl)amino)-2-(pyrido[3,4-d]pyrimidin-4-ylamino) butanoic acid. Prepared according to Scheme A using Procedure A with 2-methoxyethan-1-amine, Procedure H with 4-chloropyrido[3,4-d]pyrimidine, and Procedure P. LCMS theoretical m/z=494.3. [M+H]+, found 494.3.

Compound 18: (S)-2-((5-fluoroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-5-fluoroquinazoline, and Procedure P. LCMS theoretical m/z=511.3. [M+H]+, found 511.3.

Compound 19: (S)-2-((6-fluoroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-6-fluoroquinazoline, and Procedure P. LCMS theoretical m/z=511.3. [M+H]+, found 511.3.

Compound 20: (S)-2-((8-fluoroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-8-fluoroquinazoline, and Procedure P. LCMS theoretical m/z=511.3. [M+H]+, found 511.3.

Compound 21: (S)-2-((6,7-difluoroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-6,7-difluoroquinazoline, and Procedure P. LCMS theoretical m/z=529.3. [M+H]+, found 529.3.

Compound 22: (S)-4-((2-methoxyethyl) (4-(5,6,7,8-tetrahydro-1,8-naphthyridin-2-yl) butyl)amino)-2-((2-methyl-6-(trifluoromethyl)pyrimidin-4-yl) amino) butanoic acid. Prepared according to Scheme A using Procedure A with 2-methoxyethan-1-amine, Procedure H with 4-chloro-2-methyl-6-(trifluoromethyl)pyrimidine, and Procedure P. LCMS theoretical m/z=525.3. [M+H]+, found 525.3.

Compound 23: (S)-2-((6-(difluoromethyl)pyrimidin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-6-(difluoromethyl)pyrimidine, and Procedure P. LCMS theoretical m/z=493.3. [M+H]+, found 493.3.

Compound 24: (S)-4-((2-methoxyethyl) (4-(5,6,7,8-tetrahydro-1,8-naphthyridin-2-yl) butyl)amino)-2-((2-(trifluoromethyl)pyrimidin-4-yl) amino) butanoic acid. Prepared according to Scheme A using Procedure A with 2-methoxyethan-1-amine, Procedure H with 4-chloro-2-(trifluoromethyl)pyrimidine, and Procedure P. LCMS theoretical m/z=511.3. [M+H]+, found 511.3.

Compound 25: (S)-4-(((S)-2-methoxypropyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-(S)-2-methoxypropan-1-amine, Procedure H with 4-chloroquinazoline, and Procedure P. LCMS theoretical m/z=507.3. [M+H]+, found 507.4.

Compound 26: (S)-4-((2-methoxyethyl) (4-(5,6,7,8-tetrahydro-1,8-naphthyridin-2-yl) butyl)amino)-2-((6-methyl-2-(trifluoromethyl)pyrimidin-4-yl) amino) butanoic acid. Prepared according to Scheme A using Procedure A with 2-methoxyethan-1-amine, Procedure H with 4-chloro-6-methyl-2-(trifluoromethyl)pyrimidine, and Procedure P. LCMS theoretical m/z=525.3. [M+H]+, found 525.3.

Compound 27: (S)-4-((2-(methylsufonyl)ethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-(methylsulfonyl)ethan-1-amine, Procedure H with 4-chloroquinazoline, and Procedure P. LCMS theoretical m/z=541.3. [M+H]+, found 541.3.

Compound 28: (S)-4-((2-phenoxyethyl) (4-(5,6,7,8-tetrahydro-1,8-naphthyridin-2-yl) butyl)amino)-2-(quinazolin-4-ylamino) butanoic acid. Prepared according to Scheme D using Procedure C with (2-bromoethoxy)benzene, Procedure H with 4-chloroquinazoline, and Procedure P. LCMS theoretical m/z=555.3. [M+H]+, found 555.3.

Compound 29: (S)-4-((3,3-difluoropropyl) (4-(5,6,7,8-tetrahydro-1,8-naphthyridin-2-yl) butyl)amino)-2-(quinazolin-4-ylamino) butanoic acid. Prepared according to Scheme A using Procedure A with 3,3-difluoropropan-1-amine, Procedure H with 4-chloroquinazoline, and Procedure P. LCMS theoretical m/z=513.3. [M+H]+, found 513.4.

Compound 30: (S)-4-((3-fluoropropyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-3-fluoropropan-1-amine, Procedure H with 4-chloroquinazoline, and Procedure P. LCMS theoretical m/z=495.3. [M+H]+, found 495.3.

Compound 31: (S)-4-(((S)-2-fluoro-3-methoxypropyl) (4-(5,6,7,8-tetrahydro-1,8-naphthyridin-2-yl) butyl)amino)-2-(quinazolin-4-ylamino) butanoic acid. Prepared according to Scheme A using Procedure A with (S)-2-fluoro-3-methoxypropan-1-amine, Procedure H with 4-chloroquinazoline, and Procedure P. LCMS theoretical m/z=525.3. [M+H]+, found 525.3.

Compound 32: (S)-2-((7-fluoro-2-methylquinazolin-4-yl) amino)-4-(((S)-2-fluoro-3-methoxypropyl) (4-(5,6,7,8-tetrahydro-1,8-naphthyridin-2-yl) butyl)amino) butanoic acid. Prepared according to Scheme A using Procedure A with (S)-2-fluoro-3-methoxypropan-1-amine, Procedure H with 4-chloro-7-fluoro-2-methylquinazoline, and Procedure P. LCMS theoretical m/z=557.3. [M+H]+, found 557.4.

Compound 33: (S)-4-(((3,3-difluorocyclobutyl)methyl) (4-(5,6,7,8-tetrahydro-1,8-naphthyridin-2-yl) butyl)amino)-2-((7-fluoro-2-methylquinazolin-4-yl) amino) butanoic acid Prepared according to Scheme D using Procedure C with 3-(bromomethyl)-1,1-difluorocyclobutane, Procedure H with 4-chloro-7-fluoro-2-methylquinazoline, and Procedure P. LCMS theoretical m/z=571.3. [M+H]+, found 571.3.

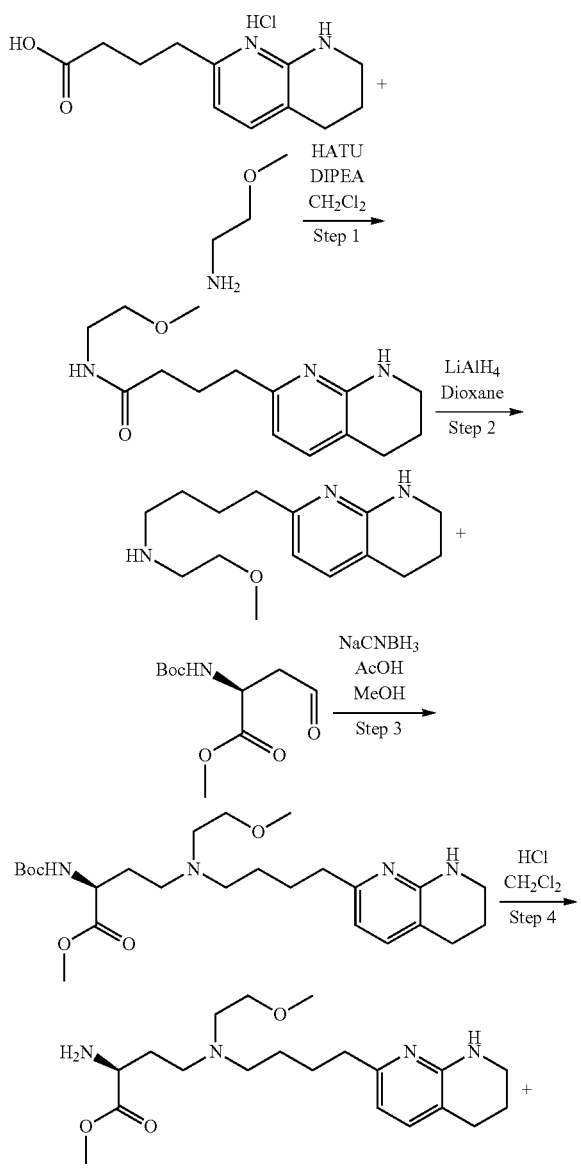

Scheme 2, Compound 34

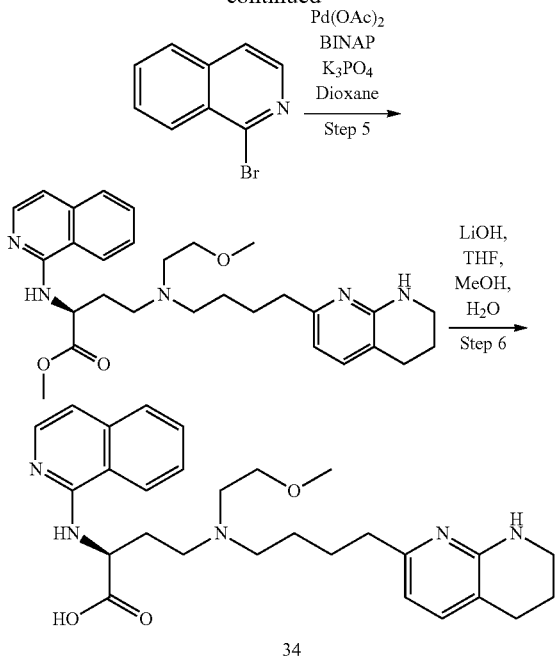

34

Step 1: N-(2-methoxyethyl)-4-(5,6,7,8-tetrahydro-1,8-naphthyridin-2-yl) butanamide To a solution of 4-(5,6,7,8-tetrahydro-1,8-naphthyridin-2-yl) butanoic acid hydrochloride (2.6 g, 10.29 mmol) in CH$_2$Cl$_2$ (26 mL) was added 2-methoxyethan-1-amine (1.3 mL, 15.44 mmol), DIPEA (5.4 mL, 30.87 mmol), then HATU (5.67 g, 14.92 mmol) and the resulting mixture was stirred at rt for 2 h and then concentrated in vacuo. The resulting crude residue was purified using normal phase silica gel chromatography to give the title compound.

Step 2: N-(2-methoxyethyl)-4-(5,6,7,8-tetrahydro-1,8-naphthyridin-2-yl) butan-1-amine To a solution of N-(2-methoxyethyl)-4-(5,6,7,8-tetrahydro-1,8-naphthyridin-2-yl) butanamide (1.1 g, 4.0 mmol) in 1,4-dioxane (11 mL) was added 2.0M LiAlH$_4$ in THF (4 mL, 8.0 mmol) and the resulting mixture was refluxed overnight and then allowed to cool to rt. The solution was carefully neutralized by the cautious addition of H$_2$O (310 µL), then 1 N NaOH (310 µL), then additional H$_2$O (310 µL) and the mixture was stirred at rt for 30 min and then dried over MgSO$_4$, filtered, and concentrated in vacuo. The resulting crude residue was used without further purification.

Step 3: methyl (S)-2-((tert-butoxycarbonyl)amino)-4-((2-methoxyethyl) (4-(5,6,7,8-tetrahydro-1,8-naphthyridin-2-yl) butyl)amino) butanoate To a solution of N-(2-methoxyethyl)-4-(5,6,7,8-tetrahydro-1,8-naphthyridin-2-yl) butan-1-amine (927 mg, 3.52 mmol) and methyl (S)-2-((tert-butoxycarbonyl)amino)-4-oxobutanoate (895 mg, 3.87 mmol) in MeOH (10 mL) at rt was added AcOH (222 µL, 3.87 mmol) then NaCNBH$_3$ (243 mg, 3.87 mmol) and the resulting mixture was stirred at rt overnight and then concentrated in vacuo. The resulting crude residue was purified by normal phase silica gel chromatography to afford the title compound.

Step 4: methyl (S)-2-amino-4-((2-methoxyethyl) (4-(5,6,7,8-tetrahydro-1,8-naphthyridin-2-yl) butyl) amino) butanoate To a solution of methyl (S)-2-((tert-butoxycarbonyl)amino)-4-((2-methoxyethyl) (4-(5,6,7,8-tetrahydro-1,8-naphthyridin-2-yl) butyl)amino) butanoate (700 mg, 1.46 mmol) in CH$_2$Cl$_2$ (3 mL) was added 4 N HCl in dioxane (5 mL) and the resulting mixture was stirred at rt for 2 h and concentrated in vacuo. The resulting crude residue was used without further purification.

Step 5: methyl (S)-2-(isoquinolin-1-ylamino)-4-((2-methoxyethyl) (4-(5,6,7,8-tetrahydro-1,8-naphthyridin-2-yl) butyl)amino) butanoate A microwave vial containing methyl (S)-2-amino-4-((2-methoxyethyl) (4-(5,6,7,8-tetrahydro-1,8-naphthyridin-2-yl) butyl)amino) butanoate (125 mg, 0.3 mmol) was charged with 1-bromoisoquinoline (65 mg, 0.3 mmol), Pd(OAc)$_2$ (6.3 mg, 0.03 mmol), rac-BINAP (35 mg, 0.6 mmol), and K$_3$PO$_4$ (210 mg, 1.0 mmol) and then diluted with dioxane (2 mL). The mixture was degassed and then sealed and heated to 100° C. for 1 h. The reaction mixture was allowed to cool to rt and then filtered and concentrated in vacuo. The crude residue was purified by normal phase silica gel chromatography to give the title compound.

Step 6: (S)-2-(isoquinolin-1-ylamino)-4-((2-methoxyethyl) (4-(5,6,7,8-tetrahydro-1,8-naphthyridin-2-yl) butyl)amino) butanoic acid To a solution of methyl (S)-2-(isoquinolin-1-ylamino)-4-((2-methoxyethyl) (4-(5,6,7,8-tetrahydro-1,8-naphthyridin-2-yl) butyl)amino) butanoate (20 mg, 0.04 mmol) in 4:1:1 THF/MeOH/H$_2$O (1.5 mL) was added LiOH (5 mg, 0.20 mmol) and the resulting mixture was stirred at rt for 1 h and then neutralized with AcOH and concentrated in vacuo. The crude residue was purified by reverse phase prep-HPLC to give the title compound. LCMS theoretical m/z=492.3. [M+H]+, found 492.4.

Compound 35: (S)-4-((2-(difluoromethoxy)ethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-(difluoromethoxy)ethan-1-amine, Procedure D, Procedure F, Procedure G, Procedure H with 4-chloroquinazoline, and Procedure P. LCMS theoretical m/z=529.3. [M+H]+, found 529.3.

Scheme 3, Compound 36

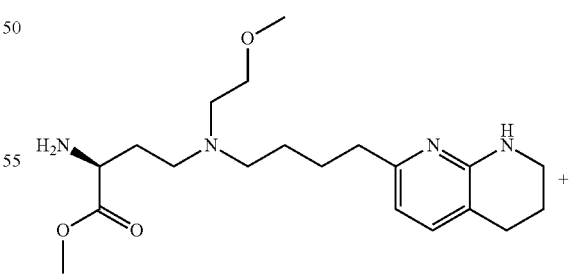

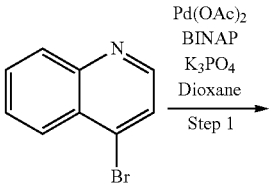

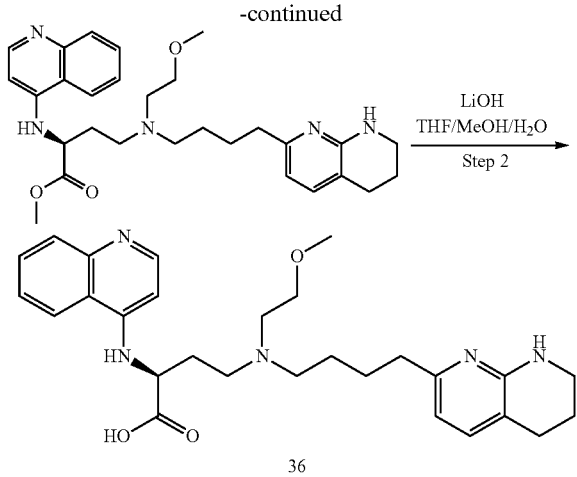

Step 1: methyl (S)-4-((2-methoxyethyl) (4-(5,6,7,8-tetrahydro-1,8-naphthyridin-2-yl) butyl)amino)-2-(quinolin-4-ylamino) butanoate A microwave vial containing methyl (S)-2-amino-4-((2-methoxyethyl) (4-(5,6,7,8-tetrahydro-1,8-naphthyridin-2-yl) butyl)amino) butanoate (125 mg, 0.3 mmol) was charged with 4-bromoquinoline (65 mg, 0.3 mmol), Pd(OAc)$_2$ (6 mg, 0.03 mmol), rac-BINAP (35 mg, 0.6 mmol), and K$_3$PO$_4$ (210 mg, 1.0 mmol) and then diluted with dioxane (2 mL). The mixture was degassed and then sealed and heated to 100° C. for 1 h. The reaction mixture was cool to rt and then filtered and concentrated in vacuo. The crude residue was purified by normal phase silica gel chromatography to give methyl (S)-4-((2-methoxyethyl) (4-(5,6,7,8-tetrahydro-1,8-naphthyridin-2-yl) butyl)amino)-2-(quinolin-4-ylamino) butanoate.

Step 2: (S)-4-((2-methoxyethyl) (4-(5,6,7,8-tetrahydro-1,8-naphthyridin-2-yl) butyl)amino)-2-(quinolin-4-ylamino) butanoic acid To a solution of methyl (S)-4-((2-methoxyethyl) (4-(5,6,7,8-tetrahydro-1,8-naphthyridin-2-yl) butyl)amino)-2-(quinolin-4-ylamino) butanoate (54 mg, 0.11 mmol) in 4:1:1 THF/MeOH/H$_2$O (3 mL) was added LiOH (25.5 mg, 1.1 mmol) and the resulting mixture was stirred at rt for 1 h and then neutralized with AcOH and concentrated in vacuo. The resulting crude residue was purified by reverse phase prep-HPLC to give the title compound. LCMS theoretical m/z=492.3. [M+H]+, found 492.3.

Compound 37: (S)-2-((7-chloroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4,7-dichloroquinazoline, and Procedure P. LCMS theoretical m/z=527.3. [M+H]+, found 527.3.

Compound 38: (S)-2-((8-chloroquinazolin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4,8-dichloroquinazoline, and Procedure P. LCMS theoretical m/z=527.3. [M+H]+, found 527.3.

Compound 39: (S)-2-(quinazolin-4-ylamino)-4-((4-(5,6,7,8-tetrahydro-1,8-naphthyridin-2-yl) butyl) (2-(2,2,2-trifluoroethoxy)ethyl)amino) butanoic acid. Prepared according to Scheme A using Procedure A with 2-(2,2,2-trifluoroethoxy)ethan-1-amine, Procedure H with 4-chloroquinazoline, and Procedure P. LCMS theoretical m/z=561.3. [M+H]+, found 561.3.

Compound 40: (S)-2-((7-fluoro-2-methylquinazolin-4-yl) amino)-4-((2-(4-fluorophenoxy)ethyl) (4-(5,6,7,8-tetrahydro-1,8-naphthyridin-2-yl) butyl)amino) butanoic acid
Prepared according to Scheme D using Procedure C with 1-(2-bromoethoxy)-4-fluorobenzene, Procedure H with 4-chloro-7-fluoro-2-methylquinazoline, and Procedure P. LCMS theoretical m/z=605.3. [M+H]+, found 605.3.

Compound 41: (S)-4-((3-fluoropropyl) (4-(5,6,7,8-tetrahydro-1,8-naphthyridin-2-yl) butyl)amino)-2-((7-methoxyquinazolin-4-yl) amino) butanoic acid. Prepared according to Scheme A using Procedure A with 3-fluoropropan-1-amine, Procedure H with 4-chloro-7-methoxyquinazoline, and Procedure P. LCMS theoretical m/z=525.3. [M+H]+, found 525.3.

Compound 42: (2S)-4-((2-(2,2-difluorocyclopropoxy) ethyl) (4-(5,6,7,8-tetrahydro-1,8-naphthyridin-2-yl) butyl) amino)-2-((7-fluoro-2-methylquinazolin-4-yl) amino) butanoic acid
Prepared according to Scheme D using Procedure C with 2-(2-bromoethoxy)-1,1-difluorocyclopropane, Procedure H with 4-chloro-7-fluoro-2-methylquinazoline, and Procedure P. LCMS theoretical m/z=587.3. [M+H]+, found 587.3.

Compound 43: (S)-4-((3-fluoropropyl) (4-(5,6,7,8-tetrahydro-1,8-naphthyridin-2-yl) butyl)amino)-2-((8-methoxyquinazolin-4-yl) amino) butanoic acid. Prepared according to Scheme A using Procedure A with 3-fluoropropan-1-amine, Procedure H with 4-chloro-8-methoxyquinazoline, and Procedure P. LCMS theoretical m/z=525.3. [M+H]+, found 525.3.

Compound 44: (S)-2-((6-(1H-pyrazol-1-yl) pyrimidin-4-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 4-chloro-6-(1H-pyrazol-1-yl) pyrimidine and Procedure P. LCMS theoretical m/z=509.3. [M+H]+, found 509.3.

Compound 45: (S)-4-((2-(3,5-dimethyl-1H-pyrazol-1-yl) ethyl) (4-(5,6,7,8-tetrahydro-1,8-naphthyridin-2-yl) butyl) amino)-2-(quinazolin-4-ylamino) butanoic acid. Prepared according to Scheme D using Procedure C with 1-(2-bromoethyl)-3,5-dimethyl-1H- pyrazole, Procedure H with 4-chloroquinazoline, and Procedure P. LCMS theoretical m/z=557.3. [M+H]+, found 557.3.

Compound 46: (S)-4-(((S)-2-fluoro-3-methoxypropyl) (4-(5,6,7,8-tetrahydro-1,8-naphthyridin-2-yl) butyl)amino)-2-((2-methylquinazolin-4-yl) amino) butanoic acid. Prepared according to Scheme A using Procedure A with (S)-2-fluoro-3-methoxypropan-1-amine, Procedure H with 4-chloro-2-methylquinazoline, and Procedure P. LCMS theoretical m/z=539.3. [M+H]+, found 539.3.

Compound 47: (S)-4-((2-(3,5-difluorophenoxy)ethyl) (4-(5,6,7,8-tetrahydro-1,8-naphthyridin-2-yl) butyl)amino)-2-(quinazolin-4-ylamino) butanoic acid. Prepared according to Scheme C using Procedure B with 2-(3,5-difluorophenoxy) acetic acid, Procedure H with 4-chloroquinazoline, and Procedure P. LCMS theoretical m/z=591.3. [M+H]+, found 591.3.

Compound 48: (S)-2-((8-chloroquinazolin-4-yl) amino)-4-((2-(pyridin-2-yloxy)ethyl) (4-(5,6,7,8-tetrahydro-1,8-naphthyridin-2-yl) butyl)amino) butanoic acid. Prepared according to Scheme C using Procedure B with 2-(pyridin- 2-yloxy)acetic acid, Procedure H with 4,8-dichloroquinazoline, and Procedure P. LCMS theoretical m/z=590.3. [M+H]+, found 590.3.

Compound 49: (S)-4-((2-(pyridin-2-yloxy)ethyl) (4-(5,6,7,8-tetrahydro-1,8-naphthyridin-2-yl) butyl)amino)-2-(quinazolin-4-ylamino) butanoic acid. Prepared according to Scheme C using Procedure B with 2-(pyridin-2-yloxy)acetic acid, Procedure H with 4-chloroquinazoline, and Procedure P. LCMS theoretical m/z=556.3. [M+H]+, found 556.3.

Compound 50: (S)-4-((2-(2,2-difluoroethoxy)ethyl) (4-(5,6,7,8-tetrahydro-1,8-naphthyridin-2-yl) butyl)amino)-2-(quinazolin-4-ylamino) butanoic acid. Prepared according to Scheme C using Procedure B with 2-(2,2-difluoroethoxy)acetic acid, Procedure H with 4-chloroquinazoline, and Procedure P. LCMS theoretical m/z=543.3. [M+H]+, found 543.3.

Compound 51: (S)-2-(pyrido[3,2-d]pyrimidin-4-ylamino)-4-((4-(5,6,7,8-tetrahydro-1,8-naphthyridin-2-yl) butyl) (2-(2,2,2-trifluoroethoxy)ethyl)amino) butanoic acid Prepared according to Scheme A using Procedure A with 2-(2,2,2-trifluoroethoxy)ethan-1-amine, Procedure G, Procedure H with 4-chloropyrido[3,2-d]pyrimidine, and Procedure P. LCMS theoretical m/z=562.3. [M+H]+, found 562.3.

Compound 52: (S)-4-((2-((2-methylpyridin-3-yl) oxy) ethyl) (4-(5,6,7,8-tetrahydro-1,8-naphthyridin-2-yl) butyl) amino)-2-(quinazolin-4-ylamino) butanoic acid. Prepared according to Scheme C using Procedure B with 2-((2-methylpyridin-3-yl) oxy)acetic acid, Procedure H with 4-chloroquinazoline, and Procedure P. LCMS theoretical m/z=570.3. [M+H]+, found 570.3.

Compound 53: (S)-2-((7-fluoro-2-methylquinazolin-4-yl) amino)-4-((2-((2-methylpyridin-3-yl) oxy)ethyl) (4-(5,6,7,8-tetrahydro-1,8-naphthyridin-2-yl) butyl)amino) butanoic acid. Prepared according to Scheme C using Procedure B with 2-((2-methylpyridin-3-yl) oxy)acetic acid, Procedure H with 4-chloro-7-fluoro-2-methylquinazoline, and Procedure P. LCMS theoretical m/z=602.3. [M+H]+, found 602.3.

Compound 54: (S)-4-((2-((2-methylpyridin-3-yl) oxy) ethyl) (4-(5,6,7,8-tetrahydro-1,8-naphthyridin-2-yl) butyl) amino)-2-(pyrido[3,2-d]pyrimidin-4-ylamino) butanoic acid. Prepared according to Scheme C using Procedure B with 2-((2-methylpyridin-3-yl) oxy)acetic acid, Procedure H with 4-chloropyrido[3,2-d]pyrimidine, and Procedure P. LCMS theoretical m/z=571.3. [M+H]+, found 571.3.

Compound 55: (S)-4-((2-ethoxyethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-ethoxyethan-1-amine, Procedure H with 4-chloroquinazoline, and Procedure P. LCMS theoretical m/z=507.3. [M+H]+, found 507.3.

Compound 56: (S)-2-((7-fluoro-2-methylquinazolin-4-yl) amino)-4-((2-((6-methylpyridin-3-yl) oxy)ethyl) (4-(5,6,7,8-tetrahydro-1,8-naphthyridin-2-yl) butyl)amino) butanoic acid. Prepared according to Scheme C using Procedure B with 2-((6-methylpyridin-3-yl) oxy)acetic acid, Procedure H with 4-chloro-7-fluoro-2-methylquinazoline, and Procedure P. LCMS theoretical m/z=602.3. [M+H]+, found 602.3.

Compound 57: (S)-4-((2-((6-methylpyridin-3-yl) oxy) ethyl) (4-(5,6,7,8-tetrahydro-1,8-naphthyridin-2-yl) butyl) amino)-2-(pyrido[3,2-d]pyrimidin-4-ylamino) butanoic acid. Prepared according to Scheme C using Procedure B with 2-((6-methylpyridin-3-yl) oxy)acetic acid, Procedure H with 4-chloropyrido[3,2-d]pyrimidine, and Procedure P. LCMS theoretical m/z=571.3. [M+H]+, found 571.3.

Compound 58: (S)-4-((2-((5-fluoropyridin-3-yl) oxy) ethyl) (4-(5,6,7,8-tetrahydro-1,8-naphthyridin-2-yl) butyl) amino)-2-(quinazolin-4-ylamino) butanoic acid. Prepared according to Scheme C using Procedure B with 2-((5-fluoropyridin-3-yl) oxy)acetic acid, Procedure H with 4-chloroquinazoline, and Procedure P. LCMS theoretical m/z=574.3. [M+H]+, 574.3.

Compound 59: (S)-4-((2-((6-methylpyridin-3-yl) oxy) ethyl) (4-(5,6,7,8-tetrahydro-1,8-naphthyridin-2-yl) butyl) amino)-2-(quinazolin-4-ylamino) butanoic acid. Prepared according to Scheme C using Procedure B with 2-((6-methylpyridin-3-yl) oxy)acetic acid, Procedure H with 4-chloroquinazoline, and Procedure P. LCMS theoretical m/z=570.3. [M+H]+, found 570.3.

Compound 60: (S)-4-((2-((5-fluoropyridin-3-yl) oxy) ethyl) (4-(5,6,7,8-tetrahydro-1,8-naphthyridin-2-yl) butyl) amino)-2-(pyrido[3,2-d]pyrimidin-4-ylamino) butanoic acid. Prepared according to Scheme C using Procedure B with 2-((5-fluoropyridin-3-yl) oxy)acetic acid, Procedure H with 4-chloropyrido[3,2-d]pyrimidine, and Procedure P. LCMS theoretical m/z=575.3. [M+H]+, found 575.3.

Compound 61: (S)-2-((7-fluoro-2-methylquinazolin-4-yl) amino)-4-((2-((5-fluoropyridin-3-yl) oxy)ethyl) (4-(5,6,7,8-tetrahydro-1,8-naphthyridin-2-yl) butyl)amino) butanoic acid. Prepared according to Scheme C using Procedure B with 2-((5-fluoropyridin-3-yl) oxy)acetic acid, Procedure H with 4-chloro-7-fluoro-2-methylquinazoline, and Procedure P. LCMS theoretical m/z=606.3. [M+H]+, found 606.3.

Compound 62: (S)-4-(((R)-2-methoxypropyl) (4-(5,6,7,8-tetrahydro-1,8-naphthyridin-2-yl) butyl)amino)-2-(quinazolin-4-ylamino) butanoic acid. Prepared according to Scheme C using Procedure B with (R)-2-methoxypropanoic acid, Procedure H with 4-chloroquinazoline, and Procedure P. LCMS theoretical m/z=507.3. [M+H]+, found 507.3.

Compound 63: (S)-4-((2-acetamidoethyl) (4-(5,6,7,8-tetrahydro-1,8-naphthyridin-2-yl) butyl)amino)-2-(quinazolin-4-ylamino) butanoic acid. Prepared according to Scheme B using Procedure F with N-(2-aminoethyl)acetamide, Procedure H with 4-chloroquinazoline, and Procedure P. LCMS theoretical m/z=520.3. [M+H]+, found 520.3.

Compound 64: (S)-4-((2-(dimethylamino)-2-oxoethyl) (4-(5,6,7,8-tetrahydro-1,8-naphthyridin-2-yl) butyl)amino)-2-(quinazolin-4-ylamino) butanoic acid. Prepared according to Scheme B using Procedure F with 2-amino-N,N-dimethylacetamide, Procedure H with 4-chloroquinazoline, and Procedure P. LCMS theoretical m/z=520.3. [M+H]+, found 520.3.

Compound 65: (S)-2-((7-fluoro-2-methylquinazolin-4-yl) amino)-4-(((R)-2-methoxypropyl) (4-(5,6,7,8-tetrahydro-1,8-naphthyridin-2-yl) butyl)amino) butanoic acid. Prepared according to Scheme C using Procedure B with (R)-2-methoxypropanoic acid, Procedure H with 4-chloro-7-fluoro-2-methylquinazoline, and Procedure P. LCMS theoretical m/z=539.3. [M+H]+, found 539.3.

Compound 66: (S)-4-(((R)-2-methoxypropyl) (4-(5,6,7,8-tetrahydro-1,8-naphthyridin-2-yl) butyl)amino)-2-((2-methylquinazolin-4-yl) amino) butanoic acid.

Prepared according to Scheme C using Procedure B with (R)-2-methoxypropanoic acid, Procedure H with 4-chloro-2-methylquinazoline, and Procedure P. LCMS theoretical m/z=521.3. [M+H]+, found 521.3.

Compound 67: (S)-2-((3-cyanopyrazin-2-yl) amino)-4-((2-methoxyethyl) (4-(5,6,7,8-tetrahydro-1,8-naphthyridin-2-yl) butyl)amino) butanoic acid. Prepared according to Scheme A using Procedure A with 2-methoxyethan-1-amine, Procedure H with 3-chloropyrazine-2-carbonitrile and Procedure P. LCMS theoretical m/z=468.3. [M+H]+, found 468.3.

Scheme 4, Compound 68

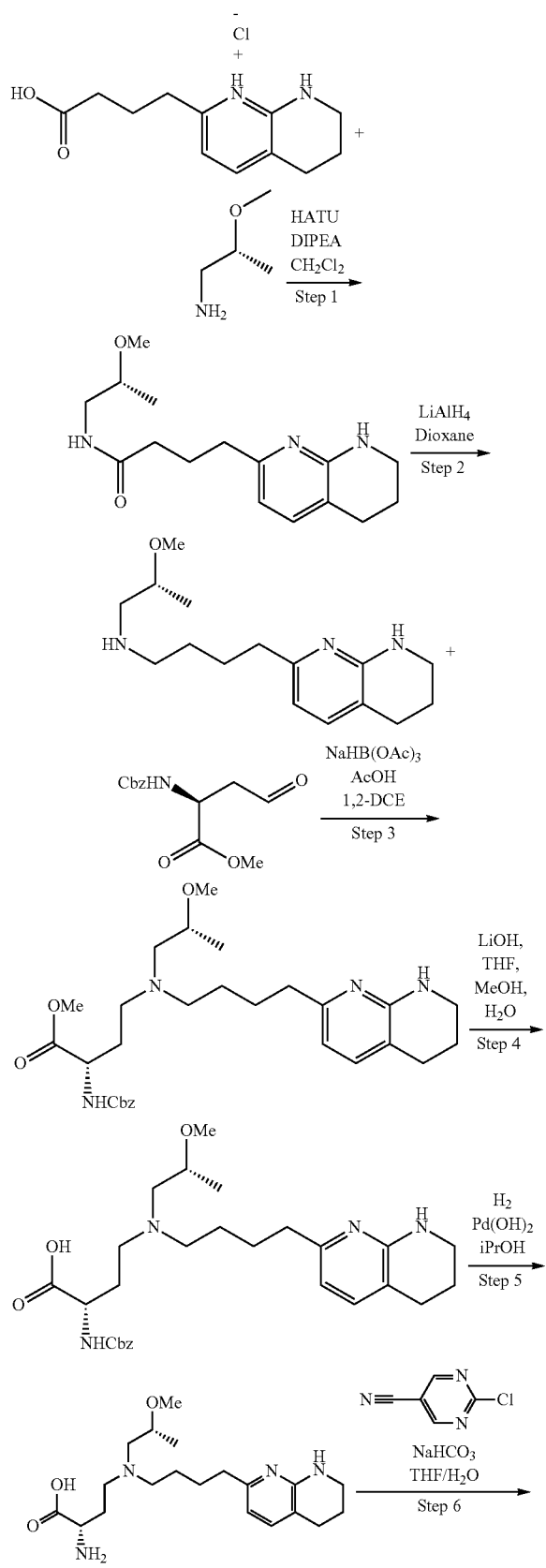

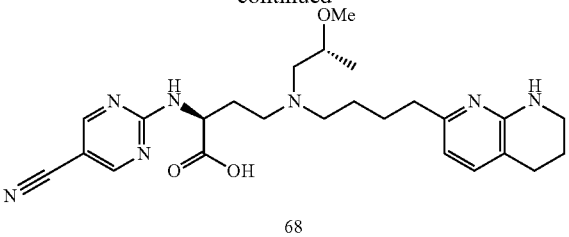

Step 1: (R)—N-(2-methoxypropyl)-4-(5,6,7,8-tetra-hydro-1,8-naphthyridin-2-yl) butanamide To a solution of 4-(5,6,7,8-tetrahydro-1,8-naphthyridin-2-yl) butanoic acid hydrochloride (2.6 g, 10.29 mmol) in CH$_2$Cl$_2$ (26 mL) was added (R)-2-methoxypropan-1-amine (1.38 g, 15.44 mmol), DIPEA (5.4 mL, 30.87 mmol), then HATU (5.67 g, 14.92 mmol) and the resulting mixture was stirred at rt for 2 h and then concentrated in vacuo. The resulting crude residue was purified using normal phase silica gel chromatography to give the title compound.

Step 2: (R)—N-(2-methoxypropyl)-4-(5,6,7,8-tetra-hydro-1,8-naphthyridin-2-yl) butan-1-amine To a solution of (R)—N-(2-methoxypropyl)-4-(5,6,7,8-tetrahydro-1,8-naphthyridin-2-yl) butanamide (1.2 g, 4.0 mmol) in 1,4-dioxane (11 mL) was added 2.0M LiAlH$_4$ in THF (4 mL, 8.0 mmol) and the resulting mixture was refluxed overnight and then allowed to cool to rt. The solution was carefully neutralized by the cautious addition of H$_2$O (310 μL), then 1 N NaOH (310 μL), then additional H$_2$O (310 μL) and the mixture was stirred at rt for 30 min and then dried over MgSO$_4$, filtered, and concentrated in vacuo. The resulting crude residue was used without further purification.

Step 3: methyl (S)-2-(((benzyloxy)carbonyl)amino)-4-(((R)-2-methoxypropyl) (4-(5,6,7,8-tetrahydro-1,8-naphthyridin-2-yl) butyl)amino) butanoate To a mixture of (R)—N-(2-methoxypropyl)-4-(5,6,7,8-tetrahydro-1,8-naphthyridin-2-yl) butan-1-amine (10 g, 36.05 mmol) and methyl (S)-2-(((benzyloxy)carbonyl) amino)-4-oxobutanoate (10.52 g, 39.65 mmol) in 1,2-DCE (100 mL) at 0° C. was added AcOH (3.09 mL, 54.07 mmol) then NaBH(OAc)$_3$ (11.46 g, 54.07 mmol) was added and the resulting mixture was stirred at rt for 1 h. The resulting mixture was diluted with MeOH and then was concentrated in vacuo. The residue was taken back up in CH$_2$Cl$_2$ and sat. aq. NaHCO$_3$ and then the layers were separated and the aqueous layer was extracted with CH$_2$Cl$_2$. The combined organic extracts were dried over Na$_2$SO$_4$, filtered, and concentrated in vacuo. The resulting crude residue was purified by normal phase silica gel chromatography to give the title compound. LCMS (ESI+): m/z=527.5 (M+H)$^+$.

Step 4: (S)-2-(((benzyloxy)carbonyl)amino)-4-(((R)-2-methoxypropyl) (4-(5,6,7,8-tetrahydro-1,8-naph-thyridin-2-yl) butyl)amino) butanoic acid To a mixture of methyl (S)-2-(((benzyloxy)carbonyl) amino)-4-(((R)-2-methoxypropyl) (4-(5,6,7,8-tetrahydro-1,8-naphthyridin-2-yl) butyl)amino) butanoate (6 g, 11.39 mmol) in 1:1:1 THF/MeOH/H$_2$O (60 mL) was added LiOH.H₂O (956 mg, 22.78 mmol) and the resulting mixture was stirred at rt for 1 h. The mixture was then adjusted to pH=6 by the addition of AcOH and then concentrated in vacuo to give the title compound as the acetate salt that was used without further purification. LCMS (ESI+): m/z=513.2 (M+H)⁺.

Step 5: (S)-2-amino-4-(((R)-2-methoxypropyl) (4-(5,6,7,8-tetrahydro-1,8-naphthyridin-2-yl) butyl) amino) butanoic acid To a solution of (S)-2-(((benzyloxy)carbonyl)amino)-4-(((R)-2-methoxypropyl) (4-(5,6,7,8-tetrahydro-1,8-naphthyridin-2-yl) butyl)amino) butanoic acid acetate (8 g, 13.97 mmol) in i-PrOH (50 mL) was added 20 wt % Pd(OH)₂/C (1.96 g) and the resulting suspension was evacuated and backfilled with H₂ several times. The resulting mixture was stirred under an H₂ atmosphere at rt for 2 h and then the mixture was filtered and concentrated under reduced pressure to give the title compound as the acetate salt that was used without further purification. LCMS (ESI+): m/z=379.2 (M+H)⁺.

Step 6: (S)-2-((5-cyanopyrimidin-2-yl) amino)-4-(((R)-2-methoxypropyl) (4-(5,6,7,8-tetrahydro-1,8-naphthyridin-2-yl) butyl)amino) butanoic acid To a solution of (S)-2-amino-4-(((R)-2-methoxypropyl) (4-(5,6,7,8-tetrahydro-1,8-naphthyridin-2-yl) butyl)amino) butanoic acid acetate (100 mg, 228 µmol) in 4:1 THF/H₂O (2.5 mL) was added solid NaHCO₃ (57 mg, 684 µmol) followed by 2-chloropyrimidine-5-carbonitrile (33 mg, 239 µmol). The resulting mixture was stirred at 70° C. for 1 h and then allowed to cool to rt. The mixture was adjusted to pH=6 by the addition of aq. 1 M HCl and then concentrated in vacuo. The resulting crude residue was purified by reverse phase prep-HPLC to give the title compound. LCMS (ESI+): m/z=482.3 (M+H)⁺. ¹H NMR (400 MHz, Methanol-d₄) δ ppm 8.48-8.64 (m, 2H) 7.21 (d, J=7.28 Hz, 1H) 6.42 (d, J=7.28 Hz, 1H) 4.41 (dd, J=6.62, 4.85 Hz, 1H) 3.71 (ddd, J=9.26, 6.06, 3.20 Hz, 1H) 3.36-3.41 (m, 2H) 3.32-3.34 (m, 1H) 3.33 (s, 2H) 3.26 (br dd, J=13.78, 6.73 Hz, 1H) 3.02-3.12 (m, 2H) 2.87-3.01 (m, 3H) 2.71 (t, J=6.06 Hz, 2H) 2.59 (br t, J=7.06 Hz, 2H) 2.22-2.32 (m, 1H) 2.06-2.16 (m, 1H) 1.88 (dt, J=11.52, 6.04 Hz, 2H) 1.72 (br s, 4H) 1.17 (d, J=6.17 Hz, 3H).

Compound 69: (S)-4-(((R)-2-methoxypropyl) (4-(5,6,7,8-tetrahydro-1,8-naphthyridin-2-yl) butyl)amino)-2-((5-(trifluoromethyl)pyrimidin-2-yl) amino) butanoic acid. (S)-2-amino-4-(((R)-2-methoxypropyl) (4-(5,6,7,8-tetrahydro-1, 8-naphthyridin-2-yl) butyl)amino) butanoic acid acetate (100 mg, 228 µmol) in 4:1 THF/H₂O (2.5 mL) was added solid NaHCO₃ (38 mg, 456 µmol) followed by 2-chloro-5-(trifluoromethyl)pyrimidine (44 mg, 239.42 µmol). The resulting mixture was stirred at 70° C. for 1 h, cooled to rt, adjusted to pH=6 by the addition of 1 M HCl, and then concentrated in vacuo. The resulting crude residue was purified by reverse phase prep-HPLC to give the title compound. LCMS (ESI+): m/z=525.2 (M+H)⁺. ¹H NMR (400 MHz, DMSO-d₆) δ ppm 9.72-10.42 (m, 1H) 8.65 (s, 2H) 8.05-8.33 (m, 2H) 7.59 (d, J=7.34 Hz, 1H) 6.62 (d, J=7.34 Hz, 1H) 4.57 (br s, 1H) 3.88 (ddd, J=8.99, 6.11, 3.12 Hz, 1H) 3.45 (t, J=5.56 Hz, 2H) 3.24-3.38 (m, 4H) 3.06-3.23 (m, 5H) 2.69-2.80 (m, 4H) 2.23-2.43 (m, 3H) 1.81-1.90 (m, 2H) 1.70-1.80 (m, 4H) 1.14 (d, J=6.24 Hz, 3H).

Compound 70: (S)-2-((5-bromopyrimidin-2-yl) amino)-4-(((R)-2-methoxypropyl) (4-(5,6,7,8-tetrahydro-1,8-naphthyridin-2-yl) butyl)amino) butanoic acid: (S)-2-amino-4-(((R)-2-methoxypropyl) (4-(5,6,7,8-tetrahydro-1,8-naphthyridin-2-yl) butyl)amino) butanoic acid acetate (100 mg, 228 µmol) in 4:1 THF/H₂O (2.5 mL) was added solid NaHCO₃ (57 mg, 684 µmol) followed by 5-bromo-2-chloropyrimidine (46 mg, 239 µmol). The resulting mixture was stirred at 70° C. for 1 h and then allowed to cool to rt. The mixture was adjusted to pH=6 by the addition of aq. 1 M HCl and then concentrated in vacuo. The resulting crude residue was purified by reverse phase prep-HPLC to give the title compound. LCMS (ESI+): m/z=535.2 (M+H)⁺. ¹H NMR (400 MHz, Methanol-d₄) δ ppm 8.47-8.55 (m, 2H) 7.59 (d, J=7.28 Hz, 1H) 6.65 (d, J=7.50 Hz, 1H) 4.70 (dt, J=8.49, 4.35 Hz, 1H) 3.82 (br s, 1H) 3.49-3.53 (m, 2H) 3.37 (d, J=12.13 Hz, 4H) 3.13-3.29 (m, 4H) 2.76-2.85 (m, 4H) 2.41-2.51 (m, 2H) 2.30 (br d, J=10.80 Hz, 1H) 1.90-2.00 (m, 2H) 1.79 (br s, 4H) 1.21 (t, J=5.29 Hz, 3H).

Compound 71: (S)-2-((1H-pyrazolo[3,4-d]pyrimidin-4-yl) amino)-4-(((R)-2-methoxypropyl) (4-(5,6,7,8-tetrahydro-1,8-naphthyridin-2-yl) butyl)amino) butanoic acid: (S)-2-amino-4-(((R)-2-methoxypropyl) (4-(5,6,7,8-tetrahydro-1,8-naphthyridin-2-yl) butyl)amino) butanoic acid acetate (150 mg, 342 µmol) in 4:1 THF/H₂O (2.5 mL) was added NaHCO₃ (86 mg, 1.03 mmol) followed by 4-chloro-1H-pyrazolo[3,4-d]pyrimidine (56 mg, 359 µmol). The resulting mixture was stirred at 70° C. for 1 h and then allowed to cool to rt. The mixture was adjusted to pH=6 by the addition of aq. 1 M HCl and then concentrated in vacuo. The resulting crude residue was purified by reverse phase prep-HPLC to give the title compound. LCMS (ESI+): m/z=497.3 (M+H)⁺. ¹H NMR (400 MHz, DMSO-d₆) δ ppm 14.34 (br s, 1H) 9.83-10.11 (m, 1H) 8.93 (br s, 1H) 8.54 (br s, 1H) 8.11 (br s, 1H) 7.60 (d, J=7.28 Hz, 1H) 6.63 (d, J=7.50 Hz, 1H) 4.93 (br s, 1H) 3.88 (br s, 1H) 3.42 (br s, 2H) 3.26-3.39 (m, 2H) 3.24 (s, 3H) 3.17 (br s, 4H) 2.72 (br d, J=5.95 Hz, 4H) 2.42 (br s, 2H) 1.64-1.86 (m, 6H) 1.11 (d, J=5.95 Hz, 3H).

Compound 72: (S)-4-(((R)-2-methoxypropyl) (4-(5,6,7,8-tetrahydro-1,8-naphthyridin-2-yl) butyl)amino)-2-((2-(trifluoromethyl)pyrimidin-4-yl) amino) butanoic acid. (S)-2-amino-4-(((R)-2-methoxypropyl) (4-(5,6,7,8-tetrahydro-1, 8-naphthyridin-2-yl) butyl)amino) butanoic acid acetate (100 mg, 228 µmol) in 4:1 THF/H₂O (2.5 mL) was added NaHCO₃ (57 mg, 684 µmol) followed by 4-chloro-2-(trifluoromethyl)pyrimidine (44 mg, 239 µmol). The resulting mixture was stirred at 70° C. for 1 h and then allowed to cool to rt. The mixture was adjusted to pH=6 by the addition of aq. 1 M HCl and then concentrated in vacuo. The resulting crude residue was purified by reverse phase prep-HPLC to give the title compound. LCMS (ESI+): m/z=525.3 (M+H)⁺. ¹H NMR (400 MHz, Methanol-d₄) δ ppm 8.27 (br d, J=5.51 Hz, 1H) 7.60 (d, J=7.28 Hz, 1H) 6.96 (d, J=6.39 Hz, 1H) 6.65 (d, J=7.28 Hz, 1H) 4.86 (br s, 1H) 3.82 (br d, J=5.95 Hz, 1H) 3.42-3.55 (m, 3H) 3.37 (d, J=8.38 Hz, 4H) 3.12-3.30 (m, 4H) 2.72-2.86 (m, 4H) 2.48 (dt, J=11.85, 5.87 Hz, 1H) 2.26-2.39 (m, 1H) 1.95 (q, J=5.90 Hz, 2H) 1.73-1.90 (m, 4H) 1.22 (dd, J=6.06, 1.87 Hz, 3H).

Compound 73: (S)-4-(((R)-2-methoxypropyl) (4-(5,6,7,8-tetrahydro-1,8-naphthyridin-2-yl) butyl)amino)-2-((2-phenylpyrimidin-4-yl) amino) butanoic acid: (S)-2-amino-4-(((R)-2-methoxypropyl) (4-(5,6,7,8-tetrahydro-1,8-naphthyridin-2-yl) butyl)amino) butanoic acid acetate (150 mg, 342 µmol), 4-chloro-2-phenylpyrimidine (65 mg, 342 µmol) in DMA (2 mL) was added DIPEA (179 µL, 1.03 mmol) and the resulting mixture was stirred at 100° C. for 2 h. The mixture was cooled to rt and then adjusted to pH=6 by aq. 1 M HCl and then concentrated in vacuo. The resulting crude residue was purified by reverse phase prep-HPLC to afford the title compound. LCMS (ESI+): m/z=533.3 (M+H)+. $^1$H NMR (400 MHz, Methanol-d$_4$) δ ppm 8.24 (br d, J=5.95 Hz, 2H) 8.11 (br s, 1H) 7.37-7.48 (m, 3H) 7.16 (br d, J=5.51 Hz, 1H) 6.49 (br s, 1H) 6.38 (d, J=7.50 Hz, 1H) 4.65 (br s, 1H) 3.68 (br d, J=5.95 Hz, 1H) 3.36 (br s, 1H) 3.23-3.30 (m, 5H) 2.82-3.18 (m, 5H) 2.52-2.69 (m, 4H) 2.35 (br s, 1H) 2.13-2.21 (m, 1H) 1.62-1.86 (m, 6H) 1.14 (d, J=6.17 Hz, 3H).

Compound 74: (S)-4-(((R)-2-methoxypropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid: (S)-2-amino-4-(((R)-2-methoxypropyl) (4-(5,6,7,8-tetrahydro-1,8-naphthyridin-2-yl) butyl)amino) butanoic acid acetate (100 mg, 228 µmol) in 4:1 THF/H$_2$O (2.5 mL) was added NaHCO$_3$ (57 mg, 684 µmol) followed by 4-chloro-1-methyl-pyrazolo[3,4-d]pyrimidine (40 mg, 239 µmol) and the resulting mixture was stirred at 70° C. for 1 h. The mixture was cooled to rt and then adjusted to pH=6 by aq. 1 M HCl and then concentrated in vacuo. The resulting crude residue was purified by reverse phase prep-HPLC to give the title compound. LCMS (ESI+): m/z=511.3 (M+H)+. $^1$H NMR (400 MHz, Methanol-d$_4$) δ ppm 8.60 (br d, J=16.54 Hz, 1H) 8.50 (s, 1H) 7.59 (d, J=7.50 Hz, 1H) 6.66 (d, J=7.28 Hz, 1H) 5.07 (br dd, J=8.05, 5.62 Hz, 1H) 4.09 (s, 3H) 3.87 (br s, 1H) 3.59 (br d, J=16.76 Hz, 1H) 3.43-3.53 (m, 4H) 3.39 (s, 3H) 3.33-3.36 (m, 1H) 3.15-3.29 (m, 2H) 2.77-2.85 (m, 4H) 2.51-2.68 (m, 2H) 1.78-1.98 (m, 6H) 1.23 (d, J=5.95 Hz, 3H).

Compound 75: (S)-4-((2-hydroxyethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-aminoethan-1-ol, Procedure H with 4-chloroquinazoline, and Procedure P. LCMS theoretical m/z=479.3. [M+H]+, found 479.3.

Compound 76: (S)-2-((3-cyanopyrazin-2-yl) amino)-4-(((R)-2-methoxypropyl) (4-(5,6,7,8-tetrahydro-1,8-naphthyridin-2-yl) butyl)amino) butanoic acid: (S)-2-amino-4-(((R)-2-methoxypropyl) (4-(5,6,7,8-tetrahydro-1,8-naphthyridin-2-yl) butyl)amino) butanoic acid acetate (100 mg, 228 µmol) in i-PrOH (2 mL) was added DPIEA (199 µL, 1.14 mmol) and 3-chloropyrazine-2-carbonitrile (35 mg, 250.82 µmol) and the resulting mixture was stirred at 70° C. for 12 h. The mixture was cooled to rt and then adjusted to pH=6 by aq. 1 M HCl and then concentrated in vacuo. The resulting crude residue was purified by reverse phase prep-HPLC to give the title compound. LCMS (ESI+): m/z=482.2 (M+H)+. $^1$H NMR (400 MHz, Methanol-d$_4$) δ ppm 8.23 (d, J=2.32 Hz, 1H) 7.87 (d, J=2.32 Hz, 1H) 7.15 (d, J=7.34 Hz, 1H) 6.38 (d, J=7.34 Hz, 1H) 4.40 (t, J=5.50 Hz, 1H) 3.63-3.73 (m, 1H) 3.35-3.39 (m, 2H) 3.31-3.32 (m, 3H) 3.12-3.22 (m, 1H) 2.81-3.03 (m, 5H) 2.69 (t, J=6.17 Hz, 2H) 2.51-2.60 (m, 2H) 2.26 (dq, J=14.35, 6.99 Hz, 1H) 2.06-2.16 (m, 1H) 1.86 (q, J=5.90 Hz, 2H) 1.67 (br s, 4H) 1.15 (d, J=5.99 Hz, 3H).

Compound 77: (S)-2-((6-(1H-pyrazol-1-yl) pyrimidin-4-yl) amino)-4-(((R)-2-methoxypropyl) (4-(5,6,7,8-tetrahydro-1,8-naphthyridin-2-yl) butyl)amino) butanoic acid: (S)-2-amino-4-(((R)-2-methoxypropyl) (4-(5,6,7,8-tetrahydro-1,8-naphthyridin-2-yl) butyl)amino) butanoic acid acetate (100 mg, 228 µmol) in DMA (2 mL) was added DIPEA (119 µL, 684 µmol) followed by 4-chloro-6-pyrazol-1-yl-pyrimidine (45 mg, 251 µmol) and the resulting mixture was stirred at 100° C. for 2 h. The mixture was cooled to rt and then adjusted to pH=6 by 1 M HCl and then concentrated in vacuo. The resulting crude residue was purified by reverse phase prep-HPLC to give the title compound. LCMS (ESI+): m/z=523.3 (M+H)+. $^1$H NMR (400 MHz, Methanol-d$_4$) δ ppm 8.51 (d, J=2.21 Hz, 1H) 8.33 (s, 1H) 7.75 (s, 1H) 7.16 (d, J=7.28 Hz, 1H) 7.00 (br s, 1H) 6.52 (d, J=1.76 Hz, 1H) 6.39 (d, J=7.28 Hz, 1H) 4.49 (br s, 1H) 3.75 (br s, 1H) 3.33-3.42 (m, 6H) 3.00-3.15 (m, 3H) 2.86-2.98 (m, 2H) 2.67 (br t, J=6.17 Hz, 2H) 2.56-2.62 (m, 2H) 2.23-2.35 (m, 1H) 2.11 (br dd, J=14.44, 5.40 Hz, 1H) 1.85 (q, J=5.95 Hz, 2H) 1.72 (br d, J=3.75 Hz, 4H) 1.18 (d, J=5.95 Hz, 3H).

Compound 78: (S)-2-((5-fluoropyrimidin-2-yl) amino)-4-(((R)-2-methoxypropyl) (4-(5,6,7,8-tetrahydro-1,8-naphthyridin-2-yl) butyl)amino) butanoic acid: (S)-2-amino-4-(((R)-2-methoxypropyl) (4-(5,6,7,8-tetrahydro-1,8-naphthyridin-2-yl) butyl)amino) butanoic acid acetate (150 mg, 342 µmol), 2-chloro-5-fluoropyrimidine (50 mg, 376 µmol) in DMA (2 mL) was added DIPEA (179 µL, 1.03 mmol) and the resulting mixture was stirred at 100° C. for 2 h. The mixture was cooled to rt and then adjusted to pH=6 by aq. 1 M HCl and then concentrated in vacuo. The resulting crude residue was purified by reverse phase prep-HPLC to give the title compound. LCMS (ESI+): m/z=475.2 (M+H)+. $^1$H NMR (400 MHz, Methanol-d$_4$) δ ppm 8.33 (s, 2H) 7.60 (d, J=7.28 Hz, 1H) 6.61-6.67 (m, 1H) 4.57-4.66 (m, 1H) 3.74-3.87 (m, 1H) 3.48-3.53 (m, 2H) 3.39-3.48 (m, 1H) 3.32-3.39 (m, 4H) 3.12-3.29 (m, 4H) 2.80 (dt, J=17.81, 6.64 Hz, 4H) 2.37-2.50 (m, 1H) 2.25 (br dd, J=9.04, 3.53 Hz, 1H) 1.95 (dt, J=11.91, 5.95 Hz, 2H) 1.79 (br d, J=5.73 Hz, 4H) 1.21 (t, J=6.28 Hz, 3H).

Compound 79: (S)-2-((1H-pyrazolo[4,3-d]pyrimidin-7-yl) amino)-4-(((R)-2-methoxypropyl) (4-(5,6,7,8-tetrahydro-1,8-naphthyridin-2-yl) butyl)amino) butanoic acid: (S)-2-amino-4-(((R)-2-methoxypropyl) (4-(5,6,7,8-tetrahydro-1,8-naphthyridin-2-yl) butyl)amino) butanoic acid acetate (100 mg, 241 µmol) in 4:1 THF/H$_2$O (2.5 mL) was added NaHCO$_3$ (57 mg, 684 µmol) followed by 7-chloro-1H-pyrazolo[4,3-d]pyrimidine (45 mg, 289 µmol) and the resulting mixture was stirred at 70° C. for 12 h. The mixture was cooled to rt and then adjusted to pH=6 by aq. 1 M HCl and then concentrated in vacuo. The resulting crude residue was purified by reverse phase prep-HPLC to give the title compound. LCMS (ESI+): m/z=497.3 (M+H)+. $^1$H NMR (400 MHz, Methanol-d$_4$) δ ppm 8.18-8.48 (m, 2H) 7.60 (d, J=7.21 Hz, 1H) 6.59 (d, J=7.21 Hz, 1H) 4.87 (br s, 1H) 3.73 (br s, 1H) 3.41 (br s, 2H) 3.25-3.37 (m, 1H) 3.19-3.24 (m, 3H) 3.02-3.19 (m, 5H) 2.63-2.77 (m, 4H) 2.33 (br s, 1H) 2.20 (br d, J=10.15 Hz, 1H) 1.59-1.87 (m, 6H) 1.10 (br d, J=5.87 Hz, 3H).

Compound 80: (S)-4-(((R)-2-methoxypropyl) (4-(5,6,7,8-tetrahydro-1,8-naphthyridin-2-yl) butyl)amino)-2-((6-phenylpyrimidin-4-yl) amino) butanoic acid: To a solution of (S)-2-amino-4-(((R)-2-methoxypropyl) (4-(5,6,7,8-tetrahydro-1,8-naphthyridin-2-yl) butyl)amino) butanoic acid hydrochloride (100 mg, 241 µmol) and 4-chloro-6-phenylpyrimidine (51 mg, 265 µmol) in 4:1 THF/H$_2$O (2.5 mL) was added NaHCO$_3$ (61 mg, 723 µmol) and the resulting mixture was stirred at 70° C. for 12 h. The mixture was cooled to rt and then adjusted to pH=6 by aq. 1 M HCl and then concentrated in vacuo. The resulting crude residue was purified by reverse phase prep-HPLC to give the title compound. LCMS (ESI+): m/z=533.3 (M+H)+. $^1$H NMR (400 MHz, Methanol-d$_4$) δ ppm 8.47 (s, 1H) 7.81-7.92 (m, 2H) 7.44-7.53 (m, 3H) 7.15 (d, J=7.50 Hz, 1H) 6.93-7.05 (m, 1H) 6.39 (d, J=7.50 Hz, 1H) 4.47 (br s, 1H) 3.75 (br s, 1H) 3.32-3.39 (m, 6H) 2.84-3.21 (m, 5H) 2.66 (t, J=6.17 Hz, 2H) 2.56-2.62 (m, 2H) 2.24-2.35 (m, 1H) 2.05-2.17 (m, 1H) 1.84 (q, J=5.90 Hz, 2H) 1.72 (br s, 4H) 1.18 (d, J=6.17 Hz, 3H).

Scheme 5, Compound 81

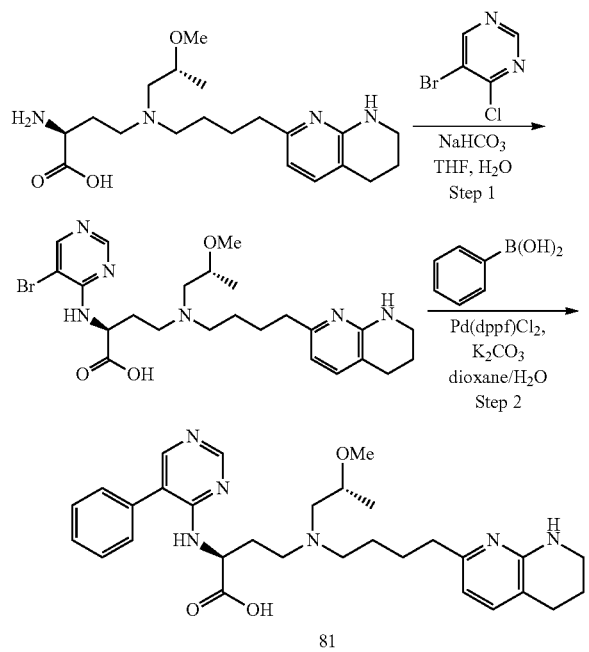

81

Scheme 6, Compound 82

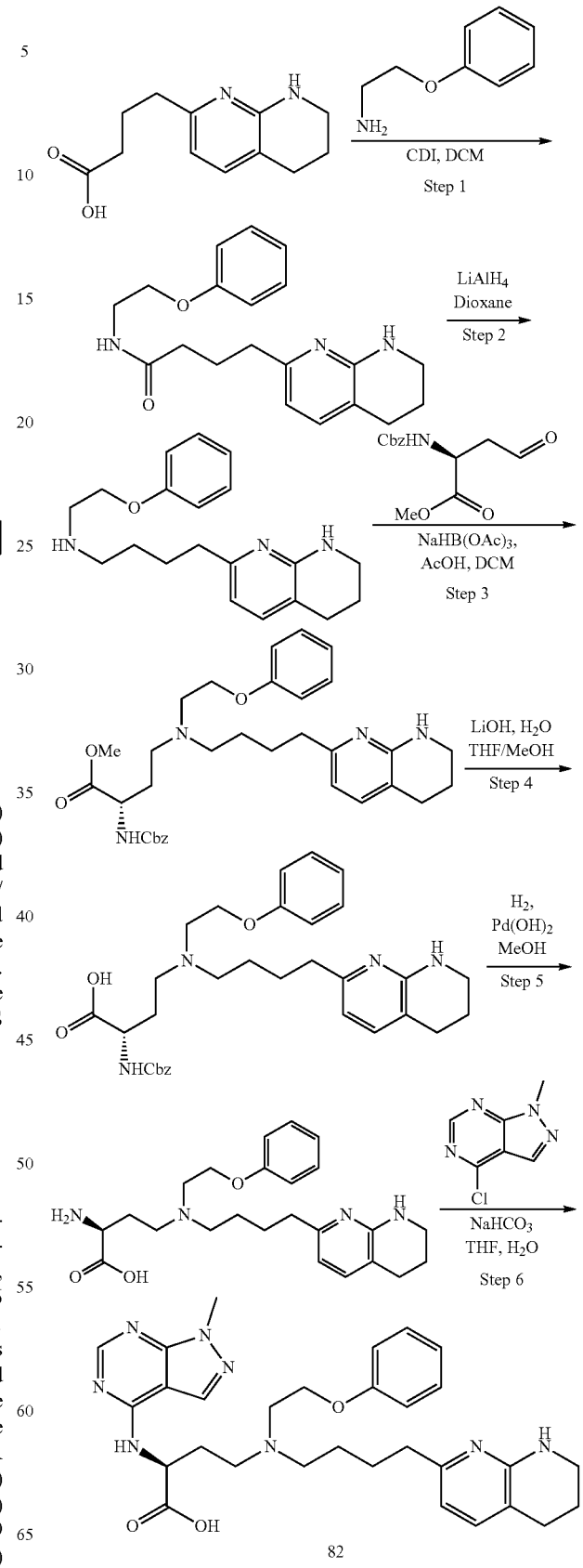

82

Step 1: (S)-2-((5-bromopyrimidin-4-yl) amino)-4-(((R)-2-methoxypropyl) (4-(5,6,7,8-tetrahydro-1,8-naphthyridin-2-yl) butyl)amino) butanoic acid To a solution of (S)-2-amino-4-(((R)-2-methoxypropyl) (4-(5,6,7,8-tetrahydro-1,8-naphthyridin-2-yl) butyl)amino) butanoic acid hydrochloride (100 mg, 241 µmol) and 5-bromo-4-chloropyrimidine (51 mg, 265 µmol) in 4:1 THF/$H_2O$ (2.5 mL) was added $NaHCO_3$ (101 mg, 1.20 mmol) and the resulting mixture was stirred at 70° C. for 2 h. The mixture was cooled to rt and then adjusted to pH=6 by aq. 1 M HCl and then concentrated in vacuo to give the title compound that was used without further purification. LCMS (ESI+): m/z=535.3 (M+H)+.

Step 2: (S)-4-(((R)-2-methoxypropyl) (4-(5,6,7,8-tetrahydro-1,8-naphthyridin-2-yl) butyl)amino)-2-((5-phenylpyrimidin-4-yl) amino) butanoic acid A mixture of (S)-2-((5-bromopyrimidin-4-yl) amino)-4-(((R)-2-methoxypropyl) (4-(5,6,7,8-tetrahydro-1,8-naphthyridin-2-yl) butyl)amino) butanoic acid (30 mg, 56 µmol), phenylboronic acid (8 mg, 67 µmol), $Pd(dppf)Cl_2$ (4 mg, 6 µmol), and $K_2CO_3$ (15 mg, 112 µmol) were diluted in 4:1 dioxane/$H_2O$ (1.25 mL) and the resulting mixture was stirred at 100° C. for 2 h. The mixture was cooled to rt and then filtered and concentrated in vacuo. The crude residue was purified by reverse phase prep-HPLC to afford the title compound. LCMS (ESI+): m/z=533.3 (M+H)+. $^1$H NMR (400 MHz, Methanol-$d_4$) δ ppm 8.86 (s, 1H) 8.22 (s, 1H) 7.53-7.66 (m, 6H) 6.66 (br d, J=6.84 Hz, 1H) 5.11 (br s, 1H) 3.84 (br s, 1H) 3.48-3.54 (m, 2H) 3.46 (br s, 1H) 3.34-3.39 (m, 3H) 3.08-3.29 (m, 4H) 2.74-2.86 (m, 5H) 2.56 (br s, 1H) 2.37 (br s, 1H) 1.76-2.00 (m, 6H) 1.21 (br d, J=5.29 Hz, 3H).

Step 1: N-(2-phenoxyethyl)-4-(5,6,7,8-tetrahydro-1,8-naphthyridin-2-yl) butanamide To a mixture of 4-(5,6,7,8-tetrahydro-1,8-naphthyridin-2-yl) butanoic acid (5 g, 15.89 mmol) in DCM (70 mL) was added CDI (2.83 g, 17.48 mmol) at 0° C. and the resulting mixture was stirred at rt for 1 h, at which time, 2-phenoxyethanamine (2.40 g, 17.48 mmol) was added and stirred for an additional 1 h at rt. The mixture was diluted with $H_2O$ and the layers were separated. The aqueous layer was extracted with DCM and the combined organic extracts were dried over $Na_2SO_4$, filtered, and concentrated in vacuo to give the title compound that was used without further purification. LCMS (ESI+): m/z=339.9 (M+H)$^+$.

Step 2: N-(2-phenoxyethyl)-4-(5,6,7,8-tetrahydro-1,8-naphthyridin-2-yl) butan-1-amine To a mixture of LiAlH$_4$ (1.21 g, 31.79 mmol) in 1,4-dioxane (50 mL) at rt was added N-(2-phenoxyethyl)-4-(5,6,7,8-tetrahydro-1,8-naphthyridin-2-yl) butanamide (5 g, 14.45 mmol) and the resulting mixture was heated to reflux for 30 min and then allowed to cool to rt. The mixture was carefully neutralized by the dropwise addition of $H_2O$ (1.2 mL), then 1 M aq. NaOH (1.2 mL), and then $H_2O$ (3.6 mL) again, followed by drying over MgSO$_4$. The mixture was filtered and concentrated in vacuo to give the title compound that was used without further purification. LCMS (ESI+): m/z=326.1 (M+H)$^+$.

Step 3: methyl (S)-2-(((benzyloxy)carbonyl)amino)-4-((2-phenoxyethyl) (4-(5,6,7,8-tetrahydro-1,8-naphthyridin-2-yl) butyl)amino) butanoate To a mixture of N-(2-phenoxyethyl)-4-(5,6,7,8-tetrahydro-1,8-naphthyridin-2-yl) butan-1-amine (5 g, 12.84 mmol) and (S)-methyl 2-(((benzyloxy)carbonyl)amino)-4-oxobutanoate (3.75 g, 14.12 mmol) in DCE (75 mL) at 0° C. was added AcOH (1.10 mL, 19.26 mmol) and NaBH(OAc)$_3$ (4.08 g, 19.26 mmol) and the resulting mixture was stirred for 3 h at rt. The mixture was diluted with MeOH (50 mL) and the mixture was concentrated in vacuo. The crude product was taken up in DCM and sat. aq. NaHCO$_3$ was added. The layers were separated and the aqueous layer was extracted with DCM. The combined organic extracts were dried over Na$_2$SO$_4$, filtered, and concentrated in vacuo. The crude residue was purified by normal phase silica gel chromatography to give the title compound. LCMS (ESI+): m/z=575.1 (M+H)$^+$.

Step 4: (S)-2-(((benzyloxy)carbonyl)amino)-4-((2-phenoxyethyl) (4-(5,6,7,8-tetrahydro-1,8-naphthyridin-2-yl) butyl)amino) butanoic acid To a solution of (S)-methyl 2-(((benzyloxy)carbonyl) amino)-4-((2-phenoxyethyl) (4-(5,6,7,8-tetrahydro-1,8-naphthyridin-2-yl) butyl)amino) butanoate (1 g, 1.74 mmol) in 1:1:1 THF/MeOH/H$_2$O (9 mL) was added LiOH.H$_2$O (146 mg, 3.48 mmol) at 0° C. and the resulting mixture was stirred at rt for 40 min. The mixture was adjusted to pH=6 by the addition of AcOH and then was concentrated in vacuo to give the title compound that was used without further purification. LCMS (ESI+): m/z=561.1 (M+H)$^+$.

Step 5: (S)-2-amino-4-((2-phenoxyethyl) (4-(5,6,7,8-tetrahydro-1,8-naphthyridin-2-yl) butyl)amino) butanoic acid To a solution of (S)-2-(((benzyloxy)carbonyl)amino)-4-((2-phenoxyethyl) (4-(5,6,7,8-tetrahydro-1,8-naphthyridin-2-yl) butyl)amino) butanoic acid (3.78 g, 6.74 mmol) in MeOH (300 mL) was added 20 wt % Pd(OH)$_2$/C (2.9 g) and the resulting mixture was stirred under an H$_2$ atmosphere for 2 h at rt. The mixture was filtered and concentrated in vacuo to give the title compound that was used without further purification. LCMS (ESI+): m/z=427.2 (M+H)$^+$.

Step 6: (S)-2-((1-methyl-1H-pyrazolo[3,4-d]pyrimidin-4-yl) amino)-4-((2-phenoxyethyl) (4-(5,6,7,8-tetrahydro-1,8-naphthyridin-2-yl) butyl)amino) butanoic acid To a solution of 4-chloro-1-methyl-1H-pyrazolo[3,4-d] pyrimidine (43 mg, 258 µmol) in 4:1 THF/H$_2$O (2 mL) was added (S)-2-amino-4-((2-phenoxyethyl) (4-(5,6,7,8-tetrahydro-1,8-naphthyridin-2-yl) butyl)amino) butanoic acid (100 mg, 234 µmol) and NaHCO$_3$ (59 mg, 703 µmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=559.3 (M+H)$^+$. $^1$H NMR (400 MHz, DMSO-d$_6$) δ ppm 14.37 (br s, 1H) 10.79-11.21 (m, 1H) 9.88-10.34 (m, 1H) 8.64 (s, 1H) 8.40 (s, 1H) 8.14 (br s, 1H) 7.58 (d, J=7.45 Hz, 1H) 7.20-7.32 (m, 2H) 6.87-7.03 (m, 3H) 6.62 (d, J=7.45 Hz, 1H) 5.01 (br s, 1H) 4.37-4.51 (m, 2H) 3.96 (s, 3H) 3.34-3.72 (m, 5H) 3.26 (br s, 2H) 2.71 (br t, J=6.14 Hz, 4H) 2.50 (br s, 3H) 1.64-1.94 (m, 5H).

Compound 83: (S)-2-((5-bromopyrimidin-2-yl) amino)-4-((2-phenoxyethyl) (4-(5,6,7,8-tetrahydro-1,8-naphthyridin-2-yl) butyl)amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 µmol) in 4:1 THF/H$_2$O (2 mL) was added 5-bromo-2-fluoropyrimidine (46 mg, 258 µmol) and NaHCO$_3$ (59 mg, 703 µmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=583.2 (M+H)$^+$. $^1$H NMR (400 MHz, Methanol-d$_4$) δ ppm 8.16 (s, 2H) 7.29 (d, J=7.45 Hz, 1H) 7.16-7.25 (m, 2H) 6.90 (t, J=7.24 Hz, 1H) 6.84 (d, J=7.89 Hz, 2H) 6.46 (d, J=7.45 Hz, 1H) 4.32 (t, J=6.14 Hz, 1H) 4.18 (t, J=5.26 Hz, 2H) 3.33-3.43 (m, 2H) 3.05-3.27 (m, 4H) 2.94 (br s, 2H) 2.59-2.75 (m, 4H) 2.05-2.27 (m, 2H) 1.69-1.93 (m, 6H).

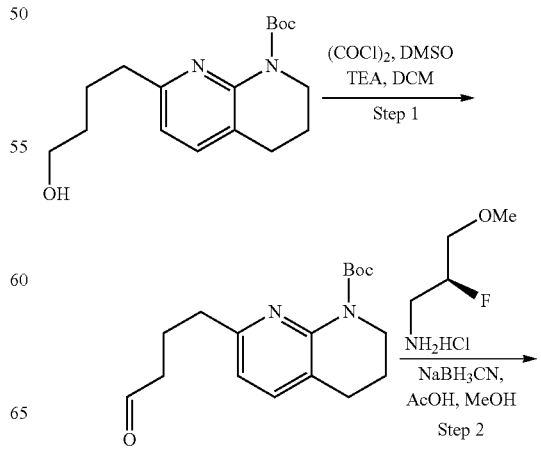

Scheme 7, Compound 84

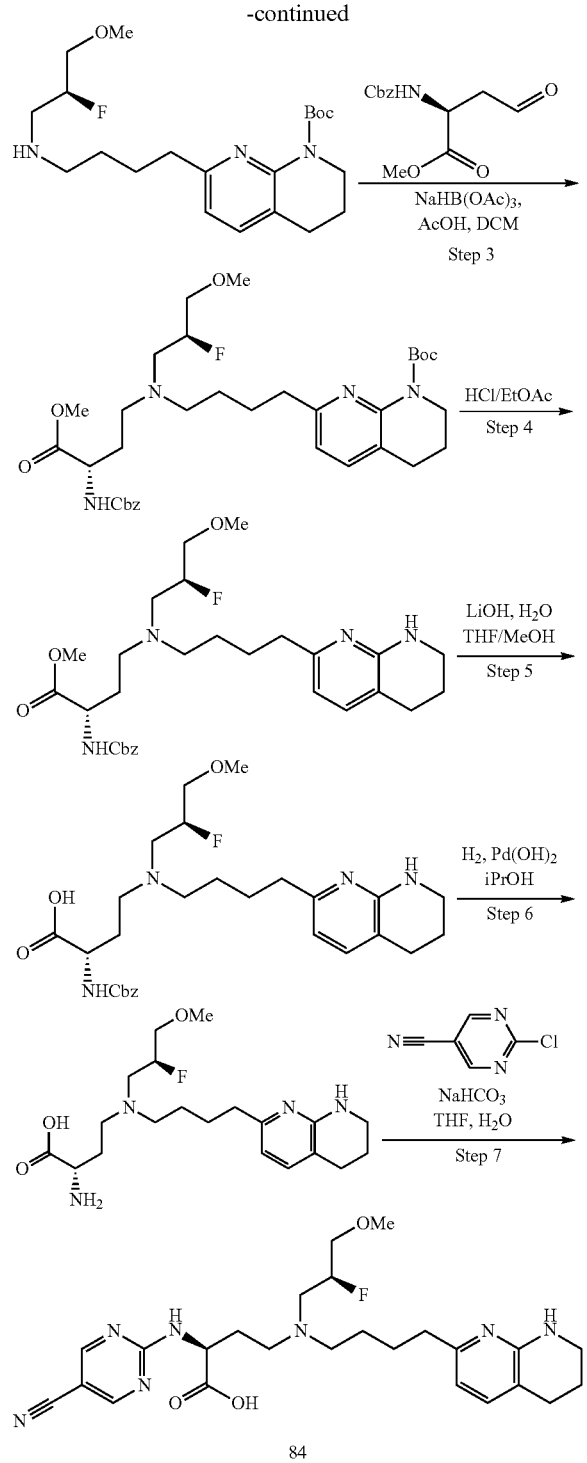

84

Step 1: tert-butyl 7-(4-oxobutyl)-3,4-dihydro-1,8-naphthyridine-1(2H)-carboxylate To a mixture of oxalyl chloride (16.00 g, 126.04 mmol) in DCM (200 mL) was added DMSO (15.15 g, 193.91 mmol) at −78° C. and the resulting mixture was stirred at −78° C. for 30 min, at which time, a solution of tert-butyl 7-(4-hydroxybutyl)-3,4-dihydro-1,8-naphthyridine-1(2H)-carboxylate (29.71 g, 96.95 mmol) in DCM (100 mL) was added. The reaction mixture was stirred at −78° C. for 1 h and then triethylamine (67.5 mL, 484.77 mmol) was added and the mixture was stirred at −78° C. for another 30 min and then slowly warmed to −40° C. and then diluted with H₂O and allowed to warm to rt. The layers were separated and the aqueous layer was extracted with DCM. The combined organic extracts were washed with brine, dried over Na₂SO₄, filtered, and concentrated in vacuo to give the title compound that was used without further purification.

Step 2: tert-butyl (S)-7-(4-((2-fluoro-3-methoxypropyl)amino) butyl)-3,4-dihydro-1,8-naphthyridine-1(2H)-carboxylate To a solution of tert-butyl 7-(4-oxobutyl)-3,4-dihydro-1,8-naphthyridine-1(2H)-carboxylate (15 g, 49.28 mmol) in MeOH (50 mL) was added (S)-2-fluoro-3-methoxypropan-1-amine hydrochloride (10.61 g, 73.92 mmol), AcOH (2.82 mL, 49.28 mmol), and NaBH₃CN (6.19 g, 98.56 mmol) at 0° C. and stirred at rt for 12 h. The resulting mixture was concentrated in vacuo and then diluted with sat. aq. NaHCO₃ and extracted with ethyl acetate. The combined organic extracts were washed with brine, dried over Na₂SO₄, filtered, and concentrated in vacuo. The crude residue was purified by normal phase silica gel chromatography to give the title compound. LCMS (ESI+): m/z=396.2 (M+H)⁺.

Step 3: tert-butyl 7-(4-(((S)-3-(((benzyloxy)carbonyl)amino)-4-methoxy-4-oxobutyl) ((S)-2-fluoro-3-methoxypropyl)amino) butyl)-3,4-dihydro-1,8-naphthyridine-1(2H)-carboxylate To a mixture of tert-butyl (S)-7-(4-((2-fluoro-3-methoxypropyl)amino)butyl)-3,4-dihydro-1,8-naphthyridine-1(2H)-carboxylate (2.00 g, 6.77 mmol) and methyl (S)-2-(((benzyloxy)carbonyl)amino)-4-oxobutanoate (1.98 g, 7.45 mmol) in DCE (20 mL) was added AcOH (581 µL, 10.16 mmol) and NaBH(OAc)₃ (2.15 g, 10.16 mmol) at 0° C. and the resulting mixture was stirred at rt for 1 h. The mixture was diluted with MeOH and then concentrated in vacuo. The crude residue was diluted with DCM and sat. aq. NaHCO₃ and the layers were separated. The aqueous layer was extracted with DCM and the combined organic extracts were dried over Na₂SO₄, filtered, and concentrated in vacuo. The crude residue was purified by normal phase silica gel chromatography to give the title compound. LCMS (ESI+): m/z=645.5 (M+H)⁺.

Step 4: methyl (S)-2-(((benzyloxy)carbonyl)amino)-4-(((S)-2-fluoro-3-methoxypropyl) (4-(5,6,7,8-tetrahydro-1,8-naphthyridin-2-yl) butyl)amino) butanoate tert-butyl 7-(4-(((S)-3-(((benzyloxy)carbonyl)amino)-4-methoxy-4-oxobutyl) ((S)-2-fluoro-3-methoxypropyl) amino)butyl)-3,4-dihydro-1,8-naphthyridine-1(2H)-carboxylate (1.8 g, 2.79 mmol) was taken up in 4 M HCl in EtOAc (20 mL) and the mixture was stirred at rt for 15 h and then concentrated in vacuo to give the title compound which was used without further purification. LCMS (ESI+): m/z=545.4 (M+H)⁺.

Step 5: (S)-2-(((benzyloxy)carbonyl)amino)-4-(((S)-2-fluoro-3-methoxypropyl) (4-(5,6,7,8-tetrahydro-1,8-naphthyridin-2-yl) butyl)amino) butanoic acid A mixture of methyl (S)-2-(((benzyloxy)carbonyl) amino)-4-(((S)-2-fluoro-3-methoxypropyl) (4-(5,6,7,8-tetrahydro-1,8-naphthyridin-2-yl) butyl)amino) butanoate hydrochloride (500 mg, 860 μmol), in 1:1:1 THF/H$_2$O/MeOH (3 mL) was added LiOH.H$_2$O (72 mg, 1.72 mmol) and the resulting mixture was stirred at rt for 1 h and then diluted with MeOH and adjusted to pH=6 by the addition of AcOH and then concentrated in vacuo to give the title compound that was used without further purification. LCMS (ESI+): m/z=531.4 (M+H)$^+$.

Step 6: (S)-2-amino-4-(((S)-2-fluoro-3-methoxypropyl) (4-(5,6,7,8-tetrahydro-1,8-naphthyridin-2-yl) butyl)amino) butanoic acid To a solution of (S)-2-(((benzyloxy)carbonyl)amino)-4-(((S)-2-fluoro-3-methoxypropyl) (4-(5,6,7,8-tetrahydro-1,8-naphthyridin-2-yl) butyl)amino) butanoic acid acetate (1 g, 1.69 mmol) in i-PrOH (10 mL) was added 20 wt % Pd(OH)$_2$/C (238 mg) and the resulting mixture was stirred under an H$_2$ atmosphere for 2 h. The mixture was filtered and concentrated under in vacuo. The crude residue was purified by reverse phase prep-HPLC to give the title compound. LCMS (ESI+): m/z=397.2 (M+H)$^+$.

Step 7: (S)-2-((5-cyanopyrimidin-2-yl) amino)-4-(((S)-2-fluoro-3-methoxypropyl) (4-(5,6,7,8-tetrahydro-1,8-naphthyridin-2-yl) butyl)amino) butanoic acid To a solution of (S)-2-amino-4-(((S)-2-fluoro-3-methoxypropyl) (4-(5,6,7,8-tetrahydro-1,8-naphthyridin-2-yl) butyl) amino) butanoic acid hydrochloride (120 mg, 277 μmol) in THF (2 mL) and H$_2$O (0.5 mL) was added NaHCO$_3$ (70 mg, 831 μmol), and then 2-chloropyrimidine-5-carbonitrile (43 mg, 305 μmol) and the resulting mixture was stirred at 70° C. for 1 h and then allowed to cool to rt. The mixture was adjusted to pH=6 by the addition of 1 M aq. HCl and then concentrated in vacuo. The crude residue was purified by reverse phase prep-HPLC to give the title compound. LCMS (ESI+): m/z=500.2 (M+H)$^+$. $^1$H NMR (400 MHz, Methanol-d$_4$) δ ppm 8.56 (br s, 1H) 8.45 (br s, 1H) 7.42 (br d, J=7.28 Hz, 1H) 6.52 (d, J=7.50 Hz, 1H) 4.75 (br d, J=3.31 Hz, 1H) 4.51 (t, J=5.84 Hz, 1H) 3.57 (d, J=3.97 Hz, 1H) 3.49-3.53 (m, 1H) 3.37-3.46 (m, 2H) 3.33-3.37 (m, 3H) 2.84-2.96 (m, 2H) 2.65-2.83 (m, 8H) 2.15-2.24 (m, 1H) 2.04-2.14 (m, 1H) 1.87-1.94 (m, 1H) 1.81 (br dd, J=13.78, 6.73 Hz, 2H) 1.58-1.69 (m, 2H).

Compound 85: (S)-4-(((S)-2-fluoro-3-methoxypropyl) (4-(5,6,7,8-tetrahydro-1,8-naphthyridin-2-yl) butyl)amino)-2-((5-(trifluoromethyl)pyrimidin-2-yl) amino) butanoic acid To a solution of (S)-2-amino-4-(((S)-2-fluoro-3-methoxypropyl) (4-(5,6,7,8-tetrahydro-1,8-naphthyridin-2-yl) butyl) amino) butanoic acid (100 mg, 252 μmol) in THF (2 mL) and H$_2$O (0.5 mL) was added NaHCO$_3$ (64 mg, 757 μmol) and then 2-chloro-5-(trifluoromethyl)pyrimidine (51 mg, 277 μmol) and the resulting mixture was stirred at 70° C. for 1 h and then cooled to rt. The mixture was adjusted to pH=6 by the addition of 1 M aq. HCl and then concentrated in vacuo. The crude residue was purified by reverse phase prep-HPLC to give the title compound. LCMS (ESI+): m/z=543.2 (M+H)$^+$. $^1$H NMR (400 MHz, Methanol-d$_4$) δ ppm 8.64 (s, 2H) 7.59 (d, J=7.46 Hz, 1H) 6.65 (d, J=7.34 Hz, 1H) 5.10-5.28 (m, 1H) 4.79 (br s, 1H) 3.54-3.74 (m, 4H) 3.42-3.54 (m, 4H) 3.40 (s, 3H) 3.33-3.39 (m, 2H) 2.75-2.86 (m, 4H) 2.43-2.57 (m, 1H) 2.35 (br s, 1H) 1.74-2.00 (m, 6H).

Compound 86: (S)-2-((5-bromopyrimidin-2-yl) amino)-4-(((S)-2-fluoro-3-methoxypropyl) (4-(5,6,7,8-tetrahydro-1,8-naphthyridin-2-yl) butyl)amino) butanoic acid: (S)-2-amino-4-(((S)-2-fluoro-3-methoxypropyl) (4-(5,6,7,8-tetrahydro-1,8-naphthyridin-2-yl) butyl)amino) butanoic acid hydrochloride (100 mg, 231 μmol) in THF (1 mL) and H$_2$O (0.25 mL) was added NaHCO$_3$ (58 mg, 693 μmol) and 5-bromo-2-fluoropyrimidine (49 mg, 277 μmol) and the resulting mixture was stirred at 70° C. for 1 h and then allowed to cool to rt. The mixture was adjusted to pH=6 by the addition of 1 M aq. HCl and then concentrated in vacuo. The crude residue was purified by reverse phase prep-HPLC to give the title compound. LCMS (ESI+): m/z=553.2 (M+H)$^+$. $^1$H NMR (400 MHz, Methanol-d$_4$) δ ppm 8.24 (s, 2H) 7.40 (d, J=7.50 Hz, 1H) 6.52 (d, J=7.28 Hz, 1H) 4.77 (br d, J=3.53 Hz, 1H) 4.36 (t, J=6.17 Hz, 1H) 3.58 (d, J=4.41 Hz, 1H) 3.52 (d, J=4.19 Hz, 1H) 3.35-3.44 (m, 2H) 3.33 (s, 3H) 2.83-2.95 (m, 4H) 2.66-2.76 (m, 6H) 2.05-2.18 (m, 2H) 1.84-1.91 (m, 3H) 1.75-1.83 (m, 1H) 1.61-1.71 (m, 2H).

Compound 87: (S)-4-(((S)-2-fluoro-3-methoxypropyl) (4-(5,6,7,8-tetrahydro-1,8-naphthyridin-2-yl) butyl)amino)-2-((2-(trifluoromethyl)pyrimidin-4-yl) amino) butanoic acid. (S)-2-amino-4-(((S)-2-fluoro-3-methoxypropyl) (4-(5,6,7,8-tetrahydro-1,8-naphthyridin-2-yl) butyl)amino) butanoic acid hydrochloride (100 mg, 231 μmol) in THF (2 mL) and H$_2$O (0.5 mL) was added NaHCO$_3$ (58 mg, 693 μmol) and 4-chloro-2-(trifluoromethyl)pyrimidine (46 mg, 254 μmol) and the resulting mixture was stirred at 70° C. for 1 hr and then cooled to rt. The mixture was adjusted to pH=6 by the addition of 1 M aq. HCl and then concentrated in vacuo. The crude residue was purified by reverse phase prep-HPLC to give the title compound. LCMS (ESI+): m/z=543.2 (M+H)$^+$. $^1$H NMR (400 MHz, Methanol-d$_4$) δ ppm 8.06 (br d, J=5.26 Hz, 1H) 7.42 (d, J=7.34 Hz, 1H) 6.66 (br d, J=5.62 Hz, 1H) 6.51 (d, J=7.34 Hz, 1H) 4.71-4.78 (m, 1H) 4.68 (br s, 1H) 3.46-3.61 (m, 2H) 3.36-3.44 (m, 2H) 3.31 (s, 3H) 2.95 (br d, J=4.89 Hz, 2H) 2.54-2.85 (m, 8H) 2.23 (br s, 1H) 2.06 (br d, J=4.52 Hz, 1H) 1.73-1.94 (m, 4H) 1.51-1.73 (m, 2H).

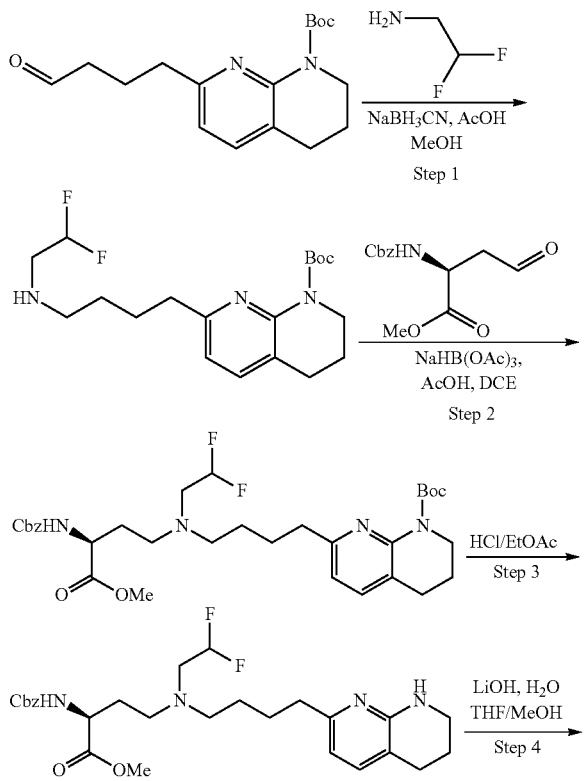

Scheme 8, Compound 88

-continued

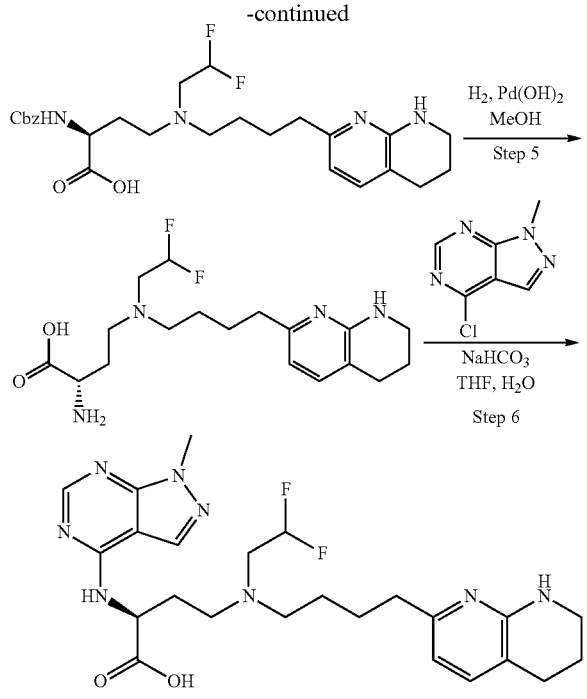

88

Step 1: tert-butyl 7-(4-((2,2-difluoroethyl)amino) butyl)-3,4-dihydro-1,8-naphthyridine-1(2H)-carboxylate To a mixture of 2,2-difluoroethanamine (3.99 g, 49.28 mmol, 1.5 eq) in MeOH (80 mL) was added AcOH (1.88 mL, 32.85 mmol), NaBH$_3$CN (4.13 g, 65.71 mmol), and then a solution of tert-butyl 7-(4-oxobutyl)-3,4-dihydro-1,8-naphthyridine-1(2H)-carboxylate (10 g, 32.85 mmol) in MeOH (30 mL) at 0° C. The resulting mixture was stirred at rt for 3 h and then dilute with sat. aq. NaHCO$_3$ and concentrated in vacuo to remove the volatiles. The remaining aqueous phase was extracted with EtOAc and the combined organic extracts were dried over Na$_2$SO$_4$, filtered, and concentrated in vacuo. The crude residue was purified by reverse phase HPLC to give the title compound. LCMS (ESI+): m/z=370.2.

Step 2: (S)-tert-butyl 7-(4-((3-(((benzyloxy)carbonyl)amino)-4-methoxy-4-oxobutyl) (2,2-difluoroethyl)amino) butyl)-3,4-dihydro-1,8-naphthyridine-1 (2H)-carboxylate To a mixture of tert-butyl 7-(4-((2,2-difluoroethyl)amino) butyl)-3,4-dihydro-1,8-naphthyridine-(2H)-carboxylate (5.7 g, 15.43 mmol) and (S)-methyl 2-(((benzyloxy)carbonyl) amino)-4-oxobutanoate (4.50 g, 16.97 mmol) in DCE (60 mL) was added AcOH (1.32 mL, 23.14 mmol), NaBH(OAc)$_3$ (4.90 g, 23.14 mmol) at 0° C. and the resulting mixture was stirred at rt for 1 h. The mixture was diluted with sat. aq. NaHCO$_3$ and DCM and the layers were separated. The aqueous layer was extracted with DCM and the combined organic extracts were dried over Na$_2$SO$_4$, filtered and concentrated in vacuo. The crude residue was purified by normal phase silica gel chromatography to give the title compound. LCMS (ESI+): m/z=619.2.

Step 3: (S)-methyl 2-(((benzyloxy)carbonyl)amino)-4-((2,2-difluoroethyl) (4-(5,6,7,8-tetrahydro-1,8-naphthyridin-2-yl) butyl)amino) butanoate (S)-tert-butyl 7-(4-((3-(((benzyloxy)carbonyl)amino)-4-methoxy-4-oxobutyl) (2,2-difluoroethyl)amino)butyl)-3,4-dihydro-1,8-naphthyridine-1(2H)-carboxylate (3 g, 4.85 mmol) was diluted in 4 M HCl in EtOAc (5 mL) and stirred at rt for 16 h and then concentrated in vacuo to give the title compound that was used without further purification. LCMS (ESI+): m/z=519.2.

Step 4: (S)-2-(((benzyloxy)carbonyl)amino)-4-((2,2-difluoroethyl) (4-(5,6,7,8-tetrahydro-1,8-naphthyridin-2-yl) butyl)amino) butanoic acid To a mixture of (S)-methyl 2-(((benzyloxy)carbonyl) amino)-4-((2,2-difluoroethyl) (4-(5,6,7,8-tetrahydro-1,8-naphthyridin-2-yl) butyl)amino) butanoate hydrochloride (2.7 g, 4.86 mmol) in 1:1:1 THF/H$_2$O/MeOH (25 mL) was added LiOH.H$_2$O (408 mg, 9.73 mmol) at 0° C. and the resulting mixture was stirred at rt for 1 h. The mixture was adjusted to pH=6 by the addition of 1 M aq. HCl and concentrated in vacuo to give the title compound. LCMS (ESI+): m/z=505.3.

Step 5: (S)-2-amino-4-((2,2-difluoroethyl) (4-(5,6,7,8-tetrahydro-1,8-naphthyridin-2-yl) butyl)amino) butanoic acid To a solution of (S)-2-(((benzyloxy)carbonyl)amino)-4-((2,2-difluoroethyl) (4-(5,6,7,8-tetrahydro-1,8-naphthyridin-2-yl) butyl)amino) butanoic acid (2.9 g, 5.75 mmol) in MeOH (20 mL) was added 20 wt % Pd(OH)$_2$/C (1.29 g) and the resulting mixture was stirred under an H$_2$ atmosphere for 2 h. The mixture was filtered and concentrated in vacuo to give the title compound that was used without further purification. LCMS (ESI+): m/z=371.4.

Step 6: (S)-4-((2,2-difluoroethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid To a mixture of (S)-2-amino-4-((2,2-difluoroethyl) (4-(5, 6,7,8-tetrahydro-1,8-naphthyridin-2-yl) butyl)amino) butanoic acid (110 mg, 297 μmol) and 4-chloro-1-methyl-1H-pyrazolo[3,4-d]pyrimidine (55 mg, 327 μmol) in THF (2 mL) and H$_2$O (0.5 mL) was added NaHCO$_3$ (50 mg, 594 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=503.3. $^1$H NMR (400 MHz, Methanol-d$_4$) δ ppm 8.63 (s, 1H) 8.49 (s, 1H) 7.59 (br d, J=6.61 Hz, 1H) 6.37-6.71 (m, 2H) 5.10 (br s, 1H) 4.09 (s, 3H) 3.86 (br t, J=14.22 Hz, 2H) 3.55-3.76 (m, 2H) 3.36-3.54 (m, 4H) 2.82 (br d, J=5.95 Hz, 4H) 2.54-2.75 (m, 2H) 1.76-2.00 (m, 6H).

Compound 89: (S)-4-((2-phenoxyethyl) (4-(5,6,7,8-tetrahydro-1,8-naphthyridin-2-yl) butyl)amino)-2-((5-(trifluoromethyl)pyrimidin-2-yl) amino) butanoic acid: (S)-2-amino-4-((2-phenoxyethyl) (4-(5,6,7,8-tetrahydro-1,8-naphthyridin-2-yl) butyl)amino) butanoic acid (100 mg, 234 μmol) in 4:1 THF/H$_2$O (2 mL) was added 2-chloro-5-(trifluoromethyl)pyrimidine (47 mg, 258 μmol) and NaHCO$_3$ (59 mg, 703 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=573.3 (M+H)⁺. ¹H NMR (400 MHz, Methanol-$d_4$) δ ppm 8.57 (s, 2H) 7.58 (d, J=7.34 Hz, 1H) 7.30 (br t, J=7.15 Hz, 2H) 6.93-7.05 (m, 3H) 6.63 (d, J=7.21 Hz, 1H) 4.79 (dd, J=8.38, 5.07 Hz, 1H) 4.38 (br s, 2H) 3.63-3.78 (m, 2H) 3.46 (br s, 3H) 3.42-3.60 (m, 1H) 3.37 (br d, J=8.80 Hz, 2H) 2.74-2.85 (m, 4H) 2.51-2.62 (m, 1H) 2.37 (br s, 1H) 1.75-1.99 (m, 6H).

Compound 90: (S)-2-((1H-pyrazolo[3,4-d]pyrimidin-4-yl) amino)-4-((2-phenoxyethyl) (4-(5,6,7,8-tetrahydro-1,8-naphthyridin-2-yl) butyl)amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 μmol) in 4:1 THF/H₂O (2 mL) was added 4-chloro-1H-pyrazolo[3,4-d]pyrimidine (40 mg, 258 μmol) and NaHCO₃ (59 mg, 703 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=545.0 (M+H)⁺. ¹H NMR (400 MHz, Methanol-$d_4$) δ ppm 8.78 (br d, J=19.07 Hz, 1H) 8.59 (s, 1H) 7.58 (d, J=7.46 Hz, 1H) 7.25 (br t, J=7.89 Hz, 2H) 6.90-7.02 (m, 3H) 6.64 (d, J=7.34 Hz, 1H) 5.29 (br s, 1H) 4.40 (br d, J=5.01 Hz, 2H) 3.73 (br s, 2H) 3.48-3.68 (m, 4H) 3.42 (br t, J=7.76 Hz, 2H) 2.75-2.85 (m, 4H) 2.71 (br s, 1H) 2.54 (br s, 1H) 1.88-2.03 (m, 4H) 1.71-1.87 (m, 2H).

Compound 91: (S)-2-((6-(1H-pyrazol-1-yl) pyrimidin-4-yl) amino)-4-((2-phenoxyethyl) (4-(5,6,7,8-tetrahydro-1,8-naphthyridin-2-yl) butyl)amino) butanoic acid: To a solution of (S)-2-amino-4-((2-phenoxyethyl) (4-(5,6,7,8-tetrahydro-1,8-naphthyridin-2-yl) butyl)amino) butanoic acid hydrochloride (100 mg, 216 μmol) in DMA (2 mL) was added DIPEA (188 μL, 1.08 mmol) and then 4-chloro-6-(1H-pyrazol-1-yl) pyrimidine (43 mg, 238 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=571.3 (M+H)⁺. ¹H NMR (400 MHz, Methanol-$d_4$) δ ppm 8.46 (d, J=2.44 Hz, 1H) 8.23 (br s, 1H) 7.72 (d, J=0.98 Hz, 1H) 7.24 (br s, 1H) 7.12 (dd, J=8.56, 7.46 Hz, 2H) 6.78-6.89 (m, 4H) 6.51 (dd, J=2.57, 1.71 Hz, 1H) 6.46 (d, J=7.34 Hz, 1H) 4.56 (br s, 1H) 4.12-4.22 (m, 2H) 3.08-3.29 (m, 7H) 2.54-2.74 (m, 5H) 2.20-2.35 (m, 1H) 2.04-2.16 (m, 1H) 1.73-1.88 (m, 6H).

Compound 92: (S)-4-((2-phenoxyethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 μmol) in 4:1 THF/H₂O (2 mL) was added 4-chloro-2-(trifluoromethyl)pyrimidine (47 mg, 258 μmol) and NaHCO₃ (59 mg, 703 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=573.2 (M+H)⁺. ¹H NMR (400 MHz, Methanol-$d_4$) δ ppm 8.21 (br d, J=5.75 Hz, 1H) 7.57 (d, J=7.34 Hz, 1H) 7.30 (t, J=7.89 Hz, 2H) 6.92-7.07 (m, 3H) 6.81 (d, J=6.11 Hz, 1H) 6.63 (d, J=7.21 Hz, 1H) 4.81-4.85 (m, 1H) 4.38 (br t, J=4.22 Hz, 2H) 3.70 (br d, J=3.91 Hz, 2H) 3.34-3.60 (m, 6H) 2.72-2.87 (m, 4H) 2.49-2.63 (m, 1H) 2.28-2.44 (m, 1H) 1.72-2.03 (m, 6H).

Compound 93: (S)-4-((2-phenoxyethyl) (4-(5,6,7,8-tetrahydro-1,8-naphthyridin-2-yl) butyl)amino)-2-((6-phenylpyrimidin-4-yl) amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 μmol) in 4:1 THF/H₂O (2 mL) was added 4-chloro-6-phenylpyrimidine (49 mg, 258 μmol) and NaHCO₃ (59 mg, 703 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=581.3 (M+H)⁺. ¹H NMR (400 MHz, Methanol-$d_4$) δ ppm 8.74 (s, 1H) 7.83 (br d, J=7.21 Hz, 2H) 7.62-7.74 (m, 3H) 7.57 (d, J=7.34 Hz, 1H) 7.18-7.31 (m, 3H) 6.93-7.03 (m, 3H) 6.64 (d, J=7.34 Hz, 1H) 5.09 (br s, 1H) 4.40 (br s, 2H) 3.47-3.73 (m, 4H) 3.38-3.46 (m, 2H) 2.80 (q, J=5.87 Hz, 4H) 2.65 (br s, 1H) 2.45 (br s, 1H) 1.87-2.00 (m, 4H).

Compound 94: (S)-4-((2-phenoxyethyl) (4-(5,6,7,8-tetrahydro-1,8-naphthyridin-2-yl) butyl)amino)-2-((2-(pyridin-3-yl) quinazolin-4-yl) amino) butanoic acid: To a solution of (S)-2-amino-4-((2-phenoxyethyl) (4-(5,6,7,8-tetrahydro-1,8-naphthyridin-2-yl) butyl)amino) butanoic acid hydrochloride (100 mg, 216 μmol) in DMA (2 mL) was added DIPEA (188 μL, 1.08 mmol) and then 4-chloro-2-(pyridin-3-yl) quinazoline (57 mg, 238 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=632.3 (M+H)⁺. ¹H NMR (400 MHz, Methanol-$d_4$) δ ppm 9.52 (d, J=1.35 Hz, 1H) 8.78 (dt, J=7.98, 1.88 Hz, 1H) 8.58 (dd, J=4.89, 1.71 Hz, 1H) 8.03 (d, J=8.44 Hz, 1H) 7.77-7.84 (m, 1H) 7.68-7.76 (m, 1H) 7.46 (dd, J=7.58, 4.52 Hz, 1H) 7.35 (t, J=8.13 Hz, 1H) 7.19 (d, J=6.97 Hz, 1H) 7.01-7.09 (m, 2H) 6.79 (t, J=7.34 Hz, 1H) 6.71 (d, J=7.82 Hz, 2H) 6.36 (d, J=7.21 Hz, 1H) 5.00 (t, J=5.93 Hz, 1H) 4.10-4.21 (m, 2H) 2.81-3.27 (m, 8H) 2.60 (br d, J=6.72 Hz, 4H) 2.46 (br s, 1H) 2.29 (br dd, J=15.04, 4.89 Hz, 1H) 1.70-1.90 (m, 6H).

Compound 95: (S)-4-((2,2-difluoroethyl) (4-(5,6,7,8-tetrahydro-1,8-naphthyridin-2-yl) butyl)amino)-2-((5-(trifluoromethyl)pyrimidin-2-yl) amino) butanoic acid: To a mixture of (S)-2-amino-4-((2,2-difluoroethyl) (4-(5,6,7,8-tetrahydro-1,8-naphthyridin-2-yl) butyl)amino) butanoic acid (160 mg, 432 μmol) and 2-chloro-5-(trifluoromethyl) pyrimidine (87 mg, 475 μmol) in H₂O (0.5 mL) and THF (2 mL) was added NaHCO₃ (73 mg, 864 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=517.2. ¹H NMR (400 MHz, Methanol-$d_4$) δ ppm 8.62 (s, 2H) 7.60 (d, J=7.50 Hz, 1H) 6.65 (d, J=7.28 Hz, 1H) 6.33-6.64 (m, 1H) 4.78 (dd, J=8.49, 5.18 Hz, 1H) 3.83 (td, J=15.05, 3.42 Hz, 2H) 3.35-3.62 (m, 6H) 2.76-2.88 (m, 4H) 2.46-2.59 (m, 1H) 2.30-2.43 (m, 1H) 1.74-2.02 (m, 6H).

Compound 96: (S)-2-((5-bromopyrimidin-2-yl) amino)-4-((2,2-difluoroethyl) (4-(5,6,7,8-tetrahydro-1,8-naphthyridin-2-yl) butyl)amino) butanoic acid: To a mixture of (S)-2-amino-4-((2,2-difluoroethyl) (4-(5,6,7,8-tetrahydro-1,8-naphthyridin-2-yl) butyl)amino) butanoic acid (160 mg, 432 μmol) and 5-bromo-2-chloropyrimidine (84 mg, 475 μmol) in THF (2 mL), H₂O (0.5 mL) was added NaHCO₃ (73 mg, 864 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=527.1. ¹H NMR (400 MHz, Methanol-$d_4$) δ ppm 8.55 (s, 2H) 7.59 (d, J=7.28 Hz, 1H) 6.32-6.71 (m, 2H) 4.73 (dd, J=8.38, 5.07 Hz, 1H) 3.82 (td, J=14.88, 3.31 Hz, 2H) 3.35-3.60 (m, 6H) 2.75-2.85 (m, 4H) 2.46-2.60 (m, 1H) 2.29-2.43 (m, 1H) 1.74-2.00 (m, 6H).

Compound 97: (S)-4-((2,2-difluoroethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((2,2-difluoroethyl) (4-(5,6,7,8-tetrahydro-1,8-naphthyridin-2-yl) butyl)amino) butanoic acid (160 mg, 432 μmol) and 4-chloro-2-(trifluoromethyl) pyrimidine (87 mg, 475 μmol) in THF (2 mL), H$_2$O (0.5 mL) was added NaHCO$_3$ (73 mg, 864 μmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=517.2. $^1$H NMR (400 MHz, Methanol-d$_4$) δ ppm 8.29 (br d, J=6.39 Hz, 1H) 7.60 (d, J=7.50 Hz, 1H) 6.98-7.09 (m, 1H) 6.31-6.70 (m, 2H) 4.85-4.91 (m, 1H) 3.83 (td, J=14.94, 3.20 Hz, 2H) 3.36-3.64 (m, 6H) 2.76-2.85 (m, 4H) 2.49-2.62 (m, 1H) 2.33-2.46 (m, 1H) 1.75-1.99 (m, 6H).

Compound 98: (S)-2-((6-(1H-pyrazol-1-yl) pyrimidin-4-yl) amino)-4-((2,2-difluoroethyl) (4-(5,6,7,8-tetrahydro-1,8-naphthyridin-2-yl) butyl)amino) butanoic acid To a mixture of (S)-2-amino-4-((2,2-difluoroethyl) (4-(5,6,7,8-tetrahydro-1,8-naphthyridin-2-yl) butyl)amino) butanoic acid (100 mg, 270 μmol) and 4-chloro-6-(1H-pyrazol-1-yl) pyrimidine (54 mg, 297 μmol) in DMA (2 mL) was added DIPEA (235 μL, 1.35 mmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=515.2. $^1$H NMR (400 MHz, Methanol-d$_4$) δ ppm 8.61 (br s, 2H) 7.93 (s, 1H) 7.59 (d, J=7.28 Hz, 1H) 7.31 (br s, 1H) 6.35-6.74 (m, 3H) 4.98 (br s, 1H) 3.85 (td, J=14.99, 3.31 Hz, 2H) 3.39-3.66 (m, 6H) 2.75-2.87 (m, 4H) 2.36-2.70 (m, 2H) 1.75-2.01 (m, 6H).

Compound 99: (S)-4-((2,2-difluoroethyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-((2,2-difluoroethyl) (4-(5,6,7,8-tetrahydro-1,8-naphthyridin-2-yl) butyl)amino) butanoic acid (100 mg, 270 μmol) and 4-chloro-2-(pyridin-3-yl) quinazoline (72 mg, 297 μmol) in DMA (2 mL) was added DPIEA (235 μL, 1.35 mmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=576.3. $^1$H NMR (400 MHz, Methanol-d$_4$) δ ppm 9.88 (d, J=1.76 Hz, 1H) 9.52 (d, J=8.38 Hz, 1H) 9.16 (d, J=5.51 Hz, 1H) 8.73 (d, J=8.38 Hz, 1H) 8.35 (dd, J=8.27, 5.84 Hz, 1H) 8.12-8.21 (m, 2H) 7.88-7.96 (m, 1H) 7.59 (d, J=7.28 Hz, 1H) 6.36-6.69 (m, 2H) 5.54 (dd, J=8.60, 5.51 Hz, 1H) 3.59-3.93 (m, 4H) 3.40-3.54 (m, 4H) 2.65-2.88 (m, 6H) 1.75-2.01 (m, 6H).

Compound 100: (S)-4-(((R)-2-methoxypropyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-(((R)-2-methoxypropyl) (4-(5,6,7,8-tetrahydro- 1,8-naphthyridin-2-yl) butyl)amino) butanoic acid (100 mg, 264 μmol) in DMA (2 mL) was added DIPEA (171 mg, 1.32 mmol) and 4-chloro-2-(pyridin-3-yl) quinazoline (70 mg, 291 μmol) and the resulting mixture was heated to 100° C. for 2 h and then allowed to cool to rt and concentrated in vacuo. The resulting crude residue was purified by reverse phase prep-HPLC to give the title compound. LCMS (ESI+): m/z=584.3 (M+H)$^+$. $^1$H NMR (400 MHz, Methanol-d$_4$) δ ppm 9.57 (s, 1H) 8.85 (br d, J=7.95 Hz, 1H) 8.63 (d, J=4.40 Hz, 1H) 8.16 (d, J=8.19 Hz, 1H) 7.77-7.90 (m, 2H) 7.51-7.59 (m, 2H) 7.12 (br d, J=7.34 Hz, 1H) 6.32 (d, J=7.21 Hz, 1H) 3.75 (br s, 1H) 3.37-3.49 (m, 1H) 3.27 (s, 5H) 2.88-3.25 (m, 6H) 2.64 (br t, J=5.93 Hz, 2H) 2.45-2.57 (m, 3H) 2.32 (br dd, J=14.79, 5.14 Hz, 1H) 1.77-1.86 (m, 2H) 1.71 (br s, 4H) 1.10-1.20 (m, 3H).

Scheme 9, Compound 101

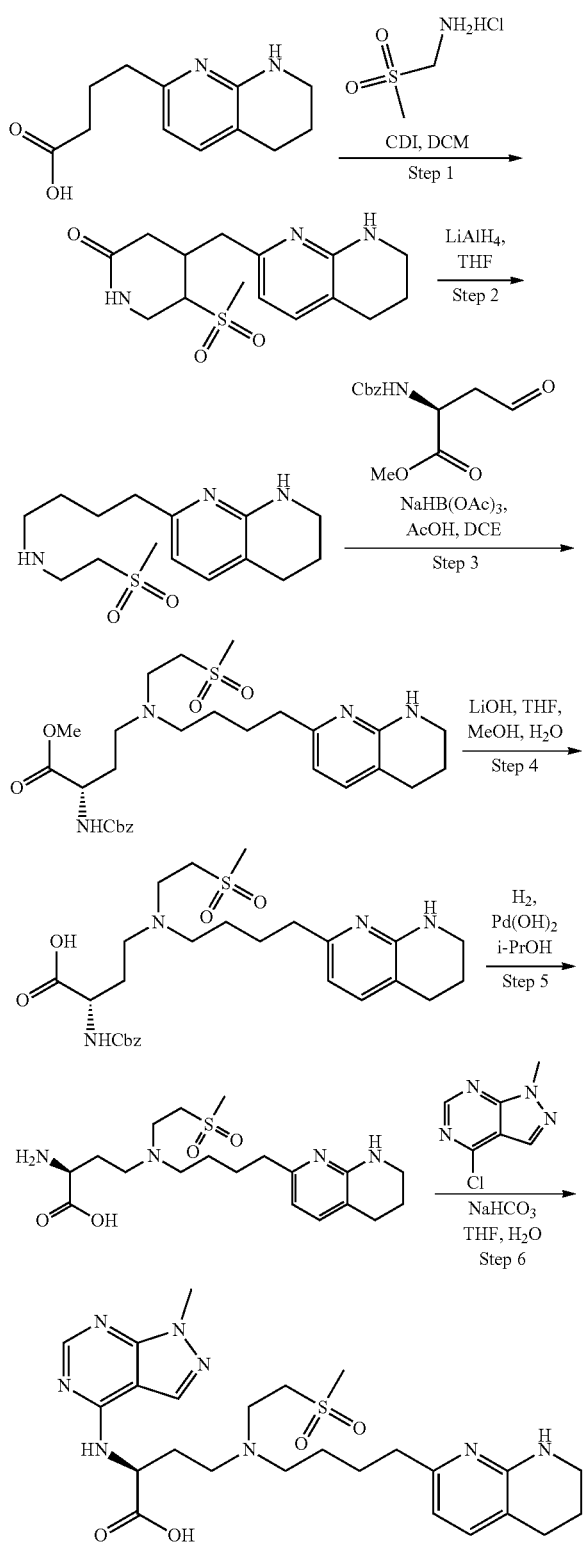

101

Step 1: N-(2-(methylsulfonyl)ethyl)-4-(5,6,7,8-tetrahydro-1,8-naphthyridin-2-yl) butanamide To a mixture of 4-(5,6,7,8-tetrahydro-1,8-naphthyridin-2-yl) butanoic acid (20 g, 63.56 mmol) in DCM (400 mL) was added CDI (11.34 g, 69.92 mmol) at 0° C. and the resulting mixture was stirred at rt for 1 h, at which time, 2-(methylsulfonyl)ethanamine hydrochloride (11.16 g, 69.92 mmol) was added and stirred at rt for an additional 2 h. The mixture was diluted with H$_2$O and the layers were separated. The aqueous layer was extracted with DCM and the combine organic extracts were dried over Na$_2$SO$_4$, filtered, and concentrated in vacuo. The crude residue was re-dissolved in EtOAc (80 mL) and then heated to reflux, at which time, hexanes (20 mL) was added and the mixture was cooled to rt causing a precipitate to form. The solid was filtered and the filtrate was concentrated in vacuo to give the title compound. LCMS (ESI+): m/z=325.9 (M+H)$^+$.

Step 2: N-(2-(methylsulfonyl)ethyl)-4-(5,6,7,8-tetrahydro-1,8-naphthyridin-2-yl) butan-1-amine To a solution of LiAlH$_4$ (1.28 g, 33.80 mmol) in THF (20 mL) at 0° C. was added N-(2-(methylsulfonyl)ethyl)-4-(5,6,7,8-tetrahydro-1,8-naphthyridin-2-yl) butanamide (5 g, 15.36 mmol) and the resulting mixture was heated to reflux for 12 h and then cooled to rt. The mixture carefully neutralized by the addition of H$_2$O (1.3 mL), 1 M aq. NaOH (1.3 mL), then H$_2$O (1.3 mL) again, followed by drying over MgSO$_4$. The mixture was filtered and concentrated under reduced pressure to give the title compound that was used without further purification. LCMS (ESI+): m/z=311.9 (M+H)$^+$.

Step 3: (S)-methyl 2-(((benzyloxy)carbonyl)amino)-4-((2-(methylsulfonyl)ethyl) (4-(5,6,7,8-tetrahydro-1,8-naphthyridin-2-yl) butyl)amino) butanoate To a mixture of N-(2-(methylsulfonyl)ethyl)-4-(5,6,7,8-tetrahydro-1,8-naphthyridin-2-yl) butan-1-amine (3 g, 9.63 mmol) and (S)-methyl 2-(((benzyloxy)carbonyl)amino)-4-oxobutanoate (2.56 g, 9.63 mmol) in DCE (30 mL) at 0° C. was added AcOH (862 µL, 14.45 mmol) then NaBH(OAc)$_3$ (3.06 g, 14.45 mmol) and the resulting mixture was stirred at rt for 1 hr. The mixture was diluted with MeOH and then concentrated under reduced pressure. The crude residue was taken up in DCM and sat. aq. NaHCO$_3$ and the layers were separated. The aqueous layer was extracted with DCM and the combined organic extracts were dried over Na$_2$SO$_4$, filtered, and concentrated under reduced pressure. The crude residue was purified by normal phase silica gel chromatography to give the title compound. LCMS (ESI+): m/z=561.4 (M+H)$^+$.

Step 4: (S)-2-(((benzyloxy)carbonyl)amino)-4-((2-(methylsulfonyl)ethyl) (4-(5,6,7,8-tetrahydro-1,8-naphthyridin-2-yl) butyl)amino) butanoic acid To a mixture of (S)-methyl 2-(((benzyloxy)carbonyl)amino)-4-((2-(methylsulfonyl)ethyl) (4-(5,6,7,8-tetrahydro-1,8-naphthyridin-2-yl) butyl)amino) butanoate (1 g, 1.78 mmol) in 1:1:1 THF/MeOH/H$_2$O (9 mL) was added LiOH.H$_2$O (150 mg, 3.57 mmol) and the resulting mixture was stirred at rt for 1 h. The mixture was adjusted to pH=6 by the addition of 1 M aq. HCl and then concentrated in vacuo to give the title compound that was used without further purification. LCMS (ESI+): m/z=547.2 (M+H)$^+$.

Step 5: (S)-2-amino-4-((2-(methylsulfonyl)ethyl) (4-(5,6,7,8-tetrahydro-1,8-naphthyridin-2-yl) butyl) amino) butanoic acid To a solution of (S)-2-(((benzyloxy)carbonyl)amino)-4-((2-(methylsulfonyl)ethyl) (4-(5,6,7,8-tetrahydro-1,8-naphthyridin-2-yl) butyl)amino) butanoic acid hydrochloride (1 g, 1.71 mmol) in i-PrOH (20 mL) was added 20 wt % Pd(OH)$_2$/C (241 mg) and the resulting mixture was stirred under an H$_2$ atmosphere for 12 h. The mixture was filtered and concentrated in vacuo to give the title compound that was used without further purification. LCMS (ESI+): m/z=413.1 (M+H)$^+$.

Step 6: (S)-2-((1-methyl-1H-pyrazolo[3,4-d]pyrimidin-4-yl) amino)-4-((2-(methylsulfonyl)ethyl) (4-(5,6,7,8-tetrahydro-1,8-naphthyridin-2-yl) butyl)amino) butanoic acid To a mixture of (S)-2-amino-4-((2-(methylsulfonyl)ethyl) (4-(5,6,7,8-tetrahydro-1,8-naphthyridin-2-yl) butyl)amino) butanoic acid (100 mg, 242) in THF (2 mL) and H$_2$O (0.5 mL) was added NaHCO$_3$ (61 mg, 727) followed by 4-chloro-1-methyl-H-pyrazolo[3,4-d]pyrimidine (49 mg, 291 µmol) and the resulting mixture was stirred at 70° C. for 18 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=545.2 (M+H)$^+$. $^1$H NMR (400 MHz, Methanol-d$_4$) δ ppm 8.61 (s, 1H) 8.50 (s, 1H) 7.59 (d, J=7.28 Hz, 1H) 6.67 (d, J=7.50 Hz, 1H) 5.10 (br dd, J=8.05, 5.18 Hz, 1H) 4.10 (s, 3H) 3.70-3.90 (m, 4H) 3.53-3.68 (m, 2H) 3.49-3.53 (m, 2H) 3.35-3.43 (m, 2H) 3.13 (s, 3H) 2.77-2.86 (m, 4H) 2.53-2.77 (m, 2H) 1.77-2.00 (m, 6H).

Compound 102: (S)-4-((2-(methylsulfonyl)ethyl) (4-(5,6,7,8-tetrahydro-1,8-naphthyridin-2-yl) butyl)amino)-2-((5-(trifluoromethyl)pyrimidin-2-yl) amino) butanoic acid: To a solution of (S)-2-amino-4-((2-(methylsulfonyl)ethyl) (4-(5,6,7,8-tetrahydro-1,8-naphthyridin-2-yl) butyl)amino) butanoic acid (100 mg, 242 µmol) in THF (2 mL) and H$_2$O (0.5 mL) was added NaHCO$_3$ (61 mg, 727 µmol) followed by 2-chloro-5-(trifluoromethyl)pyrimidine (53 mg, 291 µmol) and the resulting mixture was stirred at 70° C. for 18 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=559.2 (M+H)$^+$. $^1$H NMR (400 MHz, Methanol-d$_4$) δ ppm 8.60 (s, 2H) 7.59 (br d, J=7.21 Hz, 1H) 6.65 (d, J=7.34 Hz, 1H) 4.77 (br dd, J=8.01, 4.95 Hz, 1H) 3.67-3.82 (m, 4H) 3.49-3.54 (m, 2H) 3.32-3.49 (m, 4H) 3.13 (s, 3H) 2.75-2.86 (m, 4H) 2.46-2.58 (m, 1H) 2.36 (br s, 1H) 1.92-1.99 (m, 2H) 1.84 (br s, 4H).

Compound 103: (S)-2-((5-bromopyrimidin-2-yl) amino)-4-((2-(methylsulfonyl)ethyl) (4-(5,6,7,8-tetrahydro-1,8-naphthyridin-2-yl) butyl)amino) butanoic acid: To a mixture of (S)-2-amino-4-((2-(methylsulfonyl)ethyl) (4-(5,6,7,8-tetrahydro-1,8-naphthyridin-2-yl) butyl)amino) butanoic acid (100 mg, 242 µmol) in THF (2 mL) and H$_2$O (0.5 mL) was added NaHCO$_3$ (61 mg, 727 µmol), followed by 5-bromo-2-chloro-pyrimidine (51 mg, 291 µmol) and the resulting mixture was stirred at 70° C. for 18 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=569.0 (M+H)+. $^1$H NMR (400 MHz, Methanol-d$_4$) δ ppm 8.44-8.56 (m, 2H) 7.59 (d, J=7.28 Hz, 1H) 6.66 (d, J=7.28 Hz, 1H) 4.68-4.77 (m, 1H) 3.68-3.82 (m, 4H) 3.49-3.55 (m, 2H) 3.32-3.49 (m, 4H) 3.13 (s, 3H) 2.76-2.87 (m, 4H) 2.46-2.58 (m, 1H) 2.28-2.43 (m, 1H) 1.96 (q, J=5.90 Hz, 2H) 1.83 (br s, 4H).

Compound 104: (S)-4-((2-(methylsulfonyl)ethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((2-(methylsulfonyl)ethyl) (4-(5,6,7,8-tetrahydro-1,8-naphthyridin-2-yl) butyl)amino) butanoic acid (100 mg, 242 µmol) in THF (2 mL) and H$_2$O (0.5 mL) was added NaHCO$_3$ (61 mg, 727 µmol) followed by 4-chloro-2-(trifluoromethyl)pyrimidine (53 mg, 291 µmol) and the resulting mixture was stirred at 70° C. for 18 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=559.1 (M+H)+. $^1$H NMR (400 MHz, Methanol-d$_4$) δ ppm 8.26 (br d, J=5.95 Hz, 1H) 7.59 (d, J=7.28 Hz, 1H) 6.92 (d, J=6.39 Hz, 1H) 6.65 (d, J=7.50 Hz, 1H) 4.83-4.87 (m, 1H) 3.69-3.80 (m, 4H) 3.49-3.53 (m, 2H) 3.32-3.49 (m, 4H) 3.12 (s, 3H) 2.81 (dt, J=12.29, 6.31 Hz, 4H) 2.48-2.59 (m, 1H) 2.30-2.42 (m, 1H) 1.92-2.00 (m, 2H) 1.83 (br s, 4H).

Compound 105: (S)-4-(((S)-2-fluoro-3-methoxypropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid: To a solution of (S)-2-amino-4-(((S)-2-fluoro-3-methoxypropyl) (4-(5,6,7,8-tetrahydro-1,8-naphthyridin-2-yl) butyl)amino) butanoic acid hydrochloride (100 mg, 231 µmol) in THF (2 mL) and H$_2$O (0.5 mL) was added NaHCO$_3$ (58 mg, 693 µmol), and then 4-chloro-1-methyl-1H-pyrazolo[3,4-d]pyrimidine (43 mg, 254 µmol) and the resulting mixture was stirred at 70° C. for 1 h and then allowed to cool to rt. The mixture was adjusted to pH=6 by the addition of 1 M aq. HCl and then concentrated in vacuo. The crude residue was purified by reverse phase prep-HPLC to give the title compound. LCMS (ESI+): m/z=529.3 (M+H)+. $^1$H NMR (400 MHz, Methanol-d$_4$) δ ppm 8.63 (s, 1H) 8.50 (s, 1H) 7.59 (d, J=7.28 Hz, 1H) 6.67 (d, J=7.50 Hz, 1H) 5.15-5.34 (m, 1H) 5.08 (br dd, J=8.49, 5.40 Hz, 1H) 4.10 (s, 3H) 3.63-3.74 (m, 4H) 3.49-3.63 (m, 4H) 3.41 (s, 5H) 2.76-2.88 (m, 4H) 2.55-2.73 (m, 2H) 1.75-2.02 (m, 6H).

Scheme 10, Compound 106

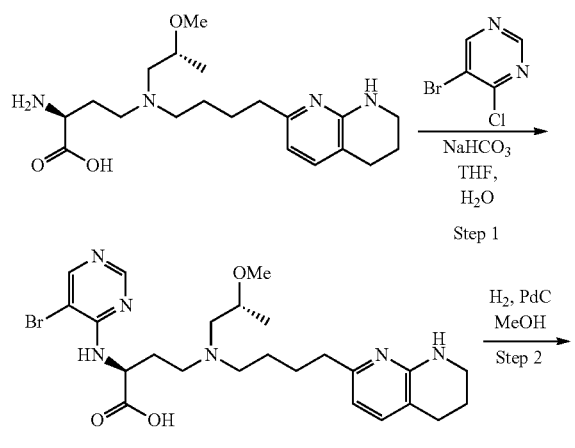

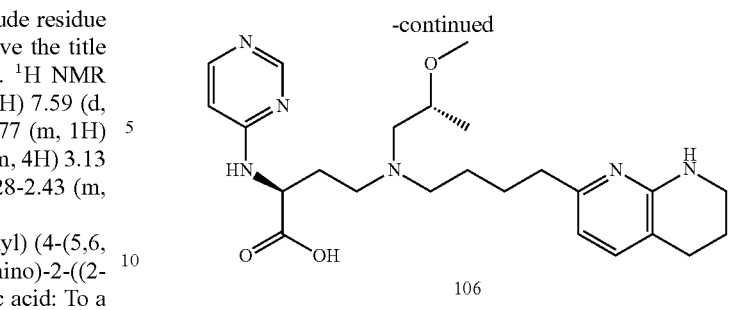

Step 1: (S)-2-((5-bromopyrimidin-4-yl)amino)-4-(((R)-2-methoxypropyl) (4-(5,6,7,8-tetrahydro-1,8-naphthyridin-2-yl) butyl)amino) butanoic acid To a solution of (S)-2-amino-4-(((R)-2-methoxypropyl) (4-(5,6,7,8-tetrahydro-1,8-naphthyridin-2-yl) butyl)amino) butanoic acid hydrochloride (200 mg, 482 µmol) and 5-bromo-4-chloropyrimidine (102 mg, 530 µmol) in THF (4 mL) and H$_2$O (1 mL) was added NaHCO$_3$ (202 mg, 2.4 mmol) and the resulting mixture was stirred at 70° C. for 2 h and then cooled to rt and concentrated in vacuo to give the title compound that was used without further purification. LCMS (ESI+): m/z=535.3 (M+H)+.

Step 2: (S)-4-(((R)-2-methoxypropyl) (4-(5,6,7,8-tetrahydro-1,8-naphthyridin-2-yl) butyl)amino)-2-(pyrimidin-4-ylamino) butanoic acid To a solution of (S)-2-((5-bromopyrimidin-4-yl) amino)-4-(((R)-2-methoxypropyl) (4-(5,6,7,8-tetrahydro-1,8-naphthyridin-2-yl) butyl)amino) butanoic acid (150 mg, 280 µmol) in MeOH (2 mL) was added 10 wt % Pd/C (297 mg) and the resulting mixture was stirred under an H$_2$ atmosphere for 15 h. The mixture was filtered and concentrated in vacuo. The crude residue was purified by reverse phase prep-HPLC to give the title compound. LCMS (ESI+): m/z=457.3 (M+H)+. $^1$H NMR (400 MHz, Methanol-d$_4$) δ ppm 8.41 (s, 1H) 8.03 (br d, J=6.11 Hz, 1H) 7.21 (d, J=7.34 Hz, 1H) 6.63 (br d, J=5.99 Hz, 1H) 6.43 (d, J=7.34 Hz, 1H) 4.43 (br s, 1H) 3.76 (br s, 1H) 3.37-3.42 (m, 3H) 3.35 (s, 3H) 2.91-3.18 (m, 5H) 2.72 (t, J=6.11 Hz, 2H) 2.60 (br s, 2H) 2.21-2.34 (m, 1H) 2.03-2.15 (m, 1H) 1.89 (dt, J=11.74, 5.99 Hz, 2H) 1.73 (br s, 4H) 1.20 (d, J=6.11 Hz, 3H).

Compound 107: (S)-4-((2-(methylsufonyl)ethyl) (4-(5,6,7,8-tetrahydro-1,8-naphthyridin-2-yl) butyl)amino)-2-((2-(pyridin-3-yl) quinazolin-4-yl) amino) butanoic acid: To a solution of (S)-2-amino-4-((2-(methylsulfonyl)ethyl) (4-(5,6,7,8-tetrahydro-1,8-naphthyridin-2-yl) butyl)amino) butanoic acid (100 mg, 242 µmol) in DMA (2 mL) was added DIPEA (210 µL, 1.21 mmol) and 4-chloro-2-(pyridin-3-yl) quinazoline (59 mg, 242 µmol and the resulting mixture was stirred at 100° C. for 2 h and then allowed to cool to rt and then concentrated in vacuo. The crude residue was purified by reverse phase prep-HPLC to give the title compound. LCMS (ESI+): m/z=618.3 (M+H)+. $^1$H NMR (400 MHz, Methanol-d$_4$) δ ppm 9.57 (d, J=1.47 Hz, 1H) 8.84 (dt, J=8.04, 1.85 Hz, 1H) 8.61 (dd, J=4.89, 1.71 Hz, 1H) 8.12 (d, J=7.70 Hz, 1H) 7.83-7.88 (m, 1H) 7.76-7.82 (m, 1H) 7.48-7.55 (m, 2H) 7.34 (d, J=7.34 Hz, 1H) 6.45 (d, J=7.34 Hz, 1H) 5.05 (t, J=6.05 Hz, 1H) 3.26-3.31 (m, 2H) 3.24 (t, J=5.56 Hz, 2H) 3.01-3.17 (m, 2H) 2.84-2.93 (m, 4H) 2.61-2.77 (m, 7H) 2.36-2.46 (m, 1H) 2.22-2.32 (m, 1H) 1.76-1.91 (m, 4H) 1.57-1.72 (m, 2H).

Compound 108: (S)-2-((6-(1H-pyrazol-1-yl) pyrimidin-4-yl) amino)-4-(((S)-2-fluoro-3-methoxypropyl) (4-(5,6,7,8-tetrahydro-1,8-naphthyridin-2-yl) butyl)amino) butanoic acid: To a mixture of 4-chloro-6-(1H-pyrazol-1-yl) pyrimidine (50 mg, 277 μmol) in DMA (2 mL) and was added DIPEA (201 μL, 1.15 mmol) then (S)-2-amino-4-(((S)-2-fluoro-3-methoxypropyl) (4-(5,6,7,8-tetrahydro-1,8-naphthyridin-2-yl) butyl)amino) butanoic acid hydrochloride (100 mg, 231 μmol) and the resulting mixture was stirred at 70° C. for 18 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=541.3 (M+H)$^+$. $^1$H NMR (400 MHz, Methanol-d$_4$) δ ppm 8.49 (br s, 1H) 8.28 (br s, 1H) 7.72 (s, 1H) 7.26 (br s, 1H) 6.87 (s, 1H) 6.42-6.53 (m, 2H) 4.76 (br s, 1H) 4.66 (br s, 1H) 3.46-3.59 (m, 2H) 3.32-3.32 (m, 3H) 2.90 (br s, 2H) 2.65 (br d, J=6.60 Hz, 10H) 2.19 (br s, 1H) 2.09 (br d, J=5.01 Hz, 1H) 1.82 (br s, 4H) 1.62 (br d, J=6.72 Hz, 2H).

Compound 109: (S)-4-(((S)-2-fluoro-3-methoxypropyl) (4-(5,6,7,8-tetrahydro-1,8-naphthyridin-2-yl) butyl)amino)-2-((2-(pyridin-3-yl) quinazolin-4-yl) amino) butanoic acid: To a mixture of 4-chloro-2-(pyridin-3-yl) quinazoline (67 mg, 277 μmol) in DMA (2 mL) and was added DIPEA (201 μL, 1.15 mmol) then (S)-2-amino-4-(((S)-2-fluoro-3-methoxypropyl) (4-(5,6,7,8-tetrahydro-1,8-naphthyridin-2-yl) butyl)amino) butanoic acid hydrochloride (100 mg, 231 μmol) and the resulting mixture was stirred at 70° C. for 18 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=602.3 (M+H)$^+$. $^1$H NMR (400 MHz, Methanol-d$_4$) δ ppm 9.56 (d, J=1.47 Hz, 1H) 8.83 (dt, J=8.04, 1.85 Hz, 1H) 8.60 (dd, J=4.89, 1.59 Hz, 1H) 8.07 (d, J=8.19 Hz, 1H) 7.81-7.85 (m, 1H) 7.73-7.79 (m, 1H) 7.44-7.52 (m, 2H) 7.25 (d, J=7.21 Hz, 1H) 6.39 (d, J=7.34 Hz, 1H) 5.09 (br t, J=5.69 Hz, 1H) 4.79 (br s, 1H) 3.40-3.59 (m, 2H) 3.22 (s, 3H) 3.10-3.16 (m, 2H) 3.03 (dt, J=14.03, 9.00 Hz, 2H) 2.80-2.89 (m, 1H) 2.67-2.76 (m, 2H) 2.58-2.66 (m, 5H) 2.37-2.45 (m, 1H) 2.21-2.29 (m, 1H) 1.79-1.92 (m, 2H) 1.74 (br dd, J=12.53, 5.81 Hz, 3H) 1.59-1.66 (m, 1H).

Compound 110: (S)-4-(((S)-2-fluoro-3-methoxypropyl) (4-(5,6,7,8-tetrahydro-1,8-naphthyridin-2-yl) butyl)amino)-2-((5-phenylpyrimidin-4-yl) amino) butanoic acid: To a solution of (S)-2-((5-bromopyrimidin-4-yl) amino)-4-(((S)-2-fluoro-3-methoxypropyl) (4-(5,6,7,8-tetrahydro-1,8-naphthyridin-2-yl) butyl)amino) butanoic acid (200 mg, 361 μmol) and phenylboronic acid (53 mg, 434 μmol) in 1,4-dioxane (2 mL) and H$_2$O (1 mL) was added Pd(dppf)Cl$_2$ (26 mg, 36 μmol) and K$_2$CO$_3$ (50 mg, 361 μmol) and the resulting mixture was stirred at 100° C. for 1 h and then allowed to cool to rt and concentrated in vacuo. The crude residue was purified by reverse phase prep-HPLC to give the title compound. LCMS (ESI+): m/z=551.3 (M+H)$^+$. $^1$H NMR (400 MHz, Methanol-d$_4$) δ ppm 8.84 (s, 1H) 8.21 (s, 1H) 7.56-7.63 (m, 6H) 6.65 (d, J=7.34 Hz, 1H) 5.09-5.28 (m, 2H) 3.70 (br d, J=3.42 Hz, 1H) 3.54-3.68 (m, 3H) 3.48-3.53 (m, 3H) 3.39 (s, 3H) 3.34 (br s, 3H) 2.80 (dt, J=12.81, 6.37 Hz, 4H) 2.58 (br t, J=11.98 Hz, 1H) 2.39 (br d, J=6.24 Hz, 1H) 1.94 (q, J=5.90 Hz, 2H) 1.80 (br s, 4H).

Compound 111: (S)-2-((5-cyanopyrimidin-2-yl) amino)-4-((2-phenoxyethyl) (4-(5,6,7,8-tetrahydro-1,8-naphthyridin-2-yl) butyl)amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 μmol) in 4:1 THF/H$_2$O (2 mL) was added 2-chloropyrimidine-5-carbonitrile (36 mg, 258 μmol) and NaHCO$_3$ (59 mg, 703 μmol) and the resulting mixture was stirred at 70° C. for 1 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=530.2 (M+H)$^+$. $^1$H NMR (400 MHz, Methanol-d$_4$) δ ppm 8.43 (br s, 1H) 8.35 (br s, 1H) 7.33 (d, J=7.34 Hz, 1H) 7.16-7.24 (m, 2H) 6.87-6.97 (m, 1H) 6.78-6.85 (m, 2H) 6.48 (d, J=7.34 Hz, 1H) 4.47 (t, J=6.17 Hz, 1H) 4.15 (t, J=5.26 Hz, 2H) 3.35-3.43 (m, 2H) 2.99-3.24 (m, 4H) 2.97-2.99 (m, 1H) 2.92 (br d, J=5.75 Hz, 2H) 2.63-2.76 (m, 4H) 2.20-2.33 (m, 1H) 2.04-2.15 ((m, 1H) 1.70-1.91 (m, 6H).

Compound 112: (S)-2-((1H-pyrazolo[3,4-d]pyrimidin-4-yl) amino)-4-((2,2-difluoroethyl) (4-(5,6,7,8-tetrahydro-1,8-naphthyridin-2-yl) butyl)amino) butanoic acid To a mixture of (S)-2-amino-4-((2,2-difluoroethyl) (4-(5,6,7,8-tetrahydro-1,8-naphthyridin-2-yl) butyl)amino) butanoic acid (100 mg, 270 μmol) and 4-chloro-1H-pyrazolo[3,4-d]pyrimidine (46 mg, 2975 μmol) in H$_2$O (0.5 mL) and THF (2 mL) was added NaHCO$_3$ (45 mg, 540 μmol) and the resulting mixture was stirred at 70° C. for 15 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=489.2 (M+H)$^+$. $^1$H NMR (400 MHz, Methanol-d$_4$) δ ppm 8.18 (s, 1H) 8.01 (s, 1H) 7.42 (br d, J=7.50 Hz, 1H) 6.50 (d, J=7.28 Hz, 1H) 5.68-6.13 (m, 1H) 4.89-4.98 (m, 1H) 3.38 (br d, J=5.51 Hz, 2H) 2.82-2.95 (m, 2H) 2.56-2.77 (m, 8H) 2.24 (br s, 1H) 2.13 (br d, J=6.17 Hz, 1H) 1.78-1.97 (m, 4H) 1.49-1.75 (m, 2H).

Compound 113: (S)-4-(cyclopropyl(4-(5,6,7,8-tetrahydro-1,8-naphthyridin-2-yl) butyl)amino)-2-((1-methyl-1H-pyrazolo[3,4-d]pyrimidin-4-yl) amino) butanoic acid: To a mixture of (S)-2-amino-4-(cyclopropyl(4-(5,6,7,8-tetrahydro-1,8-naphthyridin-2-yl) butyl)amino) butanoic acid hydrochloride (170 mg, 444 μmol) in 4:1 THF/H$_2$O (2.5 mL) was added 4-chloro-1-methyl-1H-pyrazolo[3,4-d]pyrimidine (75 mg, 444 μmol) and NaHCO$_3$ (112 mg, 1.33 mmol) and the resulting mixture was stirred at 70° C. for 1 h and then allowed to cool to rt and concentrated in vacuo. The crude residue was purified by reverse phase prep-HPLC to give the title compound as the hydrochloride salt. LCMS (ESI+): m/z=479.2 (M+H)$^+$. $^1$H NMR (400 MHz, D$_2$O): δ ppm 8.32-8.47 (m, 2H) 7.51 (br d, J=6.60 Hz, 1H) 6.56 (br s, 1H) 4.85 (br s, 1H) 4.03 (br s, 3H) 3.29-3.63 (m, 6H) 2.38-2.91 (m, 7H) 1.64-1.95 (m, 6H) 0.90-1.09 (m, 4H).

Compound 114: (S)-4-(cyclopropyl(4-(5,6,7,8-tetrahydro-1,8-naphthyridin-2-yl) butyl)amino)-2-((5-(trifluoromethyl)pyrimidin-2-yl) amino) butanoic acid: To a mixture of (S)-2-amino-4-(cyclopropyl(4-(5,6,7,8-tetrahydro-1,8-naphthyridin-2-yl) butyl)amino) butanoic acid hydrochloride (170 mg, 444 μmol) in 4:1 THF/H$_2$O (2 mL) was added 2-chloro-5-(trifluoromethyl)pyrimidine (89 mg, 488 μmol) and NaHCO$_3$ (112 mg, 1.33 mmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=493.2 (M+H)$^+$. $^1$H NMR (400 MHz, D$_2$O): δ ppm 8.61 (br s, 2H) 7.49 (d, J=7.34 Hz, 1H) 6.53 (d, J=7.21 Hz, 1H) 4.56-4.68 (m, 1H) 3.24-3.58 (m, 6H) 2.61-2.93 (m, 5H) 2.50 (br s, 1H) 2.35 (br s, 1H) 1.63-1.95 (m, 6H) 0.96 (br dd, J=12.59, 7.58 Hz, 4H).

Compound 115: (S)-4-(cyclopropyl(4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-(cyclopropyl(4-(5,6,7,8-tetrahydro-1,8-naphthyridin-2-yl) butyl)amino) butanoic acid hydrochloride (170 mg, 444 µmol) in 4:1 THF/H$_2$O (2 mL) was added 4-chloro-2-(trifluoromethyl)pyrimidine (89 mg, 488 µmol) and NaHCO$_3$ (112 mg, 1.33 mmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=493.2 (M+H)$^+$. $^1$H NMR (400 MHz, Methanol-d$_4$): δ ppm 8.09 (br s, 1H) 7.34 (br d, J=7.28 Hz, 1H) 6.71 (br s, 1H) 6.48 (br d, J=6.84 Hz, 1H) 6.41-6.41 (m, 1H) 4.56 (br s, 1H) 3.39 (br s, 2H) 2.82-3.16 (m, 4H) 2.58-2.73 (m, 4H) 2.25 (br d, J=5.95 Hz, 1H) 2.09 (br d, J=11.47 Hz, 2H) 1.65-1.89 (m, 6H) 0.44-0.76 (m, 4H).

Compound 116: (S)-2-((1H-pyrazolo[3,4-d]pyrimidin-4-yl) amino)-4-(cyclopropyl(4-(5,6,7,8-tetrahydro-1,8-naphthyridin-2-yl) butyl)amino) butanoic acid: To a mixture of (S)-2-amino-4-(cyclopropyl(4-(5,6,7,8-tetrahydro-1,8-naphthyridin-2-yl) butyl)amino) butanoic acid hydrochloride (170 mg, 491 µmol) in 4:1 THF/H$_2$O (2 mL) was added 4-chloro-1H-pyrazolo[3,4-d]pyrimidine (83 mg, 540 µmol) and NaHCO$_3$ (124 mg, 1.47 mmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=465.2 (M+H)$^+$. $^1$H NMR (400 MHz, D$_2$O): δ ppm 8.65 (s, 1H) 8.56 (s, 1H) 7.52 (br d, J=7.34 Hz, 1H) 6.56 (br d, J=7.34 Hz, 1H) 5.02 (br s, 1H) 3.30-3.60 (m, 6H) 2.37-2.88 (m, 7H) 1.68-1.94 (m, 6H) 0.91-1.07 (m, 4H).

Compound 117: (S)-2-((5-cyclopropylpyrimidin-2-yl) amino)-4-((2-phenoxyethyl) (4-(5,6,7,8-tetrahydro-1,8-naphthyridin-2-yl) butyl)amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 µmol) in 4:1 THF/H$_2$O (2 mL) was added 5-cyclopropyl-2-fluoropyrimidine (36 mg, 258 µmol) and NaHCO$_3$ (59 mg, 703 µmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=545.3 (M+H)$^+$. $^1$H NMR (400 MHz, Deutertum Oxide) δ ppm 8.27 (br s, 2H) 7.48 (br d, J=7.21 Hz, 1H) 7.28-7.39 (m, 2H) 7.02-7.12 (m, 1H) 6.91 (br d, J=7.95 Hz, 2H) 6.52 (d, J=7.34 Hz, 1H) 4.63-4.72 (m, 1H) 4.33 (br s, 2H) 3.65 (br s, 2H) 3.28-3.54 (m, 6H) 2.65-2.80 (m, 4H) 2.53 (br s, 1H) 2.31 (br d, J=7.70 Hz, 1H) 1.70-1.94 (m, 7H) 0.98-1.09 (m, 2H) 0.67 (q, J=5.09 Hz, 2H).

Compound 118: (S)-2-((5-cyanopyrimidin-2-yl) amino)-4-((2,2-difluoroethyl) (4-(5,6,7,8-tetrahydro-1,8-naphthyridin-2-yl) butyl)amino) butanoic acid: To a mixture of (S)-2-amino-4-((2,2-difluoroethyl) (4-(5,6,7,8-tetrahydro-1,8-naphthyridin-2-yl) butyl)amino) butanoic acid (100 mg, 270 µmol, 1 eq) and 2-chloropyrimidine-5-carbonitrile (41 mg, 297 µmol) in H$_2$O (0.5 mL) and THF (2 mL) was added NaHCO$_3$ (45 mg, 540 µmol) and the resulting mixture was stirred at 50° C. for 1 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=474.3. $^1$H NMR (400 MHz, Methanol-d$_4$) δ ppm 8.64 (br, s, 2H) 7.60 (d, J=7.34 Hz, 1H) 6.25-6.74 (m, 2H) 4.78 (dd, J=8.56, 5.26 Hz, 1H) 3.82 (td, J=15.07, 3.36 Hz, 2H) 3.35-3.62 (m, 6H) 2.73-2.89 (m, 4H) 2.45-2.59 (m, 1H) 2.26-2.41 (m, 1H) 1.72-2.02 (m, 6H).

Scheme 11, Compound 119

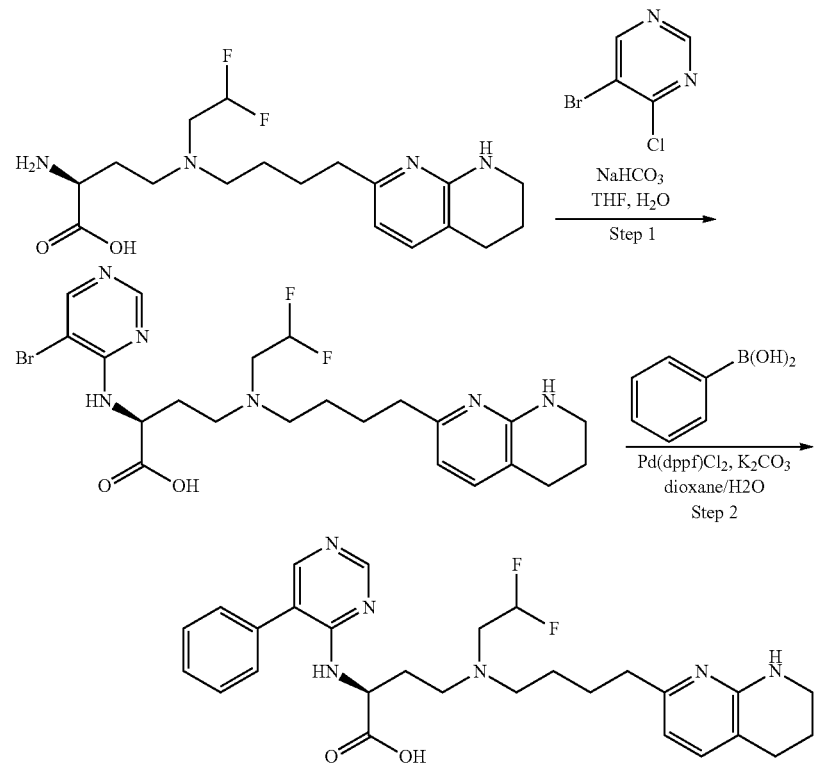

119

Step 1: (S)-2-((5-bromopyrimidin-4-yl) amino)-4-((2,2-difluoroethyl) (4-(5,6,7,8-tetrahydro-1,8-naphthyridin-2-yl) butyl)amino) butanoic acid To a solution of (S)-2-amino-4-((2,2-difluoroethyl) (4-(5,6,7,8-tetrahydro-1,8-naphthyridin-2-yl) butyl)amino) butanoic acid (150 mg, 405 μmol) and 5-bromo-4-chloropyrimidine (94 mg, 486 μmol) in THF (1.2 mL) and H$_2$O (0.3 mL) was added NaHCO$_3$ (170 mg, 2.02 mmol) and the resulting mixture was stirred at 70° C. for 1 h and then allowed to cool to rt and then adjusted to pH=6 by the addition of 1 M aq. HCl and concentrated in vacuo to give the title compound that was used without further purification. LCMS (ESI+): m/z=527.2 (M+H)$^+$.

Step 2: (S)-4-((2,2-difluoroethyl) (4-(5,6,7,8-tetrahydro-1,8-naphthyridin-2-yl) butyl)amino)-2-((5-phenylpyrimidin-4-yl) amino) butanoic acid To a solution of (S)-2-((5-bromopyrimidin-4-yl) amino)-4-((2,2-difluoroethyl) (4-(5,6,7,8-tetrahydro-1,8-naphthyridin-2-yl) butyl)amino) butanoic acid (213 mg, 404 μmol) and phenylboronic acid (59 mg, 485 μmol) in 1,4-dioxane (1 mL) H$_2$O (0.25 mL) was added Pd(dppf)Cl$_2$ (30 mg, 40 μmol) and K$_2$CO$_3$ (112 mg, 808 μmol) and the resulting mixture was stirred at 100° C. for 2 h and then allowed to cool to rt and concentrated in vacuo. The crude residue was purified by reverse phase prep-HPLC to give the title compound. LCMS (ESI+): m/z=525.3 (M+H)$^+$. $^1$H NMR (400 MHz, Methanol-d$_4$) δ ppm 8.85 (s, 1H) 8.22 (s, 1H) 7.61 (s, 3H) 7.60-7.68 (m, 1H) 7.59 (br s, 2H) 6.63-6.69 (m, 1H) 6.30-6.62 (m, 1H) 5.13 (br t, J=6.05 Hz, 1H) 3.78 (br t, J=13.75 Hz, 2H) 3.47-3.60 (m, 3H) 3.35-3.44 (m, 3H) 2.71-2.92 (m, 4H) 2.53-2.68 (m, 1H) 2.40 (br s, 1H) 1.92-2.06 (m, 1H) 1.92-2.01 (m, 1H) 1.67-1.92 (m, 4H).

Scheme 12, Compound 120

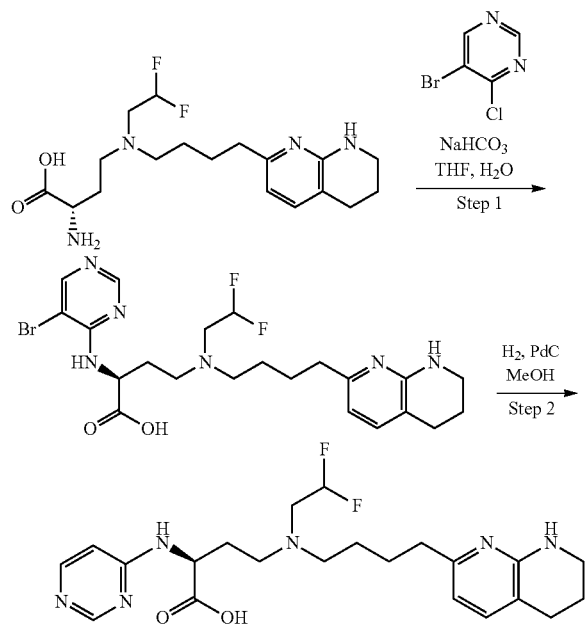

120

Step 1: (S)-2-((5-bromopyrimidin-4-yl) amino)-4-((2,2-difluoroethyl) (4-(5,6,7,8-tetrahydro-1,8-naphthyridin-2-yl) butyl)amino) butanoic acid To a solution of (S)-2-amino-4-((2,2-difluoroethyl) (4-(5,6,7,8-tetrahydro-1,8-naphthyridin-2-yl) butyl)amino) butanoic acid (150 mg, 405 μmol) and 5-bromo-4-chloropyrimidine (94 mg, 486 μmol) in THF (1.2 mL) and H$_2$O (0.3 mL) was added NaHCO$_3$ (170 mg, 2.02 mmol) and the resulting mixture was stirred at 70° C. for 1 h and then allowed to cool to rt and then adjusted to pH=6 by the addition of 1 M aq. HCl and concentrated in vacuo to give the title compound that was used without further purification. LCMS (ESI+): m/z=527.2 (M+H)$^+$.

Step 2: (S)-4-((2,2-difluoroethyl) (4-(5,6,7,8-tetrahydro-1,8-naphthyridin-2-yl) butyl)amino)-2-(pyrimidin-4-ylamino) butanoic acid To a solution of (S)-2-((5-bromopyrimidin-4-yl) amino)-4-((2,2-difluoroethyl) (4-(5,6,7,8-tetrahydro-1,8-naphthyridin-2-yl) butyl)amino) butanoic acid (213 mg, 404 μmol) in MeOH (3 mL) was added 10 wt % Pd/C (60 mg) and the resulting mixture was stirred under an H$_2$ atmosphere for 5 h and then filtered and concentrated in vacuo. The crude residue was purified by reverse phase prep-HPLC to give the title compound. LCMS (ESI+): m/z=449.2 (M+H)$^+$. $^1$H NMR (400 MHz, Methanol-d$_4$) δ ppm 8.78 (s, 1H) 8.21 (dd, J=7.34, 1.35 Hz, 1H) 7.60 (d, J=7.34 Hz, 1H) 7.00-7.08 (m, 1H) 6.28-6.73 (m, 2H) 4.99-5.09 (m, 1H) 3.83 (td, J=15.07, 3.36 Hz, 2H) 3.36-3.65 (m, 6H) 2.75-2.89 (m, 4H) 2.51-2.64 (m, 1H) 2.34-2.48 (m, 1H) 1.73-2.05 (m, 6H).

Compound 121: (S)-4-((2,2-difluoroethyl) (4-(5,6,7,8-tetrahydro-1,8-naphthyridin-2-yl) butyl)amino)-2-((5-fluoropyrimidin-2-yl) amino) butanoic acid: To a solution of (S)-2-amino-4-((2,2-difluoroethyl) (4-(5,6,7,8-tetrahydro-1,8-naphthyridin-2-yl) butyl)amino) butanoic acid (200 mg, 540 μmol) and 2-chloro-5-fluoropyrimidine (74 μL, 594 μmol) in DMA (3 mL) was added DIPEA (470 μL, 2.70 mmol) and the resulting mixture was stirred at 70° C. for 15 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=467.2 (M+H)$^+$. $^1$H NMR (400 MHz, Methanol-d$_4$) δ ppm 8.16 (s, 2H) 7.46 (d, J=7.34 Hz, 1H) 6.54 (d, J=7.34 Hz, 1H) 5.68-6.08 (m, 1H) 4.34-4.49 (m, 1H) 3.36-3.50 (m, 2H) 2.65-2.82 (m, 9H) 2.51-2.60 (m, 1H) 1.98-2.17 (m, 2H) 1.76-1.96 (m, 4H) 1.58 (q, J=6.60 Hz, 2H).

Compound 122: (S)-4-((2,2-difluoroethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid: To a solution of (S)-2-amino-4-((2,2-difluoroethyl) (4-(5,6,7,8-tetrahydro-1,8-naphthyridin-2-yl) butyl)amino) butanoic acid (150 mg, 405 μmol) and 4-chloro-6-methyl-2-(pyridin-4-yl) pyrimidine (92 mg, 445 μmol) in DMA (2 mL) was added DIPEA (71 μL, 405 μmol) and the resulting mixture was stirred at 70° C. for 12 h and then allowed to cool to rt and then concentrated in vacuo. The crude residue was purified by reverse phase prep-HPLC to give the title compound. LCMS (ESI+): m/z=540.3 (M+H)$^+$. $^1$H NMR (400 MHz, Methanol-d$_4$) δ ppm 8.54 (br d, J=4.85 Hz, 2H) 8.23 (br s, 2H) 7.43 (br s, 1H) 6.44-6.65 (m, 1H) 6.24 (s, 1H) 5.63-6.12 (m, 1H) 4.61-4.83 (m, 1H) 4.73 (br s, 1H) 2.92-3.26 (m, 2H) 2.51-2.67 (m, 3H) 2.51-2.91 (m, 7H) 2.24-2.50 (m, 3H) 2.17 (br s, 1H) 2.06 (br s, 1H) 1.92 (br d, J=5.95 Hz, 2H) 1.60-1.79 (m, 3H).

Scheme 13, Compound 123

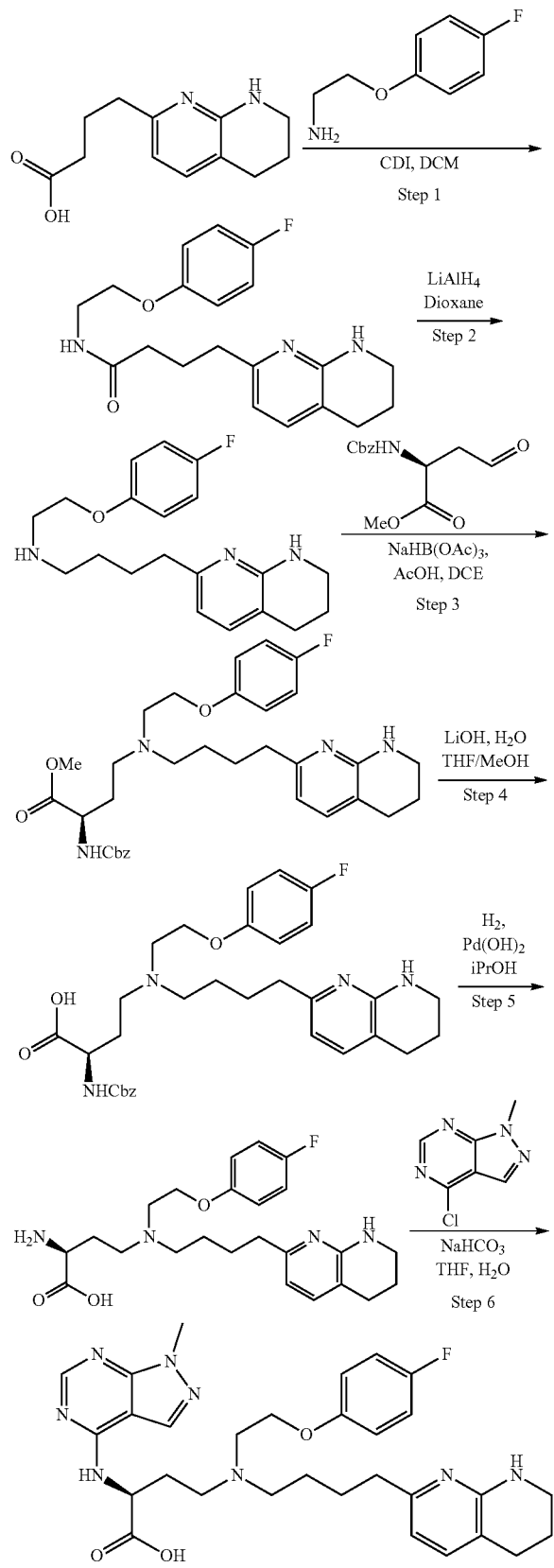

Step 1: N-(2-(4-fluorophenoxy)ethyl)-4-(5,6,7,8-tetrahydro-1,8-naphthyridin-2-yl) butanamide To a mixture of 4-(5,6,7,8-tetrahydro-1,8-naphthyridin-2-yl) butanoic acid (5 g, 15.89 mmol) in DCM (75 mL) was added CDI (2.83 g, 17.48 mmol) at 0° C. and the resulting mixture was stirred for 1 h. To this was then added 2-(4-fluorophenoxy)ethanamine hydrochloride (11.4 mL, 17.48 mmol) and the resulting mixture was stirred at rt for 2 h and then diluted with $H_2O$. The layers were separated and the aqueous layers was extracted with DCM and the combined organic extracts were dried over $Na_2SO_4$, filtered, and concentrated in vacuo. The crude residue was re-dissolved in EtOAc (40 mL) and then heated to reflux. Hexanes (15 mL) was then added and the solution was cooled to rt causing a precipitate to form. The solid was filtered and the filtrated was concentrated in vacuo to give the title compound. LCMS (ESI+): m/z=358.0 (M+H)$^+$.

Step 2: N-(2-(4-fluorophenoxy)ethyl)-4-(5,6,7,8-tetrahydro-1,8-naphthyridin-2-yl) butan-1-amine To a mixture of $LiAlH_4$ (590 mg, 15.56 mmol) in 1,4-dioxane (30 mL) was added N-(2-(4-fluorophenoxy)ethyl)-4-(5,6,7,8-tetrahydro-1,8-naphthyridin-2-yl) butanamide (2.78 g, 7.78 mmol) and the resulting mixture was heated to reflux for 30 min. and then allowed to cool to rt. The mixture was cooled to 10° C. and then neutralized by the cautious addition of $H_2O$ (0.6 mL), 1 M NaOH (0.6 mL), then $H_2O$ (0.6 mL), followed by drying over $MgSO_4$. The mixture was filtered and concentrated in vacuo to give the title compound that was used without further purification. LCMS (ESI+): m/z=344.2 (M+H)$^+$.

Step 3: (S)-methyl 2-(((benzyloxy)carbonyl)amino)-4-((2-(4-fluorophenoxy)ethyl) (4-(5,6,7,8-tetrahydro-1,8-naphthyridin-2-yl) butyl)amino) butanoate To a mixture of N-(2-(4-fluorophenoxy)ethyl)-4-(5,6,7,8-tetrahydro-1,8-naphthyridin-2-yl) butan-1-amine (2.67 g, 7.77 mmol) and methyl (2S)-2-(benzyloxycarbonylamino)-4-oxo-butanoate (2.17 g, 8.16 mmol) in DCE (50 mL) at 0° C. was added AcOH (667 μL, 11.66 mmol) then NaBH(OAc)$_3$, (2.47 g, 11.66 mmol) the resulting mixture was stirred at rt for 1 h. The mixture was diluted with sat. aq. $NaHCO_3$ and then extracted with DCM. The combined organic extracts were dried over $Na_2SO_4$, filtered, and concentrated in vacuo. The crude residue was purified by normal phase silica gel chromatography to give the title compound. LCMS (ESI+): m/z=593.4 (M+H)$^+$.

Step 4: (S)-2-(((benzyloxy)carbonyl)amino)-4-((2-(4-fluorophenoxy)ethyl) (4-(5,6,7,8-tetrahydro-1,8-naphthyridin-2-yl) butyl)amino) butanoic acid To a mixture of (S)-methyl 2-(((benzyloxy)carbonyl) amino)-4-((2-(4-fluorophenoxy)ethyl) (4-(5,6,7,8-tetrahydro-1,8-naphthyridin-2-yl) butyl)amino) butanoate (4 g, 6.75 mmol) in 1:1:1 THF/MeOH/$H_2O$ (37.5 mL) was added LiOH.$H_2O$ (566 mg, 13.50 mmol) and the resulting mixture was stirred at rt for 1 h. The mixture was adjusted to pH=6 by the addition of 1 M aq. HCl and concentrated in vacuo to give the title compound that was used without further purification. LCMS (ESI+): m/z=579.5 (M+H)$^+$.

Step 5: (S)-2-amino-4-((2-(4-fluorophenoxy)ethyl) (4-(5,6,7,8-tetrahydro-1,8-naphthyridin-2-yl) butyl) amino) butanoic acid To a solution of (S)-2-(((benzyloxy)carbonyl)amino)-4-((2-(4-fluorophenoxy)ethyl) (4-(5,6,7,8-tetrahydro-1,8-naphthyridin-2-yl) butyl)amino) butanoic acid (4 g, 6.91 mmol) in i-PrOH (30 mL) was added 10 wt % Pd(OH)$_2$/C (1.9 g) and the resulting mixture was stirred under an H$_2$ atmosphere for 48 h. The mixture was filtered and then concentrated in vacuo to give the title compound that was used without further purification. LCMS (ESI+): m/z=445.4 (M+H)$^+$.

Step 6: (S)-4-((2-(4-fluorophenoxy)ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid To a solution of (S)-2-amino-4-((2-(4-fluorophenoxy) ethyl) (4-(5,6,7,8-tetrahydro-1,8-naphthyridin-2-yl) butyl) amino) butanoic acid (80 mg, 180 µmol) and 4-chloro-1-methyl-pyrazolo[3,4-d]pyrimidine (33 mg, 198 µmol) in H$_2$O (0.5 mL) and THF (2 mL) was added NaHCO$_3$ (76 mg, 900 µmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=577.2 (M+H)$^+$. $^1$H NMR (400 MHz, Methanol-d$_4$) δ ppm 8.15 (s, 1H) 7.97 (s, 1H) 7.21-7.46 (m, 1H) 6.76-6.90 (m, 2H) 6.71 (br s, 2H) 6.46 (br d, J=7.02 Hz, 1H) 4.61-4.82 (m, 1H) 4.09 (br s, 2H) 3.92 (s, 3H) 3.38 (br s, 2H) 3.21-3.30 (m, 4H) 2.90-3.11 (m, 3H) 2.86 (br s, 1H) 2.63-2.75 (m, 4H) 2.36 (br s, 1H) 2.07-2.18 (m, 1H) 1.68-1.90 (m, 6H).

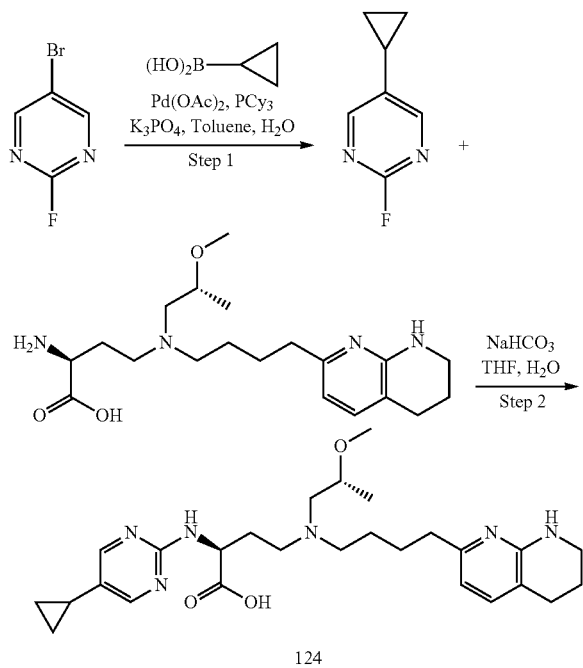

Scheme 14, Compound 124

Step 1: 5-cyclopropyl-2-fluoropyrimidine

To a solution of 5-bromo-2-fluoro-pyrimidine (5 g, 28.25 mmol) and cyclopropylboronic acid (2.91 g, 33.90 mmol) in toluene (100 mL) was added K$_3$PO$_4$ (17.99 g, 84.76 mmol), PCy$_3$ (916 µL, 2.83 mmol) and Pd(OAc)$_2$ (317 mg, 1.41 mmol) and the resulting mixture was stirred at 100° C. for 10 h and then cooled to rt. The mixture was poured into H$_2$O and the resulting mixture was extracted with ethyl acetate. The combined organic extracts were washed with brine, dried over Na$_2$SO$_4$, filtered, and concentrated in vacuo. The crude residue was purified by normal phase silica gel chromatography to give the title compound.

Step 2: (S)-2-((5-cyclopropylpyrimidin-2-yl)amino)-4-(((R)-2-methoxypropyl) (4-(5,6,7,8-tetrahydro-1, 8-naphthyridin-2-yl) butyl)amino) butanoic acid To a solution of (S)-2-amino-4-(((R)-2-methoxypropyl) (4-(5,6,7,8-tetrahydro-1,8-naphthyridin-2-yl) butyl)amino) butanoic acid hydrochloride (100 mg, 241 µmol) and 5-cyclopropyl-2-fluoropyrimidine (36.62 mg, 265.08 µmol, 1.1 eq) in THF (2 mL) and H$_2$O (0.5 mL) was added NaHCO$_3$ (101 mg, 1.20 mmol) and the resulting mixture was stirred at 70° C. for 12 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=497.3 (M+H)$^+$. $^1$H NMR (400 MHz, Methanol-d$_4$) δ ppm 8.56 (br s, 2H) 7.60 (br d, J=6.85 Hz, 1H) 6.67 (br d, J=7.09 Hz, 1H) 4.86-4.92 (m, 1H) 3.87 (br s, 1H) 3.50-3.54 (m, 2H) 3.39 (s, 4H) 3.08-3.31 (m, 5H) 2.77-2.85 (m, 4H) 2.54 (br s, 1H) 2.42 (br s, 1H) 2.20-2.25 (m, 1H) 1.92-2.00 (m, 3H) 1.81 (br s, 3H) 1.22 (br d, J=5.50 Hz, 3H) 1.05-1.11 (m, 2H) 0.82 (br d, J=4.77 Hz, 2H).

Compound 125: (S)-2-((1H-pyrazolo[3,4-d]pyrimidin-4-yl) amino)-4-((2-(methylsulfonyl)ethyl) (4-(5,6,7,8-tetrahydro-1,8-naphthyridin-2-yl) butyl)amino) butanoic acid:
To a mixture of (S)-2-amino-4-((2-(methylsulfonyl)ethyl) (4-(5,6,7,8-tetrahydro-1,8-naphthyridin-2-yl) butyl)amino) butanoic acid (100 mg, 242 µmol) in THF (2 mL) and H$_2$O (0.5 mL) was added NaHCO$_3$ (61 mg, 727 µmol) followed by 4-chloro-H-pyrazolo[3,4-d]pyrimidine (45 mg, 291 µmol) and the resulting mixture was stirred at 70° C. for 18 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=531.2 (M+H)$^+$. $^1$H NMR (400 MHz, Methanol-d$_4$) δ ppm 8.84 (s, 1H) 8.61 (s, 1H) 7.58 (d, J=7.34 Hz, 1H) 6.66 (d, J=7.34 Hz, 1H) 5.27 (br dd, J=8.31, 5.01 Hz, 1H) 3.81 (br d, J=6.85 Hz, 2H) 3.69-3.77 (m, 2H) 3.53-3.58 (m, 1H) 3.45-3.53 (m, 3H) 3.37 (br t, J=7.40 Hz, 2H) 3.12 (s, 3H) 2.77-2.84 (m, 4H) 2.61-2.71 (m, 1H) 2.47-2.59 (m, 1H) 1.95 (q, J=5.90 Hz, 2H) 1.85 (td, J=13.11, 6.17 Hz, 4H).

Compound 126: (S)-2-((6-(1H-pyrazol-1-yl) pyrimidin-4-yl) amino)-4-((2-(methylsulfonyl)ethyl) (4-(5,6,7,8-tetrahydro-1,8-naphthyridin-2-yl) butyl)amino) butanoic acid:
To a mixture of (S)-2-amino-4-((2-(methylsulfonyl)ethyl) (4-(5,6,7,8-tetrahydro-1,8-naphthyridin-2-yl) butyl)amino) butanoic acid (100 mg, 242 µmol) in DMA (2 mL) was added DIPEA (211 µL, 1.21 mmol) followed by 4-chloro-6-(1H-pyrazol-1-yl) pyrimidine (48 mg, 267 µmol) and the resulting mixture was stirred at 100° C. for 2 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=557.2 (M+H)$^+$. $^1$H NMR (400 MHz, Methanol-d$_4$) δ ppm 8.51-8.64 (m, 2H) 7.89 (s, 1H) 7.58 (d, J=7.06 Hz, 1H) 7.25 (br s, 1H) 6.65 (br d, J=7.06 Hz, 2H) 4.95 (br s, 1H) 3.77 (br dd, J=19.96, 5.62

Hz, 4H) 3.47-3.55 (m, 3H) 3.45 (br s, 1H) 3.35 (br d, J=7.50 Hz, 2H) 3.13 (s, 3H) 2.76-2.85 (m, 4H) 2.58 (br s, 1H) 2.41 (br s, 1H) 1.77-2.00 (m, 6H).

Step 1: (S)-2-((5-bromopyrimidin-4-yl) amino)-4-(((S)-2-fluoro-3-methoxypropyl) (4-(5,6,7,8-tetrahydro-1,8-naphthyridin-2-yl) butyl)amino) butanoic acid To a solution of (S)-2-amino-4-(((S)-2-fluoro-3-methoxypropyl) (4-(5,6,7,8-tetrahydro-1,8-naphthyridin-2-yl) butyl) amino) butanoic acid hydrochloride (250 mg, 577 μmol) and 5-bromo-4-chloropyrimidine (134 mg, 693 μmol) in THF (2 mL) and H₂O (0.5 mL) was added NaHCO₃ (243 mg, 2.89 mmol) and the resulting mixture was stirred at 70° C. for 1 h and then allowed to cool to rt and then adjusted to pH=6 by the addition of 1 M aq. HCl and concentrated in vacuo to give the title compound that was used without further purification. LCMS (ESI+): m/z=554.2 (M+H)⁺.

Step 2: (S)-4-(((S)-2-fluoro-3-methoxypropyl) (4-(5,6,7,8-tetrahydro-1,8-naphthyridin-2-yl) butyl) amino)-2-(pyrimidin-4-ylamino) butanoic acid To a solution of (S)-2-((5-bromopyrimidin-4-yl) amino)-4-(((S)-2-fluoro-3-methoxypropyl) (4-(5,6,7,8-tetrahydro-1,8-naphthyridin-2-yl) butyl)amino) butanoic acid (200 mg, 361 μmol) in MeOH (5 mL) was added 20 wt % Pd/C (38 mg) and the resulting mixture was stirred under an H₂ atmosphere for 5 h and then filtered and concentrated in vacuo. The crude residue was purified by reverse phase prep-HPLC to give the title compound. LCMS (ESI+): m/z=475.3 (M+H)⁺. ¹H NMR (400 MHz, Methanol-d₄) δ ppm 8.33 (s, 1H) 7.94 (br s, 1H) 7.40 (d, J=7.28 Hz, 1H) 6.44-6.55 (m, 2H) 4.80-4.83 (m, 1H) 4.55-4.79 (m, 1H) 3.53-3.58 (m, 1H) 3.50 (dd, J=6.95, 4.52 Hz, 1H) 3.39 (q, J=5.59 Hz, 2H) 3.33 (s, 3H) 2.93 (br s, 2H) 2.63-2.76 (m, 8H) 2.14-2.24 (m, 1H) 2.02-2.11 (m, 1H) 1.76-1.92 (m, 4H) 1.57-1.69 (m, 2H).

Scheme 15, Compound 127

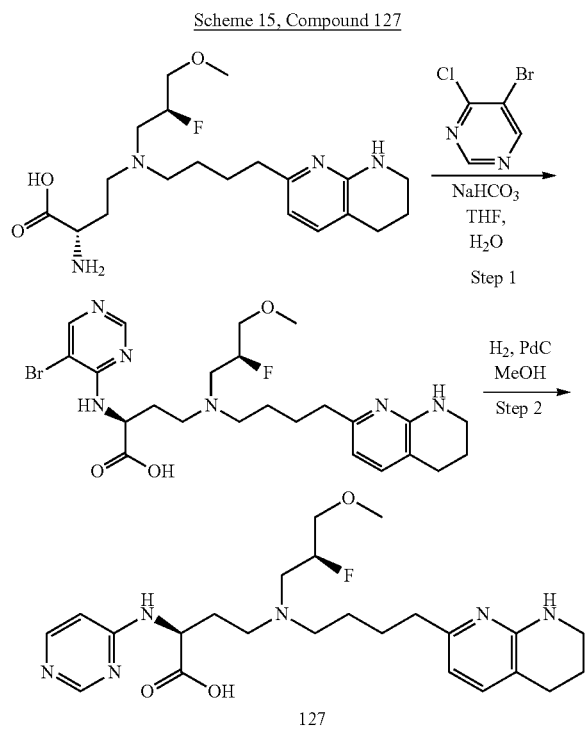

Scheme 16, Compound 128

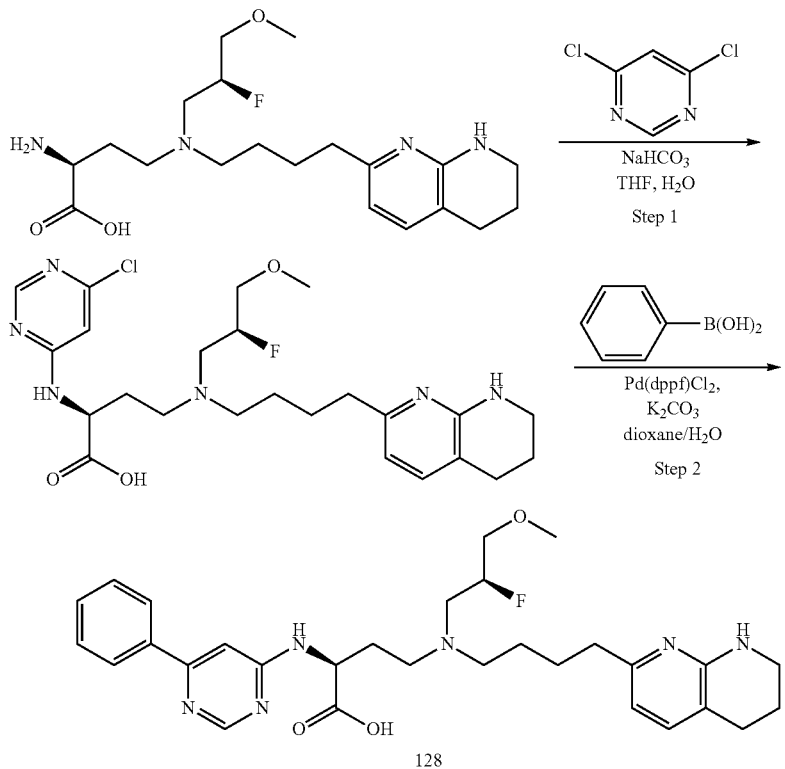

Step 1: (S)-2-((6-chloropyrimidin-4-yl) amino)-4-(((S)-2-fluoro-3-methoxypropyl) (4-(5,6,7,8-tetrahydro-1,8-naphthyridin-2-yl) butyl)amino) butanoic acid To a solution of (S)-2-amino-4-(((S)-2-fluoro-3-methoxypropyl) (4-(5,6,7,8-tetrahydro-1,8-naphthyridin-2-yl) butyl) amino) butanoic acid hydrochloride (100 mg, 231 μmol) and 4,6-dichloropyrimidine (41 mg, 277 μmol) in THF (2 mL) and H₂O (0.5 mL) was added NaHCO₃ (97 mg, 1.15 mmol) and the resulting mixture was stirred at 70° C. for 18 h and then allowed to cool to rt and then adjusted to pH=6 by the addition of 1 M aq. HCl and concentrated in vacuo to give the title compound that was used without further purification. LCMS (ESI+): m/z=510.3 (M+H)⁺.

Step 2: (S)-4-(((S)-2-fluoro-3-methoxypropyl) (4-(5,6,7,8-tetrahydro-1,8-naphthyridin-2-yl) butyl) amino)-2-((6-phenylpyrimidin-4-yl) amino) butanoic acid To a solution of (S)-2-((6-chloropyrimidin-4-yl) amino)-4-(((S)-2-fluoro-3-methoxypropyl) (4-(5,6,7,8-tetrahydro-1,8-naphthyridin-2-yl) butyl)amino) butanoic acid (100 mg, 196 μmol) and phenylboronic acid (29 mg, 236 μmol) in 1,4-dioxane (2 mL) and H₂O (1 mL) was added Pd(dppf)Cl₂ (14 mg, 20 μmol) and K₂CO₃ (81 mg, 589 μmol) and the resulting mixture was stirred at 100° C. for 2 h and then cooled to rt. The mixture was filtered and then concentrated in vacuo. The crude residue was purified by reverse phase prep-HPLC to give the title compound. LCMS (ESI+): m/z=551.3 (M+H)⁺. ¹H NMR (400 MHz, Methanol-d₄) δ ppm 8.81 (s, 1H) 7.88 (br d, J=7.46 Hz, 2H) 7.63-7.74 (m, 3H) 7.59 (br d, J=6.97 Hz, 1H) 7.30 (br s, 1H) 6.67 (br d, J=7.21 Hz, 1H) 5.14-5.34 (m, 1H) 5.10 (br s, 1H) 3.63-3.77 (m, 4H) 3.57 (br d, J=8.68 Hz, 2H) 3.48-3.53 (m, 3H) 3.41 (s, 4H) 2.81 (br d, J=4.89 Hz, 4H) 2.40-2.64 (m, 2H) 1.79-1.97 (m, 6H).

Compound 129: (2S)-4-((oxetan-2-ylmethyl) (4-(5,6,7,8-tetrahydro-1,8-naphthyridin-2-yl) butyl)amino)-2-(quinazolin-4-ylamino) butanoic acid. Prepared according to Scheme B using Procedure F with oxetan-2-ylmethanamine, Procedure H with 4-chloroquinazoline, and Procedure P. LCMS theoretical m/z=505.3. [M+H]+, found 505.3.

Compound 130: (S)-4-((3-hydroxy-2-(hydroxymethyl) propyl) (4-(5,6,7,8-tetrahydro-1,8-naphthyridin-2-yl) butyl) amino)-2-(quinazolin-4-ylamino) butanoic acid. Prepared according to Scheme B using Procedure F with 2-(aminomethyl)propane-1,3-diol, Procedure H with 4-chloroquinazoline, and Procedure P. LCMS theoretical m/z=523.3; [M+H]⁺ found 523.3.

Scheme 17, Compound 131

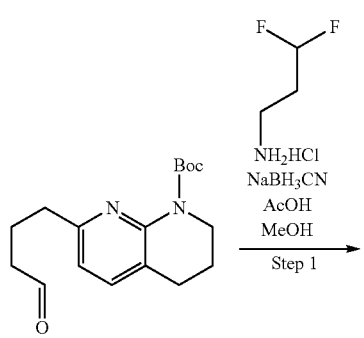

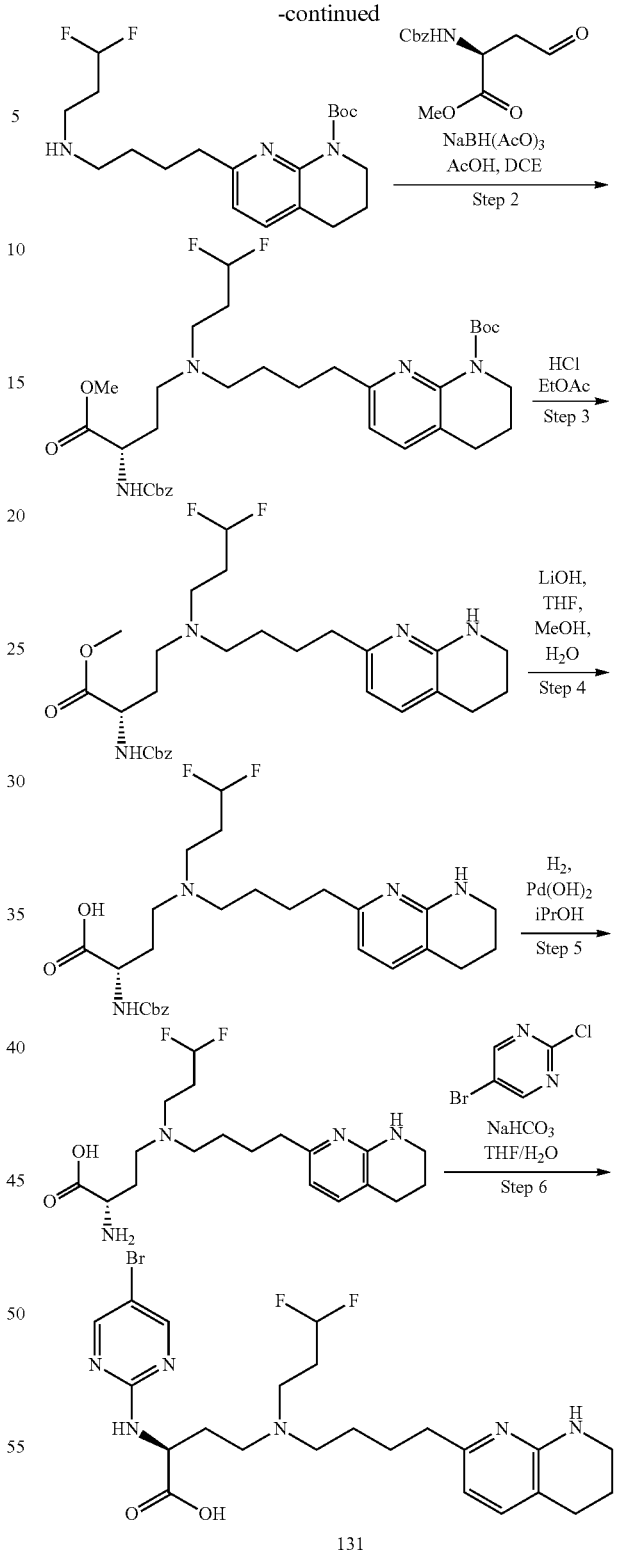

Step 1: tert-butyl 7-(4-((3,3-difluoropropyl)amino) butyl)-3,4-dihydro-1,8-naphthyridine-1(2H)-carboxylate To a solution of 3,3-difluoropropan-1-amine hydrochloride (12.04 g, 82.39 mmol) in MeOH (200 mL) at 0° C. was added AcOH (3.2 mL, 56.18 mmol), NaBH$_3$CN (4.71 g, 74.90 mmol), then a solution of tert-butyl 7-(4-oxobutyl)-3,4-dihydro-2H-1,8-naphthyridine-1-carboxylate (12 g, 37.45 mmol) in MeOH (100 mL) and the resulting mixture was stirred for 2 h at rt. The mixture was diluted with sat. aq. NaHCO$_3$ and then extracted with EtOAc. The combined organic extracts were dried over Na$_2$SO$_4$, filtered, and concentrated in vacuo. The crude residue was purified by reverse phase prep-HPLC to give the title compound. LCMS (ESI+): m/z=384.1 (M+H)$^+$ Step 2: (S)-tert-butyl7-(4-((3-(((benzyloxy)carbonyl) amino)-4-methoxy-4-oxobutyl) (3,3-difluoropropyl) amino) butyl)-3,4-dihydro-1,8-naphthyridine-1(2H)-carboxylate To a solution of tert-butyl 7-(4-((3,3-difluoropropyl) amino)butyl)-3,4-dihydro-1,8-naphthyridine-(2H)-carboxylate (19 g, 44.59 mmol) and (S)-methyl 2-(((benzyloxy) carbonyl)amino)-4-oxobutanoate (13.70 g, 49.05 mmol) in DCE (200 mL) at 0° C. was added AcOH (3.8 mL, 66.89 mmol) then NaBH(OAc)$_3$ (14.18 g, 66.89 mmol) and the resulting mixture was stirred at rt for 2 h. The mixture was diluted with sat. aq. NaHCO$_3$ and the layers were separated. The aqueous layer was extracted with DCM and the combined organic extracts were dried over Na$_2$SO$_4$, filtered, and concentrated in vacuo. The crude residue was purified by column chromatography on alumina to give the title compound. LCMS (ESI+): m/z=633.3 (M+H)$^+$ Step 3: (S)-methyl 2-(((benzyloxy)carbonyl)amino)-4-((3,3-difluoropropyl) (4-(5,6,7,8-tetrahydro-1,8-naphthyridin-2-yl) butyl)amino) butanoate To a mixture of (S)-tert-butyl7-(4-((3-(((benzyloxy)carbonyl)amino)-4-methoxy-4-oxobutyl) (3,3-difluoropropyl) amino)butyl)-3,4-dihydro-1,8-naphthyridine-1(2H)-carboxylate (26 g, 36.98 mmol) in 4 M HCl in EtOAc (300 mL) was stirred for 16 h at rt and then concentrated in vacuo. The crude residue was taken up in water and then washed with MTBE. The aqueous layer was adjusted to pH=8 by the addition of 1 M NaOH and then extracted with DCM. The combined organic extracts were dried over Na$_2$SO$_4$, filtered, and concentrated in vacuo to give the title compound. LCMS (ESI+): m/z=533.3 (M+H)$^+$;

Step 4: (S)-2-(((benzyloxy)carbonyl)amino)-4-((4-(8-(tert-butoxycarbonyl)-5,6,7,8-tetrahydro-1,8-naphthyridin-2-yl) butyl) (3,3-difluoropropyl)amino) butanoic acid To a solution of (S)-methyl 2-(((benzyloxy)carbonyl) amino)-4-((3,3-difluoropropyl) (4-(5,6,7,8-tetrahydro-1,8-naphthyridin-2-yl) butyl) amino) butanoate (5 g, 8.45 mmol) in 4:1:1 THF/MeOH/H$_2$O (60 mL) was added LiOH.H$_2$O (709 mg, 16.90 mmol) and the resulting mixture was stirred for 16 h at rt. The mixture was adjusted to pH=6 by the addition of 1 M aq. HCl and then concentrated in vacuo to give the title compound that was used without further purification. LCMS (ESI+): m/z=519.4 (M+H)+;

Step 5: (S)-2-amino-4-((3,3-difluoropropyl) (4-(5,6,7,8-tetrahydro-1,8-naphthyridin-2-yl) butyl)amino) butanoic acid To a solution of (S)-2-(((benzyloxy)carbonyl)amino)-4-((4-(8-(tert-butoxycarbonyl)-5,6,7,8-tetrahydro-1,8-naphthyridin-2-yl) butyl) (3,3-difluoropropyl)amino) butanoic acid (4 g, 7.33 mmol) in i-PrOH (200 mL) was added 10 wt % Pd(OH)$_2$/C (6.0 g) and the resulting mixture stirred under an H$_2$ atmosphere (50 Psi) for 2 h and then filtered and concentrated in vacuo to give the title compound that was used without further purification. LCMS (ESI+): m/z=385.2 (M+H)$^+$ Step 6: (S)-2-((5-bromopyrimidin-2-yl) amino)-4-((3,3-difluoropropyl) (4-(5,6,7,8-tetrahydro-1,8-naphthyridin-2-yl) butyl)amino) butanoic acid To a solution of (S)-2-amino-4-((3,3-difluoropropyl) (4-(5,6,7,8-tetrahydro-1,8-naphthyridin-2-yl) butyl)amino) butanoic acid (140 mg, 327.73 μmol) in THF (4 mL) and H$_2$O (1 mL) was added 5-bromo-2-chloropyrimidine (70 mg, 361 μmol) and NaHCO$_3$ (138 mg, 1.64 mmol) and the resulting mixture was stirred at 70° C. for 5 h and then allowed to cool to rt and concentrated in vacuo. The crude residue was purified by reverse phase prep-HPLC to give the title compound. LCMS (ESI+): m/z=541.1 (M+H)$^+$. $^1$H NMR (400 MHz, D$_2$O) δ ppm 8.42 (s, 2H) 7.51 (d, J=7.46 Hz, 1H) 6.53 (br d, J=7.21 Hz, 1H) 5.91-6.26 (m, 1H) 4.56 (dd, J=5.01, 8.68 Hz, 1H) 3.30-3.48 (m, 6H) 3.22 (br d, J=7.83 Hz, 2H) 2.74 (t, J=6.11 Hz, 2H) 2.67 (br s, 2H) 2.21-2.49 (m, 4H) 1.88 (q, J=5.93 Hz, 2H) 1.70 (br s, 4H).

Compound 132: (S)-4-((3,3-difluoropropyl) (4-(5,6,7,8-tetrahydro-1,8-naphthyridin-2-yl) butyl)amino)-2-((5-(trifluoromethyl)pyrimidin-2-yl) amino) butanoic acid To a solution of (S)-2-amino-4-((3,3-difluoropropyl) (4-(5,6,7,8-tetrahydro-1,8-naphthyridin-2-yl) butyl)amino) butanoic acid (140 mg, 328 μmol) in THF (4 mL) and H$_2$O (1 mL) was added 2-chloro-5-(trifluoromethyl)pyrimidine (66 mg, 361 μmol) and NaHCO$_3$ (138 mg, 1.64 mmol) and the resulting mixture was stirred at 70° C. for 1 h and then allowed to cool to rt and concentrated in vacuo. The crude residue was purified by reverse phase prep-HPLC to give the title compound. LCMS (ESI+): m/z=531.2 (M+H)$^+$. $^1$H NMR (400 MHz, D$_2$O) δ ppm 8.66 (s, 2H) 7.54 (br d, J=7.21 Hz, 1H) 6.57 (br d, J=7.34 Hz, 1H) 5.94-6.28 (m, 1H) 4.62-4.69 (m, 1H) 3.34-3.52 (m, 6H) 3.26 (br s, 2H) 2.66-2.82 (m, 4H) 2.28-2.53 (m, 4H) 1.85-1.96 (m, 2H) 1.74 (br s, 4H).

Compound 133: (S)-4-((3,3-difluoropropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid: To a solution of (S)-2-amino-4-((3,3-difluoropropyl) (4-(5,6,7,8-tetrahydro-1,8-naphthyridin-2-yl) butyl)amino) butanoic acid (140 mg, 328 μmol) in THF (4 mL) and H$_2$O (1 mL) was added 4-chloro-1-methyl-1H-pyrazolo[3,4-d] pyrimidine (55 mg, 328 μmol) and NaHCO$_3$ (138 mg, 1.64 mmol) and the resulting mixture was stirred at 70° C. for 1 h and then concentrated in vacuo. The crude residue was purified by reverse phase prep-HPLC to give the title compound. LCMS (ESI+): m/z=517.2 (M+H)$^+$. $^1$H NMR (400 MHz, Deuterium Oxide) δ ppm 8.30-8.48 (m, 2H) 7.52 (br d, J=6.97 Hz, 1H) 6.55 (br d, J=6.85 Hz, 1H) 5.95-6.28 (m, 1H) 4.86 (br s, 1H) 4.04 (s, 3H) 3.38-3.56 (m, 6H) 3.29 (br s, 2H) 2.66-2.80 (m, 4H) 2.30-2.63 (m, 4H) 1.86-1.96 (m, 2H) 1.75 (br s, 4H).

Compound 134: (S)-4-((3,3-difluoropropyl) (4-(5,6,7,8-tetrahydro-1,8-naphthyridin-2-yl) butyl)amino)-2-((2-(trifluoromethyl)pyrimidin-4-yl) amino) butanoic acid: To a solution of (S)-2-amino-4-((3,3-difluoropropyl) (4-(5,6,7,8-tetrahydro-1,8-naphthyridin-2-yl) butyl)amino) butanoic acid (140 mg, 328 μmol) in THF (4 mL) and H$_2$O (1 mL) was added 4-chloro-2-(trifluoromethyl)pyrimidine (66 mg, 361 µmol) and NaHCO₃ (138 mg, 1.64 mmol) and the resulting mixture was stirred at 70° C. for 18 h and then allowed to cool to rt and then concentrated in vacuo. The crude residue was purified by reverse phase prep-HPLC to give the title compound. LCMS (ESI+): m/z=531.2 (M+H)⁺. ¹H NMR (400 MHz, D₂O) δ ppm 8.22 (br d, J=5.75 Hz, 1H) 7.49 (br d, J=7.09 Hz, 1H) 6.84 (d, J=6.24 Hz, 1H) 6.52 (br d, J=7.34 Hz, 1H) 5.91-6.26 (m, 1H) 4.72 (br s, 1H) 3.14-3.50 (m, 8H) 2.61-2.78 (m, 4H) 2.21-2.52 (m, 4H) 1.82-1.94 (m, 2H) 1.69 (br s, 4H).

Compound 135: (S)-2-((5-cyclopropylpyrimidin-2-yl)amino)-4-((3,3-difluoropropyl) (4-(5,6,7,8-tetrahydro-1,8-naphthyridin-2-yl) butyl)amino) butanoic acid: To a solution of (S)-2-amino-4-((3,3-difluoropropyl) (4-(5,6,7,8-tetrahydro-1,8-naphthyridin-2-yl) butyl)amino) butanoic acid (140 mg, 327.73 µmol) in THF (4 mL) and H₂O (1 mL) was added 1-cyclopropyl-4-fluorobenzene (50 mg, 361 µmol) and NaHCO₃ (138 mg, 1.64 mmol) and the resulting mixture was stirred at 70° C. for 5 h and then allowed to cool to rt and concentrated in vacuo. The crude residue was purified by reverse phase prep-HPLC to give the title compound. LCMS (ESI+): m/z=503.2 (M+H)⁺. ¹H NMR (400 MHz, D₂O) δ ppm 8.40 (br s, 2H) 7.52 (d, J=7.46 Hz, 1H) 6.56 (d, J=7.34 Hz, 1H) 5.91-6.25 (m, 1H) 4.67-4.71 (m, 1H) 3.21-3.49 (m, 8H) 2.67-2.79 (m, 4H) 2.24-2.52 (m, 4H) 1.85-1.93 (m, 3H) 1.73 (br d, J=3.67 Hz, 4H) 0.96-1.08 (m, 2H) 0.65-0.73 (m, 2H).

Scheme 18, Compound 136

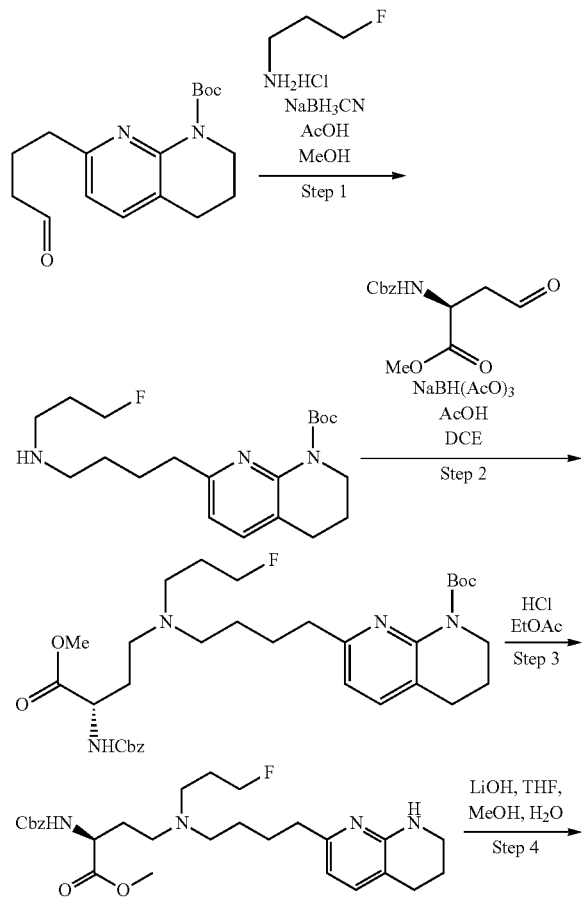

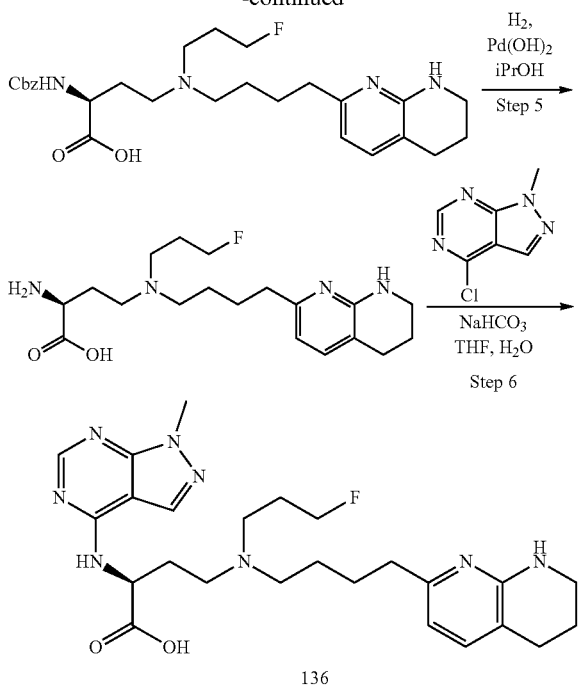

Step 1: tert-butyl 7-(4-((3-fluoropropyl)amino)butyl)-3,4-dihydro-1,8-naphthyridine-1(2H)-carboxylate To a solution of 3-fluoropropan-1-amine hydrochloride (6.72 g, 56.18 mmol) and NaBH₃CN (3.92 g, 62.42 mmol) in MeOH (100 mL) was added a solution of tert-butyl 7-(4-oxobutyl)-3,4-dihydro-1,8-naphthyridine-1(2H)-carboxylate (10 g, 31.21 mmol) in MeOH (80 mL) and the resulting mixture was stirred at rt for 2 h. The resulting solution was poured into water and then extracted with EtOAc. The combined organic extracts were dried over Na₂SO₄, filtered, and concentrated in vacuo. The crude residue was purified by reverse phase prep-HPLC to give the title compound. LCMS (ESI+): m/z=366.0 (M+H)⁺

Step 2: (S)-tert-butyl 7-(4-((3-(((benzyloxy)carbonyl)amino)-4-methoxy-4-oxobutyl) (3-fluoropropyl)amino) butyl)-3,4-dihydro-1,8-naphthyridine-1(2H)-carboxylate To a solution of tert-butyl 7-(4-((3-fluoropropyl)amino)butyl)-3,4-dihydro-1,8-naphthyridine-1(2H)-carboxylate (12 g, 30.53 mmol) and (S)-methyl 2-(((benzyloxy)carbonyl)amino)-4-oxobutanoate (11.08 g, 39.70 mmol) in DCE (150 mL) at 0° C. was added AcOH (2.62 mL, 45.80 mmol) then NaBH(OAc)₃ (9.71 g, 45.80 mmol) and the resulting mixture was stirred at rt for 1 h and then diluted with sat. aq. NaHCO₃. The layers were separated and the aqueous layer was extracted with DCM. The combined organic extracts were dried over Na₂SO₄, filtered, and concentrated in vacuo. The crude residue was purified by column chromatography on alumina to give the title compound. LCMS (ESI+): m/z=615.5 (M+H)⁺

Step 3: (S)-methyl 2-(((benzyloxy)carbonyl)amino)-4-((3-fluoropropyl) (4-(5,6,7,8-tetrahydro-1,8-naphthyridin-2-yl) butyl)amino) butanoate (S)-tert-butyl 7-(4-((3-(((benzyloxy)carbonyl)amino)-4-methoxy-4-oxobutyl) (3-fluoropropyl)amino)butyl)-3,4-dihydro-1,8-naphthyridine-1(2H)-carboxylate (14 g, 21.41 mmol) was taken up in 4 M HCl in EtOAc (150 mL) and then stirred at rt for 16 h and concentrated in vacuo. The crude residue was taken up in water and then washed with MTBE, and then adjusted to pH=8 by the addition of 1 M NaOH, and then extracted with DCM. The combined organic extracts were dried over $Na_2SO_4$, filtered, and concentrated to give the title compound that was used without further purification. LCMS (ESI+): m/z=515.2 $(M+H)^+$ Step 4: (S)-2-(((benzyloxy)carbonyl)amino)-4-((3-fluoropropyl) (4-(5,6,7,8-tetrahydro-1,8-naphthyridin-2-yl) butyl)amino) butanoic acid To a solution of (S)-methyl 2-(((benzyloxy)carbonyl) amino)-4-((3-fluoropropyl) (4-(5,6,7,8-tetrahydro-1,8-naphthyridin-2-yl) butyl)amino) butanoate (4 g, 7.00 mmol) in 4:1:1 THF/MeOH/$H_2O$ (600 mL) was added LiOH.$H_2O$ (881 mg, 20.99 mmol) and the resulting mixture was stirred at rt for 1 h and then adjusted to pH=6 by the addition of 1 M aq. HCl and then concentrated in vacuo to give the title compound that was used without further purification. LCMS (ESI+): m/z=501.2 $(M+H)^+$ Step 5: (S)-2-amino-4-((3-fluoropropyl) (4-(5,6,7,8-tetrahydro-1,8-naphthyridin-2-yl) butyl)amino) butanoic acid To a solution of (S)-2-(((benzyloxy)carbonyl)amino)-4-((3-fluoropropyl) (4-(5,6,7,8-tetrahydro-1,8-naphthyridin-2-yl) butyl)amino) butanoic acid (4.8 g, 9.01 mmol) in i-PrOH (200 mL) was added 10 wt % $Pd(OH)_2$/C (7.41 g) and the resulting mixture was stirred under an $H_2$ atmosphere (50 Psi) for 38 h and then filtered and concentrated in vacuo to give the title compound that was used without further purification. LCMS (ESI+): m/z=367.3 $(M+H)^+$ Step 6: (S)-4-((3-fluoropropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid To a solution of (S)-2-amino-4-((3-fluoropropyl) (4-(5,6,7,8-tetrahydro-1,8-naphthyridin-2-yl) butyl)amino) butanoic acid (150 mg, 368 µmol) in THF (4 mL) and $H_2O$ (1 mL) was added 4-chloro-1H-pyrazolo[3,4-d]pyrimidine (68 mg, 405 µmol) and $NaHCO_3$ (155 mg, 1.84 mmol) and the resulting mixture was stirred at 70° C. for 1 h and concentrated in vacuo. The crude residue was purified by reverse phase prep-HPLC to give the title compound. LCMS (ESI+): m/z=499.3 $(M+H)^+$. $^1$H NMR (400 MHz, $D_2O$) δ ppm 8.42 (s, 1H) 8.35 (s, 1H) 7.49 (br d, J=6.97 Hz, 1H) 6.53 (br s, 1H) 4.81-4.96 (m, 1H) 4.63 (t, J=5.20 Hz, 1H) 4.51 (t, J=5.26 Hz, 1H) 4.02 (s, 3H) 3.18-3.49 (m, 8H) 2.62-2.80 (m, 4H) 2.33-2.60 (m, 2H) 2.05-2.22 (m, 2H) 1.83-1.93 (m, 2H) 1.73 (br s, 4H).

Compound 137: (S)-4-((3-fluoropropyl) (4-(5,6,7,8-tetrahydro-1,8-naphthyridin-2-yl) butyl)amino)-2-((5-(trifluoromethyl) pyrimidin-2-yl) amino) butanoic acid: To a solution of (S)-2-amino-4-((3-fluoropropyl) (4-(5,6,7,8-tetrahydro-1,8-naphthyridin-2-yl) butyl)amino) butanoic acid (150 mg, 368 µmol) in THF (4 mL) and $H_2O$ (1 mL) was added 2-chloro-5-(trifluoromethyl)pyrimidine (74 mg, 405 µmol) and $NaHCO_3$ (155 mg, 1.84 mmol) and the resulting mixture was stirred at 70° C. for 1 h and then concentrated in vacuo. The crude residue was purified by reverse phase prep-HPLC to give the title compound. LCMS (ESI+): m/z=513.2 $(M+H)^+$. $^1$H NMR (400 MHz, $D_2O$) δ ppm 8.57 (s, 2H) 7.44 (br d, J=7.34 Hz, 1H) 6.48 (dd, J=3.85, 7.27 Hz, 1H) 4.52-4.62 (m, 2H) 4.44 (br t, J=4.34 Hz, 1H) 3.11-3.42 (m, 8H) 2.57-2.72 (m, 4H) 2.16-2.46 (m, 2H) 1.94-2.12 (m, 2H) 1.81 (q, J=5.90 Hz, 2H) 1.65 (br d, J=2.69 Hz, 4H).

Compound 138: (S)-2-((5-cyanopyrimidin-2-yl) amino)-4-((2-(4-fluorophenoxy)ethyl) (4-(5,6,7,8-tetrahydro-1,8-naphthyridin-2-yl) butyl)amino) butanoic acid: To a solution of (S)-2-amino-4-((2-(4-fluorophenoxy)ethyl) (4-(5,6,7,8-tetrahydro-1,8-naphthyridin-2-yl) butyl)amino) butanoic acid (120 mg, 270 µmol) and 2-chloropyrimidine-5-carbonitrile (41 mg, 297 µmol) in THF (2 mL) and $H_2O$ (0.5 mL) was added $NaHCO_3$ (113 mg, 1.35 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=548.3 $(M+H)^+$. $^1$H NMR (400 MHz, Methanol-$d_4$) δ ppm 8.27-8.63 (m, 2H) 7.31 (br d, J=7.21 Hz, 1H) 6.90-7.00 (m, 2H) 6.78-6.88 (m, 2H) 6.47 (d, J=7.21 Hz, 1H) 4.45-4.48 (m, 1H) 4.12 (t, J=5.20 Hz, 2H) 3.33-3.43 (m, 2H) 3.03-3.22 (m, 4H) 2.81-2.92 (m, 2H) 2.72 (br t, J=6.24 Hz, 2H) 2.65 (br t, J=7.76 Hz, 2H) 2.19-2.31 (m, 1H) 2.03-2.17 (m, 1H) 1.67-1.91 (m, 6H).

Compound 139: (S)-4-((2-(4-fluorophenoxy)ethyl) (4-(5,6,7,8-tetrahydro-1,8-naphthyridin-2-yl) butyl)amino)-2-((5-(trifluoromethyl)pyrimidin-2-yl) amino) butanoic acid: To a solution of (S)-2-amino-4-((2-(4-fluorophenoxy)ethyl) (4-(5,6,7,8-tetrahydro-1,8-naphthyridin-2-yl) butyl)amino) butanoic acid (120 mg, 270 µmol) and 2-chloropyrimidine-5-carbonitrile (120 mg, 270 µmol) and 2-chloro-5-(trifluoromethyl)pyrimidine (54 mg, 297 µmol) in THF (2 mL) and $H_2O$ (0.5 mL) was added $NaHCO_3$ (113 mg, 1.35 mmol) and the resulting mixture was stirred at 70° C. for 1 h and then concentrated in vacuo. The crude residue was purified by reverse phase prep-HPLC to give the title compound. LCMS (ESI+): m/z=591.2 $(M+H)^+$. $^1$H NMR (400 MHz, Methanol-$d_4$) δ ppm 8.25-8.61 (m, 2H) 7.34 (d, J=7.45 Hz, 1H) 6.89-6.97 (m, 2H) 6.80-6.88 (m, 2H) 6.46-6.52 (m, 1H) 4.45 (t, J=6.14 Hz, 1H) 4.18 (t, J=5.04 Hz, 2H) 3.32-3.45 (m, 2H) 3.09-3.28 (m, 4H) 2.91-3.08 (m, 2H) 2.60-2.76 (m, 4H) 2.28 (br d, J=3.95 Hz, 1H) 2.15 (br d, J=4.82 Hz, 1H) 1.72-1.93 (m, 6H).

Scheme 19, Compound 140

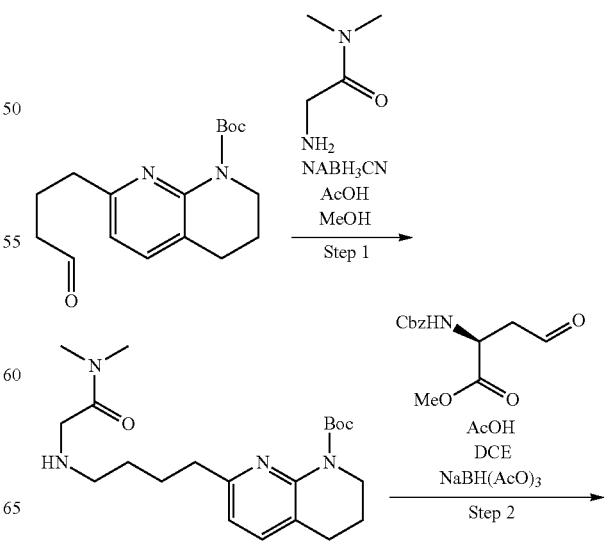

-continued

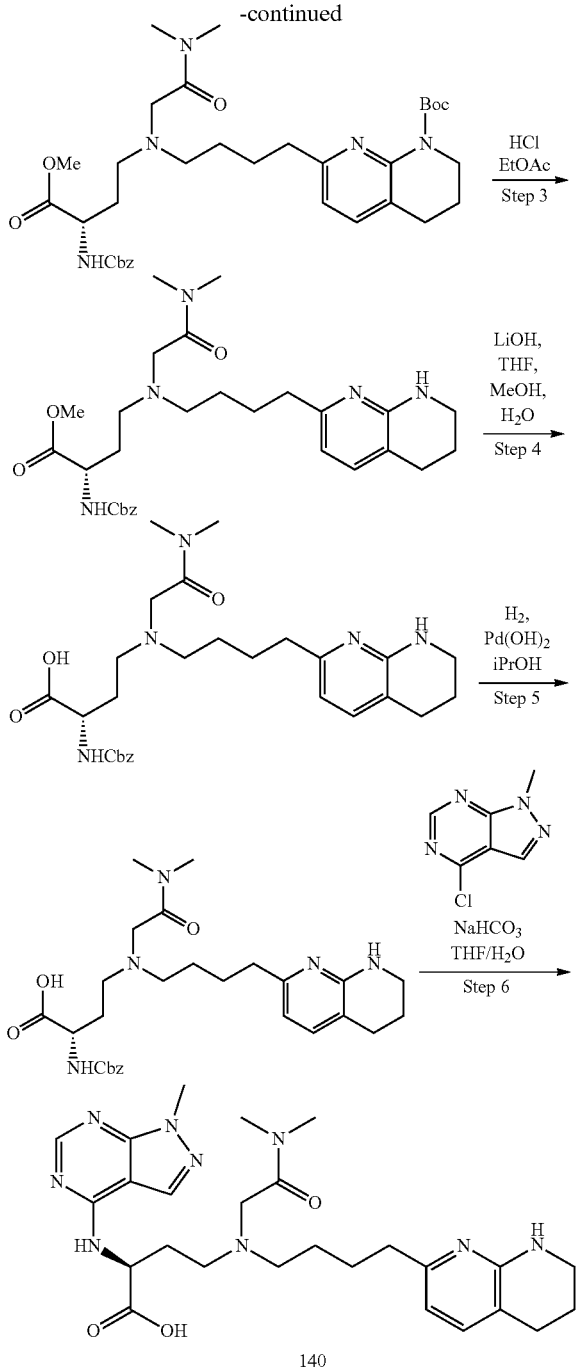

140

Step 1: tert-butyl 7-(4-((2-(dimethylamino)-2-oxo-ethyl)amino) butyl)-3,4-dihydro-1,8-naphthyridine-1(2H)-carboxylate To a mixture of 2-amino-N,N-dimethylacetamide (2.01 g, 19.71 mmol) in MeOH (10 mL) at 0° C. was added NaBH₃CN (1.24 g, 19.71 mmol), AcOH (1.13 mL, 19.71 mmol), then tert-butyl 7-(4-oxobutyl)-3,4-dihydro-1,8-naphthyridine-1(2H)-carboxylate (3 g, 9.86 mmol) and the resulting mixture was stirred at rt for 3 h. The reaction mixture was then poured into sat. aq. NaHCO₃ and then concentrated in vacuo to remove volatiles. The remaining aqueous layer was extracted with EtOAc and the combined organic extracts were dried over Na₂SO₄, filtered, and concentrated in vacuo. The crude residue was purified by normal phase silica gel chromatography to give the title compound. LCMS (ESI+): m/z=391.0 (M+H)⁺.

Step 2: (S)-tert-butyl 7-(4-((3-(((benzyloxy)carbonyl)amino)-4-methoxy-4-oxobutyl) (2-(dimethylamino)-2-oxoethyl)amino) butyl)-3,4-dihydro-1,8-naphthyridine-1(2H)-carboxylate To a mixture of tert-butyl 7-(4-((2-(dimethylamino)-2-oxoethyl)amino)butyl)-3,4-dihydro-1,8-naphthyridine-1 (2H)-carboxylate (1.68 g, 4.10 mmol) and (S)-methyl 2-(((benzyloxy)carbonyl)amino)-4-oxobutanoate (1.14 g, 4.30 mmol) in DCE (15 mL) at 0° C. was added AcOH (352 μL, 6.15 mmol) then NaBH(OAc)₃ (1.30 g, 6.15 mmol) and the resulting mixture was stirred at rt for 1 h. The reaction mixture was then poured into sat. aq. NaHCO₃ and the layers were separated. The aqueous layer was extracted with DCM and the combined organic extracts were dried over Na₂SO₄, filtered, and concentrated in vacuo. The crude residue was purified by normal phase silica gel chromatography to give the title compound. LCMS (ESI+): m/z=640.5 (M+H)⁺.

Step 3: (S)-methyl 2-(((benzyloxy)carbonyl)amino)-4-((2-(dimethylamino)-2-oxoethyl) (4-(5,6,7,8-tetrahydro-1,8-naphthyridin-2-yl) butyl)amino) butanoate (S)-tert-butyl 7-(4-((3-(((benzyloxy)carbonyl)amino)-4-methoxy-4-oxobutyl) (2-(dimethylamino)-2-oxoethyl) amino)butyl)-3,4-dihydro-1,8-naphthyridine-1(2H)-carboxylate (2.5 g, 3.91 mmol) was taken up in 4 M HCl in EtOAc (40 mL) and the resulting solution was stirred at rt for 15 h and then concentrated in vacuo to give the title compound that was used without further purification. LCMS (ESI+): m/z=540.4 (M+H)⁺.

Step 4: (S)-2-(((benzyloxy)carbonyl)amino)-4-((2-(dimethylamino)-2-oxoethyl) (4-(5,6,7,8-tetrahydro-1,8-naphthyridin-2-yl) butyl)amino) butanoic acid To a mixture of (S)-methyl 2-(((benzyloxy)carbonyl) amino)-4-((2-(dimethylamino)-2-oxoethyl) (4-(5,6,7,8-tetrahydro-1,8-naphthyridin-2-yl) butyl)amino) butanoate (2.11 g, 3.91 mmol) in 2:2:1 THF/MeOH/H₂O (37.5 mL) was added LiOH.H₂O (328 mg, 7.82 mmol) and the resulting mixture was stirred at rt for 1 h. The reaction mixture was adjusted to pH=6 by the addition of 1 M aq. HCl and concentrated in vacuo to give the title compound that was used without further purification. LCMS (ESI+): m/z=526.2 (M+H)⁺.

Step 5: (S)-2-amino-4-((2-(dimethylamino)-2-oxoethyl) (4-(5,6,7,8-tetrahydro-1,8-naphthyridin-2-yl) butyl)amino) butanoic acid To a mixture of (S)-2-(((benzyloxy)carbonyl)amino)-4-((2-(dimethylamino)-2-oxoethyl) (4-(5,6,7,8-tetrahydro-1,8-naphthyridin-2-yl) butyl)amino) butanoic acid (2.06 g, 3.82 mmol) in i-PrOH (50 mL) was added 20 wt % Pd(OH)₂/C (700 mg) and the resulting mixture was stirred under an H₂ atmosphere overnight and then the reaction mixture was filtered and concentrated in vacuo to give the title compound that was used without further purification. LCMS (ESI+): m/z=392.4 (M+H)⁺.

Step 6: (S)-4-((2-(dimethylamino)-2-oxoethyl) (4-(5,6,7,8-tetrahydro-1,8-naphthyridin-2-yl) butyl) amino)-2-((1-methyl-1H-pyrazolo[3,4-d]pyrimidin-4-yl) amino) butanoic acid To a mixture of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 μmol) and 4-chloro-1-methyl-1H-pyrazolo[3,4-d]pyrimidine (71 mg, 421 μmol) in THF (2 mL) and H$_2$O (0.5 mL) was added NaHCO$_3$ (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=524.5 (M+H)$^+$. $^1$H NMR (400 MHz, Methanol-d$_4$) δ ppm 8.27 (br d, J=22 Hz, 2H) 7.29 (br d, J=6.97 Hz, 1H) 6.41 (d, J=7.21 Hz, 1H) 4.47-4.78 (m, 1H) 3.93 (s, 3H) 3.58-3.69 (m, 1H) 3.50 (br d, J=15.04 Hz, 1H) 3.32-3.41 (m, 2H) 3.02 (s, 3H) 2.52-2.97 (m, 11H) 2.13-2.32 (m, 2H) 1.47-1.98 (m, 6H).

Compound 141: (S)-4-((2-(dimethylamino)-2-oxoethyl) (4-(5,6,7,8-tetrahydro-1,8-naphthyridin-2-yl) butyl)amino)-2-((5-(trifluoromethyl)pyrimidin-2-yl) amino) butanoic acid: To a mixture of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 μmol) and 2-chloro-5-(trifluoromethyl)pyrimidine (70 mg, 383 μmol) in THF (2 mL) and H$_2$O (0.5 mL) was added NaHCO$_3$ (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=538.2 (M+H)$^+$. $^1$H NMR (400 MHz, ethanol-d$_4$) δ ppm 8.52 (br s, 2H) 7.28 (d, J=7.46 Hz, 1H) 6.45 (d, J=7.34 Hz, 1H) 4.49 (t, J=5.87 Hz, 1H) 3.55-3.73 (m, 2H) 3.36-3.45 (m, 2H) 3.06 (s, 3H) 2.85-3.00 (m, 5H) 2.69-2.83 (m, 4H) 2.52-2.67 (m, 2H) 2.23 (dq, J=13.68, 6.77 Hz, 1H) 2.04-2.13 (m, 1H) 1.90 (q, J=5.93 Hz, 2H) 1.69-1.81 (m, 2H) 1.59-1.66 (m, 2H).

Compound 142: (S)-4-((2,2-difluoroethyl) (4-(5,6,7,8-tetrahydro-1,8-naphthyridin-2-yl) butyl)amino)-2-((6-phenylpyrimidin-4-yl) amino) butanoic acid: To a mixture of (2S)-2-amino-4-[2,2-difluoroethyl-[4-(5,6,7,8-tetrahydro-1,8-naphthyridin-2-yl) butyl]amino]butanoic acid (200 mg, 486 μmol) and 4-chloro-6-phenyl-pyrimidine (111 mg, 583 μmol) in THF (2 mL) H$_2$O (0.5 mL) was added NaHCO$_3$ (204 mg, 2.43 mmol) and the resulting mixture was stirred at 70° C. for 1 h and then concentrated in vacuo. The crude residue was purified by reverse phase prep-HPLC to give the title compound. LCMS (ESI+): m/z=525.2 (M+H)$^+$. $^1$H NMR (400 MHz, Methanol-d$_4$) δ ppm 8.41 (br s, 1H) 7.81 (br s, 2H) 7.41-7.50 (m, 3H) 7.38 (br d, J=6.62 Hz, 1H) 6.78 (s, 1H) 6.53 (d, J=7.28 Hz, 1H) 5.76-6.12 (m, 1H) 4.66 (br s, 1H) 3.33-3.47 (m, 2H) 2.78-2.88 (m, 3H) 2.56-2.78 (m, 7H) 2.13-2.25 (m, 1H) 2.09 (br s, 1H) 1.75-1.96 (m, 4H) 1.64 (q, J=6.39 Hz, 2H).

Compound 143: (S)-2-((1H-pyrazolo[3,4-d]pyrimidin-4-yl) amino)-4-((2-(4-fluorophenoxy)ethyl) (4-(5,6,7,8-tetrahydro-1,8-naphthyridin-2-yl) butyl)amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid (120 mg, 270 μmol) and 4-chloro-1H-pyrazolo[3,4-d]pyrimidine (50 mg, 324 μmol) in THF (1.2 mL) and H$_2$O (0.3 mL) was added NaHCO$_3$ (113 mg, 1.35 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=563.3 (M+H)$^+$. $^1$H NMR (400 MHz, Methanol-d$_4$) δ ppm 8.15 (s, 1H) 8.03 (s, 1H) 7.27 (br d, J=7.28 Hz, 1H) 6.79-6.91 (m, 1H) 6.73 (br s, 2H) 6.43 (br d, J=7.28 Hz, 1H) 6.38-6.47 (m, 1H) 4.11 (br s, 2H) 3.36 (br s, 2H) 3.27 (br s, 2H) 2.92-3.14 (m, 3H) 2.92-3.14 (m, 1H) 2.87 (br s, 1H) 2.63-2.76 (m, 2H) 2.54-2.76 (m, 1H) 2.54-2.76 (m, 1H) 2.37 (br d, J=5.73 Hz, 1H) 2.06-2.23 (m, 1H) 1.69-1.92 (m, 6H) 1.63-1.88 (m, 1H).

Compound 144: (S)-2-((5-bromopyrimidin-2-yl) amino)-4-((2-(4-fluorophenoxy)ethyl) (4-(5,6,7,8-tetrahydro-1,8-naphthyridin-2-yl) butyl)amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid (120 mg, 270 μmol) and 5-bromo-2-chloro-pyrimidine (63 mg, 324 μmol) in THF (1.2 mL) and H$_2$O (0.3 mL) was added NaHCO$_3$ (113 mg, 1.35 mmol) and the resulting mixture was stirred at 70° C. for 1 h and then concentrated in vacuo. The crude residue was purified by reverse phase prep-HPLC to give the title compound. LCMS (ESI+): m/z=601.2 (M+H)$^+$. $^1$H NMR (400 MHz, Methanol-d$_4$) δ ppm 8.17 (s, 2H) 7.30 (d, J=7.50 Hz, 1H) 6.89-6.97 (m, 2H) 6.79-6.87 (m, 2H) 6.47 (d, J=7.28 Hz, 1H) 4.32 (t, J=6.06 Hz, 1H) 4.14 (t, J=5.18 Hz, 2H) 3.32-3.42 (m, 2H) 3.00-3.25 (m, 4H) 2.82-2.98 (m, 1H) 2.91 (br s, 1H) 2.58-2.75 (m, 4H) 2.16-2.29 (m, 1H) 2.00-2.15 (m, 1H) 1.63-1.96 (m, 1H) 1.63-1.96 (m, 5H).

Compound 145: (S)-4-((2-(dimethylamino)-2-oxoethyl) (4-(5,6,7,8-tetrahydro-1,8-naphthyridin-2-yl) butyl)amino)-2-((2-(trifluoromethyl)pyrimidin-4-yl) amino) butanoic acid: To a solution of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 μmol) and 4-chloro-2-(trifluoromethyl)pyrimidine (84 mg, 460 μmol) in THF (2 mL) and H$_2$O (0.5 mL) was added NaHCO$_3$ (161 mg, 1.92 mmol) and the resulting mixture was stirred at 70° C. for 1 h and then concentrated in vacuo. The crude residue was purified by reverse phase prep-HPLC to give the title compound. LCMS (ESI+): m/z=538.2 (M+H)$^+$. $^1$H NMR (400 MHz, ethanol-d$_4$) δ ppm 8.02 (br d, J=5.29 Hz, 1H) 7.37 (br d, J=7.28 Hz, 1H) 6.74 (br d, J=5.73 Hz, 1H) 6.48 (d, J=7.28 Hz, 1H) 4.66-4.76 (m, 1H) 3.67 (br d, J=15.88 Hz, 1H) 3.47 (br d, J=15.21 Hz, 1H) 3.32-3.39 (m, 2H) 2.93-3.05 (m, 4H) 2.87 (s, 3H) 2.67-2.83 (m, 6H) 2.56-2.67 (m, 1H) 2.03-2.27 (m, 1H) 1.82-1.93 (m, 3H) 1.50-1.82 (m, 2H) 1.58 (br s, 1H).

Compound 146: (S)-2-((5-cyclopropylpyrimidin-2-yl) amino)-4-((2,2-difluoroethyl) (4-(5,6,7,8-tetrahydro-1,8-naphthyridin-2-yl) butyl)amino) butanoic acid: To a mixture of (S)-2-amino-4-((2,2-difluoroethyl) (4-(5,6,7,8-tetrahydro-1,8-naphthyridin-2-yl) butyl)amino) butanoic acid (200 mg, 486 μmol) and 5-cyclopropyl-2-fluoropyrimidine (81 mg, 583 μmol) in THF (1.6 mL) and H$_2$O (0.4 mL) were added NaHCO$_3$ (204 mg, 2.43 mmol) and the resulting mixture was stirred at 70° C. for 1 h and then concentrated in vacuo. The crude residue was purified by reverse phase prep-HPLC to give the title compound. LCMS (ESI+): m/z=489.2 (M+H)$^+$. $^1$H NMR (400 MHz, Methanol-d$_4$) δ ppm 8.02 (s, 2H) 7.47 (d, J=7.50 Hz, 1H) 6.54 (d, J=7.28 Hz, 1H) 5.72-6.07 (m, 1H) 4.44 (t, J=5.84 Hz, 1H) 3.35-3.44 (m, 2H) 2.63-2.85 (m, 9H) 2.51-2.62 (m, 1H) 1.98-2.18 (m, 2H) 1.81-1.93 (m, 4H) 1.69-1.79 (m, 1H) 1.58 (q, J=6.62 Hz, 2H) 0.86-0.97 (m, 2H) 0.53-0.67 (m, 2H).

Compound 147: (S)-4-(((3-fluorooxetan-3-yl) methyl) (4-(5,6,7,8-tetrahydro-1,8-naphthyridin-2-yl) butyl)amino)-2-(quinazolin-4-ylamino) butanoic acid. Prepared according to Scheme B using Procedure F with (3-fluorooxetan-3-yl)

methanamine, Procedure H with 4-chloroquinazoline, and Procedure P. LCMS theoretical m/z=523.3; [M+H]+ found 523.3.

Compound 148: (S)-4-(cyclopropyl(4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 149: (S)-2-((5-cyanopyrimidin-2-yl) amino)-4-(cyclopropyl(4-(5,6,7,8-tetrahydro-1,8-naphthyridin-2-yl) butyl)amino) butanoic acid: To a mixture of (S)-2-amino-4-(cyclopropyl(4-(5,6,7,8-tetrahydro-1,8-naphthyridin-2-yl) butyl)amino) butanoic acid trifluoroacetate (100 mg, 217 μmol) in 4:1 THF/H$_2$O (2 mL) was added 2-chloropyrimidine-5-carbonitrile (33 mg, 239 μmol) and NaHCO$_3$ (55 mg, 651 μmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=450.2 (M+H)+. $^1$H NMR (400 MHz, Methanol-d$_4$): δ ppm 8.58 (br s, 1H) 8.47 (br s, 1H) 7.36 (d, J=7.34 Hz, 1H) 6.50 (d, J=7.34 Hz, 1H) 4.42 (t, J=6.05 Hz, 1H) 3.35-3.45 (m, 2H) 2.93-3.12 (m, 2H) 2.80-2.92 (m, 2H) 2.74 (t, J=6.24 Hz, 2H) 2.64 (br dd, J=7.83, 5.75 Hz, 2H) 2.21-2.32 (m, 1H) 2.00-2.18 (m, 2H) 1.84-1.93 (m, 2H) 1.66-1.82 (m, 4H) 0.56-0.70 (m, 4H).

Compound 150: 4-(cyclopropyl(4-(5,6,7,8-tetrahydro-1,8-naphthyridin-2-yl) butyl)amino)-2-((5-(trifluoromethyl) pyrimidin-2-yl) amino) butanoic acid.

Compound 151: (S)-2-((1H-pyrazolo[3,4-d]pyrimidin-4-yl) amino)-4-(cyclopropyl(4-(5,6,7,8-tetrahydro-1,8-naphthyridin-2-yl) butyl)amino) butanoic acid.

Compound 152: (S)-2-((5-bromopyrimidin-2-yl) amino)-4-(cyclopropyl(4-(5,6,7,8-tetrahydro-1,8-naphthyridin-2-yl) butyl)amino) butanoic acid: To a mixture of 5-bromo-2-fluoro-pyrimidine (42 mg, 239 μmol) in 4:1 THF/H$_2$O (2 mL) was added (S)-2-amino-4-(cyclopropyl(4-(5,6,7,8-tetrahydro-1,8-naphthyridin-2-yl) butyl)amino) butanoic acid trifluoroacetate (100 mg, 217 μmol) and NaHCO$_3$ (55 mg, 651 μmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=503.1 (M+H)+. $^1$H NMR (400 MHz, D$_2$O): δ ppm 8.39 (s, 2H) 7.49 (d, J=7.34 Hz, 1H) 6.52 (br d, J=6.24 Hz, 1H) 4.52 (dd, J=8.93, 4.89 Hz, 1H) 3.23-3.53 (m, 6H) 2.58-2.90 (m, 5H) 2.40-2.54 (m, 1H) 2.23-2.39 (m, 1H) 1.57-1.96 (m, 6H) 0.84-1.05 (m, 4H).

Compound 153: 2-((7H-pyrrolo[2,3-d]pyrimidin-4-yl) amino)-4-(cyclopropyl(4-(5,6,7,8-tetrahydro-1,8-naphthyridin-2-yl) butyl)amino) butanoic acid.

Compound 154: (S)-2-((6-(1H-pyrazol-1-yl) pyrimidin-4-yl) amino)-4-(cyclopropyl(4-(5,6,7,8-tetrahydro-1,8-naphthyridin-2-yl) butyl)amino) butanoic acid: (S)-2-amino-4-(cyclopropyl(4-(5,6,7,8-tetrahydro-1,8-naphthyridin-2-yl) butyl)amino) butanoic acid trifluoroacetate (100 mg, 217 μmol) was taken up in DMA (2 mL) and to this was added DIPEA (189 μL, 1.09 mmol) and 4-chloro-6-(1H-pyrazol-1-yl) pyrimidine (43 mg, 239 μmol) and the resulting mixture was stirred at 70° C. for 17 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=491.3 (M+H)+. $^1$H NMR (400 MHz, D$_2$O): δ ppm 8.34 (br s, 2H) 7.81 (s, 1H) 7.35 (br s, 1H) 6.90 (s, 1H) 6.56 (br s, 1H) 6.39 (br s, 1H) 4.53-4.68 (m, 1H) 3.14-3.57 (m, 6H) 2.20-2.85 (m, 7H) 1.47-1.94 (m, 6H) 0.79-1.02 (m, 4H).

Compound 155: (S)-4-(cyclopropyl(4-(5,6,7,8-tetrahydro-1,8-naphthyridin-2-yl) butyl)amino)-2-((2-(trifluoromethyl)pyrimidin-4-yl) amino) butanoic acid.

Compound 156: (S)-4-(cyclopropyl(4-(5,6,7,8-tetrahydro-1,8-naphthyridin-2-yl) butyl)amino)-2-((5-cyclopropylpyrimidin-2-yl) amino) butanoic acid: To a mixture of (S)-2-amino-4-(cyclopropyl(4-(5,6,7,8-tetrahydro-1,8-naphthyridin-2-yl) butyl)amino) butanoic acid trifluoroacetate (100 mg, 217 μmol) in 4:1 THF/H$_2$O (2 mL) was added 5-cyclopropyl-2-fluoro-pyrimidine (33 mg, 239 μmol) and NaHCO$_3$ (55 mg, 651 μmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=465.3 (M+H)+. $^1$H NMR (400 MHz, D$_2$O): δ ppm 8.36 (br s, 2H) 7.50 (d, J=7.34 Hz, 1H) 6.54 (d, J=7.34 Hz, 1H) 4.63 (br t, J=6.66 Hz, 1H) 3.26-3.51 (m, 6H) 2.64-2.86 (m, 5H) 2.48 (br s, 1H) 2.33 (br s, 1H) 1.63-1.96 (m, 7H) 0.88-1.07 (m, 6H) 0.62-0.75 (m, 2H).

Compound 157: 4-(cyclopropyl(4-(5,6,7,8-tetrahydro-1,8-naphthyridin-2-yl) butyl)amino)-2-(pyrimidin-2-ylamino) butanoic acid.

Compound 158: (S)-4-(cyclopropyl(4-(5,6,7,8-tetrahydro-1,8-naphthyridin-2-yl) butyl)amino)-2-((6-phenylpyrimidin-4-yl) amino) butanoic acid: (S)-2-amino-4-(cyclopropyl(4-(5,6,7,8-tetrahydro-1,8-naphthyridin-2-yl) butyl) amino) butanoic acid trifluoroacetate (100 mg, 217 μmol) was taken up in 4:1 THF/H$_2$O (2 mL) and to this was added 4-chloro-6-phenylpyrimidine (46 mg, 239 μmol) and NaHCO$_3$ (55 mg, 651 μmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=501.3 (M+H)+. $^1$H NMR (400 MHz, DMSO-d$_6$): δ ppm 8.70 (s, 1H) 7.76 (br d, J=7.50 Hz, 2H) 7.57-7.71 (m, 3H) 7.48 (br d, J=7.28 Hz, 1H) 7.12 (s, 1H) 6.53 (br d, J=7.28 Hz, 1H) 4.90 (br s, 1H) 3.25-3.57 (m, 6H) 2.26-2.87 (m, 7H) 1.63-1.98 (m, 6H) 0.99 (br s, 4H).

Compound 159: (S)-4-(cyclopropyl(4-(5,6,7,8-tetrahydro-1,8-naphthyridin-2-yl) butyl)amino)-2-((5-phenylpyrimidin-4-yl) amino) butanoic acid: To a mixture of (S)-2-((5-bromopyrimidin-4-yl) amino)-4-(cyclopropyl(4-(5,6,7,8-tetrahydro-1,8-naphthyridin-2-yl) butyl)amino) butanoic acid (163, 324.41 μmol) in 3:1 dioxane/H$_2$O (3 mL) was added K$_2$CO$_3$ (90 mg, 649 μmol), phenylboronic acid (99 mg, 811 μmol), then Pd(dppf)Cl$_2$ (24 mg, 32 μmol) and the resulting mixture was heated to 100° C. for 2 h and then cooled to rt and concentrated in vacuo. The crude residue was purified by prep-HPLC to give the title compound. LCMS (ESI+): m/z=501.3 (M+H)+. $^1$H NMR (400 MHz, Methanol-d$_4$): δ ppm 8.85 (s, 1H) 8.22 (s, 1H) 7.55-7.71 (m, 6H) 6.66 (d, J=7.21 Hz, 1H) 5.13 (br s, 1H) 3.46-3.60 (m, 3H) 3.33-3.45 (m, 3H) 2.74-3.04 (m, 5H) 2.66 (br s, 1H) 2.48 (br s, 1H) 1.70-2.06 (m, 6H) 0.92-1.23 (m, 4H).

Compound 160: (S)-2-((1H-pyrazolo[4,3-d]pyrimidin-7-yl) amino)-4-(cyclopropyl(4-(5,6,7,8-tetrahydro-1,8-naphthyridin-2-yl) butyl)amino) butanoic acid.

Compound 161: (S)-4-(cyclopropyl(4-(5,6,7,8-tetrahydro-1,8-naphthyridin-2-yl) butyl)amino)-2-((2-methoxypyrimidin-4-yl) amino) butanoic acid.

Compound 162: (S)-4-(cyclopropyl(4-(5,6,7,8-tetrahydro-1,8-naphthyridin-2-yl) butyl)amino)-2-((2-(pyridin-3-yl) quinazolin-4-yl) amino) butanoic acid: To a solution of (2S)-2-amino-4-[cyclopropyl-[4-(5,6,7,8-tetrahydro-1,8-naphthyridin-2-yl) butyl]amino]butanoic acid trifluoroacetate (100 mg, 217 μmol) in DMA (2 mL) was added DIPEA (189 μL, 1.09 mmol) then 4-chloro-2-(pyridin-3-yl) quinazoline (58 mg, 239 µmol) and the resulting mixture was stirred at 70° C. for 1 h and then allowed to cool to rt and then adjusted to pH=6 by the addition of 1 M aq. HCl and then concentrated in vacuo. The crude residue was purified by reverse phase prep-HPLC to give the title compound. LCMS (ESI+): m/z=552.2 (M+H)+. $^1$H NMR (400 MHz, Methanol-d$_4$): δ ppm 9.58 (br s, 1H) 8.84 (br d, J=7.70 Hz, 1H) 8.62 (br s, 1H) 8.00 (d, J=8.07 Hz, 1H) 7.81-7.87 (m, 1H) 7.73-7.80 (m, 1H) 7.54 (br s, 1H) 7.42-7.49 (m, 1H) 7.21 (d, J=7.21 Hz, 1H) 6.36 (br d, J=7.21 Hz, 1H) 4.93 (br s, 1H) 3.12-3.29 (m, 3H) 2.82-3.08 (m, 3H) 2.46-2.66 (m, 5H) 2.24-2.36 (m, 1H) 2.06 (br s, 1H) 1.75 (br dd, J=11.37, 5.50 Hz, 6H) 0.43-0.87 (m, 4H).

Compound 163: (S)-4-(cyclopropyl(4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-(cyclopropyl(4-(5,6,7,8-tetrahydro-1,8-naphthyridin-2-yl) butyl)amino) butanoic acid trifluoroacetate (100 mg, 217 µmol) in 4:1 THF/H$_2$O (2 mL) was added 7-chloro-2-methyl-2H-pyrazolo[4,3-d]pyrimidine (40 mg, 239 µmol) and NaHCO$_3$ (55 mg, 651 µmol) and the resulting mixture was heated to 70° C. for 1 h and then cooled to rt and concentrated in vacuo. The crude residue was purified by prep-HPLC to give the title compound. LCMS (ESI+): m/z=479.2 (M+H)+. $^1$H NMR (400 MHz, Methanol-d$_4$): δ ppm 8.59 (s, 1H) 8.49 (s, 1H) 7.59 (d, J=7.21 Hz, 1H) 6.67 (d, J=7.34 Hz, 1H) 5.07 (br dd, J=8.25, 5.20 Hz, 1H) 4.09 (s, 3H) 3.36-3.74 (m, 6H) 2.48-3.05 (m, 7H) 1.66-2.12 (m, 6H) 0.94-1.31 (m, 4H).

Compound 164: 4-((2,2-difluoroethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 165: 2-((5-cyanopyrimidin-2-yl) amino)-4-((2,2-difluoroethyl) (4-(5,6,7,8-tetrahydro-1,8-naphthyridin-2-yl) butyl)amino) butanoic acid.

Compound 166: 4-((2,2-difluoroethyl) (4-(5,6,7,8-tetrahydro-1,8-naphthyridin-2-yl) butyl)amino)-2-((5-(trifluoromethyl)pyrimidin-2-yl) amino) butanoic acid.

Compound 167: 2-((1H-pyrazolo[3,4-d]pyrimidin-4-yl) amino)-4-((2,2-difluoroethyl) (4-(5,6,7,8-tetrahydro-1,8-naphthyridin-2-yl) butyl)amino) butanoic acid.

Compound 168: 2-((5-bromopyrimidin-2-yl) amino)-4-((2,2-difluoroethyl) (4-(5,6,7,8-tetrahydro-1,8-naphthyridin-2-yl) butyl)amino) butanoic acid.

Compound 169: 2-((6-(1H-pyrazol-1-yl) pyrimidin-4-yl) amino)-4-((2,2-difluoroethyl) (4-(5,6,7,8-tetrahydro-1,8-naphthyridin-2-yl) butyl)amino) butanoic acid.

Compound 170: 4-((2,2-difluoroethyl) (4-(5,6,7,8-tetrahydro-1,8-naphthyridin-2-yl) butyl)amino)-2-((2-(trifluoromethyl)pyrimidin-4-yl) amino) butanoic acid.

Compound 171: 2-((5-cyclopropylpyrimidin-2-yl) amino)-4-((2,2-difluoroethyl) (4-(5,6,7,8-tetrahydro-1,8-naphthyridin-2-yl) butyl)amino) butanoic acid.

Compound 172: (S)-4-((2,2-difluoroethyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-((2,2-difluoroethyl) (4-(5,6,7,8-tetrahydro-1,8-naphthyridin-2-yl) butyl)amino) butanoic acid (150 mg, 405 µmol) and 7-chloro-2-methyl-2H-pyrazolo[4,3-d]pyrimidine (75 mg, 445 µmol) in THF (2 mL) and H$_2$O (0.5 mL) were added NaHCO$_3$ (170 mg, 2.02 mmol) and the resulting mixture was heated to 70° C. for 1 h and then cooled to rt and concentrated in vacuo. The crude residue was purified by prep-HPLC to give the title compound. LCMS (ESI+): m/z=503.2. $^1$H NMR (400 MHz, Methanol-d$_4$) δ ppm 8.38-8.68 (m, 2H) 7.59 (d, J=7.45 Hz, 1H) 6.24-6.72 (m, 2H) 5.02-5.17 (m, 1H) 4.08 (s, 3H) 3.84 (br s, 2H) 3.56-3.73 (m, 2H) 3.49-3.53 (m, 2H) 3.38-3.47 (m, 2H) 2.78-2.87 (m, 4H) 2.48-2.74 (m, 2H) 1.75-2.01 (m, 6H).

Compound 173: 4-((2,2-difluoroethyl) (4-(5,6,7,8-tetrahydro-1,8-naphthyridin-2-yl) butyl)amino)-2-((2-(pyridin-3-yl) quinazolin-4-yl) amino) butanoic acid.

Compound 174: 4-((2,2-difluoroethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid.

Compound 175: 4-((2,2-difluoroethyl) (4-(5,6,7,8-tetrahydro-1,8-naphthyridin-2-yl) butyl)amino)-2-((5-phenylpyrimidin-4-yl) amino) butanoic acid.

Compound 176: 4-((2,2-difluoroethyl) (4-(5,6,7,8-tetrahydro-1,8-naphthyridin-2-yl) butyl)amino)-2-((6-phenylpyrimidin-4-yl) amino) butanoic acid.

Compound 177: 4-((2,2-difluoroethyl) (4-(5,6,7,8-tetrahydro-1,8-naphthyridin-2-yl) butyl)amino)-2-((2-phenylpyrimidin-4-yl) amino) butanoic acid.

Compound 178: (S)-2-((3-cyanopyrazin-2-yl) amino)-4-((2,2-difluoroethyl) (4-(5,6,7,8-tetrahydro-1,8-naphthyridin-2-yl) butyl)amino) butanoic acid: To a mixture of (S)-2-amino-4-((2,2-difluoroethyl) (4-(5,6,7,8-tetrahydro-1,8-naphthyridin-2-yl) butyl)amino) butanoic acid (200 mg, 540 µmol) and 3-chloropyrazine-2-carbonitrile (83 mg, 594 µmol) in i-PrOH (4 mL) was added DIPEA (470 µL, 2.70 mmol) and the resulting mixture was stirred at 70° C. for 12 h and then allowed to cool to rt and then concentrated in vacuo. The crude residue was purified by reverse phase prep-HPLC to give the title compound. LCMS (ESI+): m/z=474.2 (M+H)+. $^1$H NMR (400 MHz, Methanol-d$_4$) δ ppm 8.22 (d, J=2.20 Hz, 1H) 7.84 (d, J=2.21 Hz, 1H) 7.49 (d, J=7.28 Hz, 1H) 6.55 (d, J=7.28 Hz, 1H) 5.78-6.18 (m, 1H) 4.62 (t, J=5.07 Hz, 1H) 3.34-3.47 (m, 2H) 2.54-2.92 (m, 1H) 2.54-2.92 (m, 9H) 2.10-2.27 (m, 2H) 1.85-1.96 (m, 3H) 1.79 (td, J=14.72, 6.50 Hz, 1H) 1.46-1.68 (m, 2H).

Compound 179: 4-((2,2-difluoroethyl) (4-(5,6,7,8-tetrahydro-1,8-naphthyridin-2-yl) butyl)amino)-2-(pyrimidin-4-ylamino) butanoic acid.

Compound 180: 4-((2,2-difluoroethyl) (4-(5,6,7,8-tetrahydro-1,8-naphthyridin-2-yl) butyl)amino)-2-((5-fluoropyrimidin-2-yl) amino) butanoic acid.

Compound 181: (S)-4-((3,3-difluorocyclobutyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 µmol) in THF (4 mL) and H$_2$O (1 mL) was added 4-chloro-1-methyl-H-pyrazolo[3,4-d]pyrimidine (42 mg, 247 µmol) and NaHCO$_3$ (104 mg, 1.24 mmol) and the resulting mixture was heated to 70° C. for 1 h, cooled to rt, and then concentrated in vacuo. The crude residue was purified by prep-HPLC to give the title compound. LCMS (ESI+): m/z=529.3 (M+H)+. $^1$H NMR (400 MHz, DMSO-d$_6$) δ ppm 8.41 (d, J=7.70 Hz, 1H) 8.22 (d, J=19.93 Hz, 2H) 7.01 (d, J=7.21 Hz, 1H) 6.48 (br s, 1H) 6.20 (d, J=7.21 Hz, 1H) 4.71-4.83 (m, 1H) 3.90 (s, 3H) 3.18-3.27 (m, 2H) 2.96-3.07 (m, 1H) 2.55-2.67 (m, 5H) 2.13-2.44 (m, 7H) 1.81-2.07 (m, 2H) 1.74 (q, J=5.81 Hz, 2H) 1.51 (q, J=7.34 Hz, 2H) 1.28-1.42 (m, 2H). Note: (S)-2-amino-4-((3,3-difluorocyclobutyl) (4-(5,6,7,8-tetrahydro-1,8-naphthyridin-2-yl) butyl)amino) butanoic acid was prepared in an analogous manner to Compound 140.

Compound 182: (S)-2-((5-cyanopyrimidin-2-yl) amino)-4-((3,3-difluorocyclobutyl) (4-(5,6,7,8-tetrahydro-1,8-naphthyridin-2-yl) butyl)amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (400 mg, 706 μmol) and 2-chloropyrimidine-5-carbonitrile (99 mg, 706 μmol) in THF (4 mL) and H₂O (1 mL) was added NaHCO₃ (59 mg, 706 μmol) and the resulting mixture was heated to 50° C. for 1 h, cooled to rt, and then concentrated in vacuo. The crude residue was purified by prep-HPLC to give the title compound. LCMS (ESI+): m/z=500.2 (M+H)⁺. ¹H NMR (400 MHz, DMSO-d₆) δ ppm 8.65-8.78 (m, 2H) 8.52 (br d, J=7.46 Hz, 1H) 7.04 (d, J=7.34 Hz, 1H) 6.48 (br s, 1H) 6.23 (d, J=7.21 Hz, 1H) 4.39-4.48 (m, 1H) 3.24 (br s, 2H) 3.01 (br d, J=7.09 Hz, 1H) 2.54-2.69 (m, 5H) 2.14-2.44 (m, 7H) 1.90-2.00 (m, 1H) 1.83 (br d, J=7.34 Hz, 1H) 1.75 (q, J=5.84 Hz, 2H) 1.51 (q, J=7.37 Hz, 2H) 1.34 (br d, J=4.40 Hz, 2H).

Compound 183: (S)-4-((3,3-difluorocyclobutyl) (4-(5,6,7,8-tetrahydro-1,8-naphthyridin-2-yl) butyl)amino)-2-((5-(trifluoromethyl)pyrimidin-2-yl) amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 μmol) in THF (4 mL) and H₂O (1 mL) was added 2-chloro-5-(trifluoromethyl)pyrimidine (50 mg, 272 μmol) and NaHCO₃ (104 mg, 1.24 mmol) and the resulting mixture was heated to 70° C. for 1 h, cooled to rt, and then concentrated in vacuo. The crude residue was purified by prep-HPLC to give the title compound. LCMS (ESI+): m/z=543.2 (M+H)⁺. ¹H NMR (400 MHz, Methanol-d₄) δ ppm 8.53 (br s, 2H) 7.48 (d, J=7.21 Hz, 1H) 6.55 (d, J=7.34 Hz, 1H) 4.52 (dd, J=6.60, 5.26 Hz, 1H) 3.38-3.53 (m, 2H) 3.07-3.21 (m, 1H) 2.41-2.80 (m, 12H) 2.00-2.23 (m, 2H) 1.87-1.98 (m, 2H) 1.70-1.85 (m, 2H) 1.58 (q, J=7.00 Hz, 2H).

Compound 184: (S)-2-((1H-pyrazolo[3,4-d]pyrimidin-4-yl) amino)-4-((3,3-difluorocyclobutyl) (4-(5,6,7,8-tetrahydro-1,8-naphthyridin-2-yl) butyl)amino) butanoic acid.

Compound 185: (S)-2-((5-bromopyrimidin-2-yl) amino)-4-((3,3-difluorocyclobutyl) (4-(5,6,7,8-tetrahydro-1,8-naphthyridin-2-yl) butyl)amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 μmol) in THF (4 mL) and H₂O (1 mL) was added 5-bromo-2-chloropyrimidine (53 mg, 272 μmol) and NaHCO₃ (104 mg, 1.24 mmol) and the resulting mixture was heated to 70° C. for 1 h, cooled to rt, and then concentrated in vacuo. The crude residue was purified by prep-HPLC to give the title compound. LCMS (ESI+): m/z=553.1 (M+H)⁺. ¹H NMR (400 MHz, DMSO-d₆) δ ppm 8.39 (s, 2H) 7.71 (d, J=7.70 Hz, 1H) 7.02 (d, J=7.21 Hz, 1H) 6.42 (br s, 1H) 6.22 (d, J=7.21 Hz, 1H) 4.27-4.37 (m, 1H) 3.23 (br t, J=5.32 Hz, 2H) 3.01 (br d, J=6.72 Hz, 1H) 2.53-2.70 (m, 5H) 2.14-2.47 (m, 7H) 1.67-1.98 (m, 4H) 1.51 (q, J=7.46 Hz, 2H) 1.26-1.41 (m, 2H).

Compound 186: (S)-2-((6-(1H-pyrazol-1-yl) pyrimidin-4-yl) amino)-4-((3,3-difluorocyclobutyl) (4-(5,6,7,8-tetrahydro-1,8-naphthyridin-2-yl) butyl)amino) butanoic acid:

To a mixture of (S)-2-amino-4-((3,3-difluorocyclobutyl) (4-(5,6,7,8-tetrahydro-1,8-naphthyridin-2-yl) butyl)amino) butanoic acid (200 mg, 353 μmol) in DMA (3 mL) was added 4-chloro-6-(1H-pyrazol-1-yl) pyrimidine (70 mg, 388 μmol) and DIPEA (308 μL, 1.77 mmol) and the resulting mixture was heated to 70° C. for 2 h, cooled to rt, and then concentrated in vacuo. The crude residue was purified by prep-HPLC to give the title compound. LCMS (ESI+): m/z=541.3 (M+H)⁺. ¹H NMR (400 MHz, Methanol-d₄) δ ppm 8.51 (d, J=2.32 Hz, 1H) 8.31 (s, 1H) 7.76 (d, J=1.22 Hz, 1H) 7.43 (d, J=7.34 Hz, 1H) 6.99 (br s, 1H) 6.49-6.57 (m, 2H) 4.64 (br s, 1H) 3.43 (br s, 2H) 3.06-3.20 (m, 1H) 2.57-2.82 (m, 10H) 2.47 (br s, 2H) 1.98-2.25 (m, 2H) 1.72-1.94 (m, 4H) 1.50-1.64 (m, 2H).

Compound 187: (S)-4-((3,3-difluorocyclobutyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 μmol) in THF (4 mL) and H₂O (1 mL) was added 4-chloro-2-(trifluoromethyl)pyrimidine (50 mg, 272 μmol) and NaHCO₃ (104 mg, 1.24 mmol) and the resulting mixture was heated to 70° C. for 1 h, cooled to rt, and then concentrated in vacuo. The crude residue was purified by prep-HPLC to give the title compound. LCMS (ESI+): m/z=543.2 (M+H)⁺. ¹H NMR (400 MHz, Methanol-d₄) δ ppm 8.11 (br d, J=6.24 Hz, 1H) 7.49 (d, J=7.34 Hz, 1H) 6.74 (br d, J=5.50 Hz, 1H) 6.56 (d, J=7.34 Hz, 1H) 4.70 (br s, 1H) 3.46 (br s, 2H) 3.06-3.19 (m, 1H) 2.55-2.84 (m, 10H) 2.41 (br s, 2H) 2.18 (br s, 1H) 1.65-2.05 (m, 5H) 1.47-1.62 (m, 2H).

Compound 188: (S)-2-((5-cyclopropylpyrimidin-2-yl) amino)-4-((3,3-difluorocyclobutyl) (4-(5,6,7,8-tetrahydro-1,8-naphthyridin-2-yl) butyl)amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 μmol) in THF (4 mL) and H₂O (1 mL) was added 1-cyclopropyl-4-fluorobenzene (38 mg, 272 μmol) and NaHCO₃ (104 mg, 1.24 mmol) and the resulting mixture was heated to 70° C. for 6 h, cooled to rt, and then concentrated in vacuo. The crude residue was purified by prep-HPLC to give the title compound. LCMS (ESI+): m/z=515.3 (M+H)⁺. ¹H NMR (400 MHz, Methanol-d₄) δ ppm 8.09 (s, 2H) 7.45 (d, J=7.46 Hz, 1H) 6.54 (d, J=7.34 Hz, 1H) 4.42 (t, J=5.75 Hz, 1H) 3.42-3.47 (m, 2H) 3.09-3.19 (m, 1H) 2.45-2.82 (m, 12H) 2.00-2.17 (m, 2H) 1.86-1.96 (m, 2H) 1.69-1.85 (m, 3H) 1.52-1.62 (m, 2H) 0.88-1.00 (m, 2H) 0.57-0.67 (m, 2H).

Compound 189: (S)-4-((3,3-difluorocyclobutyl) (4-(5,6,7,8-tetrahydro-1,8-naphthyridin-2-yl) butyl)amino)-2-((2-(pyridin-3-yl) quinazolin-4-yl) amino) butanoic acid.

Scheme 20, Compound 190

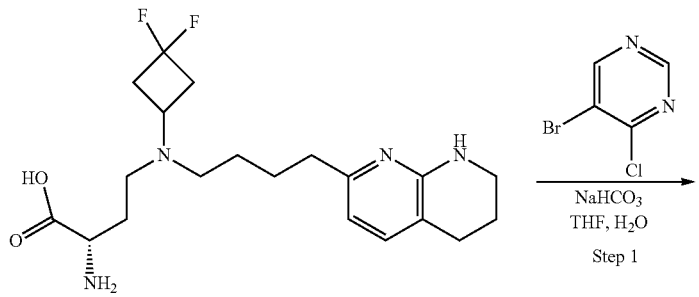

Step 1

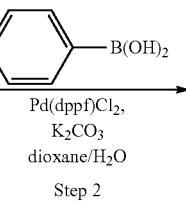
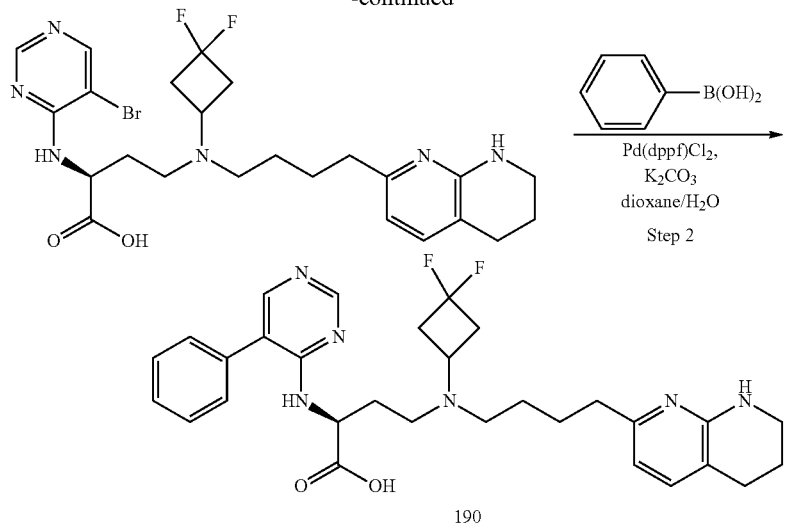

190

Step 1: (S)-2-((5-bromopyrimidin-4-yl) amino)-4-((3,3-difluorocyclobutyl) (4-(5,6,7,8-tetrahydro-1,8-naphthyridin-2-yl) butyl)amino) butanoic acid To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 µmol) in THF (4 mL) and H₂O (1 mL) was added 5-bromo-4-chloropyrimidine (53 mg, 272 µmol) and NaHCO₃ (104 mg, 1.24 mmol) and the resulting mixture was heated to 70° C. for 1 h, cooled to rt, and then concentrated in vacuo to give the title compound that was used without further purification. LCMS (ESI+): m/z=553.0 (M+H)⁺.

Step 2: (S)-4-((3,3-difluorocyclobutyl) (4-(5,6,7,8-tetrahydro-1,8-naphthyridin-2-yl) butyl)amino)-2-((5-phenylpyrimidin-4-yl) amino) butanoic acid To a mixture of (S)-2-((5-bromopyrimidin-4-yl) amino)-4-((3,3-difluorocyclobutyl) (4-(5,6,7,8-tetrahydro-1,8-naphthyridin-2-yl) butyl)amino) butanoic acid (136 mg, 246 µmol) in dioxane (4 mL) and H₂O (1 mL) was added phenylboronic acid (45 mg, 369 µmol), K₂CO₃ (68 mg, 491 µmol) and Pd(dppf)Cl₂ (18 mg, 25 µmol) and the resulting mixture was heated to 100° C. for 2 h, cooled to rt, and then concentrated in vacuo. The crude residue was purified by prep-HPLC to give the title compound. LCMS (ESI+): m/z=551.3 (M+H)⁺. ¹H NMR (400 MHz, Methanol-d₄) δ ppm 8.46 (s, 1H) 7.96 (s, 1H) 7.43-7.56 (m, 6H) 6.53 (d, J=7.34 Hz, 1H) 4.64 (br t, J=4.95 Hz, 1H) 3.39-3.48 (m, 2H) 3.02-3.13 (m, 1H) 2.47-2.81 (m, 10H) 2.06-2.43 (m, 4H) 1.92 (q, J=5.90 Hz, 2H) 1.64 (tq, J=14.24, 6.89 Hz, 2H) 1.45 (q, J=7.12 Hz, 2H).

Scheme 21, Compound 191

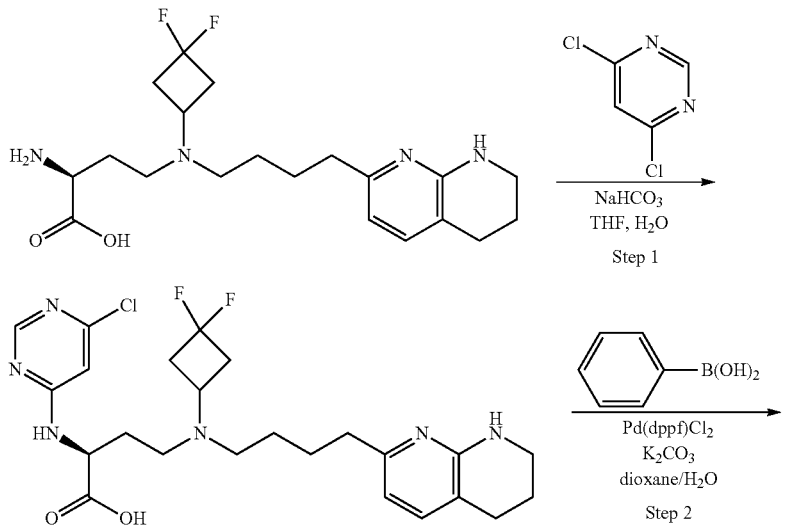

-continued

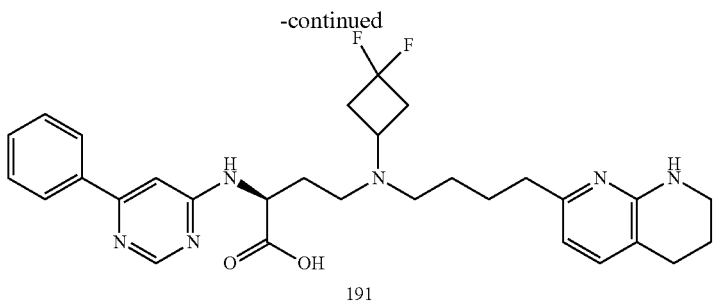

191

Step 1: (S)-2-((6-chloropyrimidin-4-yl) amino)-4-((3,3-difluorocyclobutyl) (4-(5,6,7,8-tetrahydro-1,8-naphthyridin-2-yl) butyl)amino) butanoic acid To a mixture of (S)-2-amino-4-((3,3-difluorocyclobutyl) (4-(5,6,7,8-tetrahydro-1,8-naphthyridin-2-yl) butyl)amino) butanoic acid (140 mg, 247 μmol) in THF (4 mL) and H₂O (1 mL) was added 4,6-dichloropyrimidine (41 mg, 272 μmol) and NaHCO₃ (104 mg, 1.24 mmol) and the resulting mixture was heated to 70° C. for 1 h, cooled to rt, and then concentrated in vacuo to give the title compound that was used without further purification. LCMS (ESI+): m/z=509.0 (M+H)⁺.

Step 2: (S)-4-((3,3-difluorocyclobutyl) (4-(5,6,7,8-tetrahydro-1,8-naphthyridin-2-yl) butyl)amino)-2-((6-phenylpyrimidin-4-yl) amino) butanoic acid To a mixture of (S)-2-((6-chloropyrimidin-4-yl) amino)-4-((3,3-difluorocyclobutyl) (4-(5,6,7,8-tetrahydro-1,8-naphthyridin-2-yl) butyl)amino) butanoic acid (125 mg, 246 μmol) in dioxane (4 mL) and H₂O (1 mL) was added phenylboronic acid (45 mg, 368 μmol), K₂CO₃ (68 mg, 491 μmol) and Pd(dppf)Cl₂ (18 mg, 25 μmol) and the resulting mixture was heated to 100° C. for 2 h, cooled to rt, and then concentrated in vacuo. The crude residue was purified by prep-HPLC to give the title compound. LCMS (ESI+): m/z=551.3 (M+H)⁺. ¹H NMR (400 MHz, Methanol-d₄) δ ppm 8.44 (d, J=0.73 Hz, 1H) 7.88 (br s, 2H) 7.42-7.52 (m, 4H) 6.97 (br s, 1H) 6.52 (d, J=7.34 Hz, 1H) 4.45-4.72 (m, 1H) 3.36-3.51 (m, 2H) 3.15 (br dd, J=3.30, 1.71 Hz, 1H) 2.58-2.84 (m, 10H) 2.34-2.53 (m, 2H) 2.00-2.28 (m, 2H) 1.72-1.94 (m, 4H) 1.48-1.62 (m, 2H).

Compound 192: (S)-4-((3,3-difluorocyclobutyl) (4-(5,6,7,8-tetrahydro-1,8-naphthyridin-2-yl) butyl)amino)-2-((2-phenylpyrimidin-4-yl) amino) butanoic acid: To a mixture of (S)-2-amino-4-((3,3-difluorocyclobutyl) (4-(5,6,7,8-tetrahydro-1,8-naphthyridin-2-yl) butyl)amino) butanoic acid (200 mg, 353 μmol) in DMA (3 mL) was added 4-chloro-2-phenylpyrimidine (82 mg, 388 μmol) and DIPEA (308 μL, 1.77 mmol) and the resulting mixture was heated to 70° C. for 16 h, cooled to rt, and then concentrated in vacuo. The crude residue was purified by prep-HPLC to give the title compound. LCMS (ESI+): m/z=551.3 (M+H)⁺. ¹H NMR (400 MHz, Methanol-d₄) δ ppm 8.09-8.28 (m, 3H) 7.36-7.47 (m, 4H) 6.49 (br d, J=7.21 Hz, 2H) 4.78 (br s, 1H) 3.29 (br d, J=5.26 Hz, 2H) 3.10-3.19 (m, 1H) 2.57-2.84 (m, 10H) 2.46 (br s, 2H) 2.23 (br s, 1H) 2.05 (br d, J=4.89 Hz, 1H) 1.71-1.90 (m, 4H) 1.51-1.66 (m, 2H).

Compound 193: (S)-2-((3-cyanopyrazin-2-yl) amino)-4-((3,3-difluorocyclobutyl) (4-(5,6,7,8-tetrahydro-1,8-naphthyridin-2-yl) butyl)amino) butanoic acid: To a mixture of (S)-2-amino-4-((3,3-difluoropropyl) (4-(5,6,7,8-tetrahydro-1,8-naphthyridin-2-yl) butyl)amino) butanoic acid (200 mg, 353 μmol) in i-PrOH (3 mL) was added 3-chloropyrazine-2-carbonitrile (54 mg, 388 μmol) and DIPEA (308 μL, 1.77 mmol) and the resulting mixture was heated to 70° C. for 1 h, cooled to rt, and then concentrated in vacuo. The crude residue was purified by prep-HPLC to give the title compound. LCMS (ESI+): m/z=500.2 (M+H)⁺. ¹H NMR (400 MHz, Methanol-d₄) δ ppm 8.26 (d, J=2.32 Hz, 1H) 7.88 (d, J=2.45 Hz, 1H) 7.48 (d, J=7.34 Hz, 1H) 6.56 (d, J=7.34 Hz, 1H) 4.58 (t, J=5.26 Hz, 1H) 3.38-3.49 (m, 2H) 3.08-3.20 (m, 1H) 2.55-2.84 (m, 12H) 2.08-2.27 (m, 2H) 1.74-1.97 (m, 4H) 1.59 (q, J=7.31 Hz, 2H).

Scheme 22, Compound 194

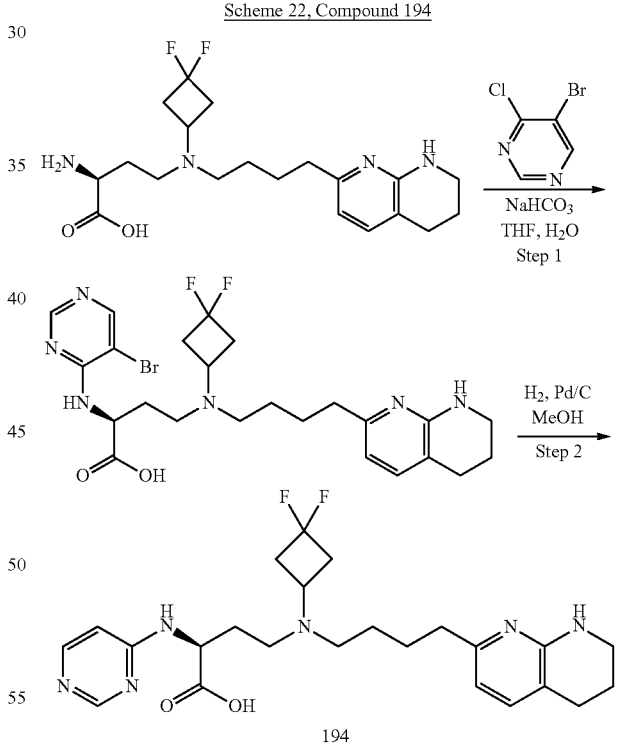

194

Step 1: (S)-2-((5-bromopyrimidin-4-yl) amino)-4-((3,3-difluorocyclobutyl) (4-(5,6,7,8-tetrahydro-1,8-naphthyridin-2-yl) butyl)amino) butanoic acid To a mixture of (S)-2-amino-4-((3,3-difluoropropyl) (4-(5,6,7,8-tetrahydro-1,8-naphthyridin-2-yl) butyl)amino) butanoic acid (300 mg, 530 μmol) in THF (4 mL) and H₂O (1 mL) was added 5-bromo-4-chloropyrimidine (113 mg, 583 µmol) and NaHCO₃ (222 mg, 2.65 mmol) and the resulting mixture was heated to 70° C. for 1 h, cooled to rt, and then concentrated in vacuo to give the title compound that was used without further purification. LCMS (ESI+): m/z=552.9 (M+H)⁺.

Step 2: (S)-4-((3,3-difluorocyclobutyl) (4-(5,6,7,8-tetrahydro-1,8-naphthyridin-2-yl) butyl)amino)-2-(pyrimidin-4-ylamino) butanoic acid To a mixture of (S)-2-((5-bromopyrimidin-4-yl) amino)-4-((3,3-difluorocyclobutyl) (4-(5,6,7,8-tetrahydro-1,8-naphthyridin-2-yl) butyl)amino) butanoic acid (293 mg, 529 µmol) in MeOH (10 mL) was added 10 wt % Pd/C (200 mg) and the resulting mixture was stirred under an H₂ atmosphere for 3 h and then filtered and concentrated in vacuo. The crude residue was purified by reverse phase prep-HPLC to give the title compound. LCMS (ESI+): m/z=475.2 (M+H)⁺. ¹H NMR (400 MHz, DMSO-d₆) δ ppm 8.39 (s, 1H) 8.05 (br d, J=5.50 Hz, 1H) 7.61 (br s, 1H) 7.04 (d, J=7.34 Hz, 1H) 6.55 (br d, J=13.57 Hz, 2H) 6.24 (d, J=7.34 Hz, 1H) 4.48 (br s, 1H) 3.21-3.29 (m, 2H) 3.01 (br d, J=6.11 Hz, 1H) 2.60 (br t, J=6.05 Hz, 4H) 2.17-2.48 (m, 8H) 1.93 (br dd, J=13.27, 4.95 Hz, 1H) 1.68-1.83 (m, 3H) 1.52 (q, J=7.37 Hz, 2H) 1.28-1.42 (m, 2H).

Compound 195: (S)-4-(((R)-2-methoxypropyl) (4-(5,6,7,8-tetrahydro-1,8-naphthyridin-2-yl)butyl)amino)-2-((5-methylpyrimidin-2-yl)amino)butanoic acid: To a solution of tert-butyl (S)-2-amino-4-(((R)-2-methoxypropyl) (4-(5,6,7,8-tetrahydro-1,8-naphthyridin-2-yl) butyl)amino) butanoate (100 mg, 230 µmol) and 2-chloro-5-methyl-pyrimidine (25 mg, 192 µmol) in t-AmOH (2 mL) was added 2.0M t-BuONa in THF (192 µL, 384 µmol) and tBuXPhos-Pd-G3 (15 mg, 19 µmol) and the resulting mixture was heated to 100° C. for 14 h and then cooled to rt and then concentrated in vacuo to give (S)-tert-butyl 4-(((S)-2-methoxypropyl) (4-(5,6,7,8-tetrahydro-1,8-naphthyridin-2-yl) butyl)amino)-2-((5-methylpyrimidin-2-yl) amino) butanoate intermediate, which was used without further purification, Of the butanoate intermediate, 80 mg, 152 µmol was taken up in DCM (2 mL) to which was added TFA (165 µL) and the resulting mixture was stirred at rt for 6 h and concentrated in vacuo. The crude residue was purified by prep-HPLC to give the title compound. LCMS (ESI+): m/z=471.2 (M+H)⁺. ¹H NMR (400 MHz, Methanol-d₄) δ ppm 8.57 (br s, 2H) 7.60 (d, J=7.28 Hz, 1H) 6.67 (d, J=7.28 Hz, 1H) 4.81-4.86 (m, 1H) 3.86 (br s, 1H) 3.41-3.59 (m, 4H) 3.39 (s, 3H) 3.33-3.38 (m, 1H) 3.12-3.30 (m, 3H) 2.76-2.86 (m, 4H) 2.54 (br s, 1H) 2.39 (br d, J=8.82 Hz, 1H) 2.30 (s, 3H) 1.76-1.99 (m, 6H) 1.22 (d, J=5.95 Hz, 3H).

Compound 196: (S)-4-(((R)-2-methoxypropyl) (4-(5,6,7,8-tetrahydro-1,8-naphthyridin-2-yl) butyl)amino)-2-(pyridin-3-ylamino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (100 mg, 230.09 µmol) and 3-bromopyridine (30 mg, 192 µmol) in t-AmOH (2 mL) was added 2.0M t-BuONa in THF (192 µL, 384 µmol) and tBuXPhos-Pd-G3 (15 mg, 19 µmol) and tBuXPhos-Pd-G3 (15 mg, 19 µmol) and the resulting mixture was heated to 100° C. for 14 h and then cooled to rt and then concentrated in vacuo to give a (S)-tert-butyl 4-(((R)-2-methoxypropyl) (4-(5,6,7,8-tetrahydro-1,8-naphthyridin-2-yl) butyl)amino)-2-(pyridin-3-ylamino) butanoate intermediate, LCMS (ESI+): m/z=512.3 (M+H)⁺, which was used without further purification. Of the butanoate intermediate, 80 mg, 156 µmol, was taken up in DCM (2 mL) and TFA (200 µL) and the resulting mixture was stirred at rt for 6 h and concentrated in vacuo. The crude residue was purified by prep-HPLC to give the title compound. LCMS (ESI+): m/z=456.4 (M+H)⁺. ¹H NMR (400 MHz, Methanol-d₄) δ ppm 7.93 (dd, J=11.03, 2.65 Hz, 1H) 7.79 (d, J=4.63 Hz, 1H) 7.13-7.24 (m, 2H) 7.03 (td, J=8.99, 1.43 Hz, 1H) 6.42 (dd, J=7.39, 1.87 Hz, 1H) 3.90 (t, J=5.84 Hz, 1H) 3.66-3.76 (m, 1H) 3.36 (br dd, J=11.03, 5.95 Hz, 3H) 3.27-3.31 (m, 3H) 3.08-3.25 (m, 2H) 2.94-3.06 (m, 3H) 2.69 (q, J=6.10 Hz, 2H) 2.60 (br s, 2H) 2.05-2.23 (m, 2H) 1.81-1.90 (m, 2H) 1.67-1.79 (m, 4H) 1.16 (dd, J=9.92, 5.95 Hz, 3H).

Compound 197: 4-(((R)-2-methoxypropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 198: 2-((5-cyanopyrimidin-2-yl) amino)-4-(((R)-2-methoxypropyl) (4-(5,6,7,8-tetrahydro-1,8-naphthyridin-2-yl) butyl)amino) butanoic acid.

Compound 199: 4-(((R)-2-methoxypropyl) (4-(5,6,7,8-tetrahydro-1,8-naphthyridin-2-yl) butyl)amino)-2-((5-(trifluoromethyl)pyrimidin-2-yl) amino) butanoic acid

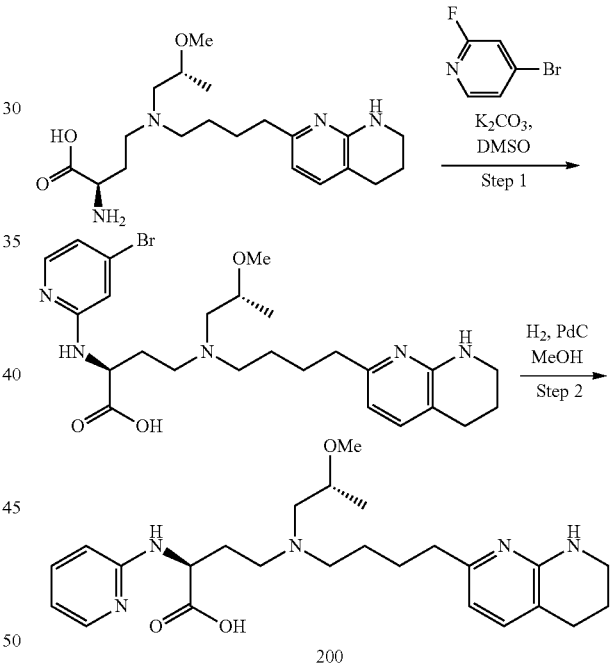

Scheme 23, Compound 200

Step 1: (S)-2-((4-bromopyridin-2-yl)amino)-4-(((R)-2-methoxypropyl) (4-(5,6,7,8-tetrahydro-1,8-naphthyridin-2-yl) butyl)amino) butanoic acid To a solution of (S)-2-amino-4-(((R)-2-methoxypropyl) (4-(5,6,7,8-tetrahydro-1,8-naphthyridin-2-yl) butyl)amino) butanoic acid hydrochloride (300 mg, 723 µmol) and 4-bromo-2-fluoropyridine (140 mg, 795 µmol) in DMSO (4 mL) was added K₂CO₃ (500 mg, 3.61 mmol) and the resulting mixture was stirred at 130° C. for 3 h and then allowed to cool to rt and concentrated in vacuo. The crude residue was purified by reverse phase prep-HPLC to give the title compound. LCMS (ESI+): m/z=534.3 (M+H)⁺.

Step 2: (S)-4-(((R)-2-methoxypropyl) (4-(5,6,7,8-tetrahydro-1,8-naphthyridin-2-yl) butyl)amino)-2-(pyridin-2-ylamino) butanoic acid To a mixture of (S)-2-((4-bromopyridin-2-yl) amino)-4-(((R)-2-methoxypropyl) (4-(5,6,7,8-tetrahydro-1,8-naphthyridin-2-yl) butyl)amino) butanoic acid (200 mg, 374 μmol) in MeOH (5 mL) was added 10 wt % Pd/C (39 mg) and the resulting mixture was stirred under an $H_2$ atmosphere for 12 h. The mixture was filtered and concentrated in vacuo. The crude residue was purified by reverse phase prep-HPLC to give the title compound. LCMS (ESI+): m/z=456.2 (M+H)$^+$. $^1$H NMR (400 MHz, Methanol-d$_4$) δ ppm 7.92 (d, J=5.07 Hz, 1H) 7.43-7.49 (m, 1H) 7.15 (d, J=7.28 Hz, 1H) 6.58-6.67 (m, 2H) 6.37 (d, J=7.28 Hz, 1H) 4.19 (t, J=6.28 Hz, 1H) 3.79 (ddd, J=9.65, 6.23, 3.09 Hz, 1H) 3.35-3.40 (m, 2H) 3.34 (s, 3H) 3.28 (br d, J=5.29 Hz, 1H) 3.08-3.23 (m, 3H) 2.97-3.06 (m, 2H) 2.70 (t, J=6.17 Hz, 2H) 2.55 (br t, J=6.84 Hz, 2H) 2.28-2.39 (m, 1H) 1.93-2.04 (m, 1H) 1.87 (q, J=5.95 Hz, 2H) 1.63-1.74 (m, 4H) 1.21 (d, J=6.17 Hz, 3H).

Compound 201: 2-((1H-pyrazolo[3,4-d]pyrimidin-4-yl) amino)-4-(((R)-2-methoxypropyl) (4-(5,6,7,8-tetrahydro-1,8-naphthyridin-2-yl) butyl)amino) butanoic acid.

Compound 202: 2-((5-bromopyrimidin-2-yl) amino)-4-(((R)-2-methoxypropyl) (4-(5,6,7,8-tetrahydro-1,8-naphthyridin-2-yl) butyl)amino) butanoic acid.

Compound 203: 2-((1H-pyrazolo[4,3-d]pyrimidin-7-yl) amino)-4-(((R)-2-methoxypropyl) (4-(5,6,7,8-tetrahydro-1,8-naphthyridin-2-yl) butyl)amino) butanoic acid.

Compound 204: (S)-4-(((R)-2-methoxypropyl) (4-(5,6,7,8-tetrahydro-1,8-naphthyridin-2-yl) butyl)amino)-2-((2-methoxypyrimidin-4-yl) amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (101 mg, 232 μmol) and 4-chloro-2-methoxypyrimidine (28 mg, 194 μmol) in t-AmOH (2 mL) was added 2.0M t-BuONa in THF (194 μL, 388 μL) and tBuXPhos-Pd-G3 (15 mg, 19 μmol) and the resulting mixture was heated to 100° C. for 15 h, cooled to rt, and then concentrated in vacuo to give a ((S)-tert-butyl 4-(((R)-2-methoxypropyl) (4-(5,6,7,8-tetrahydro-1,8-naphthyridin-2-yl) butyl)amino)-2-((2-methoxypyrimidin-4-yl) amino) butanoate intermediate, LCMS (ESI+): m/z=543.4 (M+H)$^+$, which was used without further purification. Of the butanoate intermediate, 100 mg, 184 μmol, was taken up in DCM (2 mL) was added TFA (333 μL) and the resulting mixture was stirred at rt for 3 h and then concentrated in vacuo. The crude residue was purified by reverse phase prep-HPLC to give the title compound. LCMS (ESI+): m/z=487.3 (M+H)$^+$. $^1$H NMR (400 MHz, DMSO-d$_6$) δ ppm 7.81 (br s, 1H) 7.47-7.62 (m, 1H) 7.01 (br d, J=7.21 Hz, 1H) 6.35 (br d, J=13.57 Hz, 1H) 6.18-6.28 (m, 2H) 4.31 (br s, 1H) 3.73 (s, 3H) 3.23 (br s, 2H) 3.19 (s, 4H) 2.67 (br s, 1H) 2.59 (br t, J=6.11 Hz, 4H) 2.31-2.43 (m, 5H) 1.86-1.97 (m, 1H) 1.71-1.78 (m, 3H) 1.54 (br dd, J=14.73, 7.40 Hz, 2H) 1.41 (br d, J=7.21 Hz, 2H) 1.03 (t, J=5.50 Hz, 3H).

Compound 205: (S)-4-(((R)-2-methoxypropyl) (4-(5,6,7,8-tetrahydro-1,8-naphthyridin-2-yl) butyl)amino)-2-((6-methylpyrazin-2-yl) amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (203 mg, 467 μmol), 2-chloro-6-methyl-pyrazine (50 mg, 389 μmol) in t-AmOH (3 mL) was added 2.0M NaO-tBu (389 μL, 778 μmol) then tBuXPhos-Pd-G3 (31 mg, 39 μmol) and the resulting mixture was heated to 100° C. for 15 h and then cooled to rt and then concentrated in vacuo to give a (S)-tert-butyl 4-(((R)-2-methoxypropyl) (4-(5,6,7,8-tetrahydro-1,8-naphthyridin-2-yl) butyl)amino)-2-((6-methylpyrazin-2-yl) amino) butanoate intermediate, LCMS (ESI+): m/z=527.3 (M+H)$^+$, which was used without further purification. Of the butanoate intermediate, 260 mg, 494 μmol, was taken up into DCM (2 mL) and TFA (1.5 mL) and the resulting mixture was stirred at rt for 6 h and concentrated in vacuo. The crude residue was purified by prep-HPLC to give the title compound. LCMS (ESI+): m/z=471.1 (M+H)$^+$. $^1$H NMR (400 MHz, Methanol-d$_4$) δ ppm 8.11 (d, J=2.43 Hz, 1H) 7.85 (s, 1H) 7.60 (d, J=7.28 Hz, 1H) 6.67 (d, J=7.28 Hz, 1H) 4.80-4.87 (m, 1H) 3.85 (br d, J=2.87 Hz, 1H) 3.41-3.56 (m, 4H) 3.39 (dd, J=2.65, 1.76 Hz, 3H) 3.32-3.38 (m, 1H) 3.13-3.30 (m, 3H) 2.77-2.85 (m, 4H) 2.54-2.58 (m, 3H) 2.44-2.54 (m, 1H) 2.29-2.42 (m, 1H) 1.95 (q, J=5.84 Hz, 2H) 1.81 (br d, J=4.63 Hz, 4H) 1.23 (d, J=5.95 Hz, 3H).

Compound 206: 2-((3-cyanopyrazin-2-yl) amino)-4-(((R)-2-methoxypropyl) (4-(5,6,7,8-tetrahydro-1,8-naphthyridin-2-yl) butyl)amino) butanoic acid.

Compound 207: 4-(((R)-2-methoxypropyl) (4-(5,6,7,8-tetrahydro-1,8-naphthyridin-2-yl) butyl)amino)-2-(pyrimidin-4-ylamino) butanoic acid.

Compound 208: 2-((5-fluoropyrimidin-2-yl) amino)-4-(((R)-2-methoxypropyl) (4-(5,6,7,8-tetrahydro-1,8-naphthyridin-2-yl) butyl)amino) butanoic acid.

Compound 209: (S)-4-(((R)-2-methoxypropyl) (4-(5,6,7,8-tetrahydro-1,8-naphthyridin-2-yl) butyl)amino)-2-((7-methyl-7H-pyrrolo[2,3-d]pyrimidin-4-yl)amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (149 mg, 344 μmol) and 4-chloro-7-methyl-7H-pyrrolo[2,3-d]pyrimidine (48 mg, 286.40 μmol) in t-AmOH (3 mL) was added 2.0M t-BuONa in THF (286 μL, 572 μmol) and tBuXPhos-Pd-G3 (23 mg, 29 μmol) and the resulting mixture was heated to 100° C. for 15 h. The reaction mixture was cooled to rt and then concentrated in vacuo to give a (S)-tert-butyl 4-(((R)-2-methoxypropyl) (4-(5,6,7,8-tetrahydro-1,8-naphthyridin-2-yl) butyl)amino)-2-((7-methyl-7H-pyrrolo[2,3-d]pyrimidin-4-yl) amino) butanoate intermediate, LCMS (ESI+): m/z=566.5 (M+H)$^+$, which was used without further purification. Of the butanoate intermediate, 80 mg, 141 μmol, was taken up in DCM (1 mL) and TFA (400 μL) and the resulting mixture was stirred at rt for 6 h and then concentrated in vacuo. The crude residue was purified by chiral SFC to give a first fraction containing the title compound. LCMS (ESI+): m/z=510.3 (M+H)$^+$. $^1$H NMR (400 MHz, Methanol-d$_4$) δ ppm 8.18 (s, 1H) 7.19 (d, J=7.28 Hz, 1H) 7.08 (d, J=3.53 Hz, 1H) 6.59 (d, J=3.53 Hz, 1H) 6.40 (d, J=7.28 Hz, 1H) 4.61 (t, J=6.17 Hz, 1H) 3.76 (s, 4H) 3.34-3.40 (m, 3H) 3.33 (s, 3H) 3.22-3.29 (m, 1H) 2.99-3.19 (m, 4H) 2.69 (t, J=6.17 Hz, 2H) 2.58 (br s, 2H) 2.32-2.43 (m, 1H) 2.11-2.21 (m, 1H) 1.86 (dt, J=11.52, 6.04 Hz, 2H) 1.74 (br s, 4H) 1.16 (d, J=5.95 Hz, 3H).

Compound 210: (R)-2-((6-(tert-butyl)pyrimidin-4-yl) amino)-4-(((R)-2-methoxypropyl) (4-(5,6,7,8-tetrahydro-1,8-naphthyridin-2-yl) butyl)amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (153 mg, 352 μmol) and 4-tert-butyl-6-chloropyrimidine (50 mg 293 μmol) in t-AmOH (3 mL) was added 2.0M t-BuONa in THF (293 μL, 586 mmol) then tBuXPhos-Pd-G3 (23 mg, 29 umol) and the resulting mixture was heated to 100° C. for 15 h. The reaction mixture was cooled to rt and then concentrated in vacuo to give a (S)-tert-butyl 2-((6-(tert-butyl)pyrimidin-4-yl) amino)-4-(((R)-2-methoxypropyl) (4-(5,6,7,8-tetrahydro-1,8-naphthyridin-2-yl) butyl)amino) butanoate intermediate, LCMS (ESI+): m/z=569.6 (M+H)$^+$, which was used without further purification. Of the butanoate intermediate, 75 mg, 132 μmol, was taken up in DCM (1 mL) and TFA (400 μL) and the resulting mixture was stirred at rt for 6 h and then concentrated in vacuo. The crude residue was purified by chiral SFC to give the title compound. LCMS (ESI+): m/z=513.3

(M+H)⁺. ¹H NMR (400 MHz, Methanol-d₄) δ ppm 8.35 (s, 1H) 7.20 (d, J=7.28 Hz, 1H) 6.60 (s, 1H) 6.41 (d, J=7.28 Hz, 1H) 4.42 (br s, 1H) 3.70 (br s, 1H) 3.35-3.40 (m, 2H) 3.33 (s, 3H) 3.25 (br s, 1H) 3.11-3.20 (m, 1H) 2.92-3.10 (m, 4H) 2.70 (t, J=6.17 Hz, 2H) 2.59 (br t, J=6.95 Hz, 2H) 2.24 (dq, J=14.22, 7.09 Hz, 1H) 2.06 (br dd, J=14.22, 5.62 Hz, 1H) 1.83-1.91 (m, 2H) 1.73 (br s, 4H) 1.26 (s, 9H) 1.16 (d, J=6.17 Hz, 3H).

Compound 211: 2-((5-cyclopropylpyrimidin-2-yl) amino)-4-(((R)-2-methoxypropyl) (4-(5,6,7,8-tetrahydro-1,8-naphthyridin-2-yl) butyl)amino) butanoic acid.

Compound 212: (S)-4-(((R)-2-methoxypropyl) (4-(5,6,7,8-tetrahydro-1,8-naphthyridin-2-yl) butyl)amino)-2-((6-(trifluoromethyl)pyrimidin-4-yl) amino) butanoic acid.

Scheme 24, Compound 213

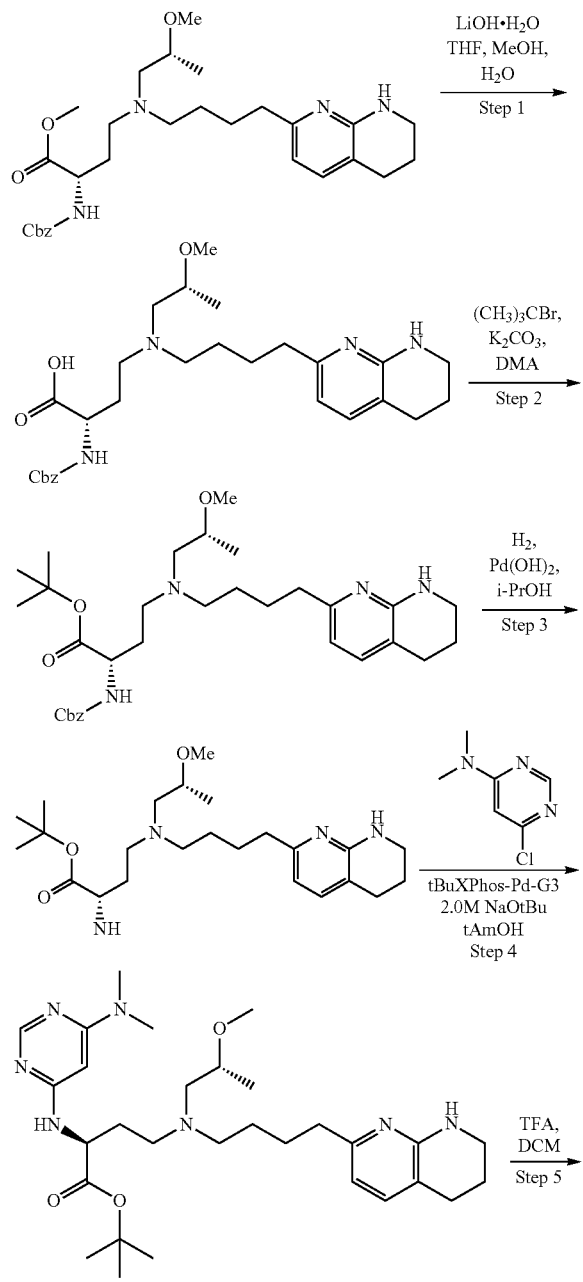

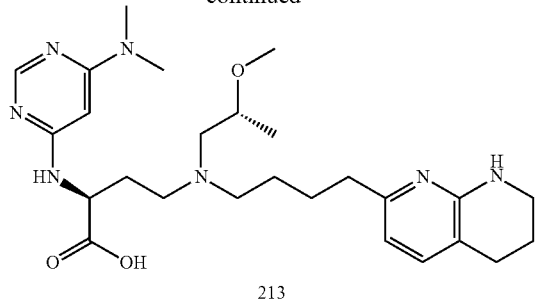

213

Step 1: (S)-2-(((benzyloxy)carbonyl)amino)-4-(((R)-2-methoxypropyl) (4-(5,6,7,8-tetrahydro-1,8-naphthyridin-2-yl) butyl)amino) butanoic acid A mixture of methyl (S)-2-(((benzyloxy)carbonyl) amino)-4-(((R)-2-methoxypropyl) (4-(5,6,7,8-tetrahydro-1, 8-naphthyridin-2-yl) butyl)amino) butanoate (1 g, 1.90 mmol) in 1:1:1 H₂O/THF/MeOH (9 mL) was added LiOH.H₂O (159 mg, 3.80 mmol) and the resulting mixture was stirred at rt for 1 h and then adjusted to pH=6 by the addition of AcOH and concentrated in vacuo to give the title compound that was used without further purification. LCMS (ESI+): m/z=513.5 (M+H)⁺.

Step 2: (S)-tert-butyl 2-(((benzyloxy)carbonyl) amino)-4-(((R)-2-methoxypropyl) (4-(5,6,7,8-tetrahydro-1,8-naphthyridin-2-yl) butyl)amino) butanoate To a solution of (S)-2-(((benzyloxy)carbonyl)amino)-4-(((R)-2-methoxypropyl) (4-(5,6,7,8-tetrahydro-1,8-naphthyridin-2-yl) butyl)amino) butanoic acid acetate (300 mg, 524 µmol) in DMA (4 mL) was added benzyltriethylammonium chloride (119 mg, 524 umol), K₂CO₃ (1.88 g, 1362 mmol), 2-bromo-2-methylpropane (2.92 mL, 25.14 mmol) and the resulting mixture was stirred at 55° C. for 18 h and then allowed to cool to rt. The reaction mixture was diluted with H₂O and then extracted with EtOAc. The combined organic extracts were washed with brine, dried over Na₂SO₄, filtered, and concentrated in vacuo. The crude product was purified by normal phase silica gel chromatography to give the title compound. LCMS (ESI+): m/z=569.3 (M+H)⁺.

Step 3: tert-butyl (S)-2-amino-4-(((R)-2-methoxypropyl) (4-(5,6,7,8-tetrahydro-1,8-naphthyridin-2-yl) butyl)amino) butanoate To a solution of tert-butyl (S)-2-(((benzyloxy)carbonyl) amino)-4-(((R)-2-methoxypropyl) (4-(5,6,7,8-tetrahydro-1, 8-naphthyridin-2-yl) butyl)amino) butanoate (107 mg, 188 µmol) in i-PrOH (2 mL) was added 20 wt % Pd(OH)₂/C (26 mg) and the resulting mixture was stirred under an H₂ atmosphere at rt for 15 h. The mixture was filtered and concentrated under reduced pressure to give the title compound that was used without further purification. LCMS (ESI+): m/z=435.5 (M+H)⁺.

Step 4: (S)-tert-butyl2-((6-(dimethylamino)pyrimidin-4-yl)amino)-4-(((R)-2-methoxypropyl) (4-(5,6,7, 8-tetrahydro-1,8-naphthyridin-2-yl) butyl)amino) butanoate To a mixture of tert-butyl (S)-2-amino-4-(((R)-2-methoxypropyl) (4-(5,6,7,8-tetrahydro-1,8-naphthyridin-2- yl) butyl)amino) butanoate (152 mg, 349 μmol) and 6-chloro-N,N-dimethyl-pyrimidin-4-amine (46 mg, 291 μmol) in t-AmOH (3 mL) was added 2.0M t-BuONa in THF (291 μL, 582 μmol) then tBuXPhos-Pd-G3 (23 mg, 29 μmol) and the resulting mixture was heated to 100° C. for 2 h. The reaction mixture was cooled to rt and then concentrated in vacuo to give the title compound that was used without further purification. LCMS (ESI+): m/z=556.6 (M+H)+.

Step 5: (S)-2-((6-(dimethylamino)pyrimidin-4-yl) amino)-4-(((R)-2-methoxypropyl) (4-(5,6,7,8-tetrahydro-1,8-naphthyridin-2-yl) butyl)amino) butanoic acid (S)-tert-butyl 2-((6-(dimethylamino)pyrimidin-4-yl) amino)-4-(((R)-2-methoxypropyl) (4-(5,6,7,8-tetrahydro-1, 8-naphthyridin-2-yl) butyl)amino) butanoate (80 mg, 144 μmol) was taken up in DCM (1 mL) and TFA (200 μL) and the resulting mixture was stirred for 6 h at rt and then concentrated in vacuo. The crude residue was purified by chiral SFC to give the title compound. LCMS (ESI+): m/z=500.3 (M+H)+. $^1$H NMR (400 MHz, Methanol-$d_4$) δ ppm 8.00 (s, 1H) 7.21 (d, J=7.28 Hz, 1H) 6.42 (d, J=7.28 Hz, 1H) 5.58 (s, 1H) 4.22 (br t, J=5.18 Hz, 1H) 3.74 (ddd, J=9.37, 6.17, 3.42 Hz, 1H) 3.36-3.40 (m, 2H) 3.35 (s, 3H) 3.16-3.29 (m, 2H) 3.04-3.14 (m, 3H) 3.02 (s, 6H) 2.96-3.01 (m, 1H) 2.70 (t, J=6.17 Hz, 2H) 2.60 (br t, J=6.73 Hz, 2H) 2.19-2.30 (m, 1H) 2.03 (br dd, J=14.66, 5.84 Hz, 1H) 1.87 (q, J=5.95 Hz, 2H) 1.73 (br s, 4H) 1.17 (d, J=5.95 Hz, 3H).

Compound 214: 2-((6-(1H-pyrazol-1-yl) pyrimidin-4-yl) amino)-4-(((R)-2-methoxypropyl) (4-(5,6,7,8-tetrahydro-1, 8-naphthyridin-2-yl) butyl)amino) butanoic acid.

Compound 215: (S)-4-(((R)-2-methoxypropyl) (4-(5,6,7, 8-tetrahydro-1,8-naphthyridin-2-yl) butyl)amino)-2-(quinoxalin-2-ylamino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (203 mg, 467 μmol), 2-chloroquinoxaline (64 mg, 389 μmol) in t-AmOH (3 mL) was added 2.0M t-BuONa in THF (389 μL, 778 μmol) then tBuXPhos-Pd-G3 (31 mg, 39 μmol) the resulting mixture was stirred for 15 h at the 100° C. and then cooled to rt and concentrated in vacuo to give (S)-isopropyl 4-(((R)-2-methoxypropyl) (4-(5,6,7,8-tetrahydro-1,8-naphthyridin-2-yl) butyl)amino)-2-(quinoxalin-2-ylamino) butanoate intermediate, LCMS (ESI+): m/z=563.3 (M+H)+, which was used without further purification. Of the butanoate intermediate, 300 mg, 533 μmol) in DCM (2 mL) and TFA (1.60 mL) and the resulting mixture was stirred at rt for 6 h and then concentrated in vacuo. The crude residue was purified by reverse phase prep-HPLC to give the title compound. LCMS (ESI+): m/z=507.3 (M+H)+. $^1$H NMR (400 MHz, Methanol-$d_4$) δ ppm 8.33 (d, J=9.70 Hz, 1H) 7.78 (d, J=8.16 Hz, 1H) 7.59-7.64 (m, 1H) 7.52-7.59 (m, 1H) 7.33-7.40 (m, 1H) 7.15 (d, J=7.50 Hz, 1H) 6.36 (t, J=6.84 Hz, 1H) 4.56 (t, J=5.73 Hz, 1H) 3.69-3.84 (m, 1H) 3.35-3.45 (m, 1H) 3.32-3.35 (m, 3H) 3.02-3.30 (m, 5H) 2.93-3.02 (m, 2H) 2.65 (q, J=6.25 Hz, 2H) 2.55 (br d, J=5.29 Hz, 2H) 2.27-2.44 (m, 1H) 2.18 (td, J=9.76, 5.18 Hz, 1H) 1.76-1.87 (m, 2H) 1.71 (br d, J=5.73 Hz, 4H) 1.16 (dd, J=15.10, 6.06 Hz, 3H).

Compound 216: (S)-4-(((R)-2-methoxypropyl) (4-(5,6,7, 8-tetrahydro-1,8-naphthyridin-2-yl) butyl)amino)-2-((5-methoxypyrazine-2-yl) amino) butanoic acid.

Compound 217: 4-(((R)-2-methoxypropyl) (4-(5,6,7,8-tetrahydro-1,8-naphthyridin-2-yl) butyl)amino)-2-((6-phenylpyrimidin-4-yl) amino) butanoic acid.

Compound 218: 4-(((R)-2-methoxypropyl) (4-(5,6,7,8-tetrahydro-1,8-naphthyridin-2-yl) butyl)amino)-2-((2-phenylpyrimidin-4-yl) amino) butanoic acid.

Compound 219: 4-(((R)-2-methoxypropyl) (4-(5,6,7,8-tetrahydro-1,8-naphthyridin-2-yl) butyl)amino)-2-((5-phenylpyrimidin-4-yl) amino) butanoic acid.

Compound 220: (S)-4-(((R)-2-methoxypropyl) (4-(5,6,7, 8-tetrahydro-1,8-naphthyridin-2-yl) butyl)amino)-2-((6-methyl-2-(pyridin-4-yl) pyrimidin-4-yl) amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (203 mg, 467 μmol), 4-chloro-6-methyl-2-(4-pyridyl)pyrimidine (80 mg, 389 μmol) in t-AmOH (3 mL) was added 2.0M NaO-tBu (389 μL, 778 μmol) then [2-(2-aminophenyl) phenyl]-methylsulfonyloxy-palladium; ditert-butyl-[2-(2,4,6-triisopropylphenyl)phenyl] phosphane (31 mg, 39 μmol) and the resulting mixture was heated to 100° C. for 15 h and then cooled to rt and then concentrated in vacuo to give a (S)-tert-butyl 4-(((R)-2-methoxypropyl) (4-(5,6,7,8-tetrahydro-1,8-naphthyridin-2-yl) butyl)amino)-2-((6-methyl-2-(pyridin-4-yl) pyrimidin-4-yl) amino) butanoate intermediate, LCMS (ESI+): m/z=604.3 (M+H)+, which was used without further purification. Of the butanoate intermediate, 270 mg, 447 μmol, was taken up in DCM (2 mL), and TFA (1.4) and the resulting mixture was stirred at rt for 6 h and concentrated in vacuo. The crude residue was purified by prep-HPLC to give the title compound. LCMS (ESI+): m/z=548.3 (M+H)+. $^1$H NMR (400 MHz, Methanol-$d_4$) δ ppm 8.61 (br s, 2H) 8.27 (d, J=5.73 Hz, 2H) 7.52 (d, J=7.28 Hz, 1H) 6.59 (d, J=7.28 Hz, 1H) 6.55 (s, 1H) 4.64 (br s, 1H) 3.88 (br s, 1H) 3.71 (br t, J=10.03 Hz, 1H) 3.60 (br s, 1H) 3.37-3.51 (m, 4H) 3.35 (s, 3H) 3.14-3.28 (m, 2H) 2.72-2.83 (m, 4H) 2.61 (br s, 1H) 2.41 (s, 3H) 2.21 (br d, J=11.69 Hz, 1H) 1.75-2.07 (m, 6H) 1.24 (d, J=5.95 Hz, 3H).

Compound 221: 4-(((R)-2-methoxypropyl) (4-(5,6,7,8-tetrahydro-1,8-naphthyridin-2-yl) butyl)amino)-2-((2-(pyridin-3-yl) quinazolin-4-yl) amino) butanoic acid.

Compound 222: (S)-4-(((R)-2-methoxypropyl) (4-(5,6,7, 8-tetrahydro-1,8-naphthyridin-2-yl) butyl)amino)-2-((6-(pyridin-4-yl) pyrazin-2-yl) amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (199 mg, 457 μmol) and 2-chloro-6-(4-pyridyl) pyrazine (73 mg, 381 μmol) in t-AmOH (3 mL) was added 2.0M t-BuONa in THF (381 μL, 762 μmol) and then tBuXPhos-Pd-G3 (30 mg, 38 μmol) and the resulting mixture was heated to 100° C. for 15 h and then cooled to rt and concentrated in vacuo to give a (S)-tert-butyl 4-(((R)-2-methoxypropyl) (4-(5,6,7,8-tetrahydro-1,8-naphthyridin-2-yl) butyl)amino)-2-((6-(pyridin-4-yl) pyrazin-2-yl) amino) butanoate intermediate, LCMS (ESI+): m/z=590.5 (M+H)+, which was used without further purification. Of the butanoate intermediate, 270 mg, 458 μmol, was taken up in DCM (2 mL) and TFA (1.4 mL) and the resulting mixture was stirred at rt for 6 h and then concentrated in vacuo. The crude residue was purified by reverse phase prep-HPLC to give the title compound. LCMS (ESI+): m/z=534.3 (M+H)+. $^1$H NMR (400 MHz, Methanol-$d_4$) δ ppm 8.96 (d, J=5.87 Hz, 2H) 8.70-8.82 (m, 3H) 8.33-8.37 (m, 1H) 7.60 (d, J=6.72 Hz, 1H) 6.66 (d, J=7.34 Hz, 1H) 4.80-4.86 (m, 1H) 3.85 (br d, J=2.45 Hz, 1H) 3.44-3.58 (m, 4H) 3.32-3.44 (m, 5H) 3.27 (br d, J=7.46 Hz, 1H) 3.14-3.24 (m, 1H) 2.75-2.86 (m, 4H) 2.47-2.62 (m, 1H) 2.31-2.46 (m, 1H) 1.95 (dt, J=11.68, 6.02 Hz, 2H) 1.74-1.90 (m, 4H) 1.21 (d, J=5.99 Hz, 3H).

Compound 223: (S)-4-(((R)-2-methoxypropyl) (4-(5,6,7,8-tetrahydro-1,8-naphthyridin-2-yl) butyl)amino)-2-((5-phenylpyrazin-2-yl) amino) butanoic acid.

Compound 224: (S)-4-(((R)-2-methoxypropyl) (4-(5,6,7,8-tetrahydro-1,8-naphthyridin-2-yl) butyl) amino)-2-((6-phenylpyrazin-2-yl)amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (200 mg, 460 µmol) and 2-chloro-6-phenylpyrazine (73 mg, 383 µmol) in t-AmOH (3 mL) was added 2.0M NaO-tBu (382 µL, 764 µmol) then tBuXPhos-Pd-G3 (30 mg, 38 µmol) and the resulting mixture was heated to 100° C. for 15 h and then cooled to rt and then concentrated in vacuo to give a (S)-tert-butyl 4-(((R)-2-methoxypropyl) (4-(5,6,7,8-tetrahydro-1,8-naphthyridin-2-yl) butyl)amino)-2-((6-phenylpyrazin-2-yl) amino) butanoate intermediate, LCMS (ESI+): m/z=589.5 (M+H)+, which was used without further purification. Of the butanoate intermediate, 280 mg, 476 µmol was taken up into DCM (2 mL), and TFA (1.1 mL) and the resulting mixture was stirred at rt for 6 h and concentrated in vacuo. The crude residue was purified by prep-HPLC to give the title compound. LCMS (ESI+): m/z=533.3 (M+H)+. $^1$H NMR (400 MHz, Methanol-d$_4$) δ ppm 8.21 (s, 1H) 7.97-8.04 (m, 2H) 7.90 (s, 1H) 7.38-7.47 (m, 3H) 7.23 (d, J=7.28 Hz, 1H) 6.43 (d, J=7.28 Hz, 1H) 4.54 (dd, J=7.17, 4.74 Hz, 1H) 3.69-3.79 (m, 1H) 3.32-3.48 (m, 2H) 3.30 (s, 3H) 3.23-3.29 (m, 2H) 2.98-3.15 (m, 4H) 2.56-2.70 (m, 4H) 2.30-2.42 (m, 1H) 2.13-2.25 (m, 1H) 1.70-1.86 (m, 6H) 1.13 (d, J=6.17 Hz, 3H).

Compounds 225: (S)-4-(((R)-2-methoxypropyl) (4-(5,6,7,8-tetrahydro-1,8-naphthyridin-2-yl) butyl)amino)-2-((1-methyl-1H-pyrazol-5-yl) amino) butanoic acid.

Compound 226: (S)-2-(benzo[d]oxazol-2-ylamino)-4-(((R)-2-methoxypropyl) (4-(5,6,7,8-tetrahydro-1,8-naphthyridin-2-yl) butyl)amino) butanoic acid.

Compound 227: (S)-4-(((R)-2-methoxypropyl) (4-(5,6,7,8-tetrahydro-1,8-naphthyridin-2-yl) butyl)amino)-2-((1-methyl-1H-benzo[d]imidazol-2-yl) amino) butanoic acid.

Compound 228: (S)-2-(benzo[d]thiazol-2-ylamino)-4-(((R)-2-methoxypropyl) (4-(5,6,7,8-tetrahydro-1,8-naphthyridin-2-yl) butyl)amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (150 mg, 345 µmol) and 2-chlorobenzo[d]thiazole (49 mg, 288 µmol) in t-AmOH (3 mL) was added 2.0M t-BuONa in THF (288 µL, 576 µmol) then tBuXPhos-Pd-G3 (23 mg, 29 µmol) and the resulting mixture was stirred 100° C. for 14 h and then cooled to rt and concentrated in vacuo to give a (S)-tert-butyl 2-(benzo[d]thiazol-2-ylamino)-4-(((R)-2-methoxypropyl) (4-(5,6,7,8-tetrahydro-1,8-naphthyridin-2-yl) butyl)amino) butanoate intermediate, LCMS (ESI+): m/z=568.5 (M+H)+, which was used without further purification. Of the butanoate intermediate, 100 mg, 176 µmol, was taken up in DCM (2 mL) and TFA (200 µL) and the resulting mixture was stirred at rt for 6 h and concentrated in vacuo. The crude residue was purified by reverse phase prep-HPLC to give the title compound. LCMS (ESI+): m/z=512.2 (M+H)+. $^1$H NMR (400 MHz, Methanol-d$_4$) δ ppm 7.86 (d, J=7.95 Hz, 1H) 7.62-7.66 (m, 1H) 7.59 (br d, J=7.34 Hz, 1H) 7.52-7.57 (m, 1H) 7.39-7.45 (m, 1H) 6.66 (d, J=7.21 Hz, 1H) 4.86-4.88 (m, 1H) 3.83-3.94 (m, 1H) 3.60 (br d, J=17.12 Hz, 1H) 3.49-3.52 (m, 2H) 3.48 (br s, 1H) 3.40 (s, 3H) 3.35 (br s, 2H) 3.23 (br d, J=6.97 Hz, 2H) 2.77-2.85 (m, 4H) 2.55-2.67 (m, 1H) 2.48 (br s, 1H) 1.76-1.98 (m, 6H) 1.23 (d, J=5.87 Hz, 3H).

Compound 229: (S)-4-(((R)-2-methoxypropyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-(((R)-2-methoxypropyl) (4-(5,6,7,8-tetrahydro-1,8-naphthyridin-2-yl) butyl) amino) butanoic acid hydrochloride (100 mg, 264 µmol) and 7-chloro-2-methyl-2H-pyrazolo[4,3-d]pyrimidine (49 mg, 291 µmol) in THF (2 mL) was added NaHCO$_3$ (111 mg, 1.32 mmol) and the resulting mixture was heated to 70° C. for 1 h, cooled to rt, and then concentrated in vacuo. The crude residue was purified by prep-HPLC to give the title compound. LCMS (ESI+): m/z=511.3 (M+H)+. $^1$H NMR (400 MHz, Methanol-d$_4$) δ ppm 8.60 (br d, J=11.49 Hz, 1H) 8.48 (s, 1H) 7.54 (d, J=7.34 Hz, 1H) 6.66 (d, J=7.21 Hz, 1H) 5.03-5.13 (m, 1H) 4.08 (s, 3H) 3.81-3.95 (m, 1H) 3.57 (br s, 1H) 3.49-3.53 (m, 2H) 3.41-3.49 (m, 1H) 3.39 (s, 3H) 3.32-3.38 (m, 2H) 3.15-3.30 (m, 2H) 2.73-2.87 (m, 4H) 2.47-2.72 (m, 2H) 1.76-1.99 (m, 6H) 1.23 (d, J=5.75 Hz, 3H).

Compound 230: (S)-2-((9H-purin-6-yl)amino)-4-(((R)-2-methoxypropyl) (4-(5,6,7,8-tetrahydro-1,8-naphthyridin-2-yl) butyl)amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (199 mg, 458 µmol) and 6-chloro-9H-purine (59 mg, 382 µmol) in t-AmOH (3 mL) was added 2.0M t-BuONa in THF (382 µL, 764 µmol) then tBuXPhos-Pd-G3 (30 mg, 38 µmol) and the resulting mixture was stirred for 15 h at 100° C. and then cooled to rt and concentrated in vacuo to give a (S)-tert-butyl 2-((9H-purin-6-yl) amino)-4-(((R)-2-methoxypropyl) (4-(5,6,7,8-tetrahydro-1,8-naphthyridin-2-yl) butyl)amino) butanoate intermediate, LCMS (ESI+): m/z=553.5 (M+H)+, that was used without further purification. Of the butanoate intermediate, 270 mg, 489 µmol, was taken up in DCM (2 mL) and TFA (512 µL) and the resulting mixture was stirred at rt for 6 h and then concentrated in vacuo. The resulting crude residue was purified by reverse phase prep-HPLC to give the title compound. LCMS (ESI+): m/z=497.3 (M+H)+. $^1$H NMR (400 MHz, Methanol-d$_4$) δ ppm 8.26 (d, J=2.08 Hz, 1H) 8.09 (d, J=3.06 Hz, 1H) 7.14-7.21 (m, 1H) 6.39 (d, J=7.21 Hz, 1H) 4.63 (br s, 1H) 3.67-3.87 (m, 1H) 3.35-3.39 (m, 2H) 3.33 (s, 3H) 3.18-3.29 (m, 2H) 2.99-3.18 (m, 4H) 2.69 (q, J=5.62 Hz, 2H) 2.57 (br s, 2H) 2.28-2.49 (m, 1H) 2.14-2.26 (m, 1H) 1.80-1.91 (m, 2H) 1.73 (br s, 4H) 1.18 (dd, J=15.47, 6.05 Hz, 3H).

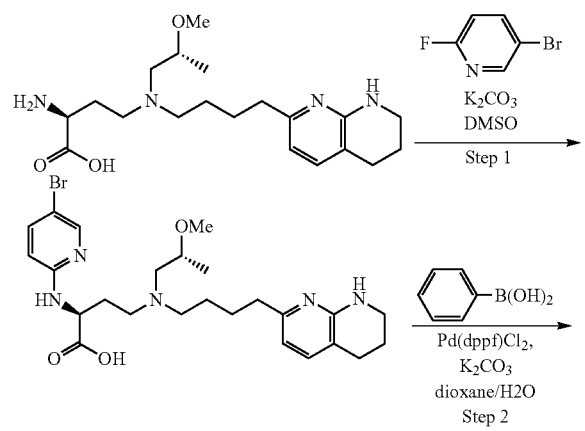

Scheme 25, Compound 231

-continued

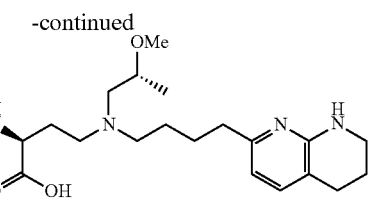

231

Step 1: (S)-2-((5-bromopyridin-2-yl) amino)-4-(((R)-2-methoxypropyl) (4-(5,6,7,8-tetrahydro-1,8-naphthyridin-2-yl) butyl)amino) butanoic acid To a mixture of (S)-2-amino-4-(((R)-2-methoxypropyl) (4-(5,6,7,8-tetrahydro-1,8-naphthyridin-2-yl) butyl)amino) butanoic acid hydrochloride (300 mg, 723 μmol) and 5-bromo-2-fluoropyridine (140 mg, 795 μmol) in DMSO (4 mL) was added K₂CO₃ (500 mg, 3.61 mmol) and the resulting mixture was stirred at 130° C. for 3 h, cooled to rt, and then concentrated in vacuo. The crude residue was purified by reverse phase prep-HPLC to afford the title compound. LCMS (ESI+): m/z=534.3 (M+H)⁺.

Step 2: (S)-4-(((R)-2-methoxypropyl) (4-(5,6,7,8-tetrahydro-1,8-naphthyridin-2-yl) butyl)amino)-2-((5-phenylpyridin-2-yl) amino) butanoic acid To a mixture of (S)-2-((5-bromopyridin-2-yl) amino)-4-(((R)-2-methoxypropyl) (4-(5,6,7,8-tetrahydro-1,8-naphthyridin-2-yl) butyl)amino) butanoic acid (100 mg, 187 μmol) and phenylboronic acid (46 mg, 374 μmol) in dioxane (1 mL) and H₂O (0.25 mL) was added K₂CO₃ (129 mg, 936 μmol) and Pd(dppf)Cl₂.CH₂Cl₂ (15 mg, 19 μmol) and the resulting mixture was stirred at 100° C. for 2 h, cooled to rt, and then concentrated in vacuo. The crude residue was purified by reverse phase prep-HPLC to afford the title compound. LCMS (ESI+): m/z=532.3 (M+H)⁺. ¹H NMR (400 MHz, Methanol-d₄) δ ppm 8.37 (dd, J=9.37, 2.09 Hz, 1H) 8.18 (s, 1H) 7.65 (d, J=7.28 Hz, 2H) 7.59 (d, J=7.28 Hz, 1H) 7.48-7.54 (m, 2H) 7.42-7.47 (m, 1H) 7.40 (br d, J=9.26 Hz, 1H) 6.67 (d, J=7.28 Hz, 1H) 4.80-4.85 (m, 1H) 3.89 (br s, 1H) 3.58 (br s, 1H) 3.43-3.54 (m, 3H) 3.41 (s, 3H) 3.35 (br s, 2H) 3.17-3.30 (m, 2H) 2.82 (br d, J=5.73 Hz, 4H) 2.53-2.66 (m, 1H) 2.37-2.50 (m, 1H) 1.78-1.98 (m, 6H) 1.24 (d, J=6.17 Hz, 3H).

Compound 232: (S)-4-(((R)-2-methoxypropyl) (4-(5,6,7,8-tetrahydro-1,8-naphthyridin-2-yl) butyl)amino)-2-((4-phenylpyridin-2-yl) amino) butanoic acid.

Compound 233: (S)-4-(((R)-2-methoxypropyl) (4-(5,6,7,8-tetrahydro-1,8-naphthyridin-2-yl) butyl)amino)-2-((1-methyl-1H-indazol-3-yl) amino) butanoic acid: To a mixture of tert-butyl (S)-2-amino-4-(((R)-2-methoxypropyl) (4-(5,6,7,8-tetrahydro-1,8-naphthyridin-2-yl) butyl)amino) butanoate (104 mg, 240 μmol) and 3-bromo-1-methyl-1H-indazole (42 mg, 200 μmol) in THF (2 mL) was added 2.0M t-BuONa in THF (200 μL, 400 μmol) then tBuXPhos-Pd-G3 (16 mg, 20 μmol) and the resulting mixture was heated to 100° C. for 15 h, cooled to rt, and then concentrated in vacuo. The crude residue was purified by reverse phase prep-HPLC to give the title compound. LCMS (ESI+): m/z=509.3 (M+H)⁺. ¹H NMR (400 MHz, DMSO-d₆) δ ppm 7.73 (d, J=8.07 Hz, 1H) 7.24-7.34 (m, 2H) 6.99 (d, J=7.21 Hz, 1H) 6.91 (td, J=7.21, 1.10 Hz, 1H) 6.30 (br d, J=11.62 Hz, 1H) 6.20 (dd, J=7.27, 5.32 Hz, 1H) 4.13 (q, J=6.28 Hz, 1H) 3.71 (s, 3H) 3.43 (br d, J=6.11 Hz, 1H) 3.20-3.23 (m, 2H) 3.17 (d, J=9.78 Hz, 3H) 2.73-2.87 (m, 1H) 2.53-2.73 (m, 5H) 2.31-2.46 (m, 4H) 1.83-2.02 (m, 2H) 1.68-1.78 (m, 2H) 1.36-1.62 (m, 4H) 1.03 (t, J=6.60 Hz, 3H).

Compound 234: (S)-4-(((R)-2-methoxypropyl) (4-(5,6,7,8-tetrahydro-1,8-naphthyridin-2-yl) butyl)amino)-2-((1-methyl-1H-indol-3-yl) amino) butanoic acid.

Compound 235: 2-((1-methyl-1H-pyrazolo[3,4-d]pyrimidin-4-yl) amino)-4-((2-(methylsulfonyl)ethyl) (4-(5,6,7,8-tetrahydro-1,8-naphthyridin-2-yl) butyl)amino) butanoic acid.

Compound 236: (S)-2-((5-cyanopyrimidin-2-yl) amino)-4-((2-(methylsulfonyl)ethyl) (4-(5,6,7,8-tetrahydro-1,8-naphthyridin-2-yl) butyl)amino) butanoic acid: To a mixture of (S)-2-amino-4-((2-(methylsulfonyl)ethyl) (4-(5,6,7,8-tetrahydro-1,8-naphthyridin-2-yl) butyl)amino) butanoic acid hydrochloride (100 mg, 223 μmol) in THF (2 mL) and H₂O (0.5 mL) was added NaHCO₃ (94 mg, 1.11 mmol) then 2-chloropyrimidine-5-carbonitrile (37 mg, 267 μmol) and the resulting mixture was heated to 70° C. for 1 h and then cooled to rt and adjusted to pH=6 by the addition of 1 M aq. HCl and then concentrated in vacuo. The crude residue was purified by reverse phase prep-HPLC to give the title compound. LCMS (ESI+): m/z=516.2 (M+H)⁺. ¹H NMR (400 MHz, Methanol-d₄) δ ppm 8.63 (s, 2H) 7.59 (d, J=7.28 Hz, 1H) 6.66 (d, J=7.28 Hz, 1H) 4.75-4.82 (m, 1H) 3.66-3.84 (m, 4H) 3.32-3.55 (m, 6H) 3.13 (s, 3H) 2.75-2.85 (m, 4H) 2.30-2.55 (m, 2H) 1.96 (q, J=5.84 Hz, 2H) 1.83 (br s, 4H).

Compound 237: 4-((2-(methylsulfonyl)ethyl) (4-(5,6,7,8-tetrahydro-1,8-naphthyridin-2-yl) butyl)amino)-2-((5-(trifluoromethyl)pyrimidin-2-yl) amino) butanoic acid.

Compound 238: 2-((1H-pyrazolo[3,4-d]pyrimidin-4-yl) amino)-4-((2-(methylsulfonyl)ethyl) (4-(5,6,7,8-tetrahydro-1,8-naphthyridin-2-yl) butyl)amino) butanoic acid.

Compound 239: 2-((5-bromopyrimidin-2-yl) amino)-4-((2-(methylsufonyl)ethyl) (4-(5,6,7,8-tetrahydro-1,8-naphthyridin-2-yl) butyl)amino) butanoic acid.

Compound 240: 2-((6-(1H-pyrazol-1-yl) pyrimidin-4-yl) amino)-4-((2-(methylsulfonyl)ethyl) (4-(5,6,7,8-tetrahydro-1,8-naphthyridin-2-yl) butyl)amino) butanoic acid.

Compound 241: 4-((2-(methylsulfonyl)ethyl) (4-(5,6,7,8-tetrahydro-1,8-naphthyridin-2-yl) butyl)amino)-2-((2-(trifluoromethyl)pyrimidin-4-yl) amino) butanoic acid.

Compound 242: (S)-2-((5-cyclopropylpyrimidin-2-yl) amino)-4-((2-(methylsulfonyl)ethyl) (4-(5,6,7,8-tetrahydro-1,8-naphthyridin-2-yl) butyl)amino) butanoic acid.

Compound 243: (S)-2-((3-cyanopyrazin-2-yl) amino)-4-((2-(methylsufonyl)ethyl) (4-(5,6,7,8-tetrahydro-1,8-naphthyridin-2-yl) butyl)amino) butanoic acid: To a mixture of (S)-2-amino-4-((2-(methylsulfonyl)ethyl) (4-(5,6,7,8-tetrahydro-1,8-naphthyridin-2-yl) butyl)amino) butanoic acid hydrochloride (100 mg, 223 μmol) in i-PrOH (2 mL) was added DIPEA (194 μL, 1.11 mmol) then 3-chloropyrazine-2-carbonitrile (35 mg, 251 μmol) and the resulting mixture was heated to 70° C. for 1 h and then cooled to rt and adjusted to pH=6 by the addition of 1 M aq. HCl and then concentrated in vacuo. The crude residue was purified by reverse phase prep-HPLC to give the title compound. LCMS (ESI+): m/z=516.2 (M+H)⁺. ¹H NMR (400 MHz, Methanol-d₄) δ ppm 8.30 (d, J=2.20 Hz, 1H) 8.00 (d, J=2.43 Hz, 1H) 7.59 (d, J=7.50 Hz, 1H) 6.65 (d, J=7.50 Hz, 1H) 4.81-4.85 (m, 1H) 3.65-3.83 (m, 4H) 3.32-3.54 (m, 6H) 3.12 (s, 3H) 2.76-2.86 (m, 4H) 2.51-2.61 (m, 1H) 2.34-2.44 (m, 1H) 1.92-2.00 (m, 2H) 1.82 (br d, J=6.17 Hz, 4H).

Compound 244: 4-((2-(methylsulfonyl)ethyl) (4-(5,6,7,8-tetrahydro-1,8-naphthyridin-2-yl) butyl)amino)-2-((2-(pyridin-3-yl) quinazolin-4-yl) amino) butanoic acid.

Compound 245: 4-((3,3-difluoropropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 246: (S)-2-((5-cyanopyrimidin-2-yl) amino)-4-((3,3-difluoropropyl) (4-(5,6,7,8-tetrahydro-1,8-naphthyridin-2-yl) butyl)amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 μmol) in THF (4 mL) and H₂O (1 mL) was added 2-chloropyrimidine-5-carbonitrile (49 mg, 353 μmol) and NaHCO₃ (135 mg, 1.61 mmol) and the resulting mixture was stirred at 50° C. for 1 h and then concentrated in vacuo. The crude residue was purified by reverse phase prep-HPLC to give the title compound. LCMS (ESI+): m/z=488.2 (M+H)⁺. ¹H NMR (400 MHz, D₂O) δ ppm 8.59 (s, 2H) 7.47 (d, J=7.34 Hz, 1H) 6.50 (d, J=7.46 Hz, 1H) 5.86-6.21 (m, 1H) 4.58 (dd, J=5.38, 8.07 Hz, 1H) 3.13-3.46 (m, 8H) 2.56-2.80 (m, 4H) 2.18-2.44 (m, 4H) 1.78-1.88 (m, 2H) 1.57-1.75 (m, 4H).

Compound 247: 4-((3,3-difluoropropyl) (4-(5,6,7,8-tetrahydro-1,8-naphthyridin-2-yl) butyl)amino)-2-((5-(trifluoromethyl)pyrimidin-2-yl) amino) butanoic acid.

Compound 248: (S)-2-((1H-pyrazolo[3,4-d]pyrimidin-4-yl) amino)-4-((3,3-difluoropropyl) (4-(5,6,7,8-tetrahydro-1,8-naphthyridin-2-yl) butyl)amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 μmol) in THF (4 mL) and H₂O (1 mL) was added 4-chloro-1H-pyrazolo[3,4-d]pyrimidine (55 mg, 353 μmol) and NaHCO₃ (135 mg, 1.61 mmol) and the resulting mixture was heated to 70° C. for 1 h and then cooled to rt and then concentrated in vacuo. The crude residue was purified by prep-HPLC to give the title compound. LCMS (ESI+): m/z=503.3 (M+H)⁺. ¹H NMR (400 MHz, Methanol-d₄) δ ppm 8.21 (s, 1H) 8.14 (s, 1H) 7.37 (br d, J=7.09 Hz, 1H) 6.50 (d, J=7.34 Hz, 1H) 5.78-6.17 (m, 1H) 4.86 (br s, 1H) 3.42 (br s, 2H) 2.63-3.09 (m, 10H) 2.26-2.42 (m, 1H) 1.97-2.20 (m, 3H) 1.57-1.96 (m, 6H).

Compound 249: 2-((5-bromopyrimidin-2-yl) amino)-4-((3,3-difluoropropyl) (4-(5,6,7,8-tetrahydro-1,8-naphthyridin-2-yl) butyl)amino) butanoic acid.

Compound 250: (S)-2-((6-(1H-pyrazol-1-yl) pyrimidin-4-yl) amino)-4-((3,3-difluoropropyl) (4-(5,6,7,8-tetrahydro-1,8-naphthyridin-2-yl) butyl)amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 μmol) in DMA (3 mL) was added 4-chloro-6-(1H-pyrazol-1-yl) pyrimidine (64 mg, 353 μmol) and DIPEA (280 μL, 1.61 mmol) and the resulting mixture was stirred at 70° C. for 16 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=529.2 (M+H)⁺. ¹H NMR (400 MHz, Methanol-d₄) δ ppm 8.52 (d, J=2.57 Hz, 1H) 8.30 (br s, 1H) 7.77 (d, J=1.10 Hz, 1H) 7.32 (br d, J=6.60 Hz, 1H) 6.96 (br s, 1H) 6.47-6.58 (m, 2H) 5.83-6.16 (m, 1H) 4.39-4.62 (m, 1H) 3.36-3.45 (m, 2H) 2.65-2.96 (m, 10H) 2.03-2.26 (m, 4H) 1.84 (br d, J=17.12 Hz, 4H) 1.63-1.74 (m, 2H).

Compound 251: 4-((3,3-difluoropropyl) (4-(5,6,7,8-tetrahydro-1,8-naphthyridin-2-yl) butyl)amino)-2-((2-(trifluoromethyl)pyrimidin-4-yl) amino) butanoic acid.

Compound 252: 2-((5-cyclopropylpyrimidin-2-yl) amino)-4-((3,3-difluoropropyl) (4-(5,6,7,8-tetrahydro-1,8-naphthyridin-2-yl) butyl)amino) butanoic acid.

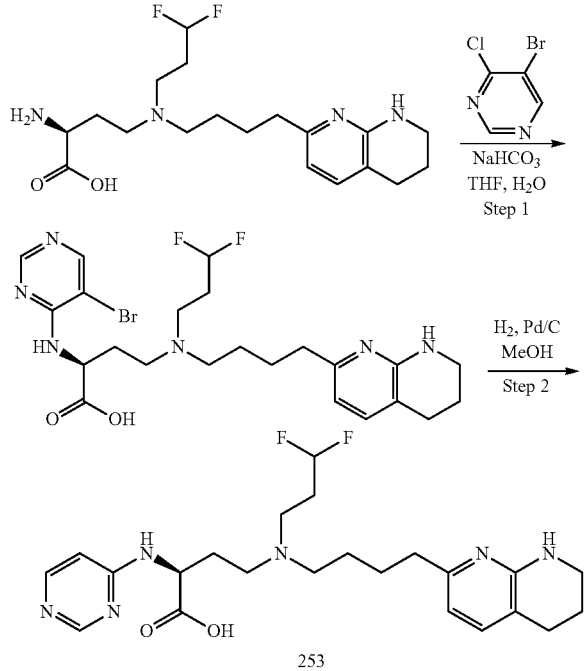

Scheme 26, Compound 253

Step 1: (S)-2-((5-bromopyrimidin-4-yl) amino)-4-((3,3-difluoropropyl) (4-(5,6,7,8-tetrahydro-1,8-naphthyridin-2-yl) butyl)amino) butanoic acid To a solution of (S)-2-amino-4-((3,3-difluoropropyl) (4-(5,6,7,8-tetrahydro-1,8-naphthyridin-2-yl) butyl)amino) butanoic acid (140 mg, 344 μmol) in THF (4 mL) and H₂O (1 mL) was added 5-bromo-4-chloropyrimidine (73 mg, 378 μmol) and NaHCO₃ (144 mg, 1.72 mmol) and the resulting mixture was heated to 60° C. for 17 h and then cooled to rt and then concentrated in vacuo. The crude residue was used without further purification. LCMS (ESI+): m/z=540.9 (M+H)⁺.

Step 2: (S)-4-((3,3-difluoropropyl) (4-(5,6,7,8-tetrahydro-1,8-naphthyridin-2-yl) butyl)amino)-2-(pyrimidin-4-ylamino) butanoic acid To a mixture of (S)-2-((5-bromopyrimidin-4-yl) amino)-4-((3,3-difluoropropyl) (4-(5,6,7,8-tetrahydro-1,8-naphthyridin-2-yl) butyl)amino) butanoic acid (186 mg, 344 μmol) in MeOH (10 mL) was 10 wt % added Pd/C (100 mg) and the resulting mixture was stirred under an H₂ atmosphere for 16 h. The mixture was filtered and then concentrated in vacuo. The crude residue was purified by reverse phase prep-HPLC to give the title compound. LCMS (ESI+): m/z=463.2 (M+H)⁺. ¹H NMR (400 MHz, Methanol-d₄) δ ppm 8.35 (s, 1H) 8.00 (br s, 1H) 7.35 (d, J=7.34 Hz, 1H) 6.57 (br d, J=4.52 Hz, 1H) 6.49 (d, J=7.34 Hz, 1H) 5.80-6.13 (m, 1H) 4.54 (br s, 1H) 3.37-3.47 (m, 2H) 2.58-3.01 (m, 10H) 1.61-2.26 (m, 10H).

Compound 254: (S)-2-((3-cyanopyrazin-2-yl) amino)-4-((3,3-difluoropropyl) (4-(5,6,7,8-tetrahydro-1,8-naphthyridin-2-yl) butyl)amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 μmol) in i-PrOH (3 mL) was added 3-chloropyrazine-2-carbonitrile (49 mg, 353 μmol) and DIPEA (280 μL, 1.61 mmol) and the resulting mixture was stirred at 70° C. for 1 h and then concentrated in vacuo. The crude residue was purified by reverse phase prep-HPLC to give the title compound. LCMS (ESI+): m/z=488.1 (M+H)+. 1H NMR (400 MHz, Methanol-d4) δ ppm 8.25 (d, J=2.45 Hz, 1H) 7.88 (d, J=2.45 Hz, 1H) 7.39 (d, J=7.34 Hz, 1H) 6.52 (d, J=7.34 Hz, 1H) 5.81-6.16 (m, 1H) 4.57 (t, J=5.38 Hz, 1H) 3.39-3.47 (m, 1H) 3.39-3.47 (m, 1H) 2.90-3.02 (m, 2H) 2.64-2.82 (m, 8H) 2.08-2.30 (m, 4H) 1.74-1.94 (m, 4H) 1.59-1.69 (m, 2H).

Compound 255: (S)-4-((3,3-difluoropropyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 μmol) in THF (4 mL) and H2O (1 mL) was added 7-chloro-2-methyl-2H-pyrazolo[4,3-d]pyrimidine (66 mg, 353 μmol) and NaHCO3 (134.93 mg, 1.61 mmol) and the resulting mixture was heated to 70° C. for 1 h and then cooled to rt and then concentrated in vacuo. The crude residue was purified by prep-HPLC to give the title compound. LCMS (ESI+): m/z=517.3 (M+H)+. 1H NMR (400 MHz, Methanol-d4) δ ppm 8.21 (s, 1H) 8.04 (s, 1H) 7.38 (d, J=7.34 Hz, 1H) 6.50 (d, J=7.21 Hz, 1H) 5.73-6.17 (m, 1H) 4.76-4.87 (m, 1H) 3.94 (s, 3H) 3.43 (br t, J=5.07 Hz, 2H) 2.59-3.07 (m, 10H) 2.26-2.45 (m, 1H) 1.61-2.19 (m, 9H).

Compound 256: (S)-4-((3,3-difluoropropyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 μmol) in DMA (3 mL) was added 4-chloro-2-(pyridin-3-yl) quinazoline (95 mg, 353 μmol) and DIPEA (280 μL, 1.61 mmol) and the resulting mixture was stirred at 70° C. for 16 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=590.2 (M+H)+. 1H NMR (400 MHz, Methanol-d4) δ ppm 9.55 (dd, J=0.67, 2.02 Hz, 1H) 8.81 (td, J=1.91, 8.04 Hz, 1H) 8.61 (dd, J=1.71, 4.89 Hz, 1H) 8.12 (d, J=7.58 Hz, 1H) 7.76-7.92 (m, 2H) 7.44-7.57 (m, 2H) 7.27 (d, J=7.34 Hz, 1H) 6.42 (d, J=7.34 Hz, 1H) 5.77-6.14 (m, 1H) 5.00 (t, J=6.11 Hz, 1H) 3.24 (t, J=5.62 Hz, 2H) 2.60-3.09 (m, 10H) 2.23-2.51 (m, 2H) 2.00-2.17 (m, 2H) 1.74-1.90 (m, 4H) 1.55-1.72 (m, 2H).

Scheme 27, Compound 257

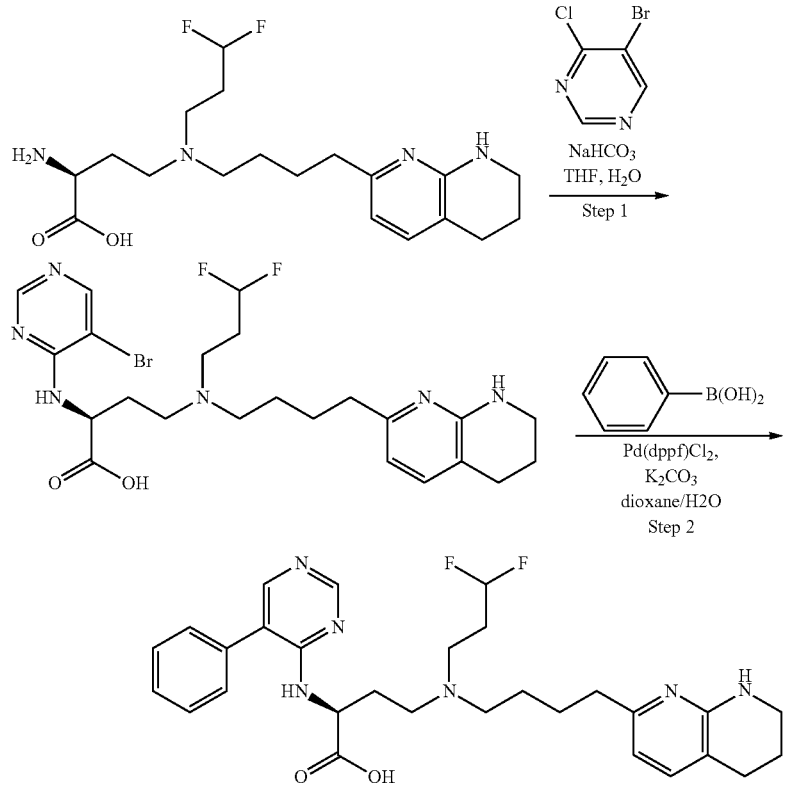

257

Step 1: (S)-2-((5-bromopyrimidin-4-yl) amino)-4-((3,3-difluoropropyl) (4-(5,6,7,8-tetrahydro-1,8-naphthyridin-2-yl) butyl)amino) butanoic acid To a mixture of (S)-2-amino-4-((3,3-difluoropropyl) (4-(5,6,7,8-tetrahydro-1,8-naphthyridin-2-yl) butyl)amino) butanoic acid (140 mg, 344 µmol) in THF (4 mL) and H$_2$O (1 mL) was added 5-bromo-4-chloropyrimidine (73 mg, 378 µmol) and NaHCO$_3$ (144 mg, 1.72 mmol) and the resulting mixture was stirred for 17 h at 60° C. and then cooled to rt and concentrated in vacuo to give the title compound that was used without further purification. LCMS (ESI+): m/z=541.0 (M+H)$^+$.

Step 2: (S)-4-((3,3-difluoropropyl) (4-(5,6,7,8-tetrahydro-1,8-naphthyridin-2-yl) butyl)amino)-2-((5-phenylpyrimidin-4-yl) amino) butanoic acid To a mixture of (S)-2-((5-bromopyrimidin-4-yl) amino)-4-((3,3-difluoropropyl) (4-(5,6,7,8-tetrahydro-1,8-naphthyridin-2-yl) butyl)amino) butanoic acid (186 mg, 344 µmol) in dioxane (4 mL) and H$_2$O (1 mL) was added phenylboronic acid (63 mg, 515 µmol), K$_2$CO$_3$ (95 mg, 687 µmol) and Pd(dppf)Cl$_2$ (25 mg, 34 µmol), the mixture was stirred for 2 h at 100° C. and then cooled to rt and concentrated in vacuo. The crude residue was purified by reverse phase prep-HPLC to give the title compound. LCMS (ESI+): m/z=539.9 (M+H)$^+$. $^1$H NMR (400 MHz, Methanol-d$_4$) δ ppm 8.45 (s, 1H) 7.95 (s, 1H) 7.32-7.57 (m, 6H) 6.48 (d, J=7.34 Hz, 1H) 5.79-6.12 (m, 1H) 4.61 (t, J=5.26 Hz, 1H) 3.36-3.45 (m, 2H) 2.53-2.98 (m, 10H) 1.85-2.25 (m, 6H) 1.45-1.71 (m, 4H).

Compound 258: (S)-4-((3,3-difluoropropyl) (4-(5,6,7,8-tetrahydro-1,8-naphthyridin-2-yl) butyl)amino)-2-((6-phenylpyrimidin-4-yl) amino) butanoic acid: To a mixture of (S)-2-amino-4-((3,3-difluoropropyl) (4-(5,6,7,8-tetrahydro-1,8-naphthyridin-2-yl) butyl)amino) butanoic acid (130 mg, 321 µmol) in THF (4 mL) and H$_2$O (1 mL) was added 4-chloro-6-phenylpyrimidine (67 mg, 353 µmol) and NaHCO$_3$ (135 mg, 1.61 mmol) and the resulting mixture was stirred for 17 h at 70° C. and then cooled to rt and concentrated in vacuo. The crude residue was purified by chiral SFC top give the title compound. LCMS (ESI+): m/z=539.2 (M+H)$^+$. $^1$H NMR (400 MHz, Methanol-d$_4$) δ ppm 8.45 (s, 1H) 7.95 (s, 1H) 7.32-7.57 (m, 6H) 6.48 (d, J=7.34 Hz, 1H) 5.79-6.12 (m, 1H) 4.61 (t, J=5.26 Hz, 1H) 3.36-3.45 (m, 2H) 2.53-2.98 (m, 10H) 1.85-2.25 (m, 6H) 1.45-1.71 (m, 4H).

Compound 259: (S)-4-((3,3-difluoropropyl) (4-(5,6,7,8-tetrahydro-1,8-naphthyridin-2-yl) butyl)amino)-2-((2-phenylpyrimidin-4-yl) amino) butanoic acid.

Compound 260: 4-((3-fluoropropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 261: (S)-2-((5-cyanopyrimidin-2-yl) amino)-4-((3-fluoropropyl) (4-(5,6,7,8-tetrahydro-1,8-naphthyridin-2-yl) butyl)amino) butanoic acid: To a mixture of (S)-2-amino-4-((3-fluoropropyl) (4-(5,6,7,8-tetrahydro-1,8-naphthyridin-2-yl) butyl)amino) butanoic acid (140 mg, 344 µmol) in THF (1 mL) and H$_2$O (0.25 mL) was added 2-chloropyrimidine-5-carbonitrile (53 mg, 378 µmol) and NaHCO$_3$ (144 mg, 1.72 mmol) and the resulting mixture was stirred at 50° C. for 1 h and then concentrated in vacuo. The crude residue was purified by reverse phase prep-HPLC to give the title compound. LCMS (ESI+): m/z=470.1 (M+H)$^+$. $^1$H NMR (400 MHz, Methanol-d$_4$) δ ppm 8.50-8.65 (m, 2H) 7.28 (d, J=7.21 Hz, 1H) 6.47 (d, J=7.34 Hz, 1H) 4.58 (t, J=5.62 Hz, 1H) 4.37-4.49 (m, 2H) 3.38-3.45 (m, 2H) 2.90-3.23 (m, 6H) 2.73 (t, J=6.24 Hz, 2H) 2.58-2.67 (m, 2H) 1.98-2.31 (m, 4H) 1.88-1.94 (m, 2H) 1.66-1.83 (m, 4H).

Compound 262: 4-((3-fluoropropyl) (4-(5,6,7,8-tetrahydro-1,8-naphthyridin-2-yl) butyl)amino)-2-((5-(trifluoromethyl)pyrimidin-2-yl) amino) butanoic acid.

Compound 263: (S)-2-((1H-pyrazolo[3,4-d]pyrimidin-4-yl) amino)-4-((3-fluoropropyl) (4-(5,6,7,8-tetrahydro-1,8-naphthyridin-2-yl) butyl)amino) butanoic acid: To a mixture of (S)-2-amino-4-((3-fluoropropyl) (4-(5,6,7,8-tetrahydro-1,8-naphthyridin-2-yl) butyl)amino) butanoic acid (100 mg, 259 µmol) in THF (1 mL) and H$_2$O (0.25 mL) was added 4-chloro-1H-pyrazolo[3,4-d]pyrimidine (44 mg, 285 µmol) and NaHCO$_3$ (109 mg, 1.30 mmol) and the resulting mixture was heated to 70° C. for 1 h and then cooled to rt and then concentrated in vacuo. The crude residue was purified by prep-HPLC to give the title compound. LCMS (ESI+): m/z=485.3 (M+H)$^+$. $^1$H NMR (400 MHz, Methanol-d$_4$) δ ppm 8.25 (br s, 1H) 8.17 (s, 1H) 7.23 (br d, J=7.09 Hz, 1H) 6.43 (d, J=7.34 Hz, 1H) 4.78 (br s, 1H) 4.40-4.64 (m, 2H) 3.39 (br s, 2H) 2.88-3.29 (m, 6H) 2.61-2.75 (m, 4H) 2.29-2.43 (m, 1H) 2.18 (td, J=5.00, 14.95 Hz, 1H) 1.95-2.11 (m, 2H) 1.68-1.92 (m, 6H).

Compound 264: (S)-2-((5-bromopyrimidin-2-yl) amino)-4-((3-fluoropropyl) (4-(5,6,7,8-tetrahydro-1,8-naphthyridin-2-yl) butyl)amino) butanoic acid: To a solution of (S)-2-amino-4-((3-fluoropropyl) (4-(5,6,7,8-tetrahydro-1,8-naphthyridin-2-yl) butyl)amino) butanoic acid (140 mg, 344 µmol) in THF (2 mL) and H$_2$O (0.5 mL) was added 5-bromo-2-chloro-pyrimidine (73 mg, 378 µmol) and NaHCO$_3$ (144 mg, 1.72 mmol) and the resulting mixture was stirred at 70° C. for 6 h and then concentrated in vacuo. The crude residue was purified by reverse phase prep-HPLC to give the title compound LCMS (ESI+): m/z=523.1 (M+H)$^+$. $^1$H NMR (400 MHz, D$_2$O) δ ppm 8.38 (d, J=2.20 Hz, 2H) 7.45 (d, J=7.34 Hz, 1H) 6.48 (dd, J=4.59, 7.27 Hz, 1H) 4.42-4.63 (m, 3H) 3.26-3.40 (m, 6H) 3.16 (br d, J=7.58 Hz, 2H) 2.69 (br t, J=6.11 Hz, 2H) 2.62 (br d, J=4.28 Hz, 2H) 2.38 (qd, J=5.43, 18.94 Hz, 1H) 2.17-2.28 (m, 1H) 1.98-2.13 (m, 2H) 1.82 (q, J=5.93 Hz, 2H) 1.65 (br d, J=3.30 Hz, 4H).

Compound 265: 2-((6-(1H-pyrazol-1-yl) pyrimidin-4-yl) amino)-4-((3-fluoropropyl) (4-(5,6,7,8-tetrahydro-1,8-naphthyridin-2-yl) butyl)amino) butanoic acid.

Compound 266: (S)-4-((3-fluoropropyl) (4-(5,6,7,8-tetrahydro-1,8-naphthyridin-2-yl)butyl) amino)-2-((2-(trifluoromethyl)pyrimidin-4-yl) amino)butanoic acid: To a solution of (S)-2-amino-4-((3-fluoropropyl) (4-(5,6,7,8-tetrahydro-1,8-naphthyridin-2-yl) butyl)amino) butanoic acid (150 mg, 368 µmol) in THF (4 mL) and H₂O (1 mL) was added 4-chloro-2-(trifluoromethyl)pyrimidine (74 mg, 405 µmol) and NaHCO₃ (155 mg, 1.84 mmol) and the resulting mixture was stirred at 70° C. for 1 h and then concentrated in vacuo. The crude residue was purified by reverse phase prep-HPLC to give the title compound. LCMS (ESI+): m/z=513.1 (M+H)⁺. ¹H NMR (400 MHz, D₂O) δ ppm 8.22 (br d, J=5.75 Hz, 1H) 7.49 (br d, J=7.09 Hz, 1H) 6.84 (d, J=6.24 Hz, 1H) 6.52 (br d, J=7.34 Hz, 1H) 5.91-6.26 (m, 1H) 4.72 (br s, 1H) 3.14-3.50 (m, 8H) 2.61-2.78 (m, 4H) 2.21-2.52 (m, 4H) 1.82-1.94 (m, 2H) 1.69 (br s, 4H).

Compound 267: (S)-2-((5-cyclopropylpyrimidin-2-yl) amino)-4-((3-fluoropropyl) (4-(5,6,7,8-tetrahydro-1,8-naphthyridin-2-yl) butyl)amino) butanoic acid: To a mixture of (S)-2-amino-4-((3-fluoropropyl) (4-(5,6,7,8-tetrahydro-1,8-naphthyridin-2-yl) butyl)amino) butanoic acid (150 mg, 368 µmol) in THF (4 mL) and H₂O (1 mL) was added 1-cyclopropyl-4-fluorobenzene (56 mg, 405 µmol) and NaHCO₃ (155 mg, 1.84 mmol) and the resulting mixture was stirred at 70° C. for 6 h and then allowed to cool to rt and then concentrated in vacuo. The crude residue was purified by reverse phase prep-HPLC to give the title compound. LCMS (ESI+): m/z=485.2 (M+H)⁺. ¹H NMR (400 MHz, D₂O) δ ppm 8.32 (s, 2H) 7.45 (d, J=7.34 Hz, 1H) 6.49 (d, J=7.34 Hz, 1H) 4.54-4.64 (m, 2H) 4.45 (t, J=5.44 Hz, 1H) 3.13-3.40 (m, 8H) 2.60-2.72 (m, 4H) 1.97-2.44 (m, 4H) 1.78-1.86 (m, 3H) 1.66 (br d, J=3.67 Hz, 4H) 0.90-1.00 (m, 2H) 0.57-0.68 (m, 2H).

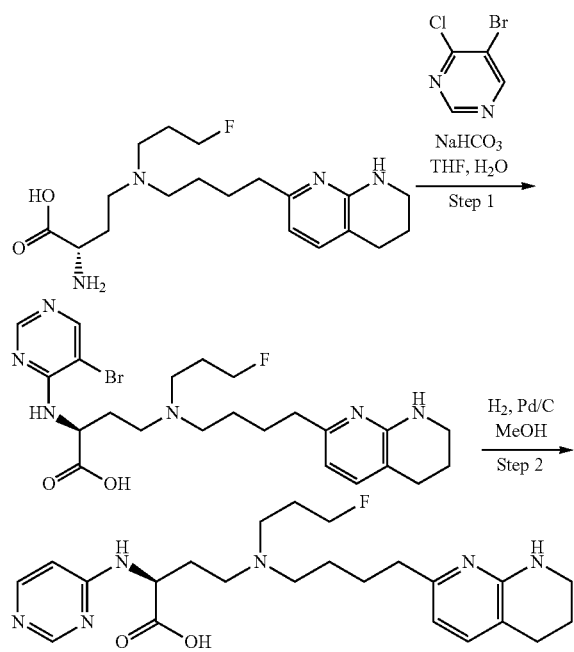

Scheme 28, Compound 268

268

Step 1: (S)-2-((5-bromopyrimidin-4-yl) amino)-4-((3-fluoropropyl) (4-(5,6,7,8-tetrahydro-1,8-naphthyridin-2-yl) butyl)amino) butanoic acid To a solution of (S)-2-amino-4-((3-fluoropropyl) (4-(5,6,7,8-tetrahydro-1,8-naphthyridin-2-yl) butyl)amino) butanoic acid (140 mg, 344 µmol) in THF (4 mL) and H₂O (1 mL) was added 5-bromo-4-chloropyrimidine (73 mg, 378 µmol) and NaHCO₃ (144 mg, 1.72 mmol) and the resulting mixture was stirred for 17 h at 60° C. and then cooled to rt and concentrated in vacuo to give the title compound that was used without further purification. LCMS (ESI+): m/z=523.2 (M+H)⁺.

Step 2: (S)-4-((3-fluoropropyl) (4-(5,6,7,8-tetrahydro-1,8-naphthyridin-2-yl) butyl)amino)-2-(pyrimidin-4-ylamino) butanoic acid To a mixture of (S)-2-((5-bromopyrimidin-4-yl) amino)-4-((3-fluoropropyl) (4-(5,6,7,8-tetrahydro-1,8-naphthyridin-2-yl) butyl)amino) butanoic acid (170 mg, 325 µmol) in MeOH (10 mL) was added 10 wt % Pd/C (200 mg) and the resulting mixture was stirred under an H₂ atmosphere for 16 h and then filtered and concentrated in vacuo. The crude residue was purified by reverse phase prep-HPLC to give the title compound. LCMS (ESI+): m/z=445.2 (M+H)⁺. ¹H NMR (400 MHz, Methanol-d₄) δ ppm 8.40 (s, 1H) 8.02 (br d, J=5.26 Hz, 1H) 7.24 (d, J=7.21 Hz, 1H) 6.61 (br d, J=5.87 Hz, 1H) 6.45 (d, J=7.34 Hz, 1H) 4.54-4.63 (m, 1H) 4.33-4.51 (m, 2H) 3.36-3.43 (m, 2H) 2.89-3.27 (m, 6H) 2.72 (t, J=6.30 Hz, 2H) 2.57-2.66 (m, 2H) 1.96-2.29 (m, 4H) 1.85-1.94 (m, 2H) 1.68-1.81 (m, 4H).

Compound 269: (S)-2-((3-cyanopyrazin-2-yl) amino)-4-((3-fluoropropyl) (4-(5,6,7,8-tetrahydro-1,8-naphthyridin-2-yl) butyl)amino) butanoic acid: To a mixture of (S)-2-amino-4-((3-fluoropropyl) (4-(5,6,7,8-tetrahydro-1,8-naphthyridin-2-yl) butyl)amino) butanoic acid (140 mg, 344 µmol) in i-PrOH (3 mL) was added 3-chloropyrazine-2-carbonitrile (53 mg, 378 µmol) and DIPEA (299 µL, 1.72 mmol) and the resulting mixture was stirred at 70° C. for 1 h and then concentrated in vacuo. The crude residue was purified by reverse phase prep-HPLC to give the title compound. LCMS (ESI+): m/z=470.1 (M+H)⁺. ¹H NMR (400 MHz, Methanol-d₄) δ ppm 8.26 (d, J=2.45 Hz, 1H) 7.90 (d, J=2.45 Hz, 1H) 7.25 (d, J=7.34 Hz, 1H) 6.45 (d, J=7.34 Hz, 1H) 4.59 (t, J=5.69 Hz, 1H) 4.44-4.49 (m, 2H) 3.37-3.42 (m, 2H) 2.83-3.23 (m, 6H) 2.72 (t, J=6.17 Hz, 2H) 2.59-2.66 (m, 2H) 1.98-2.31 (m, 4H) 1.86-1.93 (m, 2H) 1.65-1.82 (m, 4H).

Compound 270: (S)-4-((3-fluoropropyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a solution of (S)-2-amino-4-((3-fluoropropyl) (4-(5,6,7,8-tetrahydro-1,8-naphthyridin-2-yl) butyl)amino) butanoic acid (100 mg, 259 µmol) in THF (1 mL) and H₂O (0.25 mL) was added 7-chloro-2-methyl-2H-pyrazolo[4,3-d]pyrimidine (53 mg, 285 µmol) and NaHCO₃ (109 mg, 1.30 mmol) and the resulting mixture was heated to 70° C. for 1 h and then cooled to rt and then concentrated in vacuo. The crude residue was purified by prep-HPLC to give the title compound. LCMS (ESI+): m/z=499.3 (M+H)⁺. ¹H NMR (400 MHz, Methanol-d₄) δ ppm 8.27 (s, 1H) 8.07-8.16 (m, 1H) 7.24 (br d, J=7.21 Hz, 1H) 6.44 (d, J=7.34 Hz, 1H) 4.78 (br s, 1H) 4.41-4.62 (m, 2H) 3.97 (s, 3H) 3.39 (br s, 2H) 2.84-3.29 (m, 6H) 2.58-2.78 (m, 4H) 2.26-2.44 (m, 1H) 1.95-2.22 (m, 3H) 1.65-1.93 (m, 6H).

Compound 271: 4-((3-fluoropropyl) (4-(5,6,7,8-tetrahydro-1,8-naphthyridin-2-yl) butyl)amino)-2-((2-(pyridin-3-yl) quinazolin-4-yl) amino) butanoic acid.

Scheme 29, Compound 272

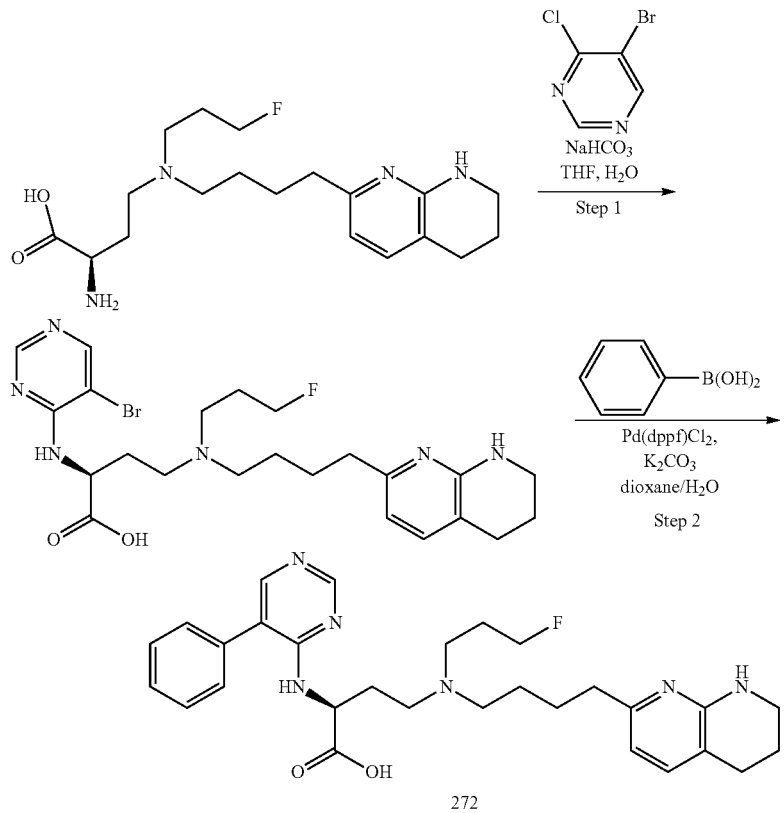

Step 1: (S)-2-((5-bromopyrimidin-4-yl) amino)-4-((3-fluoropropyl) (4-(5,6,7,8-tetrahydro-1,8-naphthyridin-2-yl) butyl)amino) butanoic acid To a mixture of (S)-2-amino-4-((3-fluoropropyl) (4-(5,6,7,8-tetrahydro-1,8-naphthyridin-2-yl) butyl)amino) butanoic acid (140 mg, 344 µmol) in THF (4 mL) and H$_2$O (1 mL) was added 5-bromo-4-chloropyrimidine (73 mg, 378 µmol) and NaHCO$_3$ (144 mg, 1.72 mmol) and the resulting mixture was stirred for 17 h at 60° C. and then cooled to rt and concentrated in vacuo to give the title compound that was used without further purification. LCMS (ESI+): m/z=523.2 (M+H)$^+$.

Step 2: (S)-4-((3-fluoropropyl) (4-(5,6,7,8-tetrahydro-1,8-naphthyridin-2-yl) butyl)amino)-2-((5-phenylpyrimidin-4-yl) amino) butanoic acid To a mixture of (S)-2-((5-bromopyrimidin-4-yl) amino)-4-((3-fluoropropyl) (4-(5,6,7,8-tetrahydro-1,8-naphthyridin-2-yl) butyl)amino) butanoic acid (170 mg, 325 µmol) in dioxane (4 mL) and H$_2$O (1 mL) was added phenylboronic acid (59 mg, 487 µmol), K$_2$CO$_3$ (90 mg, 650 µmol) and Pd(dppf)Cl$_2$ (24 mg, 32 µmol) and the resulting mixture was stirred for 2 h at 100° C. and then cooled to rt and then concentrated in vacuo. The crude residue was purified by reverse phase prep-HPLC to give the title compound. LCMS (ESI+): m/z=521.3 (M+H)$^+$. $^1$H NMR (400 MHz, Methanol-d$_4$) δ ppm 8.47 (s, 1H) 7.99 (s, 1H) 7.51-7.58 (m, 2H) 7.41-7.49 (m, 3H) 7.19-7.24 (m, 1H) 6.42 (d, J=7.34 Hz, 1H) 4.56 (t, J=5.62 Hz, 1H) 4.42-4.49 (m, 2H) 3.37 (dd, J=4.83, 6.42 Hz, 2H) 2.84-3.25 (m, 6H) 2.70 (t, J=6.24 Hz, 2H) 2.57 (br t, J=6.72 Hz, 2H) 2.19 (q, J=5.75 Hz, 2H) 1.83-2.09 (m, 4H) 1.58-1.77 (m, 4H).

Scheme 30, Compound 273

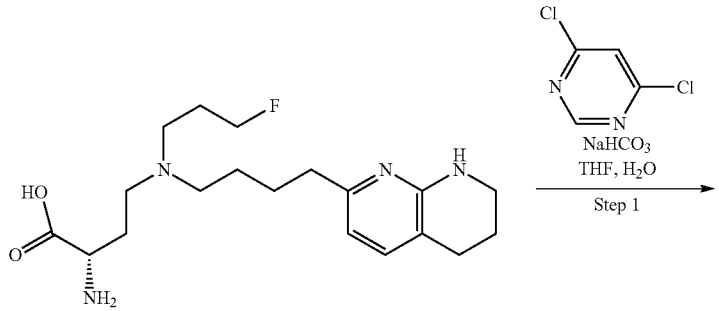

-continued

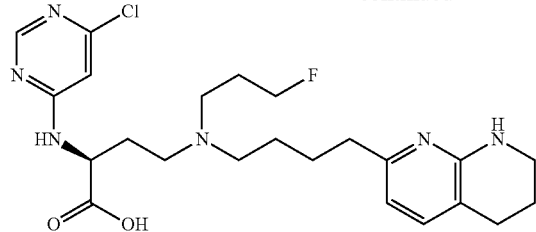 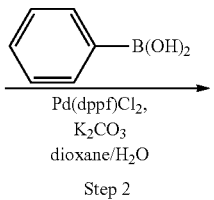

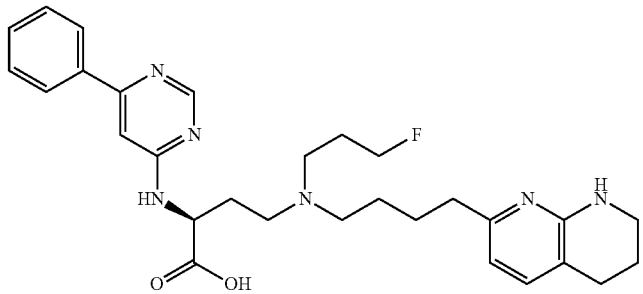

273

(S)-2-((6-chloropyrimidin-4-yl) amino)-4-((3-fluoro-propyl) (4-(5,6,7,8-tetrahydro-1,8-naphthyridin-2-yl) butyl)amino) butanoic acid To a solution of (S)-2-amino-4-((3-fluoropropyl) (4-(5,6,7,8-tetrahydro-1,8-naphthyridin-2-yl) butyl)amino) butanoic acid (140 mg, 344 μmol) in THF (4 mL) and $H_2O$ (1 mL) was added 4,6-dichloropyrimidine (56 mg, 378 μmol) and $NaHCO_3$ (144 mg, 1.72 mmol) and the resulting mixture was stirred at 60° C. for 17 h and then allowed to cool to rt and then concentrated in vacuo to give the title compound that was used without further purification. LCMS (ESI+): m/z=479.3 (M+H)+.

(S)-4-((3-fluoropropyl) (4-(5,6,7,8-tetrahydro-1,8-naphthyridin-2-yl) butyl)amino)-2-((6-phenylpyrimidin-4-yl) amino) butanoic acid To a mixture of (S)-2-((6-chloropyrimidin-4-yl) amino)-4-((3-fluoropropyl) (4-(5,6,7,8-tetrahydro-1,8-naphthyridin-2-yl) butyl)amino) butanoic acid (164 mg, 342 μmol) in dioxane (4 mL) and $H_2O$ (1 mL) was added phenylboronic acid (63 mg, 514 μmol), $K_2CO_3$ (95 mg, 685 μmol) and $Pd(dppf)Cl_2$ (25 mg, 34 μmol) and the resulting mixture was stirred for 2 h at 100° C. and then cooled to rt and concentrated in vacuo. The crude residue was purified by reverse phase prep-HPLC to give the title compound. LCMS (ESI+): m/z=539.9 (M+H)+. $^1H$ NMR (400 MHz, Methanol-$d_4$) δ ppm 8.45 (s, 1H) 7.95 (s, 1H) 7.32-7.57 (m, 6H) 6.48 (d, J=7.34 Hz, 1H) 5.79-6.12 (m, 1H) 4.61 (t, J=5.26 Hz, 1H) 3.36-3.45 (m, 2H) 2.53-2.98 (m, 10H) 1.85-2.25 (m, 6H) 1.45-1.71 (m, 4H).

Compound 274: 4-(((S)-2-fluoro-3-methoxypropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 275: 2-((5-cyanopyrimidin-2-yl) amino)-4-(((S)-2-fluoro-3-methoxypropyl) (4-(5,6,7,8-tetrahydro-1,8-naphthyridin-2-yl) butyl)amino) butanoic acid.

Compound 276: 4-(((S)-2-fluoro-3-methoxypropyl) (4-(5,6,7,8-tetrahydro-1,8-naphthyridin-2-yl) butyl)amino)-2-((5-(trifluoromethyl)pyrimidin-2-yl) amino) butanoic acid.

Compound 277: (S)-4-(((S)-2-fluoro-3-methoxypropyl) (4-(5,6,7,8-tetrahydro-1,8-naphthyridin-2-yl) butyl)amino)-2-(pyridin-2-ylamino) butanoic acid.

Compound 278: (S)-2-((1H-pyrazolo[3,4-d]pyrimidin-4-yl) amino)-4-(((S)-2-fluoro-3-methoxypropyl) (4-(5,6,7,8-tetrahydro-1,8-naphthyridin-2-yl) butyl)amino) butanoic acid: To a mixture of (S)-2-amino-4-(((S)-2-fluoro-3-methoxypropyl) (4-(5,6,7,8-tetrahydro-1,8-naphthyridin-2-yl) butyl)amino) butanoic acid hydrochloride (200 mg, 462 μmol) in THF (2 mL) and $H_2O$ (0.5 mL) was added $NaHCO_3$ (116 mg, 1.39 mmol) then 4-chloro-1H-pyrazolo[3,4-d]pyrimidine (79 mg, 508 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=515.2 (M+H)+. $^1H$ NMR (400 MHz, Methanol-$d_4$) δ ppm 8.93 (br s, 1H) 8.65 (s, 1H) 7.59 (d, J=7.28 Hz, 1H) 6.67 (d, J=7.28 Hz, 1H) 5.15-5.33 (m, 2H) 3.72 (d, J=3.53 Hz, 1H) 3.64-3.70 (m, 2H) 3.55-3.63 (m, 2H) 3.48-3.54 (m, 3H) 3.40 (s, 5H) 2.77-2.84 (m, 4H) 2.49-2.69 (m, 2H) 1.79-1.98 (m, 6H).

Compound 279: 2-((5-bromopyrimidin-2-yl) amino)-4-(((S)-2-fluoro-3-methoxypropyl) (4-(5,6,7,8-tetrahydro-1,8-naphthyridin-2-yl) butyl)amino) butanoic acid.

Compound 280: 2-((6-(1H-pyrazol-1-yl) pyrimidin-4-yl) amino)-4-(((S)-2-fluoro-3-methoxypropyl) (4-(5,6,7,8-tetrahydro-1,8-naphthyridin-2-yl) butyl)amino) butanoic acid.

Compound 281: 4-(((S)-2-fluoro-3-methoxypropyl) (4-(5,6,7,8-tetrahydro-1,8-naphthyridin-2-yl) butyl)amino)-2-((2-(trifluoromethyl)pyrimidin-4-yl) amino) butanoic acid.

Compound 282: (S)-2-((5-cyclopropylpyrimidin-2-yl) amino)-4-(((S)-2-fluoro-3-methoxypropyl) (4-(5,6,7,8-tetrahydro-1,8-naphthyridin-2-yl) butyl)amino) butanoic acid: To a mixture of (S)-2-amino-4-(((S)-2-fluoro-3-methoxypropyl) (4-(5,6,7,8-tetrahydro-1,8-naphthyridin-2-yl) butyl) amino) butanoic acid hydrochloride (100 mg, 252 µmol) in THF (1 mL) and H₂O (0.25 mL) was added NaHCO₃ (106 mg, 1.26 mmol) then 5-cyclopropyl-2-fluoropyrimidine (38 mg, 277 µmol) and the resulting mixture was heated to 70° C. for 1 h and then cooled to rt and adjusted to pH=6 by the addition of 1 M aq. HCl and then concentrated in vacuo. The crude residue was purified by reverse phase prep-HPLC to give the title compound. LCMS (ESI+): m/z=515.2 (M+H)⁺. ¹H NMR (400 MHz, Methanol-d₄) δ ppm 8.03 (s, 2H) 7.35 (d, J=7.28 Hz, 1H) 6.48 (d, J=7.50 Hz, 1H) 4.75-4.81 (m, 1H) 4.35 (t, J=5.95 Hz, 1H) 3.57 (d, J=4.19 Hz, 1H) 3.49-3.53 (m, 1H) 3.37 (dt, J=8.65, 5.82 Hz, 2H) 3.32 (s, 3H) 2.81-2.95 (m, 4H) 2.76-2.80 (m, 1H) 2.72 (br t, J=6.28 Hz, 3H) 2.66 (t, J=7.83 Hz, 2H) 2.02-2.20 (m, 2H) 1.80-1.91 (m, 3H) 1.69-1.79 (m, 2H) 1.57-1.68 (m, 2H) 0.91 (br dd, J=8.38, 1.54 Hz, 2H) 0.55-0.62 (m, 2H).

Compound 283: 4-(((S)-2-fluoro-3-methoxypropyl) (4-(5,6,7,8-tetrahydro-1,8-naphthyridin-2-yl) butyl)amino)-2-(pyrimidin-4-ylamino) butanoic acid.

Compound 284: (S)-2-((3-cyanopyrazin-2-yl) amino)-4-(((S)-2-fluoro-3-methoxypropyl) (4-(5,6,7,8-tetrahydro-1,8-naphthyridin-2-yl) butyl)amino) butanoic acid: To a mixture of (S)-2-amino-4-(((S)-2-fluoro-3-methoxypropyl) (4-(5,6,7,8-tetrahydro-1,8-naphthyridin-2-yl) butyl)amino) butanoic acid hydrochloride (200 mg, 462 µmol) in i-PrOH (2 mL) was added DIPEA (402 µL, 2.31 mmol) then 3-chloropyrazine-2-carbonitrile (71 mg, 508 µmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound LCMS (ESI+): m/z=500.2 (M+H)⁺. ¹H NMR (400 MHz, Methanol-d₄) δ ppm 8.30 (d, J=2.43 Hz, 1H) 8.00 (d, J=2.43 Hz, 1H) 7.59 (d, J=7.50 Hz, 1H) 6.64 (d, J=7.28 Hz, 1H) 5.09-5.28 (m, 1H) 4.81 (dd, J=8.82, 5.29 Hz, 1H) 3.62-3.73 (m, 3H) 3.54-3.62 (m, 1H) 3.42-3.54 (m, 4H) 3.40 (s, 3H) 3.32-3.39 (m, 2H) 2.76-2.85 (m, 4H) 2.49-2.60 (m, 1H) 2.33-2.45 (m, 1H) 1.96 (dt, J=11.74, 5.93 Hz, 2H) 1.74-1.92 (m, 4H).

Compound 285: (S)-4-(((S)-2-fluoro-3-methoxypropyl) (4-(5,6,7,8-tetrahydro-1,8-naphthyridin-2-yl) butyl)amino)-2-((3-methyl-1H-pyrazolo[4,3-d]pyrimidin-7-yl) amino) butanoic acid.

Compound 286: (S)-4-(((S)-2-fluoro-3-methoxypropyl) (4-(5,6,7,8-tetrahydro-1,8-naphthyridin-2-yl) butyl)amino)-2-((5-phenylpyridin-2-yl) amino) butanoic acid.

Scheme 31, Compound 287

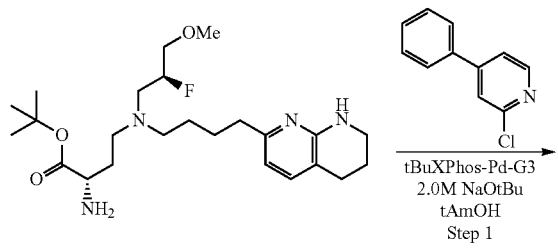

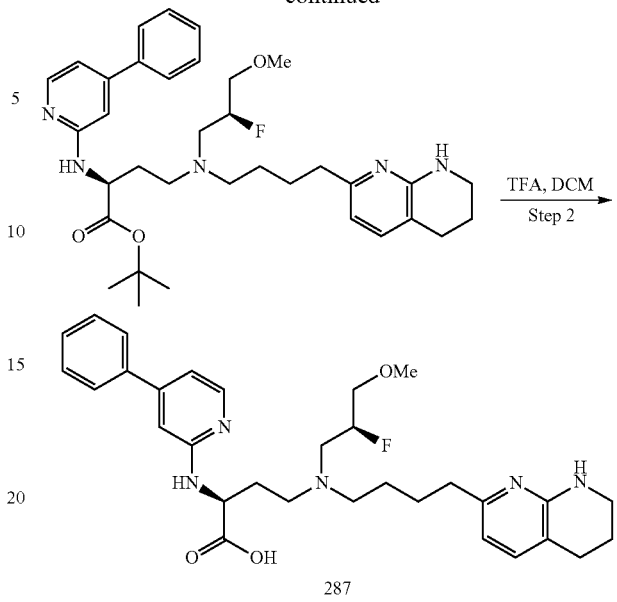

Step 1: (S)-tert-butyl4-(((S)-2-fluoro-3-methoxypropyl) (4-(5,6,7,8-tetrahydro-1,8-naphthyridin-2-yl) butyl)amino)-2-((4-phenylpyridin-2-yl) amino) butanoate To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 µmol) and 2-chloro-4-phenylpyridine (52 mg, 276 µmol) in t-AmOH (3 mL) was added 2.0M t-BuONa in THF (276 µL, 552 µmol) and t-BuXPhos Pd G3 (22 mg, 28 µmol) and the resulting mixture was heated to 100° C. for 5 h, cooled to rt, and then concentrated in vacuo to give the title compound that was used without further purification. LCMS (ESI+): m/z=606.3 (M+H)⁺. Note: The t-butyl ester was prepared in an analogous manner to Compound 213.

Step 2: (S)-4-(((S)-2-fluoro-3-methoxypropyl) (4-(5,6,7,8-tetrahydro-1,8-naphthyridin-2-yl) butyl) amino)-2-((4-phenylpyridin-2-yl) amino) butanoic acid (S)-tert-butyl 4-(((S)-2-fluoro-3-methoxypropyl) (4-(5,6,7,8-tetrahydro-1,8-naphthyridin-2-yl) butyl)amino)-2-((4-phenylpyridin-2-yl) amino) butanoate (167 mg, 276 µmol) was taken up in in 3:1 DCM/TFA (4 mL) and the resulting mixture was stirred at rt for 16 h and then concentrated in vacuo. The crude residue was purified by reverse phase prep-HPLC to give the title compound. LCMS (ESI+): m/z=550.3 (M+H)⁺. ¹H NMR (400 MHz, DMSO-d₆) δ ppm 8.06 (br d, J=6.48 Hz, 1H) 7.82 (br d, J=3.55 Hz, 2H) 7.54-7.62 (m, 4H) 7.45 (br s, 1H) 7.29 (br d, J=6.36 Hz, 1H) 6.62 (d, J=7.34 Hz, 1H) 5.17-5.40 (m, 1H) 4.81 (br s, 1H) 3.32-3.55 (m, 8H) 3.30 (s, 3H) 3.23 (br s, 2H) 2.70 (br d, J=6.24 Hz, 4H) 2.44 (br s, 1H) 2.27 (br d, J=8.93 Hz, 1H) 1.59-1.85 (m, 6H).

Scheme 32, Compound 288

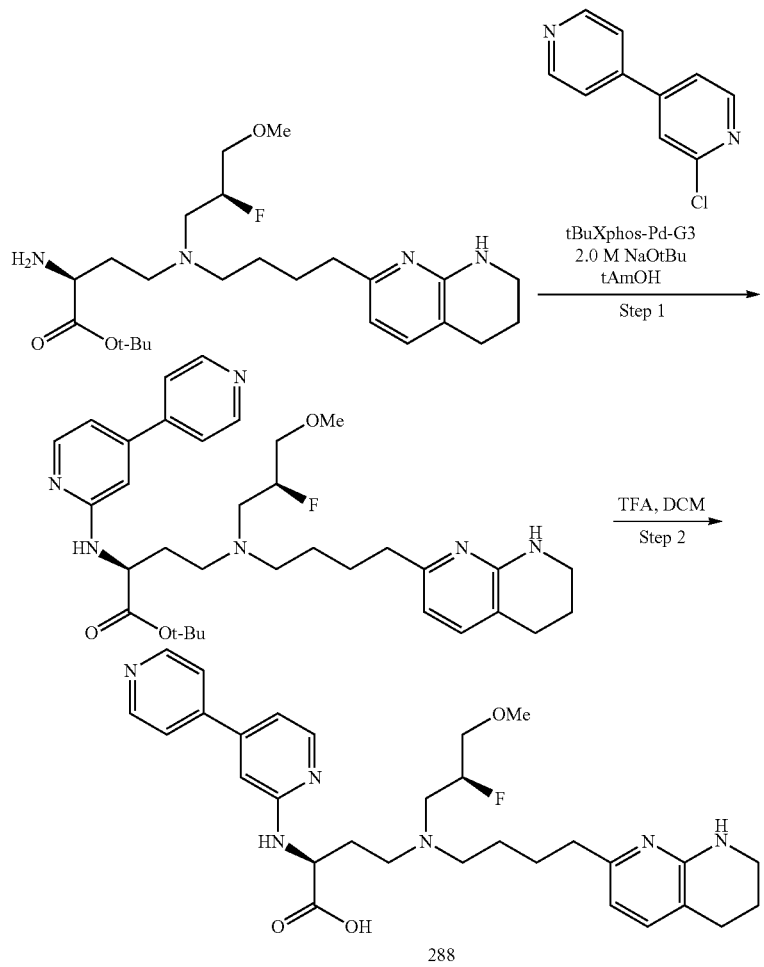

Step 1: (S)-tert-butyl4-(((S)-2-fluoro-3-methoxypropyl) (4-(5,6,7,8-tetrahydro-1,8-naphthyridin-2-yl) butyl)amino)-2-((6-phenylpyrazin-2-yl) amino) butanoate To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 μmol) and 2-chloro-6-phenylpyrazine (53 mg, 276 μmol) in t-AmOH (3 mL) was added 2.0M t-BuONa in THF (276 μL, 552 μmol) then t-BuXPhos Pd G3 (22 mg, 28 μmol) and the resulting mixture was heated to 100° C. for 5 h, cooled to rt, and then concentrated in vacuo to give the title compound that was used without further purification. LCMS (ESI+): m/z=607.2 (M+H)+.

Step 2: (S)-4-(((S)-2-fluoro-3-methoxypropyl) (4-(5, 6,7,8-tetrahydro-1,8-naphthyridin-2-yl) butyl) amino)-2-((6-phenylpyrazin-2-yl) amino) butanoic acid (S)-tert-butyl 4-(((S)-2-fluoro-3-methoxypropyl) (4-(5,6, 7,8-tetrahydro-1,8-naphthyridin-2-yl) butyl)amino)-2-((6-phenylpyrazin-2-yl) amino) butanoate (200 mg, 330 μmol) was taken up in 3:1 DCM/TFA (2 mL) and the resulting mixture was stirred at rt for 16 h and then concentrated in vacuo. The crude residue was purified by reverse phase prep-HPLC to give the title compound. LCMS (ESI+): m/z=551.3 (M+H)+. 1H NMR (400 MHz, DMSO-$d_6$) δ ppm 8.26 (s, 1H) 7.90-8.02 (m, 3H) 7.37-7.46 (m, 3H) 6.99 (d, J=7.06 Hz, 1H) 6.18 (dd, J=7.28, 2.43 Hz, 1H) 4.55-4.80 (m, 1H) 4.43 (br d, J=5.73 Hz, 1H) 3.36-3.50 (m, 2H) 3.09-3.24 (m, 5H) 2.52-2.77 (m, 7H) 2.29-2.47 (m, 3H) 2.00 (br dd, J=13.34, 6.50 Hz, 1H) 1.77-1.88 (m, 1H) 1.64-1.74 (m, 2H) 1.45-1.56 (m, 2H) 1.31-1.41 (m, 2H).

Compound 289: 4-(((S)-2-fluoro-3-methoxypropyl) (4-(5, 6,7,8-tetrahydro-1,8-naphthyridin-2-yl) butyl)amino)-2-((2-(pyridin-3-yl) quinazolin-4-yl) amino) butanoic acid.

Compound 290: 4-(((S)-2-fluoro-3-methoxypropyl) (4-(5, 6,7,8-tetrahydro-1,8-naphthyridin-2-yl) butyl)amino)-2-((5-phenylpyrimidin-4-yl) amino) butanoic acid.

Compound 291: 4-(((S)-2-fluoro-3-methoxypropyl) (4-(5, 6,7,8-tetrahydro-1,8-naphthyridin-2-yl) butyl)amino)-2-((6-phenylpyrimidin-4-yl) amino) butanoic acid.

Compound 292: 2-((1-methyl-1H-pyrazolo[3,4-d]pyrimidin-4-yl) amino)-4-((2-phenoxyethyl) (4-(5,6,7,8-tetrahydro-1,8-naphthyridin-2-yl) butyl)amino) butanoic acid.

Compound 293: 2-((5-cyanopyrimidin-2-yl) amino)-4-((2-phenoxyethyl) (4-(5,6,7,8-tetrahydro-1,8-naphthyridin-2-yl) butyl)amino) butanoic acid.

Compound 294: 4-((2-phenoxyethyl) (4-(5,6,7,8-tetrahydro-1,8-naphthyridin-2-yl) butyl)amino)-2-((5-(trifluoromethyl)pyrimidin-2-yl) amino) butanoic acid.

Compound 295: 2-((1H-pyrazolo[3,4-d]pyrimidin-4-yl) amino)-4-((2-phenoxyethyl) (4-(5,6,7,8-tetrahydro-1,8-naphthyridin-2-yl) butyl)amino) butanoic acid.

Compound 296: 2-((5-bromopyrimidin-2-yl) amino)-4-((2-phenoxyethyl) (4-(5,6,7,8-tetrahydro-1,8-naphthyridin-2-yl) butyl)amino) butanoic acid.

Compound 297: 2-((6-(1H-pyrazol-1-yl) pyrimidin-4-yl) amino)-4-((2-phenoxyethyl) (4-(5,6,7,8-tetrahydro-1,8-naphthyridin-2-yl) butyl)amino) butanoic acid.

Compound 298: 4-((2-phenoxyethyl) (4-(5,6,7,8-tetrahydro-1,8-naphthyridin-2-yl) butyl)amino)-2-((2-(trifluoromethyl)pyrimidin-4-yl) amino) butanoic acid.

Compound 299: 2-((5-cyclopropylpyrimidin-2-yl) amino)-4-((2-phenoxyethyl) (4-(5,6,7,8-tetrahydro-1,8-naphthyridin-2-yl) butyl)amino) butanoic acid.

Compound 300: (S)-4-((2-phenoxyethyl) (4-(5,6,7,8-tetrahydro-1,8-naphthyridin-2-yl) butyl)amino)-2-(pyrimidin-4-ylamino) butanoic acid.

Compound 301: 4-((2-phenoxyethyl) (4-(5,6,7,8-tetrahydro-1,8-naphthyridin-2-yl) butyl)amino)-2-((6-phenylpyrimidin-4-yl) amino) butanoic acid.

Compound 302: (S)-4-((2-phenoxyethyl) (4-(5,6,7,8-tetrahydro-1,8-naphthyridin-2-yl) butyl)amino)-2-((5-phenylpyrimidin-4-yl) amino) butanoic acid: To a (S)-2-amino-4-((2-phenoxyethyl) (4-(5,6,7,8-tetrahydro-1,8-naphthyridin-2-yl) butyl)amino) butanoic acid hydrochloride (150 mg, 324 µmol) in 4:1 THF/H$_2$O (2 mL) was added 5-bromo-4-chloropyrimidine (69 mg, 356 µmol) and NaHCO$_3$ (136, 1.62 mmol) and the resulting mixture was stirred at 70° C. for 2 h. The reaction mixture was cooled to rt and then concentrated in vacuo to give a (S)-2-((5-bromopyrimidin-4-yl) amino)-4-((2-phenoxyethyl) (4-(5,6,7,8-tetrahydro-1,8-naphthyridin-2-yl) butyl) amino) butanoic acid intermediate, which was used without further purification. Of the butanoic acid intermediate, 189 mg, 324 µmol, was mixed with phenylboronic acid (43 mg, 356 µmol) in 3:1 dioxane/H$_2$O (3 mL), to which was added K$_2$CO$_3$ (90 mg, 649 µmol) then Pd(dppf)Cl$_2$ (24 mg, 32 µmol) and the resulting mixture was heated to 100° C. for 2 h. The reaction mixture was cooled to rt and then concentrated in vacuo. The crude residue was purified by reverse phase prep-HPLC to give the title compound. LCMS (ESI+): m/z=581.3 (M+H)$^+$. $^1$H NMR (400 MHz, Methanol-d$_4$) δ ppm 8.42 (s, 1H) 7.94 (s, 1H) 7.45-7.51 (m, 2H) 7.38-7.45 (m, 3H) 7.20-7.30 (m, 3H) 6.83-7.00 (m, 3H) 6.42 (d, J=7.34 Hz, 1H) 4.52 (dd, J=6.79, 4.22 Hz, 1H) 4.19 (t, J=5.14 Hz, 2H) 3.33-3.41 (m, 3H) 3.20-3.30 (m, 2H) 2.88-3.11 (m, 3H) 2.70 (t, J=6.17 Hz, 2H) 2.57 (br t, J=6.97 Hz, 2H) 2.22-2.32 (m, 1H) 2.12-2.20 (m, 1H) 1.86 (q, J=5.90 Hz, 2H) 1.55-1.72 (m, 4H).

Compound 303: 4-((2-phenoxyethyl) (4-(5,6,7,8-tetrahydro-1,8-naphthyridin-2-yl) butyl)amino)-2-((2-(pyridin-3-yl) quinazolin-4-yl) amino) butanoic acid.

Compound 304: 4-((2-(4-fluorophenoxy)ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 305: 2-((5-cyanopyrimidin-2-yl) amino)-4-((2-(4-fluorophenoxy)ethyl) (4-(5,6,7,8-tetrahydro-1,8-naphthyridin-2-yl) butyl)amino) butanoic acid.

Compound 306: 4-((2-(4-fluorophenoxy)ethyl) (4-(5,6,7,8-tetrahydro-1,8-naphthyridin-2-yl) butyl)amino)-2-((5-(trifluoromethyl)pyrimidin-2-yl) amino) butanoic acid.

Compound 307: 2-((1H-pyrazolo[3,4-d]pyrimidin-4-yl) amino)-4-((2-(4-fluorophenoxy)ethyl) (4-(5,6,7,8-tetrahydro-1,8-naphthyridin-2-yl) butyl)amino) butanoic acid.

Compound 308: 2-((5-bromopyrimidin-2-yl) amino)-4-((2-(4-fluorophenoxy)ethyl) (4-(5,6,7,8-tetrahydro-1,8-naphthyridin-2-yl) butyl)amino) butanoic acid.

Compound 309: (S)-2-((6-(1H-pyrazol-1-yl) pyrimidin-4-yl) amino)-4-((2-(4-fluorophenoxy)ethyl) (4-(5,6,7,8-tetrahydro-1,8-naphthyridin-2-yl) butyl)amino) butanoic acid.

Compound 310: (S)-4-((2-(4-fluorophenoxy)ethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid (120 mg, 270 µmol) and 4-chloro-2-(trifluoromethyl)pyrimidine (59 mg, 324 µmol) in THF (2 mL) H$_2$O (0.5 mL) was added NaHCO$_3$ (113 mg, 1.35 mmol) and the resulting mixture was stirred at 70° C. for 1 h and then concentrated in vacuo. The crude residue was purified by reverse phase prep-HPLC to give the title compound. LCMS (ESI+): m/z=591.3 (M+H)$^+$. $^1$H NMR (400 MHz, Methanol-d$_4$) δ ppm 8.01 (br s, 1H) 7.32 (br d, J=6.84 Hz, 1H) 6.91 (br d, J=7.94 Hz, 2H) 6.81 (br s, 2H) 6.60 (br s, 1H) 6.47 (br d, J=7.50 Hz, 1H) 4.61 (br s, 1H) 4.10 (br d, J=3.97 Hz, 2H) 3.38 (br s, 2H) 3.25 (br s, 2H) 3.11 (br s, 1H) 3.00 (br d, J=5.95 Hz, 2H) 2.88 (br s, 1H) 2.59-2.80 (m, 4H) 2.28 (br s, 1H) 2.06 (br s, 2H) 1.67-1.90 (m, 5H).

Compound 311: (S)-2-((5-cyclopropylpyrimidin-2-yl) amino)-4-((2-(4-fluorophenoxy)ethyl) (4-(5,6,7,8-tetrahydro-1,8-naphthyridin-2-yl) butyl)amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid (150 mg, 337 µmol) in 4:1 THF/H$_2$O (2 mL) was added 5-cyclopropyl-2-fluoropyrimidine (51 mg, 371 µmol) and NaHCO$_3$ (85 mg, 1.01 mmol) and the resulting mixture was heated to 70° C. for 1 h and then cooled to rt and then concentrated in vacuo. The crude residue was purified by prep-HPLC to give the title compound. LCMS (ESI+): m/z=563.2 (M+H)$^+$. $^1$H NMR (400 MHz, Methanol-d$_4$) δ ppm 8.29 (s, 2H) 7.58 (d, J=7.34 Hz, 1H) 6.94-7.09 (m, 4H) 6.64 (d, J=7.34 Hz, 1H) 4.76 (dd, J=8.38, 5.20 Hz, 1H) 4.35 (br t, J=4.52 Hz, 2H) 3.33-3.78 (m, 8H) 2.73-2.86 (m, 4H) 2.52-2.65 (m, 1H) 2.30-2.43 (m, 1H) 1.70-2.01 (m, 7H) 0.93-1.11 (m, 2H) 0.61-0.76 (m, 2H).

Compound 312: (S)-4-((2-(4-fluorophenoxy)ethyl) (4-(5,6,7,8-tetrahydro-1,8-naphthyridin-2-yl) butyl)amino)-2-((6-phenylpyrimidin-4-yl) amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid (120 mg, 270 µmol) and 4-chloro-6-phenyl-pyrimidine (62 mg, 324 µmol) in THF (2 mL) and H$_2$O (0.5 mL) was added NaHCO$_3$ (113 mg, 1.35 mmol) and the resulting mixture was stirred at 70° C. for 1 h and then concentrated in vacuo. The crude residue was purified by reverse phase prep-HPLC to give the title compound. LCMS (ESI+): m/z=599.3 (M+H)$^+$. $^1$H NMR (400 MHz, Methanol-d$_4$) δ ppm 8.29-8.45 (m, 1H) 7.70 (br s, 1H) 7.60-7.80 (m, 1H) 7.40-7.47 (m, 3H) 7.19-7.29 (m, 1H) 6.78-6.85 (m, 4H) 6.69 (s, 1H) 6.47 (d, J=7.50 Hz, 1H) 4.57 (br s, 1H) 4.10-4.17 (m, 2H) 3.34-3.48 (m, 2H) 3.13 (br s, 2H) 3.08 (br s, 1H) 3.00 (br s, 1H) 2.93-2.94 (m, 1H) 2.80-2.93 (m, 1H) 2.50-2.75 (m, 4H) 2.27 (br s, 1H) 2.14 (br d, J=5.29 Hz, 1H) 1.86 (br dd, J=13.89, 6.84 Hz, 2H) 1.93 (br s, 1H) 1.78 (br s, 3H).

Compound 313: (S)-4-((2-(4-fluorophenoxy)ethyl) (4-(5,6,7,8-tetrahydro-1,8-naphthyridin-2-yl) butyl)amino)-2-((5-phenylpyrimidin-4-yl) amino) butanoic acid: To a mixture of (S)-2-((5-bromopyrimidin-4-yl) amino)-4-((2-(4-fluorophenoxy)ethyl) (4-(5,6,7,8-tetrahydro-1,8-naphthyridin-2-yl) butyl)amino) butanoic acid (202 mg, 336 µmol) in 3:1 dioxane/H$_2$O (2 mL) was added K$_2$CO$_3$ (93 mg, 672 µmol), phenylboronic acid (102 mg, 840 µmol), then Pd(dppf)Cl$_2$ (25 mg, 34 µmol) and the resulting mixture was heated to 100° C. for 2 h, cooled to rt, and then concentrated in vacuo. The crude residue was purified by prep-HPLC to give the title compound. LCMS (ESI+): m/z=599.3 (M+H)$^+$. $^1$H NMR (400 MHz, Methanol-d$_4$) δ ppm 8.43 (br s, 1H) 7.95 (br s, 1H) 7.38-7.55 (m, 5H) 7.26 (d, J=7.28 Hz, 1H) 6.95-7.04 (m, 2H) 6.83-6.93 (m, 2H) 6.42 (d, J=7.28 Hz, 1H) 4.49-4.58 (m, 1H) 4.16 (t, J=5.18 Hz, 2H) 3.34-3.40 (m, 2H) 3.16-3.30 (m, 3H) 2.84-3.11 (m, 3H) 2.71 (t, J=6.17 Hz, 2H) 2.49-2.61 (m, 2H) 2.10-2.34 (m, 2H) 1.82-1.94 (m, 2H) 1.49-1.75 (m, 4H).

Compound 314: (S)-4-((2-(4-fluorophenoxy)ethyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid hydrochloride (150 mg, 312 µmol) in DMA (2 mL) was added DIPEA (272 µL, 1.56 mmol) and then 4-chloro-2-(pyridin-3-yl) quinazoline (83 mg, 343 µmol) and the resulting mixture was heated to 70° C. for 1 h and then cooled to rt, adjusted to pH=6 by the addition of 1 M aq. HCl, and then concentrated in vacuo. The crude residue was purified by prep-HPLC to give the title compound. LCMS (ESI+): m/z=650.3 (M+H)$^+$. $^1$H NMR (400 MHz, Methanol-d$_4$) δ ppm 9.51 (d, J=1.59 Hz, 1H) 8.77 (dt, J=8.01, 1.86 Hz, 1H) 8.58 (dd, J=4.89, 1.59 Hz, 1H) 8.03 (d, J=7.70 Hz, 1H) 7.78-7.85 (m, 1H) 7.68-7.75 (m, 1H) 7.46 (dd, J=7.95, 4.89 Hz, 1H) 7.31-7.38 (m, 1H) 7.20 (d, J=7.21 Hz, 1H) 6.70-6.78 (m, 2H) 6.62-6.70 (m, 2H) 6.37 (d, J=7.34 Hz, 1H) 5.01 (t, J=5.93 Hz, 1H) 4.04-4.18 (m, 2H) 3.12-3.29 (m, 4H) 3.09-3.11 (m, 1H) 2.93-3.09 (m, 3H) 2.77-2.87 (m, 1H) 2.57-2.68 (m, 4H) 2.46 (ddt, J=14.72, 9.77, 5.00, 5.00 Hz, 1H) 2.22-2.33 (m, 1H) 1.65-1.86 (m, 6H).

Compound 315: (S)-4-((2-(4-fluorophenoxy)ethyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-((2-(4-fluorophenoxy) ethyl) (4-(5,6,7,8-tetrahydro-1,8-naphthyridin-2-yl) butyl) amino) butanoic acid (150 mg, 337 µmol) in 4:1 THF/H$_2$O (2 mL) was added 7-chloro-2-methyl-2H-pyrazolo[4,3-d] pyrimidine (63 mg, 371 µmol) and NaHCO$_3$ (85 mg, 1.01 mmol) and the resulting mixture was heated to 70° C. for 1 h and then cooled to rt and then concentrated in vacuo. The crude residue was purified by prep-HPLC to give the title compound. LCMS (ESI+): m/z=577.3 (M+H)$^+$. $^1$H NMR (400 MHz, Methanol-d$_4$) δ ppm 8.46 (d, J=19.81 Hz, 2H) 7.58 (d, J=7.34 Hz, 1H) 6.93-7.03 (m, 4H) 6.65 (d, J=7.34 Hz, 1H) 5.11 (dd, J=8.62, 5.07 Hz, 1H) 4.32-4.45 (m, 2H) 4.06 (s, 3 H) 3.48-3.77 (m, 5H) 3.42 (br t, J=7.95 Hz, 2H) 2.66-2.86 (m, 5H) 2.49-2.62 (m, 1H) 1.77-2.01 (m, 1H) 1.68-2.03 (m, 6H).

Compound 316: (S)-4-((2-ethoxyethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid: To a mixture of (S)-2-amino-4-((2-ethoxyethyl) (4-(5,6,7,8-tetrahydro-1,8-naphthyridin-2-yl) butyl)amino) butanoic acid (150 mg, 396 µmol) and 4-chloro-1-methyl-H-pyrazolo [3,4-d]pyrimidine (73 mg, 436 µmol) in THF (2 mL) and H$_2$O (0.5 mL) was added NaHCO$_3$ (166 mg, 1.98 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=511.3 (M+H)$^+$. $^1$H NMR (400 MHz, Methanol-d$_4$) δ ppm 8.25 (s, 1H) 8.08 (s, 1H) 7.18 (d, J=7.45 Hz, 1H) 6.38 (d, J=7.02 Hz, 1H) 4.77 (br s, 1H) 3.95 (s, 3H) 3.69 (br s, 2H) 3.48 (q, J=6.72 Hz, 2H) 3.35 (br d, J=5.26 Hz, 3H) 3.25 (br d, J=14.47 Hz, 1H) 2.92-3.18 (m, 4H) 2.68 (t, J=6.14 Hz, 2H) 2.57 (br t, J=7.02 Hz, 2H) 2.28-2.44 (m, 1H) 2.13 (br dd, J=14.69, 5.48 Hz, 1H) 1.85 (q, J=5.92 Hz, 2H) 1.72 (br s, 4H) 1.13 (t, J=7.02 Hz, 3H).

Compound 317: (S)-2-((5-cyanopyrimidin-2-yl) amino)-4-((2-ethoxyethyl) (4-(5,6,7,8-tetrahydro-1,8-naphthyridin-2-yl) butyl)amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) in 4:1 THF/H$_2$O (2 mL) was added 2-chloropyrimidine-5-carbonitrile (55 mg, 398 µmol) and NaHCO$_3$ (91 mg, 1.08 mmol) and the resulting mixture was heated to 70° C. for 1 h, cooled to rt, and then concentrated in vacuo. The crude residue was purified by prep-HPLC to give the title compound. LCMS (ESI+): m/z=482.2 (M+H)$^+$. $^1$H NMR (400 MHz, Methanol-d$_4$) δ ppm 8.48-8.63 (m, 2H) 7.19 (d, J=7.45 Hz, 1H) 6.40 (d, J=7.45 Hz, 1H) 4.42 (t, J=5.92 Hz, 1H) 3.66 (t, J=5.26 Hz, 2H) 3.49 (q, J=7.02 Hz, 2H) 3.34-3.41 (m, 2H) 2.87-3.26 (m, 6H) 2.70 (t, J=6.14 Hz, 2H) 2.52-2.62 (m, 2H) 2.23 (dq, J=14.03, 7.02 Hz, 1H) 2.02-2.14 (m, 1H) 1.82-1.93 (m, 2H) 1.70 (br s, 4H) 1.11-1.20 (m, 1H) 1.16 (t, J=7.02 Hz, 2H).

Scheme 33, Compound 318

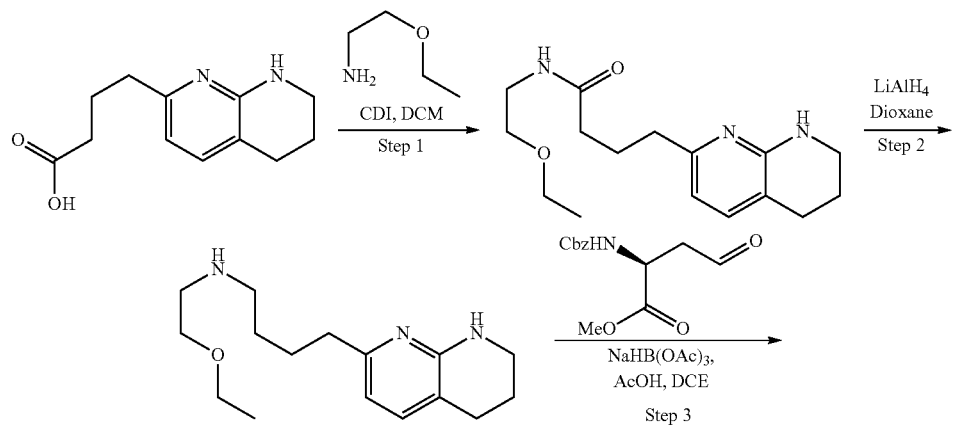

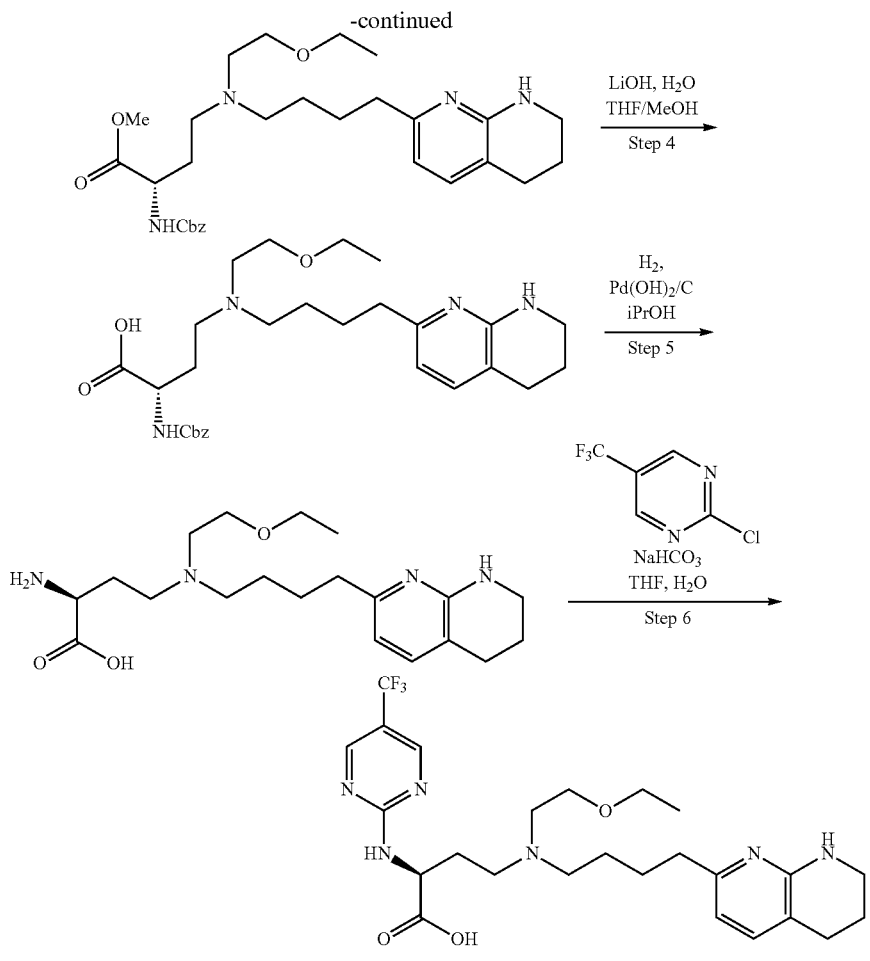

Step 1: N-(2-ethoxyethyl)-4-(5,6,7,8-tetrahydro-1,8-naphthyridin-2-yl) butanamide To a solution of 4-(5,6,7,8-tetrahydro-1,8-naphthyridin-2-yl) butanoic acid (15 g, 47.67 mmol) in DCM (150 mL) at 0° C. was added CDI (8.50 g, 52.44 mmol) and then 2-ethoxyethanamine (4.67 g, 52.44 mmol) and the resulting mixture was stirred at rt for 2 h. The reaction mixture was diluted with H$_2$O and the layers were separated. The aqueous layers was extracted with DCM and the combined organic extracts were washed with brine, dried over Na$_2$SO$_4$, filtered, and concentrated in vacuo. The crude product was triturated with MTBE and then the solid was filtered off and the filtrate was concentrated in vacuo to give the title compound. LCMS (ESI+): m/z=291.7 (M+H)$^+$. $^1$H NMR (400 MHz, CDCl$_3$) δ ppm 7.71 (br s, 1H) 7.07 (d, J=7.02 Hz, 1H) 6.34 (d, J=7.02 Hz, 1H) 5.14 (br s, 1H) 3.52-3.60 (m, 4H) 3.46-3.52 (m, 2H) 3.36-3.43 (m, 2H) 2.70 (t, J=6.36 Hz, 2H) 2.60 (t, J=6.80 Hz, 2H) 2.17-2.25 (m, 2H) 1.86-2.04 (m, 4H) 1.17-1.27 (m, 3H).

Step 2: N-(2-ethoxyethyl)-4-(5,6,7,8-tetrahydro-1,8-naphthyridin-2-yl) butan-1-amine To a mixture of LiAlH$_4$ (2.15 g, 56.63 mmol) in dioxane (120 mL) at 10° C. was added N-(2-ethoxyethyl)-4-(5,6,7,8-tetrahydro-1,8-naphthyridin-2-yl) butanamide (7.5 g, 25.74 mmol) and the resulting mixture was heated to reflux for 30 min and then cooled to rt. The mixture was then carefully neutralized by the cautious addition of H$_2$O (2.6 mL), 1 M aq. NaOH (2.6 mL), then H$_2$O (2.6 mL) again, followed by drying over MgSO$_4$. The mixture was filtered and then concentrated in vacuo to give the title compound that was used without further purification. LCMS (ESI+): m/z=277.9 (M+H)$^+$. $^1$H NMR (400 MHz, CDCl$_3$) δ ppm 7.05 (d, J=7.28 Hz, 1H) 6.34 (d, J=7.28 Hz, 1H) 4.78 (br s, 1H) 3.71 (s, 1H) 3.45-3.56 (m, 4H) 3.36-3.43 (m, 2H) 2.77 (t, J=5.18 Hz, 2H) 2.61-2.71 (m, 4H) 2.55 (t, J=7.72 Hz, 2H) 1.84-1.95 (m, 2H) 1.69 (q, J=7.61 Hz, 2H) 1.51-1.61 (m, 2H) 1.15-1.23 (m, 3H).

Step 3: (S)-methyl 2-(((benzyloxy)carbonyl)amino)-4-((2-ethoxyethyl) (4-(5,6,7,8-tetrahydro-1,8-naphthyridin-2-yl) butyl)amino) butanoate To a solution of N-(2-ethoxyethyl)-4-(5,6,7,8-tetrahydro-1,8-naphthyridin-2-yl) butan-1-amine (11 g, 39.65 mmol) and methyl (S)-methyl 2-(((benzyloxy)carbonyl)amino)-4-oxobutanoate (11.57 g, 43.62 mmol) in DCE (170 mL) at 0° C. was added AcOH (3.40 mL, 59.48 mmol) then NaBH(OAc)$_3$ (12.61 g, 59.48 mmol) and the resulting mixture was stirred at 100° C. for 1 h. The reaction mixture was diluted with MeOH and then concentrated in vacuo. The crude residue was taken up in DCM and sat. aq. NaHCO$_3$ and the layers were separated. The aqueous layer was extracted with DCM and the combined organic extracts were dried over Na$_2$SO$_4$, filtered, and concentrated in vacuo. The crude residue was purified by normal phase silica gel chromatography to give the title compound. LCMS (ESI+): m/z=527.4 (M+H)$^+$. $^1$H NMR (400 MHz, Methanol-d$_4$) δ ppm 7.24-7.39 (m, 5H) 7.07-7.14 (m, 1H) 6.36 (d, J=7.50 Hz, 1H) 4.99-5.13 (m, 2H) 4.29 (dd, J=8.16, 4.41 Hz, 1H) 3.71 (s, 1H) 3.68-3.73 (m, 1H) 3.39-3.52 (m, 4H) 3.35 (dd, J=6.17, 5.07 Hz, 2H) 2.39-2.75 (m, 10H) 2.02-2.09 (m, 1H) 1.96-2.00 (m, 1H) 1.80-1.88 (m, 2H) 1.78 (br d, J=7.28 Hz, 1H) 1.55-1.70 (m, 2H) 1.48 (q, J=7.50 Hz, 2H) 1.12 (t, J=7.06 Hz, 3H).

Step 4: (S)-2-(((benzyloxy)carbonyl)amino)-4-((2-ethoxyethyl) (4-(5,6,7,8-tetrahydro-1,8-naphthyridin-2-yl) butyl)amino) butanoic acid To a solution of (S)-methyl 2-(((benzyloxy)carbonyl)amino)-4-((2-ethoxyethyl) (4-(5,6,7,8-tetrahydro-1,8-naphthyridin-2-yl) butyl)amino) butanoate (7 g, 13.29 mmol) in 1:1 THF/MeOH (50 mL) was added LiOH.H$_2$O (1.12 g, 26.58 mmol) and the resulting mixture was stirred at rt for 1 h. The reaction mixture was adjusted to pH=6 by the addition of 1 M aq. HCl and then concentrated in vacuo to give the title compound that was used without further purification. LCMS (ESI+): m/z=513.5 (M+H)$^+$. $^1$H NMR (400 MHz, Methanol-d$_4$) δ ppm 7.58 (d, J=7.50 Hz, 1H) 7.24-7.41 (m, 5H) 6.60-6.68 (m, 1H) 5.05-5.17 (m, 1H) 5.05-5.17 (m, 1H) 4.22-4.36 (m, 1H) 3.75 (br s, 2H) 3.48-3.59 (m, 4H) 3.33-3.45 (m, 3H) 3.27 (br d, J=7.28 Hz, 2H) 2.68-2.89 (m, 4H) 2.26-2.45 (m, 1H) 2.05-2.23 (m, 1H) 1.89-2.03 (m, 3H) 1.79 (br s, 4H) 1.12-1.26 (m, 3H).

Step 5: (S)-2-amino-4-((2-ethoxyethyl) (4-(5,6,7,8-tetrahydro-1,8-naphthyridin-2-yl) butyl)amino) butanoic acid To a solution of (S)-2-(((benzyloxy)carbonyl)amino)-4-((2-ethoxyethyl) (4-(5,6,7,8-tetrahydro-1,8-naphthyridin-2-yl) butyl)amino) butanoic acid (4 g, 7.80 mmol) in i-PrOH (40 mL) was added 10 wt % Pd(OH)$_2$/C (2 g) and the resulting mixture was stirred under an H$_2$ atmosphere for 12 h. The reaction mixture was filtered and concentrated in vacuo to give the title compound that was used without further purification. LCMS (ESI+): m/z=379.4 (M+H)$^+$. $^1$H NMR (400 MHz, Methanol-d$_4$) δ ppm 7.52-7.64 (m, 1H) 6.64 (d, J=7.28 Hz, 1H) 4.05 (br d, J=7.28 Hz, 1H) 3.80 (br s, 2H) 3.63 (br s, 1H) 3.41-3.60 (m, 8H) 2.69-2.86 (m, 4H) 2.38-2.58 (m, 1H) 2.18-2.35 (m, 1H) 1.86-2.02 (m, 5H) 1.74-1.86 (m, 2H) 1.12-1.21 (m, 3H).

Step 6: (S)-4-((2-ethoxyethyl) (4-(5,6,7,8-tetrahydro-1,8-naphthyridin-2-yl) butyl)amino)-2-((5-(trifluoromethyl)pyrimidin-2-yl) amino) butanoic acid To a solution of (S)-2-amino-4-((2-ethoxyethyl) (4-(5,6,7,8-tetrahydro-1,8-naphthyridin-2-yl) butyl)amino) butanoic acid (150 mg, 396 μmol) and 2-chloro-5-(trifluoromethyl)pyrimidine (80 mg, 436 μmol) in 4:1 THF/H$_2$O (2 mL) was added NaHCO$_3$ (166 mg, 1.98 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=525.3 (M+H)$^+$. $^1$H NMR (400 MHz, Methanol-d$_4$) δ ppm 8.53 (br s, 2H) 7.20 (d, J=7.28 Hz, 1H) 6.42 (d, J=7.28 Hz, 1H) 4.42 (dd, J=6.84, 4.85 Hz, 1H) 3.69 (t, J=5.18 Hz, 2H) 3.50 (q, J=6.76 Hz, 2H) 3.37 (td, J=5.46, 2.32 Hz, 2H) 2.96-3.28 (m, 6H) 2.66-2.76 (m, 1H) 2.70 (t, J=6.28 Hz, 1H) 2.55-2.64 (m, 2H) 2.26 (dq, J=14.19, 7.18 Hz, 1H) 2.06-2.17 (m, 1H) 1.86 (q, J=5.95 Hz, 2H) 1.73 (br s, 4H) 1.16 (t, J=7.06 Hz, 3H).

Compound 319: (S)-2-((1H-pyrazolo[3,4-d]pyrimidin-4-yl) amino)-4-((2-ethoxyethyl) (4-(5,6,7,8-tetrahydro-1,8-naphthyridin-2-yl) butyl)amino) butanoic acid: To a mixture of (S)-2-amino-4-((2-ethoxyethyl) (4-(5,6,7,8-tetrahydro-1,8-naphthyridin-2-yl) butyl)amino) butanoic acid (150 mg, 396 μmol) and 4-chloro-1H-pyrazolo[3,4-d]pyrimidine (67 mg, 436 μmol) in THF (2 mL) and H$_2$O (0.5 mL) was added NaHCO$_3$ (166 mg, 1.98 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=497.3 (M+H)$^+$. $^1$H NMR (400 MHz, Methanol-d$_4$) δ ppm 8.24 (s, 1H) 8.13-8.17 (m, 1H) 7.12-7.21 (m, 1H) 6.39 (d, J=7.50 Hz, 1H) 4.75 (br s, 1H) 3.62-3.77 (m, 1H) 3.69 (br s, 1H) 3.48 (q, J=6.84 Hz, 2H) 3.35 (br d, J=5.51 Hz, 3H) 3.24 (br s, 1H) 3.13 (br s, 3H) 3.01 (br s, 1H) 2.68 (t, J=6.17 Hz, 2H) 2.53-2.62 (m, 2H) 2.28-2.44 (m, 1H) 2.14 (br dd, J=14.66, 5.40 Hz, 1H) 1.85 (q, J=5.84 Hz, 2H) 1.73 (br s, 4H) 1.12 (t, J=7.06 Hz, 3H).

Compound 320: (S)-2-((5-bromopyrimidin-2-yl) amino)-4-((2-ethoxyethyl) (4-(5,6,7,8-tetrahydro-1,8-naphthyridin-2-yl) butyl)amino) butanoic acid: To a mixture of (S)-2-amino-4-((2-ethoxyethyl) (4-(5,6,7,8-tetrahydro-1,8-naphthyridin-2-yl) butyl)amino) butanoic acid (150 mg, 396 μmol) and 5-bromo-2-chloropyrimidine (84 mg, 436 μmol) in THF (2 mL) and H$_2$O (0.5 mL) was added NaHCO$_3$ (166 mg, 1.98 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=535.2 (M+H)$^+$. $^1$H NMR (400 MHz, Methanol-d$_4$) δ ppm 8.31 (s, 2H) 7.15-7.23 (m, 1H) 6.40 (d, J=7.28 Hz, 1H) 4.28 (t, J=5.84 Hz, 1H) 3.67 (t, J=5.18 Hz, 2H) 3.46-3.54 (m, 2H) 3.33-3.39 (m, 2H) 2.92-3.29 (m, 6H) 2.70 (t, J=6.28 Hz, 2H) 2.50-2.63 (m, 2H) 2.15-2.27 (m, 1H) 2.02-2.13 (m, 1H) 1.81-1.94 (m, 2H) 1.62-1.80 (m, 4H) 1.16 (t, J=7.06 Hz, 3H).

Compound 321: (S)-2-((6-(1H-pyrazol-1-yl) pyrimidin-4-yl) amino)-4-((2-ethoxyethyl) (4-(5,6,7,8-tetrahydro-1,8-naphthyridin-2-yl) butyl)amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 μmol) in DMA (2 mL) was added DIPEA (315 μL, 1.81 mmol) then 4-chloro-6-(1H-pyrazol-1-yl) pyrimidine (72 mg, 398 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=523.2 (M+H)$^+$. $^1$H NMR (400 MHz, Methanol-d$_4$) δ ppm 8.51 (d, J=2.63 Hz, 1H) 8.33 (s, 1H) 7.75 (d, J=1.32 Hz, 1H) 7.16 (d, J=7.02 Hz, 1H) 6.99 (br s, 1H) 6.52 (dd, J=2.63, 1.75 Hz, 1H) 6.40 (d, J=7.45 Hz, 1H) 4.51 (br s, 1H) 3.69 (t, J=5.26 Hz, 2H) 3.51 (q, J=6.72 Hz, 2H) 3.33-3.42 (m, 2H) 2.92-3.30 (m, 6H) 2.54-2.77 (m, 4H) 2.22-2.34 (m, 1H) 1.99-2.16 (m, 1H) 1.67-1.90 (m, 6H) 1.15 (t, J=7.02 Hz, 3H).

Compound 322: (S)-4-((2-ethoxyethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) in 4:1 THF/H$_2$O (2 mL) was added 4-chloro-2-(trifluoromethyl)pyrimidine (73 mg, 398 µmol) and NaHCO$_3$ (91 mg, 1.08 mmol) and the resulting mixture was heated to 70° C. for 1 h, cooled to rt, and then concentrated in vacuo. LCMS (ESI+): m/z=525.2 (M+H)$^+$. $^1$H NMR (400 MHz, Methanol-d$_4$) δ ppm 8.12 (br s, 1H) 7.21 (br d, J=7.45 Hz, 1H) 6.74 (br s, 1H) 6.42 (d, J=7.45 Hz, 1H) 4.54 (br s, 1H) 3.68 (br s, 2H) 3.44-3.54 (m, 2H) 3.33-3.42 (m, 3H) 2.90-3.28 (m, 5H) 2.70 (t, J=6.36 Hz, 2H) 2.60 (br t, J=7.24 Hz, 2H) 2.24 (br s, 1H) 2.02-2.12 (m, 1H) 1.83-1.90 (m, 2H) 1.73 (br s, 4H) 1.15 (t, J=7.02 Hz, 3H).

Compound 323: (S)-2-((5-cyclopropylpyrimidin-2-yl) amino)-4-((2-ethoxyethyl) (4-(5,6,7,8-tetrahydro-1,8-naphthyridin-2-yl) butyl)amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) 4:1 in THF/H$_2$O (2 mL) was added 5-cyclopropyl-2-fluoropyrimidine (55 mg, 398 µmol) and NaHCO$_3$ (91 mg, 1.08 mmol) and the resulting mixture was heated to 70° C. for 1 h, cooled to rt, and then concentrated in vacuo. The crude residue was purified by prep-HPLC to give the title compound. LCMS (ESI+): m/z=497.2 (M+H)$^+$. $^1$H NMR (400 MHz, Methanol-d$_4$) δ ppm 8.32-8.44 (m, 2H) 7.60 (d, J=7.45 Hz, 1H) 6.65 (d, J=7.45 Hz, 1H) 4.78 (dd, J=8.11, 5.04 Hz, 1H) 3.78 (t, J=4.60 Hz, 2H) 3.37-3.64 (m, 8H) 3.30 (br s, 1H) 3.28 (br s, 2H) 2.73-2.87 (m, 4H) 2.47-2.60 (m, 1H) 2.28-2.41 (m, 1H) 1.71-2.01 (m, 6H) 1.19 (t, J=7.02 Hz, 3H) 1.00-1.08 (m, 2H) 0.70-0.78 (m, 2H).

Scheme 34, Compound 324

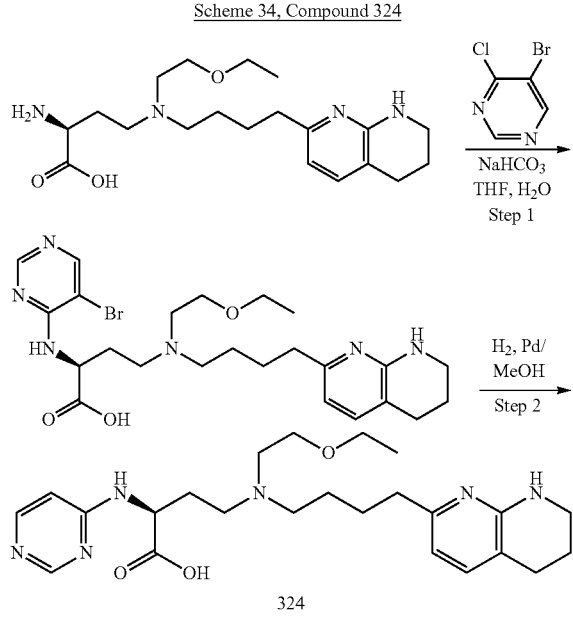

324

Step 1: (S)-2-((5-bromopyrimidin-4-yl) amino)-4-((2-ethoxyethyl) (4-(5,6,7,8-tetrahydro-1,8-naphthyridin-2-yl) butyl)amino) butanoic acid To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) in 4:1 THF/H$_2$O (3 mL) was added 5-bromo-4-chloropyrimidine (77 mg, 398 µmol) and NaHCO$_3$ (152 mg, 1.81 mmol) and the resulting mixture was heated to 70° C. for 1 h, cooled to rt, and then concentrated in vacuo to give the title compound that was used without further purification. LCMS (ESI+): m/z=535.0 (M+H)$^+$.

Step 2: (S)-4-((2-ethoxyethyl) (4-(5,6,7,8-tetrahydro-1,8-naphthyridin-2-yl) butyl)amino)-2-(pyrimidin-4-ylamino) butanoic acid To a mixture of (S)-2-((5-bromopyrimidin-4-yl) amino)-4-((2-ethoxyethyl) (4-(5,6,7,8-tetrahydro-1,8-naphthyridin-2-yl) butyl)amino) butanoic acid (387 mg, 723 µmol) in MeOH (20 mL) was added 20 wt % Pd/C (200 mg) and the resulting mixture was stirred under an H$_2$ atmosphere for 3 h and then filtered and concentrated in vacuo. The crude residue was purified by reverse phase prep-HPLC to give the title compound. LCMS (ESI+): m/z=457.3 (M+H)$^+$. $^1$H NMR (400 MHz, Methanol-d$_4$) δ ppm 8.78 (s, 1H) 8.20 (d, J=6.17 Hz, 1H) 7.59 (d, J=7.28 Hz, 1H) 7.04 (d, J=7.28 Hz, 1H) 6.66 (d, J=7.28 Hz, 1H) 5.01 (br s, 1H) 3.78 (br d, J=4.19 Hz, 2H) 3.32-3.63 (m, 10H) 2.75-2.87 (m, 4H) 2.47-2.61 (m, 1H) 2.37 (br s, 1H) 1.74-2.00 (m, 6H) 1.17 (t, J=7.06 Hz, 3H).

Compound 325: (S)-2-((3-cyanopyrazin-2-yl) amino)-4-((2-ethoxyethyl) (4-(5,6,7,8-tetrahydro-1,8-naphthyridin-2-yl) butyl)amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) in i-PrOH (3 mL) was added 3-chloropyrazine-2-carbonitrile (55 mg, 398 µmol) and DIPEA (315 µL, 1.81 mmol) and the resulting mixture was heated to 70° C. for 1 h, cooled to rt, and then concentrated in vacuo. The crude residue was purified by prep-HPLC to give the title compound. LCMS (ESI+): m/z=482.3 (M+H)$^+$. $^1$H NMR (400 MHz, Methanol-d$_4$) δ ppm 8.25 (d, J=2.63 Hz, 1H) 7.89 (d, J=2.19 Hz, 1H) 7.21 (d, J=7.02 Hz, 1H) 6.42 (d, J=7.45 Hz, 1H) 4.45 (dd, J=7.02, 4.38 Hz, 1H) 3.71 (t, J=5.26 Hz, 2H) 3.51 (q, J=7.02 Hz, 2H) 3.33-3.40 (m, 3H) 2.90-3.29 (m, 5H) 2.71 (t, J=6.14 Hz, 2H) 2.60 (br d, J=2.63 Hz, 2H) 2.22-2.36 (m, 1H) 2.09-2.19 (m, 1H) 1.83-1.93 (m, 2H) 1.68-1.79 (m, 4H) 1.16 (t, J=7.02 Hz, 3H).

Compound 326: (S)-4-((2-ethoxyethyl) (4-(5,6,7,8-tetrahydro-1,8-naphthyridin-2-yl) butyl)amino)-2-((6-phenylpyrimidin-4-yl) amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) in 4:1 THF/H$_2$O (2 mL) was added 4-chloro-6-phenylpyrimidine (76 mg, 398 µmol) and NaHCO$_3$ (91 mg, 1.08 mmol) and the resulting mixture was heated to 70° C. for 1 h, cooled to rt, and then concentrated in vacuo. The crude residue was purified by prep-HPLC to give the title compound. LCMS (ESI+): m/z=533.3 (M+H)$^+$. $^1$H NMR (400 MHz, Methanol-d$_4$) δ ppm 8.81 (s, 1H) 7.87 (d, J=7.09 Hz, 2H) 7.63-7.73 (m, 3H) 7.59 (d, J=7.21 Hz, 1H) 7.29 (s, 1H) 6.66 (d, J=7.34 Hz, 1H) 5.04-5.12 (m, 1H) 3.80 (br s, 2H) 3.44-3.62 (m, 8H) 3.33-3.38 (m, 2H) 2.77-2.86 (m, 4H) 2.58 (br s, 1H) 2.42 (br d, J=6.24 Hz, 1H) 1.78-1.98 (m, 6H) 1.21 (t, J=6.91 Hz, 3H).

Compound 327: (S)-4-((2-ethoxyethyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 361 µmol) in 4:1 THF/H$_2$O (2 mL) was added 7-chloro-2-methyl-2H-pyrazolo[4,3-d]pyrimidine (67 mg, 398 µmol) and NaHCO$_3$ (91 mg, 1.08 mmol) and the resulting mixture was heated to 70° C. for 1 h, cooled to rt, and then concentrated in vacuo. The crude residue was purified by prep-HPLC to give the title compound. LCMS (ESI+): m/z=511.3 (M+H)$^+$. $^1$H NMR (400 MHz, Methanol-d$_4$) δ ppm 8.57 (br s, 1H) 8.49 (s, 1H) 7.59

(d, J=7.34 Hz, 1H) 6.66 (d, J=7.46 Hz, 1H) 5.07 (br s, 1H) 4.09 (s, 3H) 3.81 (br s, 2H) 3.44-3.67 (m, 8H) 3.33-3.40 (m, 2H) 2.76-2.86 (m, 4H) 2.62-2.74 (m, 1H) 2.52 (br d, J=11.00 Hz, 1H) 1.72-2.05 (m, 6H) 1.19 (t, J=6.97 Hz, 3H).

Compound 328: (S)-4-((2-ethoxyethyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-((2-ethoxyethyl) (4-(5,6,7,8-tetrahydro-1,8-naphthyridin-2-yl) butyl)amino) butanoic acid hydrochloride (150 mg, 362 µmol) in DMA (2 mL) was added DIPEA (315 µL, 1.81 mmol) then 4-chloro-2-(pyridin-3-yl) quinazoline (96 mg, 398 µmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=584.3 (M+H)$^+$. $^1$H NMR (400 MHz, Methanol-d$_4$) δ ppm 9.56 (d, J=1.32 Hz, 1H) 8.83 (dt, J=8.11, 1.86 Hz, 1H) 8.58-8.66 (m, 1H) 8.13 (d, J=7.89 Hz, 1H) 7.72-7.89 (m, 2H) 7.45-7.60 (m, 2H) 7.12 (d, J=7.45 Hz, 1H) 6.33 (d, J=7.45 Hz, 1H) 4.92 (br s, 1H) 3.70 (t, J=5.04 Hz, 2H) 3.44 (q, J=7.02 Hz, 3H) 3.09-3.29 (m, 5H) 2.94-3.02 (m, 1H) 2.61 (t, J=6.14 Hz, 2H) 2.41-2.57 (m, 3H) 2.26-2.36 (m, 1H) 1.66-1.83 (m, 6H) 1.03-1.08 (m, 1H) 1.06 (t, J=7.02 Hz, 2H) 1.02-1.10 (m, 1H).

Compound 329: (S)-4-((2-ethoxyethyl) (4-(5,6,7,8-tetrahydro-1,8-naphthyridin-2-yl) butyl)amino)-2-((5-phenylpyrimidin-4-yl) amino) butanoic acid: To a mixture of (S)-2-((5-bromopyrimidin-4-yl) amino)-4-((2-ethoxyethyl) (4-(5,6,7,8-tetrahydro-1,8-naphthyridin-2-yl) butyl)amino) butanoic acid (387 mg, 723 µmol) was in 3:1 dioxane/H$_2$O (2 mL) was added K$_2$CO$_3$ (300 mg, 2.17 mmol), phenylboronic acid (220 mg, 1.81 mmol), then Pd(dppf)Cl$_2$ (53 mg, 72 µmol) and the resulting mixture was heated to 100° C. for 2 h, cooled to rt, and then concentrated in vacuo. The crude residue was purified by prep-HPLC to give the title compound. LCMS (ESI+): m/z=533.3 (M+H)$^+$. $^1$H NMR (400 MHz, Methanol-d$_4$) δ ppm 8.46 (br s, 1H) 7.98 (br s, 1H) 7.42-7.57 (m, 5H) 7.10-7.20 (m, 1H) 6.34-6.41 (m, 1H) 4.41-4.48 (m, 1H) 3.66 (t, J=5.18 Hz, 2H) 3.47-3.52 (m, 3H) 3.30 (br s, 2H) 2.88-3.29 (m, 5H) 2.68 (t, J=6.06 Hz, 2H) 2.52-2.60 (m, 2H) 2.08-2.29 (m, 2H) 1.82-1.90 (m, 2H) 1.54-1.79 (m, 4H) 1.13-1.19 (m, J=7.02 Hz, 3H).

Scheme 35, Compound 330

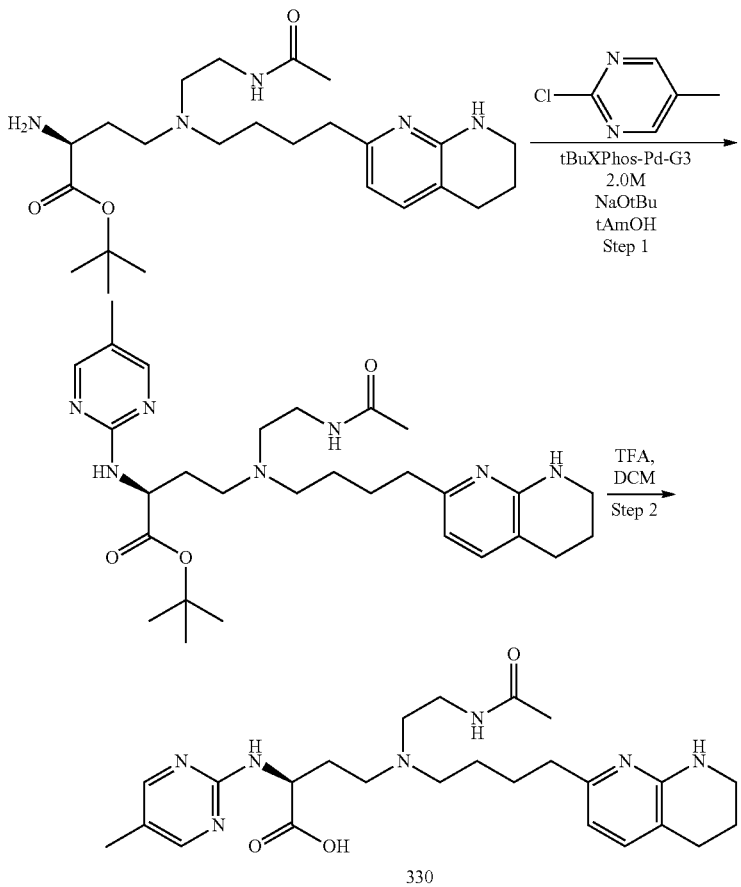

Step 1: (S)-tert-butyl 4-((2-acetamidoethyl) (4-(5,6,7,8-tetrahydro-1,8-naphthyridin-2-yl) butyl)amino)-2-((5-methylpyrimidin-2-yl) amino) butanoate To a mixture of (S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 2-chloro-5-methylpyrimidine (36 mg, 279 µmol) in t-AmOH (2 mL) was added 2.0M t-BuONa in THF (279 µL, 558 µmol) then t-BuXPhos-Pd-G3 (22 mg, 28 µmol) and the resulting mixture was heated to 100° C. for 14 h, cooled to rt, and then concentrated in vacuo to give the title compound that was used without further purification. LCMS (ESI+): m/z=540.1 (M+H)$^+$. Note: The t-butyl ester starting material was prepared in an analogous manner to example 213.

Step 2: (S)-4-(((S)-2-methoxypropyl) (4-(5,6,7,8-tetrahydro-1,8-naphthyridin-2-yl) butyl)amino)-2-((5-methylpyrimidin-2-yl)amino) butanoic acid (S)-tert-butyl 4-((2-acetamidoethyl) (4-(5,6,7,8-tetrahydro-1,8-naphthyridin-2-yl) butyl)amino)-2-((5-methylpyrimidin-2-yl) amino) butanoate (200 mg, 371 μmol) was taken up in 5:1 DCM/TFA (2 mL) and the resulting mixture was stirred at rt for 5 h and then concentrated in vacuo. The crude residue was purified by reverse phase prep-HPLC to give the title compound. LCMS (ESI+): m/z=484.2 (M+H)+. $^1$H NMR (400 MHz, DMSO-$d_6$) δ ppm 8.22 (s, 2H) 7.87 (br s, 1H) 7.14 (br d, J=6.62 Hz, 1H) 7.01 (br d, J=6.39 Hz, 1H) 6.63 (br s, 1H) 6.34 (br d, J=7.28 Hz, 1H) 4.31 (br s, 1H) 3.33 (br s, 2H) 3.22 (br s, 2H) 2.70 (br s, 4H) 2.60 (br s, 6H) 2.15 (br s, 3H) 1.99 (br d, J=5.95 Hz, 2H) 1.79-1.91 (m, 5H) 1.63 (br s, 2H) 1.48 (br s, 2H).

Compound 331: (S)-4-((2-acetamidoethyl) (4-(5,6,7,8-tetrahydro-1,8-naphthyridin-2-yl) butyl)amino)-2-(pyridin-3-ylamino) butanoic acid.

Compound 332: (S)-4-((2-acetamidoethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid (150 mg, 383 μmol) and 4-chloro-1-methyl-1H-pyrazolo[3,4-d]pyrimidine (71 mg, 421 μmol) in THF (2 mL) and H$_2$O (0.5 mL) was added NaHCO$_3$ (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=524.3 (M+H)+. $^1$H NMR (400 MHz, Methanol-$d_4$) δ ppm 8.24 (br s, 1H) 7.99-8.13 (m, 1H) 7.27 (br d, J=7.21 Hz, 1H) 6.43 (br d, J=7.34 Hz, 1H) 4.56 (br s, 1H) 3.95 (s, 3H) 3.37 (br d, J=6.60 Hz, 4H) 2.94-3.06 (m, 1H) 2.65-2.94 (m, 7H) 2.61 (br t, J=7.52 Hz, 2H) 2.24-2.38 (m, 1H) 2.07-2.22 (m, 1H) 1.55-2.03 (m, 9H).

Compound 333: (S)-4-((2-acetamidoethyl) (4-(5,6,7,8-tetrahydro-1,8-naphthyridin-2-yl) butyl)amino)-2-((5-cyanopyrimidin-2-yl) amino) butanoic acid.

Compound 334: (S)-4-((2-acetamidoethyl) (4-(5,6,7,8-tetrahydro-1,8-naphthyridin-2-yl) butyl)amino)-2-((5-(trifluoromethyl)pyrimidin-2-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid (150 mg, 383 μmol) and 2-chloro-5-(trifluoromethyl)pyrimidine (77 mg, 421 μmol) in THF (2 mL) and H$_2$O (0.5 mL) was added NaHCO$_3$ (161 mg, 1.98 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=538.2 (M+H)+. $^1$H NMR (400 MHz, Methanol-$d_4$) δ ppm 8.52 (br s, 2H) 7.34 (d, J=7.45 Hz, 1H) 6.49 (d, J=7.02 Hz, 1H) 4.45 (t, J=5.48 Hz, 1H) 3.32-3.50 (m, 4H) 2.87 (t, J=5.92 Hz, 2H) 2.60-2.82 (m, 8H) 2.10-2.25 (m, 2H) 1.93 (s, 3H) 1.83-1.90 (m, 2H) 1.69-1.82 (m, 2H) 1.56-1.67 (m, 2H).

Compound 335: (S)-2-((1H-pyrazolo[3,4-d]pyrimidin-4-yl) amino)-4-((2-acetamidoethyl) (4-(5,6,7,8-tetrahydro-1,8-naphthyridin-2-yl) butyl)amino) butanoic acid: To a mixture of (S)-4-((2-acetamidoethyl) (4-(5,6,7,8-tetrahydro-1,8-naphthyridin-2-yl) butyl)amino)-2-aminobutanoic acid (150 mg, 383 μmol) and 4-chloro-1H-pyrazolo[3,4-d]pyrimidine (65 mg, 421 μmol) in THF (2 mL) and H$_2$O (0.5 mL) was added NaHCO$_3$ (161 mg, 1.92 mmol) and the resulting mixture was stirred at 70° C. for 1 h and then concentrated in vacuo. The crude residue was purified by reverse phase prep-HPLC to give the title compound. LCMS (ESI+): m/z=510.2 (M+H)+. $^1$H NMR (400 MHz, Methanol-$d_4$) δ ppm 8.06-8.29 (m, 2H) 7.23-7.39 (m, 1H) 6.40-6.54 (m, 1H) 4.76-4.83 (m, 1H) 3.33-3.42 (m, 4H) 3.03 (br s, 1H) 2.78-2.97 (m, 4H) 2.58-2.74 (m, 5H) 2.31 (br d, J=5.70 Hz, 1H) 2.11-2.22 (m, 1H) 1.82-1.95 (m, 5H) 1.76 (br s, 2H) 1.65 (br d, J=4.82 Hz, 2H).

Scheme 36, Compound 336

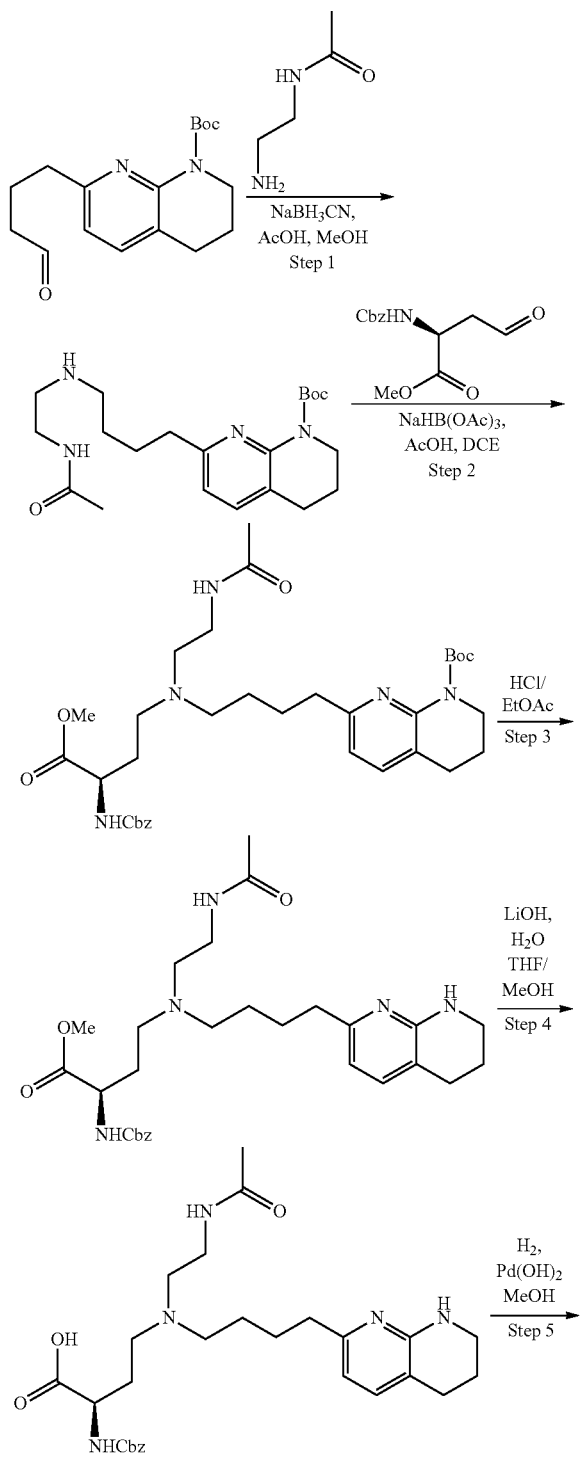

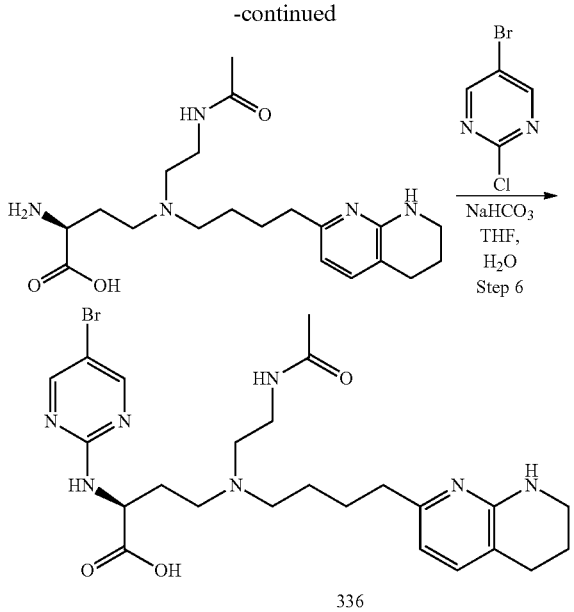

Step 1: tert-butyl 7-(4-((2-acetamidoethyl)amino) butyl)-3,4-dihydro-1,8-naphthyridine-1(2H)-carboxylate To a mixture of N-(2-aminoethyl)acetamide (18.8 mL, 197.12 mmol) and NaBH₃CN (8.26 g, 131.41 mmol) in MeOH (300 mL) at 0° C. was added AcOH (37.6 mL, 657.07 mmol) then a solution of tert-butyl 7-(4-oxobutyl)-3,4-dihydro-1,8-naphthyridine-1(2H)-carboxylate (20 g, 65.71 mmol) in MeOH (100 mL) and the resulting mixture was stirred at rt for 16 h. The reaction mixture was poured into sat. aq. NaHCO₃ and then concentrated in vacuo. The crude residue was purified by reverse phase prep-HPLC to give the title compound. LCMS (ESI+): m/z=391.4 (M+H)⁺.

Step 2: (S)-tert-butyl 7-(4-((2-acetamidoethyl) (3-(((benzyloxy)carbonyl)amino)-4-methoxy-4-oxobutyl)amino) butyl)-3,4-dihydro-1,8-naphthyridine-1(2H)-carboxylate To a mixture of tert-butyl 7-(4-((2-acetamidoethyl)amino) butyl)-3,4-dihydro-1,8-naphthyridine-1(2H)-carboxylate (18 g, 46.09 mmol) and methyl (2S)-2-(benzyloxycarbonylamino)-4-oxo-butanoate (13.45 g, 50.70 mmol) in DCE (200 mL) at 0° C. was added AcOH (4.0 mL, 69.14 mmol) then NaBH(OAc)₃ (14.65 g, 69.14 mmol) was added in portions and the resulting mixture was stirred at rt for 12 h. The reaction mixture was poured into sat. aq. NaHCO₃ (200 mL) and then extracted with ethyl acetate. The combined organic extracts were washed with brine, dried over Na₂SO₄, filtered, and concentrated in vacuo. The crude residue was purified by normal phase silica gel chromatography to give the title compound. LCMS (ESI+): m/z=640.5 (M+H)⁺.

Step 3: (S)-methyl 4-((2-acetamidoethyl) (4-(5,6,7, 8-tetrahydro-1,8-naphthyridin-2-yl) butyl)amino)-2-(((benzyl oxy)carbonyl)amino) butanoate (S)-tert-butyl 7-(4-((2-acetamidoethyl) (3-(((benzyloxy) carbonyl)amino)-4-methoxy-4-oxobutyl)amino)butyl)-3,4-dihydro-1,8-naphthyridine-1(2H)-carboxylate (3.47 g, 5.42 mmol) was taken up in 4 M HCl in EtOAc (30 mL) and the resulting mixture was stirred at rt for 1.5 h and then concentrated in vacuo to give the title compound that was used without further purification. LCMS (ESI+): m/z=540.4 (M+H)⁺.

Step 4: (S)-4-((2-acetamidoethyl) (4-(5,6,7,8-tetrahydro-1,8-naphthyridin-2-yl) butyl)amino)-2-(((benzyloxy) carbonyl)amino) butanoic acid To a mixture of (S)-methyl 4-((2-acetamidoethyl) (4-(5, 6,7,8-tetrahydro-1,8-naphthyridin-2-yl) butyl)amino)-2-(((benzyloxy)carbonyl)amino) butanoate (3.5 g, 6.49 mmol) in 2:2:1 THF/MeOH/H₂O (50 mL) was added LiOH.H₂O (1.09 g, 25.94 mmol) and the resulting mixture was stirred at rt for 1 h and then adjusted to pH=4 by the addition of 1 M aq. HCl and concentrated in vacuo to give the title compound that was used without further purification. LCMS (ESI+): m/z=526.4 (M+H)⁺.

Step 5: (S)-4-((2-acetamidoethyl) (4-(5,6,7,8-tetrahydro-1,8-naphthyridin-2-yl) butyl)amino)-2-aminobutanoic acid To a mixture of (S)-4-((2-acetamidoethyl) (4-(5,6,7,8-tetrahydro-1,8-naphthyridin-2-yl) butyl)amino)-2-(((benzyloxy)carbonyl)amino) butanoic acid (2 g, 3.80 mmol) in i-PrOH (30 mL) was added 10 wt % Pd(OH)₂/C (2 g) and the resulting mixture was stirred under an H₂ atmosphere for 16 h. The reaction mixture was filtered and then concentrated in vacuo to give the title compound that was used without further purification. LCMS (ESI+): m/z=392.2 (M+H)⁺.

Step 6: (S)-4-((2-acetamidoethyl) (4-(5,6,7,8-tetrahydro-1,8-naphthyridin-2-yl) butyl)amino)-2-((5-bromopyrimidin-2-yl) amino) butanoic acid To a solution of (2S)-4-[2-acetamidoethyl-[4-(5,6,7,8-tetrahydro-1,8-naphthyridin-2-yl) butyl]amino]-2-aminobutanoic acid (150 mg, 383 μmol) and 5-bromo-2-chloropyrimidine (89 mg, 460 μmol) in THF (2 mL) and H₂O (0.5 mL) was added NaHCO₃ (161 mg, 1.92 mmol) and the resulting mixture was stirred at 70° C. for 1 h, cooled to rt, and then concentrated in vacuo. The crude residue was purified by reverse phase prep-HPLC to give the title compound. LCMS (ESI+): m/z=548.2 (M+H)⁺. ¹H NMR (400 MHz, Methanol-d₄) δ ppm 8.28 (s, 2H) 7.34 (d, J=7.28 Hz, 1H) 6.49 (d, J=7.50 Hz, 1H) 4.32 (t, J=5.73 Hz, 1H) 3.48 (br s, 1H) 3.32-3.51 (m, 3H) 2.76-2.91 (m, 3H) 2.73 (br t, J=6.17 Hz, 3H) 2.65 (br t, J=7.39 Hz, 2H) 2.60-2.68 (m, 1H) 2.60-2.92 (m, 1H) 2.15 (br d, J=3.09 Hz, 2H) 1.92 (s, 3H) 1.87 (q, J=5.79 Hz, 2H) 1.69-1.84 (m, 2H) 1.58-1.69 (m, 1H) 1.58-1.69 (m, 1H).

Compound 337: (S)-2-((7H-pyrrolo[2,3-d]pyrimidin-4-yl) amino)-4-((2-acetamidoethyl) (4-(5,6,7,8-tetrahydro-1, 8-naphthyridin-2-yl) butyl)amino) butanoic acid.

Compound 338: (S)-2-((1H-pyrazolo[4,3-d]pyrimidin-7-yl) amino)-4-((2-acetamidoethyl) (4-(5,6,7,8-tetrahydro-1, 8-naphthyridin-2-yl) butyl)amino) butanoic acid.

Compound 339: (S)-4-((2-acetamidoethyl) (4-(5,6,7,8-tetrahydro-1,8-naphthyridin-2-yl) butyl)amino)-2-((2-methoxypyrimidin-4-yl) amino) butanoic acid.

Scheme 37, Compound 340

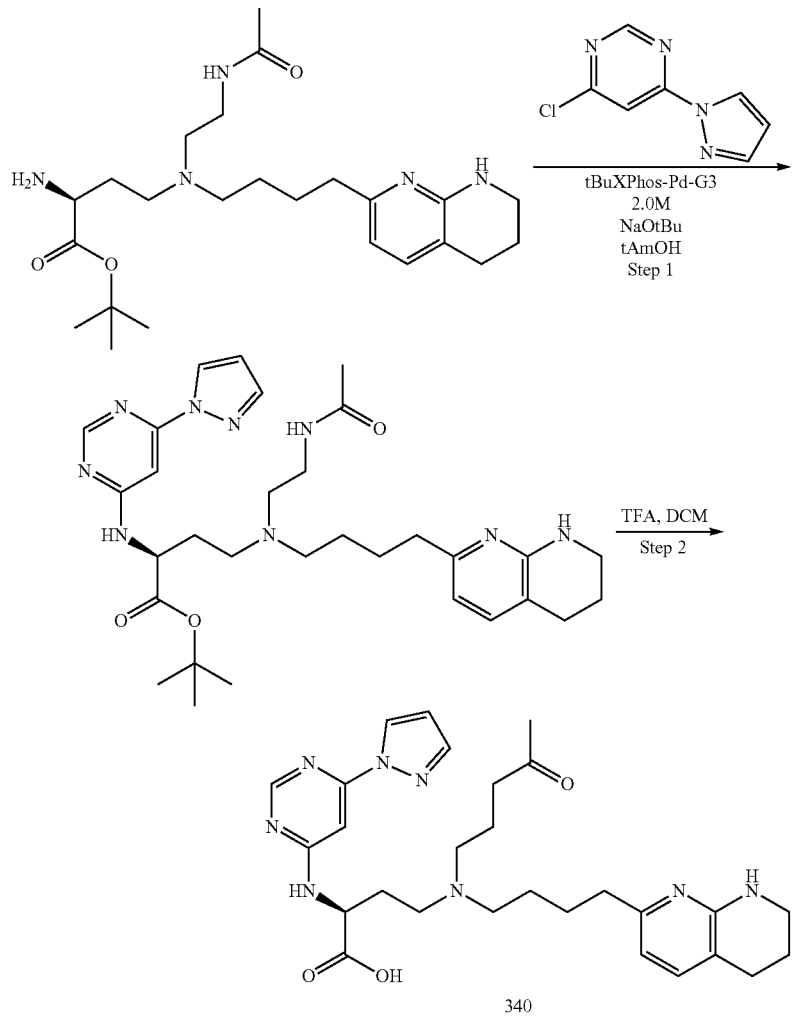

Step 1: (S)-tert-butyl 2-((6-(1H-pyrazol-1-yl) pyrimidin-4-yl) amino)-4-((2-acetamidoethyl) (4-(5, 6,7,8-tetrahydro-1,8-naphthyridin-2-yl) butyl)amino) butanoate To a mixture of (S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 4-chloro-6-(1H-pyrazol-1-yl) pyrimidine (50 mg, 279 µmol) in t-AmOH (3 mL) was added t-BuONa (279 µL, 558 µmol) then t-BuXPhos-Pd-G3 (22 mg, 28 µmol) and the resulting mixture was heated to 100° C. for 5 h, cooled to rt, and then concentrated in vacuo to give the title compound that was used without further purification. LCMS (ESI+): m/z=592.5 (M+H)+.

Step 2: (S)-2-((6-(1H-pyrazol-1-yl) pyrimidin-4-yl) amino)-4-((2-acetamidoethyl) (4-(5,6,7,8-tetrahydro-1,8-naphthyridin-2-yl) butyl)amino) butanoic acid (S)-tert-butyl 2-((6-(1H-pyrazol-1-yl) pyrimidin-4-yl) amino)-4-((2-acetamidoethyl) (4-(5,6,7,8-tetrahydro-1,8-naphthyridin-2-yl) butyl)amino) butanoate (148 mg, 249 µmol) was taken up in 3:1 DCM/TFA (2 mL) and the resulting mixture was stirred at rt for 1.5 h and then concentrated in vacuo. The crude residue was purified by reverse phase prep-HPLC to give the title compound. LCMS (ESI+): m/z=536.3 (M+H)+. $^1$H NMR (400 MHz, DMSO-$d_6$) δ ppm 14.23 (br s, 1H) 10.63 (br s, 1H) 8.55 (d, J=2.44 Hz, 1H) 8.41 (d, J=0.73 Hz, 1H) 8.31 (br s, 2H) 8.07 (br s, 1H) 7.86 (d, J=0.98 Hz, 1H) 7.59 (d, J=7.34 Hz, 1H) 7.08-7.13 (m, 1H) 6.63 (d, J=7.34 Hz, 1H) 6.57 (dd, J=2.57, 1.71 Hz, 1H) 4.63 (br s, 1H) 3.43 (br d, J=4.77 Hz, 4H) 3.31 (br s, 1H) 3.16 (br s, 5H) 2.63-2.78 (m, 4H) 2.32 (br t, J=12.29 Hz, 1H) 2.18 (br s, 1H) 1.78-1.86 (m, 5H) 1.66-1.76 (m, 4H).

Compound 341: (S)-4-((2-acetamidoethyl) (4-(5,6,7,8-tetrahydro-1,8-naphthyridin-2-yl) butyl)amino)-2-((6-(dimethylamino)pyrimidin-4-yl) amino) butanoic acid: To a mixture of (S)-tert-butyl 4-((2-acetamidoethyl) (4-(5,6,7,8-tetrahydro-1,8-naphthyridin-2-yl) butyl)amino)-2-aminobutanoate (100 mg, 223 µmol) and 6-chloro-N,N-dimethylpyrimidin-4-amine (29 mg, 186 µmol) in t-AmOH (2 mL) was added 2.0M t-BuONa in THF (186 µL, 372 µL) then tBuXPhos-Pd-G3 (15 mg, 19 µmol) and the resulting mixture was heated to 100° C. for 14 h, cooled to rt, and then concentrated in vacuo to give a (S)-tert-butyl 4-((2-acetamidoethyl) (4-(5,6,7,8-tetrahydro-1,8-naphthyridin-2-yl) butyl)amino)-2-((6-(dimethylamino)pyrimidin-4-yl) amino) butanoate intermediate, LCMS (ESI+): m/z=569.6 (M+H)+, which was used without further purification. Of the butanoate intermediate, 130 mg, 229 μmol, was taken up in DCM (2 mL) was added TFA (400 μL) and the resulting mixture was stirred at rt for 3 h and then concentrated in vacuo. The crude residue was purified by reverse phase prep-HPLC to give the title compound. LCMS (ESI+): m/z=513.3 (M+H)+. 1H NMR (400 MHz, DMSO-d6) δ ppm 7.96 (s, 1H) 7.76 (br s, 1H) 6.93-7.12 (m, 1H) 6.71 (br s, 1H) 6.55 (br s, 1H) 6.25 (d, J=7.21 Hz, 1H) 5.55 (br s, 1H) 4.26 (br s, 1H) 3.22 (br d, J=5.38 Hz, 2H) 3.10-3.14 (m, 2H) 2.93 (s, 6H) 2.54-2.68 (m, 5H) 2.33-2.45 (m, 3H) 1.67-1.96 (m, 7H) 1.48-1.60 (m, 2H) 1.31-1.47 (m, 2H).

Compound 342: (S)-4-((2-acetamidoethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid (150 mg, 383 μmol) and 4-fluoro-2-(trifluoromethyl)pyrimidine (76 mg, 460 μmol) in THF (2 mL) and H2O (0.5 mL) was added NaHCO3 (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=538.3 (M+H)+. 1H NMR (400 MHz, Methanol-d4) δ ppm 8.09 (br s, 1H) 7.24-7.34 (m, 1H) 6.71 (br s, 1H) 6.45 (d, J=7.28 Hz, 1H) 4.58 (br s, 1H) 3.32-3.43 (m, 3H) 3.32-3.44 (m, 1H) 2.84 (br s, 1H) 2.73 (br d, J=5.51 Hz, 6H) 2.47-2.66 (m, 1H) 2.62 (br t, J=7.50 Hz, 2H) 2.19 (br s, 1H) 2.02-2.14 (m, 1H) 1.81-1.94 (m, 5H) 1.71 (br s, 2H) 1.52-1.65 (m, 2H).

Compound 343: (S)-4-((2-acetamidoethyl) (4-(5,6,7,8-tetrahydro-1,8-naphthyridin-2-yl) butyl)amino)-2-((5-cyclopropylpyrimidin-2-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid (150 mg, 383 μmol) and 5-cyclopropyl-2-fluoropyrimidine (64 mg, 460 μmol) in THF (2 mL) and H2O (0.5 mL) was added NaHCO3 (161 mg, 1.92 mmol) and the resulting mixture was stirred at 70° C. for 1 h, cooled to rt, and then concentrated in vacuo. The crude residue was purified by reverse phase prep-HPLC to give the title compound. LCMS (ESI+): m/z=510.3 (M+H)+. 1H NMR (400 MHz, Methanol-d4) δ ppm 8.06 (s, 2H) 7.27 (d, J=7.28 Hz, 1H) 6.44 (d, J=7.28 Hz, 1H) 4.32 (t, J=5.73 Hz, 1H) 3.34-3.44 (m, 3H) 3.22-3.30 (m, 1H) 2.78-2.86 ((m, 1H) 2.78-2.89 (m, 1H) 2.66-2.77 (m, 5H) 2.56-2.65 (m, 3H) 2.05-2.25 (m, 2H) 1.92 (s, 3H) 1.81-1.90 (m, 2H) 1.66-1.79 (m, 3H) 1.52-1.64 (m, 2H) 0.85-0.97 (m, 2H) 0.53-0.64 (m, 2H).

Compound 344: (S)-4-((2-acetamidoethyl)-tetrahydro-1,8-naphthyridin-2-yl) butyl)amino)-2-((6-(tert-butyl)pyrimidin-4-yl) amino) butanoic acid: To a mixture of (S)-tert-butyl 4-((2-acetamidoethyl) (4-(5,6,7,8-tetrahydro-1,8-naphthyridin-2-yl) butyl)amino)-2-aminobutanoate (100 mg, 223 μmol) and 4-(tert-butyl)-6-chloropyrimidine (32 mg, 186 μmol) in t-AmOH (2 mL) was added 2.0M t-BuONa in THF (186 μL, 372 μmol) and tBuXPhos-Pd-G3 (15 mg, 19 μmol) and the resulting mixture was heated to 100° C. for 14 h, cooled to rt, and then concentrated in vacuo to give a (S)-tert-butyl 4-((2-acetamidoethyl) (4-(5,6,7,8-tetrahydro-1,8-naphthyridin-2-yl) butyl)amino)-2-((6-(tert-butyl)pyrimidin-4-yl) amino) butanoate intermediate, LCMS (ESI+): m/z=582.5 (M+H)+, which was used without further purification. Of the butanoate intermediate, 130 mg, 223 μmol, was taken up in DCM (2 mL) was added TFA (400 μL) and the resulting mixture was stirred at rt for 5 h and then concentrated in vacuo. The crude residue was purified by reverse phase prep-HPLC to give the title compound. LCMS (ESI+): m/z=526.3 (M+H)+. 1H NMR (400 MHz, Methanol-d4) δ ppm 8.35 (s, 1H) 7.72 (br t, J=5.18 Hz, 1H) 7.36 (br s, 1H) 7.04 (d, J=7.28 Hz, 1H) 6.57 (br d, J=11.69 Hz, 2H) 6.24 (d, J=7.28 Hz, 1H) 4.38 (br s, 1H) 3.23 (br d, J=5.07 Hz, 3H) 3.05-3.18 (m, 2H) 2.52-2.72 (m, 6H) 2.32-2.49 (m, 4H) 1.67-1.99 (m, 7H) 1.49-1.64 (m, 2H) 1.39 (dt, J=13.89, 6.73 Hz, 2H) 1.20 (s, 9H).

Compound 345: (S)-4-((2-acetamidoethyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid: To a mixture of (S)-tert-butyl 4-((2-acetamidoethyl) (4-(5,6,7,8-tetrahydro-1,8-naphthyridin-2-yl) butyl)amino)-2-aminobutanoate (100 mg, 223 μmol) and 4-chloro-7-methyl-7H-pyrrolo[2,3-d]pyrimidine (31 mg, 186 μmol) in t-AmOH (2 mL) was added 2.0M t-BuONa in THF (186 μL, 372 μmol) the tBuXPhos-Pd-G3 (15 mg, 19 μmol) and the resulting mixture was heated to 100° C. for 14 h, cooled to rt, and then concentrated in vacuo to give a (S)-tert-butyl 4-((2-acetamidoethyl) (4-(5,6,7,8-tetrahydro-1,8-naphthyridin-2-yl) butyl)amino)-2-((7-methyl-7H-pyrrolo[2,3-d]pyrimidin-4-yl) amino) butanoate intermediate, LCMS (ESI+): m/z=579.5 (M+H)+, which was used without further purification. Of the butanoate intermediate, 130 mg, 225 μmol, was taken up in DCM (2 mL) and TFA (500 μL) and the resulting mixture was stirred at rt for 5 h and then concentrated in vacuo. The crude residue was purified by reverse phase prep-HPLC to give the title compound. LCMS (ESI+): m/z=523.2 (M+H)+. 1H NMR (400 MHz, Methanol-d4) δ ppm 13.95-14.35 (m, 1H) 10.36-10.81 (m, 1H) 8.22-8.45 (m, 2H) 8.04 (br s, 1H) 7.60 (d, J=7.28 Hz, 1H) 7.40 (br s, 1H) 7.00-7.13 (m, 1H) 6.63 (d, J=7.28 Hz, 1H) 4.94 (br s, 1H) 3.80 (s, 3H) 3.40-3.47 (m, 6H) 3.10-3.27 (m, 4H) 2.64-2.81 (m, 4H) 2.27-2.46 (m, 2H) 1.63-1.88 (m, 9H).

Scheme 38, Compound 346

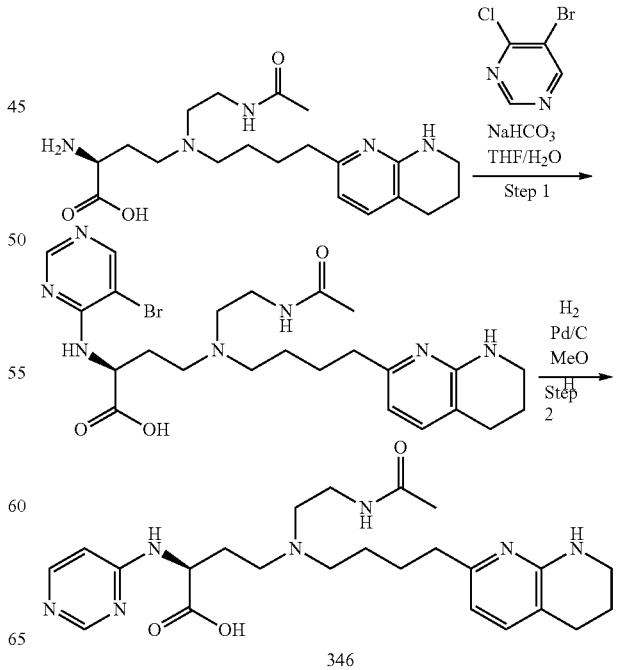

346

Step 1: (S)-4-((2-acetamidoethyl) (4-(5,6,7,8-tetrahydro-1,8-naphthyridin-2-yl) butyl)amino)-2-((5-bromopyrimidin-4-yl) amino) butanoic acid To a mixture of (S)-4-((2-acetamidoethyl) (4-(5,6,7,8-tetrahydro-1,8-naphthyridin-2-yl) butyl)amino)-2-aminobutanoic acid (200 mg, 511 µmol) and 5-bromo-4-chloropyrimidine (109 mg, 562 µmol) in THF (2 mL) and H$_2$O (0.5 mL) was added NaHCO$_3$ (215 mg, 2.55 mmol) and the resulting mixture was heated to 70° C. for 1 h and then cooled to rt and then concentrated in vacuo to give the title compound that was used without further purification. LCMS (ESI+): m/z=548.3 (M+H)$^+$.

Step 2: (S)-4-((2-acetamidoethyl) (4-(5,6,7,8-tetrahydro-1,8-naphthyridin-2-yl) butyl)amino)-2-(pyrimidin-4-ylamino) butanoic acid To a mixture of (S)-4-((2-acetamidoethyl) (4-(5,6,7,8-tetrahydro-1,8-naphthyridin-2-yl) butyl)amino)-2-((5-bromopyrimidin-4-yl) amino) butanoic acid (200 mg, 364.65 µmol, 1 eq) in MeOH (20 mL) was added 20 wt % Pd/C (200 mg) and the resulting mixture was stirred under an H$_2$ atmosphere for 3 h and then filtered and concentrated in vacuo. The crude residue was purified by reverse phase prep-HPLC to give the title compound. LCMS (ESI+): m/z=470.2 (M+H)$^+$. $^1$H NMR (400 MHz, Methanol-d$_4$) δ ppm 8.37 (br s, 1H) 8.04 (br s, 1H) 7.34 (d, J=7.34 Hz, 1H) 6.59 (br s, 1H) 6.48 (d, J=7.34 Hz, 1H) 4.49 (br s, 1H) 3.34-3.48 (m, 4H) 2.59-3.06 (m, 10H) 2.06-2.26 (m, 2H) 1.83-1.98 (m, 5H) 1.59-1.81 (m, 4H).

Compound 347: (S)-4-((2-acetamidoethyl) (4-(5,6,7,8-tetrahydro-1,8-naphthyridin-2-yl) butyl)amino)-2-((3-cyanopyrazin-2-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid hydrochloride (150 mg, 350 µmol) in i-PrOH (3 mL) was added 3-chloropyrazine-2-carbonitrile (54 mg, 386 µmol) and DIPEA (305 µL, 1.75 mmol) and the resulting mixture was heated to 70° C. for 1 h, cooled to rt, and then concentrated in vacuo. The crude residue was purified by reverse phase prep-HPLC to give the title compound. LCMS (ESI+): m/z=495.2 (M+H)$^+$. $^1$H NMR (400 MHz, Methanol-d$_4$) δ ppm 8.25 (d, J=2.43 Hz, 1H) 7.87 (d, J=2.43 Hz, 1H) 7.37 (d, J=7.28 Hz, 1H) 6.50 (d, J=7.28 Hz, 1H) 4.49 (t, J=5.07 Hz, 1H) 3.33-3.49 (m, 4H) 2.64-2.88 (m, 10H) 2.25 (q, J=5.44 Hz, 2H) 1.85-1.96 (m, 5H) 1.50-1.81 (m, 4H).

Scheme 39, Compound 348

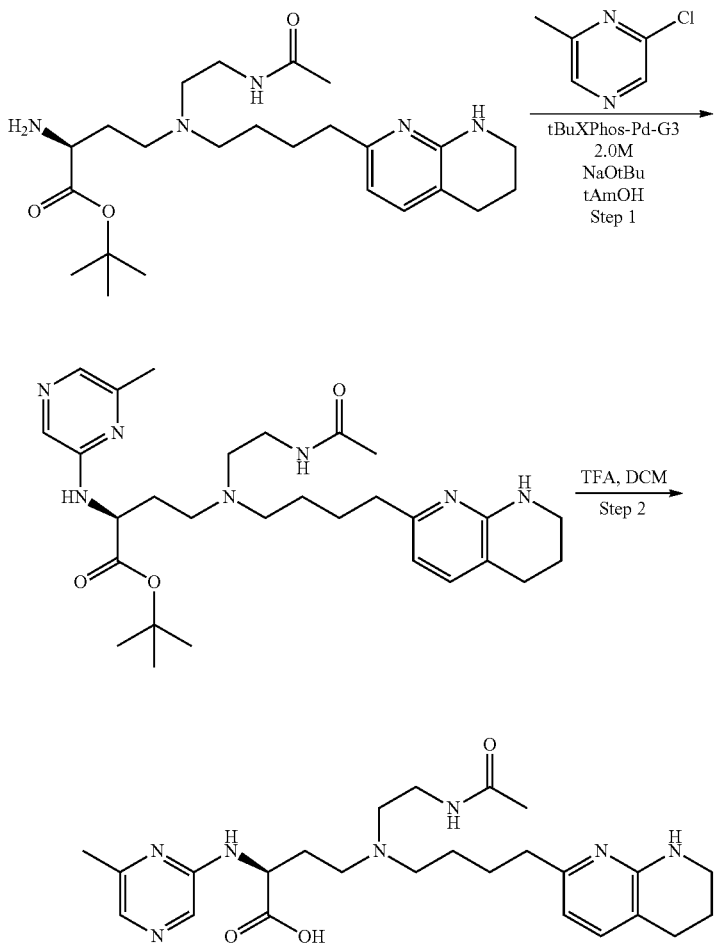

348

Step 1: (S)-tert-butyl 4-((2-acetamidoethyl) (4-(5,6,7,8-tetrahydro-1,8-naphthyridin-2-yl) butyl)amino)-2-((6-methylpyrazin-2-yl) amino) butanoate To a mixture of ((S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 2-chloro-6-methylpyrimidine (36 mg, 279 µmol) in t-AmOH (2 mL) was added 2.0M t-BuONa in THF (279 µL, 558 µmol) then t-BuXphos Pd G3 (22 mg, 28 µmol)) and the resulting mixture was heated to 100° C. for 15 h, cooled to rt, and then concentrated in vacuo to give the title compound that was used without further purification. LCMS (ESI+): m/z=540.1 (M+H)+.

Step 2: (S)-4-((2-acetamidoethyl) (4-(5,6,7,8-tetrahydro-1,8-naphthyridin-2-yl) butyl)amino)-2-((6-methylpyrazin-2-yl) amino) butanoic acid (S)-tert-butyl 4-((2-acetamidoethyl) (4-(5,6,7,8-tetrahydro-1,8-naphthyridin-2-yl) butyl)amino)-2-((6-methylpyrazin-2-yl) amino) butanoate (200 mg, 371 µmol) was taken up in 3:1 DCM/TFA=3:1 (2 mL) and the resulting mixture was stirred at rt for 5 h and then concentrated in vacuo. The crude residue was purified by reverse phase prep-HPLC to give the title compound. LCMS (ESI+): m/z=484.2 (M+H)+. 1H NMR (400 MHz, DMSO-d6) δ ppm 7.81 (s, 1H) 7.74 (br t, J=5.38 Hz, 1H) 7.56 (s, 1H) 6.99-7.06 (m, 2H) 6.51 (br s, 1H) 6.24 (d, J=7.21 Hz, 1H) 4.27 (q, J=6.11 Hz, 1H) 3.22-3.25 (m, 2H) 3.09-3.16 (m, 2H) 2.51-2.84 (m, 7H) 2.44-2.49 (m, 1H) 2.36-2.43 (m, 2H) 2.20 (s, 3H) 1.92 (dt, J=13.33, 6.79 Hz, 1H) 1.79-1.85 (m, 1H) 1.71-1.79 (m, 5H) 1.53 (q, J=7.27 Hz, 2H) 1.35-1.45 (m, 2H).

Scheme 40, Compound 349

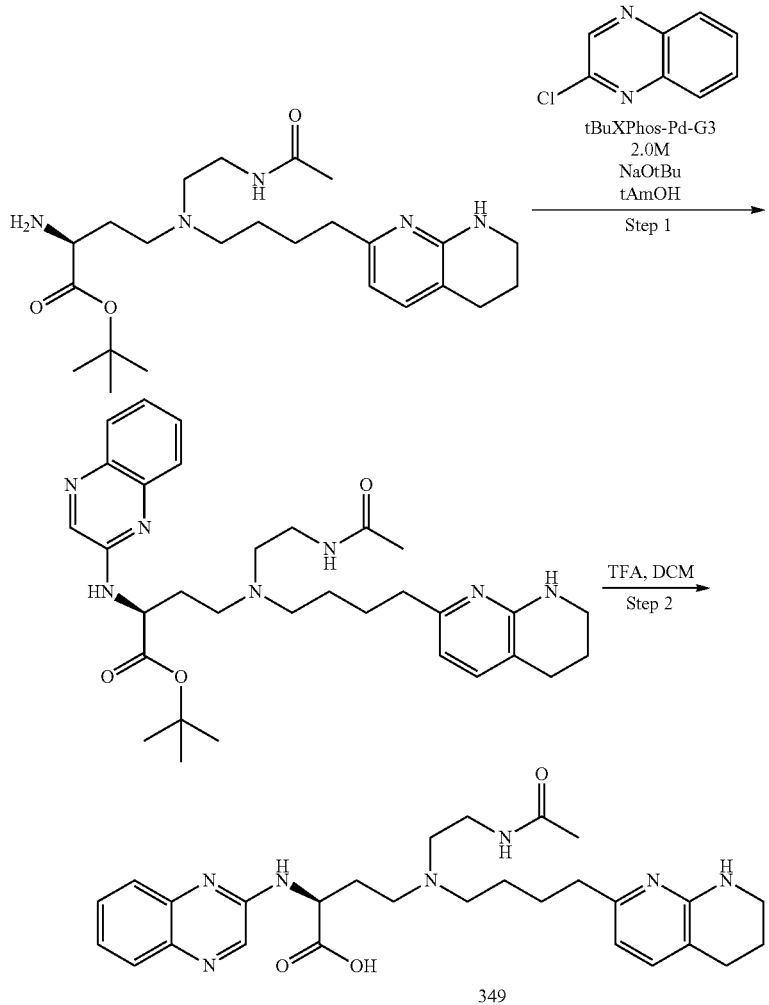

Step 1: (S)-tert-butyl 4-((2-acetamidoethyl) (4-(5,6,7,8-tetrahydro-1,8-naphthyridin-2-yl) butyl)amino)-2-(quinoxalin-2-ylamino) butanoate To a mixture of ((S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 2-chloroquinoxaline (46 mg, 279 µmol) in t-AmOH (2 mL) was added 2.0M t-BuONa (279 µL, 558 µmol) then t-BuXphos Pd G3 (22 mg, 28 µmol) and the resulting mixture was heated to 100° C. for 15 h, cooled to rt, and then concentrated in vacuo to give the title compound that was used without further purification. LCMS (ESI+): m/z=576.1 (M+H)+.

Step 2: (S)-4-((2-acetamidoethyl) (4-(5,6,7,8-tetra-hydro-1,8-naphthyridin-2-yl) butyl)amino)-2-(quinoxalin-2-ylamino) butanoic acid ((S)-tert-butyl 4-((2-acetamidoethyl) (4-(5,6,7,8-tetra-hydro-1,8-naphthyridin-2-yl) butyl)amino)-2-(quinoxalin-2-ylamino) butanoate (200 mg, 347 µmol) was taken up in 3:1 DCM/TFA (2 mL) and the resulting mixture was stirred at rt for 5 h and then concentrated in vacuo. The crude residue was purified by reverse phase prep-HPLC to give the title compound. LCMS (ESI+): m/z=520.2 (M+H)⁺. ¹H NMR (400 MHz, DMSO-d₆) δ ppm 8.44 (s, 1H) 7.86 (br s, 1H) 7.74 (d, J=7.72 Hz, 1H) 7.66 (br d, J=7.06 Hz, 1H) 7.47-7.53 (m, 2H) 7.30 (ddd, J=8.16, 5.62, 2.54 Hz, 1H) 6.98 (d, J=7.28 Hz, 1H) 6.48 (br s, 1H) 6.19 (d, J=7.28 Hz, 1H) 4.35-4.43 (m, 1H) 3.22 (br d, J=5.07 Hz, 2H) 3.10-3.15 (m, 2H) 2.52-2.71 (m, 7H) 2.33-2.48 (m, 3H) 1.86-2.05 (m, 2H) 1.71-1.77 (m, 5H) 1.48-1.59 (m, 2H) 1.34-1.46 (m, 2H).

nylpyrimidine (53 mg, 279 µmol) in t-AmOH (3 mL) was added 2.0M t-BuONa in THF (279 µL, 558 µmol) then t-BuXphos Pd (22 mg, 28 µmol) and the resulting mixture was heated to 100° C. for 15 h, cooled to rt, and then concentrated in vacuo to give the title compound that was used without further purification. LCMS (ESI+): m/z=602.5 (M+H)⁺.

Step 2: (S)-4-((2-acetamidoethyl) (4-(5,6,7,8-tetra-hydro-1,8-naphthyridin-2-yl) butyl)amino)-2-((2-phenylpyrimidin-4-yl) amino) butanoic acid (S)-tert-butyl 4-((2-acetamidoethyl) (4-(5,6,7,8-tetra-hydro-1,8-naphthyridin-2-yl) butyl)amino)-2-((2-phenylpyrimidin-4-yl) amino) butanoate (150 mg, 249 µmol) was

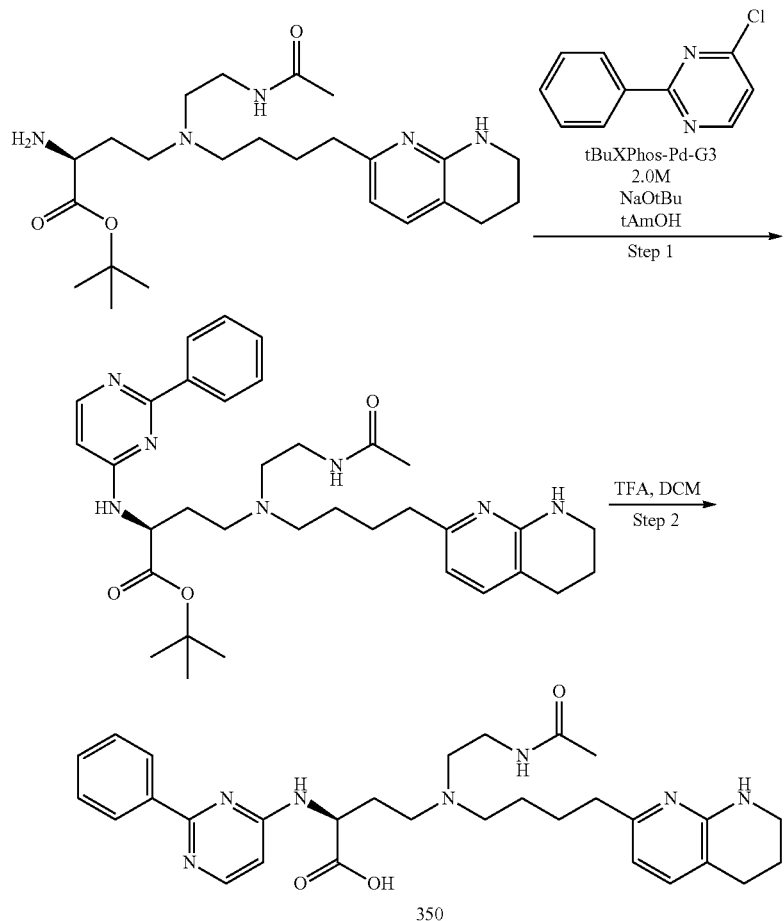

Scheme 41, Compound 350

Step 1: (S)-tert-butyl 4-((2-acetamidoethyl) (4-(5,6,7,8-tetrahydro-1,8-naphthyridin-2-yl) butyl)amino)-2-((2-phenylpyrimidin-4-yl) amino) butanoate To a mixture of (S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 4-chloro-2-phetaken up in DCM/TFA (2 mL) and the resulting mixture was stirred at rt for 5 h and then concentrated in vacuo. The crude residue was purified by reverse phase prep-HPLC to give the title compound. LCMS (ESI+): m/z=546.3 (M+H)⁺. ¹H NMR (400 MHz, DMSO-d₆) δ ppm 8.27-8.35 (m, 2H) 8.14-8.20 (m, 1H) 7.73 (br s, 1H) 7.62 (br s, 1H) 7.44 (br d, J=3.55 Hz, 3H) 6.99 (br d, J=7.21 Hz, 1H) 6.39-6.61 (m, 2H) 6.21 (d, J=7.21 Hz, 1H) 4.50 (br s, 1H) 3.01-3.25 (m, 4H)

2.66 (br dd, J=13.39, 6.66 Hz, 2H) 2.58 (br t, J=5.75 Hz, 4H) 2.31-2.43 (m, 2H) 1.86-2.05 (m, 2H) 1.71-1.78 (m, 5H) 1.33-1.62 (m, 6H).

Compound 351: (S)-4-((2-acetamidoethyl) (4-(5,6,7,8-tetrahydro-1,8-naphthyridin-2-yl) butyl)amino)-2-((6-phenylpyrimidin-4-yl) amino) butanoic acid.

Compound 352: (S)-4-((2-acetamidoethyl) (4-(5,6,7,8-tetrahydro-1,8-naphthyridin-2-yl) butyl)amino)-2-((5-phenylpyrimidin-4-yl) amino) butanoic acid: To a mixture of (S)-4-((2-acetamidoethyl) (4-(5,6,7,8-tetrahydro-1,8-naphthyridin-2-yl) butyl)amino)-2-((5-bromopyrimidin-4-yl) amino) butanoic acid (100 mg, 171 μmol) in 3:1 dioxane/H$_2$O (2 mL) was added K$_2$CO$_3$ (71 mg, 513 μmol) and phenylboronic acid (31 mg, 256 μmol) then Pd(dppf)Cl$_2$ (13 mg, 17 μmol) and the resulting mixture was heated to 100° C. for 2 h, cooled to rt, and then concentrated in vacuo. The crude residue was purified by prep-HPLC to give the title compound. LCMS (ESI+): m/z=546.3 (M+H)$^+$. $^1$H NMR (400 MHz, Methanol-d$_4$) δ ppm δ ppm 8.85 (s, 1H) 8.22 (s, 1H) 7.61 (s, 6H) 6.66 (d, J=7.34 Hz, 1H) 5.14 (br t, J=6.24 Hz, 1H) 3.33-3.60 (m, 10H) 2.73-2.88 (m, 4H) 2.57 (br s, 1H) 2.39 (br d, J=7.09 Hz, 1H) 1.94-2.10 (m, 5H) 1.83 (br s, 4H).

Step 1: (S)-tert-butyl 4-((2-acetamidoethyl) (4-(5,6,7,8-tetrahydro-1,8-naphthyridin-2-yl) butyl)amino)-2-((6-methyl-2-(pyridin-4-yl) pyrimidin-4-yl) amino) butanoate To a mixture of ((S)-tert-butyl 4-((2-acetamidoethyl) (4-(5,6,7,8-tetrahydro-1,8-naphthyridin-2-yl) butyl)amino)-2-aminobutanoate (150 mg, 335 μmol) and 4-chloro-6-methyl-2-(pyridin-4-yl) pyrimidine (57 mg, 279 μmol) in t-AmOH (2 mL) was added 2.0M t-BuONa in THF (279 μL, 558 μmol) then t-BuXphos Pd G3 (22 mg, 28 μmol) and the resulting mixture was heated to 100° C. for 15 h, cooled to rt, and then concentrated in vacuo to give the title compound that was used without further purification. LCMS (ESI+): m/z=617.2 (M+H)$^+$.

Step 2: (S)-4-((2-acetamidoethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid (S)-tert-butyl 4-((2-acetamidoethyl) (4-(5,6,7,8-tetrahydro-1,8-naphthyridin-2-yl) butyl)amino)-2-((6-methyl-2-

Scheme 42, Compound 353

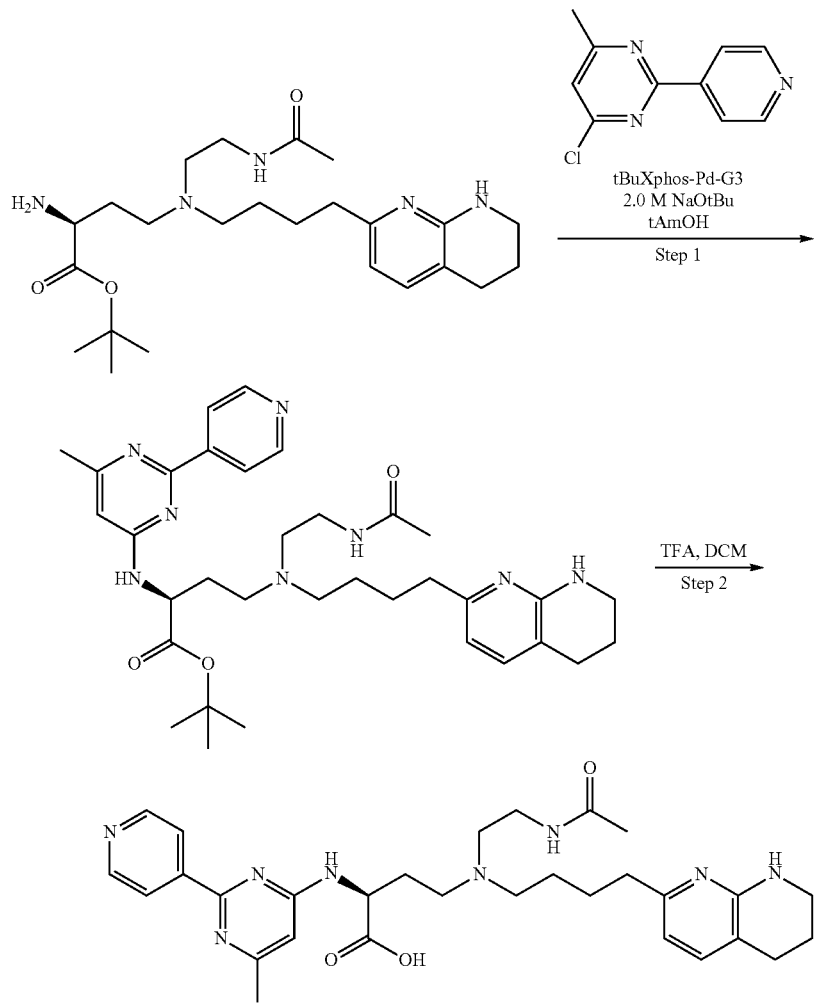

353

(pyridin-4-yl) pyrimidin-4-yl) amino) butanoate (200 mg, 324 µmol) was taken up in 3:1 DCM/TFA (2 mL) and the resulting mixture was stirred at rt for 5 h and then concentrated in vacuo. The crude residue was purified by reverse phase prep-HPLC to give the title compound. LCMS (ESI+): m/z=561.2 (M+H)+. $^1$H NMR (400 MHz, DMSO-d$_6$) δ ppm 8.66 (d, J=5.87 Hz, 2H) 8.13-8.19 (m, 2H) 7.73 (br s, 1H) 7.64 (br s, 1H) 6.97-7.05 (m, 1H) 6.50 (br s, 2H) 6.20 (d, J=7.21 Hz, 1H) 4.51 (br s, 1H) 3.20-3.24 (m, 2H) 3.11-3.18 (m, 2H) 2.51-2.80 (m, 8H) 2.39 (br t, J=7.34 Hz, 2H) 2.32 (s, 3H) 1.99 (dq, J=13.66, 6.73 Hz, 1H) 1.84-1.94 (m, 1H) 1.68-1.79 (m, 5H) 1.49-1.59 (m, 2H) 1.36-1.46 (m, 2H).

(400 MHz, Methanol-d$_4$) δ ppm 8.62 (br s, 1H) 8.50 (s, 1H) 7.60 (d, J=7.34 Hz, 1H) 6.67 (d, J=7.34 Hz, 1H) 5.07 (br dd, J=8.31, 5.26 Hz, 1H) 4.10 (s, 3H) 3.60 (br t, J=5.69 Hz, 3H) 3.45-3.55 (m, 3H) 3.33-3.44 (m, 4H) 2.77-2.89 (m, 4H) 2.61-2.74 (m, 1H) 2.56 (br s, 1H) 1.75-2.10 (m, 9H).

Compound 355: (S)-4-((2-acetamidoethyl) (4-(5,6,7,8-tetrahydro-1,8-naphthyridin-2-yl) butyl)amino)-2-((4-phenylpyridin-2-yl) amino) butanoic acid.

Compound 356: (S)-2-([4,4'-bipyridin]-2-ylamino)-4-((2-acetamidoethyl) (4-(5,6,7,8-tetrahydro-1,8-naphthyridin-2-yl) butyl)amino) butanoic acid.

Scheme 43, Compound 357

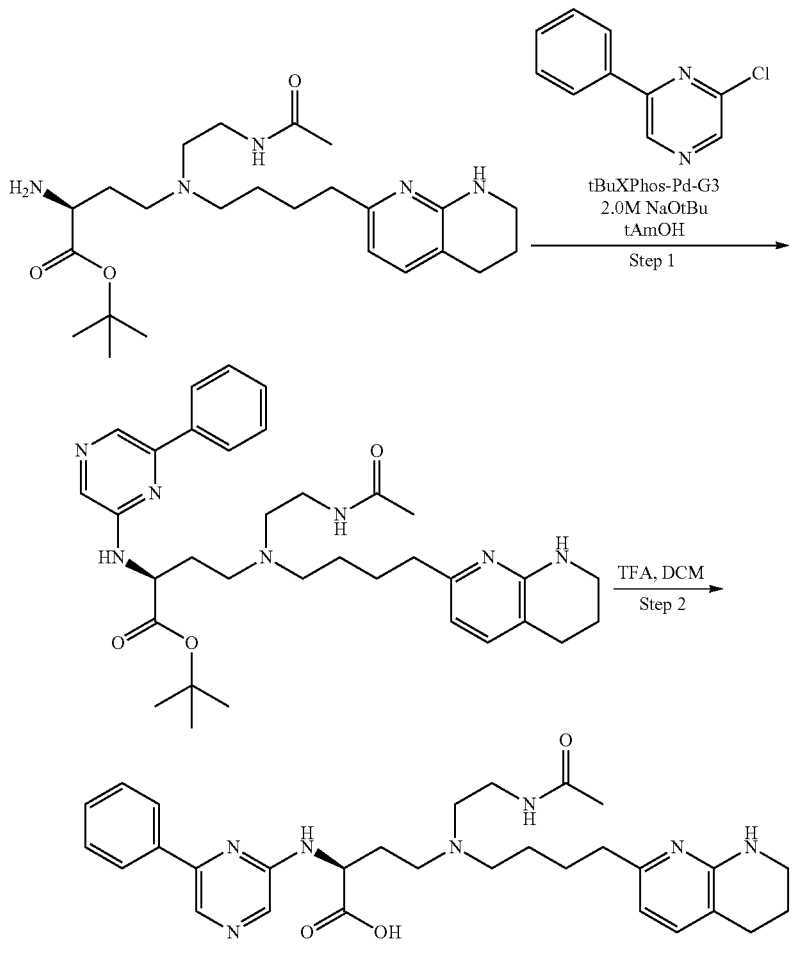

357

Compound 354: (S)-4-((2-acetamidoethyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid (200 mg, 511 µmol) and 7-chloro-2-methyl-2H-pyrazolo[4,3-d]pyrimidine (95 mg, 562 µmol) in THF (2 mL) H$_2$O (0.5 mL) was added NaHCO$_3$ (215 mg, 2.55 mmol) and the resulting mixture was heated to 70° C. for 2 h and then cooled to rt and then concentrated in vacuo. The crude residue was purified by prep-HPLC to give the title compound. LCMS (ESI+): m/z=524.3 (M+H)+. $^1$H NMR Step 1: (S)-tert-butyl 4-((2-acetamidoethyl) (4-(5,6,7,8-tetrahydro-1,8-naphthyridin-2-yl) butyl)amino)-2-((6-phenylpyrazin-2-yl) amino) butanoate To a mixture of ((S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 2-chloro-6-phenylpyrazine (53 mg, 279 µmol) in t-AmOH (3 mL) was added 2.0M t-BuONa (279 µL, 558 µmol) then t-BuXphos Pd G3 (22 mg, 28 µmol) and the resulting mixture was heated to 100° C. for 15 h, cooled to rt, and then concentrated in vacuo to give the title compound that was used without further purification. LCMS (ESI+): m/z=602.5 (M+H)⁺.

Step 2: (S)-4-((2-acetamidoethyl) (4-(5,6,7,8-tetrahydro-1,8-naphthyridin-2-yl) butyl)amino)-2-((6-phenylpyrazin-2-yl) amino) butanoic acid (S)-tert-butyl 4-((2-acetamidoethyl) (4-(5,6,7,8-tetrahydro-1,8-naphthyridin-2-yl) butyl)amino)-2-((6-phenylpyrazin-2-yl) amino) butanoate (200 mg, 371 µmol) was taken up in 5:1 DCM/TFA (2 mL) and the resulting mixture was stirred at rt for 5 h and then concentrated in vacuo. The crude residue was purified by reverse phase prep-HPLC to give the title compound. LCMS (ESI+): m/z=546.3 (M+H)⁺. ¹H NMR (400 MHz, DMSO-d₆) δ ppm 8.31 (s, 1H) 8.02 (br s, 3H) 7.74 (br s, 1H) 7.33-7.50 (m, 4H) 6.99 (br d, J=7.21 Hz, 1H) 6.50 (br s, 1H) 6.20 (br d, J=7.09 Hz, 1H) 4.38 (br d, J=5.99 Hz, 1H) 3.21 (br s, 2H) 3.14 (br s, 2H) 2.52-2.80 (m, 8H) 2.33-2.43 (m, 2H) 1.83-2.08 (m, 2H) 1.68-1.81 (m, 5H) 1.53 (br d, J=7.09 Hz, 4H).

Compound 358: (S)-4-((2-acetamidoethyl) (4-(5,6,7,8-tetrahydro-1,8-naphthyridin-2-yl) butyl)amino)-2-((5-phenylpyrazin-2-yl) amino) butanoic acid.

Compound 359: (S)-4-((2-acetamidoethyl) (4-(5,6,7,8-tetrahydro-1,8-naphthyridin-2-yl) butyl)amino)-2-((6-(pyridin-4-yl) pyrazin-2-yl) amino) butanoic acid.

Compound 360: (S)-4-((2-acetamidoethyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-4-((2-acetamidoethyl) (4-(5,6,7,8-tetrahydro-1,8-naphthyridin-2-yl) butyl)amino)-2-aminobutanoic acid hydrochloride (150 mg, 383 µmol) in DMA (2 mL) was added DIPEA (334 uL, 1.92 mmol) then 4-chloro-2-(pyridin-3-yl) quinazoline (102 mg, 421 µmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=597.3 (M+H)⁺. ¹H NMR (400 MHz, Methanol-d₄) δ ppm 9.79 (s, 1H) 9.38 (br d, J=7.45 Hz, 1H) 9.07 (d, J=5.70 Hz, 1H) 8.64 (t, J=8.11 Hz, 1H) 8.21 (dd, J=8.11, 5.48 Hz, 1H) 8.06-8.15 (m, 2H) 7.87 (t, J=6.80 Hz, 1H) 7.58 (br s, 1H) 6.64 (t, J=7.45 Hz, 1H) 5.44 (br d, J=7.89 Hz, 1H) 3.47-3.62 (m, 6H) 3.33-3.40 (m, 4H) 2.54-2.85 (m, 6H) 1.92-1.99 (m, 5H) 1.74-1.90 (m, 4H).

Compound 361: 4-((2-(dimethylamino)-2-oxoethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 362: (S)-2-((5-cyanopyrimidin-2-yl) amino)-4-((2-(dimethylamino)-2-oxoethyl) (4-(5,6,7,8-tetrahydro-1,8-naphthyridin-2-yl) butyl)amino) butanoic acid: To a mixture of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 µmol) and 2-chloropyrimidine-5-carbonitrile (59 mg, 421 µmol) in THF (2 mL) and H₂O (0.5 mL) was added NaHCO₃ (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=495.2 (M+H)⁺. ¹H NMR (400 MHz, Methanol-d₄) δ ppm 8.33-8.76 (m, 2H) 7.34 (d, J=7.02 Hz, 1H) 6.47 (d, J=7.02 Hz, 1H) 4.44-4.55 (m, 1H) 3.69 (br d, J=9.65 Hz, 1H) 3.37-3.46 (m, 2H) 2.85-3.05 (m, 10H) 2.72-2.77 (m, 2H) 2.60-2.67 (m, 2H) 2.04-2.28 (m, 2H) 1.84-1.94 (m, 2H) 1.60-1.80 (m, 4H).

Compound 363: 4-((2-(dimethylamino)-2-oxoethyl) (4-(5,6,7,8-tetrahydro-1,8-naphthyridin-2-yl) butyl)amino)-2-((5-(trifluoromethyl)pyrimidin-2-yl) amino) butanoic acid.

Compound 364: (S)-2-((1H-pyrazolo[3,4-d]pyrimidin-4-yl) amino)-4-((2-(dimethylamino)-2-oxoethyl) (4-(5,6,7,8-tetrahydro-1,8-naphthyridin-2-yl) butyl)amino) butanoic acid: To a mixture of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 µmol) and 4-chloro-1H-pyrazolo[3,4-d]pyrimidine (40 µL, 421 µmol) in THF (2 mL) and H₂O (0.5 mL) as added NaHCO₃ (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=510.2 (M+H)⁺. ¹H NMR (400 MHz, ethanol-d₄) δ ppm 8.35 (s, 1H) 8.22 (s, 1H) 7.28 (d, J=7.45 Hz, 1H) 6.41 (d, J=7.45 Hz, 1H) 4.91-4.94 (m, 1H) 3.60-3.71 (m, 1H) 3.45-3.55 (m, 1H) 3.32-3.39 (m, 2H) 3.01 (s, 3H) 2.91-2.99 (m, 1H) 2.88 (s, 3H) 2.81 (br d, J=13.59 Hz, 1H) 2.75 (br t, J=6.14 Hz, 2H) 2.56-2.71 (m, 4H) 2.24 (br d, J=4.82 Hz, 2H) 1.87-2.01 (m, 1H) 1.64-1.87 (m, 4H) 1.50-1.62 (m, 1H).

Compound 365: (S)-2-((5-bromopyrimidin-2-yl) amino)-4-((2-(dimethylamino)-2-oxoethyl) (4-(5,6,7,8-tetrahydro-1,8-naphthyridin-2-yl) butyl)amino) butanoic acid: To a solution of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 µmol) and 5-bromo-2-chloropyrimidine (89 mg, 460 µmol) in THF (2 mL) and H₂O (0.5 mL) was added NaHCO₃ (161 mg, 1.92 mmol) and the resulting mixture was stirred at 70° C. for 1 h, cooled to rt, and then concentrated in vacuo. The crude residue was purified by reverse phase prep-HPLC to give the title compound. LCMS (ESI+): m/z=548.2 (M+H)⁺. ¹H NMR (400 MHz, ethanol-d₄) δ ppm 8.28 (s, 2H) 7.30 (d, J=7.28 Hz, 1H) 6.45 (d, J=7.28 Hz, 1H) 4.36 (t, J=6.06 Hz, 1H) 3.66-3.79 (m, 2H) 3.36-3.42 (m, 2H) 3.03 (s, 3H) 2.98 (br dd, J=13.78, 7.17 Hz, 2H) 2.85-2.92 (m, 5H) 2.73 (t, J=5.95 Hz, 2H) 2.62 (br t, J=7.39 Hz, 2H) 2.14-2.27 (m, 1H) 2.01-2.12 (m, 1H) 1.88 (q, J=5.90 Hz, 2H) 1.70-1.80 (m, 2H) 1.59-1.69 (m, 2H).

Compound 366: (S)-2-((1H-pyrazolo[4,3-d]pyrimidin-7-yl) amino)-4-((2-(dimethylamino)-2-oxoethyl) (4-(5,6,7,8-tetrahydro-1,8-naphthyridin-2-yl) butyl)amino) butanoic acid.

Compound 367: (S)-2-((6-(1H-pyrazol-1-yl) pyrimidin-4-yl) amino)-4-((2-(dimethylamino)-2-oxoethyl) (4-(5,6,7,8-tetrahydro-1,8-naphthyridin-2-yl) butyl)amino) butanoic acid.

Compound 368: 4-((2-(dimethylamino)-2-oxoethyl) (4-(5,6,7,8-tetrahydro-1,8-naphthyridin-2-yl) butyl)amino)-2-((2-(trifluoromethyl)pyrimidin-4-yl) amino) butanoic acid.

Compound 369: (S)-2-((5-cyclopropylpyrimidin-2-yl) amino)-4-((2-(dimethylamino)-2-oxoethyl) (4-(5,6,7,8-tetrahydro-1,8-naphthyridin-2-yl) butyl)amino) butanoic acid: To a mixture of (S)-2-amino-4-((2-(dimethylamino)-2-oxoethyl) (4-(5,6,7,8-tetrahydro-1,8-naphthyridin-2-yl) butyl) amino) butanoic acid (150 mg, 383 µmol) and 5-cyclopropyl-2-fluoropyrimidine (64 mg, 460 µmol) in THF (2 mL) and H₂O (0.5 mL) was added NaHCO₃ (161 mg, 1.92 mmol) and the resulting mixture was stirred at 70° C. for 1 h and then allowed to cool to rt and then concentrated in vacuo. The crude residue was purified by reverse phase prep-HPLC to give the title compound. LCMS (ESI+): m/z=510.3 (M+H)⁺. ¹H NMR (400 MHz, ethanol-d₄) δ ppm 8.07 (s, 2H) 7.20 (d, J=7.28 Hz, 1H) 6.39 (d, J=7.28 Hz, 1H) 4.33 (t, J=5.73 Hz, 1H) 3.55-3.72 (m, 2H) 3.35-3.40 (m, 2H) 3.04 (s, 3H) 2.92-3.00 (m, 1H) 2.82-2.92 (m, 4H) 2.78 (br t, J=7.17 Hz, 2H) 2.71 (t, J=6.17 Hz, 2H) 2.55 (t, J=7.50 Hz, 2H) 2.15-2.27 (m, 1H) 1.94-2.06 (m, 1H) 1.87 (q, J=5.79 Hz, 2H) 1.71-1.79 (m, 1H) 1.62-1.71 (m, 2H) 1.52-1.62 (m, 2H) 0.84-0.97 (m, 2H) 0.51-0.67 (m, 2H).

Compound 370: (S)-4-((2-(dimethylamino)-2-oxoethyl) (4-(5,6,7,8-tetrahydro-1,8-naphthyridin-2-yl) butyl)amino)-2-((5-fluoropyrimidin-2-yl) amino) butanoic acid.

Scheme 44, Compound 371

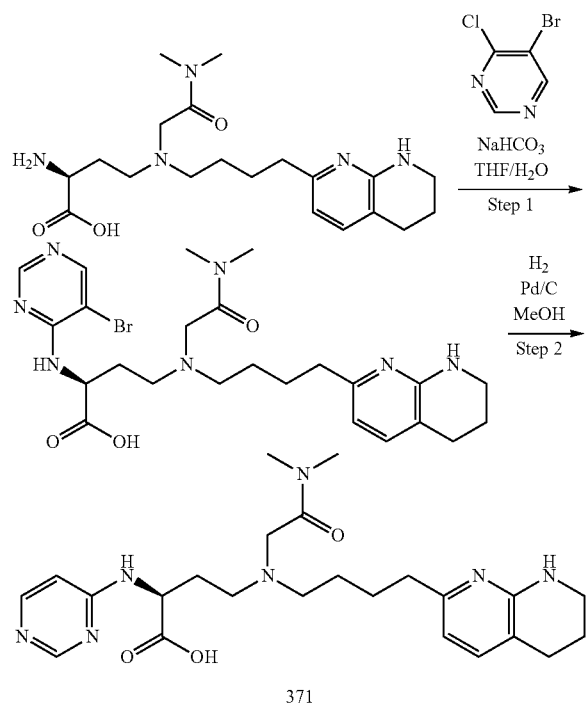

371

Step 1: (S)-2-((5-bromopyrimidin-4-yl) amino)-4-((2-(dimethylamino)-2-oxoethyl) (4-(5,6,7,8-tetrahydro-1,8-naphthyridin-2-yl) butyl)amino) butanoic acid To a mixture of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 µmol) and 5-bromo-4-chloro-pyrimidine (89 mg, 460 µmol) in THF (2 mL) and H$_2$O (0.5 mL) was added NaHCO$_3$ (161 mg, 1.92 mmol) and the resulting mixture was stirred at 70° C. for 2 h and then allowed to cool to rt and then concentrated in vacuo to give the title compound that was used without further purification. LCMS (ESI+): m/z=548.4 (M+H)$^+$.

Step 2: (S)-4-((2-(dimethylamino)-2-oxoethyl) (4-(5,6,7,8-tetrahydro-1,8-naphthyridin-2-yl) butyl) amino)-2-(pyrimidin-4-ylamino) butanoic acid To a mixture of (S)-2-((5-bromopyrimidin-4-yl) amino)-4-((2-(dimethylamino)-2-oxoethyl) (4-(5,6,7,8-tetrahydro-1,8-naphthyridin-2-yl) butyl)amino) butanoic acid (210 mg, 383 µmol) in MeOH (4 mL) was added 10 wt % Pd/C (50 mg) and the resulting mixture was stirred under an H$_2$ atmosphere for 5 h. The reaction mixture was filtered and concentrated in vacuo. The crude residue was purified by reverse phase prep-HPLC to give the title compound. LCMS (ESI+): m/z=470.2 (M+H)$^+$. $^1$H NMR (400 MHz, ethanol-d$_4$) δ ppm 8.34 (s, 1H) 7.91 (br s, 1H) 7.26 (br d, J=7.06 Hz, 1H) 6.58 (br s, 1H) 6.42 (d, J=7.28 Hz, 1H) 4.54 (br s, 1H) 3.58 (br d, J=15.66 Hz, 1H) 3.34-3.46 (m, 3H) 3.04 (s, 3H) 2.85-2.92 (m, 4H) 2.51-2.79 (m, 7H) 2.16 (br s, 1H) 2.05 (br d, J=5.95 Hz, 1H) 1.87 (q, J=5.95 Hz, 2H) 1.65-1.82 (m, 2H) 1.47-1.65 (m, 2H).

Compound 372: (S)-2-((3-cyanopyrazin-2-yl) amino)-4-((2-(dimethylamino)-2-oxoethyl) (4-(5,6,7,8-tetrahydro-1,8-naphthyridin-2-yl) butyl)amino) butanoic acid: To a mixture of (S)-2-amino-4-((2-(dimethylamino)-2-oxoethyl) (4-(5,6,7,8-tetrahydro-1,8-naphthyridin-2-yl) butyl)amino) butanoic acid (200 mg, 511 µmol) and 3-chloropyrazine-2-carbonitrile (86 mg, 613 µmol) in i-PrOH (4 mL) was added DIPEA (445 µL, 2.55 mmol) and the resulting mixture was stirred at 70° C. for 12 h and then allowed to cool to rt and then concentrated in vacuo. The crude residue was purified by reverse phase prep-HPLC to give the title compound. LCMS (ESI+): m/z=495.3 (M+H)$^+$. $^1$H NMR (400 MHz, Methanol-d$_4$) δ ppm 9.57 (s, 1H) 8.85 (br d, J=7.72 Hz, 1H) 8.56-8.65 (m, 1H) 8.29 (d, J=7.94 Hz, 1H) 7.72-7.85 (m, 2H) 7.45-7.54 (m, 2H) 7.18 (d, J=7.28 Hz, 1H) 6.33 (d, J=7.28 Hz, 1H) 5.04 (t, J=5.51 Hz, 1H) 3.68 (br d, J=15.66 Hz, 1H) 3.50 (br d, J=15.21 Hz, 1H) 3.11-3.25 (m, 2H) 3.05 (br d, J=4.63 Hz, 1H) 2.97 (s, 3H) 2.86 (br dd, J=11.91, 5.73 Hz, 2H) 2.78 (s, 3H) 2.70-2.76 (m, 1H) 2.50-2.68 (m, 4H) 2.40 (br d, J=6.39 Hz, 1H) 2.22-2.33 (m, 1H) 1.50-1.92 (m, 6H).

Compound 373: (S)-4-((2-(dimethylamino)-2-oxoethyl) (4-(5,6,7,8-tetrahydro-1,8-naphthyridin-2-yl) butyl)amino)-2-((2-phenylpyrimidin-4-yl) amino) butanoic acid.

Compound 374: (S)-4-((2-(dimethylamino)-2-oxoethyl) (4-(5,6,7,8-tetrahydro-1,8-naphthyridin-2-yl) butyl)amino)-2-((6-phenylpyrimidin-4-yl) amino) butanoic acid.

Sche,e 45, Compound 375

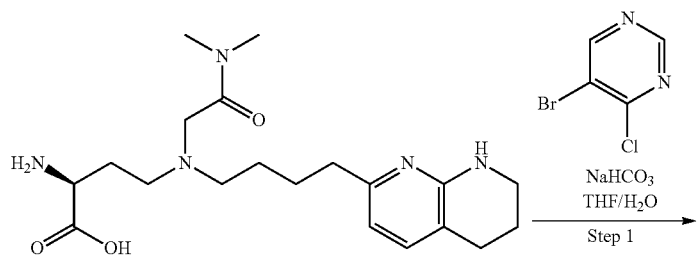

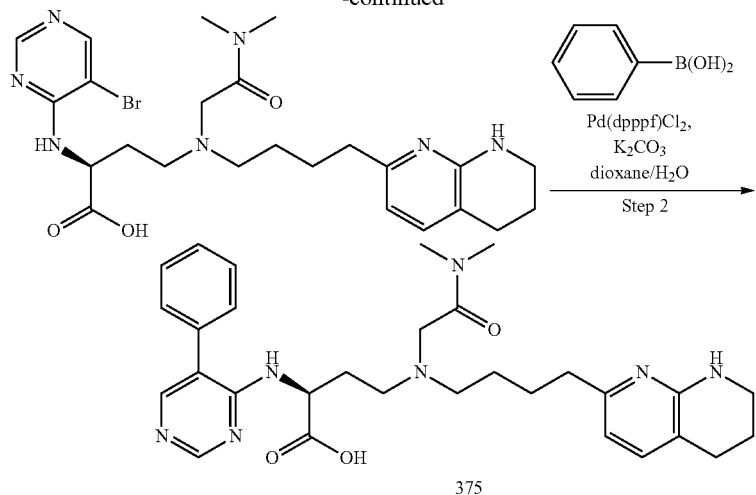

Step 1: (S)-2-((5-bromopyrimidin-4-yl) amino)-4-((2-(dimethylamino)-2-oxoethyl) (4-(5,6,7,8-tetrahydro-1,8-naphthyridin-2-yl) butyl)amino) butanoic acid To a mixture of (S)-2-amino-4-((2-(dimethylamino)-2-oxoethyl) (4-(5,6,7,8-tetrahydro-1,8-naphthyridin-2-yl) butyl)amino) butanoic acid (150 mg, 383 μmol) and 5-bromo-4-chloro-pyrimidine (89 mg, 460 μmol) in THF (1.2 mL) and H$_2$O (0.3 mL) was added NaHCO$_3$ (160.93 mg, 1.92 mmol) and the resulting mixture was stirred at 70° C. for 1 h and then allowed to cool to rt and then concentrated in vacuo to give the title compound that was used without further purification. LCMS (ESI+): m/z=548.4 (M+H)$^+$.

Step 2: (S)-4-((2-(dimethylamino)-2-oxoethyl) (4-(5,6,7,8-tetrahydro-1,8-naphthyridin-2-yl) butyl) amino)-2-((5-phenylpyrimidin-4-yl) amino) butanoic acid To a mixture of (S)-2-((5-bromopyrimidin-4-yl) amino)-4-((2-(dimethylamino)-2-oxoethyl) (4-(5,6,7,8-tetrahydro-1,8-naphthyridin-2-yl) butyl)amino) butanoic acid (210 mg, 383 μmol) and phenylboronic acid (56 mg, 459 μmol) in dioxane (2 mL) and H$_2$O (0.5 mL) was added Pd(dppf)Cl$_2$ (28 mg, 38 μmol) and K$_2$CO$_3$ (106 mg, 766 μmol) and the resulting mixture was stirred at 100° C. for 2 h and then cooled to rt and concentrated in vacuo. The crude residue was purified by rever phase prep-HPLC to give the title compound. LCMS (ESI+): m/z=546.3 (M+H)$^+$. $^1$H NMR (400 MHz, Deuterium Oxide) δ ppm 8.70 (s, 1H) 8.10 (s, 1H) 7.55-7.65 (m, 3H) 7.49 (br d, J=7.58 Hz, 3H) 6.53 (d, J=7.46 Hz, 1H) 4.77-4.78 (m, 1H) 4.13-4.28 (m, 2H) 3.35-3.45 (m, 3H) 3.18-3.31 (m, 3H) 2.84-2.99 (m, 6H) 2.62-2.79 (m, 4H) 2.41 (br s, 1H) 2.19 (br s, 1H) 1.85 (q, J=5.81 Hz, 2H) 1.70 (br s, 4H).

Compound 376: (S)-4-((2-(dimethylamino)-2-oxoethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid.

Compound 377: (S)-4-((2-(dimethylamino)-2-oxoethyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-((2-(dimethylamino)-2-oxoethyl) (4-(5,6,7,8-tetrahydro-1,8-naphthyridin-2-yl) butyl) amino) butanoic acid (150 mg, 383 μmol) and 4-chloro-2-(3-pyridyl)quinazoline (102 mg, 421 μmol) in DMA (4 mL) was added DIPEA (334 μL, 1.92 mmol) and the resulting mixture was stirred at 70° C. for 12 h and then allowed to cool to rt and then concentrated in vacuo. The crude residue was purified by reverse phase prep-HPLC to give the title compound. LCMS (ESI+): m/z=597.2 (M+H)$^+$. $^1$H NMR (400 MHz, ethanol-d$_4$) δ ppm 9.57 (s, 1H) 8.85 (br d, J=7.72 Hz, 1H) 8.56-8.65 (m, 1H) 8.29 (d, J=7.94 Hz, 1H) 7.72-7.85 (m, 2H) 7.45-7.54 (m, 2H) 7.18 (d, J=7.28 Hz, 1H) 6.33 (d, J=7.28 Hz, 1H) 5.04 (t, J=5.51 Hz, 1H) 3.68 (br d, J=15.66 Hz, 1H) 3.50 (br d, J=15.21 Hz, 1H) 3.11-3.25 (m, 2H) 3.05 (br d, J=4.63 Hz, 1H) 2.97 (s, 3H) 2.86 (br dd, J=11.91, 5.73 Hz, 2H) 2.78 (s, 3H) 2.70-2.76 (m, 1H) 2.50-2.68 (m, 4H) 2.40 (br d, J=6.39 Hz, 1H) 2.22-2.33 (m, 1H) 1.50-1.92 (m, 6H).

Compound 378: (S)-4-((2-(dimethylamino)-2-oxoethyl) (4-(5,6,7,8-tetrahydro-1,8-naphthyridin-2-yl) butyl)amino)-2-((4-phenylpyridin-2-yl) amino) butanoic acid.

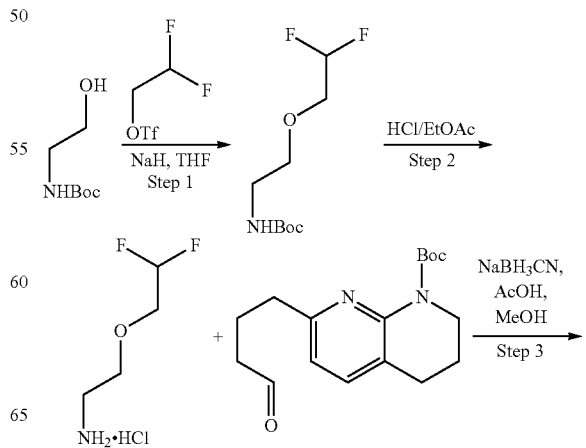

Scheme 46, Compound 379

277
-continued

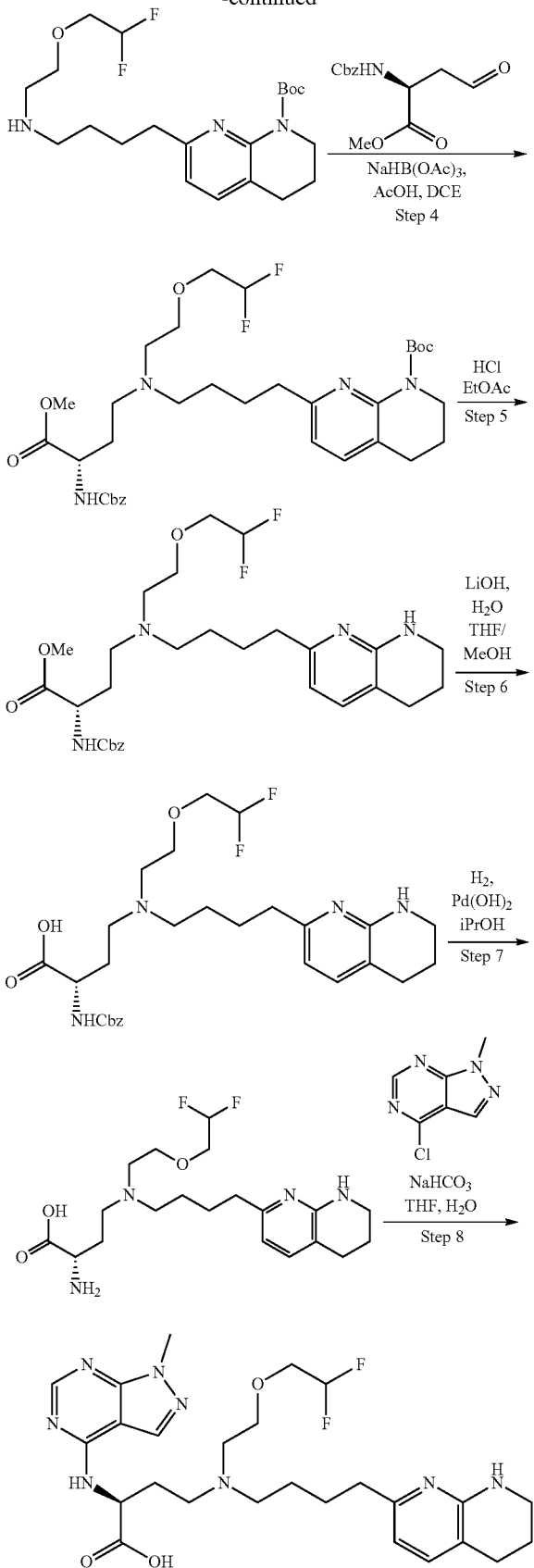

278

Step 1: tert-butyl (2-(2,2-difluoroethoxy)ethyl)carbamate

To a solution of tert-butyl (2-hydroxyethyl)carbamate (15 g, 93.05 mmol) in THF (100 mL) was added 60 wt % NaH dispersion in mineral oil (8.19 g, 204.72 mmol) at −10° C. and the resulting mixture was stirred for 30 min, at which time a solution of 2,2-difluoroethyl trifluoromethanesulfonate (19.92 g, 93.05 mmol) in THF (10 mL) was dropwise added at −10° C. The mixture was stirred at 0° C. for 1 h and then diluted with water and then extracted with EtOAc. The combined organic extracts were dried over Na$_2$SO$_4$, filtered, and concentrated under reduced pressure. The crude residue was purified by normal phase silica gel chromatography to give the title compound.

Step 2: 2-(2,2-difluoroethoxy)ethanamine hydrochloride tert-butyl (2-(2,2-difluoroethoxy)ethyl)carbamate (20 g, 88.80 mmol) was taken up in 4 M HCl in EtOAc (111 mL) and the resulting mixture was stirred at rt for 30 min and then was concentrated in vacuo to give the title compound that was used without further purification.

Step 3: tert-butyl 7-(4-((2-(2,2-difluoroethoxy)ethyl) amino) butyl)-3,4-dihydro-1,8-naphthyridine-1(2H)-carboxylate To a solution of 2-(2,2-difluoroethoxy)ethanamine hydrochloride (11.94 g, 73.92 mmol) in MeOH (100 mL) was added HOAc (5.64 mL, 98.56 mmol), NaBH$_3$CN (6.19 g, 98.56 mmol), then a solution of tert-butyl 7-(4-oxobutyl)-3,4-dihydro-1,8-naphthyridine-1(2H)-carboxylate (15 g, 49.28 mmol) in MeOH (50 mL) was added at 0° C. and the resulting mixture was stirred at rt for 1 h. The mixture was concentrated in vacuo and then diluted with sat. aq. NaHCO$_3$ and the resulting mixture was extracted with EtOAc and the combined organic extracts were dried over Na$_2$SO$_4$, filtered and concentrated in vacuo to give the title compound that was used without further purification. LCMS (ESI+): m/z=414.4 (M+H)$^+$.

Step 4: (S)-tert-butyl 7-(4-((3-(((benzyloxy)carbonyl)amino)-4-methoxy-4-oxobutyl) (2-(2,2-difluoroethoxy)ethyl)amino) butyl)-3,4-dihydro-1,8-naphthyridine-1(2H)-carboxylate To a mixture of tert-butyl 7-(4-((2-(2,2-difluoroethoxy) ethyl)amino)butyl)-3,4-dihydro-1,8-naphthyridine-1(2H)-carboxylate (19 g, 32.16 mmol) and (S)-methyl 2-(((benzyloxy)carbonyl)amino)-4-oxobutanoate (8.53 g, 32.16 mmol) in DCE (200 mL) was added AcOH (2.76 mL, 48.25 mmol) at 0° C. was added NaBH(OAc)$_3$ (10.23 g, 48.25 mmol) and the resulting mixture was stirred at rt for 2 h. The reaction mixture was diluted with MeOH and then concentrated in vacuo. The crude residue was taken up in a mixture of DCM and sat. aq. NaHCO$_3$ and the layers were separated. The aqueous layer was extracted with DCM and the combined organic extracts were dried over Na$_2$SO$_4$, filtered, and concentrated under reduced pressure to give a residue. The crude residue was purified by normal phase silica gel chromatography. LCMS (ESI+): m/z=663.5 (M+H)$^+$.

Step 5: (S)-methyl 2-(((benzyloxy)carbonyl)amino)-4-((2-(2,2-difluoroethoxy)ethyl) (4-(5,6,7,8-tetrahydro-1,8-naphthyridin-2-yl) butyl)amino) butanoate (S)-tert-butyl 7-(4-((3-(((benzyloxy)carbonyl)amino)-4-methoxy-4-oxobutyl) (2-(2,2-difluoroethoxy)ethyl)amino)

butyl)-3,4-dihydro-1,8-naphthyridine-1(2H)-carboxylate (3.5 g, 5.28 mmol) was taken up in 4 M HCl in EtOAc (13.20 mL) and the resulting mixture was stirred at rt for 8 h and then was poured into water, adjusted to pH=8 by the addition of 1 M NaOH, and extracted with EtOAc. The combined organic extracts were dried over $Na_2SO_4$, filtered and concentrated in vacuo to give the title compound. LCMS (ESI+): m/z=563.4 (M+H)+.

Step 6: (S)-2-(((benzyloxy)carbonyl)amino)-4-((2-(2,2-difluoroethoxy)ethyl) (4-(5,6,7,8-tetrahydro-1,8-naphthyridin-2-yl) butyl)amino) butanoic acid To a mixture of (S)-methyl 2-(((benzyloxy)carbonyl)amino)-4-((2-(2,2-difluoroethoxy)ethyl) (4-(5,6,7,8-tetrahydro-1,8-naphthyridin-2-yl) butyl)amino) butanoate (2.8 g, 4.98 mmol) in THF (10 mL) and $H_2O$ (10 mL) and MeOH (10 mL) was added $LiOH.H_2O$ (418 mg, 9.95 mmol) and the resulting mixture was stirred at rt for 1 h and then was adjusted to pH=6 by the addition of 1 M aq. HCl and then was concentrated under reduced pressure to give the title compound that was used without further purification. LCMS (ESI+): m/z=549.4 (M+H)+.

Step 7: (S)-2-amino-4-((2-(2,2-difluoroethoxy)ethyl) (4-(5,6,7,8-tetrahydro-1,8-naphthyridin-2-yl) butyl) amino) butanoic acid To a solution of (S)-2-(((benzyloxy)carbonyl)amino)-4-((2-(2,2-difluoroethoxy)ethyl) (4-(5,6,7,8-tetrahydro-1,8-naphthyridin-2-yl) butyl)amino) butanoic acid hydrochloride (3 g, 5.13 mmol) in i-PrOH (30 mL) was added 20 wt % $Pd(OH)_2$/C (720 mg) and the resulting mixture was stirred under an $H_2$ atmosphere for 3 h and then was filtered and concentrated in vacuo to give the title compound that was used without further purification. LCMS (ESI+): m/z=415.4 (M+H)+.

Step 8: (S)-4-((2-(2,2-difluoroethoxy)ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid To a mixture of (S)-2-amino-4-(((S)-2-fluoro-3-methoxypropyl) (4-(5,6,7,8-tetrahydro-1,8-naphthyridin-2-yl) butyl) amino) butanoic acid hydrochloride (150 mg, 333 μmol) in THF (1.6 mL) and $H_2O$ (0.4 mL) was added $NaHCO_3$ (140 mg, 1.66 mmol) then 4-chloro-1-methyl-1H-pyrazolo[3,4-d]pyrimidine (62 mg, 366 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=547.3 (M+H)+. $^1$H NMR (400 MHz, Methanol-$d_4$) δ ppm 8.56 (s, 1H) 8.48 (s, 1H) 7.59 (d, J=7.34 Hz, 1H) 6.65 (d, J=7.46 Hz, 1H) 5.85-6.16 (m, 1H) 5.07 (br dd, J=8.01, 5.32 Hz, 1H) 4.08 (s, 3H) 3.94-4.03 (m, 2H) 3.78 (td, J=14.73, 3.67 Hz, 2H) 3.49-3.64 (m, 5H) 3.32-3.40 (m, 3H) 2.74-2.88 (m, 4H) 2.46-2.73 (m, 2H) 1.75-1.99 (m, 6H).

Compound 380: (S)-2-((5-cyanopyrimidin-2-yl) amino)-4-((2-(2,2-difluoroethoxy)ethyl) (4-(5,6,7,8-tetrahydro-1,8-naphthyridin-2-yl) butyl)amino) butanoic acid.

Compound 381: (S)-4-((2-(2,2-difluoroethoxy)ethyl) (4-(5,6,7,8-tetrahydro-1,8-naphthyridin-2-yl) butyl)amino)-2-((5-(trifluoromethyl)pyrimidin-2-yl) amino) butanoic acid: To a mixture of (S)-2-amino-4-((2-(2,2-difluoroethoxy) ethyl) (4-(5,6,7,8-tetrahydro-1,8-naphthyridin-2-yl) butyl) amino) butanoic acid hydrochloride (150 mg, 333 μmol) in THF (2 mL) and $H_2O$ (0.5 mL) was added $NaHCO_3$ (56 mg, 665 μmol) then 2-chloro-5-(trifluoromethyl)pyrimidine (91 mg, 499 μmol) and the resulting mixture was heated to 70° C. for 6 h, cooled to rt, adjusted to pH=6 by the addition of 1 M aq. HCl, and then concentrated in vacuo. The crude residue was purified by reverse phase prep-HPLC to give the title compound. LCMS (ESI+): m/z=561.2 (M+H)+. $^1$H NMR (400 MHz, Methanol-$d_4$) δ ppm 8.62 (s, 2H) 7.59 (d, J=7.34 Hz, 1H) 6.64 (d, J=7.21 Hz, 1H) 5.84-6.17 (m, 1H) 4.77 (dd, J=8.50, 5.07 Hz, 1H) 3.96 (br d, J=4.40 Hz, 2H) 3.78 (br t, J=14.37 Hz, 2H) 3.44-3.55 (m, 5H) 3.32-3.44 (m, 3H) 2.72-2.88 (m, 4H) 2.44-2.56 (m, 1H) 2.24-2.38 (m, 1H) 1.73-2.00 (m, 6H).

Compound 382: (S)-2-((1H-pyrazolo[3,4-d]pyrimidin-4-yl) amino)-4-((2-(2,2-difluoroethoxy)ethyl) (4-(5,6,7,8-tetrahydro-1,8-naphthyridin-2-yl) butyl)amino) butanoic acid: To a mixture of (S)-2-amino-4-((2-(2,2-difluoroethoxy) ethyl) (4-(5,6,7,8-tetrahydro-1,8-naphthyridin-2-yl) butyl) amino) butanoic acid hydrochloride (150 mg, 333 μmol) in THF (1.6 mL) and $H_2O$ (0.4 mL) was added $NaHCO_3$ (140 mg, 1.66 mmol) and then the 4-chloro-1H-pyrazolo[3,4-d]pyrimidine (57 mg, 366 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound LCMS (ESI+): m/z=533.2 (M+H)+. $^1$H NMR (400 MHz, Methanol-$d_4$) δ ppm 8.87 (s, 1H) 8.65 (s, 1H) 7.59 (d, J=7.34 Hz, 1H) 6.65 (d, J=7.34 Hz, 1H) 5.84-6.15 (m, 1H) 5.26 (dd, J=8.68, 5.26 Hz, 1H) 3.97 (br s, 2H) 3.77 (td, J=14.79, 3.55 Hz, 2H) 3.47-3.54 (m, 5H) 3.33-3.39 (m, 3H) 2.76-2.85 (m, 4H) 2.43-2.69 (m, 2H) 1.77-1.99 (m, 6H).

Compound 383: (S)-2-((5-bromopyrimidin-2-yl) amino)-4-((2-(2,2-difluoroethoxy)ethyl) (4-(5,6,7,8-tetrahydro-1,8-naphthyridin-2-yl) butyl)amino) butanoic acid: To a mixture of (S)-2-amino-4-((2-(2,2-difluoroethoxy)ethyl) (4-(5,6,7,8-tetrahydro-1,8-naphthyridin-2-yl) butyl)amino) butanoic acid hydrochloride (150 mg, 333 μmol) in THF (1.6 mL) and $H_2O$ (0.4 mL) was added $NaHCO_3$ (140 mg, 1.66 mmol) and then 5-bromo-2-fluoropyrimidine (65 mg, 366 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=571.1 (M+H)+. $^1$H NMR (400 MHz, Methanol-$d_4$) δ ppm 8.41 (s, 2H) 7.60 (d, J=7.34 Hz, 1H) 6.64 (d, J=7.46 Hz, 1H) 5.80-6.22 (m, 1H) 4.64 (dd, J=8.62, 5.07 Hz, 1H) 3.95 (br t, J=4.65 Hz, 2H) 3.78 (td, J=14.67, 1.83 Hz, 2H) 3.47-3.55 (m, 4H) 3.32-3.46 (m, 3H) 3.25-3.30 (m, 1H) 2.75-2.86 (m, 4H) 2.41-2.52 (m, 1H) 2.21-2.34 (m, 1H) 1.96 (dt, J=11.77, 6.04 Hz, 2H) 1.80 (br d, J=2.81 Hz, 4H).

Compound 384: (S)-4-((2-(2,2-difluoroethoxy)ethyl) (4-(5,6,7,8-tetrahydro-1,8-naphthyridin-2-yl) butyl)amino)-2-((2-(trifluoromethyl)pyrimidin-4-yl) amino) butanoic acid: To a mixture of (S)-2-amino-4-((2-(2,2-difluoroethoxy) ethyl) (4-(5,6,7,8-tetrahydro-1,8-naphthyridin-2-yl) butyl) amino) butanoic acid hydrochloride (150 mg, 332 μmol) in THF (1.6 mL) and $H_2O$ (0.4 mL) was added $NaHCO_3$ (140 mg, 1.66 mmol) and then 4-chloro-2-(trifluoromethyl)pyrimidine (67 mg, 366 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=561.2 (M+H)+. $^1$H NMR (400 MHz, Methanol-$d_4$) δ ppm 8.25 (br d, J=6.11 Hz, 1H) 7.59 (d, J=7.34 Hz, 1H) 6.88 (d, J=6.11 Hz, 1H) 6.64 (d, J=7.34 Hz, 1H) 5.82-6.17 (m, 1H) 4.83 (br s, 1H) 3.95 (br s, 2H) 3.77 (td, J=14.70, 3.61 Hz, 2H) 3.45-3.57 (m, 5H) 3.32-3.45 (m, 3H) 2.72-2.90 (m, 4H) 2.43-2.56 (m, 1H) 2.25-2.40 (m, 1H) 1.70-2.03 (m, 6H).

Compound 385: (S)-4-((2-methoxyethyl) (4-(5,6,7,8-tetrahydro-1,8-naphthyridin-2-yl) butyl)amino)-2-((5-methylpyrimidin-2-yl) amino) butanoic acid.

Compound 386: (S)-4-((2-methoxyethyl) (4-(5,6,7,8-tetrahydro-1,8-naphthyridin-2-yl) butyl)amino)-2-(pyridin-3-ylamino) butanoic acid.

Compound 387: (S)-4-((2-methoxyethyl) (4-(5,6,7,8-tetrahydro-1,8-naphthyridin-2-yl) butyl)amino)-2-((1-methyl-H-pyrazolo[3,4-d]pyrimidin-4-yl) amino) butanoic acid.

Compound 388: (S)-2-((5-cyanopyrimidin-2-yl) amino)-4-((2-methoxyethyl) (4-(5,6,7,8-tetrahydro-1,8-naphthyridin-2-yl) butyl)amino) butanoic acid.

Compound 389: (S)-4-((2-methoxyethyl) (4-(5,6,7,8-tetrahydro-1,8-naphthyridin-2-yl) butyl)amino)-2-((5-(trifluoromethyl)pyrimidin-2-yl) amino) butanoic acid.

Compound 390: (S)-4-((2-methoxyethyl) (4-(5,6,7,8-tetrahydro-1,8-naphthyridin-2-yl) butyl)amino)-2-(pyridin-2-ylamino) butanoic acid.

Compound 391: (S)-2-((1H-pyrazolo[3,4-d]pyrimidin-4-yl) amino)-4-((2-methoxyethyl) (4-(5,6,7,8-tetrahydro-1,8-naphthyridin-2-yl) butyl)amino) butanoic acid.

Compound 392: (S)-2-((5-bromopyrimidin-2-yl) amino)-4-((2-methoxyethyl) (4-(5,6,7,8-tetrahydro-1,8-naphthyridin-2-yl) butyl)amino) butanoic acid.

Compound 393: (S)-2-((1H-pyrazolo[4,3-d]pyrimidin-7-yl) amino)-4-((2-methoxyethyl) (4-(5,6,7,8-tetrahydro-1,8-naphthyridin-2-yl) butyl)amino) butanoic acid.

Compound 394: (S)-4-((2-methoxyethyl) (4-(5,6,7,8-tetrahydro-1,8-naphthyridin-2-yl) butyl)amino)-2-((2-methoxypyrimidin-4-yl) amino) butanoic acid.

Compound 395: (S)-4-((2-methoxyethyl) (4-(5,6,7,8-tetrahydro-1,8-naphthyridin-2-yl) butyl)amino)-2-((6-methylpyrazin-2-yl) amino) butanoic acid.

Compound 396: 2-((3-cyanopyrazin-2-yl) amino)-4-((2-methoxyethyl) (4-(5,6,7,8-tetrahydro-1,8-naphthyridin-2-yl) butyl)amino) butanoic acid.

Compound 397: (S)-4-((2-methoxyethyl) (4-(5,6,7,8-tetrahydro-1,8-naphthyridin-2-yl) butyl)amino)-2-(pyrimidin-4-ylamino) butanoic acid.

Compound 398: (S)-2-((5-fluoropyrimidin-2-yl) amino)-4-((2-methoxyethyl) (4-(5,6,7,8-tetrahydro-1,8-naphthyridin-2-yl) butyl)amino) butanoic acid.

Compound 399: (S)-4-((2-methoxyethyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid.

Compound 400: (S)-2-((6-(tert-butyl)pyrimidin-4-yl) amino)-4-((2-methoxyethyl) (4-(5,6,7,8-tetrahydro-1,8-naphthyridin-2-yl) butyl)amino) butanoic acid.

Compound 401: (S)-2-((5-cyclopropylpyrimidin-2-yl) amino)-4-((2-methoxyethyl) (4-(5,6,7,8-tetrahydro-1,8-naphthyridin-2-yl) butyl)amino) butanoic acid.

Compound 402: (S)-4-((2-methoxyethyl) (4-(5,6,7,8-tetrahydro-1,8-naphthyridin-2-yl) butyl)amino)-2-((6-(trifluoromethyl)pyrimidin-4-yl) amino) butanoic acid.

Compound 403: (S)-2-((6-(dimethylamino)pyrimidin-4-yl) amino)-4-((2-methoxyethyl) (4-(5,6,7,8-tetrahydro-1,8-naphthyridin-2-yl) butyl)amino) butanoic acid.

Compound 404: 2-((6-(1H-pyrazol-1-yl) pyrimidin-4-yl) amino)-4-((2-methoxyethyl) (4-(5,6,7,8-tetrahydro-1,8-naphthyridin-2-yl) butyl)amino) butanoic acid.

Compound 405: 4-((2-methoxyethyl) (4-(5,6,7,8-tetrahydro-1,8-naphthyridin-2-yl) butyl)amino)-2-(quinoxalin-2-ylamino) butanoic acid.

Compound 406: (S)-4-((2-methoxyethyl) (4-(5,6,7,8-tetrahydro-1,8-naphthyridin-2-yl) butyl)amino)-2-((5-methoxypyrazin-2-yl) amino) butanoic acid.

Compound 407: (S)-4-((2-methoxyethyl) (4-(5,6,7,8-tetrahydro-1,8-naphthyridin-2-yl) butyl)amino)-2-((6-phenylpyrimidin-4-yl) amino) butanoic acid.

Compound 408: (S)-4-((2-methoxyethyl) (4-(5,6,7,8-tetrahydro-1,8-naphthyridin-2-yl) butyl)amino)-2-((2-phenylpyrimidin-4-yl) amino) butanoic acid.

Compound 409: (S)-4-((2-methoxyethyl) (4-(5,6,7,8-tetrahydro-1,8-naphthyridin-2-yl) butyl)amino)-2-((5-phenylpyrimidin-4-yl) amino) butanoic acid.

Compound 410: (S)-4-((2-methoxyethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid.

Compound 411: (S)-4-((2-methoxyethyl) (4-(5,6,7,8-tetrahydro-1,8-naphthyridin-2-yl) butyl)amino)-2-((2-(pyridin-3-yl) quinazolin-4-yl) amino) butanoic acid.

Compound 412: (S)-4-((2-methoxyethyl) (4-(5,6,7,8-tetrahydro-1,8-naphthyridin-2-yl) butyl)amino)-2-((6-(pyridin-4-yl) pyrazin-2-yl) amino) butanoic acid.

Compound 413: (S)-4-((2-methoxyethyl) (4-(5,6,7,8-tetrahydro-1,8-naphthyridin-2-yl) butyl)amino)-2-((5-phenylpyrazin-2-yl) amino) butanoic acid.

Compound 414: (S)-4-((2-methoxyethyl) (4-(5,6,7,8-tetrahydro-1,8-naphthyridin-2-yl) butyl)amino)-2-((6-phenylpyrazin-2-yl) amino) butanoic acid.

Compound 415: (S)-4-((2-methoxyethyl) (4-(5,6,7,8-tetrahydro-1,8-naphthyridin-2-yl) butyl)amino)-2-((1-methyl-1H-pyrazol-5-yl) amino) butanoic acid.

Compound 416: (S)-2-(benzo[d]oxazol-2-ylamino)-4-((2-methoxyethyl) (4-(5,6,7,8-tetrahydro-1,8-naphthyridin-2-yl) butyl)amino) butanoic acid.

Compound 417: (S)-4-((2-methoxyethyl) (4-(5,6,7,8-tetrahydro-1,8-naphthyridin-2-yl) butyl)amino)-2-((1-methyl-1H-benzo[d]imidazol-2-yl) amino) butanoic acid.

Compound 418: (S)-2-(benzo[d]thiazol-2-ylamino)-4-((2-methoxyethyl) (4-(5,6,7,8-tetrahydro-1,8-naphthyridin-2-yl) butyl)amino) butanoic acid.

Compound 419: (S)-4-((2-methoxyethyl) (4-(5,6,7,8-tetrahydro-1,8-naphthyridin-2-yl) butyl)amino)-2-((1-methyl-1H-pyrazolo[4,3-d]pyrimidin-7-yl) amino) butanoic acid.

Compound 420: (S)-2-((9H-purin-6-yl) amino)-4-((2-methoxyethyl) (4-(5,6,7,8-tetrahydro-1,8-naphthyridin-2-yl) butyl)amino) butanoic acid.

Compound 421: (S)-4-((2-methoxyethyl) (4-(5,6,7,8-tetrahydro-1,8-naphthyridin-2-yl) butyl)amino)-2-((5-phenylpyridin-2-yl) amino) butanoic acid.

Compound 422: (S)-4-((2-methoxyethyl) (4-(5,6,7,8-tetrahydro-1,8-naphthyridin-2-yl) butyl)amino)-2-((4-phenylpyridin-2-yl) amino) butanoic acid.

Compound 423: (S)-4-((2-methoxyethyl) (4-(5,6,7,8-tetrahydro-1,8-naphthyridin-2-yl) butyl)amino)-2-((1-methyl-1H-indazol-3-yl) amino) butanoic acid.

Compound 424: (S)-4-((2-methoxyethyl) (4-(5,6,7,8-tetrahydro-1,8-naphthyridin-2-yl) butyl)amino)-2-((1-methyl-1H-indol-3-yl) amino) butanoic acid.

Compound 425: (R)-4-((2-methoxyethyl) (4-(5,6,7,8-tetrahydro-1,8-naphthyridin-2-yl) butyl)amino)-2-(quinoxalin-2-ylamino) butanoic acid.

Compound 426: (S)-4-((2-((2-methylpyridin-3-yl) oxy) ethyl) (4-(5,6,7,8-tetrahydro-1,8-naphthyridin-2-yl) butyl) amino)-2-((5-methylpyrimidin-2-yl) amino) butanoic acid.

Compound 427: (S)-4-((2-((2-methylpyridin-3-yl) oxy) ethyl) (4-(5,6,7,8-tetrahydro-1,8-naphthyridin-2-yl) butyl) amino)-2-(pyridin-3-ylamino) butanoic acid.

Compound 428: (S)-2-((1-methyl-1H-pyrazolo[3,4-d]pyrimidin-4-yl) amino)-4-((2-((2-methylpyridin-3-yl) oxy)ethyl) (4-(5,6,7,8-tetrahydro-1,8-naphthyridin-2-yl) butyl) amino) butanoic acid.

Compound 429: (S)-2-((5-cyanopyrimidin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 430: (S)-4-((2-((2-methylpyridin-3-yl) oxy) ethyl) (4-(5,6,7,8-tetrahydro-1,8-naphthyridin-2-yl) butyl) amino)-2-((5-(trifluoromethyl)pyrimidin-2-yl) amino) butanoic acid.

Compound 431: (S)-4-((2-((2-methylpyridin-3-yl) oxy) ethyl) (4-(5,6,7,8-tetrahydro-1,8-naphthyridin-2-yl) butyl) amino)-2-(pyridin-2-ylamino) butanoic acid.

Compound 432: (S)-2-((1H-pyrazolo[3,4-d]pyrimidin-4-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 433: (S)-2-((5-bromopyrimidin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 434: (S)-2-((1H-pyrazolo[4,3-d]pyrimidin-7-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 435: (S)-2-((2-methoxypyrimidin-4-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 436: (S)-2-((6-methylpyrazin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 437: (S)-2-((3-cyanopyrazin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 438: (S)-4-((2-((2-methylpyridin-3-yl) oxy) ethyl) (4-(5,6,7,8-tetrahydro-1,8-naphthyridin-2-yl) butyl) amino)-2-(pyrimidin-4-ylamino) butanoic acid.

Compound 439: (S)-2-((5-fluoropyrimidin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 440: (S)-2-((7-methyl-7H-pyrrolo[2,3-d]pyrimidin-4-yl) amino)-4-((2-((2-methylpyridin-3-yl) oxy) ethyl) (4-(5,6,7,8-tetrahydro-1,8-naphthyridin-2-yl) butyl) amino) butanoic acid.

Compound 441: (S)-2-((6-(tert-butyl)pyrimidin-4-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 442: (S)-2-((5-cyclopropylpyrimidin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 443: (S)-4-((2-((2-methylpyridin-3-yl) oxy) ethyl) (4-(5,6,7,8-tetrahydro-1,8-naphthyridin-2-yl) butyl) amino)-2-((6-(trifluoromethyl)pyrimidin-4-yl) amino) butanoic acid.

Compound 444: (S)-2-((6-(dimethylamino)pyrimidin-4-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 445: (S)-2-((6-(1H-pyrazol-1-yl) pyrimidin-4-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 446: (S)-4-((2-((2-methylpyridin-3-yl) oxy) ethyl) (4-(5,6,7,8-tetrahydro-1,8-naphthyridin-2-yl) butyl) amino)-2-(quinoxalin-2-ylamino) butanoic acid.

Compound 447: (S)-2-((5-methoxypyrazin-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 448: (S)-4-((2-((2-methylpyridin-3-yl) oxy) ethyl) (4-(5,6,7,8-tetrahydro-1,8-naphthyridin-2-yl) butyl) amino)-2-((6-phenylpyrimidin-4-yl) amino) butanoic acid.

Compound 449: (S)-4-((2-((2-methylpyridin-3-yl) oxy) ethyl) (4-(5,6,7,8-tetrahydro-1,8-naphthyridin-2-yl) butyl) amino)-2-((2-phenylpyrimidin-4-yl) amino) butanoic acid.

Compound 450: (S)-4-((2-((2-methylpyridin-3-yl) oxy) ethyl) (4-(5,6,7,8-tetrahydro-1,8-naphthyridin-2-yl) butyl) amino)-2-((5-phenylpyrimidin-4-yl) amino) butanoic acid.

Compound 451: (S)-2-((6-methyl-2-(pyridin-4-yl) pyrimidin-4-yl) amino)-4-((2-((2-methylpyridin-3-yl) oxy) ethyl) (4-(5,6,7,8-tetrahydro-1,8-naphthyridin-2-yl) butyl) amino) butanoic acid.

Compound 452: (S)-4-((2-((2-methylpyridin-3-yl) oxy) ethyl) (4-(5,6,7,8-tetrahydro-1,8-naphthyridin-2-yl) butyl) amino)-2-((2-(pyridin-3-yl) quinazolin-4-yl) amino) butanoic acid.

Compound 453: (S)-4-((2-((2-methylpyridin-3-yl) oxy) ethyl) (4-(5,6,7,8-tetrahydro-1,8-naphthyridin-2-yl) butyl) amino)-2-((6-(pyridin-4-yl) pyrazin-2-yl) amino) butanoic acid.

Compound 454: (S)-4-((2-((2-methylpyridin-3-yl) oxy) ethyl) (4-(5,6,7,8-tetrahydro-1,8-naphthyridin-2-yl) butyl) amino)-2-((5-phenylpyrazin-2-yl) amino) butanoic acid.

Compound 455: (S)-4-((2-((2-methylpyridin-3-yl) oxy) ethyl) (4-(5,6,7,8-tetrahydro-1,8-naphthyridin-2-yl) butyl) amino)-2-((6-phenylpyrazin-2-yl) amino) butanoic acid.

Compound 456: (S)-4-((2-((2-methylpyridin-3-yl) oxy) ethyl) (4-(5,6,7,8-tetrahydro-1,8-naphthyridin-2-yl) butyl) amino)-2-((4-phenylpyridin-2-yl) amino) butanoic acid.

Compound 457: (S)-4-((2-((6-methylpyridin-3-yl) oxy) ethyl) (4-(5,6,7,8-tetrahydro-1,8-naphthyridin-2-yl) butyl) amino)-2-((4-phenylpyridin-2-yl) amino) butanoic acid.

Compound 458: (S)-2-((9H-purin-6-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 459: (S)-2-((1-methyl-1H-pyrazolo[4,3-d]pyrimidin-7-yl) amino)-4-((2-((2-methylpyridin-3-yl) oxy) ethyl) (4-(5,6,7,8-tetrahydro-1,8-naphthyridin-2-yl) butyl) amino) butanoic acid.

Compound 460: (S)-2-(benzo[d]thiazol-2-ylamino)-4-((2-((2-methylpyridin-3-yl) oxy)ethyl) (4-(5,6,7,8-tetrahydro-1,8-naphthyridin-2-yl) butyl)amino) butanoic acid.

Compound 461: (S)-2-((1-methyl-1H-benzo[d]imidazol-2-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 462: (S)-2-(benzo[d]oxazol-2-ylamino)-4-((2-((2-methylpyridin-3-yl) oxy)ethyl) (4-(5,6,7,8-tetrahydro-1,8-naphthyridin-2-yl) butyl)amino) butanoic acid.

Compound 463: (S)-2-((1-methyl-1H-pyrazol-5-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 464: (S)-2-((1-methyl-1H-indazol-3-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 465: (S)-2-((1-methyl-1H-indol-3-yl) amino)-4-((2-((2-methylpyridin-3-yl) oxy)ethyl) (4-(5,6,7,8-tetrahydro-1,8-naphthyridin-2-yl) butyl)amino) butanoic acid.

Compound 466: (S)-4-((2-((5-fluoropyridin-3-yl) oxy)ethyl) (4-(5,6,7,8-tetrahydro-1,8-naphthyridin-2-yl) butyl)amino)-2-((5-methylpyrimidin-2-yl) amino) butanoic acid.

Compound 467: (S)-4-((2-((5-fluoropyridin-3-yl) oxy)ethyl) (4-(5,6,7,8-tetrahydro-1,8-naphthyridin-2-yl) butyl)amino)-2-(pyridin-3-ylamino) butanoic acid.

Compound 468: (S)-4-((2-((5-fluoropyridin-3-yl) oxy)ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 469: (S)-2-((5-cyanopyrimidin-2-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 470: (S)-4-((2-((5-fluoropyridin-3-yl) oxy)ethyl) (4-(5,6,7,8-tetrahydro-1,8-naphthyridin-2-yl) butyl)amino)-2-((5-(trifluoromethyl)pyrimidin-2-yl) amino) butanoic acid.

Compound 471: (S)-4-((2-((5-fluoropyridin-3-yl) oxy)ethyl) (4-(5,6,7,8-tetrahydro-1,8-naphthyridin-2-yl) butyl)amino)-2-(pyridin-2-ylamino) butanoic acid.

Compound 472: (S)-2-((1H-pyrazolo[3,4-d]pyrimidin-4-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 473: (S)-2-((5-bromopyrimidin-2-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 474: (S)-2-((1H-pyrazolo[4,3-d]pyrimidin-7-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 475: (S)-4-((2-((5-fluoropyridin-3-yl) oxy)ethyl) (4-(5,6,7,8-tetrahydro-1,8-naphthyridin-2-yl) butyl)amino)-2-((2-methoxypyrimidin-4-yl) amino) butanoic acid.

Compound 476: (S)-2-((6-(1H-pyrazol-1-yl) pyrimidin-4-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 477: (S)-2-((6-(dimethylamino)pyrimidin-4-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 478: (S)-4-((2-((5-fluoropyridin-3-yl) oxy)ethyl) (4-(5,6,7,8-tetrahydro-1,8-naphthyridin-2-yl) butyl)amino)-2-((6-(trifluoromethyl)pyrimidin-4-yl) amino) butanoic acid.

Compound 479: (S)-2-((5-cyclopropylpyrimidin-2-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 480: (S)-2-((6-(tert-butyl)pyrimidin-4-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 481: (S)-4-((2-((5-fluoropyridin-3-yl) oxy)ethyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid.

Compound 482: (S)-4-((2-((5-fluoropyridin-3-yl) oxy)ethyl) (4-(5,6,7,8-tetrahydro-1,8-naphthyridin-2-yl) butyl)amino)-2-((5-fluoropyrimidin-2-yl) amino) butanoic acid.

Compound 483: (S)-4-((2-((5-fluoropyridin-3-yl) oxy)ethyl) (4-(5,6,7,8-tetrahydro-1,8-naphthyridin-2-yl) butyl)amino)-2-(pyrimidin-4-ylamino) butanoic acid.

Compound 484: (S)-2-((3-cyanopyrazin-2-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 485: (S)-4-((2-((5-fluoropyridin-3-yl) oxy)ethyl) (4-(5,6,7,8-tetrahydro-1,8-naphthyridin-2-yl) butyl)amino)-2-((6-methylpyrazin-2-yl) amino) butanoic acid.

Compound 486: (S)-4-((2-((5-fluoropyridin-3-yl) oxy)ethyl) (4-(5,6,7,8-tetrahydro-1,8-naphthyridin-2-yl) butyl)amino)-2-((6-phenylpyrazin-2-yl) amino) butanoic acid.

Compound 487: (S)-4-((2-((5-fluoropyridin-3-yl) oxy)ethyl) (4-(5,6,7,8-tetrahydro-1,8-naphthyridin-2-yl) butyl)amino)-2-((5-phenylpyrazin-2-yl) amino) butanoic acid.

Compound 488: (S)-4-((2-((5-fluoropyridin-3-yl) oxy)ethyl) (4-(5,6,7,8-tetrahydro-1,8-naphthyridin-2-yl) butyl)amino)-2-((6-(pyridin-4-yl) pyrazin-2-yl) amino) butanoic acid.

Compound 489: (S)-4-((2-((5-fluoropyridin-3-yl) oxy)ethyl) (4-(5,6,7,8-tetrahydro-1,8-naphthyridin-2-yl) butyl)amino)-2-((2-(pyridin-3-yl) quinazolin-4-yl) amino) butanoic acid.

Compound 490: (S)-4-((2-((5-fluoropyridin-3-yl) oxy)ethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid.

Compound 491: (S)-4-((2-((5-fluoropyridin-3-yl) oxy)ethyl) (4-(5,6,7,8-tetrahydro-1,8-naphthyridin-2-yl) butyl)amino)-2-((5-phenylpyrimidin-4-yl) amino) butanoic acid.

Compound 492: (S)-4-((2-((5-fluoropyridin-3-yl) oxy)ethyl) (4-(5,6,7,8-tetrahydro-1,8-naphthyridin-2-yl) butyl)amino)-2-((2-phenylpyrimidin-4-yl) amino) butanoic acid.

Compound 493: (S)-4-((2-((5-fluoropyridin-3-yl) oxy)ethyl) (4-(5,6,7,8-tetrahydro-1,8-naphthyridin-2-yl) butyl)amino)-2-((6-phenylpyrimidin-4-yl) amino) butanoic acid.

Compound 494: (S)-4-((2-((5-fluoropyridin-3-yl) oxy)ethyl) (4-(5,6,7,8-tetrahydro-1,8-naphthyridin-2-yl) butyl)amino)-2-((5-methoxypyrazin-2-yl) amino) butanoic acid.

Compound 495: (S)-4-((2-((5-fluoropyridin-3-yl) oxy)ethyl) (4-(5,6,7,8-tetrahydro-1,8-naphthyridin-2-yl) butyl)amino)-2-(quinoxalin-2-ylamino) butanoic acid.

Compound 496: (S)-4-((2-((5-fluoropyridin-3-yl) oxy)ethyl) (4-(5,6,7,8-tetrahydro-1,8-naphthyridin-2-yl) butyl)amino)-2-((4-phenylpyridin-2-yl) amino) butanoic acid.

Compound 497: (S)-4-((2-((5-fluoropyridin-3-yl) oxy)ethyl) (4-(5,6,7,8-tetrahydro-1,8-naphthyridin-2-yl) butyl)amino)-2-((5-phenylpyridin-2-yl) amino) butanoic acid.

Compound 498: (S)-2-((9H-purin-6-yl) amino)-4-((2-((5-fluoropyridin-3-yl) oxy)ethyl) (4-(5,6,7,8-tetrahydro-1,8-naphthyridin-2-yl) butyl)amino) butanoic acid.

Compound 499: (S)-4-((2-((5-fluoropyridin-3-yl) oxy)ethyl) (4-(5,6,7,8-tetrahydro-1,8-naphthyridin-2-yl) butyl)amino)-2-((1-methyl-1H-pyrazolo[4,3-d]pyrimidin-7-yl) amino) butanoic acid.

Compound 500: (S)-2-(benzo[d]thiazol-2-ylamino)-4-((2-((5-fluoropyridin-3-yl) oxy)ethyl) (4-(5,6,7,8-tetrahydro-1,8-naphthyridin-2-yl) butyl)amino) butanoic acid.

Compound 501: (S)-4-((2-((5-fluoropyridin-3-yl) oxy)ethyl) (4-(5,6,7,8-tetrahydro-1,8-naphthyridin-2-yl) butyl)amino)-2-((1-methyl-1H-benzo[d]imidazol-2-yl) amino) butanoic acid.

Compound 502: (S)-2-(benzo[d]oxazol-2-ylamino)-4-((2-((5-fluoropyridin-3-yl) oxy)ethyl) (4-(5,6,7,8-tetrahydro-1,8-naphthyridin-2-yl) butyl)amino) butanoic acid.

Compound 503: (S)-4-((2-((5-fluoropyridin-3-yl) oxy)ethyl) (4-(5,6,7,8-tetrahydro-1,8-naphthyridin-2-yl) butyl)amino)-2-((1-methyl-1H-pyrazol-5-yl) amino) butanoic acid.

Compound 504: (S)-4-((2-((5-fluoropyridin-3-yl) oxy) ethyl) (4-(5,6,7,8-tetrahydro-1,8-naphthyridin-2-yl) butyl) amino)-2-((1-methyl-1H-indazol-3-yl) amino) butanoic acid.

Compound 505: (S)-4-((2-((5-fluoropyridin-3-yl) oxy) ethyl) (4-(5,6,7,8-tetrahydro-1,8-naphthyridin-2-yl) butyl) amino)-2-((1-methyl-1H-indol-3-yl) amino) butanoic acid.

Compound 506: (S)-4-((2-((6-methylpyridin-3-yl) oxy) ethyl) (4-(5,6,7,8-tetrahydro-1,8-naphthyridin-2-yl) butyl) amino)-2-((5-methylpyrimidin-2-yl) amino) butanoic acid.

Compound 507: (S)-4-((2-((6-methylpyridin-3-yl) oxy) ethyl) (4-(5,6,7,8-tetrahydro-1,8-naphthyridin-2-yl) butyl) amino)-2-(pyridin-3-ylamino) butanoic acid.

Compound 508: (S)-2-((1-methyl-1H-pyrazolo[3,4-d]pyrimidin-4-yl) amino)-4-((2-((6-methylpyridin-3-yl) oxy) ethyl) (4-(5,6,7,8-tetrahydro-1,8-naphthyridin-2-yl) butyl) amino) butanoic acid.

Compound 509: (S)-2-((5-cyanopyrimidin-2-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 510: (S)-4-((2-((6-methylpyridin-3-yl) oxy) ethyl) (4-(5,6,7,8-tetrahydro-1,8-naphthyridin-2-yl) butyl) amino)-2-((5-(trifluoromethyl)pyrimidin-2-yl) amino) butanoic acid.

Compound 511: (S)-4-((2-((6-methylpyridin-3-yl) oxy) ethyl) (4-(5,6,7,8-tetrahydro-1,8-naphthyridin-2-yl) butyl) amino)-2-(pyridin-2-ylamino) butanoic acid.

Compound 512: (S)-2-((1H-pyrazolo[3,4-d]pyrimidin-4-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 513: (S)-2-((5-bromopyrimidin-2-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 514: (S)-2-((1H-pyrazolo[4,3-d]pyrimidin-7-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 515: (S)-2-((2-methoxypyrimidin-4-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 516: (S)-2-((6-methylpyrazin-2-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 517: (S)-2-((3-cyanopyrazin-2-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 518: (S)-4-((2-((6-methylpyridin-3-yl) oxy) ethyl) (4-(5,6,7,8-tetrahydro-1,8-naphthyridin-2-yl) butyl) amino)-2-(pyrimidin-4-ylamino) butanoic acid.

Compound 519: (S)-2-((5-fluoropyrimidin-2-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 520: (S)-2-((7-methyl-7H-pyrrolo[2,3-d]pyrimidin-4-yl) amino)-4-((2-((6-methylpyridin-3-yl) oxy) ethyl) (4-(5,6,7,8-tetrahydro-1,8-naphthyridin-2-yl) butyl) amino) butanoic acid.

Compound 521: (S)-2-((6-(tert-butyl)pyrimidin-4-yl) amino)-4-((2-((6-methylpyridin-3-yl) oxy)ethyl) (4-(5,6,7, 8-tetrahydro-1,8-naphthyridin-2-yl) butyl)amino) butanoic acid.

Compound 522: (S)-2-((5-cyclopropylpyrimidin-2-yl) amino)-4-((2-((6-methylpyridin-3-yl) oxy)ethyl) (4-(5,6,7, 8-tetrahydro-1,8-naphthyridin-2-yl) butyl)amino) butanoic acid.

Compound 523: (S)-4-((2-((6-methylpyridin-3-yl) oxy) ethyl) (4-(5,6,7,8-tetrahydro-1,8-naphthyridin-2-yl) butyl) amino)-2-((6-(trifluoromethyl)pyrimidin-4-yl) amino) butanoic acid.

Compound 524: (S)-2-((6-(dimethylamino)pyrimidin-4-yl) amino)-4-((2-((6-methylpyridin-3-yl) oxy)ethyl) (4-(5,6, 7,8-tetrahydro-1,8-naphthyridin-2-yl) butyl)amino) butanoic acid.

Compound 525: (S)-2-((6-(1H-pyrazol-1-yl) pyrimidin-4-yl) amino)-4-((2-((6-methylpyridin-3-yl) oxy)ethyl) (4-(5,6, 7,8-tetrahydro-1,8-naphthyridin-2-yl) butyl)amino) butanoic acid.

Compound 526: (S)-4-((2-((6-methylpyridin-3-yl) oxy) ethyl) (4-(5,6,7,8-tetrahydro-1,8-naphthyridin-2-yl) butyl) amino)-2-(quinoxalin-2-ylamino) butanoic acid.

Compound 527: (S)-2-((5-methoxypyrazin-2-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 528: (S)-4-((2-((6-methylpyridin-3-yl) oxy) ethyl) (4-(5,6,7,8-tetrahydro-1,8-naphthyridin-2-yl) butyl) amino)-2-((6-phenylpyrimidin-4-yl) amino) butanoic acid.

Compound 529: (S)-4-((2-((6-methylpyridin-3-yl) oxy) ethyl) (4-(5,6,7,8-tetrahydro-1,8-naphthyridin-2-yl) butyl) amino)-2-((2-phenylpyrimidin-4-yl) amino) butanoic acid.

Compound 530: (S)-4-((2-((6-methylpyridin-3-yl) oxy) ethyl) (4-(5,6,7,8-tetrahydro-1,8-naphthyridin-2-yl) butyl) amino)-2-((5-phenylpyrimidin-4-yl) amino) butanoic acid.

Compound 531: (S)-2-((6-methyl-2-(pyridin-4-yl) pyrimidin-4-yl) amino)-4-((2-((6-methylpyridin-3-yl) oxy) ethyl) (4-(5,6,7,8-tetrahydro-1,8-naphthyridin-2-yl) butyl) amino) butanoic acid.

Compound 532: (S)-4-((2-((6-methylpyridin-3-yl) oxy) ethyl) (4-(5,6,7,8-tetrahydro-1,8-naphthyridin-2-yl) butyl) amino)-2-((2-(pyridin-3-yl) quinazolin-4-yl) amino) butanoic acid.

Compound 533: (S)-4-((2-((6-methylpyridin-3-yl) oxy) ethyl) (4-(5,6,7,8-tetrahydro-1,8-naphthyridin-2-yl) butyl) amino)-2-((6-(pyridin-4-yl) pyrazin-2-yl) amino) butanoic acid.

Compound 534: (S)-4-((2-((6-methylpyridin-3-yl) oxy) ethyl) (4-(5,6,7,8-tetrahydro-1,8-naphthyridin-2-yl) butyl) amino)-2-((5-phenylpyrazin-2-yl) amino) butanoic acid.

Compound 535: (S)-4-((2-((6-methylpyridin-3-yl) oxy) ethyl) (4-(5,6,7,8-tetrahydro-1,8-naphthyridin-2-yl) butyl) amino)-2-((6-phenylpyrazin-2-yl) amino) butanoic acid.

Compound 536: (S)-2-((1-methyl-1H-pyrazol-5-yl) amino)-4-((2-((6-methylpyridin-3-yl) oxy) ethyl) (4-(5,6,7, 8-tetrahydro-1,8-naphthyridin-2-yl) butyl)amino) butanoic acid.

Compound 537: (S)-2-(benzo[d]oxazol-2-ylamino)-4-((2-((6-methylpyridin-3-yl) oxy)ethyl) (4-(5,6,7,8-tetrahydro-1, 8-naphthyridin-2-yl) butyl)amino) butanoic acid.

Compound 538: (S)-2-((1-methyl-1H-benzo[d]imidazol-2-yl) amino)-4-((2-((6-methylpyridin-3-yl) oxy)ethyl) (4-(5, 6,7,8-tetrahydro-1,8-naphthyridin-2-yl) butyl)amino) butanoic acid.

Compound 539: (S)-2-(benzo[d]thiazol-2-ylamino)-4-((2-((6-methylpyridin-3-yl) oxy)ethyl) (4-(5,6,7,8-tetrahydro-1,8-naphthyridin-2-yl) butyl)amino) butanoic acid.

Compound 540: (S)-2-((1-methyl-1H-pyrazolo[4,3-d]pyrimidin-7-yl) amino)-4-((2-((6-methylpyridin-3-yl) oxy) ethyl) (4-(5,6,7,8-tetrahydro-1,8-naphthyridin-2-yl) butyl) amino) butanoic acid.

Compound 541: (S)-2-((9H-purin-6-yl) amino)-4-((2-((6-methylpyridin-3-yl) oxy) ethyl) (4-(5,6,7,8-tetrahydro-1,8-naphthyridin-2-yl) butyl)amino) butanoic acid.

Compound 542: (S)-4-((2-((6-methylpyridin-3-yl) oxy) ethyl) (4-(5,6,7,8-tetrahydro-1,8-naphthyridin-2-yl) butyl) amino)-2-((5-phenylpyridin-2-yl) amino) butanoic acid.

Compound 543: (S)-4-((2-((2-methylpyridin-3-yl) oxy) ethyl) (4-(5,6,7,8-tetrahydro-1,8-naphthyridin-2-yl) butyl) amino)-2-((5-phenylpyridin-2-yl) amino) butanoic acid.

Compound 544: (S)-2-((1-methyl-1H-indazol-3-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 545: (S)-2-((1-methyl-1H-indol-3-yl) amino)-4-((2-((6-methylpyridin-3-yl) oxy)ethyl) (4-(5,6,7,8-tetrahydro-1,8-naphthyridin-2-yl) butyl)amino) butanoic acid.

Compound 546: (S)-2-((5-methylpyrimidin-2-yl) amino)-4-((2-(pyridin-2-yloxy)ethyl) (4-(5,6,7,8-tetrahydro-1,8-naphthyridin-2-yl) butyl)amino) butanoic acid.

Compound 547: (S)-4-((2-(pyridin-2-yloxy)ethyl) (4-(5,6,7,8-tetrahydro-1,8-naphthyridin-2-yl) butyl)amino)-2-(pyridin-3-ylamino) butanoic acid.

Compound 548: (S)-2-((1-methyl-1H-pyrazolo[3,4-d]pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 549: (S)-2-((5-cyanopyrimidin-2-yl) amino)-4-((2-(pyridin-2-yloxy)ethyl) (4-(5,6,7,8-tetrahydro-1,8-naphthyridin-2-yl) butyl)amino) butanoic acid.

Compound 550: (S)-4-((2-(pyridin-2-yloxy)ethyl) (4-(5,6,7,8-tetrahydro-1,8-naphthyridin-2-yl) butyl)amino)-2-((5-(trifluoromethyl)pyrimidin-2-yl) amino) butanoic acid.

Compound 551: (S)-2-(pyridin-2-ylamino)-4-((2-(pyridin-2-yloxy)ethyl) (4-(5,6,7,8-tetrahydro-1,8-naphthyridin-2-yl) butyl)amino) butanoic acid.

Compound 552: (S)-2-((1H-pyrazolo[3,4-d]pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 553: (S)-2-((5-bromopyrimidin-2-yl) amino)-4-((2-(pyridin-2-yloxy)ethyl) (4-(5,6,7,8-tetrahydro-1,8-naphthyridin-2-yl) butyl)amino) butanoic acid.

Compound 554: (S)-2-((1H-pyrazolo[4,3-d]pyrimidin-7-yl) amino)-4-((2-(pyridin-2-yloxy)ethyl) (4-(5,6,7,8-tetrahydro-1,8-naphthyridin-2-yl) butyl)amino) butanoic acid.

Compound 555: (S)-2-((2-methoxypyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 556: (S)-2-((6-methylpyrazin-2-yl) amino)-4-((2-(pyridin-2-yloxy)ethyl) (4-(5,6,7,8-tetrahydro-1,8-naphthyridin-2-yl) butyl)amino) butanoic acid.

Compound 557: (S)-2-((3-cyanopyrazin-2-yl) amino)-4-((2-(pyridin-2-yloxy)ethyl) (4-(5,6,7,8-tetrahydro-1,8-naphthyridin-2-yl) butyl)amino) butanoic acid.

Compound 558: (S)-4-((2-(pyridin-2-yloxy)ethyl) (4-(5,6,7,8-tetrahydro-1,8-naphthyridin-2-yl) butyl)amino)-2-(pyrimidin-4-ylamino) butanoic acid.

Compound 559: (S)-2-((5-fluoropyrimidin-2-yl) amino)-4-((2-(pyridin-2-yloxy)ethyl) (4-(5,6,7,8-tetrahydro-1,8-naphthyridin-2-yl) butyl)amino) butanoic acid.

Compound 560: (S)-2-((7-methyl-7H-pyrrolo[2,3-d]pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 561: (S)-2-((6-(tert-butyl)pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 562: (S)-2-((5-cyclopropylpyrimidin-2-yl) amino)-4-((2-(pyridin-2-yloxy)ethyl) (4-(5,6,7,8-tetrahydro-1,8-naphthyridin-2-yl) butyl)amino) butanoic acid.

Compound 563: (S)-4-((2-(pyridin-2-yloxy)ethyl) (4-(5,6,7,8-tetrahydro-1,8-naphthyridin-2-yl) butyl)amino)-2-((6-(trifluoromethyl)pyrimidin-4-yl) amino) butanoic acid.

Compound 564: (S)-2-((6-(dimethylamino)pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 565: (S)-2-((6-(1H-pyrazol-1-yl) pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 566: (S)-4-((2-(pyridin-2-yloxy)ethyl) (4-(5,6,7,8-tetrahydro-1,8-naphthyridin-2-yl) butyl)amino)-2-(quinoxalin-2-ylamino) butanoic acid.

Compound 567: (S)-2-((5-methoxypyrazin-2-yl) amino)-4-((2-(pyridin-2-yloxy)ethyl) (4-(5,6,7,8-tetrahydro-1,8-naphthyridin-2-yl) butyl)amino) butanoic acid.

Compound 568: (S)-2-((6-phenylpyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 569: (S)-2-((2-phenylpyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 570: (S)-2-((5-phenylpyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 571: (S)-2-((6-methyl-2-(pyridin-4-yl) pyrimidin-4-yl) amino)-4-((2-(pyridin-2-yloxy)ethyl) (4-(5,6,7,8-tetrahydro-1,8-naphthyridin-2-yl) butyl)amino) butanoic acid.

Compound 572: (S)-4-((2-(pyridin-2-yloxy)ethyl) (4-(5,6,7,8-tetrahydro-1,8-naphthyridin-2-yl) butyl)amino)-2-((2-(pyridin-3-yl) quinazolin-4-yl) amino) butanoic acid.

Compound 573: (S)-4-((2-(pyridin-2-yloxy)ethyl) (4-(5,6,7,8-tetrahydro-1,8-naphthyridin-2-yl) butyl)amino)-2-((6-(pyridin-4-yl) pyrazin-2-yl) amino) butanoic acid.

Compound 574: (S)-2-((5-phenylpyrazin-2-yl) amino)-4-((2-(pyridin-2-yloxy)ethyl) (4-(5,6,7,8-tetrahydro-1,8-naphthyridin-2-yl) butyl)amino) butanoic acid.

Compound 575: (S)-2-((6-phenylpyrazin-2-yl) amino)-4-((2-(pyridin-2-yloxy)ethyl) (4-(5,6,7,8-tetrahydro-1,8-naphthyridin-2-yl) butyl)amino) butanoic acid.

Compound 576: (S)-2-((1-methyl-1H-pyrazol-5-yl) amino)-4-((2-(pyridin-2-yloxy)ethyl) (4-(5,6,7,8-tetrahydro-1,8-naphthyridin-2-yl) butyl)amino) butanoic acid.

Compound 577: (S)-2-(benzo[d]oxazol-2-ylamino)-4-((2-(pyridin-2-yloxy)ethyl) (4-(5,6,7,8-tetrahydro-1,8-naphthyridin-2-yl) butyl)amino) butanoic acid.

Compound 578: (S)-2-((1-methyl-1H-benzo[d]imidazol-2-yl) amino)-4-((2-(pyridin-2-yloxy)ethyl) (4-(5,6,7,8-tetrahydro-1,8-naphthyridin-2-yl) butyl)amino) butanoic acid.

Compound 579: (S)-2-(benzo[d]thiazol-2-ylamino)-4-((2-(pyridin-2-yloxy)ethyl) (4-(5,6,7,8-tetrahydro-1,8-naphthyridin-2-yl) butyl)amino) butanoic acid.

Compound 580: (S)-2-((1-methyl-1H-pyrazolo[4,3-d]pyrimidin-7-yl) amino)-4-((2-(pyridin-2-yloxy)ethyl) (4-(5,6,7,8-tetrahydro-1,8-naphthyridin-2-yl) butyl)amino) butanoic acid.

Compound 581: (S)-2-((9H-purin-6-yl) amino)-4-((2-(pyridin-2-yloxy)ethyl) (4-(5,6,7,8-tetrahydro-1,8-naphthyridin-2-yl) butyl)amino) butanoic acid.

Compound 582: (S)-2-((5-phenylpyridin-2-yl) amino)-4-((2-(pyridin-2-yloxy)ethyl) (4-(5,6,7,8-tetrahydro-1,8-naphthyridin-2-yl) butyl)amino) butanoic acid.

Compound 583: (S)-2-((4-phenylpyridin-2-yl) amino)-4-((2-(pyridin-2-yloxy)ethyl) (4-(5,6,7,8-tetrahydro-1,8-naphthyridin-2-yl) butyl)amino) butanoic acid.

Compound 584: (S)-2-((1-methyl-1H-indol-3-yl) amino)-4-((2-(pyridin-2-yloxy)ethyl) (4-(5,6,7,8-tetrahydro-1,8-naphthyridin-2-yl) butyl)amino) butanoic acid.

Compound 585: (S)-2-((1-methyl-1H-indazol-3-yl) amino)-4-((2-(pyridin-2-yloxy)ethyl) (4-(5,6,7,8-tetrahydro-1,8-naphthyridin-2-yl) butyl)amino) butanoic acid.

Compound 586: (S)-4-((2-(3,5-difluorophenoxy)ethyl) (4-(5,6,7,8-tetrahydro-1,8-naphthyridin-2-yl) butyl)amino)-2-((5-methylpyrimidin-2-yl) amino) butanoic acid.

Compound 587: (S)-4-((2-(3,5-difluorophenoxy)ethyl) (4-(5,6,7,8-tetrahydro-1,8-naphthyridin-2-yl) butyl)amino)-2-(pyridin-3-ylamino) butanoic acid.

Compound 588: (S)-4-((2-(3,5-difluorophenoxy)ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 589: (S)-2-((5-cyanopyrimidin-2-yl) amino)-4-((2-(3,5-difluorophenoxy)ethyl) (4-(5,6,7,8-tetrahydro-1,8-naphthyridin-2-yl) butyl)amino) butanoic acid.

Compound 590: (S)-4-((2-(3,5-difluorophenoxy)ethyl) (4-(5,6,7,8-tetrahydro-1,8-naphthyridin-2-yl) butyl)amino)-2-((5-(trifluoromethyl)pyrimidin-2-yl) amino) butanoic acid.

Compound 591: (S)-4-((2-(3,5-difluorophenoxy)ethyl) (4-(5,6,7,8-tetrahydro-1,8-naphthyridin-2-yl) butyl)amino)-2-(pyridin-2-ylamino) butanoic acid.

Compound 592: (S)-2-((1H-pyrazolo[3,4-d]pyrimidin-4-yl) amino)-4-((2-(3,5-difluorophenoxy)ethyl) (4-(5,6,7,8-tetrahydro-1,8-naphthyridin-2-yl) butyl)amino) butanoic acid.

Compound 593: (S)-2-((5-bromopyrimidin-2-yl) amino)-4-((2-(3,5-difluorophenoxy)ethyl) (4-(5,6,7,8-tetrahydro-1,8-naphthyridin-2-yl) butyl)amino) butanoic acid.

Compound 594: (S)-2-((1H-pyrazolo[4,3-d]pyrimidin-7-yl) amino)-4-((2-(3,5-difluorophenoxy)ethyl) (4-(5,6,7,8-tetrahydro-1,8-naphthyridin-2-yl) butyl)amino) butanoic acid.

Compound 595: (S)-4-((2-(3,5-difluorophenoxy)ethyl) (4-(5,6,7,8-tetrahydro-1,8-naphthyridin-2-yl) butyl)amino)-2-((2-methoxypyrimidin-4-yl) amino) butanoic acid.

Compound 596: (S)-4-((2-(3,5-difluorophenoxy)ethyl) (4-(5,6,7,8-tetrahydro-1,8-naphthyridin-2-yl) butyl)amino)-2-((6-methylpyrazin-2-yl) amino) butanoic acid.

Compound 597: (S)-2-((3-cyanopyrazin-2-yl) amino)-4-((2-(3,5-difluorophenoxy)ethyl) (4-(5,6,7,8-tetrahydro-1,8-naphthyridin-2-yl) butyl)amino) butanoic acid.

Compound 598: (S)-4-((2-(3,5-difluorophenoxy)ethyl) (4-(5,6,7,8-tetrahydro-1,8-naphthyridin-2-yl) butyl)amino)-2-(pyrimidin-4-ylamino) butanoic acid.

Compound 599: (S)-4-((2-(3,5-difluorophenoxy)ethyl) (4-(5,6,7,8-tetrahydro-1,8-naphthyridin-2-yl) butyl)amino)-2-((5-fluoropyrimidin-2-yl) amino) butanoic acid.

Compound 600: (S)-4-((2-(3,5-difluorophenoxy)ethyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid.

Compound 601: (S)-2-((6-(tert-butyl)pyrimidin-4-yl) amino)-4-((2-(3,5-difluorophenoxy)ethyl) (4-(5,6,7,8-tetrahydro-1,8-naphthyridin-2-yl) butyl)amino) butanoic acid.

Compound 602: (S)-2-((5-cyclopropylpyrimidin-2-yl) amino)-4-((2-(3,5-difluorophenoxy)ethyl) (4-(5,6,7,8-tetrahydro-1,8-naphthyridin-2-yl) butyl)amino) butanoic acid.

Compound 603: (S)-4-((2-(3,5-difluorophenoxy)ethyl) (4-(5,6,7,8-tetrahydro-1,8-naphthyridin-2-yl) butyl)amino)-2-((6-(trifluoromethyl)pyrimidin-2-yl) amino) butanoic acid.

Compound 604: (S)-4-((2-(3,5-difluorophenoxy)ethyl) (4-(5,6,7,8-tetrahydro-1,8-naphthyridin-2-yl) butyl)amino)-2-((6-(dimethylamino)pyrimidin-4-yl) amino) butanoic acid.

Compound 605: (S)-2-((6-(1H-pyrazol-1-yl) pyrimidin-4-yl) amino)-4-((2-(3,5-difluorophenoxy)ethyl) (4-(5,6,7,8-tetrahydro-1,8-naphthyridin-2-yl) butyl)amino) butanoic acid.

Compound 606: (S)-4-((2-(3,5-difluorophenoxy)ethyl) (4-(5,6,7,8-tetrahydro-1,8-naphthyridin-2-yl) butyl)amino)-2-(quinoxalin-2-ylamino) butanoic acid.

Compound 607: (S)-4-((2-(3,5-difluorophenoxy)ethyl) (4-(5,6,7,8-tetrahydro-1,8-naphthyridin-2-yl) butyl)amino)-2-((5-methoxypyrazin-2-yl) amino) butanoic acid.

Compound 608: (S)-4-((2-(3,5-difluorophenoxy)ethyl) (4-(5,6,7,8-tetrahydro-1,8-naphthyridin-2-yl) butyl)amino)-2-((6-phenylpyrimidin-4-yl) amino) butanoic acid.

Compound 609: (S)-4-((2-(3,5-difluorophenoxy)ethyl) (4-(5,6,7,8-tetrahydro-1,8-naphthyridin-2-yl) butyl)amino)-2-((2-phenylpyrimidin-4-yl) amino) butanoic acid.

Compound 610: (S)-4-((2-(3,5-difluorophenoxy)ethyl) (4-(5,6,7,8-tetrahydro-1,8-naphthyridin-2-yl) butyl)amino)-2-((5-phenylpyrimidin-4-yl) amino) butanoic acid.

Compound 611: (S)-4-((2-(3,5-difluorophenoxy)ethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid.

Compound 612: (S)-4-((2-(3,5-difluorophenoxy)ethyl) (4-(5,6,7,8-tetrahydro-1,8-naphthyridin-2-yl) butyl)amino)-2-((2-(pyridin-3-yl) quinazolin-4-yl) amino) butanoic acid.

Compound 613: (S)-4-((2-(3,5-difluorophenoxy)ethyl) (4-(5,6,7,8-tetrahydro-1,8-naphthyridin-2-yl) butyl)amino)-2-((6-(pyridin-4-yl) pyrazin-2-yl) amino) butanoic acid.

Compound 614: (S)-4-((2-(3,5-difluorophenoxy)ethyl) (4-(5,6,7,8-tetrahydro-1,8-naphthyridin-2-yl) butyl)amino)-2-((5-phenylpyrazin-2-yl) amino) butanoic acid.

Compound 615: (S)-4-((2-(3,5-difluorophenoxy)ethyl) (4-(5,6,7,8-tetrahydro-1,8-naphthyridin-2-yl) butyl)amino)-2-((6-phenylpyrazin-2-yl) amino) butanoic acid.

Compound 616: (S)-4-((2-(3,5-difluorophenoxy)ethyl) (4-(5,6,7,8-tetrahydro-1,8-naphthyridin-2-yl) butyl)amino)-2-((1-methyl-H-pyrazol-5-yl) amino) butanoic acid.

Compound 617: (S)-2-(benzo[d]oxazol-2-ylamino)-4-((2-(3,5-difluorophenoxy)ethyl) (4-(5,6,7,8-tetrahydro-1,8-naphthyridin-2-yl) butyl)amino) butanoic acid.

Compound 618: (S)-4-((2-(3,5-difluorophenoxy)ethyl) (4-(5,6,7,8-tetrahydro-1,8-naphthyridin-2-yl) butyl)amino)-2-((1-methyl-1H-benzo[d]imidazol-2-yl) amino) butanoic acid.

Compound 619: (S)-2-(benzo[d]thiazol-2-ylamino)-4-((2-(3,5-difluorophenoxy)ethyl) (4-(5,6,7,8-tetrahydro-1,8-naphthyridin-2-yl) butyl)amino) butanoic acid.

Compound 620: (S)-4-((2-(3,5-difluorophenoxy)ethyl) (4-(5,6,7,8-tetrahydro-1,8-naphthyridin-2-yl) butyl)amino)-2-((1-methyl-1H-pyrazolo[4,3-d]pyrimidin-7-yl) amino) butanoic acid.

Compound 621: (S)-2-((9H-purin-6-yl) amino)-4-((2-(3,5-difluorophenoxy)ethyl) (4-(5,6,7,8-tetrahydro-1,8-naphthyridin-2-yl) butyl)amino) butanoic acid.

Compound 622: (S)-4-((2-(3,5-difluorophenoxy)ethyl) (4-(5,6,7,8-tetrahydro-1,8-naphthyridin-2-yl) butyl)amino)-2-((5-phenylpyridin-2-yl) amino) butanoic acid.

Compound 623: (S)-4-((2-(3,5-difluorophenoxy)ethyl) (4-(5,6,7,8-tetrahydro-1,8-naphthyridin-2-yl) butyl)amino)-2-((4-phenylpyridin-2-yl) amino) butanoic acid.

Compound 624: (S)-4-((2-(3,5-difluorophenoxy)ethyl) (4-(5,6,7,8-tetrahydro-1,8-naphthyridin-2-yl) butyl)amino)-2-((1-methyl-1H-indazol-3-yl) amino) butanoic acid.

Compound 625: (S)-4-((2-(3,5-difluorophenoxy)ethyl) (4-(5,6,7,8-tetrahydro-1,8-naphthyridin-2-yl) butyl)amino)-2-((1-methyl-1H-indol-3-yl) amino) butanoic acid.

Compound 626: (S)-4-((2-(3,5-dimethyl-1H-pyrazol-1-yl) ethyl) (4-(5,6,7,8-tetrahydro-1,8-naphthyridin-2-yl) butyl)amino)-2-((5-methylpyrimidin-2-yl) amino) butanoic acid.

Compound 627: (S)-4-((2-(3,5-dimethyl-1H-pyrazol-1-yl) ethyl) (4-(5,6,7,8-tetrahydro-1,8-naphthyridin-2-yl) butyl)amino)-2-(pyridin-3-ylamino) butanoic acid.

Compound 628: (S)-4-((2-(3,5-dimethyl-1H-pyrazol-1-yl) ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid.

Compound 629: (S)-2-((5-cyanopyrimidin-2-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 630: (S)-4-((2-(3,5-dimethyl-1H-pyrazol-1-yl) ethyl) (4-(5,6,7,8-tetrahydro-1,8-naphthyridin-2-yl) butyl)amino)-2-((5-(trifluoromethyl)pyrimidin-2-yl) amino) butanoic acid.

Compound 631: (S)-4-((2-(3,5-dimethyl-1H-pyrazol-1-yl) ethyl) (4-(5,6,7,8-tetrahydro-1,8-naphthyridin-2-yl) butyl)amino)-2-(pyridin-2-ylamino) butanoic acid.

Compound 632: (S)-2-((1H-pyrazolo[3,4-d]pyrimidin-4-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 633: (S)-2-((5-bromopyrimidin-2-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 634: (S)-2-((1H-pyrazolo[4,3-d]pyrimidin-7-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 635: (S)-4-((2-(3,5-dimethyl-1H-pyrazol-1-yl) ethyl) (4-(5,6,7,8-tetrahydro-1,8-naphthyridin-2-yl) butyl)amino)-2-((2-methoxypyrimidin-4-yl) amino) butanoic acid.

Compound 636: (S)-4-((2-(3,5-dimethyl-1H-pyrazol-1-yl) ethyl) (4-(5,6,7,8-tetrahydro-1,8-naphthyridin-2-yl) butyl)amino)-2-((6-methylpyrazin-2-yl) amino) butanoic acid.

Compound 637: (S)-2-((3-cyanopyrazin-2-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 638: (S)-4-((2-(3,5-dimethyl-1H-pyrazol-1-yl) ethyl) (4-(5,6,7,8-tetrahydro-1,8-naphthyridin-2-yl) butyl)amino)-2-(pyrimidin-4-ylamino) butanoic acid.

Compound 639: (S)-4-((2-(3,5-dimethyl-1H-pyrazol-1-yl) ethyl) (4-(5,6,7,8-tetrahydro-1,8-naphthyridin-2-yl) butyl)amino)-2-((5-fluoropyrimidin-2-yl) amino) butanoic acid.

Compound 640: (S)-4-((2-(3,5-dimethyl-1H-pyrazol-1-yl) ethyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid.

Compound 641: (S)-2-((6-(tert-butyl)pyrimidin-4-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 642: (S)-2-((5-cyclopropylpyrimidin-2-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 643: (S)-4-((2-(3,5-dimethyl-1H-pyrazol-1-yl) ethyl) (4-(5,6,7,8-tetrahydro-1,8-naphthyridin-2-yl) butyl)amino)-2-((6-(trifluoromethyl)pyrimidin-4-yl) amino) butanoic acid.

Compound 644: (S)-4-((2-(3,5-dimethyl-1H-pyrazol-1-yl) ethyl) (4-(5,6,7,8-tetrahydro-1,8-naphthyridin-2-yl) butyl)amino)-2-((6-(dimethylamino)pyrimidin-4-yl) amino) butanoic acid.

Compound 645: (S)-2-((6-(H-pyrazol-1-yl) pyrimidin-4-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 646: (S)-4-((2-(3,5-dimethyl-1H-pyrazol-1-yl) ethyl) (4-(5,6,7,8-tetrahydro-1,8-naphthyridin-2-yl) butyl)amino)-2-(quinoxalin-2-ylamino) butanoic acid.

Compound 647: (S)-4-((2-(3,5-dimethyl-1H-pyrazol-1-yl) ethyl) (4-(5,6,7,8-tetrahydro-1,8-naphthyridin-2-yl) butyl)amino)-2-((5-methoxypyrazin-2-yl) amino) butanoic acid.

Compound 648: (S)-4-((2-(3,5-dimethyl-1H-pyrazol-1-yl) ethyl) (4-(5,6,7,8-tetrahydro-1,8-naphthyridin-2-yl) butyl)amino)-2-((6-phenylpyrimidin-4-yl) amino) butanoic acid.

Compound 649: (S)-4-((2-(3,5-dimethyl-1H-pyrazol-1-yl) ethyl) (4-(5,6,7,8-tetrahydro-1,8-naphthyridin-2-yl) butyl)amino)-2-((2-phenylpyrimidin-4-yl) amino) butanoic acid.

Compound 650: (S)-4-((2-(3,5-dimethyl-1H-pyrazol-1-yl) ethyl) (4-(5,6,7,8-tetrahydro-1,8-naphthyridin-2-yl) butyl)amino)-2-((5-phenylpyrimidin-4-yl) amino) butanoic acid.

Compound 651: (S)-4-((2-(3,5-dimethyl-1H-pyrazol-1-yl) ethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid.

Compound 652: (S)-4-((2-(3,5-dimethyl-1H-pyrazol-1-yl) ethyl) (4-(5,6,7,8-tetrahydro-1,8-naphthyridin-2-yl) butyl)amino)-2-((2-(pyridin-3-yl) quinazolin-4-yl) amino) butanoic acid.

Compound 653: (S)-4-((2-(3,5-dimethyl-1H-pyrazol-1-yl) ethyl) (4-(5,6,7,8-tetrahydro-1,8-naphthyridin-2-yl) butyl)amino)-2-((6-(pyridin-4-yl) pyrazin-2-yl) amino) butanoic acid.

Compound 654: (S)-4-((2-(3,5-dimethyl-1H-pyrazol-1-yl) ethyl) (4-(5,6,7,8-tetrahydro-1,8-naphthyridin-2-yl) butyl)amino)-2-((5-phenylpyrazin-2-yl) amino) butanoic acid.

Compound 655: (S)-4-((2-(3,5-dimethyl-1H-pyrazol-1-yl) ethyl) (4-(5,6,7,8-tetrahydro-1,8-naphthyridin-2-yl) butyl)amino)-2-((6-phenylpyrazin-2-yl) amino) butanoic acid.

Compound 656: (S)-4-((2-(3,5-dimethyl-1H-pyrazol-1-yl) ethyl) (4-(5,6,7,8-tetrahydro-1,8-naphthyridin-2-yl) butyl)amino)-2-((1-methyl-1H-pyrazol-5-yl) amino) butanoic acid.

Compound 657: (S)-2-(benzo[d]oxazol-2-ylamino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 658: (S)-4-((2-(3,5-dimethyl-1H-pyrazol-1-yl) ethyl) (4-(5,6,7,8-tetrahydro-1,8-naphthyridin-2-yl) butyl)amino)-2-((1-methyl-1H-benzo[d]imidazol-2-yl) amino) butanoic acid.

Compound 659: (S)-2-(benzo[d]thiazol-2-ylamino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 660: (S)-4-((2-(3,5-dimethyl-1H-pyrazol-1-yl) ethyl) (4-(5,6,7,8-tetrahydro-1,8-naphthyridin-2-yl) butyl)amino)-2-((1-methyl-1H-pyrazolo[4,3-d]pyrimidin-7-yl) amino) butanoic acid.

Compound 661: (S)-2-((9H-purin-6-yl) amino)-4-((2-(3,5-dimethyl-1H-pyrazol-1-yl) ethyl) (4-(5,6,7,8-tetrahydro-1,8-naphthyridin-2-yl) butyl)amino) butanoic acid.

Compound 662: (S)-4-((2-(3,5-dimethyl-1H-pyrazol-1-yl) ethyl) (4-(5,6,7,8-tetrahydro-1,8-naphthyridin-2-yl) butyl)amino)-2-((5-phenylpyridin-2-yl) amino) butanoic acid.

Compound 663: (S)-4-((2-(3,5-dimethyl-1H-pyrazol-1-yl) ethyl) (4-(5,6,7,8-tetrahydro-1,8-naphthyridin-2-yl) butyl)amino)-2-((4-phenylpyridin-2-yl) amino) butanoic acid.

Compound 664: (S)-4-((2-(3,5-dimethyl-1H-pyrazol-1-yl) ethyl) (4-(5,6,7,8-tetrahydro-1,8-naphthyridin-2-yl) butyl)amino)-2-((1-methyl-1H-indazol-3-yl) amino) butanoic acid.

Compound 665: (S)-4-((2-(3,5-dimethyl-1H-pyrazol-1-yl) ethyl) (4-(5,6,7,8-tetrahydro-1,8-naphthyridin-2-yl) butyl)amino)-2-((1-methyl-1H-indol-3-yl) amino) butanoic acid.

Compound 666: (R)-4-((2-methoxyethyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-methoxyethan-1-amine, Procedure F with methyl (R)-2-((tert-butoxycarbonyl)amino)-4-oxobutanoate, Procedure H with 4-chloroquinazoline, and Procedure P. LCMS theoretical m/z=493.3. [M+H]+, found 493.3.

Compound 667: (S)-4-((2-methoxyethyl) (5-(5,6,7,8-tetrahydro-1,8-naphthyridin-2-yl) pentyl)amino)-2-(quinazolin-4-ylamino) butanoic acid. Prepared according to Scheme A using Procedure A with 2-methoxyethan-1-amine and (S)-4-((2-methoxyethyl) (5-(5,6,7,8-tetrahydro-1,8-naphthyridin-2-yl) pentyl)amino)-2-(quinazolin-4-ylamino) butanoic acid, Procedure H with 4-chloro-2-methylquinazoline, and Procedure P. LCMS theoretical m/z=507.3. [M+H]+, found 507.3.

Compound 668: (S)-4-((2-methoxyethyl) (4-(5,6,7,8-tetrahydro-1,8-naphthyridin-2-yl) butyl)amino)-2-(quinoxalin-2-ylamino) butanoic acid. Prepared according to Scheme A using Procedure A with 2-methoxyethan-1-amine, Procedure H with 2-chloroquinoxaline and Procedure P. LCMS theoretical m/z=493.3. [M+H]+, found 493.3.

Compound 669: (2S)-2-(quinazolin-4-ylamino)-4-((4-(5,6,7,8-tetrahydro-1,8-naphthyridin-2-yl) butyl) ((tetrahydrofuran-2-yl) methyl)amino) butanoic acid.

Compound 670: (S)-2-((6-(1H-pyrazol-1-yl) pyrimidin-4-yl) amino)-4-((3-fluoropropyl) (4-(5,6,7,8-tetrahydro-1,8-naphthyridin-2-yl) butyl)amino) butanoic acid: To a mixture of (S)-2-amino-4-((3-fluoropropyl) (4-(5,6,7,8-tetrahydro-1,8-naphthyridin-2-yl) butyl)amino) butanoic acid (140 mg, 344 µmol) in DMA (3 mL) was added 4-chloro-6-(1H-pyrazol-1-yl) pyrimidine (68 mg, 378 µmol) and DIPEA (299 µL, 1.72 mmol) and the resulting mixture was stirred at 70° C. for 16 h and then allowed to cool to rt and then adjusted to pH=6 by the addition of 1 M aq. HCl and concentrated in vacuo. The crude residue was purified by reverse phase prep-HPLC to give the title compound. LCMS (ESI+): m/z=511.3 (M+H)+. 1H NMR (400 MHz, Methanol-d4) δ ppm 8.53 (d, J=2.57 Hz, 1H) 8.34 (s, 1H) 7.78 (d, J=1.10 Hz, 1H) 7.20 (d, J=7.34 Hz, 1H) 7.00 (br s, 1H) 6.54 (dd, J=1.71, 2.69 Hz, 1H) 6.42 (d, J=7.34 Hz, 1H) 4.90 (br s, 1H) 4.58 (t, J=5.07 Hz, 1H) 4.43-4.49 (m, 1H) 3.35-3.41 (m, 2H) 2.80-3.19 (m, 6H) 2.59-2.72 (m, 4H) 1.94-2.31 (m, 4H) 1.86 (q, J=5.90 Hz, 2H) 1.63-1.79 (m, 4H).

Compound 671: (S)-4-((3,3-difluoropropyl) (4-(5,6,7,8-tetrahydro-1,8-naphthyridin-2-yl) butyl)amino)-2-((2-(pyridin-3-yl) quinazolin-4-yl) amino) butanoic acid: To a solution of (S)-2-amino-4-((3-fluoropropyl) (4-(5,6,7,8-tetrahydro-1,8-naphthyridin-2-yl) butyl)amino) butanoic acid (140 mg, 344 µmol) in DMA (3 mL) was added 4-chloro-2-(pyridin-3-yl) quinazoline (102 mg, 378 µmol, and DIPEA (299 µL, 1.72 mmol) and the resulting mixture was stirred at 70° C. for 16 h and then concentrated in vacuo. The crude residue was purified by reverse phase prep-HPLC to give the title compound. LCMS (ESI+): m/z=572.3 (M+H)+. 1H NMR (400 MHz, Methanol-d4) δ ppm 9.57 (dd, J=0.73, 2.08 Hz, 1H) 8.84 (td, J=1.86, 8.01 Hz, 1H) 8.63 (dd, J=1.59, 4.89 Hz, 1H) 8.14 (d, J=7.70 Hz, 1H) 7.77-7.90 (m, 2H) 7.48-7.59 (m, 2H) 7.16 (d, J=7.34 Hz, 1H) 6.36 (d, J=7.34 Hz, 1H) 4.90-4.93 (m, 1H) 4.39-4.60 (m, 2H) 3.23-3.32 (m, 3H) 2.89-3.19 (m, 5H) 2.55-2.66 (m, 4H) 2.41-2.52 (m, 1H) 2.27-2.39 (m, 1H) 1.95-2.15 (m, 2H) 1.71-1.85 (m, 6H).

Compound 672: (R)-2-((6-(dimethylamino)pyrimidin-4-yl) amino)-4-(((R)-2-methoxypropyl) (4-(5,6,7,8-tetrahydro-1,8-naphthyridin-2-yl) butyl)amino) butanoic acid. From chiral SFC separation of example 213. LCMS (ESI+): m/z=500.3 (M+H)+. 1H NMR (400 MHz, Methanol-d4) δ ppm 7.98 (s, 1H) 7.19 (d, J=7.28 Hz, 1H) 6.40 (d, J=7.28 Hz, 1H) 5.60 (s, 1H) 4.22 (br s, 1H) 3.75 (br d, J=6.62 Hz, 1H) 3.35-3.40 (m, 2H) 3.33 (s, 3H) 3.23-3.30 (m, 1H) 3.07-3.16 (m, 3H) 3.03 (s, 6H) 2.93-3.01 (m, 2H) 2.70 (t, J=6.17 Hz, 2H) 2.54-2.62 (m, 2H) 2.22-2.34 (m, 1H) 2.01 (br dd, J=14.33, 5.07 Hz, 1H) 1.87 (q, J=5.84 Hz, 2H) 1.72 (br s, 4H) 1.19 (d, J=5.95 Hz, 3H).

Compound 673: (S)-2-((6-(tert-butyl)pyrimidin-4-yl) amino)-4-(((R)-2-methoxypropyl) (4-(5,6,7,8-tetrahydro-1,8-naphthyridin-2-yl) butyl)amino) butanoic acid. From chiral SFC separation of Example 210. LCMS (ESI+): m/z=513.3 (M+H)+. 1H NMR (400 MHz, Methanol-d4) δ ppm 8.34 (s, 1H) 7.21 (d, J=7.28 Hz, 1H) 6.61 (s, 1H) 6.41 (d, J=7.28 Hz, 1H) 4.41 (br s, 1H) 3.75 (br s, 1H) 3.36-3.40 (m, 2H) 3.33 (s, 3H) 3.29-3.30 (m, 1H) 2.90-3.19 (m, 5H) 2.70 (t, J=6.17 Hz, 2H) 2.55-2.63 (m, 2H) 2.22-2.35 (m, 1H) 2.06 (br dd, J=14.77, 5.51 Hz, 1H) 1.87 (q, J=5.95 Hz, 2H) 1.73 (br s, 4H) 1.27 (s, 9H) 1.19 (d, J=5.95 Hz, 3H).

Compound 674: (R)-4-(((R)-2-methoxypropyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid. From chiral SFC separation of Example 209. LCMS (ESI+): m/z=510.3 (M+H)+. 1H NMR (400 MHz, Methanol-d4) δ ppm 8.19 (s, 1H) 7.53 (d, J=7.06 Hz, 1H) 7.12 (d, J=3.53 Hz, 1H) 6.63 (d, J=3.31 Hz, 1H) 6.58 (d, J=7.28 Hz, 1H) 4.74 (br d, J=6.39 Hz, 1H) 3.90 (br s, 1H) 3.79 (s, 3H) 3.54-3.67 (m, 1H) 3.47 (t, J=5.51 Hz, 2H) 3.38 (br s, 1H) 3.37 (s, 3H) 3.35 (s, 1H) 3.27 (br d, J=10.58 Hz, 1H) 3.02-3.22 (m, 2H) 2.69-2.85 (m, 4H) 2.54 (br s, 1H) 2.18 (br d, J=18.74 Hz, 1H) 2.04 (s, 1H) 1.85-1.97 (m, 4H) 1.78 (br s, 1H) 1.25 (d, J=5.95 Hz, 3H).

Scheme 47, Compound 675

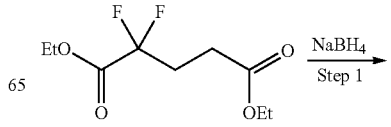

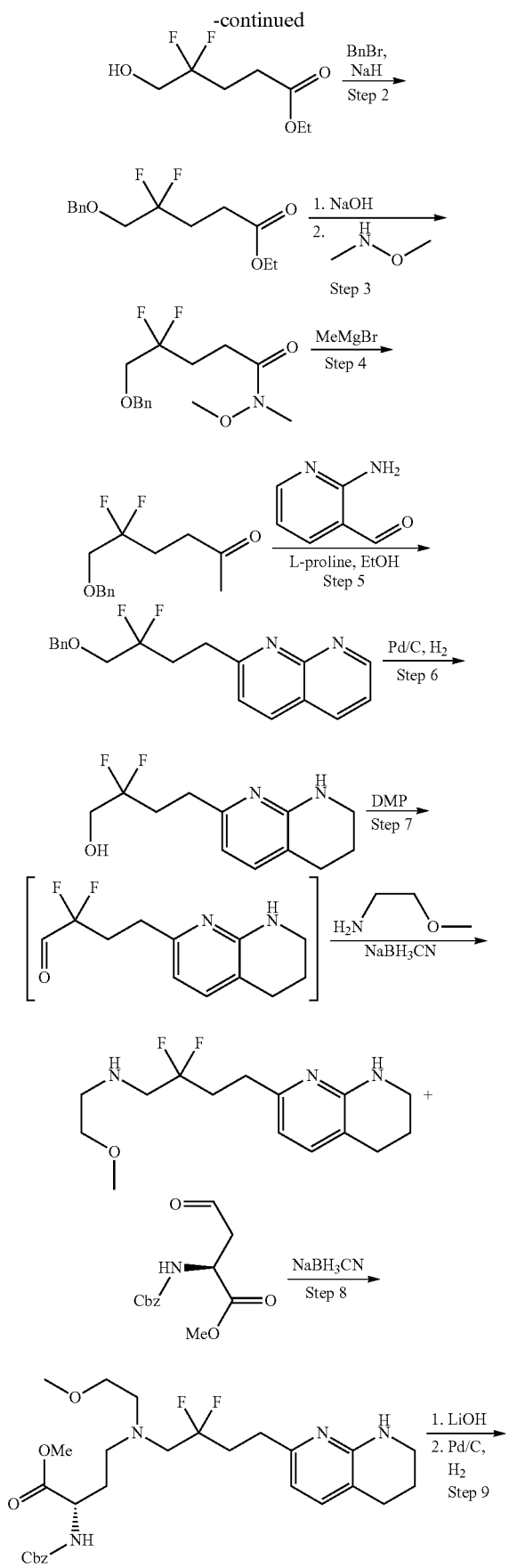

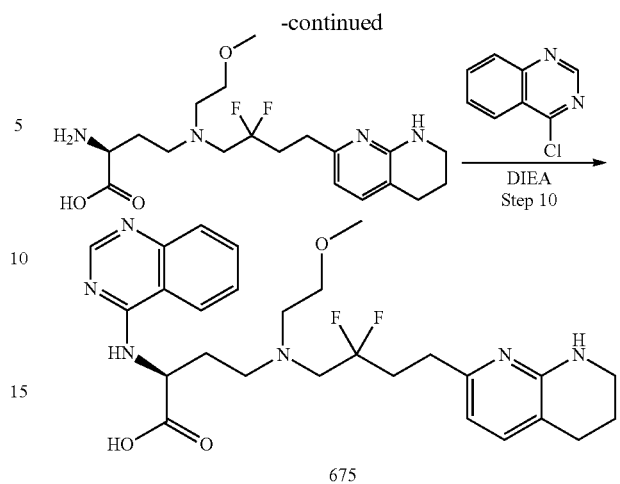

Step 1: ethyl 4,4-difluoro-5-hydroxypentanoate

At 0° C., to a solution of diethyl 2,2-difluoropentanedioate (1 g, 4.46 mmol) in THF/methanol (6/4 mL) was added sodium borohydride (253 mg, 6.7 mmol) portionwise. After addition, the mixture was allowed to stir at 0° C. for 30 min; then warmed up to rt and stirred 1 h. The reaction was quenched by addition of NH$_4$Cl solution; extracted with ethyl acetate (50 mL×2). The combined organic phase was washed with brine; dried with anhydrous Na$_2$SO$_4$, filtered and concentrated in vacuum. The residue was purified by column chromatography to give ethyl 4,4-difluoro-5-hydroxypentanoate (800 mg). LCMS (ESI+): m/z=182.08; [M+H]$^+$ found 183.4.

Step 2: ethyl 5-(benzyloxy)-4,4-difluoropentanoate

At 0° C., to a THF solution of ethyl 4,4-difluoro-5-hydroxypentanoate (800 mg, 4.4 mmol) was added NaH (60% dispersion in mineral oil, 264 mg, 6.6 mmol) and stirred for 10 min. Benzyl bromide (6.6 mmol, 784 µL) was added; slowly warmed up to rt and stirred for 1 h. The reaction was quenched by addition of NH$_4$Cl solution; extracted with ethyl acetate (30 mL×2). The combined organic phase was washed with brine; dried with anhydrous Na$_2$SO$_4$, filtered and concentrated in vacuum. The residue was purified by column chromatography to give ethyl 5-(benzyloxy)-4,4-difluoropentanoate (1.17 g, 97% yield).

Step 3: 5-(benzyloxy)-4,4-difluoro-N-methoxy-N-methylpentanamide

To a solution of ethyl 5-(benzyloxy)-4,4-difluoropentanoate (1.17 g, 4.3 mmol) in methanol was added NaOH solution (2 M, 4.3 mL) at RT. The reaction mixture was stirred for 2 h. It was acidified with 1 N HCl solution and extracted with DCM (20 mL×3). The combined organic phase was dried with anhydrous Na$_2$SO$_4$, filtered and concentrated in vacuum. The crude product was used directly for the next step without further purification.

To a mixture of 5-(benzyloxy)-4,4-difluoropentanoic acid (720 mg, 2.95 mmol) in THF (10 mL) was added HATU (1.35 g, 3.53 mmol), DIEA (1.29 mL, 7.37 mmol), and N,O-dimethylhydroxylamine hydrochloride (346 mg, 3.53 mmol), The reaction mixture was stirred at RT for 5 h. H$_2$O (10 mL) was added to the mixture; it was extracted with DCM (20 mL×2). The combined organic phase was dried with anhydrous Na$_2$SO$_4$, filtered and concentrated in vacuum. The residue was purified by column chromatography to give 5-(benzyloxy)-4,4-difluoro-N-methoxy-N-methylpentanamide (300 mg). LCMS (ESI+): m/z=287.13; [M+H]$^+$ found 288.10.

Step 4: 6-(benzyloxy)-5,5-difluorohexan-2-one

At 0° C., to a THF solution of 5-(benzyloxy)-4,4-difluoro-N-methoxy-N-methylpentanamide (300 mg, 1.0 mmol) was added methylmagnesium bromide in THF solution (3 M, 0.7 mL, 2 mmol). It was allowed to stir at 0° C. for 30 min. The reaction was quenched by addition of NH$_4$Cl solution; extracted with ethyl acetate (30 mL×2). The combined organic phase was washed with brine; dried with anhydrous Na$_2$SO$_4$, filtered and concentrated in vacuum. The residue was purified by column chromatography to give 6-(benzyloxy)-5,5-difluorohexan-2-one (200 mg).

Step 5: 2-(4-(benzyloxy)-3,3-difluorobutyl)-1,8-naphthyridine

To a mixture of 6-(benzyloxy)-5,5-difluorohexan-2-one (200 mg, 0.82 mmol) and 2-aminopyridine-3-carbaldehyde (131 mg, 1.07 mmol) in EtOH (10 mL) was added L-proline (48 mg, 0.41 mmol). The mixture was refluxed at 85° C. for 12 hs. LCMS indicated the reaction was completed. The mixture was concentrated under reduced pressure. The crude product was purified by column chromatography (Hexanes/Ethyl acetate=1/1 to 1:3) to give 2-(4-(benzyloxy)-3,3-difluorobutyl)-1,8-naphthyridine (160 mg, 59% yield) as a yellow solid. LCMS (ESI+): m/z=328.14; [M+H]$^+$ found 329.18.

Step 6: 2,2-difluoro-4-(5,6,7,8-tetrahydro-1,8-naphthyridin-2-yl) butan-1-ol A flask containing 2-(4-(benzyloxy)-3,3-difluorobutyl)-1,8-naphthyridine (160 mg, 0.49 mmol) was charged with Pd(OH)$_2$ (20 wt % on carbon, 15 mg) and then diluted with MeOH (3 mL). The flask was evacuated and backfilled with H$_2$ for 3 cycles and then stirred under an H$_2$ atmosphere for 15 h. The mixture was filtered through a pad of CELITE® and concentrated in vacuo to give 2,2-difluoro-4-(5,6,7,8-tetrahydro-1,8-naphthyridin-2-yl) butan-1-ol which was used without further purification. LCMS (ESI+): m/z=242.12; [M+H]$^+$ found 243.024.

Step 7: 2,2-difluoro-4-(5,6,7,8-tetrahydro-1,8-naphthyridin-2-yl) butanal

To a solution of 2,2-difluoro-4-(5,6,7,8-tetrahydro-1,8-naphthyridin-2-yl) butan-1-ol (35 mg, 145 µmol) in CH$_2$Cl$_2$ (2 mL) at room temperature was added Dess-Martin periodinane (64 g, 152 µmol) and the resulting mixture was stirred for an additional 2 h at room temperature. Then 2-methoxyethan-1-amine (17 mg, 219 µmol) was added followed by sodium triacetoxyborohydride (77 mg, 364 µmol). The reaction mixture was stirred at RT for 15 h. The reaction mixture was concentrated and purified by reverse phase chromatography to provide 2,2-difluoro-N-(2-methoxyethyl)-4-(5,6,7,8-tetrahydro-1,8-naphthyridin-2-yl) butan-1-amine. LCMS (ESI+): m/z=299.18; [M+H]$^+$ found 300.833.

Step 8: methyl (S)-2-(((benzyloxy)carbonyl)amino)-4-((2,2-difluoro-4-(5,6,7,8-tetrahydro-1,8-naphthyridin-2-yl) butyl) (2-methoxyethyl)amino) butanoate The reaction solution of 2,2-difluoro-N-(2-methoxyethyl)-4-(5,6,7,8-tetrahydro-1,8-naphthyridin-2-yl) butan-1-amine (15 mg, 50 µmol), methyl (S)-2-(((benzyloxy)carbonyl)amino)-4-oxobutanoate (4 mg, 60 µmol), and sodium cyanoborohydride (4 mg, 60 µmol) in DCM/MeOH (1/0.5 mL) was stirred at room temperature for 12 h. The reaction mixture was concentrated and purified by reverse phase chromatography to provide methyl (S)-2-(((benzyloxy)carbonyl)amino)-4-((2,2-difluoro-4-(5,6,7,8-tetrahydro-1,8-naphthyridin-2-yl) butyl) (2-methoxyethyl)amino) butanoate. LCMS (ESI+): m/z=548.28; [M+H]$^+$ found 549.337.

Step 9: (S)-2-amino-4-((2,2-difluoro-4-(5,6,7,8-tetrahydro-1,8-naphthyridin-2-yl) butyl) (2-methoxyethyl)amino) butanoic acid To a solution of methyl (S)-2-(((benzyloxy)carbonyl)amino)-4-((2,2-difluoro-4-(5,6,7,8-tetrahydro-1,8-naphthyridin-2-yl) butyl) (2-methoxyethyl)amino) butanoate (20 mg, 36 µmol) in 4:1:1 THF/MeOH/H$_2$O (1.0 mL) was added LiOH (3 mg, 109 µmol) and the resulting mixture was stirred at room temperature for 2 h. The mixture was then neutralized with AcOH and purified by preparative reverse phase HPLC to give (S)-2-(((benzyloxy)carbonyl)amino)-4-((2,2-difluoro-4-(5,6,7,8-tetrahydro-1,8-naphthyridin-2-yl) butyl) (2-methoxyethyl)amino) butanoic acid. LCMS (ESI+): m/z=534.27; [M+H]$^+$ found 535.184.

A flask containing (S)-2-(((benzyloxy)carbonyl)amino)-4-((2,2-difluoro-4-(5,6,7,8-tetrahydro-1,8-naphthyridin-2-yl) butyl) (2-methoxyethyl)amino) butanoic acid (14 mg, 26 µmol) in MeOH (1 mL) was charged with Pd(OH)$_2$ (20 wt % on carbon, 1 mg). The flask was evacuated and backfilled with H$_2$ for 3 cycles and then stirred under an H$_2$ atmosphere for 12 h. The mixture was filtered through a pad of CELITE® and concentrated in vacuo to give (S)-2-amino-4-((2,2-difluoro-4-(5,6,7,8-tetrahydro-1,8-naphthyridin-2-yl) butyl) (2-methoxyethyl)amino) butanoic acid. LCMS (ESI+): m/z=400.23; [M+H]$^+$ found 401.067.

Step 10: (S)-4-((2,2-difluoro-4-(5,6,7,8-tetrahydro-1,8-naphthyridin-2-yl) butyl) (2-methoxyethyl) amino)-2-(quinazolin-4-ylamino) butanoic acid A mixture of 4-chloroquinazoline (8 mg, 49 µmol), (S)-2-amino-4-((2,2-difluoro-4-(5,6,7,8-tetrahydro-1,8-naphthyridin-2-yl) butyl) (2-methoxyethyl)amino) butanoic acid (13 mg, 33 µmol), and DIEA (17 µL, 97 µmol) in $^i$PrOH (1 mL) was heated to 85° C. for 15 h. The mixture was then neutralized with AcOH and purified by preparative reverse phase HPLC to give (S)-4-((2,2-difluoro-4-(5,6,7,8-tetrahydro-1,8-naphthyridin-2-yl) butyl) (2-methoxyethyl)amino)-2-(quinazolin-4-ylamino) butanoic acid. LCMS (ESI+): m/z=528.27; [M+H]$^+$ found 529.415. $^1$H NMR (500 MHz, Methanol-d$_4$) δ 8.83 (s, 1H), 8.52 (d, J=8.4 Hz, 1H), 8.12 (t, J=7.8 Hz, 1H), 7.85 (t, J=8.0 Hz, 2H), 7.57 (d, J=7.3 Hz, 1H), 6.61 (d, J=7.4 Hz, 1H), 5.32 (dd, J=7.8, 5.0 Hz, 1H), 3.72-3.43 (m, 5H), 3.28-2.94 (m, 9H), 2.93-2.67 (m, 4H), 2.63-2.10 (m, 3H), 2.04-1.79 (m, 2H).

Compound 676: (S)-2-((2-methyl-2H-pyrazolo[4,3-d]pyrimidin-7-yl) amino)-4-((2-phenoxyethyl) (4-(5,6,7,8-tetrahydro-1,8-naphthyridin-2-yl) butyl)amino) butanoic acid: To a mixture of (S)-2-amino-4-((2-phenoxyethyl) (4-(5,6,7,8-tetrahydro-1,8-naphthyridin-2-yl) butyl)amino) butanoic acid (100 mg, 234 μmol) in 4:1 THF/H₂O (2 mL) was added 7-chloro-2-methyl-2H-pyrazolo[4,3-d]pyrimidine (43 mg, 258 μmol) and NaHCO₃ (59 mg, 703 μmol) and the resulting mixture was heated to 70° C. for 1 h and then cooled to rt and concentrated in vacuo. The crude residue was purified by prep-HPLC to give the title compound. LCMS (ESI+): m/z=559.3 (M+H)⁺. ¹H NMR (400 MHz, Methanol-d₄) δ ppm 8.28-8.65 (m, 2H) 7.57 (d, J=7.34 Hz, 1H) 7.26 (br t, J=7.95 Hz, 2H) 6.87-7.09 (m, 3H) 6.65 (d, J=7.34 Hz, 1H) 5.11 (br dd, J=8.50, 5.07 Hz, 1H) 4.41 (br d, J=4.52 Hz, 2H) 4.07 (s, 3H) 3.37-3.86 (m, 8H) 2.48-3.00 (m, 6H) 1.69-2.17 (m, 6H).

MeOH (4 mL) was added 10 wt % Pd/C (80 mg) and the resulting mixture was stirred under an H₂ atmosphere for 12 h and then filtered and concentrated in vacuo. The crude residue was purified by reverse phase prep-HPLC to give the title compound. LCMS (ESI+): m/z=448.2 (M+H)⁺. ¹H NMR (400 MHz, Methanol-d₄) δ ppm 7.89 (dd, J=5.14, 1.10 Hz, 1H) 7.55-7.60 (m, 1H) 7.40 (ddd, J=8.62, 6.97, 1.90 Hz, 1H) 7.30 (d, J=7.34 Hz, 1H) 6.50-6.57 (m, 1H) 6.46 (dd, J=10.51, 7.95 Hz, 2H) 5.68-6.08 (m, 1H) 4.25 (dd, J=7.09, 4.89 Hz, 1H) 3.33-3.39 (m, 2H) 2.50-2.84 (m, 10H) 2.03-2.14 (m, 1H) 1.92-2.03 (m, 1H) 1.81-1.91 (m, 2H) 1.68-1.80 (m, 2H) 1.58-1.59 ((m, 1H) 1.48-1.59 ((m, 1H).

Scheme 48, Compound 677

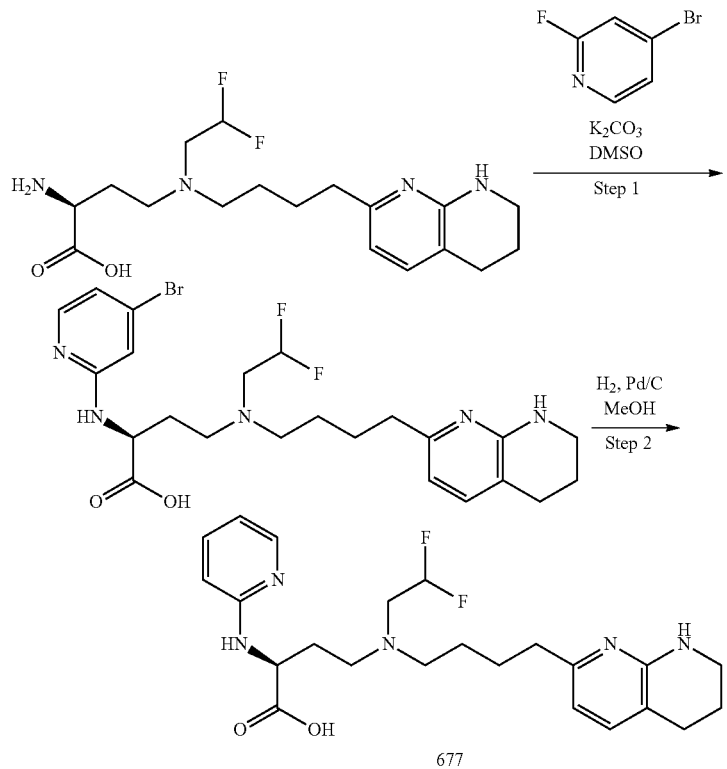

677

Step 1: (S)-2-((4-bromopyridin-2-yl) amino)-4-((2,2-difluoroethyl) (4-(5,6,7,8-tetrahydro-1,8-naphthyridin-2-yl) butyl)amino) butanoic acid To a mixture of (S)-2-amino-4-((2,2-difluoroethyl) (4-(5,6,7,8-tetrahydro-1,8-naphthyridin-2-yl) butyl)amino) butanoic acid (200 mg, 540 μmol) and 4-bromo-2-fluoropyridine (105 mg, 594 μmol) in DMSO (4 mL) was added K₂CO₃ (373 mg, 2.70 mmol) and the mixture was stirred at 100° C. for 2 h and then cooled to rt and concentrated in vacuo to give the title compound that was used without further purification. LCMS (ESI+): m/z=526.2 (M+H)⁺.

Step 2: (S)-4-((2,2-difluoroethyl) (4-(5,6,7,8-tetrahydro-1,8-naphthyridin-2-yl) butyl)amino)-2-(pyridin-2-ylamino) butanoic acid To a mixture of (S)-2-((4-bromopyridin-2-yl) amino)-4-((2,2-difluoroethyl) (4-(5,6,7,8-tetrahydro-1,8-naphthyridin-2-yl) butyl)amino) butanoic acid (200 mg, 380 μmol) in Compound 678: (S)-4-((2-(dimethylamino)-2-oxoethyl) (4-(5,6,7,8-tetrahydro-1,8-naphthyridin-2-yl)butyl)amino)-2-((2-methyl-2H-pyrazolo[4,3-d]pyrimidin-7-yl)amino)butanoic acid: To a mixture of (S)-2-amino-4-((2-(dimethylamino)-2-oxoethyl)(4-(5,6,7,8-tetrahydro-1,8-naphthyridin-2-yl)butyl)amino)butanoic acid (103 mg, 264 umol) and 7-chloro-2-methyl-2H-pyrazolo[4,3-d]pyrimidine (49 mg, 291 umol) in THF (2 mL) was added NaHCO₃ (111 mg, 1.32 mmol) and the resulting mixture was heated to 70° C. for 1 hr and then cooled to rt and concentrated in vacuo. The crude residue was purified by prep-HPLC to give the title compound. LCMS (ESI+): m/z=524.3.

Compound 679: (S)-4-(((R)-2-methoxypropyl) (4-(5,6,7,8-tetrahydro-1,8-naphthyridin-2-yl) butyl)amino)-2-((2-methyl-2H-pyrazolo[4,3-d]pyrimidin-7-yl) amino) butanoic acid: To a mixture of (S)-2-amino-4-(((R)-2-methoxypropyl) (4-(5,6,7,8-tetrahydro-1,8-naphthyridin-2-yl) butyl) amino) butanoic acid hydrochloride (100 mg, 231 μmol) and 7-chloro-2-methyl-2H-pyrazolo[4,3-d]pyrimidine (43 mg, 254 μmol) in THF (2 mL) and H₂O (0.5 mL) was added NaHCO$_3$ (97 mg, 1.15 mmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=529.2 (M+H)$^+$. $^1$H NMR (400 MHz, Methanol-d$_4$) δ ppm 8.63 (br s, 1H) 8.50 (s, 1H) 7.59 (d, J=7.34 Hz, 1H) 6.67 (d, J=7.34 Hz, 1H) 5.15-5.35 (m, 1H) 5.08 (br dd, J=8.38, 5.32 Hz, 1H) 4.10 (s, 3H) 3.54-3.75 (m, 6H) 3.49-3.53 (m, 2H) 3.41 (s, 5H) 2.77-2.85 (m, 4H) 2.53-2.74 (m, 2H) 1.79-1.99 (m, 6H).

Compound 680: (S)-4-((2-fluoro-3-hydroxy-2-(hydroxymethyl)propyl) (4-(5,6,7,8-tetrahydro-1,8-naphthyridin-2-yl) butyl)amino)-2-(quinazolin-4-ylamino) butanoic acid. A solution of (S)-4-(((3-fluorooxetan-3-yl) methyl) (4-(5,6,7,8-tetrahydro-1,8-naphthyridin-2-yl) butyl)amino)-2-(quinazolin-4-ylamino) butanoic acid (5 mg) in water (1 mL) was added sulfuric acid (0.1 mL). The reaction mixture was stirred at 80° C. for 6 h. The crude product was purified by reverse phase chromatography to provide (S)-4-((2-fluoro-3-hydroxy-2-(hydroxymethyl)propyl) (4-(5,6,7,8-tetrahydro-1,8-naphthyridin-2-yl) butyl)amino)-2-(quinazolin-4-ylamino) butanoic acid as a TFA salt. LCMS theoretical m/z=541.3; [M+H]$^+$ found 541.24. $^1$H NMR (500 MHz, Methanol-d$_4$) δ 8.84 (s, 1H), 8.50 (d, J=8.3 Hz, 1H), 8.13 (ddd, J=8.4, 7.2, 1.2 Hz, 1H), 7.93-7.80 (m, 2H), 7.58 (d, J=7.4 Hz, 1H), 6.62 (d, J=7.3 Hz, 1H), 5.40-5.23 (m, 1H), 3.92-3.63 (m, 6H), 3.63-3.41 (m, 3H), 2.95-2.62 (m, 8H), 2.41 (s, 1H), 2.06-1.66 (m, 9H).

Compound 681: (S)-4-((3-hydroxypropyl) (4-(5,6,7,8-tetrahydro-1,8-naphthyridin-2-yl) butyl)amino)-2-(quinazolin-4-ylamino) butanoic acid. Prepared according to Scheme A using Procedure A with 3-aminopropan-1-ol, Procedure H with 4-chloroquinazoline, and Procedure P. LCMS theoretical m/z=493.3. [M+H]+, found 493.2.

Scheme 49, Compound 682

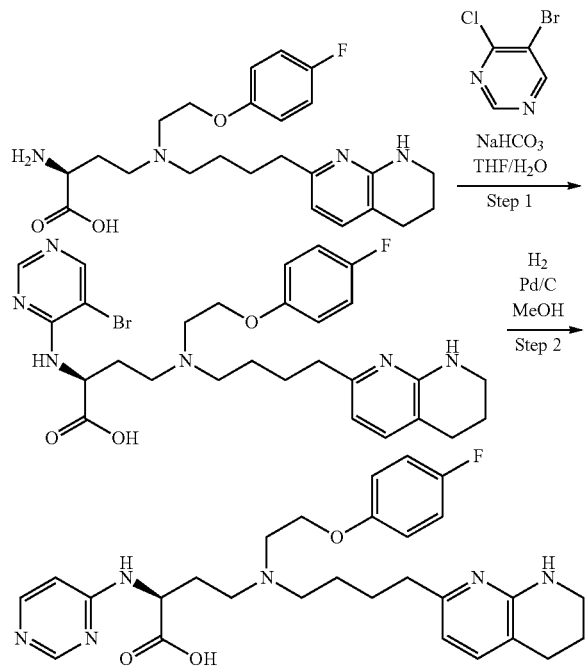

682

Step 1: (S)-2-((5-bromopyrimidin-4-yl) amino)-4-((2-(4-fluorophenoxy)ethyl) (4-(5,6,7,8-tetrahydro-1,8-naphthyridin-2-yl) butyl)amino) butanoic acid To a mixture of (S)-2-amino-4-((2-(4-fluorophenoxy)ethyl) (4-(5,6,7,8-tetrahydro-1,8-naphthyridin-2-yl) butyl) amino) butanoic acid hydrochloride (150 mg, 312 μmol) in 4:1 THF/H$_2$O (3 mL) was added 5-bromo-4-chloropyrimidine (66 mg, 343 μmol) and NaHCO$_3$ (79 mg, 936 μmol) and the resulting mixture was heated to 70° C. for 2 h and then cooled to rt and concentrated in vacuo to give the title compound that was used without further purification. LCMS (ESI+): m/z=614.9 (M+H)$^+$.

Step 2: (S)-4-((2-(4-fluorophenoxy)ethyl) (4-(5,6,7,8-tetrahydro-1,8-naphthyridin-2-yl) butyl)amino)-2-(pyrimidin-4-ylamino) butanoic acid To a mixture of (S)-2-((5-bromopyrimidin-4-yl) amino)-4-((2-(4-fluorophenoxy)ethyl) (4-(5,6,7,8-tetrahydro-1,8-naphthyridin-2-yl) butyl)amino) butanoic acid (188 mg, 312 μmol) in MeOH (20 mL) was added 10 wt % Pd/C (200 mg) and the resulting mixture was stirred under an H$_2$ atmosphere for 12 h and then filtered and concentrated in vacuo. The crude residue was purified by reverse phase prep-HPLC column to give the title compound. LCMS (ESI+): m/z=523.2 (M+H)$^+$. $^1$H NMR (400 MHz, Methanol-d$_4$) δ ppm 8.30 (s, 1H) 7.90 (br s, 1H) 7.29 (d, J=7.02 Hz, 1H) 6.90-7.01 (m, 2H) 6.81-6.89 (m, 2H) 6.46 (d, J=7.45 Hz, 2H) 4.49 (br s, 1H) 4.15 (t, J=5.26 Hz, 2H) 3.34-3.41 (m, 2H) 2.82-3.30 (m, 6H) 2.59-2.80 (m, 4H) 2.24 (br d, J=5.26 Hz, 1H) 2.00-2.12 (m, 1H) 1.66-1.96 (m, 6H).

Compound 683: (R)-4-(((R)-2-methoxypropyl) (4-(5,6,7,8-tetrahydro-1,8-naphthyridin-2-yl) butyl)amino)-2-((6-phenylpyrazin-2-yl) amino) butanoic acid. From chiral SFC separation of example 224. LCMS (ESI+): m/z=533.3 (M+H)$^+$. $^1$H NMR (400 MHz, DMSO-d$_6$) δ ppm 14.42 (br s, 1H) 9.87-10.12 (m, 1H) 8.40 (s, 1H) 8.15 (br s, 1H) 8.01-8.10 (m, 3H) 7.91 (br s, 1H) 7.60 (br d, J=6.84 Hz, 1H) 7.40-7.53 (m, 3H) 6.57-6.65 (m, 1H) 4.53 (br s, 1H) 3.84 (br s, 1H) 3.42 (br s, 2H) 3.28 (br s, 2H) 3.25 (d, J=3.09 Hz, 3H) 3.17 (br s, 4H) 2.71 (br d, J=6.39 Hz, 4H) 2.15-2.41 (m, 2H) 1.64-1.86 (m, 6H) 1.09 (br dd, J=8.27, 6.28 Hz, 3H).

Compound 684: (S)-4-((2-(2-oxopyrrolidin-1-yl) ethyl) (4-(5,6,7,8-tetrahydro-1,8-naphthyridin-2-yl) butyl)amino)-2-(quinazolin-4-ylamino) butanoic acid. Prepared according to Scheme B using Procedure F with 1-(2-aminoethyl)pyrrolidin-2-one, Procedure H with 4-chloroquinazoline, and Procedure P. LCMS theoretical m/z=546.3. [M+H]+, found 546.3.

Compound 685: (S)-2-((3-cyanopyrazin-2-yl) amino)-4-(cyclopropyl(4-(5,6,7,8-tetrahydro-1,8-naphthyridin-2-yl) butyl)amino) butanoic acid: To a mixture of (2S)-2-amino-4-[cyclopropyl-[4-(5,6,7,8-tetrahydro-1,8-naphthyridin-2-yl) butyl]amino]butanoic acid (150 mg, 433 μmol) in i-PrOH (3 mL) was added 3-chloropyrazine-2-carbonitrile (66 mg, 476 μmol) and DIPEA (377 μL, 2.16 mmol) and the resulting mixture was heated to 70° C. for 1 h, cooled to rt, and then concentrated in vacuo. The crude residue was purified by prep-HPLC to give the title compound. LCMS (ESI+): m/z=450.2 (M+H)$^+$. $^1$H NMR (400 MHz, Methanol-d$_4$): δ ppm 8.24 (d, J=2.43 Hz, 1H) 7.85 (d, J=2.43 Hz, 1H) 7.35 (d, J=7.28 Hz, 1H) 6.48 (d, J=7.50 Hz, 1H) 6.39 (d, J=7.06 Hz, 1H) 4.50 (t, J=5.29 Hz, 1H) 3.33-3.46 (m, 2H) 3.00-3.17 (m, 1H) 2.53-2.95 (m, 7H) 2.29-2.42 (m, 1H) 2.15 (dq, J=14.72, 5.02 Hz, 1H) 1.58-2.00 (m, 7H) 0.54-0.79 (m, 4H).

Compound 686: (S)-2-((3-cyanopyrazin-2-yl) amino)-4-((2-(4-fluorophenoxy)ethyl) (4-(5,6,7,8-tetrahydro-1,8-naphthyridin-2-yl) butyl)amino) butanoic acid: To a mixture of (S)-2-amino-4-((2-(4-fluorophenoxy)ethyl) (4-(5,6,7,8-tetrahydro-1,8-naphthyridin-2-yl) butyl)amino) butanoic acid hydrochloride (150 mg, 337 µmol) in i-PrOH (3 mL) was added 3-chloropyrazine-2-carbonitrile (52 mg, 371 µmol) and DIPEA (294 µL, 1.69 mmol) and the resulting mixture was heated to 70° C. for 1 h, cooled to rt, and then concentrated in vacuo. The crude residue was purified by prep-HPLC to give the title compound. LCMS (ESI+): m/z=548.2 (M+H)+. ¹H NMR (400 MHz, Methanol-d₄) δ ppm 8.18 (d, J=2.43 Hz, 1H) 7.81 (d, J=2.43 Hz, 1H) 7.31 (d, J=7.28 Hz, 1H) 6.78-7.01 (m, 4H) 6.46 (d, J=7.28 Hz, 1H) 4.52 (t, J=5.51 Hz, 1H) 4.09-4.32 (m, 2H) 3.33-3.44 (m, 2H) 2.76-3.29 (m, 6H) 2.52-2.74 (m, 4H) 2.23-2.42 (m, 1H) 2.15 (dq, J=14.75, 4.86 Hz, 1H) 1.67-1.91 (m, 6H).

thiazole (47 mg, 279 µmol) in t-AmOH (3 mL) was added 2.0M t-BuONa in THF (279 µL, 558 µmol) then t-BuXphos Pd G3 (22 mg, 28 µmol) and the resulting mixture was heated to 100° C. for 15 h, cooled to rt, and then concentrated in vacuo to give the title compound that was used without further purification. LCMS (ESI+): m/z=581.4 (M+H)+.

Step 2: (S)-4-((2-acetamidoethyl) (4-(5,6,7,8-tetrahydro-1,8-naphthyridin-2-yl) butyl)amino)-2-(benzo[d]thiazol-2-ylamino) butanoic acid (S)-tert-butyl 4-((2-acetamidoethyl) (4-(5,6,7,8-tetrahydro-1,8-naphthyridin-2-yl) butyl)amino)-2-(benzo[d]thiazol-2-ylamino) butanoate (200 mg, 332 µmol) was taken up in 5:1 DCM/TFA (2 mL) and the resulting mixture was stirred at rt for 5 h and then concentrated in vacuo. The crude

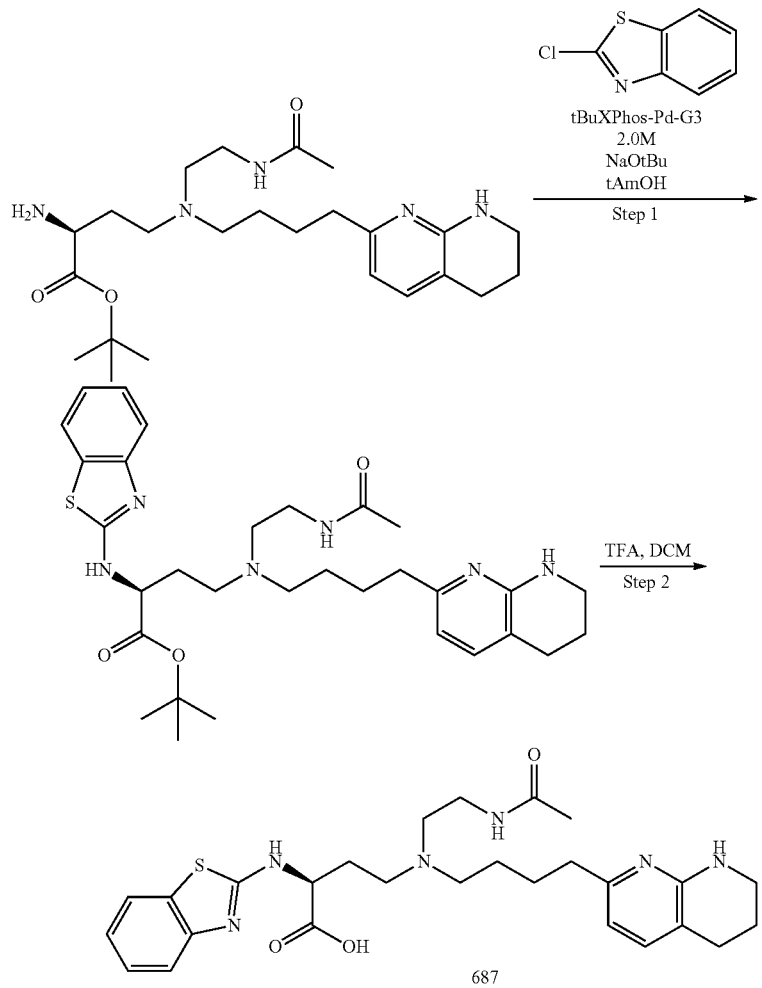

Scheme 50, Compound 687

Step 1: (S)-tert-butyl 4-((2-acetamidoethyl) (4-(5,6,7,8-tetrahydro-1,8-naphthyridin-2-yl) butyl)amino)-2-(benzo[d]thiazol-2-ylamino) butanoate To a mixture of (S)-tert-butyl 4-((2-acetamidoethyl) (4-(5,6,7,8-tetrahydro-1,8-naphthyridin-2-yl) butyl)amino)-2-aminobutanoate (150 mg, 335 µmol) and 2-chlorobenzo[d]

residue was purified by reverse phase prep-HPLC to give the title compound. LCMS (ESI+): m/z=525.2 (M+H)+. ¹H NMR (400 MHz, DMSO-d₆) δ ppm 8.17 (br d, J=5.62 Hz, 1H) 7.75 (br t, J=5.14 Hz, 1H) 7.66 (d, J=7.70 Hz, 1H) 7.36 (d, J=7.95 Hz, 1H) 7.21 (t, J=7.58 Hz, 1H) 6.96-7.08 (m, 2H) 6.72 (br s, 1H) 6.24 (d, J=7.21 Hz, 1H) 4.38 (br d, J=5.14 Hz, 1H) 3.20-3.28 (m, 2H) 3.06-3.18 (m, 2H) 2.51-2.78 (m, 8H)

2.41 (br t, J=7.34 Hz, 2H) 1.86-2.07 (m, 2H) 1.68-1.83 (m, 5H) 1.49-1.61 (m, 2H) 1.35-1.47 (m, 2H).

Compound 688: (S)-2-((1-methyl-1H-pyrazolo[3,4-d]pyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid: To a mixture of (S)-2-amino-4-((4-(5,6,7,8-tetrahydro-1,8-naphthyridin-2-yl) butyl) (2-(2,2,2-trifluoroethoxy)ethyl)amino) butanoic acid (140 mg, 259 μmol) in THF (4 mL) and H$_2$O (1 mL) was added 4-chloro-H-pyrazolo[3,4-d]pyrimidine (44 mg, 259 μmol) and NaHCO$_3$ (109 mg, 1.29 mmol)) and the resulting mixture was heated to 70° C. for 1 h, cooled to rt, and then concentrated in vacuo. The crude residue was purified by prep-HPLC to give the title compound. LCMS (ESI+): m/z=565.2 (M+H)$^+$. $^1$H NMR (400 MHz, DMSO-d$_6$) δ ppm 8.36 (br d, J=7.21 Hz, 1H) 8.23 (s, 1H) 8.18 (s, 1H) 6.99 (d, J=7.34 Hz, 1H) 6.41 (br s, 1H) 6.17 (d, J=7.34 Hz, 1H) 4.73 (br d, J=5.26 Hz, 1H) 3.98 (qd, J=9.41, 1.71 Hz, 2H) 3.89 (s, 3H) 3.63 (br t, J=5.81 Hz, 2H) 3.22 (br t, J=5.20 Hz, 2H) 2.55-2.75 (m, 7H) 2.42-2.48 (m, 1H) 2.34 (br t, J=7.46 Hz, 2H) 1.97-2.10 (m, 1H) 1.87 (br d, J=5.87 Hz, 1H) 1.73 (q, J=5.69 Hz, 2H) 1.46-1.56 (m, 2H) 1.37 (br d, J=7.09 Hz, 2H).

Compound 689: (S)-2-((5-cyclopropylpyrimidin-2-yl) amino)-4-((2-(2,2-difluoroethoxy)ethyl) (4-(5,6,7,8-tetrahydro-1,8-naphthyridin-2-yl) butyl)amino) butanoic acid: To a mixture of (S)-2-amino-4-((2-(2,2-difluoroethoxy) ethyl) (4-(5,6,7,8-tetrahydro-1,8-naphthyridin-2-yl) butyl) amino) butanoic acid (150 mg, 362 μmol) in THF (1 mL) and H$_2$O (0.25 mL) was added NaHCO$_3$ (91 mg, 1.09 mmol) then 5-cyclopropyl-2-fluoropyrimidine (100 mg, 724 μmol) and the resulting mixture was heated to 70° C. for 1 h, cooled to rt, adjusted to pH=6 by the addition of 1 M aq. HCl, and then concentrated in vacuo. The crude residue was purified by prep-HPLC to give the title compound. LCMS (ESI+): m/z=533.3 (M+H)$^+$. $^1$H NMR (400 MHz, Methanol-d$_4$) δ ppm 8.54 (br s, 2H) 7.60 (d, J=7.28 Hz, 1H) 6.66 (d, J=7.50 Hz, 1H) 5.85-6.20 (m, 1H) 4.82-4.87 (m, 1H) 3.93-4.01 (m, 2H) 3.79 (td, J=14.77, 3.53 Hz, 2H) 3.40-3.57 (m, 6H) 3.32-3.40 (m, 2H) 2.76-2.85 (m, 4H) 2.32-2.65 (m, 2H) 1.74-2.03 (m, 7H) 1.04-1.12 (m, 2H) 0.78-0.85 (m, 2H).

Compound 690: (S)-4-((2-(2,2-difluoroethoxy)ethyl) (4-(5,6,7,8-tetrahydro-1,8-naphthyridin-2-yl) butyl)amino)-2-((6-phenylpyrimidin-4-yl) amino) butanoic acid: To a mixture of (S)-2-amino-4-((2-(2,2-difluoroethoxy)ethyl) (4-(5,6,7,8-tetrahydro-1,8-naphthyridin-2-yl) butyl)amino) butanoic acid (150 mg, 362 μmol) in THF (1 mL) and H$_2$O (0.25 mL) was added NaHCO$_3$ (91 mg, 1.09 mol) then 4-chloro-6-phenylpyrimidine (138 mg, 724 μmol) and the resulting mixture was heated to 70° C. for 2 h, cooled to rt, adjusted to pH=6 by the addition of 1 M aq. HCl, and then concentrated in vacuo. The crude residue was purified by reverse phase prep-HPLC to give the title compound. LCMS (ESI+): m/z=569.3 (M+H)$^+$. $^1$H NMR (400 MHz, Methanol-d$_4$) δ ppm 8.81 (s, 1H) 7.87 (d, J=7.50 Hz, 2H) 7.54-7.77 (m, 4H) 7.29 (s, 1H) 6.66 (d, J=7.50 Hz, 1H) 5.86-6.19 (m, 1H) 5.09 (br s, 1H) 3.98 (br s, 2H) 3.79 (td, J=14.72, 3.42 Hz, 2H) 3.41-3.62 (m, 6H) 3.34 (br d, J=7.94 Hz, 2H) 2.75-2.86 (m, 4H) 2.35-2.66 (m, 2H) 1.74-2.00 (m, 6H).

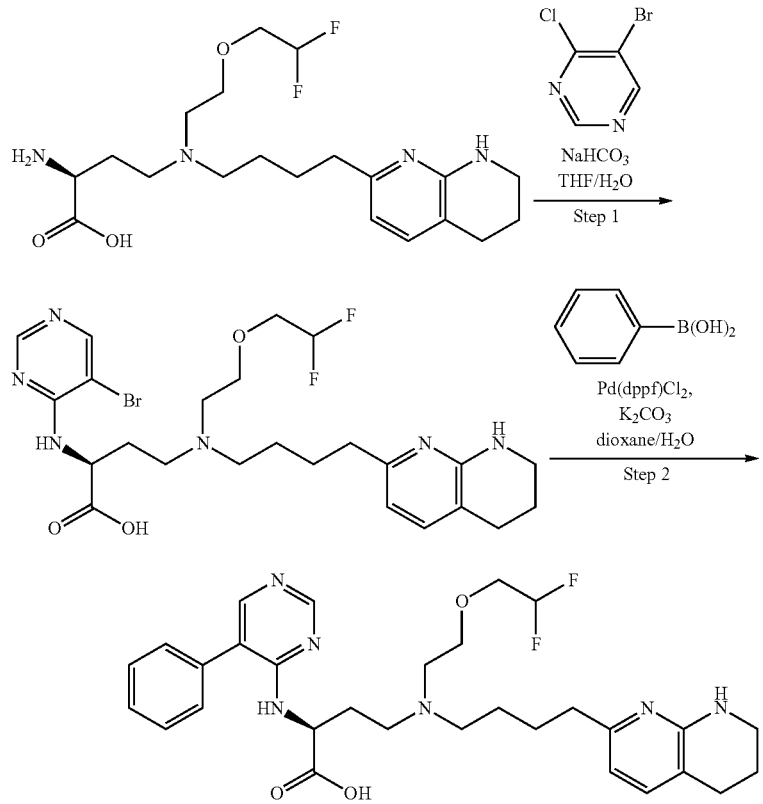

Scheme 51, Compound 691

691

Step 1: (S)-2-((5-bromopyrimidin-4-yl) amino)-4-((2-(2,2-difluoroethoxy)ethyl) (4-(5,6,7,8-tetrahydro-1,8-naphthyridin-2-yl) butyl)amino) butanoic acid To a mixture of 5-bromo-4-chloro-pyrimidine (77 mg, 398 μmol) and (S)-2-amino-4-((2-(2,2-difluoroethoxy)ethyl) (4-(5,6,7,8-tetrahydro-1,8-naphthyridin-2-yl) butyl)amino) butanoic acid (150 mg, 362 μmol) in THF (2 mL) H$_2$O (0.5 mL) was added NaHCO$_3$ (152 mg, 1.81 mmol) and the resulting mixture was heated to 70° C. for 2 h, cooled to rt, and then concentrated in vacuo to give the title compound that was used without further purification. LCMS (ESI+): m/z=571.3 (M+H)$^+$.

Step 2: (S)-4-((2-(2,2-difluoroethoxy)ethyl) (4-(5,6,7,8-tetrahydro-1,8-naphthyridin-2-yl) butyl)amino)-2-((5-phenylpyrimidin-4-yl) amino) butanoic acid To a mixture of phenylboronic acid (38 mg, 315 μmol) and (S)-2-((5-bromopyrimidin-4-yl) amino)-4-((2-(2,2-difluoroethoxy)ethyl) (4-(5,6,7,8-tetrahydro-1,8-naphthyridin-2-yl) butyl)amino) butanoic acid (150 mg, 262 μmol) in dioxane (1 mL) and H$_2$O (0.25 mL) was added Pd(dppf)Cl$_2$ (19 mg, 26 μmol) and K$_2$CO$_3$ (73 mg, 525 μmol) and the resulting mixture was heated to 70° C. for 2 h, cooled to rt, and then concentrated in vacuo. The crude residue was purified by reverse phase prep-HPLC to give the title compound. LCMS (ESI+): m/z=569.2 (M+H)$^+$. $^1$H NMR (400 MHz, DMSO-d$_6$) δ ppm 8.46 (s, 1H) 8.01 (s, 1H) 7.40-7.57 (m, 5H) 7.01-7.09 (m, 2H) 6.47 (br s, 1H) 5.90-6.31 (m, 2H) 4.34 (br d, J=4.89 Hz, 1H) 3.63 (td, J=15.22, 3.79 Hz, 2H) 3.55 (br t, J=5.38 Hz, 2H) 3.18-3.27 (m, 2H) 2.53-2.93 (m, 8H) 2.40 (t, J=7.46 Hz, 2H) 1.89-2.02 (m, 2H) 1.68-1.78 (m, 2H) 1.22-1.58 (m, 4H).

Compound 692: (S)-4-((2-(2,2-difluoroethoxy)ethyl) (4-(5,6,7,8-tetrahydro-1,8-naphthyridin-2-yl) butyl)amino)-2-((2-(pyridin-3-yl) quinazolin-4-yl) amino) butanoic acid: To a mixture of (S)-2-amino-4-((2-(2,2-difluoroethoxy)ethyl) (4-(5,6,7,8-tetrahydro-1,8-naphthyridin-2-yl) butyl)amino) butanoic acid (150 mg, 362 μmol) and 4-chloro-2-(3-pyridyl)quinazoline (96 mg, 398 μmol) in DMA (4 mL) was added DIPEA (315 μL, 1.81 mmol) and the resulting mixture was heated to 70° C. for 12 h, cooled to rt, and then concentrated in vacuo. The crude residue was purified by reverse phase prep-HPLC to give the title compound. LCMS (ESI+): m/z=620.3 (M+H)$^+$. $^1$H NMR (400 MHz, Methanol-d$_4$) δ ppm 9.56 (d, J=1.54 Hz, 1H) 8.84 (dt, J=8.10, 1.79 Hz, 1H) 8.62 (dd, J=4.96, 1.65 Hz, 1H) 8.11 (d, J=8.38 Hz, 1H) 7.75-7.91 (m, 2H) 7.46-7.58 (m, 2H) 7.15 (d, J=7.28 Hz, 1H) 6.29-6.38 (m, 1H) 5.68-6.03 (m, 1H) 4.91-4.93 (m, 1H) 3.83 (t, J=5.07 Hz, 2H) 3.58-3.69 (m, 1H) 3.63 (td, J=14.55, 3.75 Hz, 1H) 3.33-3.40 (m, 1H) 3.17-3.28 (m, 1H) 3.02-3.15 (m, 1H) 3.07 (br s, 1H) 3.01-3.28 (m, 1H) 2.88-2.99 (m, 1H) 2.51-2.64 (m, 4H) 2.37-2.50 (m, 1H) 2.25-2.37 (m, 1H) 1.61-1.86 (m, 6H).

Compound 693: (S)-2-((6-(1H-pyrazol-1-yl) pyrimidin-4-yl) amino)-4-((2-(2,2-difluoroethoxy)ethyl) (4-(5,6,7,8-tetrahydro-1,8-naphthyridin-2-yl) butyl)amino) butanoic acid: To a mixture of (S)-2-amino-4-((2-(2,2-difluoroethoxy)ethyl) (4-(5,6,7,8-tetrahydro-1,8-naphthyridin-2-yl) butyl) amino) butanoic acid hydrochloride (150 mg, 333 μmol) and 4-chloro-6-(1H-pyrazol-1-yl) pyrimidine (66 mg, 366 μmol) in DMA (4 mL) was added DIPEA (290 μL, 1.66 mmol) and the resulting mixture was heated to 70° C. for 12 h, cooled to rt, and then concentrated in vacuo. The crude residue was purified by reverse phase prep-HPLC to give the title compound. LCMS (ESI+): m/z=559.3 (M+H)$^+$. $^1$H NMR (400 MHz, Methanol-d$_4$) δ ppm 8.50 (d, J=2.43 Hz, 1H) 8.31 (br s, 1H) 7.74 (s, 1H) 7.13-7.24 (m, 1H) 6.94 (s, 1H) 6.51 (d, J=2.21 Hz, 1H) 6.42 (d, J=7.28 Hz, 1H) 5.77-6.13 (m, 1H) 4.50 (br s, 1H) 3.77-3.87 (m, 2H) 3.63-3.75 (m, 2H) 3.33-3.43 (m, 2H) 3.15 (br d, J=9.48 Hz, 2H) 2.83-3.07 (m, 4H) 2.56-2.73 (m, 4H) 2.18-2.31 (m, 1H) 2.03-2.16 (m, 1H) 1.64-1.91 (m, 6H).

Scheme 52, Compound 694

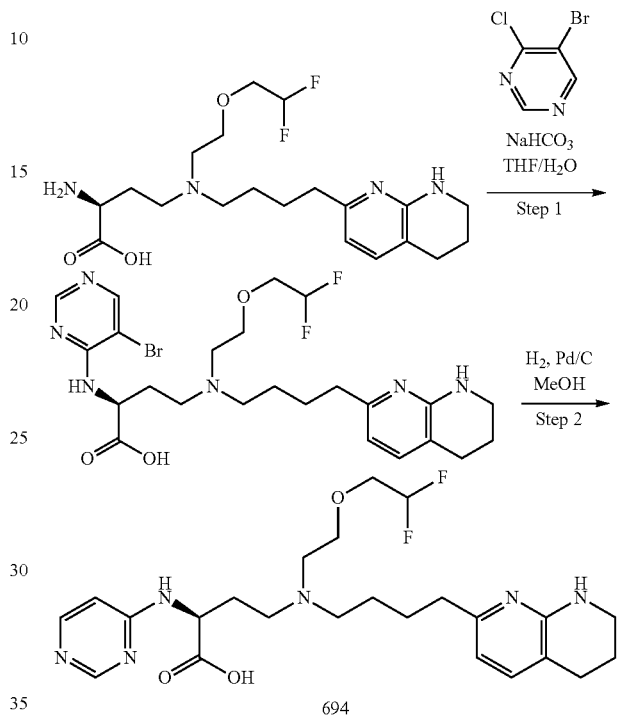

694

Step 1: (S)-2-((5-bromopyrimidin-4-yl) amino)-4-((2-(2,2-difluoroethoxy)ethyl) (4-(5,6,7,8-tetrahydro-1,8-naphthyridin-2-yl) butyl)amino) butanoic acid To a mixture of 5-bromo-4-chloro-pyrimidine (77.00 mg, 398.08 μmol, 1.1 eq) and (S)-2-amino-4-((2-(2,2-difluoroethoxy)ethyl) (4-(5,6,7,8-tetrahydro-1,8-naphthyridin-2-yl) butyl)amino) butanoic acid (150 mg, 362 μmol) in THF (2 mL) H$_2$O (0.5 mL) was added NaHCO$_3$ (152 mg, 1.81 mmol) and the resulting mixture was heated to 70° C. for 2 h, cooled to rt, and then concentrated in vacuo to give the title compound that was used without further purification. LCMS (ESI+): m/z=571.3 (M+H)$^+$.

Step 2: (S)-4-((2-(2,2-difluoroethoxy)ethyl) (4-(5,6,7,8-tetrahydro-1,8-naphthyridin-2-yl) butyl)amino)-2-(pyrimidin-4-ylamino) butanoic acid To a mixture of (S)-2-((5-bromopyrimidin-4-yl) amino)-4-((2-(2,2-difluoroethoxy)ethyl) (4-(5,6,7,8-tetrahydro-1,8-naphthyridin-2-yl) butyl)amino) butanoic acid (150 mg, 262 μmol) in MeOH (3 mL) was added 10 wt % Pd/C (50 mg) and the resulting mixture was stirred under an H$_2$ atmosphere for 5 h and then filtered and concentrated in vacuo. The crude residue was purified by reverse phase prep-HPLC to give the title compound. LCMS (ESI+): m/z=493.1 (M+H)$^+$. $^1$H NMR (400 MHz, DMSO-d$_6$) δ ppm 8.37 (s, 1H) 8.02 (br d, J=5.62 Hz, 1H) 7.51 (br s, 1H) 7.02 (d, J=7.21 Hz, 1H) 6.57 (br s, 1H) 6.39 (br s, 1H) 5.91-6.29 (m, 2H) 4.38 (br s, 1H) 3.62-3.69 (m, 2H) 3.56-3.60 (m, 2H) 3.23 (br t, J=5.38 Hz, 2H) 2.52-2.78 (m, 8H) 2.39 (t, J=7.46

Hz, 2H) 1.87-1.99 (m, 1H) 1.68-1.83 (m, 3H) 1.47-1.61 (m, 2H) 1.33-1.46 (m, 1H) 1.33-1.46 (m, 1H).

Scheme 53, Compound 695

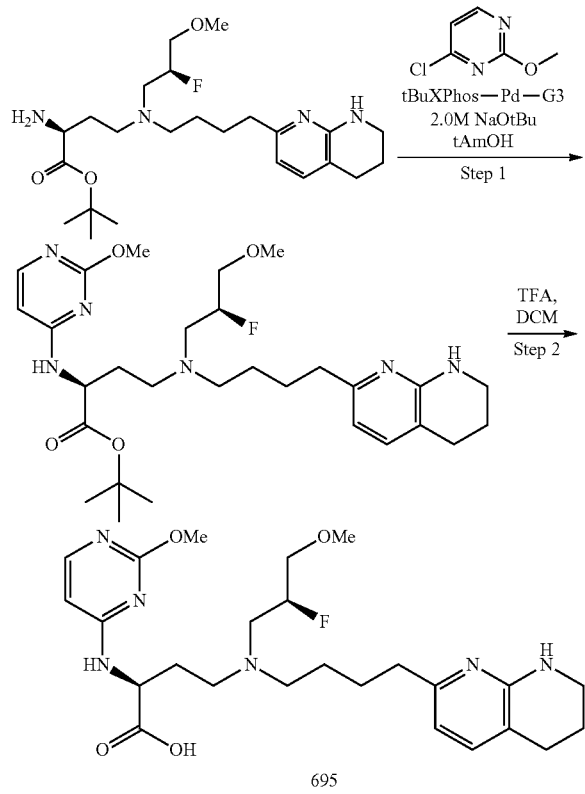

Step 1: (S)-4-(((S)-2-fluoro-3-methoxypropyl) (4-(5,6,7,8-tetrahydro-1,8-naphthyridin-2-yl) butyl) amino)-2-((2-methoxypyrimidin-4-yl) amino) butanoic acid To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 μmol) and 4-chloro-2-methoxypyrimidine (40 mg, 276 μmol) in t-AmOH (3 mL) then was added 2.0M t-BuONa in THF (276 μL, 552 μmol) and t-BuXPhos-Pd-G3 (22 mg, 28 μmol) and the resulting mixture was heated to 100° C. for 15 h, cooled to rt, and then concentrated in vacuo to give the title compound that was used without further purification. LCMS (ESI+): m/z=561.5 (M+H)+.

Step 2: (S)-4-(((S)-2-fluoro-3-methoxypropyl) (4-(5,6,7,8-tetrahydro-1,8-naphthyridin-2-yl) butyl) amino)-2-((2-methoxypyrimidin-4-yl) amino) butanoic acid (S)-tert-butyl 4-(((S)-2-fluoro-3-methoxypropyl) (4-(5,6,7,8-tetrahydro-1,8-naphthyridin-2-yl) butyl)amino)-2-((2-methoxypyrimidin-4-yl) amino) butanoate (200 mg, 357 μmol) was taken up in 3:1 DCM/TFA (2 mL) and the resulting mixture was stirred at rt for 5 h and then concentrated in vacuo. The crude residue was purified by reverse phase prep-HPLC to give the title compound. LCMS (ESI+): m/z=505.3 (M+H)+. $^1$H NMR (400 MHz, DMSO-$d_6$) δ ppm 14.33 (br s, 1H) 11.23 (br s, 1H) 10.10 (br d, J=18.58 Hz, 1H) 8.12 (br s, 1H) 8.02 (d, J=6.85 Hz, 1H) 7.61 (d, J=7.34 Hz, 1H) 6.56-6.79 (m, 2H) 5.20-5.51 (m, 1H) 4.58-4.82 (m, 1H) 4.01 (s, 3H) 3.34-3.65 (m, 8H) 3.31 (s, 3H) 3.21 (br s, 2H) 2.64-2.79 (m, 4H) 2.41 (br d, J=12.10 Hz, 1H) 2.20-2.34 (m, 1H) 1.63-1.85 (m, 6H).

Scheme 54, Compound 696

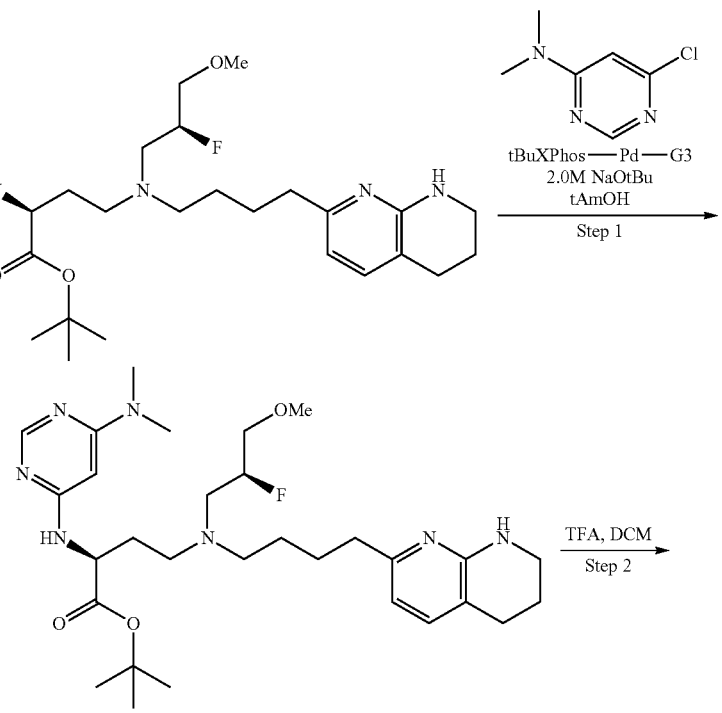

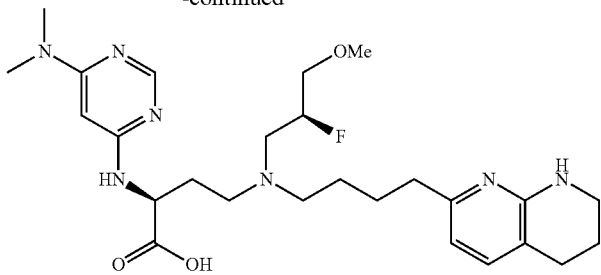

696

Step 1: (S)-4-(((S)-2-fluoro-3-methoxypropyl) (4-(5, 6,7,8-tetrahydro-1,8-naphthyridin-2-yl) butyl) amino)-2-((2-methoxypyrimidin-4-yl) amino) butanoic acid To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 μmol) and 6-chloro-N,N-dimethylpyrimidin-4-amine (44 mg, 276 μmol) in t-AmOH (3 mL) was added 2.0M t-BuONa in THF (276 μL, 552 μmol) and t-BuXPhos Pd G3 (22 mg, 28 μmol) and the resulting mixture was heated to 100° C. for 2.5 h, cooled to rt, and then concentrated in vacuo to give the title compound that was used without further purification. LCMS (ESI+): m/z=574.5 (M+H)+.

Step 2: (S)-2-((6-(dimethylamino)pyrimidin-4-yl) amino)-4-(((S)-2-fluoro-3-methoxypropyl) (4-(5,6,7, 8-tetrahydro-1,8-naphthyridin-2-yl) butyl)amino) butanoic acid (S)-tert-butyl 2-((6-(dimethylamino)pyrimidin-4-yl) amino)-4-(((S)-2-fluoro-3-methoxypropyl) (4-(5,6,7,8-tetrahydro-1,8-naphthyridin-2-yl) butyl)amino) butanoate (200 mg, 349 μmol) was taken up in 3:1 DCM/TFA (2 mL) and the resulting mixture was stirred at rt for 16 h and then concentrated in vacuo. The crude residue was purified by reverse phase prep-HPLC to give the title compound. LCMS (ESI+): m/z=518.3 (M+H)+. $^1$H NMR (400 MHz, DMSO-d$_6$) δ ppm 14.07-14.49 (m, 1H) 12.99-13.76 (m, 1H) 11.24 (br s, 1H) 8.44-8.99 (m, 1H) 8.48 (br d, J=18.46 Hz, 1H) 8.33 (s, 1H) 8.10 (br s, 1H) 7.60 (d, J=7.34 Hz, 1H) 6.64 (d, J=7.34 Hz, 1H) 5.87 (br s, 1H) 5.25-5.49 (m, 1H) 4.71 (br s, 1H) 3.34-3.64 (m, 7H) 3.31 (s, 3H) 3.19 (br d, J=3.55 Hz, 3H) 3.12 (br s, 6H) 2.64-2.79 (m, 4H) 2.31-2.45 (m, 1H) 2.21 (br s, 1H) 1.64-1.87 (m, 6H).

Scheme 55, Compound 697

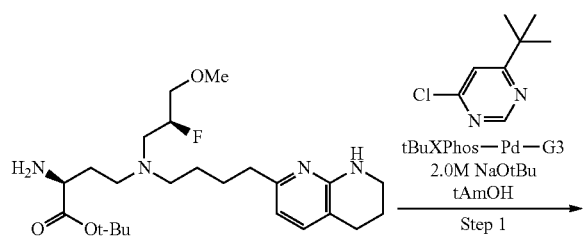

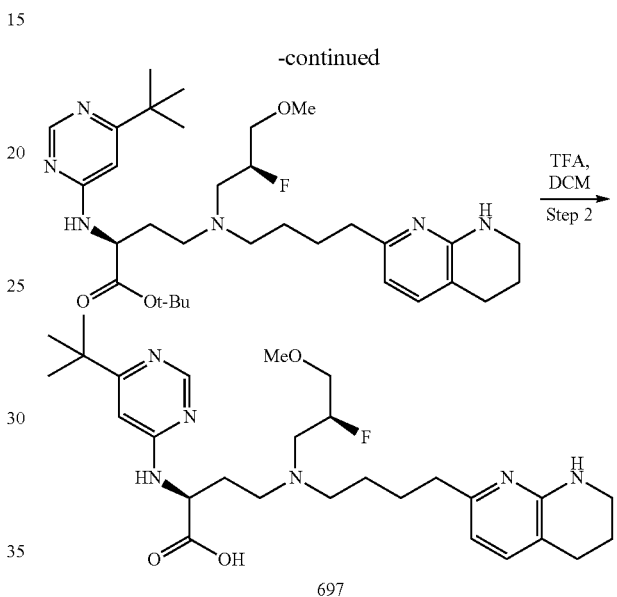

697

Step 1: (S)-tert-butyl 2-((6-(tert-butyl)pyrimidin-4-yl) amino)-4-(((S)-2-fluoro-3-methoxypropyl) (4-(5, 6,7,8-tetrahydro-1,8-naphthyridin-2-yl) butyl)amino) butanoate To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 μmol) and 4-(tert-butyl)-6-chloropyrimidine (47 mg, 276 μmol) in t-AmOH (3 mL) was added 2.0M t-BuONa in THF (276 μL, 552 μmol) then t-BuXPhos Pd G3 (22 mg, 28 μmol) and the resulting mixture was heated to 100° C. for 2.5 h, cooled to rt, and then concentrated in vacuo to give the title compound that was used without further purification. LCMS (ESI+): m/z=587.3 (M+H)+.

Step 2: (S)-2-((6-(tert-butyl)pyrimidin-4-yl) amino)-4-(((S)-2-fluoro-3-methoxypropyl) (4-(5,6,7,8-tetrahydro-1,8-naphthyridin-2-yl) butyl)amino) butanoic acid (S)-tert-butyl 2-((6-(tert-butyl)pyrimidin-4-yl) amino)-4-(((S)-2-fluoro-3-methoxypropyl) (4-(5,6,7,8-tetrahydro-1,8-naphthyridin-2-yl) butyl)amino) butanoate (200 mg, 341 μmol) was taken up in 3:1 DCM/TFA (2 mL) and the resulting mixture was stirred at rt for 16 h and then concentrated in vacuo. The crude residue was purified by reverse phase prep-HPLC to give the title compound. LCMS (ESI+): m/z=531.3 (M+H)+. $^1$H NMR (400 MHz, DMSO-d$_6$) δ ppm 14.07-14.49 (m, 1H) 12.99-13.76 (m, 1H) 11.24 (br s, 1H) 8.44-8.99 (m, 1H) 8.48 (br d, J=18.46 Hz, 1H)

8.33 (s, 1H) 8.10 (br s, 1H) 7.60 (d, J=7.34 Hz, 1H) 6.64 (d, J=7.34 Hz, 1H) 5.87 (br s, 1H) 5.25-5.49 (m, 1H) 4.71 (br s, 1H) 3.34-3.64 (m, 7H) 3.31 (s, 3H) 3.19 (br d, J=3.55 Hz, 3H) 3.12 (br s, 6H) 2.64-2.79 (m, 4H) 2.31-2.45 (m, 1H) 2.21 (br s, 1H) 1.64-1.87 (m, 6H).

Step 1: (S)-tert-butyl 4-(((S)-2-fluoro-3-methoxypropyl) (4-(5,6,7,8-tetrahydro-1,8-naphthyridin-2-yl) butyl)amino)-2-((2-phenylpyrimidin-4-yl) amino) butanoate To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 μmol) and 4-chloro-2-phenylpyrimidine (53 mg, 276 μmol) in t-AmOH (3 mL) was added 2.0M t-BuONa in THF (276 μL, 552 μmol) then t-BuXPhos Pd G3 (22 mg, 28 μmol) and the resulting mixture was heated to 100° C. for 5 h, cooled to rt, and then concentrated in vacuo to give the title compound that was used without further purification. LCMS (ESI+): m/z=607.2 (M+H)⁺.

Step 2: (S)-4-(((S)-2-fluoro-3-methoxypropyl) (4-(5,6,7,8-tetrahydro-1,8-naphthyridin-2-yl) butyl) amino)-2-((2-phenylpyrimidin-4-yl) amino) butanoic acid (S)-tert-butyl 4-(((S)-2-fluoro-3-methoxypropyl) (4-(5,6,7,8-tetrahydro-1,8-naphthyridin-2-yl) butyl)amino)-2-((2-phenylpyrimidin-4-yl) amino) butanoate (200 mg, 330 μmol) was taken up in DCM/TFA (2 mL) and the resulting mixture was stirred at rt for 16 h and then concentrated in vacuo. The crude residue was purified by reverse phase prep-HPLC to give the title compound. LCMS (ESI+): m/z=551.3 (M+H)⁺. ¹H NMR (400 MHz, DMSO-d₆) δ ppm 8.26 (br d, J=7.72 Hz, 2H) 8.15 (br d, J=6.39 Hz, 1H) 7.37-7.46 (m, 3H) 6.95 (br d, J=7.06 Hz, 1H) 6.48 (br s, 1H) 6.15 (d, J=7.28 Hz, 1H) 4.50-4.76 (m, 2H) 3.35-3.47 (m, 2H) 3.12-3.21 (m, 5H) 2.51-2.70 (m, 6H) 2.28-2.46 (m, 4H) 1.97 (br d, J=7.28 Hz, 1H) 1.80 (br s, 1H) 1.65-1.74 (m, 2H) 1.49 (br s, 2H) 1.28-1.40 (m, 2H).

Scheme 56, Compound 698

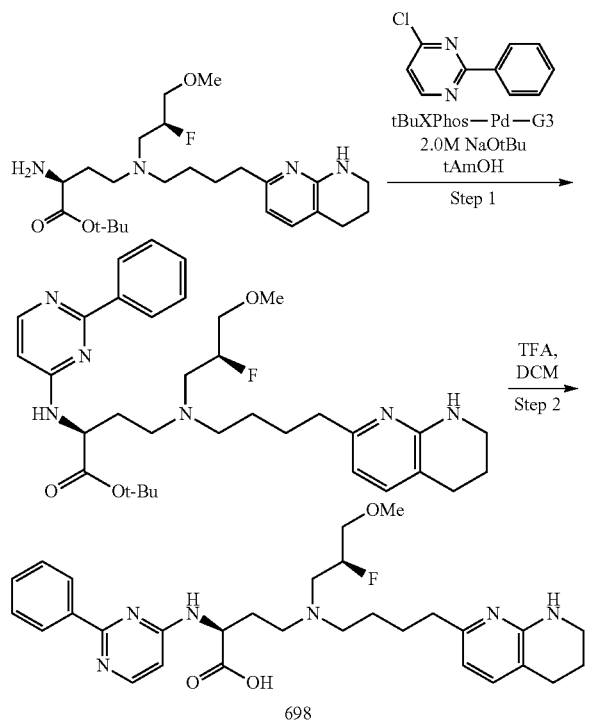

Scheme 57, Compound 699

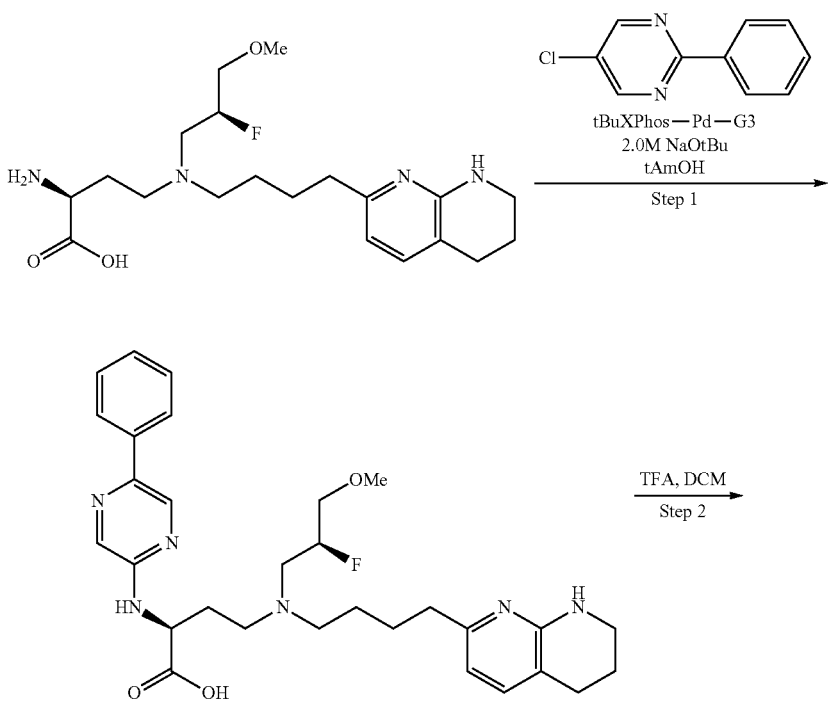

-continued

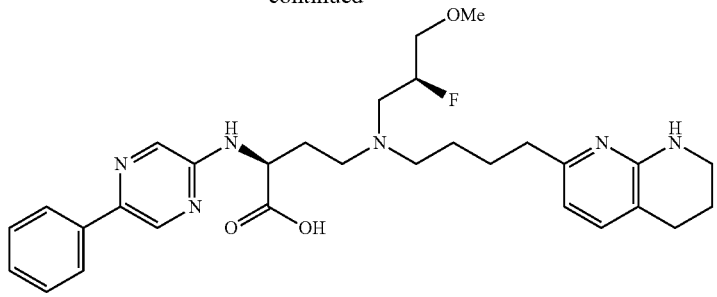

699

Step 1: (S)-tert-butyl 4-(((S)-2-fluoro-3-methoxy-propyl) (4-(5,6,7,8-tetrahydro-1,8-naphthyridin-2-yl) butyl)amino)-2-((5-phenylpyrazin-2-yl) amino) butanoate To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 μmol) and 4-chloro-2-phenylpyrimidine (53 mg, 276 μmol) in t-AmOH (3 mL) was added 2.0M t-BuONa in THF (276 μL, 552 μmol) and t-BuXPhos Pd G3 (22 mg, 28 μmol) and the resulting mixture was heated to 100° C. for 5 h, cooled to rt, and then concentrated in vacuo to give the title compound that was used without further purification. LCMS (ESI+): m/z=607.2 (M+H)+.

Step 2: (S)-4-(((S)-2-fluoro-3-methoxypropyl) (4-(5,6,7,8-tetrahydro-1,8-naphthyridin-2-yl) butyl) amino)-2-((5-phenylpyrazin-2-yl) amino) butanoic acid (S)-tert-butyl 4-(((S)-2-fluoro-3-methoxypropyl) (4-(5,6,7,8-tetrahydro-1,8-naphthyridin-2-yl) butyl)amino)-2-((5-phenylpyrazin-2-yl) amino) butanoate (200 mg, 330 μmol) was taken up in 3:1 DCM/TFA (2 mL) and the resulting mixture was stirred at rt for 16 h and then concentrated in vacuo. The crude residue was purified by reverse phase prep-HPLC to give the title compound. LCMS (ESI+): m/z=551.3 (M+H)+. $^1$H NMR (400 MHz, DMSO-d$_6$) δ ppm 14.30 (br s, 1H) 10.95 (br s, 1H) 8.56 (s, 1H) 8.17 (s, 1H) 8.10 (br s, 1H) 7.92 (d, J=7.28 Hz, 2H) 7.78 (br s, 1H) 7.58 (d, J=7.28 Hz, 1H) 7.38-7.49 (m, 2H) 7.29-7.37 (m, 1H) 6.62 (d, J=7.06 Hz, 1H) 5.22-5.48 (m, 1H) 4.50 (br s, 1H) 3.34-3.65 (m, 8H) 3.31 (s, 3H) 3.13 (s, 2H) 2.64-2.79 (m, 4H) 2.34 (br s, 1H) 2.22 (br s, 1H) 1.63-1.86 (m, 6H).

Scheme 58, Compound 700

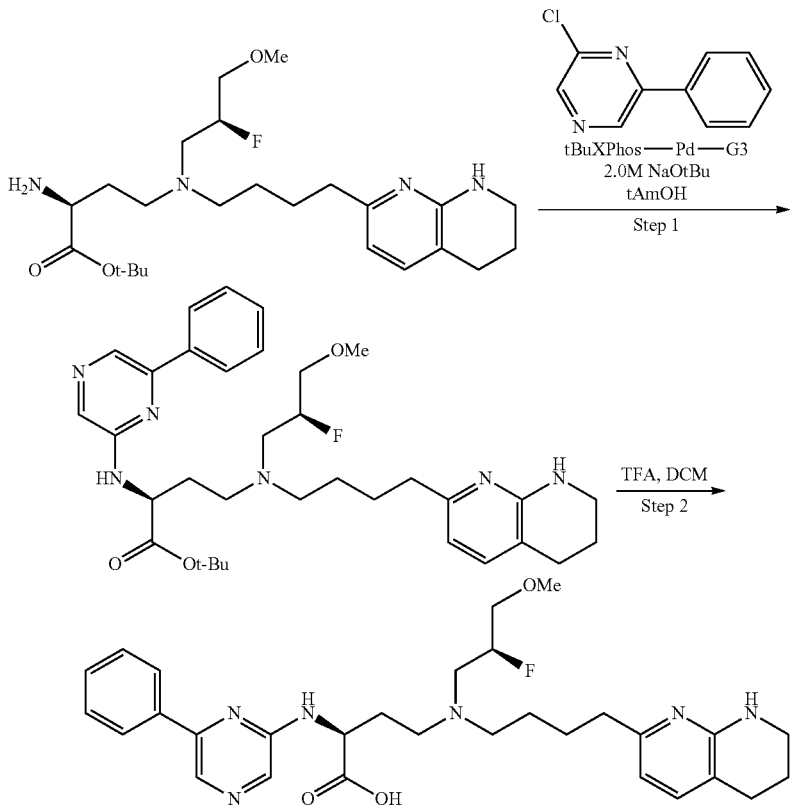

700

Step 1: (S)-tert-butyl 4-(((S)-2-fluoro-3-methoxy-propyl) (4-(5,6,7,8-tetrahydro-1,8-naphthyridin-2-yl) butyl)amino)-2-((6-phenylpyrazin-2-yl) amino) butanoate To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 µmol) and 2-chloro-6-phenylpyrazine (53 mg, 276 µmol) was added to t-AmOH (3 mL) then was added 2.0M t-BuONa in THF (276 µL, 552 µmol) and t-BuXPhos Pd G3 (22 mg, 28 µmol) and the resulting mixture was heated to 100° C. for 5 h, cooled to rt, and then concentrated in vacuo to give the title compound that was used without further purification. LCMS (ESI+): m/z=607.2 (M+H)⁺.

Step 2: (S)-4-(((S)-2-fluoro-3-methoxypropyl) (4-(5, 6,7,8-tetrahydro-1,8-naphthyridin-2-yl) butyl) amino)-2-((6-phenylpyrazin-2-yl) amino) butanoic acid (S)-tert-butyl 4-(((S)-2-fluoro-3-methoxypropyl) (4-(5,6, 7,8-tetrahydro-1,8-naphthyridin-2-yl) butyl)amino)-2-((6-phenylpyrazin-2-yl) amino) butanoate (200 mg, 330 µmol) was taken up in 3:1 DCM/TFA (2 mL) and the resulting mixture was stirred at rt for 16 h and then concentrated in vacuo. The crude residue was purified by reverse phase prep-HPLC to give the title compound. LCMS (ESI+): m/z=551.3 (M+H)⁺. ¹H NMR (400 MHz, DMSO-d₆) δ ppm 8.26 (s, 1H) 7.90-8.02 (m, 3H) 7.37-7.46 (m, 3H) 6.99 (d, J=7.06 Hz, 1H) 6.18 (dd, J=7.28, 2.43 Hz, 1H) 4.55-4.80 (m, 1H) 4.43 (br d, J=5.73 Hz, 1H) 3.36-3.50 (m, 2H) 3.09-3.24 (m, 5H) 2.52-2.77 (m, 7H) 2.29-2.47 (m, 3H) 2.00 (br dd, J=13.34, 6.50 Hz, 1H) 1.77-1.88 (m, 1H) 1.64-1.74 (m, 2H) 1.45-1.56 (m, 2H) 1.31-1.41 (m, 2H).

Compound 701: (S)-4-((4-(5,6,7,8-tetrahydro-1,8-naphthyridin-2-yl) butyl) (2-(2,2,2-trifluoroethoxy)ethyl)amino)-2-((5-(trifluoromethyl)pyrimidin-2-yl) amino) butanoic acid: To a mixture of (S)-2-amino-4-((4-(5,6,7,8-tetrahydro-1,8-naphthyridin-2-yl) butyl) (2-(2,2,2-trifluoroethoxy) ethyl)amino) butanoic acid (140 mg, 259 µmol) in THF (4 mL) and H₂O (1 mL) was added 2-chloro-5-(trifluoromethyl)pyrimidine (52 mg, 285 µmol) and NaHCO₃ (109 mg, 1.29 mmol) and the resulting mixture was heated to 70° C. for 1 h, cooled to rt, and then concentrated in vacuo. The crude residue was purified by reverse phase prep-HPLC to give the title compound. LCMS (ESI+): m/z=579.2 (M+H)⁺. ¹H NMR (400 MHz, DMSO-d₆) δ ppm 8.64 (s, 2H) 8.18 (d, J=7.21 Hz, 1H) 7.02 (d, J=7.34 Hz, 1H) 6.44 (br s, 1H) 6.19-6.27 (m, 1H) 6.19-6.27 ((m, 1H) 4.38-4.46 (m, 1H) 3.94-4.06 (m, 2H) 3.65 (br s, 2H) 3.20-3.28 (m, 2H) 2.54-2.78 (m, 7H) 2.42-2.48 (m, 1H) 2.37 (t, J=7.52 Hz, 2H) 1.94-2.05 (m, 1H) 1.81-1.91 (m, 1H) 1.70-1.79 (m, 2H) 1.53 (tq, J=13.50, 6.61 Hz, 2H) 1.32-1.43 (m, 2H).

Compound 702: (S)-2-((5-cyanopyrimidin-2-yl) amino)-4-((4-(5,6,7,8-tetrahydro-1,8-naphthyridin-2-yl) butyl) (2-(2,2,2-trifluoroethoxy)ethyl)amino) butanoic acid: To a mixture of (S)-2-amino-4-((4-(5,6,7,8-tetrahydro-1,8-naphthyridin-2-yl) butyl) (2-(2,2,2-trifluoroethoxy)ethyl) amino) butanoic acid (140 mg, 259 µmol) in THF (1 mL) and H₂O (0.25 mL) was added 2-chloropyrimidine-5-carbonitrile (40 mg, 285 µmol) and NaHCO₃ (109 mg, 1.29 mmol) and the resulting mixture was heated to 50° C. for 1 h, cooled to rt, and then concentrated in vacuo. The crude residue was purified by reverse phase prep-HPLC to give the title compound. LCMS (ESI+): m/z=536.2 (M+H)⁺. ¹H NMR (400 MHz, DMSO-d₆) 8.66-8.73 (m, 2H) 8.42 (d, J=7.46 Hz, 1H) 7.03 (d, J=7.21 Hz, 1H) 6.44 (br s, 1H) 6.22 (d, J=7.34 Hz, 1H) 4.36-4.46 (m, 1H) 3.96-4.07 (m, 2H) 3.64 (t, J=5.93 Hz, 2H) 3.24 (br t, J=5.20 Hz, 2H) 2.54-2.79 (m, 8H) 2.37 (t, J=7.52 Hz, 2H) 1.81-2.06 (m, 2H) 1.75 (q, J=5.90 Hz, 2H) 1.46-1.59 (m, 2H) 1.33-1.44 (m, 2H).

Compound 703: (S)-2-((1H-pyrazolo[3,4-d]pyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid: To a solution of (S)-2-amino-4-((4-(5,6,7,8-tetrahydro-1,8-naphthyridin-2-yl) butyl) (2-(2,2,2-trifluoroethoxy)ethyl) amino) butanoic acid (140 mg, 259 µmol) in THF (1 mL) and H₂O (0.25 mL) was added 4-chloro-1H-pyrazolo[3,4-d]pyrimidine (44 mg, 285 µmol) and NaHCO₃ (109 mg, 1.29 mmol) and the resulting mixture was heated to 70° C. for 9 h, cooled to rt, and then concentrated in vacuo. The crude residue was purified by reverse phase prep-HPLC to give the title compound. LCMS (ESI+): m/z=551.2 (M+H)⁺. ¹H NMR (400 MHz, DMSO-d₆) δ ppm 13.42 (br s, 1H) 8.31 (br d, J=7.34 Hz, 1H) 8.20 (d, J=4.16 Hz, 2H) 7.00 (d, J=7.34 Hz, 1H) 6.46 (br s, 1H) 6.18 (d, J=7.34 Hz, 1H) 4.68-4.78 (m, 1H) 3.92-4.07 (m, 2H) 3.64 (t, J=5.87 Hz, 2H) 3.23 (br t, J=5.38 Hz, 2H) 2.52-2.78 (m, 7H) 2.41-2.49 (m, 1H) 2.34 (t, J=7.46 Hz, 2H) 1.98-2.11 (m, 1H) 1.88 (br d, J=5.99 Hz, 1H) 1.68-1.78 (m, 2H) 1.46-1.58 (m, 2H) 1.31-1.43 (m, 2H).

Compound 704: (S)-2-((5-bromopyrimidin-2-yl) amino)-4-((4-(5,6,7,8-tetrahydro-1,8-naphthyridin-2-yl) butyl) (2-(2,2,2-trifluoroethoxy)ethyl)amino) butanoic acid: To a mixture of (S)-2-amino-4-((4-(5,6,7,8-tetrahydro-1,8-naphthyridin-2-yl) butyl) (2-(2,2,2-trifluoroethoxy)ethyl) amino) butanoic acid (140 mg, 259 µmol) in THF (4 mL) and H₂O (1 mL) was added 5-bromo-2-chloro-pyrimidine (55 mg, 285 µmol) and NaHCO₃ (109 mg, 1.29 mmol) and the resulting mixture was heated to 70° C. for 6 h, cooled to rt, and then concentrated in vacuo. The crude residue was purified by reverse phase prep-HPLC to give the title compound. LCMS (ESI+): m/z=589.1 (M+H)⁺. ¹H NMR (400 MHz, DMSO-d₆) δ ppm 8.37 (br s, 2H) 7.59 (br d, J=7.09 Hz, 1H) 7.02 (d, J=7.21 Hz, 1H) 6.40 (br s, 1H) 6.22 (d, J=7.21 Hz, 1H) 4.22-4.33 (m, 1H) 4.01 (q, J=9.41 Hz, 2H) 3.64 (br t, J=5.87 Hz, 2H) 3.24 (br t, J=5.07 Hz, 2H) 2.53-2.79 (m, 7H) 2.42-2.49 (m, 1H) 2.38 (br t, J=7.52 Hz, 2H) 1.79-2.00 (m, 2H) 1.69-1.78 (m, 2H) 1.47-1.59 (m, 2H) 1.33-1.45 (m, 2H).

Compound 705: (S)-4-((4-(5,6,7,8-tetrahydro-1,8-naphthyridin-2-yl) butyl) (2-(2,2,2-trifluoroethoxy)ethyl)amino)-2-((2-(trifluoromethyl)pyrimidin-4-yl) amino) butanoic acid: To a solution of (S)-2-amino-4-((4-(5,6,7,8-tetrahydro-1,8-naphthyridin-2-yl) butyl) (2-(2,2,2-trifluoroethoxy) ethyl)amino) butanoic acid (140 mg, 259 µmol) in THF (4 mL) and H₂O (1 mL) was added 4-chloro-2-(trifluoromethyl)pyrimidine (52 mg, 285 µmol) and NaHCO₃ (109 mg, 1.29 mmol) and the resulting mixture was heated to 70° C. for 9 h, cooled to rt, and then concentrated in vacuo. The crude residue was purified by reverse phase prep-HPLC to give the title compound. LCMS (ESI+): m/z=579.2 (M+H)⁺. ¹H NMR (400 MHz, DMSO-d₆) δ ppm 8.20 (br d, J=5.75 Hz, 2H) 7.03 (d, J=7.21 Hz, 1H) 6.82 (d, J=5.99 Hz, 1H) 6.55 (br s, 1H) 6.23 (d, J=7.21 Hz, 1H) 4.43 (br d, J=5.99 Hz, 1H) 3.97-4.08 (m, 2H) 3.66 (t, J=5.69 Hz, 2H) 3.24 (br t, J=5.32 Hz, 2H) 2.54-2.85 (m, 8H) 2.34-2.44 (m, 2H) 1.69-2.02 (m, 4H) 1.49-1.58 (m, 2H) 1.35-1.48 (m, 2H).

Compound 706: (S)-2-((5-cyclopropylpyrimidin-2-yl) amino)-4-((4-(5,6,7,8-tetrahydro-1,8-naphthyridin-2-yl) butyl) (2-(2,2,2-trifluoroethoxy)ethyl)amino) butanoic acid: To a mixture of (S)-2-amino-4-((4-(5,6,7,8-tetrahydro-1,8-naphthyridin-2-yl) butyl) (2-(2,2,2-trifluoroethoxy)ethyl) amino) butanoic acid (140 mg, 259 µmol) in THF (4 mL)

and H₂O (1 mL) was added 1-cyclopropyl-4-fluorobenzene (39 mg, 285 µmol) and NaHCO₃ (109 mg, 1.29 mmol) and the resulting mixture was heated to 70° C. for 6 h, cooled to rt, and then concentrated in vacuo. The crude residue was purified by reverse phase prep-HPLC to give the title compound. LCMS (ESI+): m/z=551.3 (M+H)⁺. ¹H NMR (400 MHz, DMSO-d₆) δ ppm 8.08 (s, 2H) 6.96-7.10 (m, 2H) 6.37 (br s, 1H) 6.22 (d, J=7.21 Hz, 1H) 4.21-4.32 (m, 1H) 3.95-4.07 (m, 2H) 3.64 (t, J=5.93 Hz, 2H) 3.23 (br t, J=5.20 Hz, 2H) 2.52-2.79 (m, 7H) 2.42-2.49 (m, 1H) 2.38 (t, J=7.46 Hz, 2H) 1.78-1.99 (m, 2H) 1.67-1.78 (m, 3H) 1.48-1.60 (m, 2H) 1.34-1.43 (m, 2H) 0.81-0.90 (m, 2H) 0.55-0.65 (m, 2H).

Compound 707: (S)-2-((3-cyanopyrazin-2-yl) amino)-4-((4-(5,6,7,8-tetrahydro-1,8-naphthyridin-2-yl) butyl) (2-(2,2,2-trifluoroethoxy)ethyl)amino) butanoic acid: To a mixture of (S)-2-amino-4-((4-(5,6,7,8-tetrahydro-1,8-naphthyridin-2-yl) butyl) (2-(2,2,2-trifluoroethoxy)ethyl)amino) butanoic acid (140 mg, 259 µmol) in i-PrOH (3 mL) was added 3-chloropyrazine-2-carbonitrile (40 mg, 285 µmol) and DIPEA (226 µL, 1.29 mmol) and the resulting mixture was heated to 70° C. for 1 h, cooled to rt, and then concentrated in vacuo. The crude residue was purified by reverse phase prep-HPLC to give the title compound. LCMS (ESI+): m/z=536.2 (M+H)⁺. ¹H NMR (400 MHz, Methanol-d₄) δ ppm 8.25 (d, J=2.08 Hz, 1H) 7.89 (d, J=2.08 Hz, 1H) 7.33 (br d, J=7.34 Hz, 1H) 6.48 (d, J=7.21 Hz, 1H) 4.48-4.55 (m, 1H) 3.90-4.02 (m, 4H) 3.37-3.44 (m, 2H) 3.15-3.27 (m, 2H) 2.98-3.11 (m, 3H) 2.84-2.92 (m, 1H) 2.74 (br t, J=5.99 Hz, 2H) 2.60-2.69 (m, 2H) 2.12-2.34 (m, 2H) 1.71-1.92 (m, 6H).

Compound 708: (S)-2-((2-(pyridin-3-yl) quinazolin-4-yl) amino)-4-((4-(5,6,7,8-tetrahydro-1,8-naphthyridin-2-yl) butyl) (2-(2,2,2-trifluoroethoxy)ethyl)amino) butanoic acid: To a mixture of (S)-2-amino-4-((4-(5,6,7,8-tetrahydro-1,8-naphthyridin-2-yl) butyl) (2-(2,2,2-trifluoroethoxy)ethyl)amino) butanoic acid (140 mg, 259 µmol) in DMA (3 mL) was added 4-chloro-2-(pyridin-3-yl) quinazoline (77 mg, 285 µmol) and DIPEA (226 µL, 1.29 mmol) and the resulting mixture was heated to 70° C. for 2 h, cooled to rt, and then concentrated in vacuo. The crude residue was purified by reverse phase prep-HPLC to give the title compound. LCMS (ESI+): m/z=638.3 (M+H)⁺. ¹H NMR (400 MHz, DMSO-d₆) δ ppm 9.59 (d, J=1.47 Hz, 1H) 8.55-8.76 (m, 3H) 8.33 (d, J=8.19 Hz, 1H) 7.75-7.93 (m, 2H) 7.46-7.62 (m, 2H) 6.91 (d, J=7.21 Hz, 1H) 6.24-6.37 (m, 1H) 6.09 (d, J=7.21 Hz, 1H) 4.73-4.82 (m, 1H) 3.96 (q, J=9.50 Hz, 2H) 3.66 (t, J=5.87 Hz, 2H) 3.20 (br t, J=4.95 Hz, 2H) 2.53-2.85 (m, 8H) 2.29 (t, J=7.46 Hz, 2H) 2.04-2.19 (m, 2H) 1.71 (q, J=5.84 Hz, 2H) 1.46-1.55 (m, 2H) 1.40 (br d, J=6.60 Hz, 2H).

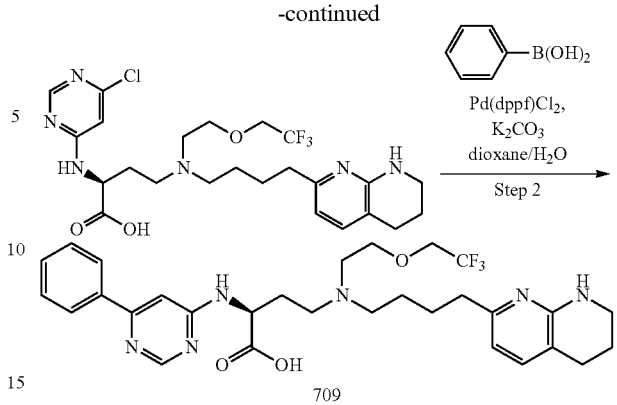

Step 1: (S)-2-((6-chloropyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid To a mixture of (S)-2-amino-4-((4-(5,6,7,8-tetrahydro-1, 8-naphthyridin-2-yl) butyl) (2-(2,2,2-trifluoroethoxy)ethyl) amino) butanoic acid (140 mg, 259 µmol) in THF (4 mL) and H₂O (1 mL) was added 4,6-dichloropyrimidine (42 mg, 285 µmol) and NaHCO₃ (109 mg, 1.29 mmol) and the resulting mixture was heated to 70° C. for 5 h, cooled to rt, and then concentrated in vacuo. The crude residue was purified by reverse phase prep-HPLC to give the title compound. LCMS (ESI+): m/z=545.3 (M+H)⁺.

Step 2: (S)-2-((6-phenylpyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid To a mixture of (S)-2-((6-chloropyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid (141 mg, 259 µmol) in dioxane (4 mL) and H₂O (1 mL) was added phenylboronic acid (47 mg, 388 µmol), K₂CO₃ (72 mg, 517 µmol), and Pd(dppf)Cl₂ (19 mg, 26 µmol) and the resulting mixture was heated to 100° C. for 2 h, cooled to rt, and then concentrated in vacuo. The crude residue was purified by reverse phase prep-HPLC to give the title compound. LCMS (ESI+): m/z=587.3 (M+H)⁺. ¹H NMR (400 MHz, DMSO-d₆) δ ppm 8.49 (s, 1H) 7.99 (br d, J=5.38 Hz, 2H) 7.60 (br s, 1H) 7.45-7.53 (m, 3H) 7.10 (br s, 1H) 6.99 (d, J=7.21 Hz, 1H) 6.43 (br s, 1H) 6.21 (d, J=7.21 Hz, 1H) 4.47 (br s, 1H) 4.02 (q, J=9.25 Hz, 2H) 3.67 (br t, J=5.75 Hz, 2H) 3.22 (br t, J=5.20 Hz, 2H) 2.53-2.83 (m, 7H) 2.44-2.48 (m, 1H) 2.39 (br t, J=7.40 Hz, 2H) 1.94-2.03 (m, 1H) 1.84 (br dd, J=13.02, 6.79 Hz, 1H) 1.70-1.78 (m, 2H) 1.54 (br d, J=4.77 Hz, 2H) 1.38-1.47 (m, 2H).

Scheme 59, Compound 709

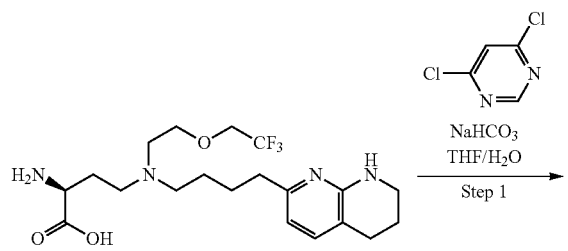

Scheme 60, Compound 710

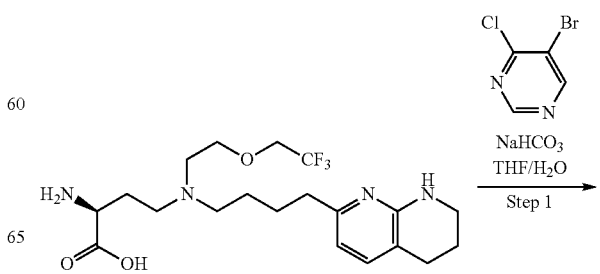

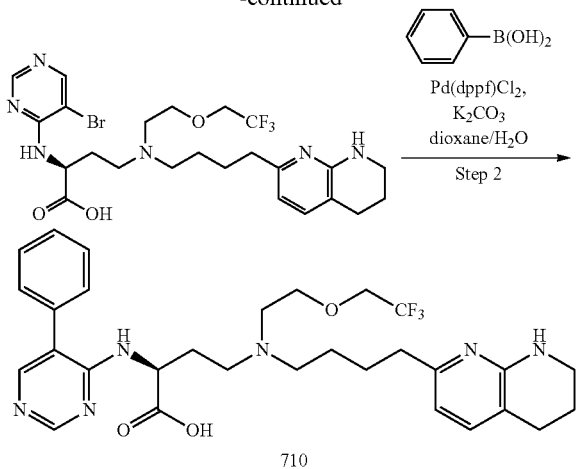

710

Step 1: (S)-2-((5-bromopyrimidin-4-yl) amino)-4-((4-(5,6,7,8-tetrahydro-1,8-naphthyridin-2-yl) butyl)(2-(2,2,2-trifluoroethoxy)ethyl)amino) butanoic acid To a mixture of (S)-2-amino-4-((4-(5,6,7,8-tetrahydro-1,8-naphthyridin-2-yl) butyl) (2-(2,2,2-trifluoroethoxy)ethyl)amino) butanoic acid (140 mg, 259 μmol) in THF (4 mL) and H$_2$O (1 mL) was added 5-bromo-4-chloropyrimidine (55 mg, 285 μmol) and NaHCO$_3$ (109 mg, 1.29 mmol) and the resulting mixture was heated to 70° C. for 3 h, cooled to rt, and then concentrated in vacuo to give the title compound that was used without further purification. LCMS (ESI+): m/z=589.1 (M+H)$^+$.

Step 2: (S)-2-((5-phenylpyrimidin-4-yl) amino)-4-((4-(5,6,7,8-tetrahydro-1,8-naphthyridin-2-yl) butyl)(2-(2,2,2-trifluoroethoxy)ethyl)amino) butanoic acid To a mixture of (S)-2-((5-bromopyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid (152 mg, 258 μmol) in dioxane (4 mL) and H$_2$O (1 mL) was added phenylboronic acid (47 mg, 387 μmol), K$_2$CO$_3$ (72 mg, 516 μmol), and Pd(dppf)Cl$_2$ (19 mg, 26 μmol) and the resulting mixture was heated to 100° C. for 2 h, cooled to rt, and then concentrated in vacuo. The crude residue was purified by reverse phase prep-HPLC to give the title compound. LCMS (ESI+): m/z=587.3 (M+H)$^+$. $^1$H NMR (400 MHz, DMSO-d$_6$) δ ppm 8.46 (s, 1H) 8.02 (s, 1H) 7.40-7.58 (m, 5H) 7.06 (br dd, J=13.27, 6.54 Hz, 2H) 6.57 (br s, 1H) 6.25 (d, J=7.21 Hz, 1H) 4.41 (br d, J=5.62 Hz, 1H) 4.00 (q, J=9.41 Hz, 2H) 3.60 (br t, J=5.50 Hz, 2H) 3.21-3.27 (m, 2H) 2.54-2.85 (m, 8H) 2.40 (br t, J=7.40 Hz, 2H) 1.97 (br d, J=5.38 Hz, 2H) 1.69-1.80 (m, 2H) 1.41-1.58 (m, 2H) 1.22-1.40 (m, 2H).

Scheme 61, compound 711

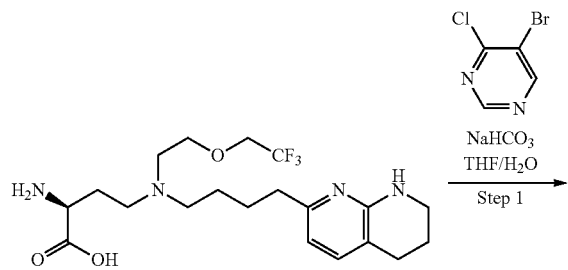

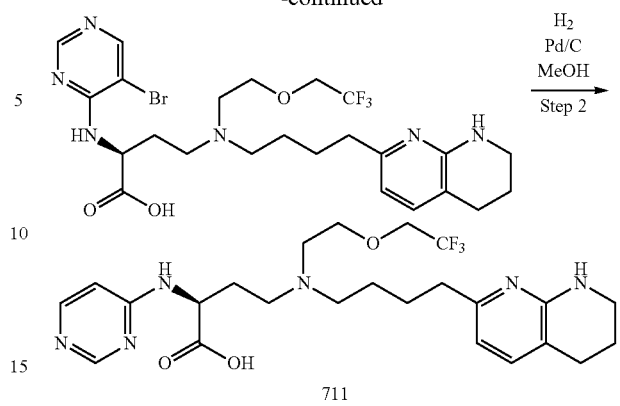

711

Step 1: (S)-2-((5-bromopyrimidin-4-yl) amino)-4-((4-(5,6,7,8-tetrahydro-1,8-naphthyridin-2-yl) butyl)(2-(2,2,2-trifluoroethoxy)ethyl)amino) butanoic acid To a mixture of (S)-2-amino-4-((4-(5,6,7,8-tetrahydro-1,8-naphthyridin-2-yl) butyl) (2-(2,2,2-trifluoroethoxy)ethyl)amino) butanoic acid (140 mg, 259 μmol) in THF (4 mL) and H$_2$O (1 mL) was added 5-bromo-4-chloropyrimidine (55 mg, 285 μmol) and NaHCO$_3$ (109 mg, 1.29 mmol) and the resulting mixture was heated to 70° C. for 6 h, cooled to rt, and then concentrated in vacuo to give the title compound that was used without further purification. LCMS (ESI+): m/z=589.1 (M+H)$^+$.

Step 2: (S)-2-(pyrimidin-4-ylamino)-4-((4-(5,6,7,8-tetrahydro-1,8-naphthyridin-2-yl) butyl) (2-(2,2,2-trifluoroethoxy)ethyl)amino) butanoic acid To a mixture of (S)-2-((5-bromopyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid (152 mg, 258 μmol) in MeOH (10 mL) was added 10 wt % Pd/C (200 mg) and the resulting mixture was stirred under an H$_2$ atmosphere for 16 h and then was filtered and concentrated in vacuo. The crude residue was purified by reverse phase prep-HPLC to give the title compound. LCMS (ESI+): m/z=511.2 (M+H)$^+$. $^1$H NMR (400 MHz, DMSO-d$_6$) δ ppm 8.38 (s, 1H) 8.03 (br d, J=5.50 Hz, 1H) 7.55 (br s, 1H) 7.04 (d, J=7.34 Hz, 1H) 6.55 (br d, J=19.56 Hz, 2H) 6.23 (d, J=7.21 Hz, 1H) 4.40 (br s, 1H) 4.01 (q, J=9.46 Hz, 2H) 3.65 (br t, J=5.75 Hz, 2H) 3.24 (br t, J=5.38 Hz, 2H) 2.55-2.76 (m, 8H) 2.40 (br t, J=7.40 Hz, 2H) 1.95 (br dd, J=13.39, 6.54 Hz, 1H) 1.71-1.84 (m, 3H) 1.49-1.58 (m, 2H) 1.35-1.45 (m, 2H).

Compound 712: (S)-2-((6-(1H-pyrazol-1-yl) pyrimidin-4-yl) amino)-4-((4-(5,6,7,8-tetrahydro-1,8-naphthyridin-2-yl) butyl) (2-(2,2,2-trifluoroethoxy)ethyl)amino) butanoic acid:
To a mixture of (S)-2-amino-4-((4-(5,6,7,8-tetrahydro-1,8-naphthyridin-2-yl) butyl) (2-(2,2,2-trifluoroethoxy)ethyl) amino) butanoic acid (140 mg, 259 μmol) in DMA (3 mL) was added 4-chloro-6-(1H-pyrazol-1-yl) pyrimidine (51 mg, 285 μmol) and DIPEA (226 μL, 1.29 mmol) and the resulting mixture was heated to 70° C. for 2 h, cooled to rt, and then concentrated in vacuo. The crude residue was purified by reverse phase prep-HPLC to give the title compound. LCMS (ESI+): m/z=577.3 (M+H)$^+$. $^1$H NMR (400 MHz, DMSO-d$_6$) δ ppm 8.54 (d, J=2.32 Hz, 1H) 8.35 (s, 1H) 7.92 (br d, J=5.75 Hz, 1H) 7.84 (d, J=0.98 Hz, 1H) 7.07 (br s, 1H) 6.99

(d, J=7.21 Hz, 1H) 6.54-6.58 (m, 1H) 6.43 (br s, 1H) 6.20 (d, J=7.34 Hz, 1H) 4.51 (br s, 1H) 3.98-4.05 (m, 2H) 3.65 (br t, J=5.87 Hz, 2H) 3.20-3.25 (m, 2H) 2.55-2.78 (m, 8H) 2.38 (br t, J=7.40 Hz, 2H) 1.94-2.03 (m, 1H) 1.80 (br s, 1H) 1.71-1.76 (m, 2H) 1.49-1.58 (m, 2H) 1.36-1.44 (m, 2H).

Compound 713: (S)-4-(((S)-2-fluoro-3-methoxypropyl) (4-(5,6,7,8-tetrahydro-1,8-naphthyridin-2-yl) butyl)amino)-2-((5-methylpyrimidin-2-yl) amino) butanoic acid: To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (152 mg, 336 µmol) and 2-chloro-5-methyl-pyrimidine (36 mg, 280 µmol) in t-AmOH (2 mL) was added 2.0M t-BuONa in THF (280 µL, 560 µmol) then t-BuXPhos-Pd-G3 (22 mg, 28 µmol) and the resulting mixture was heated to 100° C. for 5 h, cooled to rt, and then concentrated in vacuo to give a (S)-tert-butyl 4-(((S)-2-fluoro-3-methoxypropyl) (4-(5,6,7,8-tetrahydro-1, 8-naphthyridin-2-yl) butyl)amino)-2-((5-methylpyrimidin-2-yl) amino) butanoate intermediate, LCMS (ESI+): m/z=545.3 (M+H)$^+$, which was used without further purification. Of the butanoate intermediate, 180 mg, 330 µmol) was taken up in DCM (2 mL) and TFA (600 µL) and the resulting mixture was stirred at rt for 6 h and then concentrated in vacuo. The crude residue was purified by reverse phase prep-HPLC to give the title compound. LCMS (ESI+): m/z=489.3 (M+H)$^+$. $^1$H NMR (400 MHz, DMSO-d$_6$) δ ppm 14.34 (br s, 1H) 10.93 (br s, 1H) 8.30 (s, 2H) 8.13 (br s, 1H) 7.82 (br s, 1H) 7.60 (d, J=7.34 Hz, 1H) 6.63 (d, J=7.34 Hz, 1H) 5.24-5.44 (m, 1H) 4.46 (br s, 1H) 3.63 (br s, 1H) 3.49-3.59 (m, 2H) 3.33-3.48 (m, 4H) 3.31 (d, J=0.98 Hz, 3H) 3.14-3.27 (m, 3H) 2.66-2.77 (m, 4H) 2.14-2.37 (m, 2H) 2.10 (s, 3H) 1.63-1.86 (m, 6H).

Compound 714: (S)-2-((3-cyanopyrazin-2-yl) amino)-4-((2-(2,2-difluoroethoxy)ethyl) (4-(5,6,7,8-tetrahydro-1,8-naphthyridin-2-yl) butyl)amino) butanoic acid: To a mixture of (S)-2-amino-4-(((S)-2-fluoro-3-methoxypropyl) (4-(5,6,7,8-tetrahydro-1,8-naphthyridin-2-yl) butyl)amino) butanoic acid hydrochloride (150 mg, 333 µmol) in i-PrOH (2 mL) was added DIPEA (290 µL, 1.66 mmol) then 3-chloropyrazine-2-carbonitrile (93 mg, 665 µmol) and the resulting mixture was heated to 70° C. for 2 h, cooled to rt, adjusted to pH=6 by the addition of 1 M aq. HCl, and then concentrated in vacuo. The crude residue was purified by reverse phase prep-HPLC to give the title compound. LCMS (ESI+): m/z=518.2 (M+H)$^+$. $^1$H NMR (400 MHz, DMSO-d$_6$) δ ppm 14.13 (br s, 1H) 10.22 (br s, 1H) 8.37 (d, J=2.43 Hz, 1H) 8.03 (d, J=2.43 Hz, 2H) 7.84-7.90 (m, 1H) 7.61 (d, J=7.28 Hz, 1H) 6.61 (d, J=7.28 Hz, 1H) 6.00-6.33 (m, 1H) 4.54-4.66 (m, 1H) 3.90 (br t, J=4.74 Hz, 2H) 3.75 (td, J=15.27, 3.42 Hz, 2H) 3.35 (br s, 4H) 3.16 (br s, 4H) 2.67-2.76 (m, 4H) 2.28-2.41 (m, 2H) 1.76-1.87 (m, 2H) 1.63-1.75 (m, 4H).

Compound 715: (S)-2-([4,4'-bipyridin]-2-ylamino)-4-((2-(2,2-difluoroethoxy)ethyl) (4-(5,6,7,8-tetrahydro-1,8-naphthyridin-2-yl) butyl)amino) butanoic acid: To a mixture of (S)-2-((4-bromopyridin-2-yl) amino)-4-((2-(2,2-difluoroethoxy)ethyl) (4-(5,6,7,8-tetrahydro-1,8-naphthyridin-2-yl) butyl)amino) butanoic acid (50 mg, 88 µmol) and 4-pyridyl-boronic acid (32 mg, 263 µmol) in dioxane (2 mL) and H$_2$O (0.5 mL) was added Pd(dppf)Cl$_2$.CH$_2$Cl$_2$ (7 mg, 9 µmol) and K$_2$CO$_3$ (36 mg, 262 µmol) and the resulting mixture was heated to 100° C. for 2 h, cooled to rt, and then concentrated in vacuo. The crude residue was purified by reverse phase prep-HPLC to give the title compound. LCMS (ESI+): m/z=569.3 (M+H)$^+$. $^1$H NMR (400 MHz, Methanol-d$_4$) δ ppm 9.07 (d, J=6.85 Hz, 2H) 8.53 (d, J=6.85 Hz, 2H) 8.18 (d, J=6.60 Hz, 1H) 7.82 (d, J=0.98 Hz, 1H) 7.60 (d, J=7.34 Hz, 1H) 7.46 (dd, J=6.72, 1.71 Hz, 1H) 6.67 (d, J=7.34 Hz, 1H) 5.87-6.19 (m, 1H) 4.92-4.96 (m, 1H) 3.96-4.05 (m, 2H) 3.80 (td, J=14.70, 3.61 Hz, 2H) 3.60-3.69 (m, 1H) 3.51 (br dd, J=10.94, 5.44 Hz, 5H) 3.37 (br t, J=7.89 Hz, 2H) 2.78-2.85 (m, 4H) 2.61-2.72 (m, 1H) 2.41-2.53 (m, 1H) 1.78-1.99 (m, 6H).

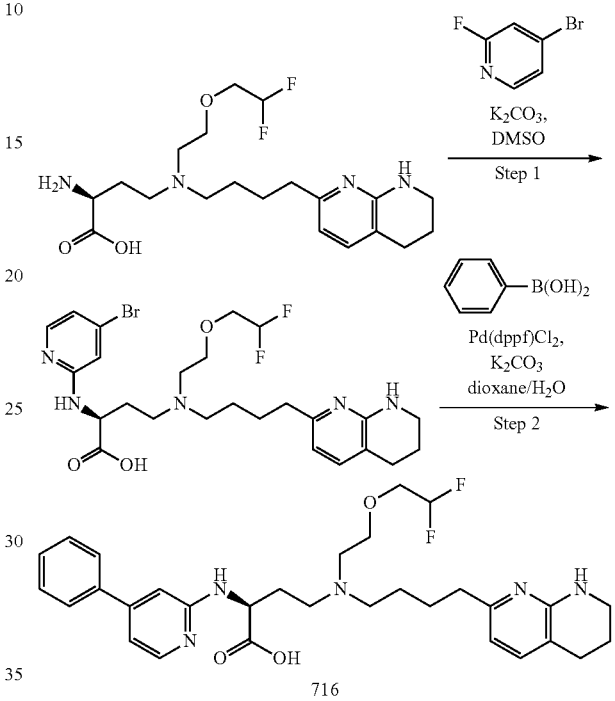

Scheme 62, Compound 716

Step 1: (S)-2-((4-bromopyridin-2-yl) amino)-4-((2-(2,2-difluoroethoxy)ethyl) (4-(5,6,7,8-tetrahydro-1, 8-naphthyridin-2-yl) butyl)amino) butanoic acid To a mixture of (S)-2-amino-4-((2-(2,2-difluoroethoxy) ethyl) (4-(5,6,7,8-tetrahydro-1,8-naphthyridin-2-yl) butyl) amino) butanoic acid hydrochloride (500 mg, 1.11 mmol) in DMSO (4 mL) was added K$_2$CO$_3$ (766 mg, 5.54 mmol) and 4-bromo-2-fluoropyridine (234 mg, 1.33 mmol) and the resulting mixture was heated to 130° C. for 1 h, cooled to rt, adjusted to pH=6 by the addition of 1 M aq. HCl, and then concentrated in vacuo. The crude residue was purified by reverse phase prep-HPLC to give the title compound. LCMS (ESI+): m/z=571.2 (M+H)$^+$.

Step 2: (S)-4-((2-(2,2-difluoroethoxy)ethyl) (4-(5,6, 7,8-tetrahydro-1,8-naphthyridin-2-yl) butyl)amino)-2-((4-phenylpyridin-2-yl) amino) butanoic acid To a mixture of (S)-2-((4-bromopyridin-2-yl) amino)-4-((2-(2,2-difluoroethoxy)ethyl) (4-(5,6,7,8-tetrahydro-1,8-naphthyridin-2-yl) butyl)amino) butanoic acid (50 mg, 88 µmol) and phenylboronic acid (32 mg, 263 µmol) in dioxane (2 mL) and H$_2$O (0.5 mL) was added Pd(dppf)Cl$_2$.CH$_2$Cl$_2$ (7 mg, 9 µmol) and K$_2$CO$_3$ (36 mg, 263 µmol) and the resulting mixture was heated to 100° C. for 2 h, cooled to rt, and then concentrated in vacuo. The crude residue was purified by reverse phase prep-HPLC to give the title compound. LCMS (ESI+): m/z=568.3 (M+H)$^+$. $^1$H NMR (400 MHz, Methanol-d$_4$) δ ppm 8.00 (d, J=6.60 Hz, 1H) 7.81-7.86 (m, 2H) 7.56-7.61 (m, 4H) 7.45 (d, J=1.34 Hz, 1H) 7.35 (dd, J=6.79, 1.65 Hz, 1H) 6.65 (d, J=7.34 Hz, 1H) 5.86-6.17 (m, 1H) 4.75-4.80 (m, 1H) 3.95-4.03 (m, 2H) 3.80 (td, J=14.76, 3.62 Hz, 2H) 3.58-3.66 (m, 1H) 3.47-3.56 (m, 5H) 3.34-3.40 (m, 2H) 2.76-2.84 (m, 4H) 2.56-2.67 (m, 1H) 2.34-2.46 (m, 1H) 1.75-1.98 (m, 6H).

Scheme 63, Compound 717

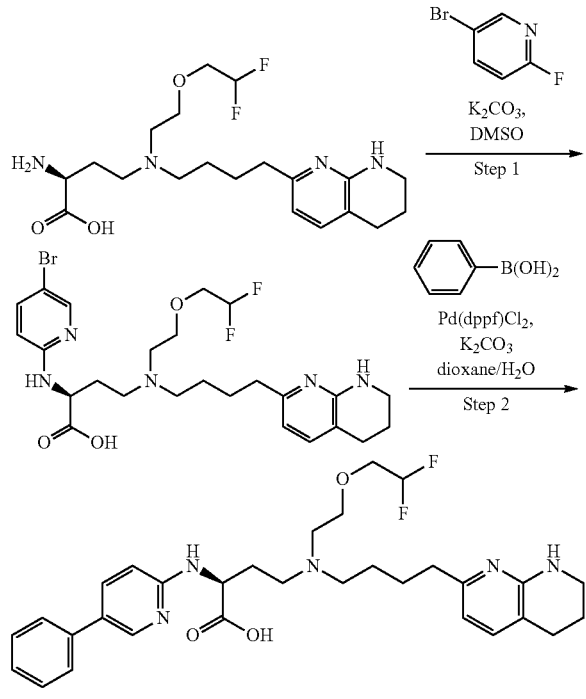

Step 1: (S)-2-((5-bromopyridin-2-yl) amino)-4-((2-(2,2-difluoroethoxy)ethyl) (4-(5,6,7,8-tetrahydro-1,8-naphthyridin-2-yl) butyl)amino) butanoic acid To a mixture of (S)-2-amino-4-((2-(2,2-difluoroethoxy)ethyl) (4-(5,6,7,8-tetrahydro-1,8-naphthyridin-2-yl) butyl) amino) butanoic acid hydrochloride (200 mg, 444 µmol) in DMSO (3 mL) was added
(306 mg, 2.22 mmol) and 5-bromo-2-fluoropyridine (94 mg, 532 µmol) and the resulting mixture was heated to 130° C. for 15 h, cooled to rt, adjusted to pH=6 by the addition of 1 M aq. HCl, and then concentrated in vacuo. The crude residue was purified by reverse phase prep-HPLC to give the title compound. LCMS (ESI+): m/z=571.2 (M+H)⁺.

Step 2: 2-((5-phenylpyridin-2-yl) amino) butanoic acid

To a mixture of (S)-2-((5-bromopyridin-2-yl) amino)-4-((2-(2,2-difluoroethoxy)ethyl) (4-(5,6,7,8-tetrahydro-1,8-naphthyridin-2-yl) butyl)amino) butanoic acid (20 mg, 35 µmol) and phenylboronic acid (13 mg, 105 µmol) in dioxane (2 mL) and H$_2$O (0.5 mL) was added Pd(dppf)Cl$_2$·CH$_2$Cl$_2$ (3 mg, 4 µmol) and K$_2$CO$_3$ (15 mg, 105 µmol) and the resulting mixture was heated to 100° C. for 2 h, cooled to rt, and then concentrated in vacuo. The crude residue was purified by reverse phase prep-HPLC to give the title compound. LCMS (ESI+): m/z=568.3 (M+H)⁺. ¹H NMR (400 MHz, Methanol-d$_4$) δ ppm 8.36 (dd, J=9.35, 2.26 Hz, 1H) 8.18 (d, J=1.83 Hz, 1H) 7.62-7.67 (m, 2H) 7.59 (d, J=7.34 Hz, 1H) 7.48-7.54 (m, 2H) 7.42-7.47 (m, 1H) 7.37 (d, J=9.29 Hz, 1H) 6.66 (d, J=7.34 Hz, 1H) 5.87-6.19 (m, 1H) 4.79 (dd, J=7.89, 5.44 Hz, 1H) 3.95-4.05 (m, 2H) 3.80 (td, J=14.76, 3.61 Hz, 2H) 3.57-3.65 (m, 1H) 3.46-3.56 (m, 5H) 3.34-3.40 (m, 2H) 2.76-2.85 (m, 4H) 2.57-2.68 (m, 1H) 2.36-2.48 (m, 1H) 1.77-1.99 (m, 6H).

Compound 718: (S)-4-(((S)-2-fluoro-3-methoxypropyl) (4-(5,6,7,8-tetrahydro-1,8-naphthyridin-2-yl) butyl)amino)-2-((7-methyl-7H-pyrrolo[2,3-d]pyrimidin-4-yl) amino) butanoic acid: To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (150 mg, 331 µmol), 4-chloro-7-methyl-7H-pyrrolo[2,3-d]pyrimidine (48 mg, 286) in t-AmOH (3 mL) was added 2.0M t-BuONa in THF (286 L, 572 µmol) then t-BuXPhos-Pd-G3 (23 mg, 29 µmol) and the resulting mixture was heated to 100° C. for 15 h, cooled to rt, and then concentrated in vacuo to give a tert-butyl (S)-4-(((S)-2-fluoro-3-methoxypropyl) (4-(5,6,7,8-tetrahydro-1,8-naphthyridin-2-yl) butyl)amino)-2-((7-methyl-7H-pyrrolo[2,3-d]pyrimidin-4-yl) amino) butanoate intermediate, LCMS (ESI+): m/z=584.4 (M+H)⁺, which was used without further purification. Of the butanoate intermediate, 80 mg, 141 µmol was taken up in DCM (1 mL) and TFA (400 µL) and the resulting mixture was stirred at rt for 6 h and then concentrated in vacuo. The crude residue was purified by reverse phase prep-HPLC to give the title compound. LCMS (ESI+): m/z=528.3 (M+H)⁺.

Compound 719: (S)-4-(((S)-2-fluoro-3-methoxypropyl) (4-(5,6,7,8-tetrahydro-1,8-naphthyridin-2-yl)butyl)amino)-2-((6-methylpyrazin-2-yl)amino)butanoic acid: To a mixture of tert-butyl (S)-2-amino-4-(((S)-2-fluoro-3-methoxypropyl) (4-(5,6,7,8-tetrahydro-1,8-naphthyridin-2-yl) butyl) amino) butanoate (211 mg, 467 µmol) and 2-chloro-6-methyl-pyrazine (50 mg, 389 µmol) in t-AmOH (3 mL) was added 2.0M t-BuONa in THF (389 µL, 778 µmol) then t-BuXPhos-Pd-G3 (31 mg, 39 µmol) and the resulting mixture was heated to 100° C. for 15 h, cooled to rt, and then concentrated in vacuo to give a tert-butyl (S)-4-(((S)-2-fluoro-3-methoxypropyl) (4-(5,6,7,8-tetrahydro-1,8-naphthyridin-2-yl) butyl)amino)-2-((6-methylpyrazin-2-yl) amino) butanoate intermediate, LCMS (ESI+): m/z=545.4 (M+H)⁺, which was used without further purification. Of the butanoate intermediate, 268 mg, 494 µmol, was taken up in DCM (2 mL) and TFA (1.5 mL) and the resulting mixture was stirred at rt for 6 h and then concentrated in vacuo. The crude residue was purified by reverse phase prep-HPLC to give the title compound. LCMS (ESI+): m/z=489.3 (M+H)⁺.

Compound 720: (S)-4-(((S)-2-fluoro-3-methoxypropyl) (4-(5,6,7,8-tetrahydro-1,8-naphthyridin-2-yl)butyl)amino)-2-(quinoxalin-2-ylamino)butanoic acid: To a mixture of tert-butyl (S)-2-amino-4-(((S)-2-fluoro-3-methoxypropyl) (4-(5,6,7,8-tetrahydro-1,8-naphthyridin-2-yl) butyl)amino) butanoate (211 mg, 467 µmol) and 2-chloroquinoxaline (64 mg, 389 µmol) in t-AmOH (3 mL) was added 2.0M t-BuONa in THF (389 µL, 778 µmol) then t-BuXPhos-Pd-G3 (31 mg, 39 µmol) and the resulting mixture was heated to 100° C. for 15 h, cooled to rt, and then concentrated in vacuo to give a tert-butyl (S)-4-(((S)-2-fluoro-3-methoxypropyl) (4-(5,6,7,8-tetrahydro-1,8-naphthyridin-2-yl) butyl) amino)-2-(quinoxalin-2-ylamino) butanoate intermediate, LCMS (ESI+): m/z=581.4 (M+H)⁺, which was used without further purification. Of the butanoate intermediate, 309 mg, 533 µmol, was taken up in DCM (2 mL) and TFA (1.5 mL) and the resulting mixture was stirred at rt for 6 h and then concentrated in vacuo. The crude residue was purified by reverse phase prep-HPLC to give the title compound. LCMS (ESI+): m/z=525.3 (M+H)⁺.

Compound 721: (S)-4-(((S)-2-fluoro-3-methoxypropyl) (4-(5,6,7,8-tetrahydro-1,8-naphthyridin-2-yl)butyl)amino)-2-((6-methyl-2-(pyridin-4-yl)pyrimidin-4-yl)amino)butanoic acid: To a mixture of tert-butyl (S)-2-amino-4-(((S)-2-fluoro-3-methoxypropyl) (4-(5,6,7,8-tetrahydro-1,8-naphthyridin-2-yl) butyl)amino) butanoate (211 mg, 467 µmol) and 4-chloro-6-methyl-2-(4-pyridyl)pyrimidine (80 mg, 389 µmol) in t-AmOH (3 mL) was added 2.0M t-BuONa in THF (389 µL, 778 µmol) then t-BuXPhos-Pd-G3 (31 mg, 39 µmol) and the resulting mixture was heated to 100° C. for 15 h, cooled to rt, and then concentrated in vacuo to give a tert-butyl (S)-4-(((S)-2-fluoro-3-methoxypropyl) (4-(5,6,7,8-tetrahydro-1,8-naphthyridin-2-yl) butyl) amino)-2-((6-methyl-2-(pyridin-4-yl) pyrimidin-4-yl) amino) butanoate intermediate, LCMS (ESI+): m/z=622.4 (M+H)⁺, which was used without further purification. Of the butanoate intermediate, 270 mg, 447 µmol, was taken up in DCM (2 mL) and TFA (1.5 mL) and the resulting mixture was stirred at rt for 6 h and then concentrated in vacuo. The crude residue was purified by reverse phase prep-HPLC to give the title compound. LCMS (ESI+): m/z=566.3 (M+H)⁺.

Compound 722: (S)-4-(((S)-2-fluoro-3-methoxypropyl) (4-(5,6,7,8-tetrahydro-1,8-naphthyridin-2-yl) butyl)amino)-2-((1-methyl-1H-indazol-3-yl) amino) butanoic acid: To a mixture of tert-butyl (S)-2-amino-4-(((S)-2-fluoro-3-methoxypropyl) (4-(5,6,7,8-tetrahydro-1,8-naphthyridin-2-yl) butyl)amino) butanoate (109 mg, 240 µmol) and 3-bromo-1-methyl-1H-indazole (42 mg, 200 µmol) in THF (2 mL) was added 2.0M t-BuONa in THF (200 µL, 400 µmol) then t-BuXPhos-Pd-G3 (31 mg, 39 µmol) and the resulting mixture was heated to 100° C. for 15 h, cooled to rt, and then concentrated in vacuo. The crude residue was purified by reverse phase prep-HPLC to give a tert-butyl (S)-4-(((S)-2-fluoro-3-methoxypropyl) (4-(5,6,7,8-tetrahydro-1,8-naphthyridin-2-yl) butyl)amino)-2-((1-methyl-1H-indazol-3-yl) amino) butanoate intermediate, LCMS (ESI+): m/z=583.4 (M+H)⁺. Of the butanoate intermediate, 150 mg, 258 µmol) was taken up in DCM (2 mL) and TFA (1.5 mL) and the resulting mixture was stirred at rt for 6 h and then concentrated in vacuo. The crude residue was purified by reverse phase prep-HPLC to give the title compound. LCMS (ESI+): m/z=527.3 (M+H)⁺.

Scheme 64, Compound 723

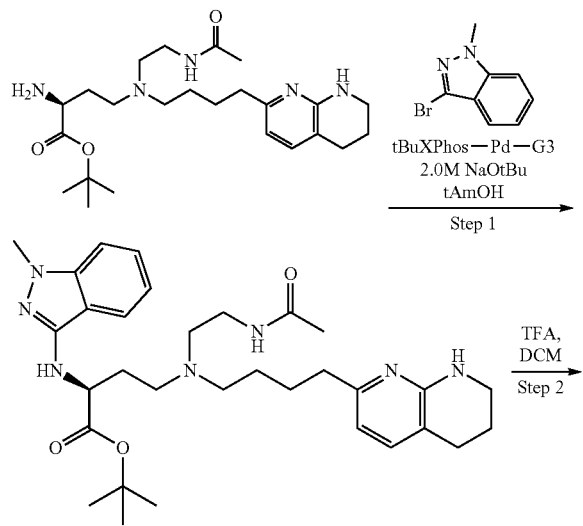

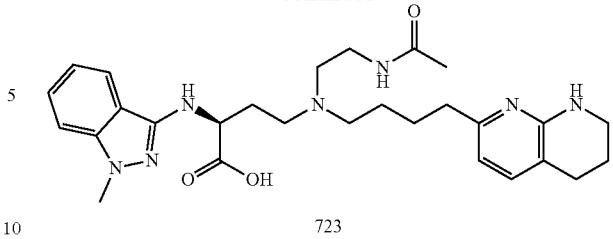

723

Step 1: (S)-tert-butyl 4-((2-acetamidoethyl) (4-(5,6,7,8-tetrahydro-1,8-naphthyridin-2-yl) butyl)amino)-2-((1-methyl-1H-indazol-3-yl) amino) butanoate To a mixture of (S)-tert-butyl 4-((2-acetamidoethyl) (4-(5,6,7,8-tetrahydro-1,8-naphthyridin-2-yl) butyl)amino)-2-aminobutanoate (130 mg, 290 µmol) and 3-bromo-1-methyl-1H-indazole (61 mg, 290 µmol) in t-AmOH (3 mL) was added 2.0M t-BuONa in THF (290 µL, 580 µmol) then t-Bu Xphos Pd G3 (23 mg, 29 µmol) and the resulting mixture was heated to 100° C. for 15 h, cooled to rt, and then concentrated in vacuo to give the title compound that was used without further purification. LCMS (ESI+): m/z=578.5 (M+H)⁺.

Step 2: (S)-4-((2-acetamidoethyl) (4-(5,6,7,8-tetrahydro-1,8-naphthyridin-2-yl) butyl)amino)-2-(benzo[d]thiazol-2-ylamino) butanoic acid (S)-tert-butyl 4-((2-acetamidoethyl) (4-(5,6,7,8-tetrahydro-1,8-naphthyridin-2-yl) butyl)amino)-2-((1-methyl-1H-indazol-3-yl) amino) butanoate (200 mg, 346 µmol) was taken up in 3:1 DCM/TFA (2 mL) and the resulting mixture was stirred at rt for 15 h and then concentrated in vacuo. The crude residue was purified by reverse phase prep-HPLC to give the title compound. LCMS (ESI+): m/z=522.3 (M+H)⁺. ¹H NMR (400 MHz, DMSO-d₆) δ ppm 7.79 (br t, J=5.40 Hz, 1H) 7.70 (d, J=8.16 Hz, 1H) 7.24-7.34 (m, 2H) 7.00 (d, J=7.28 Hz, 1H) 6.91 (t, J=6.73 Hz, 1H) 6.43 (br s, 1H) 6.22 (d, J=7.28 Hz, 1H) 4.11 (t, J=6.06 Hz, 1H) 3.71 (s, 3H) 3.22 (br t, J=5.29 Hz, 2H) 3.12 (dt, J=12.68, 6.23 Hz, 2H) 2.53-2.69 (m, 6H) 2.31-2.46 (m, 4H) 1.86-2.01 (m, 2H) 1.71-1.77 (m, 5H) 1.49-1.58 (m, 2H) 1.35-1.45 (m, 2H).

Compound 724: (S)-4-(((S)-2-fluoro-3-methoxypropyl) (4-(5,6,7,8-tetrahydro-1,8-naphthyridin-2-yl) butyl)amino)-2-(pyridin-3-ylamino) butanoic acid: To a mixture of (S)-tert-butyl 2-amino-4-(((S)-2-fluoro-3-methoxypropyl) (4-(5,6,7,8-tetrahydro-1,8-naphthyridin-2-yl) butyl)amino) butanoate (151 mg, 334 µmol) and 3-bromopyridine (44 mg, 278 µmol) in t-AmOH (2 mL) was added 2.0M t-BuONa in THF (278 µL, 556 µmol) then t-BuXPhos-Pd-G3 (22 mg, 28 µmol) and the resulting mixture was heated to 100° C. for 5 h, cooled to rt, and then concentrated in vacuo to give a (S)-tert-butyl 4-(((S)-2-fluoro-3-methoxypropyl) (4-(5,6,7,8-tetrahydro-1,8-naphthyridin-2-yl) butyl)amino)-2-(pyridin-3-ylamino) butanoate intermediate, LCMS (ESI+): m/z=530.3 (M+H)⁺, which was used without further purification. Of the butanoate intermediate, 160 mg, 302 µmol, was taken up in DCM (2 mL) was added TFA (600 µL) and the resulting mixture was stirred at rt for 6 h and then concentrated in vacuo. The crude residue was purified by reverse phase prep-HPLC to give the title compound. LCMS (ESI+): m/z=474.3 (M+H)⁺. ¹H NMR (400 MHz, DMSO-d₆) δ ppm 7.90 (d, J=2.45 Hz, 1H) 7.74 (d, J=4.40 Hz, 1H)

7.02-7.11 (m, 2H) 6.85 (dd, J=8.38, 1.53 Hz, 1H) 6.25 (d, J=7.34 Hz, 1H) 4.55-4.82 (m, 1H) 3.84-4.02 (m, 1H) 3.45-3.49 (m, 1H) 3.39-3.43 (m, 1H) 3.18-3.25 (m, 5H) 2.64-2.69 (m, 4H) 2.59 (br d, J=6.72 Hz, 4H) 2.30-2.42 (m, 2H) 1.86-1.93 (m, 1H) 1.67-1.82 (m, 3H) 1.46-1.59 (m, 2H) 1.31-1.43 (m, 2H).

Compound 725: (S)-4-((2-methoxyethyl)(4-(5,6,7,8-tetrahydro-1,8-naphthyridin-2-yl)butyl)amino)-2-(naphthalen-1-ylamino)butanoic acid: To a mixture of tert-butyl (S)-2-amino-4-((2-methoxyethyl) (4-(5,6,7,8-tetrahydro-1,8-naphthyridin-2-yl) butyl)amino) butanoate (151 mg, 334 µmol) and 1-iodonaphthalene (70 mg, 278 µmol) in t-AmOH (2 mL) was added 2.0M t-BuONa in THF (278 µL, 556 µmol) then t-BuXPhos-Pd-G3 (22 mg, 28 µmol) and the resulting mixture was heated to 100° C. for 5 h, cooled to rt, and then concentrated in vacuo to give a tert-butyl 4-((2-methoxyethyl) (4-(5,6,7,8-tetrahydro-1,8-naphthyridin-2-yl) butyl)amino)-2-(naphthalen-1-ylamino) butanoate intermediate, which was used without further purification. Of the butanoate intermediate, 160 mg, 302 µmol, was taken up in DCM (2 mL) and TFA (600 µL) and the resulting mixture was stirred at rt for 6 h and then concentrated in vacuo. The crude residue was purified by reverse phase prep-HPLC and then chiral SFC to give the title compound. LCMS (ESI+): m/z=491.3 (M+H)$^+$.

Compound 726: (S)-4-((2-morpholinoethyl) (4-(5,6,7,8-tetrahydro-1,8-naphthyridin-2-yl) butyl)amino)-2-(quinazolin-4-ylamino) butanoic acid. Prepared according to Scheme B using Procedure F with 2-morpholinoethan-1-amine, Procedure H with 4-chloroquinazoline, and Procedure P. LCMS theoretical m/z=548.3. [M+H]+, found 548.4.

Compound 727: (2S)-4-((2,3-dihydroxypropyl) (4-(5,6,7,8-tetrahydro-1,8-naphthyridin-2-yl) butyl)amino)-2-(quinazolin-4-ylamino) butanoic acid. Prepared according to Scheme B using Procedure F with 3-aminopropane-1,2-diol, Procedure H with 4-chloroquinazoline, and Procedure P. $^1$H NMR (400 MHz, Methanol-d$_4$) δ 8.87 (s, 1H), 8.54 (dd, J=8.7, 1.3 Hz, 1H), 8.19-8.05 (m, 1H), 7.97-7.79 (m, 2H), 7.58 (dd, J=7.3, 1.2 Hz, 1H), 6.62 (dd, J=7.3, 1.1 Hz, 1H), 5.37 (dd, J=8.0, 5.9 Hz, 1H), 4.02 (d, J=19.8 Hz, 1H), 3.70-3.43 (m, 6H), 2.81 (dt, J=19.3, 6.9 Hz, 6H), 2.51 (m, 1H), 2.02-1.67 (m, 8H). LCMS theoretical m/z=509.3. [M+H]+, found 509.3.

Compound 728: 4-((2-methoxyethyl) (4-(5,6,7,8-tetrahydro-1,8-naphthyridin-2-yl) butyl)amino)-2-(naphthalen-1-ylamino) butanoic acid. From chiral SFC purification of Example 329. LCMS (ESI+): m/z=491.3 (M+H)$^+$ Compound 729: (2S)-4-((3-fluoro-2-hydroxypropyl) (4-(5,6,7,8-tetrahydro-1,8-naphthyridin-2-yl) butyl)amino)-2-(quinazolin-4-ylamino) butanoic acid. Prepared according to Scheme B using Procedure F with 1-amino-3-fluoropropan-2-ol, Procedure H with 4-chloroquinazoline, and Procedure P. LCMS theoretical m/z=511.3. [M+H]+, found 511.3. $^1$H NMR (400 MHz, Methanol-d$_4$) δ 8.86 (d, J=1.3 Hz, 1H), 8.53 (d, J=8.2 Hz, 1H), 8.14 (dd, J=8.4, 6.8 Hz, 1H), 7.88 (t, J=8.3 Hz, 2H), 7.63-7.53 (m, 1H), 6.98 (t, J=8.4 Hz, 1H), 6.63 (dd, J=7.4, 2.2 Hz, 1H), 5.37 (d, J=7.5 Hz, 1H), 4.50 (d, J=3.7 Hz, 1H), 4.38 (d, J=3.8 Hz, 1H), 4.29 (m, 1H), 3.79-3.45 (m, 6H), 2.93-2.62 (m, 6H), 2.04-1.71 (m, 7H).

Compound 730: (S)-2-(quinazolin-4-ylamino)-4-((4-(5,6,7,8-tetrahydro-1,8-naphthyridin-2-yl) butyl) (thiazol-2-ylmethyl)amino) butanoic acid. Prepared according to Scheme A using Procedure A with thiazol-2-ylmethanamine, Procedure H with 4-chloroquinazoline, and Procedure P. LCMS theoretical m/z=532.2. [M+H]+, found 532.3.

Compound 731: (S)-4-((2-(3-oxomorpholino)ethyl) (4-(5,6,7,8-tetrahydro-1,8-naphthyridin-2-yl) butyl)amino)-2-(quinazolin-4-ylamino) butanoic acid. Prepared according to Scheme B using Procedure F with 4-(2-aminoethyl)morpholin-3-one, Procedure H with 4-chloroquinazoline, and Procedure P. LCMS theoretical m/z=562.3. [M+H]+, found 562.3.

Compound 732: (S)-4-(benzyl(4-(5,6,7,8-tetrahydro-1,8-naphthyridin-2-yl) butyl)amino)-2-(quinazolin-4-ylamino) butanoic acid. Prepared according to Scheme A using Procedure A with benzylamine, Procedure H with 4-chloroquinazoline, and Procedure P. LCMS theoretical m/z=525.3. [M+H]+, found 525.2.

Compound 733: (S)-4-(((R)-2-hydroxypropyl) (4-(5,6,7,8-tetrahydro-1,8-naphthyridin-2-yl) butyl)amino)-2-(quinazolin-4-ylamino) butanoic acid. Prepared according to Scheme A using Procedure A with (R)-1-aminopropan-2-ol, Procedure H with 4-chloroquinazoline, and Procedure P. LCMS theoretical m/z=493.3. [M+H]+, found 493.3.

Compound 734: (2S)-4-(((1,4-dioxan-2-yl) methyl) (4-(5,6,7,8-tetrahydro-1,8-naphthyridin-2-yl) butyl)amino)-2-(quinazolin-4-ylamino) butanoic acid. Prepared according to Scheme B using Procedure F with (1,4-dioxan-2-yl) methanamine, Procedure H with 4-chloroquinazoline, and Procedure P. LCMS [M+H]$^+$ found 535.3. 1H NMR (400 MHz, Methanol-d4) δ 8.88 (s, 1H), 8.56 (dq, J=8.5, 1.5 Hz, 1H), 8.20-8.07 (m, 1H), 7.88 (ddd, J=7.2, 3.8, 2.5 Hz, 2H), 7.58 (d, J=7.3 Hz, 1H), 6.62 (d, J=7.3 Hz, 1H), 5.35 (ddd, J=8.0, 6.1, 1.8 Hz, 1H), 4.06 (m, 1H), 3.84-3.66 (m, 4H), 3.66-3.40 (m, 5H), 3.29-3.17 (m, 2H), 2.80 (dt, J=21.2, 6.8 Hz, 5H), 2.68 (dt, J=16.3, 6.8 Hz, 1H), 2.49 (s, 1H), 2.02-1.64 (m, 8H).

Compound 735: (S)-4-(((S)-3-fluoro-2-hydroxypropyl) (4-(5,6,7,8-tetrahydro-1,8-naphthyridin-2-yl) butyl)amino)-2-(quinazolin-4-ylamino) butanoic acid. Prepared according to Scheme B using Procedure F with 1-amino-3-fluoropropan-2-ol, Procedure H with 4-chloroquinazoline, and Procedure P. LCMS [M+H]$^+$ found 511.2. 1H NMR (400 MHz, Methanol-d4) δ 8.87 (s, 1H), 8.56 (dt, J=8.8, 1.9 Hz, 1H), 8.14 (ddq, J=8.4, 7.1, 1.1 Hz, 1H), 7.94-7.80 (m, 2H), 7.58 (dt, J=7.4, 1.1 Hz, 1H), 6.62 (d, J=7.3 Hz, 1H), 5.38 (dd, J=8.3, 5.6 Hz, 1H), 4.50 (d, J=4.3 Hz, 1H), 4.38 (d, J=4.4 Hz, 1H), 4.27 (ddd, J=18.6, 9.1, 4.3 Hz, 1H), 3.75-3.41 (m, 6H), 2.92-2.63 (m, 5H), 2.54 (d, J=12.9 Hz, 1H), 2.11-1.65 (m, 7H).

Compound 736: (S)-4-(((S)-2-hydroxypropyl) (4-(5,6,7,8-tetrahydro-1,8-naphthyridin-2-yl) butyl)amino)-2-(quinazolin-4-ylamino) butanoic acid. Prepared according to Scheme A using Procedure A with (S)-1-aminopropan-2-ol, Procedure H with 4-chloroquinazoline, and Procedure P. LCMS theoretical m/z=493.3. [M+H]+, found 493.3.

Compound 737: (2S)-4-((morpholin-3-ylmethyl) (4-(5,6,7,8-tetrahydro-1,8-naphthyridin-2-yl) butyl)amino)-2-(quinazolin-4-ylamino) butanoic acid. Prepared according to Scheme B using Procedure F with morpholin-3-ylmethanamine, Procedure H with 4-chloroquinazoline, and Procedure P. LCMS [M+H]$^+$ found 534.2. $^1$H NMR (400 MHz, Methanol-d$_4$) δ 8.85 (d, J=4.2 Hz, 1H), 8.67-8.53 (m, 1H), 8.13 (ddt, J=8.5, 7.2, 1.4 Hz, 1H), 7.87 (td, J=8.1, 7.6, 1.7 Hz, 2H), 7.58 (dd, J=7.3, 1.4 Hz, 1H), 6.62 (d, J=7.3 Hz, 1H), 5.36 (ddd, J=10.3, 8.3, 5.5 Hz, 1H), 3.98 (dt, J=12.6, 3.3 Hz, 1H), 3.83 (dtd, J=16.5, 12.5, 7.2 Hz, 2H), 3.63-3.40 (m, 4H), 3.24-3.05 (m, 3H), 2.96 (dd, J=21.1, 13.3 Hz, 1H), 2.80 (dt, J=26.9, 6.4 Hz, 5H), 2.62-2.26 (m, 2H), 2.09-1.88 (m, 7H), 1.86-1.63 (m, 4H).

Compound 738: (2S)-4-((3,3-difluoro-2-hydroxypropyl) (4-(5,6,7,8-tetrahydro-1,8-naphthyridin-2-yl) butyl)amino)-2-(quinazolin-4-ylamino) butanoic acid. Prepared according to Scheme B using Procedure F with 3-amino-1,1-difluoropropan-2-ol, Procedure H with 4-chloroquinazoline, and Procedure P. LCMS theoretical m/z=529.3. [M+H]+, found 529.3.

Compound 739: (S)-4-(((S)-2,3-dihydroxypropyl) (4-(5,6,7,8-tetrahydro-1,8-naphthyridin-2-yl) butyl)amino)-2-(quinazolin-4-ylamino) butanoic acid. Prepared according to Scheme B using Procedure F with 3-amino-1,1-difluoropropan-2-ol, Procedure H with 4-chloroquinazoline, and Procedure P. LCMS [M+H]+ found 509.2. $^1$H NMR (400 MHz, Methanol-d$_4$) δ 8.86 (s, 1H), 8.64-8.48 (m, 1H), 8.22-8.06 (m, 1H), 7.95-7.80 (m, 2H), 7.58 (dd, J=7.3, 1.1 Hz, 1H), 6.62 (d, J=7.3 Hz, 1H), 5.36 (t, J=6.9 Hz, 1H), 4.06 (s, 1H), 3.76-3.40 (m, 5H), 2.81 (dt, J=18.5, 6.9 Hz, 6H), 2.49 (br s, 1H), 2.03-1.67 (m, 8H).

Compound 740: (S)-4-((2-hydroxy-2-methylpropyl) (4-(5,6,7,8-tetrahydro-1,8-naphthyridin-2-yl) butyl)amino)-2-(pyrido[2,3-d]pyrimidin-4-ylamino) butanoic acid. Prepared according to Scheme A using Procedure A with 1-amino-2-methylpropan-2-ol, Procedure H with 4-chloropyrido[2,3-d]pyrimidine, and Procedure P. LCMS theoretical m/z=508.3. [M+H]+, found 508.3.

Compound 741: (S)-4-((2-hydroxy-2-methylpropyl) (4-(5,6,7,8-tetrahydro-1,8-naphthyridin-2-yl) butyl)amino)-2-(pyrido[3,2-d]pyrimidin-4-ylamino) butanoic acid. Prepared according to Scheme A using Procedure A with 1-amino-2-methylpropan-2-ol, Procedure H with 4-chloropyrido[3,2-d]pyrimidine, and Procedure P. LCMS theoretical m/z=508.3. [M+H]+, found 508.3.

Compound 742: (S)-2-((7-fluoro-2-methylquinazolin-4-yl) amino)-4-((2-hydroxy-2-methylpropyl) (4-(5,6,7,8-tetrahydro-1,8-naphthyridin-2-yl) butyl)amino) butanoic acid. Prepared according to Scheme A using Procedure A with 1-amino-2-methylpropan-2-ol, Procedure H with 1-amino-2-methylpropan-2-ol, and Procedure P. LCMS theoretical m/z=539.3. [M+H]+, found 539.3.

Compound 743: (S)-4-((2-hydroxy-2-methylpropyl) (4-(5,6,7,8-tetrahydro-1,8-naphthyridin-2-yl) butyl)amino)-2-(quinazolin-4-ylamino) butanoic acid. Prepared according to Scheme A using Procedure A with 1-amino-2-methylpropan-2-ol, Procedure H with 4-chloroquinazoline, and Procedure P. LCMS theoretical m/z=507.3. [M+H]+, found 507.3.

Compound 744: (S)-4-(((S)-2-fluoro-3-methoxypropyl) (4-(5,6,7,8-tetrahydro-1,8-naphthyridin-2-yl) butyl)amino)-2-(pyrido[3,2-d]pyrimidin-4-ylamino) butanoic acid. Prepared according to Scheme B using Procedure F with (S)-2-fluoro-3-methoxypropan-1-amine, Procedure H with 4-chloropyrido[3,2-d]pyrimidine, and Procedure P. LCMS theoretical m/z=526.3. [M+H]+, found 526.3.

Compound 745: (S)-4-(methoxy(4-(5,6,7,8-tetrahydro-1,8-naphthyridin-2-yl) butyl)amino)-2-(quinazolin-4-ylamino) butanoic acid. Prepared according to Scheme B using Procedure F with O-methylhydroxylamine, Procedure H with 4-chloroquinazoline, and Procedure P. LCMS [M+H]+ found 465.2. $^1$H NMR (400 MHz, Methanol-d$_4$) δ 8.83 (d, J=0.9 Hz, 1H), 8.53 (dd, J=8.6, 1.3 Hz, 1H), 8.12 (ddt, J=8.4, 7.2, 1.2 Hz, 1H), 7.87 (ddd, J=8.4, 6.7, 1.1 Hz, 2H), 7.55 (dd, J=7.3, 1.2 Hz, 1H), 6.57 (d, J=7.3 Hz, 1H), 5.41 (dd, J=9.3, 4.7 Hz, 1H), 3.62 (d, J=1.2 Hz, 3H), 3.50 (t, J=5.7 Hz, 2H), 3.02-2.88 (m, 2H), 2.89-2.76 (m, 3H), 2.70 (t, J=7.7 Hz, 2H), 2.50 (ddd, J=14.6, 7.4, 5.1 Hz, 1H), 2.37-2.20 (m, 1H), 1.96 (p, J=6.1 Hz, 2H), 1.81-1.47 (m, 4H).

Compound 746: (S)-4-((2-methoxy-2-methylpropyl) (4-(5,6,7,8-tetrahydro-1,8-naphthyridin-2-yl) butyl)amino)-2-(quinazolin-4-ylamino) butanoic acid. Prepared according to Scheme A using Procedure A with 2-methoxy-2-methylpropan-1-amine, Procedure H with 4-chloroquinazoline, and Procedure P. LCMS theoretical m/z=521.3. [M+H]+, found 521.3.

Compound 747: (S)-2-((7-fluoro-2-methylquinazolin-4-yl) amino)-4-((2-methoxy-2-methylpropyl) (4-(5,6,7,8-tetrahydro-1,8-naphthyridin-2-yl) butyl)amino) butanoic acid. Prepared according to Scheme A using Procedure A with 2-methoxy-2-methylpropan-1-amine, Procedure H with 4-chloro-7-fluoro-2-methylquinazoline, and Procedure P. LCMS theoretical m/z=553.3. [M+H]+, found 553.3.

Compound 748: (S)-4-(((3-hydroxyoxetan-3-yl) methyl) (4-(5,6,7,8-tetrahydro-1,8-naphthyridin-2-yl) butyl)amino)-2-(quinazolin-4-ylamino) butanoic acid. Prepared according to Scheme B using Procedure F with 3-(aminomethyl)oxetan-3-ol, Procedure H with 4-chloroquinazoline, and Procedure P. LCMS [M+H]+ found 521.2. 1H NMR (400 MHz, Methanol-d4) δ 8.81 (s, 1H), 8.47 (d, J=8.2 Hz, 1H), 8.18-8.03 (m, 1H), 7.93-7.75 (m, 2H), 7.58 (d, J=7.3 Hz, 1H), 6.63 (d, J=7.3 Hz, 1H), 5.29 (dd, J=8.8, 4.0 Hz, 1H), 4.69 (d, J=10.4 Hz, 4H), 3.90-3.43 (m, 4H), 3.30-3.15 (m, 1H), 3.06-2.56 (m, 6H), 2.30 (s, 1H), 2.16-1.69 (m, 6H).

Compound 749: (S)-4-((2-methoxy-2-methylpropyl) (4-(5,6,7,8-tetrahydro-1,8-naphthyridin-2-yl) butyl)amino)-2-(pyrido[2,3-d]pyrimidin-4-ylamino) butanoic acid. Prepared according to Scheme A using Procedure A with 2-methoxy-2-methylpropan-1-amine, Procedure H with 4-chloropyrido[2,3-d]pyrimidine, and Procedure P. LCMS theoretical m/z=522.3. [M+H]+, found 522.3.

Compound 750: (S)-4-((2-methoxy-2-methylpropyl) (4-(5,6,7,8-tetrahydro-1,8-naphthyridin-2-yl) butyl)amino)-2-(pyrido[3,2-d]pyrimidin-4-ylamino) butanoic acid. Prepared according to Scheme A using Procedure A with 2-methoxy-2-methylpropan-1-amine, Procedure H with 4-chloropyrido[3,2-d]pyrimidine, and Procedure P. LCMS theoretical m/z=522.3. [M+H]+, found 522.3.

Compound 751: (S)-4-((2-methoxy-2-methylpropyl) (4-(5,6,7,8-tetrahydro-1,8-naphthyridin-2-yl) butyl)amino)-2-((2-methylquinazolin-4-yl) amino) butanoic acid. Prepared according to Scheme A using Procedure A with 2-methoxy-2-methylpropan-1-amine, Procedure H with 4-chloro-2-methylquinazoline, and Procedure P. LCMS theoretical m/z=535.3. [M+H]+, found 535.3.

Compound 752: (S)-4-(((1-cyanocyclopropyl)methyl) (4-(5,6,7,8-tetrahydro-1,8-naphthyridin-2-yl) butyl)amino)-2-(quinazolin-4-ylamino) butanoic acid. Prepared according to Scheme B using Procedure F with 1-(aminomethyl)cyclopropane-1-carbonitrile, Procedure H with 4-chloroquinazoline, and Procedure P. LCMS theoretical m/z=514.3. [M+H]+, found 514.3.

Compound 753: (S)-4-(((S)-3-fluoro-2-methoxypropyl) (4-(5,6,7,8-tetrahydro-1,8-naphthyridin-2-yl) butyl)amino)-2-(quinazolin-4-ylamino) butanoic acid. Prepared according to Scheme B using Procedure F with (S)-3-fluoro-2-methoxypropan-1-amine, Procedure H with 4-chloroquinazoline, and Procedure P. LCMS theoretical m/z=525.3. [M+H]+, found 525.3.

Compound 754: (S)-4-(((S)-3-fluoro-2-methoxypropyl) (4-(5,6,7,8-tetrahydro-1,8-naphthyridin-2-yl) butyl)amino)-2-((2-methylquinazolin-4-yl) amino) butanoic acid. Prepared according to Scheme B using Procedure F with (S)-3-fluoro-2-methoxypropan-1-amine, Procedure H with 4-chloro-2-methylquinazoline, and Procedure P. LCMS theoretical m/z=539.3. [M+H]+, found 539.3.

Compound 755: (S)-4-(((S)-3-fluoro-2-methoxypropyl) (4-(5,6,7,8-tetrahydro-1,8-naphthyridin-2-yl) butyl)amino)-2-((7-fluoro-2-methylquinazolin-4-yl) amino) butanoic acid. Prepared according to Scheme B using Procedure F with (S)-3-fluoro-2-methoxypropan-1-amine, Procedure H with 4-chloro-7-fluoro-2-methylquinazoline, and Procedure P. LCMS theoretical m/z=557.3. [M+H]+, found 557.3.

Compound 756: (S)-2-(quinazolin-4-ylamino)-4-((4-(5,6,7,8-tetrahydro-1,8-naphthyridin-2-yl) butyl)amino) butanoic acid: To a mixture of (S)-4-(benzyl(4-(5,6,7,8-tetrahydro-1,8-naphthyridin-2-yl) butyl)amino)-2-(quinazolin-4-ylamino) butanoic acid (87 mg, 0.17 mmol) in MeOH (3 mL) was added 1 M aq. HCl (340 µL, 0.34 mmol) then 20 wt % Pd(OH)$_2$/C (12 mg) and the resulting mixture was stirred under an H$_2$ atmosphere for 6 h and then was filtered and concentrated in vacuo. The crude residue was purified by reverse phase prep-HPLC to give the title compound. LCMS theoretical m/z=435.2. [M+H]+, found 435.2.

Compound 757: (S)-2-((8-fluoroquinazolin-4-yl) amino)-4-(((R)-2-methoxypropyl) (4-(5,6,7,8-tetrahydro-1,8-naphthyridin-2-yl) butyl)amino) butanoic acid. Prepared according to Scheme A using Procedure A with (R)-2-methoxypropan-1-amine, Procedure H with 4-chloro-8-fluoroquinazoline, and Procedure P. LCMS theoretical m/z=525.3. [M+H]+, found 525.2.

Compound 758: (S)-2-((7-fluoroquinazolin-4-yl) amino)-4-(((R)-2-methoxypropyl) (4-(5,6,7,8-tetrahydro-1,8-naphthyridin-2-yl) butyl)amino) butanoic acid. Prepared according to Scheme A using Procedure A with (R)-2-methoxypropan-1-amine, Procedure H with 4-chloro-7-fluoroquinazoline, and Procedure P. LCMS theoretical m/z=525.3. [M+H]+, found 525.3.

Compound 759: (S)-4-(((R)-2-methoxypropyl) (4-(5,6,7,8-tetrahydro-1,8-naphthyridin-2-yl) butyl)amino)-2-((8-methylquinazolin-4-yl) amino) butanoic acid. Prepared according to Scheme A using Procedure A with (R)-2-methoxypropan-1-amine, Procedure H with 4-chloro-8-methylquinazoline, and Procedure P. LCMS theoretical m/z=521.3. [M+H]+, found 521.3.

Compound 760: (S)-4-(((S)-3-fluoro-2-methoxypropyl) (4-(5,6,7,8-tetrahydro-1,8-naphthyridin-2-yl) butyl)amino)-2-((7-methylquinazolin-4-yl) amino) butanoic acid. Prepared according to Scheme B using Procedure F with (S)-3-fluoro-2-methoxypropan-1-amine, Procedure H with 4-chloro-7-methylquinazoline, and Procedure P. LCMS theoretical m/z=539.3. [M+H]+, found 539.2.

Compound 761: (S)-4-(((S)-3-fluoro-2-methoxypropyl) (4-(5,6,7,8-tetrahydro-1,8-naphthyridin-2-yl) butyl)amino)-2-((7-fluoroquinazolin-4-yl) amino) butanoic acid. Prepared according to Scheme B using Procedure F with (S)-3-fluoro-2-methoxypropan-1-amine, Procedure H with 4-chloro-7-fluoroquinazoline, and Procedure P. LCMS theoretical m/z=545.3. [M+H]+, found 545.2.

Compound 762: (S)-4-(((S)-3-fluoro-2-methoxypropyl) (4-(5,6,7,8-tetrahydro-1,8-naphthyridin-2-yl) butyl)amino)-2-((8-methylquinazolin-4-yl) amino) butanoic acid. Prepared according to Scheme B using Procedure F with (S)-3-fluoro-2-methoxypropan-1-amine, Procedure H with 4-chloro-8-methylquinazoline, and Procedure P. LCMS theoretical m/z=539.3. [M+H]+, found 539.3.

Compound 763: (S)-4-(((S)-3-fluoro-2-methoxypropyl) (4-(5,6,7,8-tetrahydro-1,8-naphthyridin-2-yl) butyl)amino)-2-((8-fluoroquinazolin-4-yl) amino) butanoic acid. Prepared according to Scheme B using Procedure F with (S)-3-fluoro-2-methoxypropan-1-amine, Procedure H with 4-chloro-8-fluoroquinazoline, and Procedure P. LCMS theoretical m/z=543.3. [M+H]+, found 543.3.

Compound 764: (S)-4-(((R)-2-methoxypropyl) (4-(5,6,7,8-tetrahydro-1,8-naphthyridin-2-yl) butyl)amino)-2-((7-methylquinazolin-4-yl) amino) butanoic acid. Prepared according to Scheme A using Procedure A with (R)-2-methoxypropan-1-amine, Procedure H with 4-chloro-7-methylquinazoline, and Procedure P. LCMS theoretical m/z=521.3. [M+H]+, found 521.3.

Compound 765: (S)-2-((6-fluoroquinazolin-4-yl) amino)-4-(((R)-2-methoxypropyl) (4-(5,6,7,8-tetrahydro-1,8-naphthyridin-2-yl) butyl)amino) butanoic acid. Prepared according to Scheme A using Procedure A with (R)-2-methoxypropan-1-amine, Procedure H with 4-chloro-6-fluoroquinazoline, and Procedure P. LCMS theoretical m/z=525.3. [M+H]+, found 525.3.

Compound 766: (S)-4-(((S)-3-fluoro-2-methoxypropyl) (4-(5,6,7,8-tetrahydro-1,8-naphthyridin-2-yl) butyl)amino)-2-((6-fluoroquinazolin-4-yl) amino) butanoic acid. Prepared according to Scheme B using Procedure F with (S)-3-fluoro-2-methoxypropan-1-amine, Procedure H with 4-chloro-6-fluoroquinazoline, and Procedure P. LCMS theoretical m/z=543.3. [M+H]+, found 545.3.

Compound 767: (S)-4-(((R)-2-methoxypropyl) (4-(5,6,7,8-tetrahydro-1,8-naphthyridin-2-yl) butyl)amino)-2-(thieno[2,3-d]pyrimidin-4-ylamino) butanoic acid. Prepared according to Scheme A using Procedure A with (R)-2-methoxypropan-1-amine, Procedure H with 4-chlorothieno[2,3-d]pyrimidine, and Procedure P. LCMS theoretical m/z=513.3. [M+H]+, found 513.2.

Compound 768: (S)-4-(((S)-3-fluoro-2-methoxypropyl) (4-(5,6,7,8-tetrahydro-1,8-naphthyridin-2-yl) butyl)amino)-2-(thieno[2,3-d]pyrimidin-4-ylamino) butanoic acid. Prepared according to Scheme B using Procedure F with (S)-3-fluoro-2-methoxypropan-1-amine, Procedure H with 4-chlorothieno[2,3-d]pyrimidine, and Procedure P. LCMS theoretical m/z=531.3. [M+H]+, found 531.2.

Compound 769: (S)-4-(((S)-3-fluoro-2-methoxypropyl) (4-(5,6,7,8-tetrahydro-1,8-naphthyridin-2-yl) butyl)amino)-2-((6-methylthieno[2,3-d]pyrimidin-4-yl) amino) butanoic acid. Prepared according to Scheme B using Procedure F with (S)-3-fluoro-2-methoxypropan-1-amine, Procedure H with 4-chloro-6-methylthieno[2,3-d]pyrimidine, and Procedure P. LCMS theoretical m/z=545.3. [M+H]+, found 545.3.

Compound 770: (S)-4-(((R)-2-methoxypropyl) (4-(5,6,7,8-tetrahydro-1,8-naphthyridin-2-yl) butyl)amino)-2-((6-methylthieno[2,3-d]pyrimidin-4-yl) amino) butanoic acid. Prepared according to Scheme A using Procedure A with (R)-2-methoxypropan-1-amine, Procedure H with 4-chloro-6-methylthieno[2,3-d]pyrimidine, and Procedure P. LCMS theoretical m/z=527.3. [M+H]+, found 527.3.

Compound 771: (S)-4-(((R)-2-methoxypropyl) (4-(5,6,7,8-tetrahydro-1,8-naphthyridin-2-yl) butyl)amino)-2-(thieno[3,2-d]pyrimidin-4-ylamino) butanoic acid. Prepared according to Scheme A using Procedure A with (R)-2-methoxypropan-1-amine, Procedure H with 4-chlorothieno[3,2-d]pyrimidine, and Procedure P. LCMS theoretical m/z=513.3. [M+H]+, found 513.2.

Compound 772: (S)-4-(((R)-2-methoxypropyl) (4-(5,6,7,8-tetrahydro-1,8-naphthyridin-2-yl) butyl)amino)-2-((6-methylthieno[3,2-d]pyrimidin-4-yl) amino) butanoic acid. Prepared according to Scheme A using Procedure A with (R)-2-methoxypropan-1-amine, Procedure H with 4-chloro-6-methylthieno[3,2-d]pyrimidine, and Procedure P. LCMS theoretical m/z=527.3. [M+H]+, found 527.3.

Compound 773: (S)-4-(((S)-3-fluoro-2-methoxypropyl) (4-(5,6,7,8-tetrahydro-1,8-naphthyridin-2-yl) butyl)amino)-2-(thieno[3,2-d]pyrimidin-4-ylamino) butanoic acid. Prepared according to Scheme B using Procedure F with (S)-3-fluoro-2-methoxypropan-1-amine, Procedure H with 4-chlorothieno[3,2-d]pyrimidine, and Procedure P. LCMS theoretical m/z=531.3. [M+H]+, found 531.2.

Compound 774: (S)-4-(((S)-3-fluoro-2-methoxypropyl)(4-(5,6,7,8-tetrahydro-1,8-naphthyridin-2-yl) butyl)amino)-2-((6-methylthieno[3,2-d]pyrimidin-4-yl) amino) butanoic acid. Prepared according to Scheme B using Procedure F with (S)-3-fluoro-2-methoxypropan-1-amine, Procedure H with 4-chloro-6-methylthieno[3,2-d]pyrimidine, and Procedure P. LCMS theoretical m/z=545.3. [M+H]+, found 545.2.

Compound 775: (S)-4-(((S)-3-fluoro-2-methoxypropyl)(4-(5,6,7,8-tetrahydro-1,8-naphthyridin-2-yl) butyl)amino)-2-((5-methylthieno[2,3-d]pyrimidin-4-yl) amino) butanoic acid. Prepared according to Scheme B using Procedure F with (S)-3-fluoro-2-methoxypropan-1-amine, Procedure H with 4-chloro-5-methylthieno[2,3-d]pyrimidine, and Procedure P. LCMS theoretical m/z=545.3. [M+H]+, found 545.2.

Compound 776: (S)-4-(((R)-2-methoxypropyl) (4-(5,6,7,8-tetrahydro-1,8-naphthyridin-2-yl) butyl)amino)-2-((5-methylthieno[2,3-d]pyrimidin-4-yl) amino) butanoic acid. Prepared according to Scheme A using Procedure A with (R)-2-methoxypropan-1-amine, Procedure H with 4-chloro-5-methylthieno[2,3-d]pyrimidine, and Procedure P. LCMS theoretical m/z=527.3. [M+H]+, found 527.2.

Compound 777: (S)-2-((7,8-difluoroquinazolin-4-yl)amino)-4-(((S)-3-fluoro-2-methoxypropyl) (4-(5,6,7,8-tetrahydro-1,8-naphthyridin-2-yl) butyl)amino) butanoic acid. Prepared according to Scheme B using Procedure F with (S)-3-fluoro-2-methoxypropan-1-amine, Procedure H with 4-chloro-7,8-difluoroquinazoline, and Procedure P. LCMS theoretical m/z=561.3. [M+H]+, found 561.3.

Compound 778: (S)-2-((7,8-difluoroquinazolin-4-yl) amino)-4-(((R)-2-methoxypropyl) (4-(5,6,7,8-tetrahydro-1,8-naphthyridin-2-yl) butyl)amino) butanoic acid. Prepared according to Scheme A using Procedure A with (R)-2-methoxypropan-1-amine, Procedure H with 4,7-dichloroquinazoline, and Procedure P. LCMS theoretical m/z=543.3. [M+H]+, found 543.3.

Compound 779: (S)-4-(((S)-3-fluoro-2-methoxypropyl)(4-(5,6,7,8-tetrahydro-1,8-naphthyridin-2-yl) butyl)amino)-2-((7-methylthieno[3,2-d]pyrimidin-4-yl) amino) butanoic acid. Prepared according to Scheme B using Procedure F with (S)-3-fluoro-2-methoxypropan-1-amine, Procedure H with 4-chloro-7-methylthieno[3,2-d]pyrimidine, and Procedure P. LCMS theoretical m/z=545.3. [M+H]+, found 545.2.

Compound 780: (S)-4-(((R)-2-methoxypropyl) (4-(5,6,7,8-tetrahydro-1,8-naphthyridin-2-yl) butyl)amino)-2-((7-methylthieno[3,2-d]pyrimidin-4-yl) amino) butanoic acid. Prepared according to Scheme A using Procedure A with (R)-2-methoxypropan-1-amine, Procedure H with 4-chloro-7-methylthieno[3,2-d]pyrimidine, and Procedure P. LCMS theoretical m/z=527.3. [M+H]+, found 527.3.

BIOLOGICAL EXAMPLES

Example B1—Solid Phase Integrin $\alpha v \beta_6$ Binding Assay

Microplates were coated with recombinant human integrin $\alpha v \beta_6$ (2 μg/mL) in PBS (100 μL/well 25° C., overnight). The coating solution was removed, washed with wash buffer (0.05% Tween 20; 0.5 mM $MnCl_2$; in 1×TBS). The plate was blocked with 200 μL/well of Block Buffer (1% BSA; 5% sucrose; 0.5 mM $MnCl_2$; in 1×TBS) at 37° C. for 2 h. Dilutions of testing compounds and recombinant $TGF\beta_1$ LAP (0.67 μg/mL) in binding buffer (0.05% BSA; 2.5% sucrose; 0.5 mM $MnCl_2$; in 1×TBS) were added. The plate was incubated for 2 hours at 25° C., washed, and incubated for 1 hour with Biotin-Anti-hLAP. Bound antibody was detected by peroxidase-conjugated streptavidin. The $IC_{50}$ values for testing compounds were calculated by four-parameter logistic regression.

The $IC_{50}$ values obtained for $\alpha v \beta_6$ integrin inhibition for a first series of selected exemplary compounds are shown in Table B-1. The $IC_{50}$ values obtained for $\alpha v \beta_6$ integrin inhibition for a second series of selected exemplary compounds are shown in Table B-2. The compounds tested were compound samples prepared according to procedures described in the Synthetic Examples section, with the stereochemical purity as indicated in the Examples. The $IC_{50}$ values in Tables B-1 and B-2 are presented in four ranges: below 50 nM; from 50 nM to 250 nM; from above 250 nM to 1000 nM; and above 1000 nM.

TABLE B-1

| Compound No. | $\alpha v \beta_6$ Inhibition $IC_{50}$ (nM)-range | Compound No. | $\alpha v \beta_6$ Inhibition $IC_{50}$ (nM)-range |
|---|---|---|---|
| 1 | 250-1000 | 2 | 250-1000 |
|   |   | 4 | 50-250 |
| 5 | <50 | 6 | 50-250 |
| 7 | <50 | 8 | 50-250 |
| 9 | >1000 | 10 | <50 |
| 11 | <50 | 12 | <50 |
| 13 | 50-250 | 14 | <50 |
| 15 | <50 | 16 | <50 |
| 17 | <50 | 18 | <50 |
| 19 | <50 | 20 | <50 |
| 21 | <50 | 22 | <50 |
| 23 | <50 | 24 | <50 |
| 25 | <50 | 26 | <50 |
| 27 | <50 | 28 | <50 |
| 29 | <50 | 30 | <50 |
| 31 | <50 | 32 | <50 |
| 33 | <50 | 34 | >1000 |
| 35 | <50 | 36 | >1000 |
| 37 | 50-250 | 38 | <50 |
| 39 | <50 | 40 | <50 |
| 41 | <50 | 42 | <50 |
| 43 | <50 | 44 | <50 |
| 45 | <50 | 46 | <50 |
| 47 | <50 | 48 | <50 |
| 49 | <50 | 50 | <50 |
| 51 | <50 | 52 | <50 |
| 53 | <50 | 54 | <50 |
| 55 | <50 | 56 | <50 |
| 57 | <50 | 58 | <50 |
| 59 | <50 | 60 | <50 |
| 61 | <50 | 62 | <50 |
| 63 | <50 | 64 | <50 |
| 65 | <50 | 66 | <50 |

TABLE B-2

| Compound No. | $\alpha v \beta_6$ Inhibition $IC_{50}$ (nM)-range | Compound No. | $\alpha v \beta_6$ Inhibition $IC_{50}$ (nM)-range |
|---|---|---|---|
| 67 | <50 | 68 | <50 |
| 69 | <50 | 70 | <50 |
| 71 | <50 | 72 | <50 |
| 73 | <50 | 74 | <50 |
| 75 | <50 | 76 | <50 |
| 77 | <50 | 78 | <50 |
| 79 | <50 | 80 | <50 |
| 81 | <50 | 82 | <50 |
| 83 | <50 | 84 | 250-1000 |
| 85 | 250-1000 | 86 | 50-250 |
| 87 | 250-1000 | 88 | >1000 |
| 89 | <50 | 90 | <50 |
| 91 | <50 | 92 | <50 |
| 93 | <50 | 94 | <50 |
| 95 | >1000 | 96 | >1000 |

TABLE B-2-continued

| Compound No. | αvβ6 Inhibition IC$_{50}$ (nM)-range | Compound No. | αvβ6 Inhibition IC$_{50}$ (nM)-range |
|---|---|---|---|
| 97 | >1000 | 98 | >1000 |
| 99 | 250-1000 | 100 | <50 |
| 101 | 50-250 | 102 | >1000 |
| 103 | >1000 | 104 | >1000 |
| 105 | <50 | 106 | <50 |
| 107 | 250-1000 | 108 | >1000 |
| 109 | <50 | 110 | <50 |
| 111 | <50 | 112 | 250-1000 |
| | | 114 | <50 |
| 115 | 50-250 | 116 | 50-250 |
| 117 | <50 | 118 | >1000 |
| 119 | >1000 | 120 | >1000 |
| 121 | >1000 | 122 | 250-1000 |
| 123 | <50 | 124 | <50 |
| 125 | 50-250 | 126 | >1000 |
| 127 | 250-1000 | 128 | >1000 |
| 129 | <50 | 130 | <50 |
| 131 | 50-250 | 132 | 50-250 |
| 133 | 50-250 | 134 | 50-250 |
| 135 | 50-250 | 136 | <50 |
| 137 | <50 | 138 | <50 |
| 139 | <50 | 140 | <50 |
| 141 | 50-250 | 142 | >1000 |
| 143 | 50-250 | 144 | 50-250 |
| 145 | <50 | 146 | >1000 |
| 147 | 50-250 | | |

Example B2—The Disclosed Compounds Potently Inhibit $α_vβ_6$ in a Solid Phase Assay A third series of exemplary compounds was selected for testing in the solid phase integrin αvβ$_6$ binding assay. The compounds tested were compound samples prepared according to procedures described in the Synthetic Examples section, with the stereochemical purity as indicated in the Examples. As in Example B1, microplates were coated with recombinant human integrin αvβ$_6$ (2 µg/mL) in PBS (100 µL/well 25° C., overnight). The coating solution was removed, washed with wash buffer (0.05% Tween 20; 0.5 mM MnCl$_2$; in 1×TBS). The plate was blocked with 200 µL/well of Block Buffer (1% BSA; 5% sucrose; 0.5 mM MnCl$_2$; in 1×TBS) at 37° C. for 2 h. Dilutions of testing compounds and recombinant TGFβ$_1$ LAP (0.67 µg/mL) in binding buffer (0.05% BSA; 2.5% sucrose; 0.5 mM MnCl$_2$; in 1×TBS) were added. The plate was incubated for 2 hours at 25° C., washed, and incubated for 1 hour with Biotin-Anti-hLAP. Bound antibody was detected by peroxidase-conjugated streptavidin. The IC$_{50}$ values for testing compounds were calculated by a four-parameter logistic regression.

Example B3—The Disclosed Compounds Potently Inhibit $α_vβ_1$ in a Solid Phase Assay A fourth series of exemplary compounds was selected for testing in a solid phase integrin αvβ$_1$ binding assay. The compounds tested were compound samples prepared according to procedures described in the Synthetic Examples section, with the stereochemical purity as indicated in the Examples. Similar to Examples B1 and B2, microplates were coated with recombinant human integrin αvβ$_1$ (2 µg/mL) in PBS (100 µL/well 25° C., overnight). The coating solution was removed, washed with wash buffer (0.05% Tween 20; 0.5 mM MnCl$_2$; in 1×TBS). The plate was blocked with 200 µL/well of Block Buffer (1% BSA; 5% sucrose; 0.5 mM MnCl$_2$; in 1×TBS) at 37° C. for 2 h. Dilutions of testing compounds and recombinant TGFβ$_1$ LAP (0.67 µg/mL) in binding buffer (0.05% BSA; 2.5% sucrose; 0.5 mM MnCl$_2$; in 1×TBS) were added. The plate was incubated for 2 hours at 25° C., washed, and incubated for 1 hour with Biotin-Anti-hLAP. Bound antibody was detected by peroxidase-conjugated streptavidin. The IC$_{50}$ values for testing compounds were calculated by a four-parameter logistic regression.

Example B4—The Disclosed Compounds Potently Inhibit Human $α_vβ_6$ Integrin

A fifth series of exemplary compounds was selected for determining biochemical potency using the ALPHASCREEN® (Perkin Elmer, Waltham, Mass.) proximity-based assay (a bead-based, non-radioactive Amplified Luminescent Proximity Homogeneous Assay) as described previously (Ullman E F et al., Luminescent oxygen channeling immunoassay: Measurement of particle binding kinetics by chemiluminescence. Proc. Natl. Acad. Sci. USA, Vol. 91, pp. 5426-5430, June 1994). To gauge the potency of inhibitors of binding to human integrin $α_vβ_6$, inhibitor compounds and integrin were incubated together with recombinant TGFβ$_1$ LAP and biotinylated anti-LAP antibody plus acceptor and donor beads, following the manufacturer's recommendations. The donor beads were coated with streptavidin. The acceptor beads had a nitrilotriacetic acid Ni chelator, for binding to a 6×His-tag on human integrin $α_vβ_6$. All incubations occurred at room temperatures in 50 mM Tris-HCl, pH 7.5, 0.1% BSA supplemented with 1 mM each CaCl$_2$) and MgCl$_2$. The order of reagent addition was as follows: 1. αvβ$_6$ integrin, test inhibitor compound, LAP, biotinylated anti-LAP antibody and acceptor beads were all added together. 2. After 2 hours, donor beads were added. After another 30 min incubation, samples were read.

Integrin binding was evaluated by exciting donor beads at 680 nm, and measuring the fluorescent signal produced, between 520-620 nm, using a Biotek Instruments (Winooski, Vt., USA) SynergyNeo2 multimode plate reader. Compound potency was assessed by determining inhibitor concentrations required to reduce fluorescent light output by 50%. Data analysis for IC$_{50}$ determinations was carried out by nonlinear four parameter logistic regression analysis using Dotmatics ELN Software (Core Informatics Inc., Branford, Conn.).

Example B5—The Disclosed Compounds Potently Inhibit Human $α_vβ_1$ Integrin

A sixth series of exemplary compounds was selected for determining biochemical potency using the ALPHASCREEN® proximity-based assay as described in Example B4. To gauge the potency of inhibitors of binding to human integrin $α_vβ_1$, inhibitor compounds and integrin were incubated together with biotinylated, purified human fibronectin plus acceptor and donor beads, following the manufacturer's recommendations. The donor beads were coated with streptavidin. The acceptor beads had a nitrilotriacetic acid Ni chelator, for binding to a 6×His-tag on human integrin αvβ$_1$. All incubations occurred at room temperatures in 50 mM Tris-HCl, pH 7.5, 0.1% BSA supplemented with 1 mM each CaCl$_2$) and MgCl$_2$. The order of reagent addition was as follows: 1. αvβ$_1$ integrin, test inhibitor compound, fibronectin-biotinylated and acceptor beads were all added together. 2. After 2 hours, donor beads were added. After another 30 min incubation, samples were read.

Integrin binding was evaluated by exciting donor beads at 680 nm, and measuring the fluorescent signal produced, between 520-620 nm, using a Biotek Instruments (Winooski, Vt., USA) SynergyNeo2 multimode plate reader. Compound potency was assessed by determining inhibitor concentrations required to reduce fluorescent light output by 50%. Data analysis for $IC_{50}$ determinations was carried out by nonlinear four parameter logistic regression analysis using Dotmatics ELN Software (Core Informatics Inc., Branford, Conn.).

Combined Inhibition Results of Examples B1, B2, B3, B4, and B5

Table B-3 (FIG. 2) shows $IC_{50}$ data from Examples B1, B2, B3, B4, and B5 for inhibition of $\alpha v\beta_1$ and $\alpha v\beta_6$ integrin in the solid phase assays and inhibition of human $\alpha v\beta_1$ and $\alpha v\beta_6$ integrin in the ALPHASCREEN® assays. The $IC_{50}$ data is shown in four ranges: below 50 nM; from 50 nM to 250 nM; from above 250 nM to 1000 nM; and above 1000 nM.

Example B6—$\alpha_v\beta_6$ and $\alpha_v\beta_1$ Inhibition Activity Shown in Normal Human Bronchial Epithelial Cells and IPF-Derived Human Lung Fibroblasts Two latency associated peptide (LAP) adhesion binding assays were devised using primary human lung cells, including normal (healthy) human bronchial epithelial cells and human lung fibroblasts (healthy and IPF).

Figure 3B:
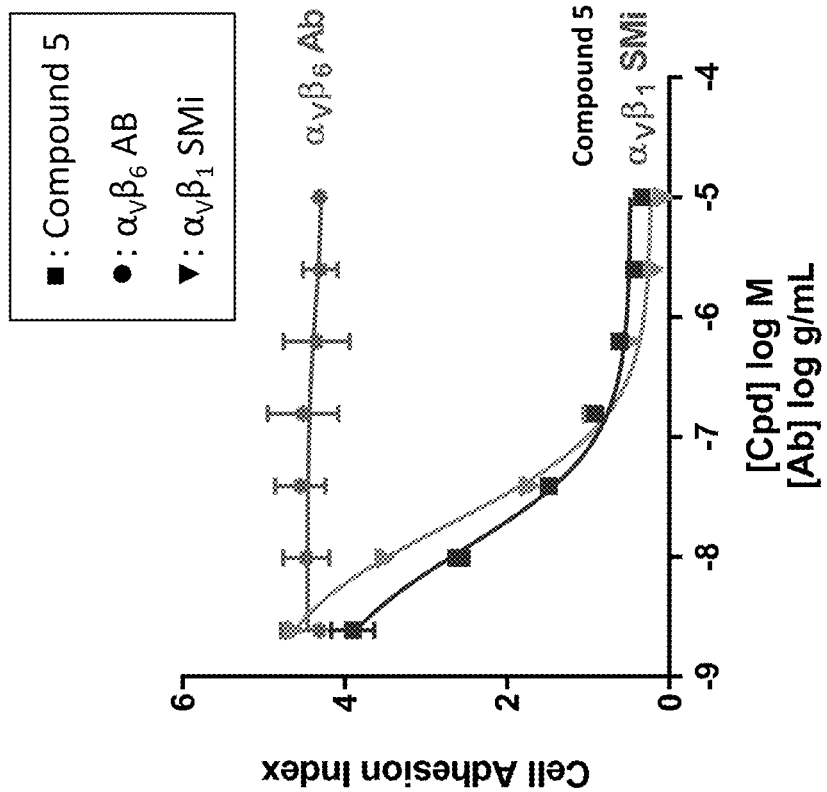
FIG. 3B shows that compound 5 and the αvβ1-selective small molecule inhibitor both substantially inhibited cell adhesion in the IPF-derived lung fibroblasts, in contrast to the selective antibody αvβ6 inhibitor, 3G9.
Figure 3A:
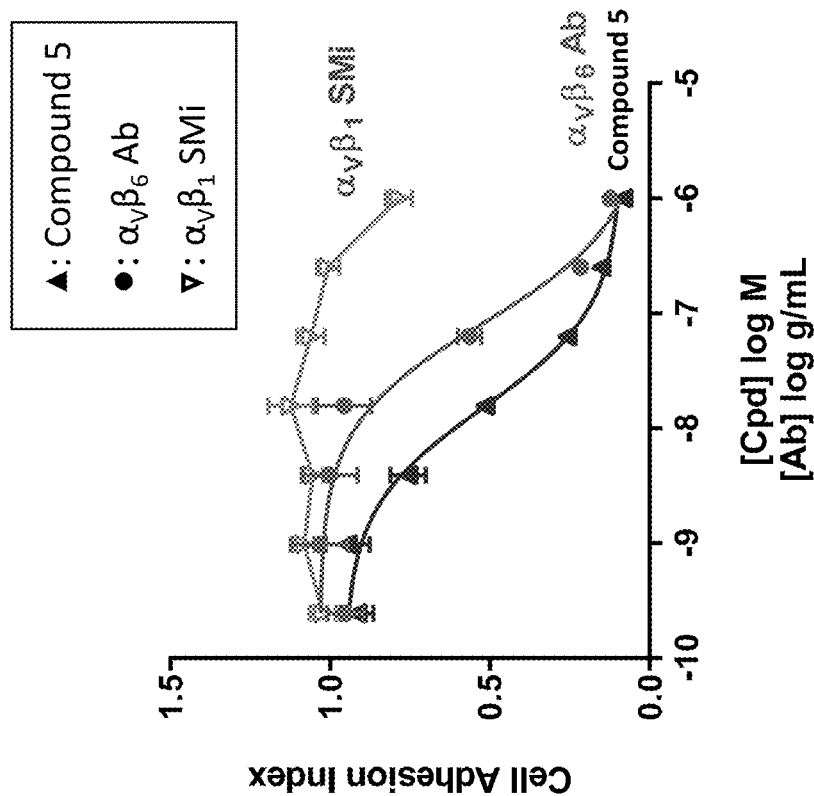
FIG. 3A is a graph showing that compound 5 and the selective antibody αvβ6 inhibitor 3G9 both substantially inhibited normal bronchial epithelial cell adhesion to LAP, in contrast with the αvβ1-selective small molecule inhibitor.

Human bronchial epithelial cells are known to express $\alpha v\beta_6$ integrin in culture. Human bronchial epithelial cells were prepared for the assay by dissociation with trypsin/EDTA and were then seeded at 20,000 cells per well on 96 well plates (ACEA Bioscience E-plate View, Acea Biosciences; San Diego, Calif.) previously coated with 5 µg/ml of recombinant human LAP (R&D Systems; Minneapolis, Minn.) and blocked with 4% bovine serum albumin. Cell index (electrical impedance) was measured to assess cell attachment/spreading every 3 minutes for 24 hours at 37° C./5% $CO_2$ using the xCELLigence RTCA MP Instrument (Acea Biosciences; San Diego, Calif.). $EC_{90}$ (time point at 90% of the peak cell index) was determined for vehicle-treated cells and $IC_{50}$ curves for test article-treated cells were generated at that time point. In the assay, the IPF-derived human bronchial epithelial cells were separately incubated with: a $\alpha v\beta_1$-selective small molecule inhibitor (characterized by sub-50 nM $IC_{50}$ for $\alpha v\beta_1$, and selective for $\alpha v\beta_1$ over $\alpha v\beta_6$ by a factor of about 25); a selective antibody $\alpha v\beta_6$ inhibitor, 3G9 (ITGB1BP2 Monoclonal Antibody (3G9), ThermoFisher Scientific, Santa Clara, Calif.); and compound 5, (S)-4-((2-methoxyethyl)(4-(5,6,7,8-tetrahydro-1,8-naphthyridin-2-yl)butyl) amino)-2-(quinazolin-4-ylamino)butanoic acid. FIG. 3A shows that compound 5 and the selective antibody $\alpha v\beta_6$ inhibitor 3G9 both substantially inhibited normal bronchial epithelial cell adhesion to LAP, in contrast with the $\alpha v\beta_1$-selective small molecule inhibitor.

Human lung fibroblasts derived from normal and IPF lung tissue are known to express $\alpha v\beta_1$ integrin. The IPF-derived human lung fibroblasts were prepared for the assay by dissociation with trypsin/EDTA, and were seeded at 20,000 cells per well on 96 well plates (ACEA Bioscience E-plate View, Acea Biosciences; San Diego, Calif.) previously coated with 5 µg/ml of recombinant human LAP (R&D Systems; Minneapolis, Minn.) and blocked with 4% bovine serum albumin. Cell index (electrical impedance) was measured to assess cell attachment/spreading every 3 minutes for 24 hours at 37° C./5% $CO_2$ using the xCELLigence RTCA MP Instrument (Acea Biosciences; San Diego, Calif.). $EC_{90}$ (time point at 90% of the peak cell index) was determined for vehicle-treated cells and $IC_{50}$ curves for test article-treated cells were generated at that time point. In the assay, the IPF-derived human lung fibroblasts were separately incubated with: the $\alpha v\beta_1$-selective small molecule inhibitor; the selective antibody $\alpha v\beta_6$ inhibitor, 3G9; and compound 5. FIG. 3B shows that compound 5 and the $\alpha v\beta_1$-selective small molecule inhibitor both substantially inhibited cell adhesion in the IPF-derived lung fibroblasts, in contrast to the selective antibody $\alpha v\beta_6$ inhibitor, 3G9.

Example B7—Dual $\alpha_v\beta_6/\alpha v\beta_1$ Inhibition Reduces Collagen Deposition in the Murine Bleomycin Model It has been previously shown that inhibition of $\alpha v\beta_6$ in the lung can be detected though measurement of phospho-SMAD (pSMAD) in alveolar macrophages. Alveolar macrophages are known to operate in a unique niche in the lung, distinct from interstitial macrophages. SMAD3 is a downstream target of the active TGF-β cytokine binding its receptor and in alveolar macrophages it is phosphorylated by homoeostatic levels of TGF-β. Accordingly, it was desirable to know whether inhibition of TGF-β activation using the disclosed compounds would result in reduced SMAD2 and SMAD3 phosphorylation.

Mice (C57BL/6) were divided into healthy (n=15), vehicle-treated (n=15), and test article-treated (n=15 per dose) groups. Mice in the vehicle and test article-treated groups were administered 3 U/kg of bleomycin (Teva Pharmaceuticals; North Wales, Pa.) via oropharyngeal aspiration while under anesthesia on day 0. Healthy animals were administered water in a similar fashion. Starting on day 7, mice in the control group were administered PBS vehicle, 130 µL, by oral gavage, BID for 14 days. Also starting on day 7, mice in the test group were administered compound 5 in PBS by oral gavage, BID for 14 days, at relative dosages of 1×, 2.5× and 5×. The absolute amount of the 1× dosage was selected at a value in mg/kg that showed significant efficacy. From day 14 through day 21, 9 of the 15 mice were administered $^2H_2O$ for labeling. All mice were sacrificed on day 21 and tissues were collected. Samples were prepared for analysis either directly from lung tissue, or by bronchoalveolar lavage, which washes out the bronchiolar and alveolar space with saline to produce a bronchoalveolar lavage fluid (BALF) in which 80-90% of cells are alveolar macrophages.

Figure 4A:
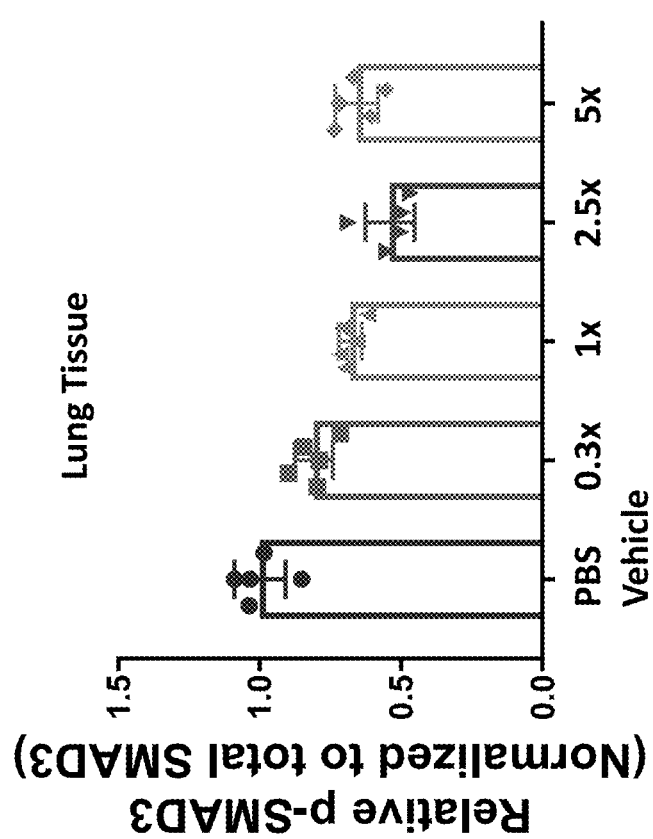
FIG. 4A is a graph of PSMAD3/SMAD3 in lung tissue from healthy mice administered PBS vehicle and varying levels of compound 5 for 4 days.
Figure 4B:
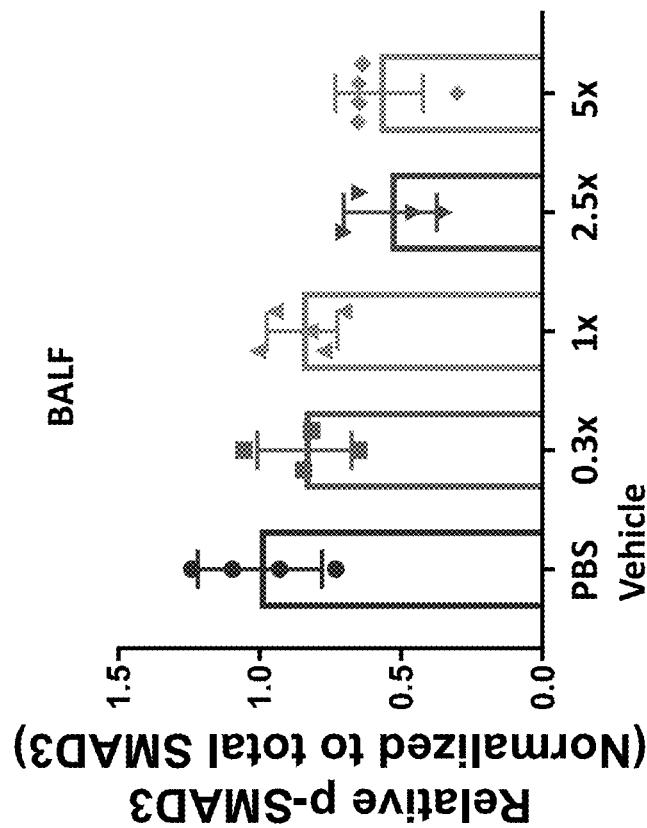
FIG. 4B is a graph of PSMAD3/SMAD3 in BALF drawn from the same healthy mice administered PBS vehicle and varying levels of compound 5 for 4 days.
Figures 4C, 4D, 4E:
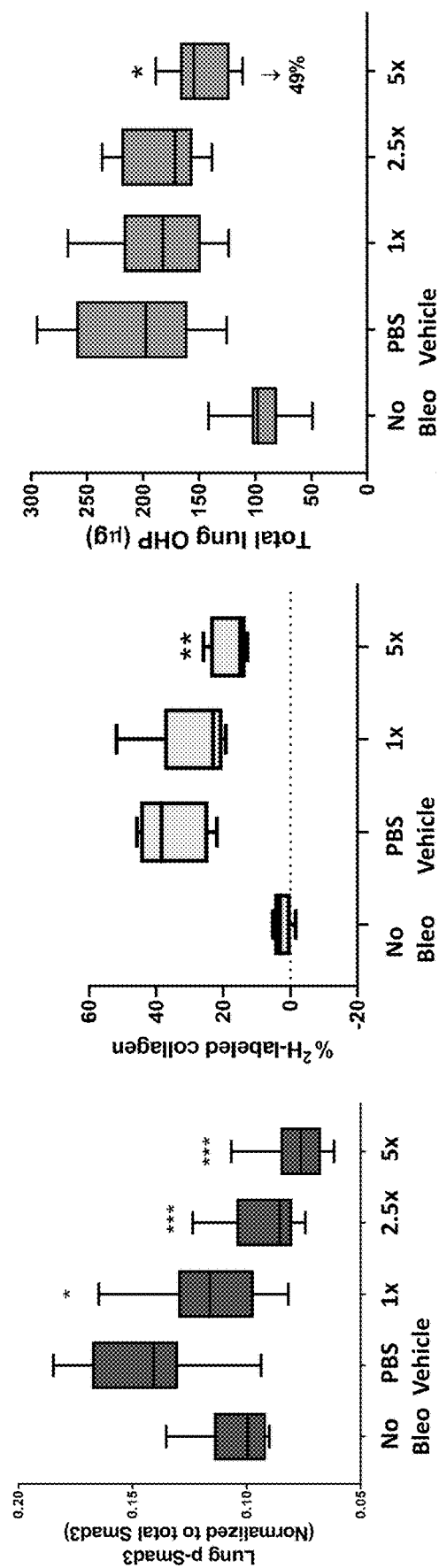
FIG. 4C is a graph showing that compared to the healthy mice, lung tissue in the vehicle-treated mice experienced a substantial increase in SMAD3 phosphorylation.
FIG. 4D is a graph showing that compared to the healthy mice, lung tissue in the vehicle-treated mice experienced a substantial accumulation of new collagen as evidenced by the percentage of lung collagen containing $^2$H-labeled hydroxyproline.
FIG. 4E shows that compared to the healthy mice, the vehicle-treated mice experienced a significant increase in total pulmonary collagen, as measured by μg of hydroxyproline.

FIG. 4A is a graph of PSMAD3/SMAD3 in lung tissue from healthy mice administered PBS vehicle and varying levels of compound 5 for 4 days. FIG. 4B is a graph of PSMAD3/SMAD3 in BALF drawn from the same healthy mice administered PBS vehicle and varying levels of compound 5 for 4 days. FIGS. 4A and 4B show that 4 days of compound 5 treatment significantly reduced SMAD3 phosphorylation in both lung tissue and cells isolated from BALF in a dose dependent manner to approximately 50% of the untreated levels FIG. 4C is a graph showing that compared to the healthy mice, lung tissue in the vehicle-treated mice experienced a substantial increase in SMAD3 phosphorylation, which is a measure of TGF-β signaling-related kinase activity. FIG. 4C also shows, compared to the vehicle-treated mice, substantial, statistically significant dose-dependent reductions in SMAD3 phosphorylation in the test article-treated mice according to the dosage of compound 5, including at 1× (p<0.05 vs vehicle), 2.5× (p<0.01 vs vehicle), and 5× mg/kg (p<0.001 vs vehicle). This time- and dose-dependent inhibition of pSMAD3 levels in the lung to approximately 50% of the untreated levels was associated with inhibition of fibrosis according to the following results. FIG. 4D is a graph showing that compared to the healthy mice, lung tissue in the vehicle-treated mice experienced a substantial accumulation of new collagen as evidenced by the percentage of lung collagen containing $^2$H-labeled hydroxyproline. FIG. 4D also shows, compared to the control mice, a dose-dependent reduction in accumulated new collagen as evidenced by the percentage of lung collagen containing $^2$H-labeled hydroxyproline in the test mice, including at 1×, and at 5× (p<0.01 vs vehicle). FIG. 4E shows that compared to the healthy mice, the vehicle-treated mice experienced a significant increase in total pulmonary collagen, as measured by μg of hydroxyproline. FIG. 4E also shows, compared to the control mice, a reduction in total pulmonary collagen in the test mice according to the dosage of compound 5, including at 1×, 2.5×, and 5× (p<0.05 vs vehicle). As shown among FIGS. 4C, 4D, and 4E, in fibrotic bleomycin-treated mice, compound 5 abrogated the increase in pSMAD3 due to bleomycin challenge, a reduction that was associated with inhibition of fibrosis.

Figure 4I:
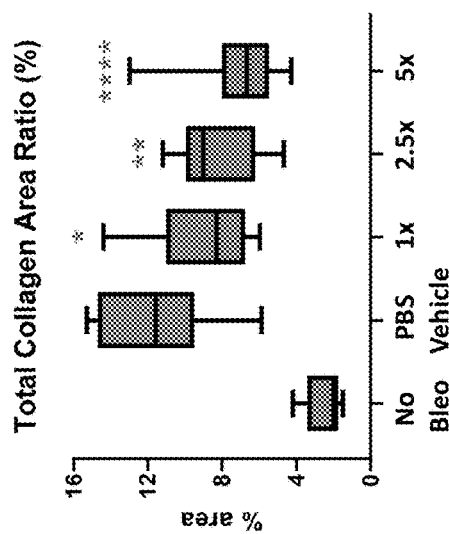
FIG. 4I is a graph showing the percent total collagen area in the second harmonic generation mouse lung images of FIGS. 4F, 4G, and 4H.
Figure 4H:
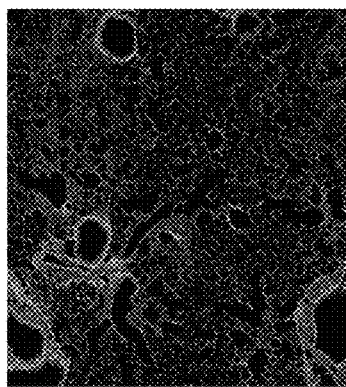
FIG. 4H is a high resolution second harmonic generation image of fibrillar collagen (collagen type I and III) taken from formalin-fixed paraffin embedded lung tissue sections from a test-article treated mouse lung (500 mg/kg BID of compound 5).
Figure 4G:
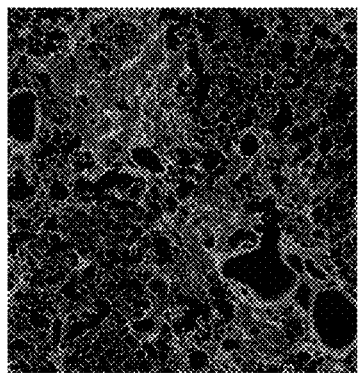
FIG. 4G is a high resolution second harmonic generation image of fibrillar collagen (collagen type I and III) taken from formalin-fixed paraffin embedded lung tissue sections from a vehicle-treated mouse lung.
Figure 4F:
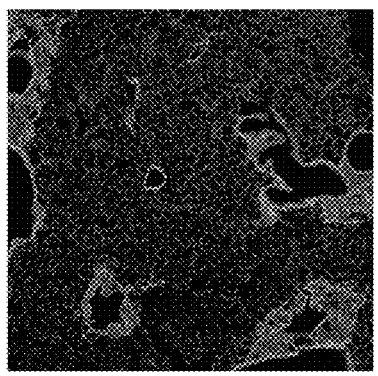
FIG. 4F is a high resolution second harmonic generation image of fibrillar collagen (collagen type I and III) taken from formalin-fixed paraffin embedded lung tissue sections from a healthy mouse lung.

FIGS. 4F, 4G, and 4H show high resolution second harmonic generation images of fibrillar collagen (collagen type I and III) taken from formalin-fixed paraffin embedded lung tissue sections from a healthy mouse lung (4F), a vehicle-treated mouse lung (4G) and a test-article treated mouse lung (4H; 500 mg/kg BID). Color scale is indicative of collagen fiber density (red=most dense; blue=least dense).

FIG. 4I is a graph showing the percent total collagen area in the second harmonic generation mouse lung images. Large structural areas of collagen found similarly in healthy and fibrotic tissues (dense collagen fibers surrounding airways were excluded from this analysis to focus on interstitial fibrotic collagen). FIG. 4I shows that compared to the healthy mice, lung tissue in the vehicle-treated mice experienced a substantial increase in total collagen area in the second harmonic generation images. FIG. 4I also shows that compared to the control mice, lung tissue in the test article-treated mice experienced a substantial, statistically significant dose-dependent reduction in total collagen area in the second harmonic generation images according to the administration of compound 5, including at 1× (p<0.05 vs vehicle), 2.5× (p<0.01 vs vehicle), and 5× (p<0.0001 vs vehicle). The 1×, 2.5×, and 5× dosages were at the same absolute values in mg/kg as in Example B7.

Figure 4K:
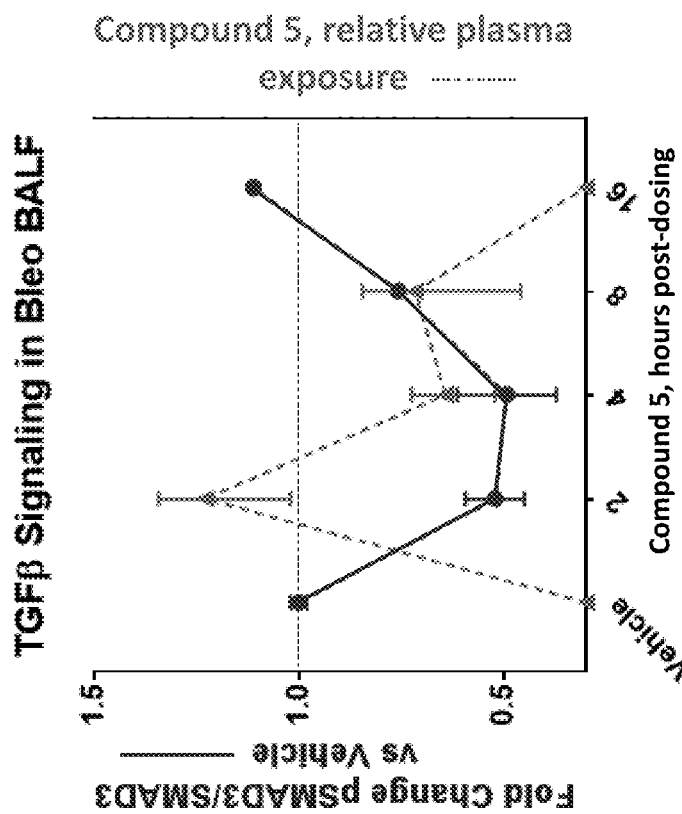
FIG. 4K is a graph of sequential measurements in bleomycin-treated mice, which demonstrated a close inverse relationship between pSMAD3 levels in BALF cells vs. plasma drug exposure.
Figure 4J:
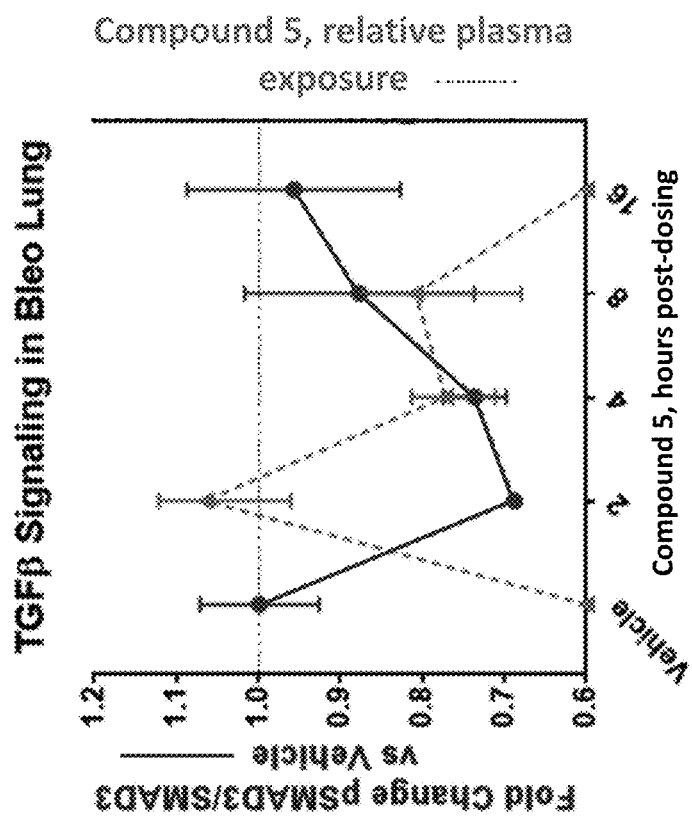
FIG. 4J is a graph of sequential measurements in bleomycin-treated mice, which demonstrated a close inverse relationship between pSMAD3 levels in lung vs. plasma drug exposure.

FIGS. 4J and 4K are graphs of sequential measurements in bleomycin-treated mice, which demonstrated a close inverse relationship between pSMAD3 levels in lung (4J) and BALF cells (4K) vs. plasma drug exposure. The data for FIGS. 4J and 4K, was obtained 14 days after bleomycin challenge in mice were treated with compound 5 at 2.5× dose (PO, BID for 1.5 days).

Example B8—Dual $\alpha_v\beta_1/\alpha_v\beta_6$ Inhibition Outperforms Single Integrin Inhibition in Precision Cut Lung Slice Assays of Mice Under Acute Bleomycin Exposure Mice (C57BL/6) were administered 3 U/kg of bleomycin (Teva Pharmaceuticals; North Wales, Pa.) on day 0 via oropharyngeal aspiration while under anesthesia. On day 14, precision cut lung slices were obtained. Following euthanization, 2% low gelling temp agarose was injected into the mouse lungs via the trachea. Lungs were excised and the inferior lobe separated by dissection. The lobes were then subjected to precision slicing to obtain samples for culture using a microtome (Compresstome VF-300-0Z, Precisionary; Greenville, N.C.). Individual slices were distributed in a multiwell culture plate and cultured for 3 days under control (DMSO) and test compound conditions. The viability of the slices over the course of culturing was confirmed by WST-1 assay of mitochondrial activity.

During the culture period, slices in the control group were treated with DMSO and slices in the test group were treated with a DMSO solution of one of a selective antibody $\alpha v\beta_6$ inhibitor, 3G9; the $\alpha v\beta_1$-selective small molecule inhibitor; compound 5; a first pan-αv small molecule inhibitor ((3S)-3-[3-(3,5-dimethyl-1H-pyrazol-1-yl)phenyl]-4-{(3S)-3-[2-(5,6,7,8-tetrahydro-1,8-naphthyridin-2-yl)ethyl]-1-pyrrolidinyl}butanoic acid, PROBECHEM®, St. Petersburg, Fla.); a second pan-αv small molecule inhibitor ((3S)—N-[3-hydroxy-5-[(1,4,5,6-tetrahydro-5-hydroxy-2-pyrimidinyl)amino]benzoyl]glycyl-3-[3-bromo-5-(1,1-dimethylethyl)phenyl]-β-alanine, Cayman Chemical, Ann Arbor, Mich.); and a small molecule ALK5 (TGF-β type I receptor) inhibitor (4-[2-Fluoro-5-[3-(6-methyl-2-pyridinyl)-1H-pyrazol-4-yl]phenyl]-1H-pyrazole-1-ethanol, Bio-Techne Corporation, Minneapolis, Minn.). Single and dual integrin inhibitors were analyzed at their respective $IC_{50}$ concentrations for inhibition of TGF-beta activation (compound 5 run at $IC_{50}$ for $\alpha v\beta_6$). The pan αv integrin inhibitors and small molecule ALK5 inhibitor were analyzed at concentrations 10× above their respective reported $IC_{50}$ values.

Figure 5B:
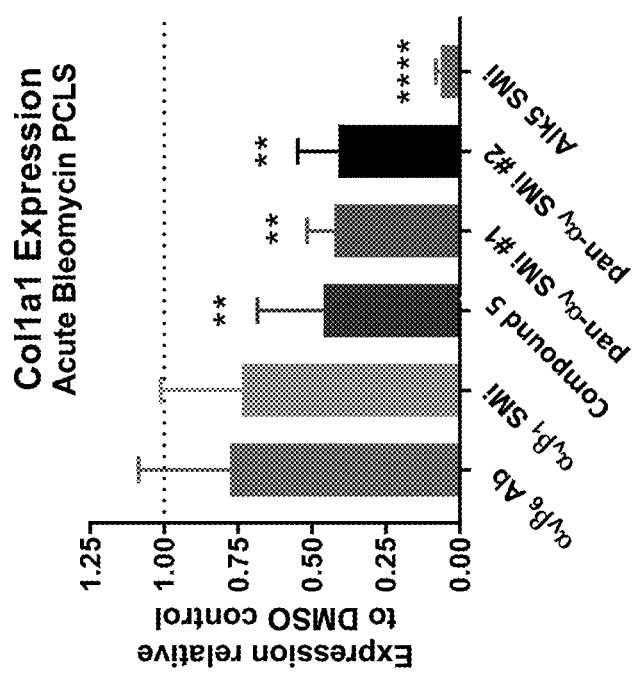
FIG. 5B is a bar graph, normalized to control slices treated with DMSO, showing that all test treatments reduced lung Col1a1 expression.
Figure 5A:
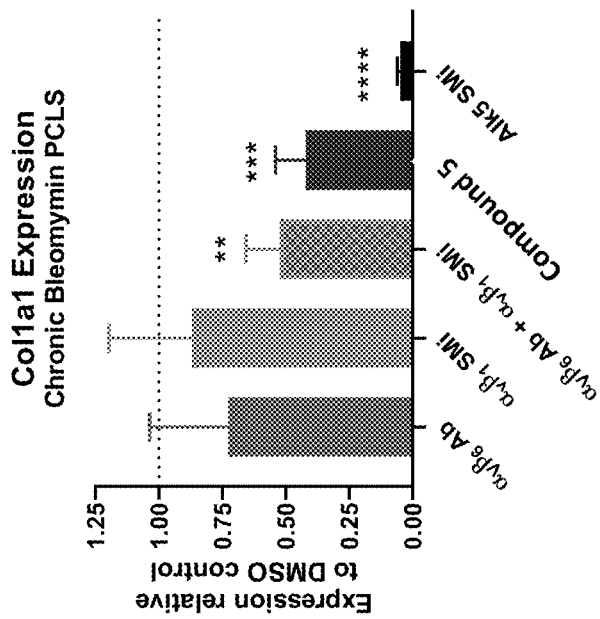
FIG. 5A is a bar graph, normalized to control slices treated with DMSO, showing that all test treatments reduced Type I Collagen gene Col1a1 expression.

FIG. 5A is a bar graph, normalized to control slices treated with DMSO, showing that all test treatments reduced Type I Collagen gene Col1a1 expression, although selective antibody $\alpha v\beta_6$ inhibitor 3G9 and the $\alpha v\beta_1$-selective small molecule inhibitor were not statistically significant. Compound 5, as a dual $\alpha v\beta_1/\alpha v\beta_6$ inhibitor, decreased Type I Collagen gene Col1a1 expression substantially (p<0.01 vs vehicle) compared to the DMSO control, the selective antibody $\alpha v\beta_6$ inhibitor, 3G9; and the $\alpha v\beta_1$-selective small molecule inhibitor. Compound 5 decreased Type I Collagen gene Col1a1 expression comparably to the first and second pan-av small molecule inhibitors (each p<0.01 compared to the DMSO control). The small molecule ALK5 inhibitor, used as a positive control representative of total TGF-beta signaling inhibition, provided the greatest decrease in Type I Collagen gene Col1a1 expression (p<0.0001 compared to the DMSO control).

Example B9—Dual $\alpha_v\beta_1/\alpha_v\beta_6$ Inhibition Outperforms Single Integrin Inhibition in Precision Cut Lung Slice Assays of Mice Under Chronic Bleomycin Exposure Mice (C57BL/6) were administered 3 U/kg of bleomycin (Teva Pharmaceuticals; North Wales, Pa.) on Day 0 and 1 U/kg of bleomycin on days 14, 28, 42 and 56 via oropharyngeal aspiration while under anesthesia. At day 70, 14 days after the final bleomycin insult, precision cut lung slices were obtained. Following euthanization, 2% low gelling temp agarose was injected into the mouse lungs via the trachea. Lungs were excised and the inferior lobe separated by dissection. The lobes were then subjected to precision slicing to obtain samples for culture using a microtome (Compresstome VF-300-0Z, Precisionary; Greenville, N.C.). Individual slices were distributed in a multiwell culture plate and cultured for 7 days under control (DMSO) and test compound conditions. The viability of the slices over the course of culturing was confirmed by WST-1 assay of mitochondrial activity.

During the culture period, slices in the control group were treated with DMSO and slices in the test group were treated with a DMSO solution of one of: the selective antibody $\alpha v \beta_6$ inhibitor 3G9; the $\alpha v \beta_1$-selective small molecule inhibitor; a combination of the selective antibody $\alpha v \beta_6$ inhibitor 3G9 and the $\alpha v \beta_1$-selective small molecule inhibitor; compound 5; and the small molecule ALK5 inhibitor. The selective $\alpha v \beta_1$ and $\alpha v \beta_6$ integrin inhibitors were analyzed at ≥their respective $IC_{90}$ concentrations for inhibition of TGF-beta activation. Compound 5 was run at approximate $IC_{50}$ for inhibition of TGF-beta activation by $\alpha v \beta_6$. The small molecule ALK5 inhibitor was analyzed at 10× its reported $IC_{50}$ value.

FIG. 5B is a bar graph, normalized to control slices treated with DMSO, showing that all test treatments reduced lung Col1a1 expression. Compound 5, as a dual $\alpha v \beta_1/\alpha v \beta_6$ inhibitor, decreased lung Col1a1 expression substantially (p<0.01 vs vehicle) compared to the DMSO control, the selective antibody $\alpha v \beta_6$ inhibitor, 3G9; and the $\alpha v \beta_1$-selective small molecule inhibitor. Compound 5 also decreased lung Col1a1 expression to a greater extent than combined administration (p<0.001 vs vehicle) of the selective antibody $\alpha v \beta_6$ inhibitor 3G9 and the $\alpha v \beta_1$-selective small molecule $\alpha v \beta_1$ inhibitor. The small molecule ALK5 inhibitor, used as a positive control representative of total TGF-beta signaling inhibition, provided the greatest decrease in Type I Collagen gene Col1a1 expression (p<0.0001 compared to the DMSO control).

Example B10—Dual $\alpha_v \beta_1/\alpha_v \beta_6$ Inhibition More Potently Blocks Collagen Gene Expression in the Murine Bleomycin Model than Pirfenidone and Nintedanib Mice (C57BL/6) were administered 3 U/kg of bleomycin (Teva Pharmaceuticals; North Wales, Pa.) on Day 0 and 1 U/kg of bleomycin on days 14, 28, 42 and 56 via oropharyngeal aspiration while under anesthesia. At day 70, 14 days following the final bleomycin insult, precision cut lung slices were obtained. Following euthanization, 2% low gelling temp agarose was injected into the mouse lungs via the trachea. Lungs were excised and the inferior lobe separated by dissection. The lobes were then subjected to precision slicing to obtain samples for culture using a microtome (Compresstome VF-300-0Z, Precisionary; Greenville, N.C.). Individual slices were distributed in a multiwell culture plate and cultured for 7 days under control (DMSO) and test compound conditions. The viability of the slices over the course of culturing was confirmed by WST-1 assay of mitochondrial activity.

During the culture period, slices in the control group were treated with DMSO and slices in the test group were treated with a DMSO solution of one of compound 5; nintedanib; pirfenidone; a combination of nintedanib and compound 5; a combination of pirfenidone and compound 5; or the small molecule ALK5 inhibitor. Compound 5 was administered to mice effective to equal or exceed its respective $IC_{50}$ values at $\alpha v \beta_6$ and $\alpha v \beta_1$. The small molecule ALK5 inhibitor was analyzed at 0x its reported $IC_{50}$ value. Nintendanib and pirfenidone were analyzed at concentrations 10× their reported therapeutic concentrations.

Figures 6A, 6B, 6C:
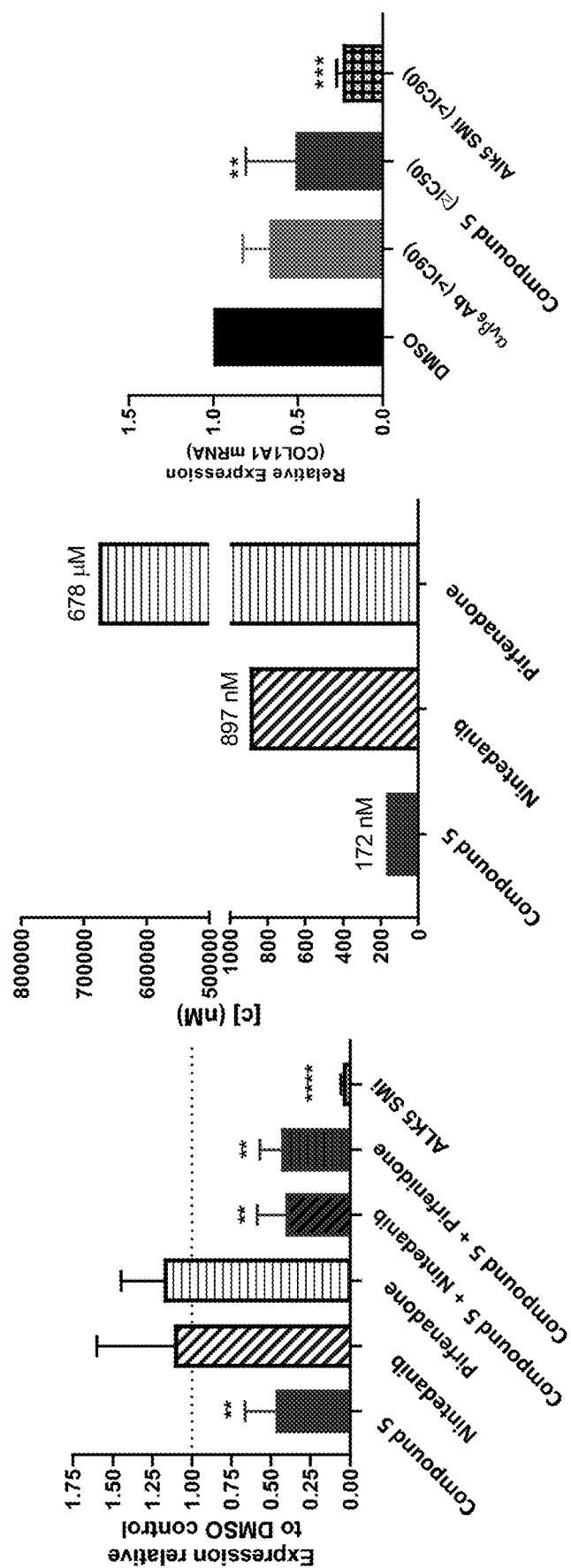
FIG. 6A is a bar graph showing that compared to the DMSO vehicle control slices, both nintedanib and pirfenidone showed a slight increase in lung Col1a1 expression.
FIG. 6B is a bar graph showing the concentration of compound needed to reduce lung slice Col1a1 expression by 50% compared to DMSO control slices.
FIG. 6C is a bar graph, normalized to control slices treated with DMSO, showing that all test treatments reduced lung Col1a1 expression.

FIG. 6A is a bar graph showing that compared to the DMSO vehicle control slices, both nintedanib and pirfenidone showed a slight increase in lung Col1a1 expression, although the increase was not shown to be statistically significant. By contrast, compound 5 both alone (p<0.01 vs vehicle) and in combination with nintedanib or pirfenidone showed a substantial, statistically significant (p<0.01 vs vehicle) decrease in lung slice Col1a1 expression. Likewise, the small molecule ALK5 inhibitor, used as a positive control representative of total TGF-beta signaling inhibition, showed a substantial, statistically significant (p<0.0001 vs vehicle) decrease in lung Col1a1 expression.

FIG. 6B is a bar graph showing the concentration of compound needed to reduce lung slice Col1a1 expression by 50% compared to DMSO control slices. Data for FIG. 6B was obtained using acute bleomycin injured lung slices prepared as described in Example B8. To match the efficacy of compound 5, nintedanib required a 5.2 fold increase in concentration over compound 5, and pirfenidone required a 3,940-fold increase in concentration over compound 5.

Example B11—Dual $\alpha_v \beta_1/\alpha_v \beta_6$ Inhibition Significantly Reduces Collagen Gene Expression in Precision Cut Lung Slices from Human IPF Explants Explanted lung tissue was obtained from human IPF subjects and inflated with agarose as described in the preceding examples. Biopsy cores were obtained from the agarose-inflated lung tissue. The biopsy cores were subjected to precision slicing to obtain several hundred μm thick. Individual slices were distributed in a multiwell culture plate and cultured for 3 days under control (DMSO) and test compound conditions. The viability of the slices over the course of culturing was confirmed by WST-1 assay of mitochondrial activity.

During the culture period, slices in the control group were treated with DMSO and slices in the test group were treated with a DMSO solution of one of: the selective antibody $\alpha c \beta_6$ inhibitor, 3G9, at ≥400 ng/mL; compound 5, at 179 nM; and the small molecule ALK5 inhibitor at 1 μM.

FIG. 6C is a bar graph, normalized to control slices treated with DMSO, showing that all test treatments reduced lung Col1a1 expression. The selective antibody $\alpha v \beta_6$ inhibitor, 3G9, slightly reduced lung Col1a1 expression, but was not statistically significant. Compound 5 showed a substantial, statistically significant (p<0.01 vs vehicle) decrease in lung Col1a1 expression, as did the small molecule ALK5 inhibitor (p<0.0001 vs vehicle). Notably, in these human IPF subject samples, compound 5 was much closer in efficacy to the small molecule ALK5 inhibitor than in the murine bleomycin model.

Figure 6D:
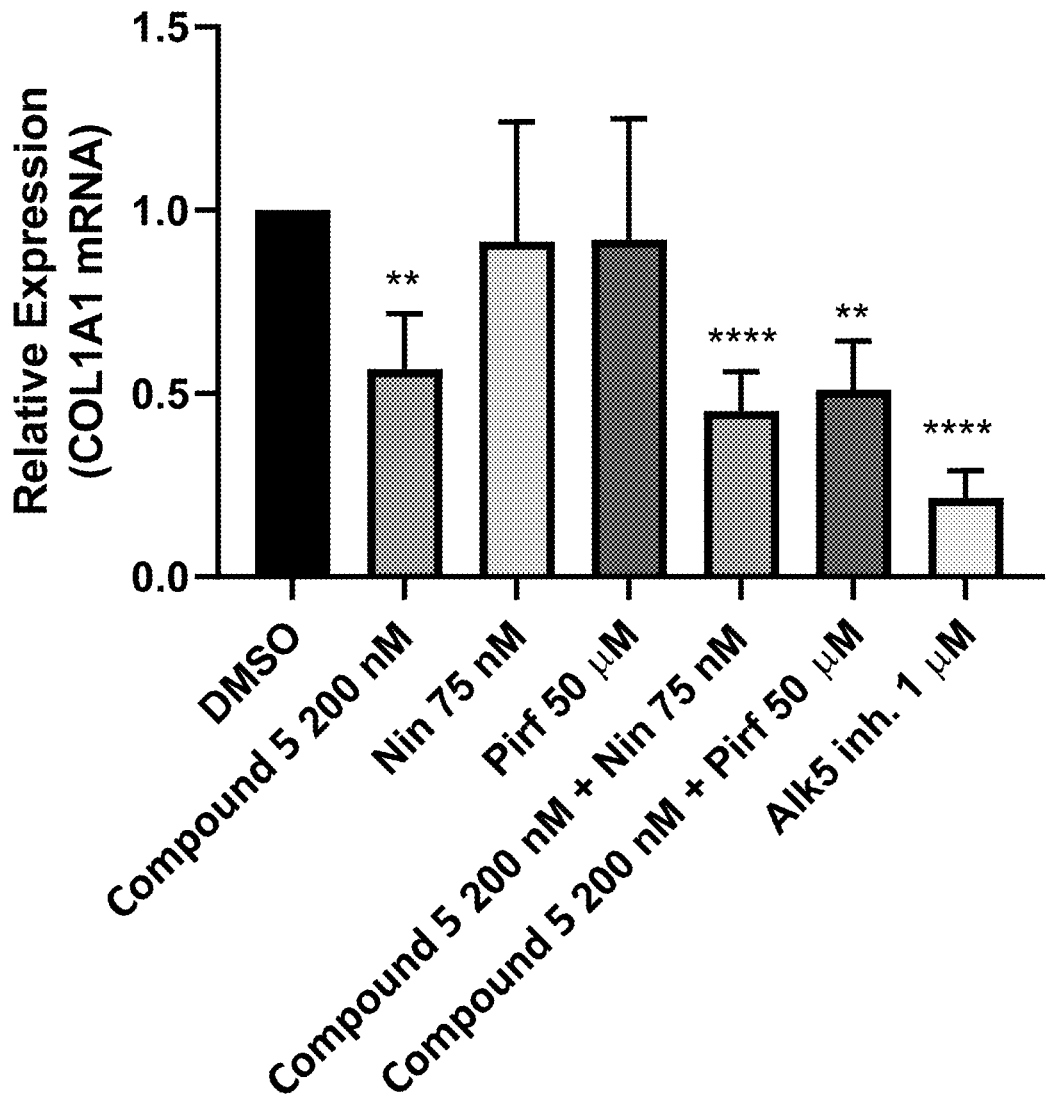
FIG. 6D is a bar graph showing relative expression of COL1A1 in precision cut lung slices (PCLS) from idopathic pulmonary fibrosis (IPF) lung tissue upon exposure to Compound 5, clinical standard of care compounds nintedanib (Nin) and pirfenidone (Pirf), and an ALK5 inhibitor, all versus DMSO control.

PCLS from 5-7 idopathic pulmonary fibrosis (IPF) lung tissue samples were cultured for seven days with one of: DMSO; Compound 5 at 200 nM; nintedanib at 75 nM; pirfenidone at 50 μm; a combination of Compound 5 at 200 nM and nintedanib at 75 nM; a combination of Compound 5 at 200 nM and pirfenidone at 50 m; or an Alk5 inhibitor at 1 μm. Compound 5 alone or in combination with nintedanib or pirfenidone reduced COL1A1 expression by 43%, 55%, and 49%, respectively. Nintedanib and pirfenidone treatment alone did not significantly reduce expression of COL1A1. FIG. 6D is a bar graph showing relative expression of COL1A1 in precision cut lung slices (PCLS) from idopathic pulmonary fibrosis (IPF) lung tissue upon exposure to Comopund 5, clinical standard of care compounds nintedanib (Nin) and pirfenidone (Pirf), and an ALK5 inhibitor, all versus DMSO control.

Figure 6E:
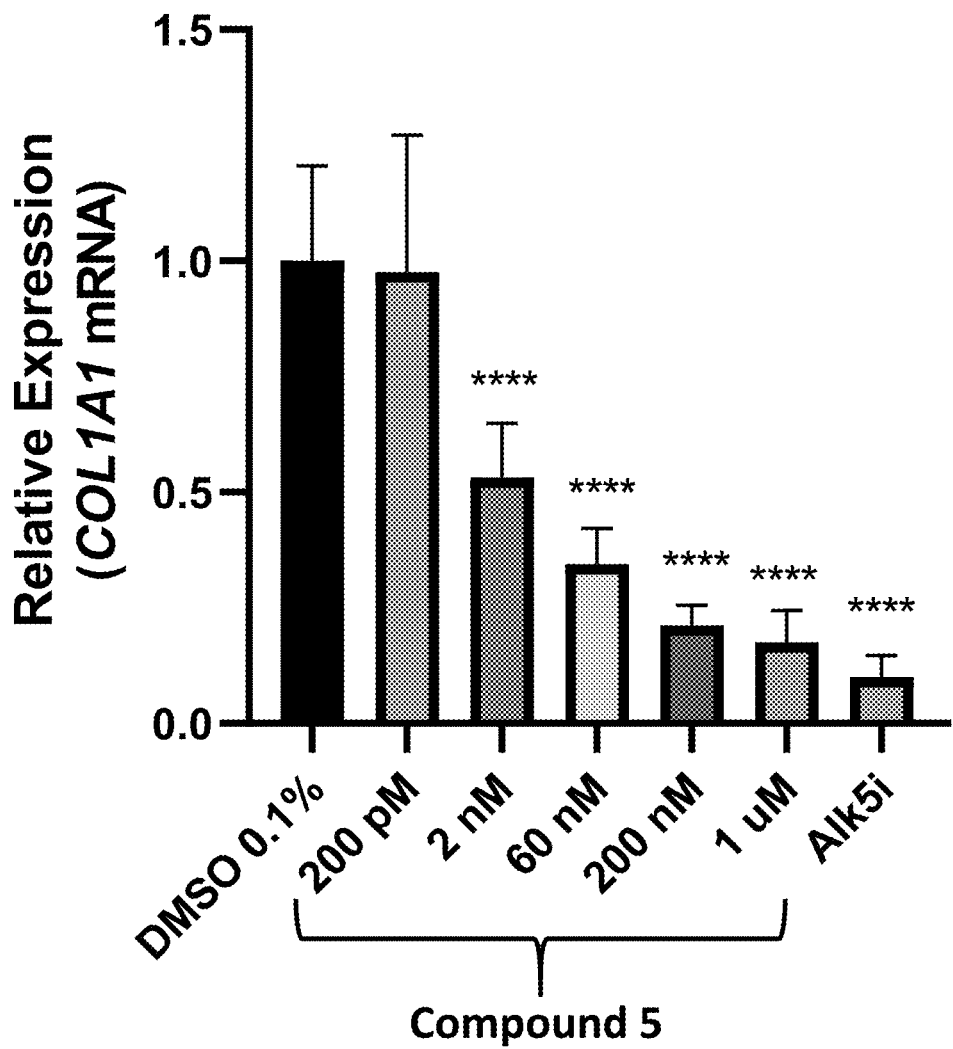
FIG. 6E is a bar graph showing a dose dependent reduction of COL1A1 expression in PCLS from human IPF lung tissue upon treatment with concentrations of compound 5 ranging from 200 pM to 1 μM. COL1A1 expression is also graphed for the PCLS in the presence of 0.1% DMSO control, and an Alk5 inhibitor at 1 μM.

PCLS from a single IPF lung tissue sample were cultured for seven days with Compound 5 at concentrations of 200

μM, 2 nM, 60 nM, 200 nM, and 1 μM, along with 0.1% DMSO control and an Alk5 inhibitor at 1 μM. There was a dose dependent reduction in COL1A1 expression with a significant reduction observed ≥2 nM (≥47% reduction). FIG. 6E is a bar graph showing a dose dependent reduction of COL1A1 expression in PCLS from human IPF lung tissue upon treatment with concentrations of compound 5 ranging from 200 pM to 1 μM. COL1A1 expression is also graphed for the PCLS in the presence of 0.1% DMSO control, and an Alk5 inhibitor at 1 μM.

Figure 6F:
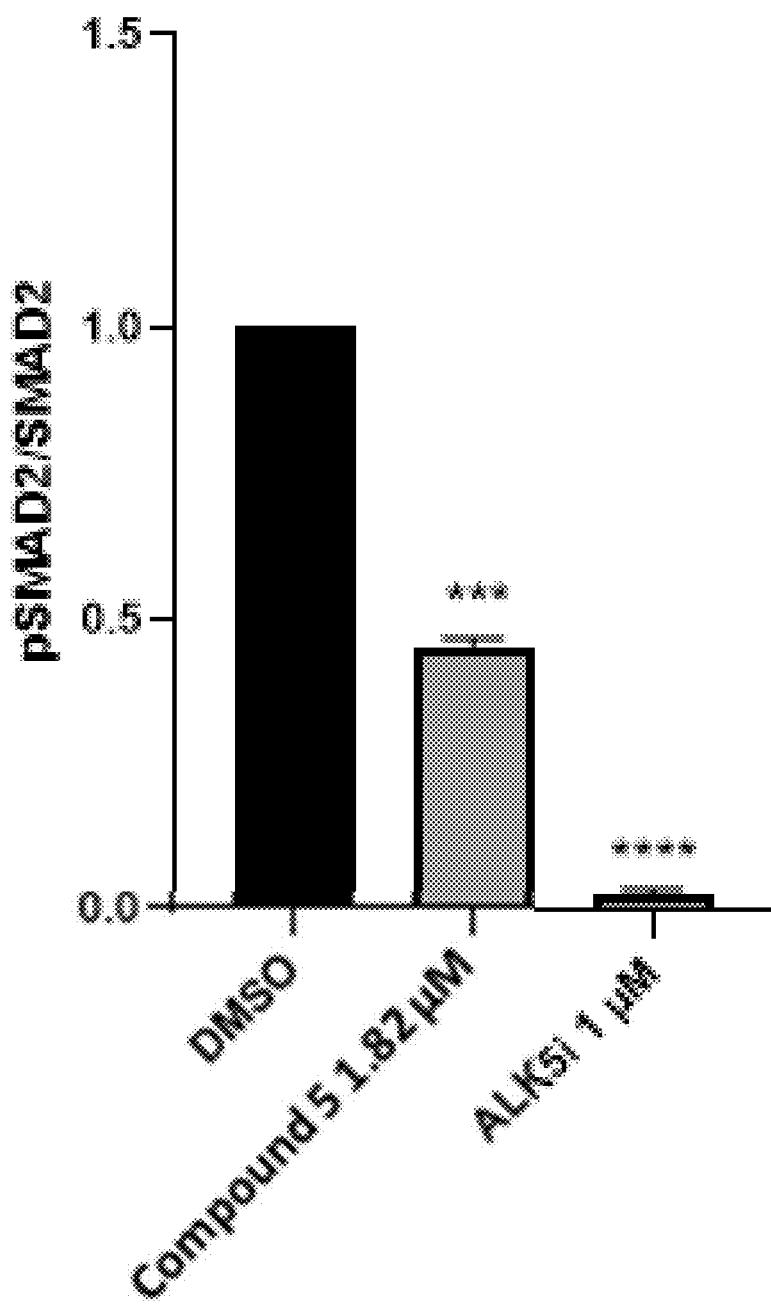
FIG. 6F is a bar graph showing the effect of dual selective αvβ6 and αvβ1 inhibition (Compound 5 at 1.82 μM) on the ratio of pSMAD2/SMAD2 in PCLS from human IPF lung tissue samples. The ratio of pSMAD2/SMAD2 is also graphed for the PCLS in the presence of 0.1% DMSO control, and an Alk5 inhibitor at 1 μM

PCLS from 3 IPF lung tissues were cultured for seven days with Compound 5. Dual inhibition of $\alpha v\beta_6$ and $\alpha v\beta_1$ with Compound 5 significantly reduced pSMAD2/SMAD2 ratio, a marker of the canonical TGF-β signaling pathway, in PCLS by approximately 50%. FIG. 6F is a bar graph showing the effect of dual selective $\alpha v\beta_6$ and $\alpha v\beta_1$ inhibition (Compound 5 at 1.82 μM) on the ratio of pSMAD2/SMAD2 in PCLS from human IPF lung tissue samples. The ratio of pSMAD2/SMAD2 is also graphed for the PCLS in the presence of 0.1% DMSO control, and an Alk5 inhibitor at 1 μM

Figure 7B:
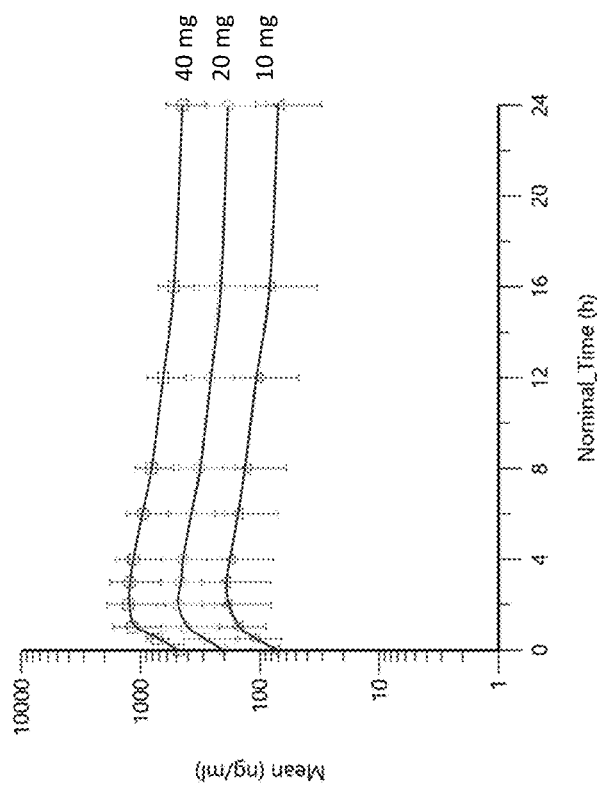
FIG. 7B shows the multiple ascending dose (MAD) study data for administration of 10, 20, and 40 mg of Compound 5.
Figure 7A:
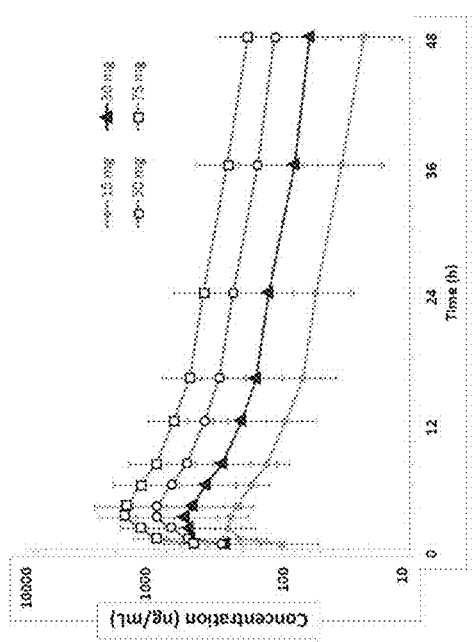
FIG. 7A shows single ascending dose (SAD) study data for administration of 15, 30, 50, and 75 mg of Compound 5.

Example B12—A Dual $\alpha_v\beta_1/\alpha_v\beta_6$ Inhibitor Demonstrates Good Oral Bioavailability and Pharmacokinetics in Healthy Human Subjects Healthy human subjects (N=85) were selected for single ascending dose (SAD) and multiple ascending dose (MAD) first-in-human studies. A solution for oral administration was prepared, containing 10 mg/mL of compound 5 in a 50:50 mixture of ORA-SWEET® SF (PERRIGO®, Allegan, Mich.) and sterile water for irrigation. Sufficient solution was administered orally to the subjects to provide between 15 mg/dose and 75 mg/dose of compound 5 in the SAD study and between 10 mg/dose and 40 mg/dose of compound 5 in the MAD study. Concentrations of compound 5 were measured in the subjects by obtaining a sample of plasma from each subject at desired intervals, and subjecting the plasma to liquid chromatography-mass spectrometry-mass spectrometry (LC-MS/MS), with quantification using a calibration curve determined from a range of solutions at standardized concentrations. The lower limit of quantitation (LLOQ) of the assay was 1 ng/mL and the calibration curve range was 1 to 500 ng/mL. FIG. 7A shows an example of the SAD study data for administration of 15, 30, 50, and 75 mg of compound 5, and further PK data for 75 mg, which is representative of the results obtained for SAD doses at 15, 30, and 50 mg. FIG. 7B shows the MAD study data for administration of 10, 20, and 40 mg of compound 5. The calculated half life of the compound varied between 18-20 hours, which supports daily administration, such as once-daily administration.

Example B13—A Dual $\alpha_v\beta_1/\alpha_v\beta_6$ Inhibitor Demonstrates Reduction of pSMAD2/SMAD2 in BAL from Healthy Human Subjects In order to evaluate the change of pSMAD2 as a biomarker of TGF-β activity following administration of an integrin inhibitor, and to determine a therapeutically effective dosage and an effective blood plasma $C_{max}$ of the integrin inhibitor, healthy subjects were administered compound 5, a dual selective $\alpha v\beta_6/\alpha v\beta_1$-integrin inhibitor, and the corresponding $C_{max}$ levels and decrease in phosphorylation levels and were determined.

Healthy non-smoking adult males without history of lung disease were selected as subjects and were randomized into 4 cohorts. Broncoalevaolar lavage samples were obtained from all subjects 1 day prior to start of treatment. Cohorts 1 and 2 were administered 20 mg of a compound daily, wherein 3 subjects were administered the dual selective $\alpha v\beta_6/\alpha v\beta_1$-integrin inhibitor (compound 5) per every 1 subject receiving a placebo compound. Cohorts 3 and 4 were administered 40 mg of a compound daily, wherein 3 subjects were administered the dual selective $\alpha v\beta_6/\alpha v\beta_1$-integrin inhibitor (compound 5) per every 1 subject receiving a placebo compound. BAL samples and blood samples were taken from all subjects on Day −1 (baseline) and on Day 7 (end of treatment).

Figure 8G:
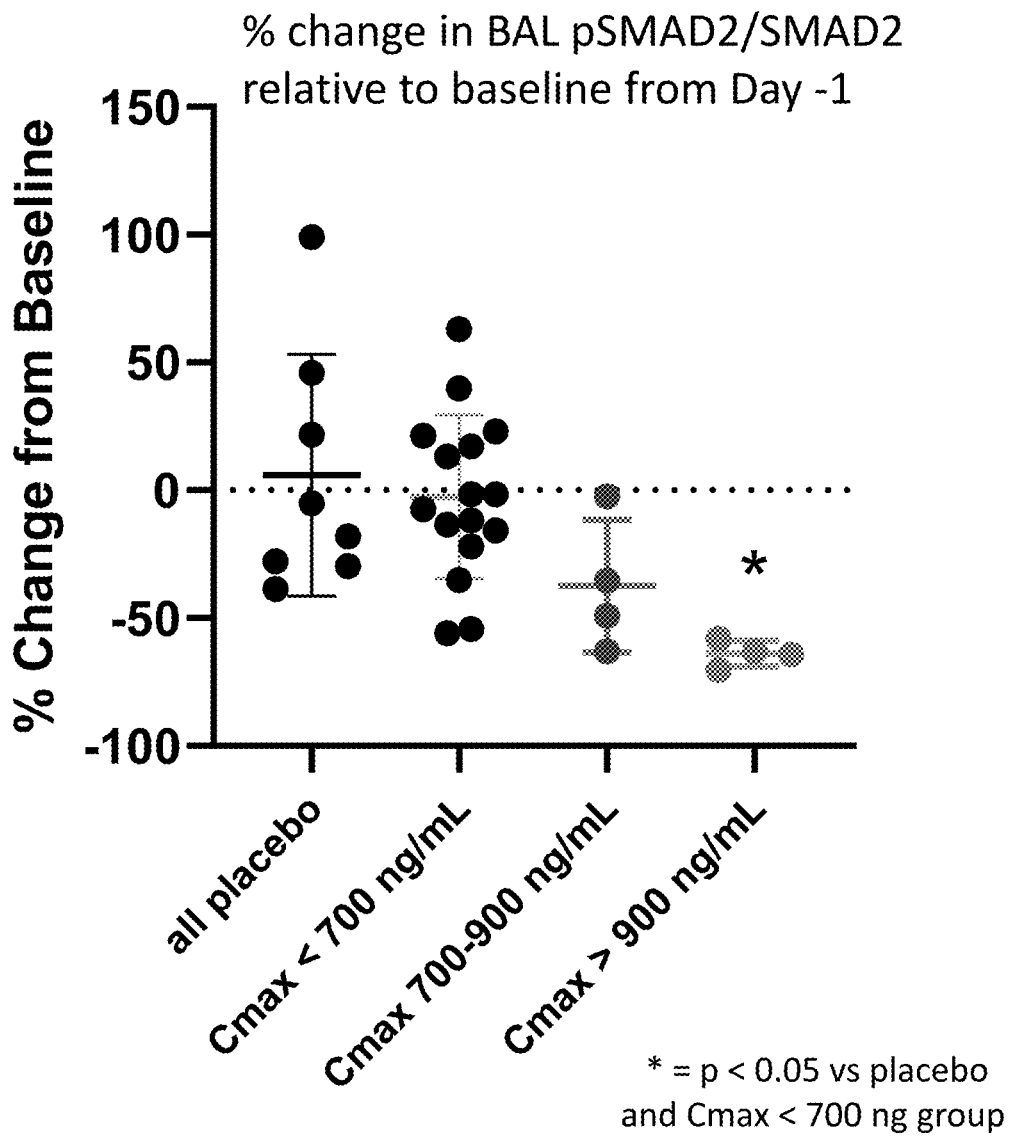
FIG. 8G shows the % change in BAL SMAD2 phosphorylation levels (pSMAD2:SMAD2 ratio) on Day 7 compared to baseline levels recorded on Day −1, for subjects receiving placebo treatment, and subjects in which the $C_{max}$ of the integrin inhibitor was measured to be less than 700 ng/mL, from 700 ng/mL to 900 ng/mL, and greater than 900 ng/mL.
Figure 8H:
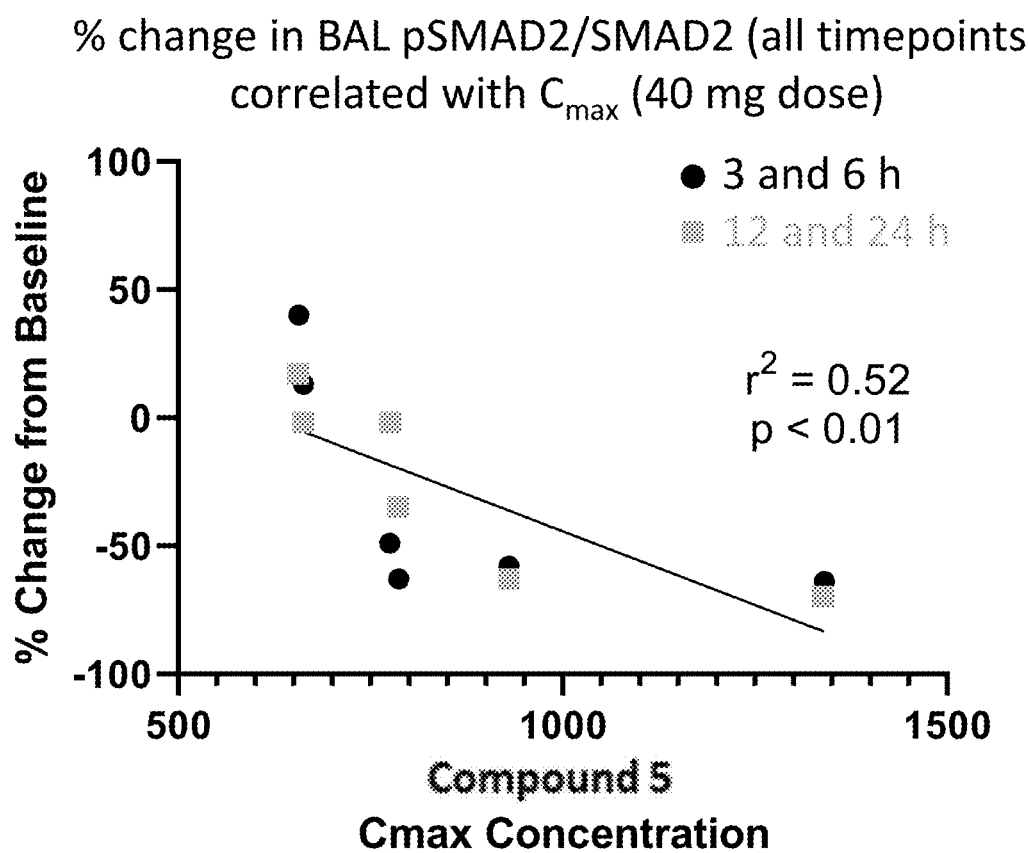
FIG. 8H shows the % change in SMAD2 phosphorylation (pSMAD2:SMAD2 ratio) (all timepoints) correlated with $C_{max}$ in subjects administered a 40 mg dose of Compound 5) compared to baseline levels recorded on Day −1.

As shown in FIG. 8A, a reduction in pSMAD2:SMAD2 ratio of about 50% or more was achieved in subjects which showed higher blood plasma $C_{max}$ of the dual selective $\alpha v\beta_6/\alpha v\beta_1$-integrin inhibitor (compound 5) (subjects 15, 9, 14, 7). All subjects with $C_{max}$ above 700 ng/mL exhibited about 50% or more reduction in pSMAD2:SMAD2 ratio when compared to the placebo group (FIG. 8G) using the dual selective $\alpha v\beta_6/\alpha v\beta_1$ integrin inhibitor (compound 5). The $C_{max}$ and pSMAD2:SMAD2 ratio modulations are plotted in FIG. 8H to further illustrate the relationships between dose and pSMAD2 levels. As shown in FIG. 8H, the plasma $C_{max}$ strongly correlated with reduction of pSMAD2: SMAD2 ratio relative to baseline at 12 h and 24 h post-administration on Day 7.

DISCUSSION

In human and murine fibrotic lung tissue, $\alpha v\beta_6$ (in epithelial cells) and $\alpha v\beta_1$ (in fibroblasts) integrin levels are elevated and contribute to the activation of TGF-β. SMAD2/3 phosphorylation in lung tissue and BAL macrophages reflects TGF-β activation and corresponds to fibrogenic activity. SMAD2/3 phosphorylation in healthy lung tissue and BAL macrophages respond to integrin inhibitors reflecting reduced TGF-β activation. Accordingly, SMAD2 phosphorylation in BAL macrophages has been used as described herein to determine dose response and duration of inhibition of integrin inhibitors in clinical studies to establish precise PK/PD models. Dual inhibition of $\alpha v\beta_6$ and $\alpha v\beta_1$ with compound 5 also significantly reduced SMAD3 phosphorylation and fibrotic collagen deposition in the bleomycin mouse model. Dual inhibition of $\alpha v\beta_6$ and $\alpha v\beta_1$ with compound 5 significantly reduces collagen gene expression in precision cut lung slices prepared from bleomycin-injured mouse lung and from human IPF subjects. Compound 5 is comparable in antifibrotic activity to pan-αv inhibitors, and may have fewer off-target effects due to selectivity for $\mu v\beta_6$ and $\alpha v\beta_1$. Further, dual inhibition of $\alpha v\beta_6$ and $\alpha v\beta_1$ with compound 5 is more effective than inhibition of either αvβ6 or αvβ1 alone. Finally, compound 5 demonstrated good oral bioavailability and pharmacokinetics in healthy subjects, offering a targeted small molecule approach for blocking TGF-β activity in pulmonary fibrosis.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed as new and desired to be protected by Letters Patent of the United States is:

1. A dosage form configured for daily administration, comprising:
a pharmaceutically acceptable carrier or excipient; and
a unit dose of a compound of formula (A)

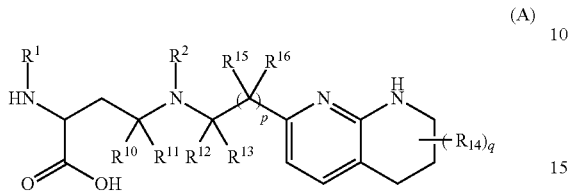

or a salt thereof, wherein:
$R^1$ is $C_6$-$C_{14}$ aryl or 5- to 10-membered heteroaryl wherein the $C_6$-$C_{14}$ aryl and 5- to 10-membered heteroaryl are optionally substituted by $R^{1a}$;
$R^2$ is hydrogen; deuterium; $C_1$-$C_6$ alkyl optionally substituted by $R^{2a}$; —OH; —O—$C_1$-$C_6$ alkyl optionally substituted by $R^{2a}$; $C_3$-$C_6$ cycloalkyl optionally substituted by $R^{2b}$; —O—$C_3$-$C_6$ cycloalkyl optionally substituted by $R^{2b}$; 3- to 12-membered heterocyclyl optionally substituted by $R^{2c}$; or —S(O)$_2$R$^{2d}$; with the proviso that any carbon atom bonded directly to a nitrogen atom is optionally substituted with an $R^{2a}$ moiety other than halogen;
each $R^{1a}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, deuterium, halogen, —CN, —OR$^3$, —SR$^3$, —NR$^4$R$^5$, —NO$_2$, —C=NH(OR$^3$), —C(O)R$^3$, —OC(O)R$^3$, —C(O)OR$^3$, —C(O)NR$^4$R$^5$, —NR$^3$C(O)R$^4$, —NR$^3$C(O)OR$^4$, —NR$^3$C(O)NR$^4$R$^5$, —S(O)R$^3$, —S(O)$_2$R$^3$, —NR$^3$S(O)R$^4$, —NR$^3$S(O)$_2$R$^4$, —S(O)NR$^4$R$^5$, —S(O)$_2$NR$^4$R$^5$, or —P(O)(OR$^4$)(OR$^5$), wherein each $R^{1a}$ is, where possible, independently optionally substituted by deuterium, halogen, oxo, —OR$^6$, —NR$^6$R$^7$, —C(O)R$^6$, —CN, —S(O)R$^6$, —S(O)$_2$R$^6$, —P(O)(OR$^6$)(OR$^7$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by deuterium, oxo, —OH or halogen;
each $R^{2a}$, $R^{2b}$, $R^{2c}$, $R^{2e}$, and $R^{2f}$ is independently oxo or $R^{1a}$;
$R^{2d}$ is $C_1$-$C_6$ alkyl optionally substituted by $R^{2e}$ or $C_3$-$C_5$ cycloalkyl optionally substituted by $R^{2f}$;
each $R^3$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl or 3- to 12-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl and 3- to 12-membered heterocyclyl of $R^3$ are independently optionally substituted by halogen, deuterium, oxo, —CN, —OR$^8$, —NR$^8$R$^9$, —P(O)(OR$^8$)(OR$^9$), or $C_1$-$C_6$ alkyl optionally substituted by deuterium, halogen, —OH or oxo;
$R^4$ and $R^5$ are each independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^4$ and $R^5$ are independently optionally substituted by deuterium, halogen, oxo, —CN, —OR$^8$, —NR$^8$R$^9$ or $C_1$-$C_6$ alkyl optionally substituted by deuterium, halogen, —OH or oxo;
or $R^4$ and $R^5$ are taken together with the atom to which they attached to form a 3- to 6-membered heterocyclyl optionally substituted by deuterium, halogen, oxo, —OR$^8$, —NR$^8$R$^9$ or $C_1$-$C_6$ alkyl optionally substituted by deuterium, halogen, oxo or —OH;
$R^6$ and $R^7$ are each independently hydrogen, deuterium, $C_1$-$C_6$ alkyl optionally substituted by deuterium, halogen, or oxo, $C_2$-$C_6$ alkenyl optionally substituted by deuterium, halogen, or oxo, or $C_2$-$C_6$ alkynyl optionally substituted by deuterium, halogen, or oxo;
or $R^6$ and $R^7$ are taken together with the atom to which they attached to form a 3- to 6-membered heterocyclyl optionally substituted by deuterium, halogen, oxo or $C_1$-$C_6$ alkyl optionally substituted by deuterium, halogen, or oxo;
$R^8$ and $R^9$ are each independently hydrogen, deuterium, $C_1$-$C_6$ alkyl optionally substituted by deuterium, halogen, or oxo, $C_2$-$C_6$ alkenyl optionally substituted by deuterium, halogen or oxo, or $C_2$-$C_6$ alkynyl optionally substituted by deuterium, halogen, or oxo;
or $R^8$ and $R^9$ are taken together with the atom to which they attached to form a 3-6 membered heterocyclyl optionally substituted by deuterium, halogen, oxo or $C_1$-$C_6$ alkyl optionally substituted by deuterium, oxo, or halogen;
each $R^{10}$, $R^{11}$, $R^{12}$ and $R^{13}$ are independently hydrogen or deuterium;
$R^{14}$ is deuterium;
q is 0, 1, 2, 3, 4, 5, 6, 7, or 8;
each $R^{15}$ is independently selected from hydrogen, deuterium, or halogen;
each $R^{16}$ is independently selected from hydrogen, deuterium, or halogen; and
p is 3, 4, 5, 6, 7, 8, or 9.

2. The dosage form of claim 1, wherein:
$R^2$ is $C_1$-$C_6$ alkyl optionally substituted by $R^{2a}$; $C_3$-$C_6$ cycloalkyl optionally substituted by $R^{2b}$; 3- to 12-membered heterocyclyl optionally substituted by $R^{2c}$; or —S(O)$_2$R$^{2d}$;
$R^3$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl of $R^3$ are independently optionally substituted by halogen, deuterium, oxo, —CN, —OR$^8$, —NR$^8$R$^9$, —P(O)(OR$^8$)(OR$^9$), or $C_1$-$C_6$ alkyl optionally substituted by deuterium, halogen, —OH or oxo;
each $R^{15}$ is hydrogen; and
each $R^{16}$ is hydrogen;

wherein the compound of Formula (A) is represented by Formula (I):

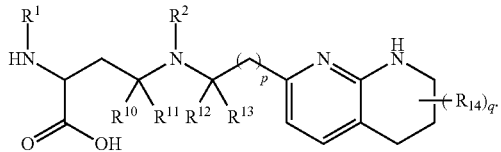

3. The dosage form of claim 1 or a salt thereof, wherein at least one of $R^{1a}$, $R^{2a}$, $R^{2b}$, $R^{2c}$, $R^{2e}$, $R^{2f}$, $R^3$, $R^4$, $R^5$, $R^6$, $R^7$, $R^8$, $R^9$, $R^{10}$, $R^{11}$, $R^{12}$, or $R^{13}$ is deuterium; or
q is 1, 2, 3, 4, 5, 6, 7, or 8.

4. The dosage form of claim 1, or a salt thereof, wherein $R^{10}$, $R^{11}$, $R^{12}$, and $R^{13}$ are hydrogen; q is 0; p is 3; and wherein the compound of Formula (A) is represented by the compound of formula (II):

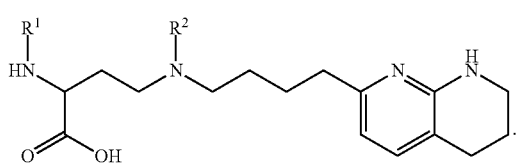

5. The dosage form of claim 1, or a salt thereof, wherein $R^1$ is 5- to 10-membered heteroaryl optionally substituted by $R^{1a}$.

6. The dosage form of claim 1, or a salt thereof, wherein $R^1$ is:
pyrimidinyl, quinazolinyl, pyrazolopyrimidinyl, pyrazinyl, quinolinyl, pyridopyrimidinyl, thienopyrimidinyl, pyridinyl, pyrrolopyrimidinyl, quinoxalinyl, indazolyl, benzothiazolyl, naphthalenyl, purinyl, or isoquinolinyl; and
wherein $R^1$ is optionally substituted by deuterium, hydroxy, $C_1$-$C_6$ alkyl, $C_1$-$C_6$ haloalkyl, $C_1$-$C_6$ perhaloalkyl, $C_1$-$C_6$ alkoxyl, $C_3$-$C_8$ cycloalkyl, $C_3$-$C_8$ halocycloalkyl, $C_3$-$C_8$ cycloalkoxyl, 5- to 10-membered heteroaryl, $C_6$-$C_{14}$ aryl, cyano, amino, alkylamino, or dialkylamino.

7. The dosage form of claim 1, or a salt thereof, wherein $R^1$ is:
pyrimidin-2-yl, pyrimidin-4-yl, quinazolin-4-yl, 1H-pyrazolo[3,4-d]pyrimidin-4-yl, 1H-pyrazolo[4,3-d]pyrimidin-7-yl, pyrazin-2-yl, quinolin-4-yl, pyrido[2,3-d]pyrimidin-4-yl, pyrido[3,2-d]pyrimidin-4-yl, pyrido[3,4-d]pyrimidin-4-yl, thieno[2,3-d]pyrimidin-4-yl, thieno[3,2-d]pyrimidin-4-yl, thienopyrimidin-4-yl, pyridin-2-yl, pyridin-3-yl, 7H-pyrrolo[2,3-d]pyrimidin-4-yl, quinoxalin-2-yl, 1H-indazol-3-yl, benzo[d]thiazol-2-yl, naphthalen-1-yl, 9H-purin-6-yl, or isoquinolin-1-yl; and
wherein $R^1$ is optionally substituted by one or more deuterium, methyl, cyclopropyl, fluoro, chloro, bromo, difluoromethyl, trifluoromethyl, methoxy, cyano, dimethylamino, phenyl, pyridin-3-yl, or pyridin-4-yl.

8. The dosage form of claim 1, or a salt thereof, wherein $R^1$ is pyrimidin-4-yl optionally substituted by $R^{1a}$, wherein each $R^{1a}$ is independently: 5- to 10-membered heteroaryl; $C_1$-$C_6$ alkyl optionally substituted by halogen; pyrazolyl; methyl; difluoromethyl; or trifluoromethyl, or $R^1$ is pyrimidin-4-yl substituted by both methyl and trifluoromethyl.

9. The dosage form of claim 1, or a salt thereof, wherein $R^1$ is quinazolin-4-yl optionally substituted by $R^{1a}$, wherein each $R^{1a}$ is independently halogen, $C_1$-$C_6$ alkyl optionally substituted by halogen, $C_1$-$C_6$ alkoxy, fluoro, chloro, methyl, trifluoromethyl or methoxy.

10. The dosage form of claim 1, or a salt thereof, wherein $R^2$ is:
hydrogen,
deuterium,
hydroxyl,
$C_1$-$C_6$ alkyl, or
—O—$C_1$-$C_6$ alkyl, and
wherein the $C_1$-$C_6$ alkyl and —O—$C_1$-$C_6$ alkyl of $R^2$ are optionally substituted with deuterium, halogen, $C_1$-$C_6$ alkyl, $C_1$-$C_6$ haloalkyl, $C_1$-$C_6$ hydroxyalkyl, $C_1$-$C_6$ alkoxyl, $C_3$-$C_8$ cycloalkyl, $C_3$-$C_8$ halocycloalkyl, $C_3$-$C_6$ cycloalkoxyl, $C_6$-$C_{14}$ aryl, $C_6$-$C_{14}$ aryloxy, 5- to 10-membered heteroaryl, 5- to 10-membered heteroaryloxy, 3- to 12-membered heterocyclyl optionally substituted with oxo, —C(O)NR$^4$R$^5$, —NR$^3$C(O)R$^4$, or —S(O)$_2$R$^3$.

11. The dosage form of claim 1, or a salt thereof, wherein $R^2$ is:
methyl, methoxy, ethyl, ethoxy, propyl, cyclopropyl, or cyclobutyl; and
wherein $R^2$ is optionally substituted with one or more of hydroxy, methoxy, ethoxy, acetamide, fluoro, fluoroalkyl, phenoxy, dimethylamide, methyl sulfonyl, cyclopropoxyl, pyridin-2-yloxy, pyridine-3-yloxy, N-morpholinyl, N-pyrrolidin-2-onyl, dimethylpyrazol-1-yl, (1,4-dioxan-2-yl) methyl, morpholin-2-yl, oxetan-3-yl, phenyl, tetrahydrofuran-2-yl, or thiazol-2-yl;
each of which is substituted with 0, 1, 2, or 3 of deuterium, hydroxy, methyl, fluoro, cyano, or oxo.

12. The dosage form of claim 1, or a salt thereof, wherein $R^2$ is:
a) $C_1$-$C_6$ alkyl optionally substituted by:
$R^{2a}$, wherein each $R^{2a}$ is independently: halogen; $C_3$-$C_8$ cycloalkyl optionally substituted by halogen; 5- to 10-membered heteroaryl optionally substituted by $C_1$-$C_6$ alkyl; —NR$^4$R$^5$; —NR$^3$C(O)R$^4$; —S(O)$_2$R$^3$; oxo; fluoro; cyclobutyl substituted by fluoro; pyrazolyl substituted by methyl; or —S(O)$_2$CH$_3$, or
—OR$^3$, wherein each R$^3$ is independently: hydrogen; $C_1$-$C_6$ alkyl optionally substituted by halogen; $C_3$-$C_6$ cycloalkyl optionally substituted by halogen; $C_6$-$C_{14}$ aryl optionally substituted by halogen; 5- to 6-membered heteroaryl optionally substituted by halogen or $C_1$-$C_6$ alkyl; methyl; ethyl; difluoromethyl; —CH$_2$CHF$_2$; —CH$_2$CF$_3$; cyclopropyl substituted by fluoro; phenyl optionally substituted by fluoro; or pyridinyl optionally substituted by fluoro or methyl,
b) $C_1$-$C_6$ alkyl substituted by both halogen and OR$^3$, wherein R$^3$ is $C_1$-$C_6$ alkyl,
c) —CH$_2$CH$_2$OCH$_3$,
d) $C_3$-$C_6$ cycloalkyl optionally substituted by $R^{2b}$, or
e) cyclopropyl.

13. The dosage form of claim 1, or a salt thereof, wherein $R^1$ is

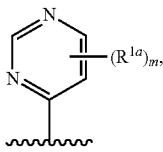

wherein m is 0, 1, 2, or 3 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

14. The dosage form of claim 13, or a salt thereof, wherein $R^1$ is

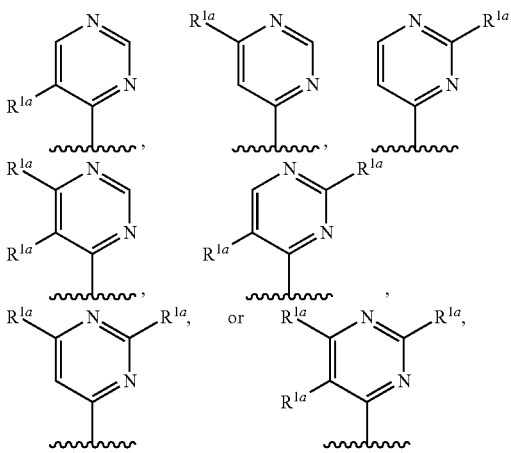

wherein each $R^{1a}$ is independently deuterium, alkyl, haloalkyl, or heteroaryl.

15. The dosage form of claim 1, or a salt thereof, wherein $R^1$ is

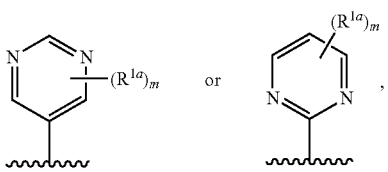

wherein m is 0, 1, 2, or 3 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

16. The dosage form of claim 1, or a salt thereof, wherein $R^1$ is

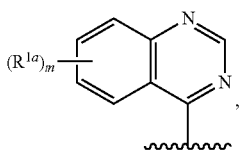

wherein m is 0, 1, 2, 3, 4, or 5 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

17. The dosage form of claim 16, or a salt thereof, wherein $R^1$ is

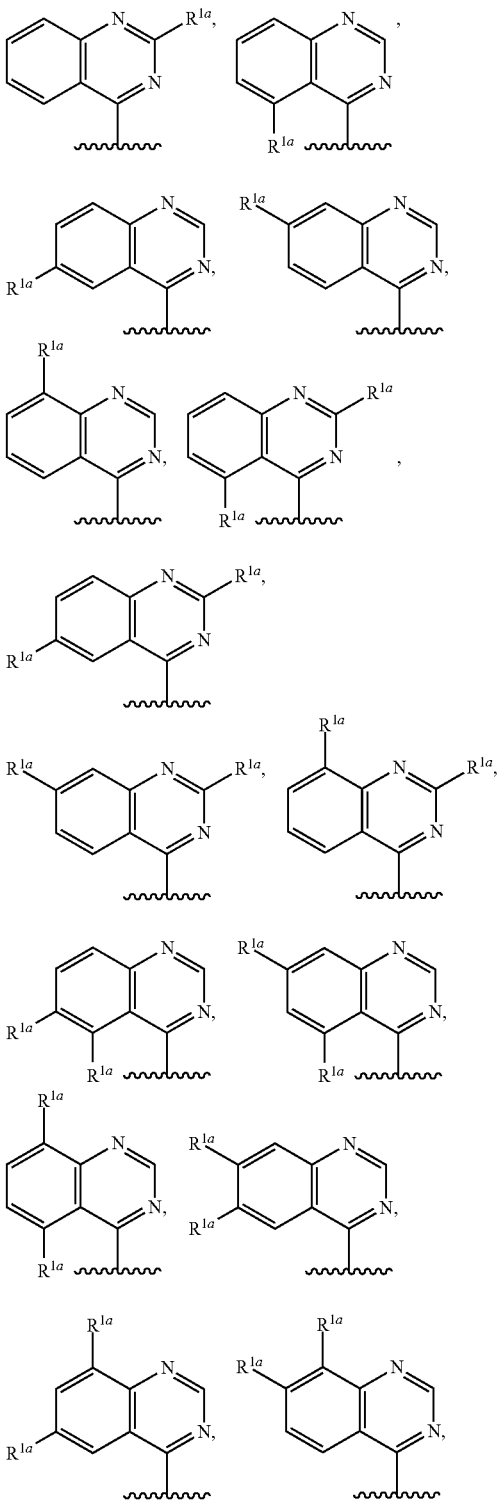

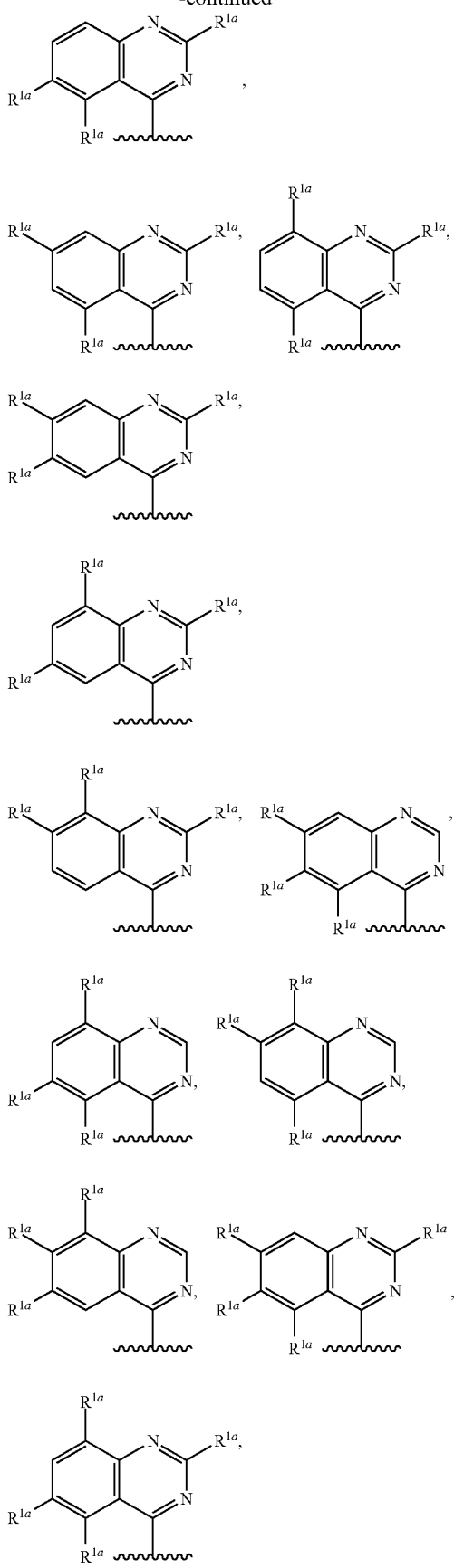
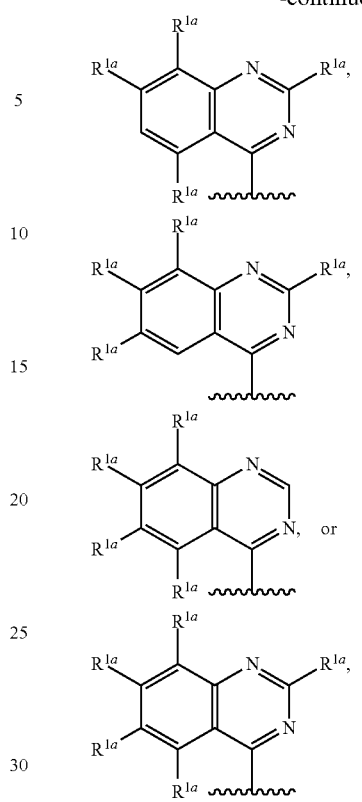
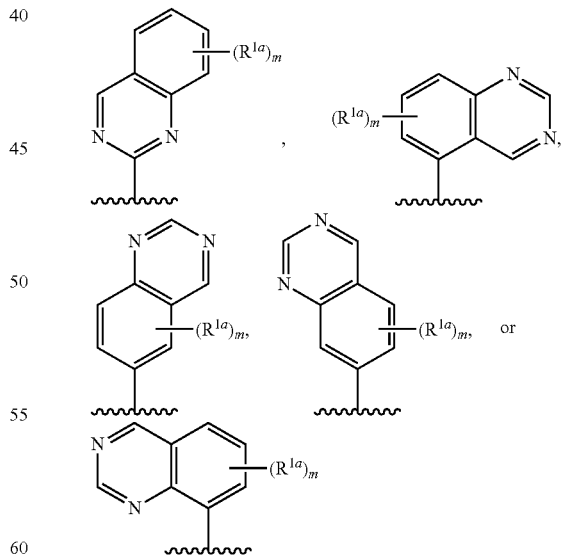

wherein each $R^{1a}$ is independently deuterium, halogen, alkyl, haloalkyl, or alkoxy.

18. The dosage form of claim 1, or a salt thereof, wherein $R^1$ is wherein m is 0, 1, 2, 3, 4, or 5 and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

19. The dosage form of claim 1, or a salt thereof, wherein $R^1$ is

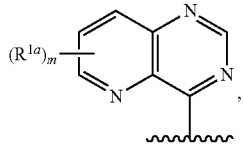

wherein m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

20. The dosage form of claim 19, or a salt thereof, wherein $R^1$ is selected from the group consisting of

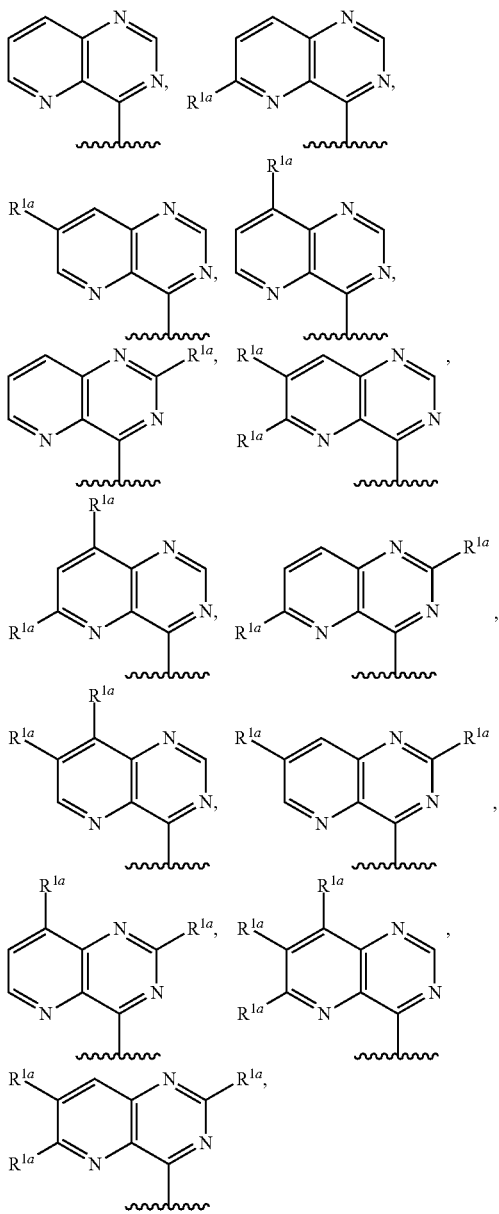

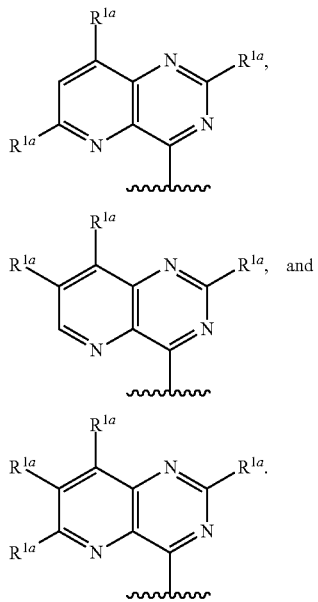

21. The dosage form of claim 1, or a salt thereof, wherein $R^1$ is

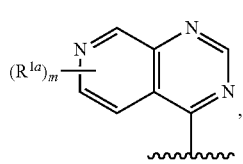

wherein m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

22. The dosage form of claim 21, or a salt thereof, wherein $R^1$ is selected from the group consisting of

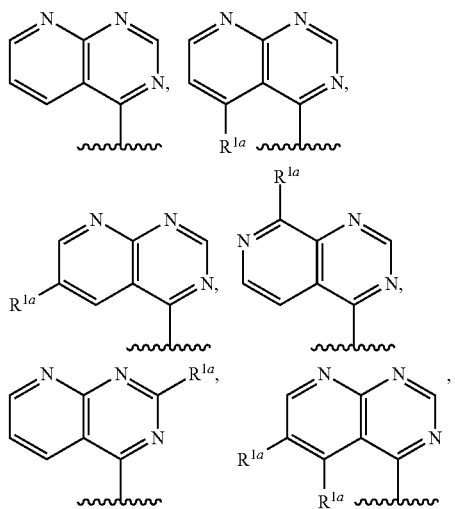

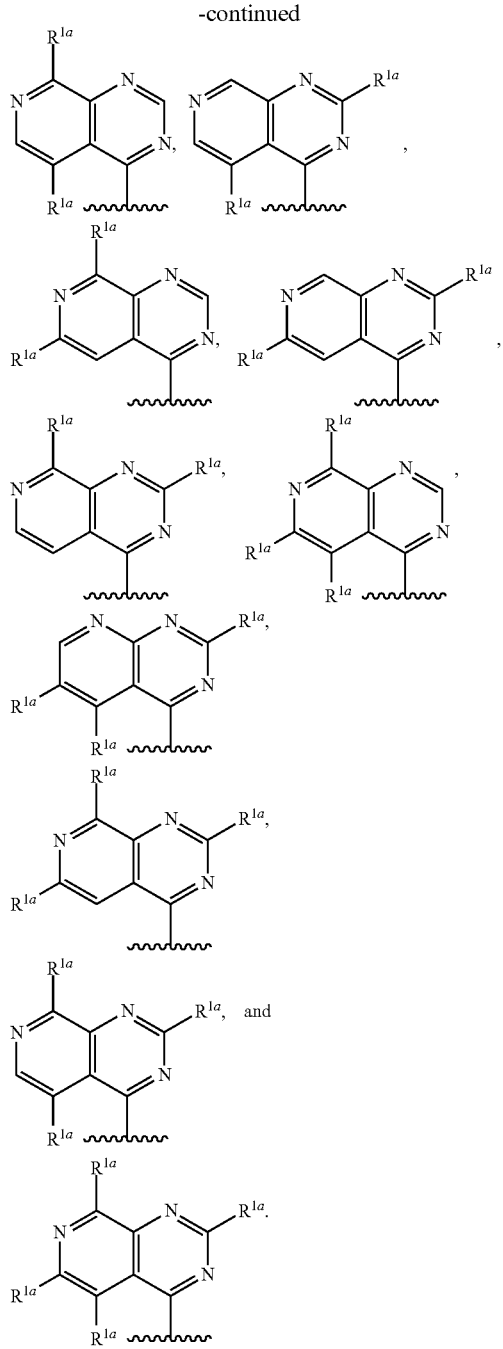

23. The dosage form of claim 1, or a salt thereof, wherein $R^1$ is wherein m is 0, 1, 2, 3, or 4, and each $R^{1a}$ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of $R^{1a}$ are independently optionally substituted by deuterium.

24. The dosage form of claim 23, or a salt thereof, wherein $R^1$ is selected from the group consisting of -continued

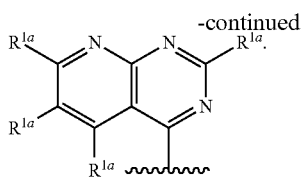

25. The dosage form of claim 1, or a salt thereof, wherein R¹ is

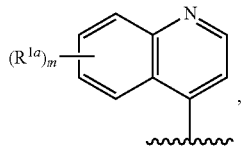

wherein m is 0, 1, 2, 3, 4, 5, or 6 and each R¹ᵃ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of R¹ᵃ are independently optionally substituted by deuterium.

26. The dosage form of claim 1, or a salt thereof, wherein R¹ is

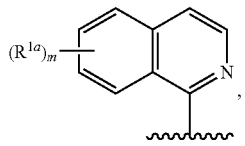

wherein m is 0, 1, 2, 3, 4, 5, or 6 and each R¹ᵃ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of R¹ᵃ are independently optionally substituted by deuterium.

27. The dosage form of claim 1, or a salt thereof, wherein R¹ is

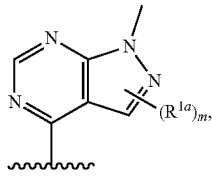

wherein m is 0, 1, or 2 and each R¹ᵃ is, where applicable, independently deuterium, halogen, alkyl, haloalkyl, alkoxy, hydroxy, —CN, or heteroaryl, wherein the alkyl, haloalkyl, alkoxy, hydroxy, and heteroaryl of R¹ᵃ are independently optionally substituted by deuterium.

28. The dosage form of claim 1, or a salt thereof, wherein R¹ is selected from the group consisting of

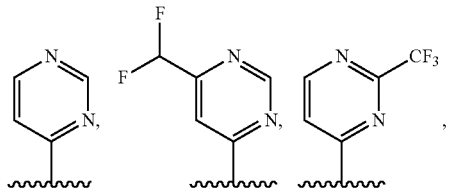

-continued

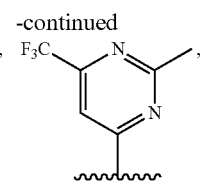

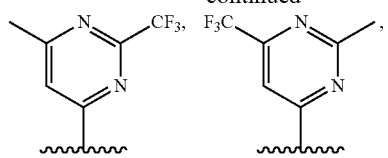

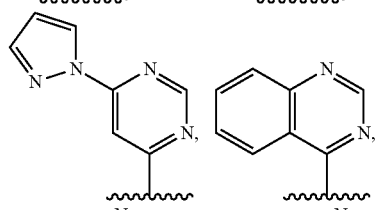

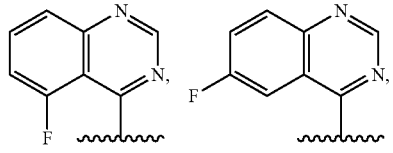

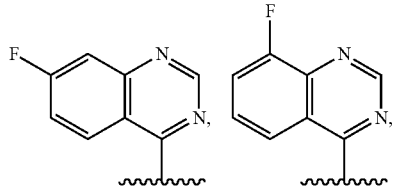

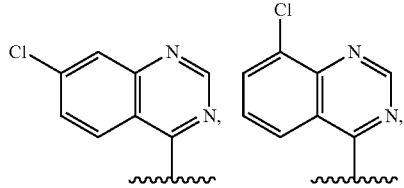

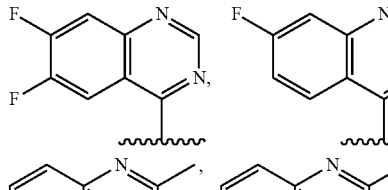

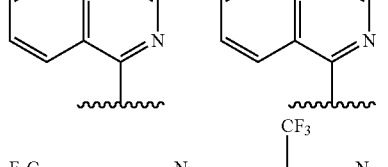

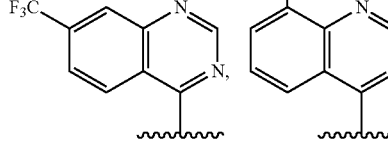

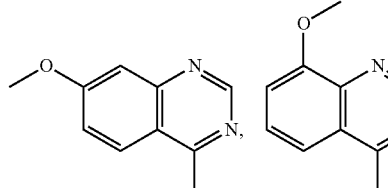

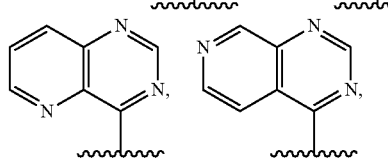

-continued
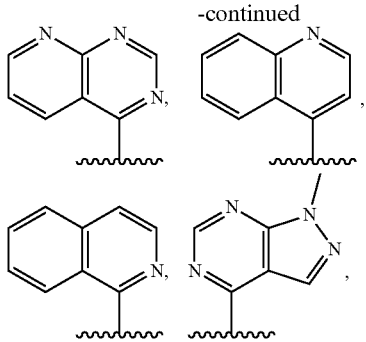
and any of the foregoing groups wherein any one or more hydrogen atom(s) are replaced with deuterium atom(s).
29. The dosage form of claim 1, or a salt thereof, wherein $R^1$ is selected from the group consisting of
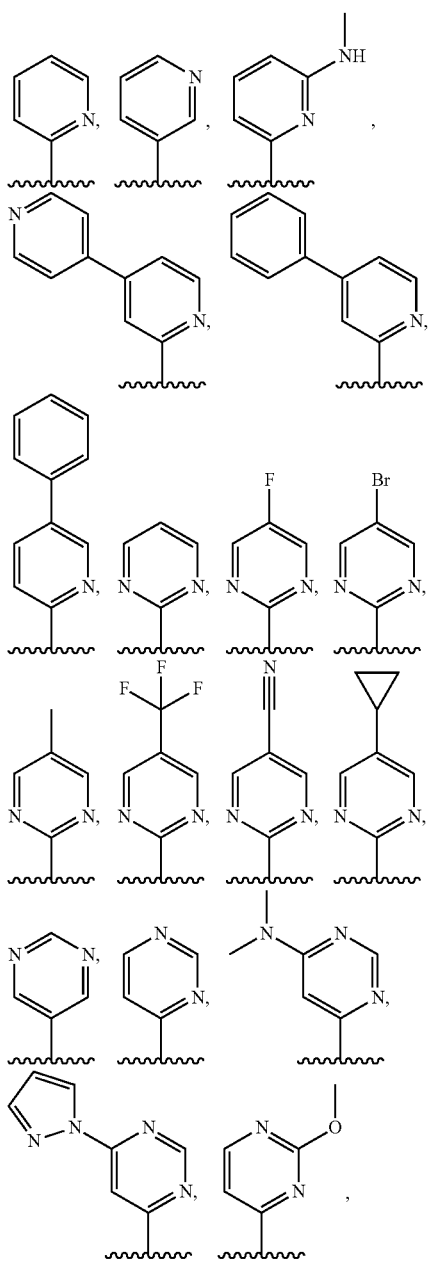
-continued
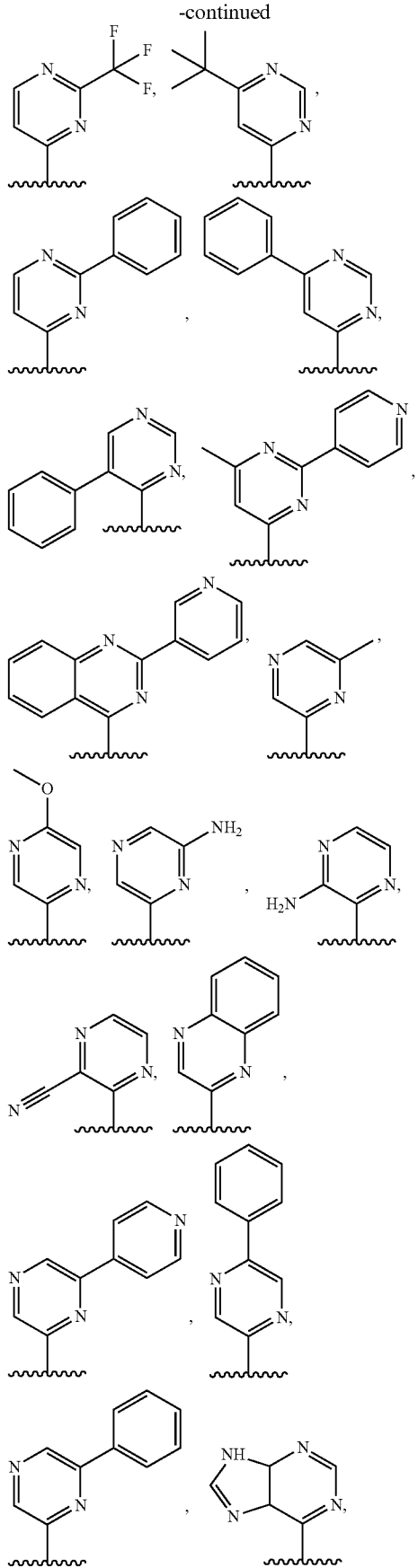

and any of the foregoing groups wherein any one or more hydrogen atom(s) are replaced with deuterium atom(s).

30. The dosage form of claim 1, or a salt thereof, wherein $R^1$ is selected from the group consisting of and any of the foregoing groups wherein any one or more hydrogen atom(s) are replaced with deuterium atom(s).

31. The dosage form of claim 1, or a salt thereof, wherein $R^1$ is selected from the group consisting of

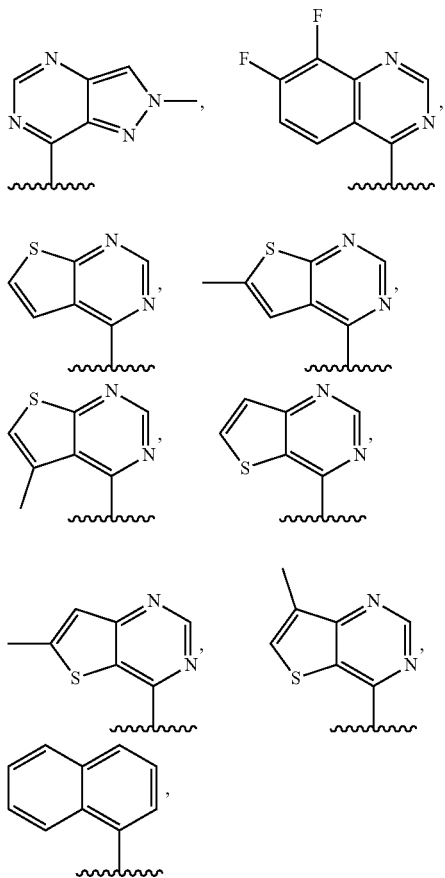

and any of the foregoing groups wherein any one or more hydrogen atom(s) are replaced with deuterium atom(s).

32. The dosage form of claim 1, or a salt thereof, wherein $R^2$ is

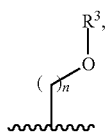

wherein n is 1, 2, 3, 4, 5, or 6, and $R^3$ is $C_1$-$C_2$ alkyl optionally substituted by fluoro; phenyl optionally substituted by fluoro; pyridinyl optionally substituted by fluoro or methyl; or cyclopropyl optionally substituted by fluoro.

33. The dosage form of claim 1, or a salt thereof, wherein $R^2$ is selected from the group consisting of

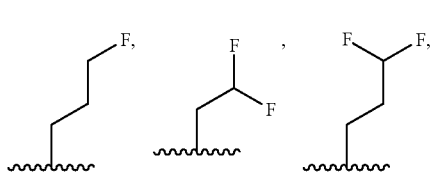

-continued

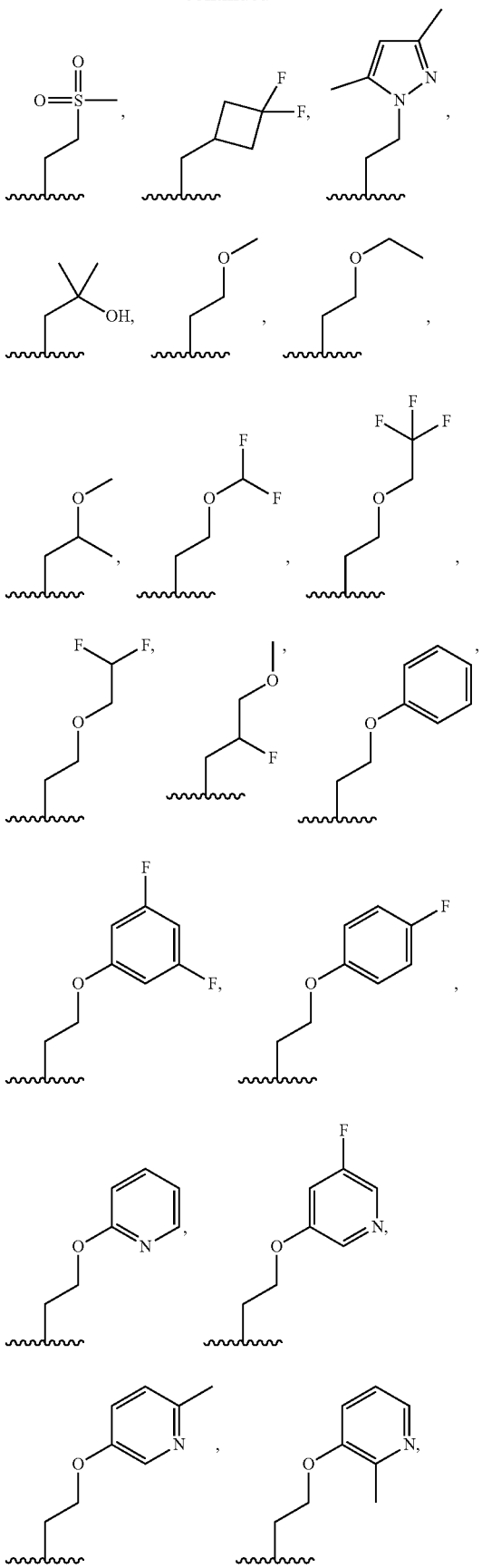

-continued

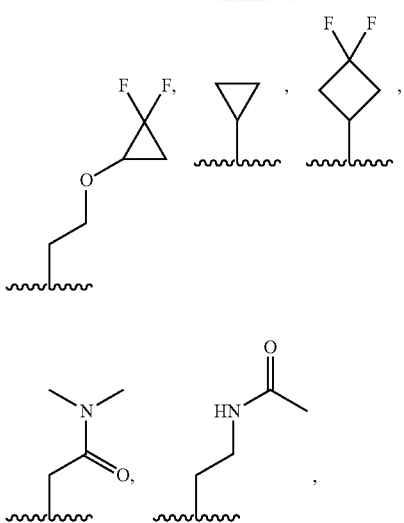

and any of the foregoing groups wherein any one or more hydrogen atom(s) are replaced with deuterium atom(s).

34. The dosage form of claim 1, or a salt thereof, wherein R² is selected from the group consisting of

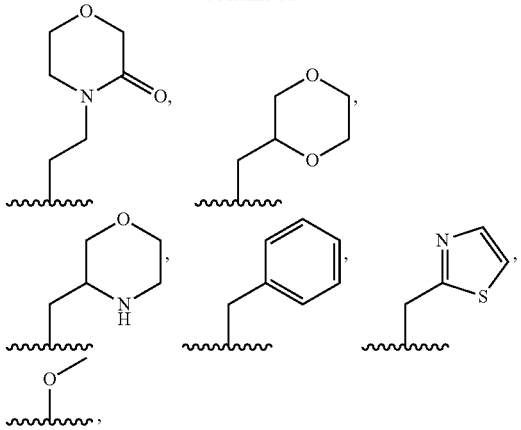

and any of the foregoing groups wherein any one or more hydrogen atom(s) are replaced with deuterium atom(s).

35. The dosage form of claim 1, or a salt thereof, wherein R² is:
 a) $C_3$-$C_5$ alkyl substituted by both fluorine and —$OCH_3$,
 b) $C_1$-$C_6$ alkyl optionally substituted by —$OR^3$, and each $R^3$ is independently: phenyl optionally substituted by fluorine; or pyridinyl optionally substituted by fluorine or methyl, or
 c) $C_1$-$C_6$ alkyl substituted by $R^{2a}$ wherein each $R^{2a}$ is independently: halogen; deuterium; 3- to 12-membered heterocyclyl optionally substituted by oxo; 4- to 5-membered heterocyclyl optionally substituted by oxo; $C_6$-$C_{14}$ aryl optionally substituted by halogen or $OR^6$; phenyl optionally substituted by halogen or —$OR^6$; 5- to 10-membered heteroaryl optionally substituted by $C_1$-$C_6$ alkyl; pyrazolyl optionally substituted by methyl; $C_3$-$C_8$ cycloalkyl optionally substituted by —CN, halogen, or —$OR^6$; or —$S(O)_2R^3$.

36. The dosage form of claim 1, or a salt thereof, wherein $R^1$ is pyridyl, indazolyl, 1H-pyrrolopyridyl, quinolinyl, phenyl, or indanyl, each of which is optionally substituted by $R^{1a}$.

37. A dosage form of claim 1 configured for daily administration, comprising a pharmaceutically acceptable carrier or excipient and a unit dose of a compound, or a salt thereof, selected from the group consisting of
 4-(cyclopropyl(4-(5,6,7,8-tetrahydro-1,8-naphthyridin-2-yl) butyl)amino)-2-((6-(difluoromethyl)pyrimidin-4-yl) amino) butanoic acid;
 4-(cyclopropyl(4-(5,6,7,8-tetrahydro-1,8-naphthyridin-2-yl) butyl)amino)-2-(pyrimidin-4-ylamino) butanoic acid;
 4-(cyclopropyl(4-(5,6,7,8-tetrahydro-1,8-naphthyridin-2-yl) butyl)amino)-2-((1-methyl-1H-pyrazolo[3,4-d]pyrimidin-4-yl) amino) butanoic acid;
 4-((2-hydroxy-2-methylpropyl) (4-(5,6,7,8-tetrahydro-1,8-naphthyridin-2-yl) butyl)amino)-2-(pyrimidin-4-ylamino) butanoic acid;
 4-((2-methoxyethyl) (4-(5,6,7,8-tetrahydro-1,8-naphthyridin-2-yl) butyl)amino)-2-(quinazolin-4-ylamino) butanoic acid;
 4-(cyclopropyl(4-(5,6,7,8-tetrahydro-1,8-naphthyridin-2-yl) butyl)amino)-2-(quinazolin-4-ylamino) butanoic acid;
 2-((7-fluoroquinazolin-4-yl) amino)-4-((2-methoxyethyl) (4-(5,6,7,8-tetrahydro-1,8-naphthyridin-2-yl) butyl) amino) butanoic acid;

4-((2,2-difluoroethyl) (4-(5,6,7,8-tetrahydro-1,8-naphthyridin-2-yl) butyl)amino)-2-(quinazolin-4-ylamino) butanoic acid;

4-((3,3-difluorocyclobutyl) (4-(5,6,7,8-tetrahydro-1,8-naphthyridin-2-yl) butyl)amino)-2-(quinazolin-4-ylamino) butanoic acid;

4-((2-methoxyethyl) (4-(5,6,7,8-tetrahydro-1,8-naphthyridin-2-yl) butyl)amino)-2-((2-methylquinazolin-4-yl) amino) butanoic acid;

4-((2-methoxyethyl) (4-(5,6,7,8-tetrahydro-1,8-naphthyridin-2-yl) butyl)amino)-2-(pyrido[2,3-d]pyrimidin-4-ylamino) butanoic acid;

2-((7-fluoro-2-methylquinazolin-4-yl) amino)-4-((2-methoxyethyl) (4-(5,6,7,8-tetrahydro-1,8-naphthyridin-2-yl) butyl)amino) butanoic acid;

4-((2-methoxyethyl) (4-(5,6,7,8-tetrahydro-1,8-naphthyridin-2-yl) butyl)amino)-2-((7-(trifluoromethyl)quinazolin-4-yl) amino) butanoic acid;

4-((2-methoxyethyl) (4-(5,6,7,8-tetrahydro-1,8-naphthyridin-2-yl) butyl)amino)-2-((2-(trifluoromethyl)quinazolin-4-yl) amino) butanoic acid;

4-((2-methoxyethyl) (4-(5,6,7,8-tetrahydro-1,8-naphthyridin-2-yl) butyl)amino)-2-((8-(trifluoromethyl)quinazolin-4-yl) amino) butanoic acid;

4-((2-methoxyethyl) (4-(5,6,7,8-tetrahydro-1,8-naphthyridin-2-yl) butyl)amino)-2-(pyrido[3,2-d]pyrimidin-4-ylamino) butanoic acid;

4-((2-methoxyethyl) (4-(5,6,7,8-tetrahydro-1,8-naphthyridin-2-yl) butyl)amino)-2-(pyrido[3,4-d]pyrimidin-4-ylamino) butanoic acid;

2-((5-fluoroquinazolin-4-yl) amino)-4-((2-methoxyethyl) (4-(5,6,7,8-tetrahydro-1,8-naphthyridin-2-yl) butyl) amino) butanoic acid;

2-((6-fluoroquinazolin-4-yl) amino)-4-((2-methoxyethyl) (4-(5,6,7,8-tetrahydro-1,8-naphthyridin-2-yl) butyl) amino) butanoic acid;

2-((8-fluoroquinazolin-4-yl) amino)-4-((2-methoxyethyl) (4-(5,6,7,8-tetrahydro-1,8-naphthyridin-2-yl) butyl) amino) butanoic acid;

2-((6,7-difluoroquinazolin-4-yl) amino)-4-((2-methoxyethyl) (4-(5,6,7,8-tetrahydro-1,8-naphthyridin-2-yl) butyl)amino) butanoic acid;

4-((2-methoxyethyl) (4-(5,6,7,8-tetrahydro-1,8-naphthyridin-2-yl) butyl)amino)-2-((2-methyl-6-(trifluoromethyl)pyrimidin-4-yl) amino) butanoic acid;

2-((6-(difluoromethyl)pyrimidin-4-yl) amino)-4-((2-methoxyethyl) (4-(5,6,7,8-tetrahydro-1,8-naphthyridin-2-yl) butyl)amino) butanoic acid;

4-((2-methoxyethyl) (4-(5,6,7,8-tetrahydro-1,8-naphthyridin-2-yl) butyl)amino)-2-((2-(trifluoromethyl)pyrimidin-4-yl) amino) butanoic acid;

4-((2-methoxypropyl) (4-(5,6,7,8-tetrahydro-1,8-naphthyridin-2-yl) butyl)amino)-2-(quinazolin-4-ylamino) butanoic acid;

4-((2-methoxyethyl) (4-(5,6,7,8-tetrahydro-1,8-naphthyridin-2-yl) butyl)amino)-2-((6-methyl-2-(trifluoromethyl)pyrimidin-4-yl) amino) butanoic acid;

4-((2-(methylsulfonyl)ethyl) (4-(5,6,7,8-tetrahydro-1,8-naphthyridin-2-yl) butyl)amino)-2-(quinazolin-4-ylamino) butanoic acid;

4-((2-phenoxyethyl) (4-(5,6,7,8-tetrahydro-1,8-naphthyridin-2-yl) butyl)amino)-2-(quinazolin-4-ylamino) butanoic acid;

4-((3,3-difluoropropyl) (4-(5,6,7,8-tetrahydro-1,8-naphthyridin-2-yl) butyl)amino)-2-(quinazolin-4-ylamino) butanoic acid;

4-((3-fluoropropyl) (4-(5,6,7,8-tetrahydro-1,8-naphthyridin-2-yl) butyl)amino)-2-(quinazolin-4-ylamino) butanoic acid;

4-((2-fluoro-3-methoxypropyl) (4-(5,6,7,8-tetrahydro-1,8-naphthyridin-2-yl) butyl)amino)-2-(quinazolin-4-ylamino) butanoic acid;

2-((7-fluoro-2-methylquinazolin-4-yl) amino)-4-((2-fluoro-3-methoxypropyl) (4-(5,6,7,8-tetrahydro-1,8-naphthyridin-2-yl) butyl)amino) butanoic acid;

4-(((3,3-difluorocyclobutyl)methyl) (4-(5,6,7,8-tetrahydro-1,8-naphthyridin-2-yl) butyl)amino)-2-((7-fluoro-2-methylquinazolin-4-yl) amino) butanoic acid;

2-(isoquinolin-1-ylamino)-4-((2-methoxyethyl) (4-(5,6,7,8-tetrahydro-1,8-naphthyridin-2-yl) butyl)amino) butanoic acid;

4-((2-(difluoromethoxy)ethyl) (4-(5,6,7,8-tetrahydro-1,8-naphthyridin-2-yl) butyl)amino)-2-(quinazolin-4-ylamino) butanoic acid;

4-((2-methoxyethyl) (4-(5,6,7,8-tetrahydro-1,8-naphthyridin-2-yl) butyl)amino)-2-(quinolin-4-ylamino) butanoic acid;

2-((7-chloroquinazolin-4-yl) amino)-4-((2-methoxyethyl) (4-(5,6,7,8-tetrahydro-1,8-naphthyridin-2-yl) butyl) amino) butanoic acid;

2-((8-chloroquinazolin-4-yl) amino)-4-((2-methoxyethyl) (4-(5,6,7,8-tetrahydro-1,8-naphthyridin-2-yl) butyl) amino) butanoic acid;

2-(quinazolin-4-ylamino)-4-((4-(5,6,7,8-tetrahydro-1,8-naphthyridin-2-yl) butyl) (2-(2,2,2-trifluoroethoxy) ethyl)amino) butanoic acid;

2-((7-fluoro-2-methylquinazolin-4-yl) amino)-4-((2-(4-fluorophenoxy)ethyl) (4-(5,6,7,8-tetrahydro-1,8-naphthyridin-2-yl) butyl)amino) butanoic acid;

4-((3-fluoropropyl) (4-(5,6,7,8-tetrahydro-1,8-naphthyridin-2-yl) butyl)amino)-2-((7-methoxyquinazolin-4-yl) amino) butanoic acid;

(2S)-4-((2-(2,2-difluorocyclopropoxy)ethyl) (4-(5,6,7,8-tetrahydro-1,8-naphthyridin-2-yl) butyl)amino)-2-((7-fluoro-2-methylquinazolin-4-yl) amino) butanoic acid;

4-((3-fluoropropyl) (4-(5,6,7,8-tetrahydro-1,8-naphthyridin-2-yl) butyl)amino)-2-((8-methoxyquinazolin-4-yl) amino) butanoic acid;

2-((6-(1H-pyrazol-1-yl) pyrimidin-4-yl) amino)-4-((2-methoxyethyl) (4-(5,6,7,8-tetrahydro-1,8-naphthyridin-2-yl) butyl)amino) butanoic acid;

4-((2-(3,5-dimethyl-1H-pyrazol-1-yl) ethyl) (4-(5,6,7,8-tetrahydro-1,8-naphthyridin-2-yl) butyl)amino)-2-(quinazolin-4-ylamino) butanoic acid;

4-((2-fluoro-3-methoxypropyl) (4-(5,6,7,8-tetrahydro-1,8-naphthyridin-2-yl) butyl)amino)-2-((2-methylquinazolin-4-yl) amino) butanoic acid;

4-((2-(3,5-difluorophenoxy)ethyl) (4-(5,6,7,8-tetrahydro-1,8-naphthyridin-2-yl) butyl)amino)-2-(quinazolin-4-ylamino) butanoic acid;

2-((8-chloroquinazolin-4-yl) amino)-4-((2-(pyridin-2-yloxy)ethyl) (4-(5,6,7,8-tetrahydro-1,8-naphthyridin-2-yl) butyl)amino) butanoic acid;

4-((2-(pyridin-2-yloxy)ethyl) (4-(5,6,7,8-tetrahydro-1,8-naphthyridin-2-yl) butyl)amino)-2-(quinazolin-4-ylamino) butanoic acid;

4-((2-(2,2-difluoroethoxy)ethyl) (4-(5,6,7,8-tetrahydro-1,8-naphthyridin-2-yl) butyl)amino)-2-(quinazolin-4-ylamino) butanoic acid;

2-(pyrido[3,2-d]pyrimidin-4-ylamino)-4-((4-(5,6,7,8-tetrahydro-1,8-naphthyridin-2-yl) butyl) (2-(2,2,2-trifluoroethoxy)ethyl)amino) butanoic acid;

4-((2-((2-methylpyridin-3-yl) oxy)ethyl) (4-(5,6,7,8-tetrahydro-1,8-naphthyridin-2-yl) butyl)amino)-2-(quinazolin-4-ylamino) butanoic acid;

2-((7-fluoro-2-methylquinazolin-4-yl) amino)-4-((2-((2-methylpyridin-3-yl) oxy)ethyl) (4-(5,6,7,8-tetrahydro-1,8-naphthyridin-2-yl) butyl)amino) butanoic acid;

4-((2-((2-methylpyridin-3-yl) oxy)ethyl) (4-(5,6,7,8-tetrahydro-1,8-naphthyridin-2-yl) butylamino)-2-(pyrido[3,2-d]pyrimidin-4-ylamino) butanoic acid;

4-((2-ethoxyethyl) (4-(5,6,7,8-tetrahydro-1,8-naphthyridin-2-yl) butyl)amino)-2-(quinazolin-4-ylamino) butanoic acid;

2-((7-fluoro-2-methylquinazolin-4-yl) amino)-4-((2-((6-methylpyridin-3-yl) oxy)ethyl) (4-(5,6,7,8-tetrahydro-1,8-naphthyridin-2-yl) butyl)amino) butanoic acid;

4-((2-((6-methylpyridin-3-yl) oxy)ethyl) (4-(5,6,7,8-tetrahydro-1,8-naphthyridin-2-yl) butyl)amino)-2-(pyrido[3,2-d]pyrimidin-4-ylamino) butanoic acid;

4-((2-((5-fluoropyridin-3-yl) oxy)ethyl) (4-(5,6,7,8-tetrahydro-1,8-naphthyridin-2-yl) butyl)amino)-2-(quinazolin-4-ylamino) butanoic acid;

4-((2-((6-methylpyridin-3-yl) oxy)ethyl) (4-(5,6,7,8-tetrahydro-1,8-naphthyridin-2-yl) butyl)amino)-2-(quinazolin-4-ylamino) butanoic acid;

4-((2-((5-fluoropyridin-3-yl) oxy)ethyl) (4-(5,6,7,8-tetrahydro-1,8-naphthyridin-2-yl) butyl)amino)-2-(pyrido[3,2-d]pyrimidin-4-ylamino) butanoic acid;

2-((7-fluoro-2-methylquinazolin-4-yl) amino)-4-((2-((5-fluoropyridin-3-yl) oxy)ethyl) (4-(5,6,7,8-tetrahydro-1,8-naphthyridin-2-yl) butyl)amino) butanoic acid;

4-((2-methoxypropyl) (4-(5,6,7,8-tetrahydro-1,8-naphthyridin-2-yl) butyl)amino)-2-(quinazolin-4-ylamino) butanoic acid;

4-((2-acetamidoethyl) (4-(5,6,7,8-tetrahydro-1,8-naphthyridin-2-yl) butyl)amino)-2-(quinazolin-4-ylamino) butanoic acid;

4-((2-(dimethylamino)-2-oxoethyl) (4-(5,6,7,8-tetrahydro-1,8-naphthyridin-2-yl) butyl)amino)-2-(quinazolin-4-ylamino) butanoic acid;

2-((7-fluoro-2-methylquinazolin-4-yl) amino)-4-((2-methoxypropyl) (4-(5,6,7,8-tetrahydro-1,8-naphthyridin-2-yl) butyl)amino) butanoic acid; and 4-((2-methoxypropyl) (4-(5,6,7,8-tetrahydro-1,8-naphthyridin-2-yl) butyl)amino)-2-((2-methylquinazolin-4-yl) amino) butanoic acid.

38. A dosage form of claim 1 configured for daily administration, comprising a pharmaceutically acceptable carrier or excipient and a unit dose of a compound, or a salt thereof, selected from the group consisting of 2-((3-cyanopyrazin-2-yl) amino)-4-((2-methoxyethyl) (4-(5,6,7,8-tetrahydro-1,8-naphthyridin-2-yl) butyl) amino) butanoic acid;

2-((5-cyanopyrimidin-2-yl) amino)-4-((2-methoxypropyl) (4-(5,6,7,8-tetrahydro-1,8-naphthyridin-2-yl) butyl)amino) butanoic acid;

4-((2-methoxypropyl) (4-(5,6,7,8-tetrahydro-1,8-naphthyridin-2-yl) butyl)amino)-2-((5-(trifluoromethyl)pyrimidin-2-yl) amino) butanoic acid;

2-((5-bromopyrimidin-2-yl) amino)-4-((2-methoxypropyl) (4-(5,6,7,8-tetrahydro-1,8-naphthyridin-2-yl) butyl)amino) butanoic acid;

2-((1H-pyrazolo[3,4-d]pyrimidin-4-yl) amino)-4-((2-methoxypropyl) (4-(5,6,7,8-tetrahydro-1,8-naphthyridin-2-yl) butyl)amino) butanoic acid;

4-((2-methoxypropyl) (4-(5,6,7,8-tetrahydro-1,8-naphthyridin-2-yl) butyl)amino)-2-((2-(trifluoromethyl)pyrimidin-4-yl) amino) butanoic acid;

4-((2-methoxypropyl) (4-(5,6,7,8-tetrahydro-1,8-naphthyridin-2-yl) butyl)amino)-2-((2-phenylpyrimidin-4-yl) amino) butanoic acid;

4-((2-methoxypropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-((2-hydroxyethyl) (4-(5,6,7,8-tetrahydro-1,8-naphthyridin-2-yl) butyl)amino)-2-(quinazolin-4-ylamino) butanoic acid;

2-((3-cyanopyrazin-2-yl) amino)-4-((2-methoxypropyl) (4-(5,6,7,8-tetrahydro-1,8-naphthyridin-2-yl) butyl) amino) butanoic acid;

2-((6-(1H-pyrazol-1-yl) pyrimidin-4-yl) amino)-4-((2-methoxypropyl) (4-(5,6,7,8-tetrahydro-1,8-naphthyridin-2-yl) butyl)amino) butanoic acid;

2-((5-fluoropyrimidin-2-yl) amino)-4-((2-methoxypropyl) (4-(5,6,7,8-tetrahydro-1,8-naphthyridin-2-yl) butyl)amino) butanoic acid;

2-((1H-pyrazolo[4,3-d]pyrimidin-7-yl) amino)-4-((2-methoxypropyl) (4-(5,6,7,8-tetrahydro-1,8-naphthyridin-2-yl) butyl)amino) butanoic acid;

4-((2-methoxypropyl) (4-(5,6,7,8-tetrahydro-1,8-naphthyridin-2-yl) butyl)amino)-2-((6-phenylpyrimidin-4-yl) amino) butanoic acid;

4-((2-methoxypropyl) (4-(5,6,7,8-tetrahydro-1,8-naphthyridin-2-yl) butyl)amino)-2-((5-phenylpyrimidin-4-yl) amino) butanoic acid;

2-((1-methyl-1H-pyrazolo[3,4-d]pyrimidin-4-yl) amino)-4-((2-phenoxyethyl) (4-(5,6,7,8-tetrahydro-1,8-naphthyridin-2-yl) butyl)amino) butanoic acid;

2-((5-bromopyrimidin-2-yl) amino)-4-((2-phenoxyethyl) (4-(5,6,7,8-tetrahydro-1,8-naphthyridin-2-yl) butyl) amino) butanoic acid;

2-((5-cyanopyrimidin-2-yl) amino)-4-((2-fluoro-3-methoxypropyl) (4-(5,6,7,8-tetrahydro-1,8-naphthyridin-2-yl) butyl)amino) butanoic acid;

4-((2-fluoro-3-methoxypropyl) (4-(5,6,7,8-tetrahydro-1,8-naphthyridin-2-yl) butyl)amino)-2-((5-(trifluoromethyl)pyrimidin-2-yl) amino) butanoic acid;

2-((5-bromopyrimidin-2-yl) amino)-4-((2-fluoro-3-methoxypropyl) (4-(5,6,7,8-tetrahydro-1,8-naphthyridin-2-yl) butyl)amino) butanoic acid;

4-((2-fluoro-3-methoxypropyl) (4-(5,6,7,8-tetrahydro-1,8-naphthyridin-2-yl) butyl)amino)-2-((2-(trifluoromethyl)pyrimidin-4-yl) amino) butanoic acid;

4-((2,2-difluoroethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-((2-phenoxyethyl) (4-(5,6,7,8-tetrahydro-1,8-naphthyridin-2-yl) butyl)amino)-2-((5-(trifluoromethyl)pyrimidin-2-yl) amino) butanoic acid;

2-((1H-pyrazolo[3,4-d]pyrimidin-4-yl) amino)-4-((2-phenoxyethyl) (4-(5,6,7,8-tetrahydro-1,8-naphthyridin-2-yl) butyl)amino) butanoic acid;

2-((6-(1H-pyrazol-1-yl) pyrimidin-4-yl) amino)-4-((2-phenoxyethyl) (4-(5,6,7,8-tetrahydro-1,8-naphthyridin-2-yl) butyl)amino) butanoic acid;

4-((2-phenoxyethyl) (4-(5,6,7,8-tetrahydro-1,8-naphthyridin-2-yl) butyl)amino)-2-((2-(trifluoromethyl)pyrimidin-4-yl) amino) butanoic acid;

4-((2-phenoxyethyl) (4-(5,6,7,8-tetrahydro-1,8-naphthyridin-2-yl) butyl)amino)-2-((6-phenylpyrimidin-4-yl) amino) butanoic acid;

4-((2-phenoxyethyl) (4-(5,6,7,8-tetrahydro-1,8-naphthyridin-2-yl) butyl)amino)-2-((2-(pyridin-3-yl) quinazolin-4-yl) amino) butanoic acid;

4-((2,2-difluoroethyl) (4-(5,6,7,8-tetrahydro-1,8-naphthyridin-2-yl) butyl)amino)-2-((5-(trifluoromethyl)pyrimidin-2-yl) amino) butanoic acid;

2-((5-bromopyrimidin-2-yl) amino)-4-((2,2-difluoroethyl) (4-(5,6,7,8-tetrahydro-1,8-naphthyridin-2-yl) butyl)amino) butanoic acid;

4-((2,2-difluoroethyl) (4-(5,6,7,8-tetrahydro-1,8-naphthyridin-2-yl) butyl)amino)-2-((2-(trifluoromethyl)pyrimidin-4-yl) amino) butanoic acid;

2-((6-(1H-pyrazol-1-yl) pyrimidin-4-yl) amino)-4-((2,2-difluoroethyl) (4-(5,6,7,8-tetrahydro-1,8-naphthyridin-2-yl) butyl)amino) butanoic acid;

4-((2,2-difluoroethyl) (4-(5,6,7,8-tetrahydro-1,8-naphthyridin-2-yl) butyl)amino)-2-((2-(pyridin-3-yl) quinazolin-4-yl) amino) butanoic acid;

4-((2-methoxypropyl) (4-(5,6,7,8-tetrahydro-1,8-naphthyridin-2-yl) butyl)amino)-2-((2-(pyridin-3-yl) quinazolin-4-yl) amino) butanoic acid;

2-((1-methyl-1H-pyrazolo[3,4-d]pyrimidin-4-yl) amino)-4-((2-(methylsulfonyl)ethyl) (4-(5,6,7,8-tetrahydro-1,8-naphthyridin-2-yl) butyl)amino) butanoic acid;

4-((2-(methylsulfonyl)ethyl) (4-(5,6,7,8-tetrahydro-1,8-naphthyridin-2-yl) butyl)amino)-2-((5-(trifluoromethyl)pyrimidin-2-yl) amino) butanoic acid;

2-((5-bromopyrimidin-2-yl) amino)-4-((2-(methylsulfonyl)ethyl) (4-(5,6,7,8-tetrahydro-1,8-naphthyridin-2-yl) butyl)amino) butanoic acid;

4-((2-(methylsulfonyl)ethyl) (4-(5,6,7,8-tetrahydro-1,8-naphthyridin-2-yl) butyl)amino)-2-((2-(trifluoromethyl)pyrimidin-4-yl) amino) butanoic acid;

4-((2-fluoro-3-methoxypropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-((2-methoxypropyl) (4-(5,6,7,8-tetrahydro-1,8-naphthyridin-2-yl) butyl)amino)-2-(pyrimidin-4-ylamino) butanoic acid;

4-((2-(methylsulfonyl)ethyl) (4-(5,6,7,8-tetrahydro-1,8-naphthyridin-2-yl) butyl)amino)-2-((2-(pyridin-3-yl) quinazolin-4-yl) amino) butanoic acid;

2-((6-(1H-pyrazol-1-yl) pyrimidin-4-yl) amino)-4-((2-fluoro-3-methoxypropyl) (4-(5,6,7,8-tetrahydro-1,8-naphthyridin-2-yl) butyl)amino) butanoic acid;

4-((2-fluoro-3-methoxypropyl) (4-(5,6,7,8-tetrahydro-1,8-naphthyridin-2-yl) butyl)amino)-2-((2-(pyridin-3-yl) quinazolin-4-yl) amino) butanoic acid;

4-((2-fluoro-3-methoxypropyl) (4-(5,6,7,8-tetrahydro-1,8-naphthyridin-2-yl) butyl)amino)-2-((5-phenylpyrimidin-4-yl) amino) butanoic acid;

2-((5-cyanopyrimidin-2-yl) amino)-4-((2-phenoxyethyl) (4-(5,6,7,8-tetrahydro-1,8-naphthyridin-2-yl) butyl) amino) butanoic acid;

2-((1H-pyrazolo[3,4-d]pyrimidin-4-yl) amino)-4-((2,2-difluoroethyl) (4-(5,6,7,8-tetrahydro-1,8-naphthyridin-2-yl) butyl)amino) butanoic acid;

4-(cyclopropyl(4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-(cyclopropyl(4-(5,6,7,8-tetrahydro-1,8-naphthyridin-2-yl) butyl)amino)-2-((5-(trifluoromethyl)pyrimidin-2-yl) amino) butanoic acid;

4-(cyclopropyl(4-(5,6,7,8-tetrahydro-1,8-naphthyridin-2-yl) butyl)amino)-2-((2-(trifluoromethyl)pyrimidin-4-yl) amino) butanoic acid;

2-((1H-pyrazolo[3,4-d]pyrimidin-4-yl) amino)-4-(cyclopropyl(4-(5,6,7,8-tetrahydro-1,8-naphthyridin-2-yl) butyl)amino) butanoic acid;

2-((5-cyclopropylpyrimidin-2-yl) amino)-4-((2-phenoxyethyl) (4-(5,6,7,8-tetrahydro-1,8-naphthyridin-2-yl) butyl)amino) butanoic acid;

2-((5-cyanopyrimidin-2-yl) amino)-4-((2,2-difluoroethyl) (4-(5,6,7,8-tetrahydro-1,8-naphthyridin-2-yl) butyl) amino) butanoic acid;

4-((2,2-difluoroethyl) (4-(5,6,7,8-tetrahydro-1,8-naphthyridin-2-yl) butyl)amino)-2-((5-phenylpyrimidin-4-yl) amino) butanoic acid;

4-((2,2-difluoroethyl) (4-(5,6,7,8-tetrahydro-1,8-naphthyridin-2-yl) butyl)amino)-2-(pyrimidin-4-ylamino) butanoic acid;

4-((2,2-difluoroethyl) (4-(5,6,7,8-tetrahydro-1,8-naphthyridin-2-yl) butyl)amino)-2-((5-fluoropyrimidin-2-yl) amino) butanoic acid;

4-((2,2-difluoroethyl) (4-(5,6,7,8-tetrahydro-1,8-naphthyridin-2-yl) butyl)amino)-2-((6-methyl-2-(pyridin-4-yl) pyrimidin-4-yl) amino) butanoic acid;

4-((2-(4-fluorophenoxy)ethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

2-((5-cyclopropylpyrimidin-2-yl)amino)-4-((2-methoxypropyl) (4-(5,6,7,8-tetrahydro-1,8-naphthyridin-2-yl) butyl)amino) butanoic acid;

2-((1H-pyrazolo[3,4-d]pyrimidin-4-yl) amino)-4-((2-(methylsulfonyl)ethyl) (4-(5,6,7,8-tetrahydro-1,8-naphthyridin-2-yl) butyl)amino) butanoic acid;

2-((6-(1H-pyrazol-1-yl) pyrimidin-4-yl) amino)-4-((2-(methylsulfonyl)ethyl) (4-(5,6,7,8-tetrahydro-1,8-naphthyridin-2-yl) butyl)amino) butanoic acid;

4-((2-fluoro-3-methoxypropyl) (4-(5,6,7,8-tetrahydro-1,8-naphthyridin-2-yl) butyl)amino)-2-(pyrimidin-4-ylamino) butanoic acid;

4-((2-fluoro-3-methoxypropyl) (4-(5,6,7,8-tetrahydro-1,8-naphthyridin-2-yl) butyl)amino)-2-((6-phenylpyrimidin-4-yl) amino) butanoic acid;

(2S)-4-((oxetan-2-ylmethyl) (4-(5,6,7,8-tetrahydro-1,8-naphthyridin-2-yl) butyl)amino)-2-(quinazolin-4-ylamino) butanoic acid;

4-((3-hydroxy-2-(hydroxymethyl)propyl) (4-(5,6,7,8-tetrahydro-1,8-naphthyridin-2-yl) butyl)amino)-2-(quinazolin-4-ylamino) butanoic acid;

2-((5-bromopyrimidin-2-yl) amino)-4-((3,3-difluoropropyl) (4-(5,6,7,8-tetrahydro-1,8-naphthyridin-2-yl) butyl)amino) butanoic acid;

4-((3,3-difluoropropyl) (4-(5,6,7,8-tetrahydro-1,8-naphthyridin-2-yl) butyl)amino)-2-((5-(trifluoromethyl)pyrimidin-2-yl) amino) butanoic acid;

4-((3,3-difluoropropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-((3,3-difluoropropyl) (4-(5,6,7,8-tetrahydro-1,8-naphthyridin-2-yl) butyl)amino)-2-((2-(trifluoromethyl)pyrimidin-4-yl) amino) butanoic acid;

2-((5-cyclopropylpyrimidin-2-yl) amino)-4-((3,3-difluoropropyl) (4-(5,6,7,8-tetrahydro-1,8-naphthyridin-2-yl) butyl)amino) butanoic acid;

4-((3-fluoropropyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-((3-fluoropropyl) (4-(5,6,7,8-tetrahydro-1,8-naphthyridin-2-yl) butyl)amino)-2-((5-(trifluoromethyl) pyrimidin-2-yl) amino) butanoic acid;

2-((5-cyanopyrimidin-2-yl) amino)-4-((2-(4-fluorophenoxy)ethyl) (4-(5,6,7,8-tetrahydro-1,8-naphthyridin-2-yl) butyl)amino) butanoic acid;

4-((2-(4-fluorophenoxy)ethyl) (4-(5,6,7,8-tetrahydro-1,8-naphthyridin-2-yl) butyl)amino)-2-((5-(trifluoromethyl)pyrimidin-2-yl) amino) butanoic acid;

4-((2-(dimethylamino)-2-oxoethyl) (4-(5,6,7,8-tetrahydro-1,8-naphthyridin-2-yl) butyl)amino)-2-((1-methyl-1H-pyrazolo[3,4-d]pyrimidin-4-yl) amino) butanoic acid;

4-((2-(dimethylamino)-2-oxoethyl) (4-(5,6,7,8-tetrahydro-1,8-naphthyridin-2-yl) butyl)amino)-2-((5-(trifluoromethyl)pyrimidin-2-yl) amino) butanoic acid;

4-((2,2-difluoroethyl) (4-(5,6,7,8-tetrahydro-1,8-naphthyridin-2-yl) butyl)amino)-2-((6-phenylpyrimidin-4-yl) amino) butanoic acid;

2-((1H-pyrazolo[3,4-d]pyrimidin-4-yl) amino)-4-((2-(4-fluorophenoxy)ethyl) (4-(5,6,7,8-tetrahydro-1,8-naphthyridin-2-yl) butyl)amino) butanoic acid;

2-((5-bromopyrimidin-2-yl) amino)-4-((2-(4-fluorophenoxy)ethyl) (4-(5,6,7,8-tetrahydro-1,8-naphthyridin-2-yl) butyl)amino) butanoic acid;

4-((2-(dimethylamino)-2-oxoethyl) (4-(5,6,7,8-tetrahydro-1,8-naphthyridin-2-yl) butyl)amino)-2-((2-(trifluoromethyl)pyrimidin-4-yl) amino) butanoic acid;

2-((5-cyclopropylpyrimidin-2-yl) amino)-4-((2,2-difluoroethyl) (4-(5,6,7,8-tetrahydro-1,8-naphthyridin-2-yl) butyl)amino) butanoic acid; and 4-(((3-fluorooxetan-3-yl) methyl) (4-(5,6,7,8-tetrahydro-1,8-naphthyridin-2-yl) butyl)amino)-2-(quinazolin-4-ylamino) butanoic acid.

39. The dosage form of claim 1, wherein the compound is (S)-4-((2-methoxyethyl)(4-(5,6,7,8-tetrahydro-1,8-naphthyridin-2-yl)butyl)amino)-2-(quinazolin-4-ylamino)butanoic acid:

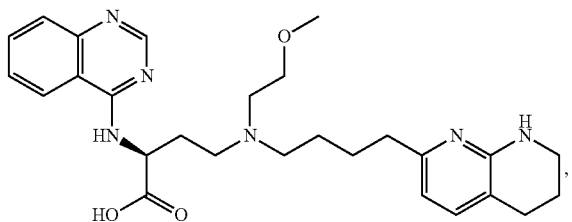 [SMILES: COCCN(CCCCc1ccc2c(n1)NCCC2)CC[C@H](Nc1ncnc2ccccc12)C(=O)O]

or a salt thereof.

40. The dosage form of claim 1, comprising about 1, 2.5, 5, 7.5, 10, 15, 20, 25, 30, 35, 40, 50, 75, 80, 85, 90, 95, 100, 105, 110, 115, 120, or 125 mg of the compound, or a range between any two of the preceding values.

41. The dosage form of claim 1, comprising an amount of the compound in mg of about one of: 1, 2.5, 5, 7.5, 10, 15, 20, 25, 30, 35, 40, 50, 75, 80, 85, 90, 95, 100, 105, 110, 115, 120, 125, 150, 175, 200, 225, or 250, or a range between any two of the preceding amounts.

42. The dosage form of claim 1, comprising the compound in an amount effective on administration to an individual to produce a $C_{max}$ in plasma of the individual in ng/mL of at least about one of 700, 750, 800, 850, 900, 950, 1000, 1050, 1100, 1150, 1200, 1250, 1300, 1350, 1400, 1450, or 1500, or a range between any two of the preceding concentrations.

43. The dosage form of claim 1, comprising the compound in an amount effective on administration to an individual to produce a $C_{max}$ in ng/mL in plasma of the individual, the $C_{max}$ corresponding to a plasma-adjusted concentration effective to inhibit a percentage of $\alpha v \beta_6$ or $\alpha v \beta_1$ in the individual of at least about one of 50, 55, 60, 65, 70, 75, 80, 85, 90, 95, or 100, or a range between any two of the preceding percentages.

44. A kit comprising a dosage form of claim 1.

45. The kit of claim 44, further comprising instructions for the treatment of a fibrotic disease.

46. The kit of claim 44, further comprising instructions for daily administration of the dosage form to an individual in need thereof.

47. The kit of claim 44, further comprising instructions for administration of the dosage form to an individual in need thereof one, two, three, or four times daily.

48. The kit of claim 44, further comprising instructions for administration of the dosage form to an individual in need thereof once daily.

49. The kit of claim 44, further comprising instructions for administration of the dosage form to an individual in need thereof to produce a $C_{max}$ in plasma of the individual in ng/mL of at least about one of 700, 750, 800, 850, 900, 950, 1000, 1050, 1100, 1150, 1200, 1250, 1300, 1350, 1400, 1450, or 1500, or a range between any two of the preceding concentrations.

50. The kit of claim 44, further comprising instructions for administration of the dosage form to an individual in need thereof to produce a $C_{max}$ in ng/mL in plasma of the individual, the $C_{max}$ corresponding to a plasma-adjusted concentration effective to inhibit a percentage of $\alpha v \beta_6$ or $\alpha v \beta_1$ in the individual of at least about one of 50, 55, 60, 65, 70, 75, 80, 85, 90, 95, or 100, or a range between any two of the preceding percentages.

51. The dosage form of claim 1 or a salt thereof for use in inhibiting $\alpha v \beta_6$ or $\alpha v \beta_1$ integrin, the use comprising administering the dosage form to an individual in need thereof in an amount effective to inhibit the $\alpha v \beta_6$ or $\alpha v \beta_1$ integrin.

52. The dosage form of claim 51, the use comprising administering the dosage form to the individual effective to produce a $C_{max}$ of the compound in plasma of the individual in ng/mL of at least about one of 700, 750, 800, 850, 900, 950, 1000, 1050, 1100, 1150, 1200, 1250, 1300, 1350, 1400, 1450, or 1500, or a range between any two of the preceding concentrations.

53. The dosage form of claim 51, the use comprising administering the dosage form to the individual effective to produce a $C_{max}$ in ng/mL in plasma of the individual, the $C_{max}$ corresponding to a plasma-adjusted concentration effective to inhibit a percentage of $\alpha v \beta_6$ or $\alpha v \beta_1$ in the individual of at least about one of 50, 55, 60, 65, 70, 75, 80, 85, 90, 95, or 100, or a range between any two of the preceding percentages.

54. The dosage form of claim 1, or a salt thereof, wherein the compound is of the formula (II-A):

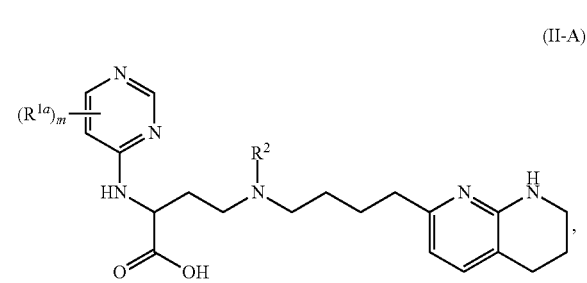

where m is 0, 1, 2, or 3.

55. The dosage form of claim 1, wherein the compound is selected from:
- (S)-2-((5-fluoropyrimidin-2-yl)amino)-4-(((R)-2-methoxypropyl)(4-(5,6,7,8-tetrahydro-1,8-naphthyridin-2-yl)butyl)amino)butanoic acid;
- (S)-2-((5-cyanopyrimidin-2-yl)amino)-4-(((S)-2-fluoro-3-methoxypropyl)(4-(5,6,7,8-tetrahydro-1,8-naphthyridin-2-yl)butyl)amino)butanoic acid;
- (S)-4-(((S)-2-fluoro-3-methoxypropyl)(4-(5,6,7,8-tetrahydro-1,8-naphthyridin-2-yl)butyl)amino)-2-((5-(trifluoromethyl)pyrimidin-2-yl)amino)butanoic acid;
- (S)-2-((5-bromopyrimidin-2-yl)amino)-4-(((S)-2-fluoro-3-methoxypropyl)(4-(5,6,7,8-tetrahydro-1,8-naphthyridin-2-yl)butyl)amino)butanoic acid;
- (S)-4-(((S)-2-fluoro-3-methoxypropyl)(4-(5,6,7,8-tetrahydro-1,8-naphthyridin-2-yl)butyl)amino)-2-((2-(trifluoromethyl)pyrimidin-4-yl)amino)butanoic acid;
- (S)-2-((6-(1H-pyrazol-1-yl)pyrimidin-4-yl)amino)-4-(((S)-2-fluoro-3-methoxypropyl)(4-(5,6,7,8-tetrahydro-1,8-naphthyridin-2-yl)butyl)amino)butanoic acid;
- (S)-4-(((S)-2-fluoro-3-methoxypropyl)(4-(5,6,7,8-tetrahydro-1,8-naphthyridin-2-yl)butyl)amino)-2-((5-phenylpyrimidin-4-yl)amino)butanoic acid;
- (S)-2-((5-cyclopropylpyrimidin-2-yl)amino)-4-(((R)-2-methoxypropyl)(4-(5,6,7,8-tetrahydro-1,8-naphthyridin-2-yl)butyl)amino)butanoic acid;
- (S)-4-(((S)-2-fluoro-3-methoxypropyl)(4-(5,6,7,8-tetrahydro-1,8-naphthyridin-2-yl)butyl)amino)-2-(pyrimidin-4-ylamino)butanoic acid;
- (S)-4-(((S)-2-fluoro-3-methoxypropyl)(4-(5,6,7,8-tetrahydro-1,8-naphthyridin-2-yl)butyl)amino)-2-((6-phenylpyrimidin-4-yl)amino)butanoic acid;
- (S)-2-((5-cyclopropylpyrimidin-2-yl)amino)-4-(((S)-2-fluoro-3-methoxypropyl)(4-(5,6,7,8-tetrahydro-1,8-naphthyridin-2-yl)butyl)amino)butanoic acid;
- (S)-4-((2-phenoxyethyl)(4-(5,6,7,8-tetrahydro-1,8-naphthyridin-2-yl)butyl)amino)-2-((5-phenylpyrimidin-4-yl)amino)butanoic acid;
- (S)-4-((2-(4-fluorophenoxy)ethyl)(4-(5,6,7,8-tetrahydro-1,8-naphthyridin-2-yl)butyl)amino)-2-((5-phenylpyrimidin-4-yl)amino)butanoic acid;
- (S)-2-((3-cyanopyrazin-2-yl)amino)-4-((2-ethoxyethyl)(4-(5,6,7,8-tetrahydro-1,8-naphthyridin-2-yl)butyl)amino)butanoic acid;
- (S)-2-((6-(1H-pyrazol-1-yl)pyrimidin-4-yl)amino)-4-((3-fluoropropyl)(4-(5,6,7,8-tetrahydro-1,8-naphthyridin-2-yl)butyl)amino)butanoic acid; and
- (S)-2-((3-cyanopyrazin-2-yl)amino)-4-((2-(4-fluorophenoxy)ethyl)(4-(5,6,7,8-tetrahydro-1,8-naphthyridin-2-yl)butyl)amino)butanoic acid, or a salt thereof.

56. The dosage form of claim 1, or a salt thereof, wherein the compound is of the formula (II-B):

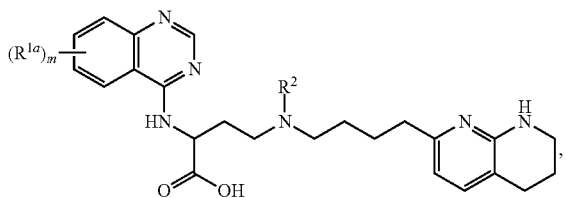

(II-B)

where m is 0, 1, 2, 3, 4, or 5.

57. The dosage form of claim 1, wherein the compound is selected from:
- (S)-2-((7-fluoroquinazolin-4-yl)amino)-4-((2-methoxyethyl)(4-(5,6,7,8-tetrahydro-1,8-naphthyridin-2-yl)butyl)amino)butanoic acid;
- (S)-2-((7-fluoro-2-methylquinazolin-4-yl)amino)-4-((2-methoxyethyl)(4-(5,6,7,8-tetrahydro-1,8-naphthyridin-2-yl)butyl)amino)butanoic acid;
- (S)-4-((2-methoxyethyl)(4-(5,6,7,8-tetrahydro-1,8-naphthyridin-2-yl)butyl)amino)-2-((8-(trifluoromethyl)quinazolin-4-yl)amino)butanoic acid;
- (S)-2-((6-fluoroquinazolin-4-yl)amino)-4-((2-methoxyethyl)(4-(5,6,7,8-tetrahydro-1,8-naphthyridin-2-yl)butyl)amino)butanoic acid;
- (S)-2-((6,7-difluoroquinazolin-4-yl)amino)-4-((2-methoxyethyl)(4-(5,6,7,8-tetrahydro-1,8-naphthyridin-2-yl)butyl)amino)butanoic acid;
- (S)-2-((7-fluoro-2-methylquinazolin-4-yl)amino)-4-((2-(4-fluorophenoxy)ethyl)(4-(5,6,7,8-tetrahydro-1,8-naphthyridin-2-yl)butyl)amino)butanoic acid;
- (2S)-4-((2-(2,2-difluorocyclopropoxy)ethyl)(4-(5,6,7,8-tetrahydro-1,8-naphthyridin-2-yl)butyl)amino)-2-((7-fluoro-2-methylquinazolin-4-yl)amino)butanoic acid;
- (S)-4-(((S)-3-fluoro-2-methoxypropyl)(4-(5,6,7,8-tetrahydro-1,8-naphthyridin-2-yl)butyl)amino)-2-((2-methylquinazolin-4-yl)amino)butanoic acid;
- (S)-2-((8-fluoroquinazolin-4-yl)amino)-4-(((R)-2-methoxypropyl)(4-(5,6,7,8-tetrahydro-1,8-naphthyridin-2-yl)butyl)amino)butanoic acid;
- (S)-2-((7-fluoroquinazolin-4-yl)amino)-4-(((R)-2-methoxypropyl)(4-(5,6,7,8-tetrahydro-1,8-naphthyridin-2-yl)butyl)amino)butanoic acid;
- (S)-4-(((R)-2-methoxypropyl)(4-(5,6,7,8-tetrahydro-1,8-naphthyridin-2-yl)butyl)amino)-2-((8-methylquinazolin-4-yl)amino)butanoic acid;
- (S)-2-((7,8-difluoroquinazolin-4-yl)amino)-4-(((R)-2-methoxypropyl)(4-(5,6,7,8-tetrahydro-1,8-naphthyridin-2-yl)butyl)amino)butanoic acid;
- (S)-4-((2-methoxyethyl)(4-(5,6,7,8-tetrahydro-1,8-naphthyridin-2-yl)butyl)amino)-2-(quinazolin-4-ylamino)butanoic acid;
- (S)-4-((2-phenoxyethyl)(4-(5,6,7,8-tetrahydro-1,8-naphthyridin-2-yl)butyl)amino)-2-(quinazolin-4-ylamino)butanoic acid;
- (S)-4-((2-(3,5-difluorophenoxy)ethyl)(4-(5,6,7,8-tetrahydro-1,8-naphthyridin-2-yl)butyl)amino)-2-(quinazolin-4-ylamino)butanoic acid;
- (S)-4-((2-(pyridin-2-yloxy)ethyl)(4-(5,6,7,8-tetrahydro-1,8-naphthyridin-2-yl)butyl)amino)-2-(quinazolin-4-ylamino)butanoic acid;
- (S)-4-((2-(2,2-difluoroethoxy)ethyl)(4-(5,6,7,8-tetrahydro-1,8-naphthyridin-2-yl)butyl)amino)-2-(quinazolin-4-ylamino)butanoic acid;
- (S)-4-((2-((6-methylpyridin-3-yl)oxy)ethyl)(4-(5,6,7,8-tetrahydro-1,8-naphthyridin-2-yl)butyl)amino)-2-(quinazolin-4-ylamino)butanoic acid;
- (S)-4-(((R)-2-methoxypropyl)(4-(5,6,7,8-tetrahydro-1,8-naphthyridin-2-yl)butyl)amino)-2-(quinazolin-4-ylamino)butanoic acid;
- (S)-4-((2-hydroxyethyl)(4-(5,6,7,8-tetrahydro-1,8-naphthyridin-2-yl)butyl)amino)-2-(quinazolin-4-ylamino)butanoic acid;
- (S)-4-(((R)-2-hydroxypropyl)(4-(5,6,7,8-tetrahydro-1,8-naphthyridin-2-yl)butyl)amino)-2-(quinazolin-4-ylamino)butanoic acid; and (S)-4-(((S)-2,3-dihydroxypropyl)(4-(5,6,7,8-tetrahydro-1,8-naphthyridin-2-yl)butyl)amino)-2-(quinazolin-4-ylamino)butanoic acid,
or a salt thereof.

58. The dosage form of claim 1, or a salt thereof, wherein the compound is of the formula (II-H):

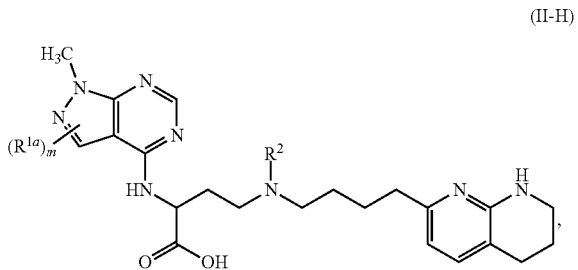

(II-H)

where m is 0, 1, or 2.

59. The dosage form of claim 1, wherein the compound is selected from:
- (S)-4-(((R)-2-methoxypropyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;
- (S)-2-((1H-pyrazolo[3,4-d]pyrimidin-4-yl)amino)-4-((2-phenoxyethyl)(4-(5,6,7,8-tetrahydro-1,8-naphthyridin-2-yl)butyl)amino)butanoic acid;
- (S)-2-((1H-pyrazolo[3,4-d]pyrimidin-4-yl)amino)-4-((2-(4-fluorophenoxy)ethyl)(4-(5,6,7,8-tetrahydro-1,8-naphthyridin-2-yl)butyl)amino)butanoic acid;
- (S)-4-((2-(4-fluorophenoxy)ethyl)(4-(5,6,7,8-tetrahydro-1,8-naphthyridin-2-yl)butyl)amino)-2-((2-methyl-2H-pyrazolo[4,3-d]pyrimidin-7-yl)amino)butanoic acid;
- (S)-4-((2-ethoxyethyl)(4-(5,6,7,8-tetrahydro-1,8-naphthyridin-2-yl)butyl)amino)-2-((2-methyl-2H-pyrazolo[4,3-d]pyrimidin-7-yl)amino)butanoic acid;
- (S)-4-((2-(2,2-difluoroethoxy)ethyl)(4-(5,6,7,8-tetrahydro-1,8-naphthyridin-2-yl)butyl)amino)-2-((1-methyl-1H-pyrazolo[3,4-d]pyrimidin-4-yl)amino)butanoic acid;
- (S)-2-((1H-pyrazolo[3,4-d]pyrimidin-4-yl)amino)-4-((2-(2,2-difluoroethoxy)ethyl)(4-(5,6,7,8-tetrahydro-1,8-naphthyridin-2-yl)butyl)amino)butanoic acid;
- (S)-2-((2-methyl-2H-pyrazolo[4,3-d]pyrimidin-7-yl)amino)-4-((2-phenoxyethyl)(4-(5,6,7,8-tetrahydro-1,8-naphthyridin-2-yl)butyl)amino)butanoic acid;
- (S)-2-((1-methyl-1H-pyrazolo[3,4-d]pyrimidin-4-yl)amino)-4-((4-(5,6,7,8-tetrahydro-1,8-naphthyridin-2-yl)butyl)(2-(2,2,2-trifluoroethoxy)ethyl)amino)butanoic acid;
- (S)-2-((1H-pyrazolo[3,4-d]pyrimidin-4-yl)amino)-4-((4-(5,6,7,8-tetrahydro-1,8-naphthyridin-2-yl)butyl)(2-(2,2,2-trifluoroethoxy)ethyl)amino)butanoic acid;
- (S)-4-(((R)-2-methoxypropyl)(4-(5,6,7,8-tetrahydro-1,8-naphthyridin-2-yl)butyl)amino)-2-(thieno[2,3-d]pyrimidin-4-ylamino)butanoic acid;
- (S)-4-(((S)-3-fluoro-2-methoxypropyl)(4-(5,6,7,8-tetrahydro-1,8-naphthyridin-2-yl)butyl)amino)-2-(thieno[2,3-d]pyrimidin-4-ylamino)butanoic acid;
- (S)-4-(((R)-2-methoxypropyl)(4-(5,6,7,8-tetrahydro-1,8-naphthyridin-2-yl)butyl)amino)-2-(thieno[3,2-d]pyrimidin-4-ylamino)butanoic acid;
- (S)-4-(((S)-3-fluoro-2-methoxypropyl)(4-(5,6,7,8-tetrahydro-1,8-naphthyridin-2-yl)butyl)amino)-2-(thieno[3,2-d]pyrimidin-4-ylamino)butanoic acid;
- (S)-4-(((S)-3-fluoro-2-methoxypropyl)(4-(5,6,7,8-tetrahydro-1,8-naphthyridin-2-yl)butyl)amino)-2-((6-methylthieno[3,2-d]pyrimidin-4-yl)amino)butanoic acid; and
- (S)-4-(((R)-2-methoxypropyl)(4-(5,6,7,8-tetrahydro-1,8-naphthyridin-2-yl)butyl)amino)-2-((5-methylthieno[2,3-d]pyrimidin-4-yl)amino)butanoic acid, or a salt thereof.

60. The dosage form of claim 1, wherein the compound is (S)-2-((7-fluoro-2-methylquinazolin-4-yl)amino)-4-((2-(4-fluorophenoxy)ethyl)(4-(5,6,7,8-tetrahydro-1,8-naphthyridin-2-yl)butyl)amino)butanoic acid, or a salt thereof.

61. The dosage form of claim 1, wherein the compound is (S)-4-((2-hydroxyethyl)(4-(5,6,7,8-tetrahydro-1,8-naphthyridin-2-yl)butyl)amino)-2-(quinazolin-4-ylamino)butanoic acid, or a salt thereof.

62. The dosage form of claim 1, wherein the compound is (S)-4-((2-(3,5-difluorophenoxy)ethyl)(4-(5,6,7,8-tetrahydro-1,8-naphthyridin-2-yl)butyl)amino)-2-(quinazolin-4-ylamino)butanoic acid, or a salt thereof.

63. The dosage form of claim 1, wherein the compound is (S)-4-((2-phenoxyethyl)(4-(5,6,7,8-tetrahydro-1,8-naphthyridin-2-yl)butyl)amino)-2-((5-phenylpyrimidin-4-yl)amino)butanoic acid, or a salt thereof.

64. The dosage form of claim 1, wherein the compound is (S)-4-((2-(4-fluorophenoxy)ethyl)(4-(5,6,7,8-tetrahydro-1,8-naphthyridin-2-yl)butyl)amino)-2-((5-phenylpyrimidin-4-yl)amino)butanoic acid, or a salt thereof.

65. The dosage form of claim 1, wherein the compound is (S)-2-((6-(1H-pyrazol-1-yl)pyrimidin-4-yl)amino)-4-((3-fluoropropyl)(4-(5,6,7,8-tetrahydro-1,8-naphthyridin-2-yl)butyl)amino)butanoic acid, or a salt thereof.

66. The dosage form of claim 1, wherein the compound is (S)-4-(((S)-3-fluoro-2-methoxypropyl)(4-(5,6,7,8-tetrahydro-1,8-naphthyridin-2-yl)butyl)amino)-2-(thieno[2,3-d]pyrimidin-4-ylamino)butanoic acid, or a salt thereof.

67. The dosage form of claim 1, wherein the compound is (S)-2-((2-methyl-2H-pyrazolo[4,3-d]pyrimidin-7-yl)amino)-4-((2-phenoxyethyl)(4-(5,6,7,8-tetrahydro-1,8-naphthyridin-2-yl)butyl)amino)butanoic acid, or a salt thereof.

68. The dosage form of claim 1, wherein the compound is (S)-2-((1H-pyrazolo[3,4-d]pyrimidin-4-yl)amino)-4-((2-phenoxyethyl)(4-(5,6,7,8-tetrahydro-1,8-naphthyridin-2-yl)butyl)amino)butanoic acid, or a salt thereof.

69. The dosage form of claim 1, wherein the compound is (S)-2-((1H-pyrazolo[3,4-d]pyrimidin-4-yl)amino)-4-((2-(4-fluorophenoxy)ethyl)(4-(5,6,7,8-tetrahydro-1,8-naphthyridin-2-yl)butyl)amino)butanoic acid, or a salt thereof.

70. The dosage form of claim 1, wherein the compound is (S)-4-((2-(4-fluorophenoxy)ethyl)(4-(5,6,7,8-tetrahydro-1,8-naphthyridin-2-yl)butyl)amino)-2-((2-methyl-2H-pyrazolo[4,3-d]pyrimidin-7-yl)amino)butanoic acid, or a salt thereof.

71. The dosage form of claim 1, or a salt thereof, wherein $R^1$ is:
pyrimidin-2-yl, pyrimidin-4-yl, quinazolin-4-yl, 1H-pyrazolo[3,4-d]pyrimidin-4-yl, 1H-pyrazolo[4,3-d]pyrimidin-7-yl, pyrazin-2-yl, quinolin-4-yl, pyrido[2,3-d]pyrimidin-4-yl, pyrido[3,2-d]pyrimidin-4-yl, pyrido[3,4-d]pyrimidin-4-yl, thieno[2,3-d]pyrimidin-4-yl, thieno[3,2-d]pyrimidin-4-yl, thienopyrimidin-4-yl, pyridin-2-yl, pyridin-3-yl, 7H-pyrrolo[2,3-d]pyrimidin-4-yl, quinoxalin-2-yl, 1H-indazol-3-yl, benzo[d]thiazol-2-yl, naphthalen-1-yl, 9H-purin-6-yl, or isoquinolin-1-yl; and
wherein $R^1$ is optionally substituted by methyl and fluoro.

72. The dosage form of claim 1, or a salt thereof, wherein $R^1$ is:
 pyrimidin-2-yl, pyrimidin-4-yl, quinazolin-4-yl, 1H-pyrazolo[3,4-d]pyrimidin-4-yl, 1H-pyrazolo[4,3-d]pyrimidin-7-yl, pyrazin-2-yl, quinolin-4-yl, pyrido[2,3-d]pyrimidin-4-yl, pyrido[3,2-d]pyrimidin-4-yl, pyrido[3,4-d]pyrimidin-4-yl, thieno[2,3-d]pyrimidin-4-yl, thieno[3,2-d]pyrimidin-4-yl, thienopyrimidin-4-yl, pyridin-2-yl, pyridin-3-yl, 7H-pyrrolo[2,3-d]pyrimidin-4-yl, quinoxalin-2-yl, 1H-indazol-3-yl, benzo[d]thiazol-2-yl, naphthalen-1-yl, 9H-purin-6-yl, or isoquinolin-1-yl; and
 wherein $R^1$ is optionally substituted by methyl and trifluoromethyl.

* * * * *

UNITED STATES PATENT AND TRADEMARK OFFICE
CERTIFICATE OF CORRECTION

PATENT NO. : 11,419,869 B2
APPLICATION NO. : 16/843824
DATED : August 23, 2022
INVENTOR(S) : Martin Decaris et al.

Page 1 of 18

It is certified that error appears in the above-identified patent and that said Letters Patent is hereby corrected as shown below:

On the Title Page

Item [74] replace:
"Morrison & Foerster LLP; Kraig Anderson; Johannes Hull"

With:
--Morrison & Foerster LLP; Kraig Anderson and Johannes Hull, Pliant Therapeutics--

In the Specification

At Column 5, Line 67: replace:
"idopathic"

With:
--idiopathic--

At Column 7, Line 19: replace:
"$C_1$-$C_2$"

With:
--"$C_1$-$C_{20}$"--

At Column 8, Line 67: replace:
"norbomenyl."

With:
--norbornenyl.--

At Column 14, Line 50: replace:
"R is"

Signed and Sealed this
Sixth Day of February, 2024

Katherine Kelly Vidal
Director of the United States Patent and Trademark Office

With:
--$R^1$ is--

At Column 14, Line 52: replace:
"$R_1NH$—"

With:
--$R^1NH$—--

At Column 15, Line 3: replace:
"$R^1$,"

With:
--$R^{15}$,--

At Column 15, Line 11: replace:
"$R^{1a}$"

With:
--$R^{1a}$.--

At Column 19, Line 2: replace:
"$R^{2b}$,"

With:
--$R^{2c}$,--

At Column 19, Line 48: replace:
"R"

With:
--$R^1$--

At Column 19, Line 51: replace:
"R variable,"

With:
--$R^1$ variable,--

At Column 35, Line 48: replace:
"H"

With:
--1H--

At Column 36, Line 57: replace:

"benzooxazolyl)."
With:
--benzoxazolyl).--
At Column 39, Line 39-44: replace:
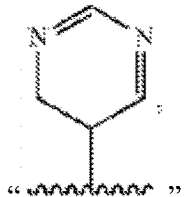
With:
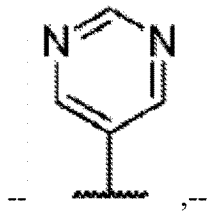
At Column 45, Line 23: replace:
"pyrimid-4-yl,"
With:
--pyrimidin-4-yl,--
At Column 45, Line 25: replace:
"pyrimid-2-yl)."
With:
--pyrimidin-2-yl).--
At Column 46, Line 65: replace:
"$C_3$—C"
With:
--$C_3$—$C_8$--
At Column 52, Line 41: replace:
"benzooxazolyl;"
With:
--benzoxazolyl;--

At Column 64, Line 14: replace:
"of"

With:
--of:--

At Column 69, Line 35: replace:
"$^{14}C\ ^{13}N$,"

With:
--$^{14}C,\ ^{13}N$,--

At Column 69, Line 67: replace:
"RI,"

With:
--$R^1$,--

At Column 71, Line 52: insert:
--$R^2$,--

After:
"$R^{1a}$,"

At Column 71, Line 55: insert:
--$R^2$,--

After:
"$R^{1a}$,"

At Column 80, Line 65: replace:
"1e"

With:
--1c--

At Column 83, Line 25: replace:
"poly-ols,"

With:
--polyols,--

At Column 91, Line 53: replace:
"$\alpha v\beta_6$"

With:

--α$_v$β$_6$--

At Column 93, Line 65: replace:
"of"

With:
--of:--

At Column 94, Line 7: replace:
"about about"

With:
--about--

At Column 103, Line 5: replace:
"mg"

With:
--mg,--

At Column 107, Line 67: replace:
"R"

With:
--R$^1$--

At Column 129, Line 16: replace:
"CH$_2$Cl$_2$"

With:
--THF/DMF--

At Column 136, Line 65: replace:
"concentracted"

With:
--concentrated--

At Column 139, Line 25: replace
"CH$_2$C$_2$."

With:
--CH$_2$Cl$_2$.--

At Column 147, Line 40: replace:
"(methylsufonyl)"

With:
--(methylsulfonyl)--
At Column 169, Line 56: replace:
"(2H)"
With:
--1(2H)--
At Column 174, Line 16-20: replace:
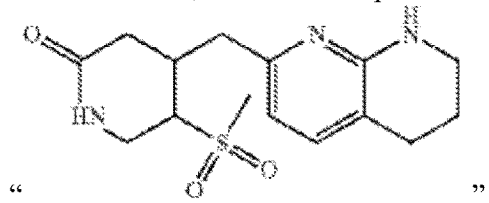
"                              "
With:
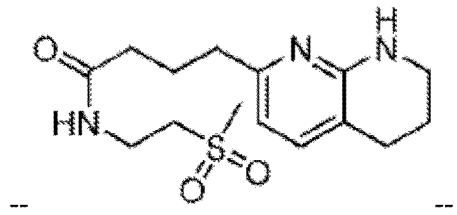
--                    --
At Column 176, Line 27: replace:
"H"
With:
--1H--
At Column 178, Line 48: replace:
"(methylsufonyl)"
With:
--(methylsulfonyl)--
At Column 178, Line 59: replace:
"compound."
With:
--compound).--
At Column 180, Line 13: replace:
"((m,"

With:
--(m,--

At Column 182, Line 1: replace:
"Deutertum"

With:
--Deuterium--

At Column 181-182, Line 41: replace:
"H2O"

With:
--$H_2O$--

At Column 188, Line 39: replace:
"H"

With:
--1H--

At Column 193, Line 10: replace:
"$(M+H)^+$"

With:
--$(M+H)^+$.--

At Column 193, Line 18: replace:
"(2H)"

With:
--1(2H)--

At Column 193, Line 29: replace:
"$(M+H)^+$"

With:
--$(M+H)^+$.--

At Column 193, Line 60: replace:
"(M+H)+;"

With:
--$(M+H)^+$;--

At Column 194, Line 7: replace:

At Column 196, Line 43: replace:
"(M+H)⁺"

With:
--(M+H)⁺.--

At Column 196, Line 43: replace:
"(M+H)⁺"

With:
--(M+H)⁺.--

At Column 196, Line 43: replace:
"(M+H)⁺"

With:
--(M+H)⁺.--

At Column 197, Line 10: replace:
"(M+H)⁺"

With:
--(M+H)⁺.--

At Column 197, Line 24: replace:
"(M+H)⁺"

With:
--(M+H)⁺.--

At Column 197, Line 37: replace:
"(M+H)⁺"

With:
--(M+H)⁺.--

At Column 198, Line 52: replace:
"NABH₃CN"

With:
--NaBH₃CN--

At Column 206, Line 48: replace:
"H"

With:
--1H--

At Column 216, Line 55: replace:
"mg"

With:
--mg,--

At Column 216, Line 57: replace:
"umol)"

With:
--μmol)--

At Column 218, Line 37: replace:
"umol),"

With:
--μmol),--

At Column 218, Line 37: replace:
"1362"

With:
--13.62--

At Column 218, Line 61: replace:
"butyl2"

With:
--butyl-2--

At Column 219, Line 64: replace:
"methoxypyrazine"

With:
--methoxypyrazin--

At Column 224, Line 39: replace:
"(methylsufonyl)"

With:
--(methylsulfonyl)--

At Column 224, Line 51: replace:
"(methylsufonyl)"

With:

--(methylsulfonyl)--

At Column 238, Line 28: replace:
"butyl4"

With:
--butyl-4--

At Column 239, Line 43: replace:
"butyl4"

With:
--butyl-4--

At Column 244, Line 7: replace:
"3 H)"

With:
--3H)--

At Column 244, Line 15: replace:
"H"

With:
--1H--

At Column 246, Line 65: replace:
"100°"

With:
--10°--

At Column 249, Line 45: replace:
"Pd/"

With:
--Pd/C--

At Column 259, Line 48: replace:
"((m,"

With:
--(m,--

At Column 260, Line 55-57: replace:

"[MeO over Step 2]"

With:

--[MeOH over Step 2]--

At Column 267-268, Line 36: replace:
"tBuXphos"

With:
--tBuXPhos--

At Column 273-274, Line 57: replace:
"Sche,e"

With:
--Scheme--

At Column 275, Line 55: replace:
"rever"

With:
--reverse--

At Column 281, Line 13: replace:
"H"

With:
--1H--

At Column 292, Line 44: replace:
"H"

With:
--1H--

At Column 294, Line 13: replace:
"((6-H"

With:
--((6-(1H--

At Column 296, Line 11: replace:
"µmol,"
With:
--µmol),--
At Column 302, Line 12: replace:
"((m,"
With:
--(m,--
At Column 302, Line 12: replace:
"((m,"
With:
--(m,--
At Column 307, Line 10: replace:
"H"
With:
--1H--
At Column 308, Line 20: replace:
"mol)"
With:
--mmol)--
At Column 315-316, Line 41-45: replace:
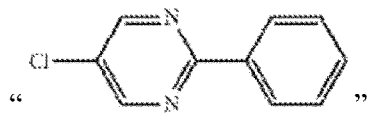
" "
With:
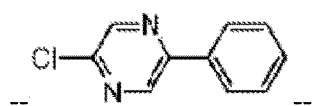
-- --
At Column 319, Line 50: replace:
"((m,"
With:
--(m,--

At Column 328, Line 17: replace:
"i-BuONa"

With:
--t-BuONa--

At Column 318, Line 18: replace:
"L,"

With:
--µL,--

At Column 330, Line 22-23: replace:
"t-Bu Xphos"

With:
--t-BuXPhos--

At Column 331, Line 47: replace:
"(M+H)$^+$"

With:
--(M+H)$^+$.--

At Column 338, Line 2: insert:
--a--

After:
"by"

At Column 338, Line 18: replace:
"αβ6"

With:
--αv$\beta_6$--

At Column 338, Line 52: replace:
"αβ6"

With:
--αv$\beta_6$--

At Column 339, Line 1 (Table B-2 -continued): replace:
"αβ6"

With:

--αvβ_6--

At Column 340, Line 33: replace:
"CaCl_2)"

With:
--CaCl_2--

At Column 340, Line 42: replace:
"SynergyNeo2"

With:
--Synergy Neo2--

At Column 340, Line 65: replace:
"CaCl_2)"

With:
--CaCl_2--

At Column 341, Line 7: replace:
"SynergyNeo2"

With:
--Synergy Neo2--

At Column 342, Line 17: replace:
"αvβ1"

With:
--α_vβ1--

At Column 342, Line 62: replace:
"levels"

With:
--levels.--

At Column 344, Line 14: replace:
"of a"

With:
--of: a--

At Column 344, Line 20: replace:
"pan-av"

With:
--pan-αv--

At Column 344, Line 44: replace:
"pan-av"

With:
--pan- αv--

At Column 345, Line 20: replace:
"α$_v$β$_6$"

With:
--αvβ$_6$--

At Column 345, Line 57: replace:
"one of"

With:
--one of:--

At Column 345, Line 63: replace:
"Ox"

With:
--10x--

At Column 345, Line 63: replace:
"Nintendanib"

With:
--Nintedanib--

At Column 346, Line 36: replace:
"αcβ$_6$"

With:
--αvβ$_6$--

At Column 346, Line 50: replace:
"idopathic"

With:
--idiopathic--

At Column 346, Line number 55: please replace:

"m;"

With:
--µm,--

At Column 346, Line 62: replace:
"idopathic"

With:
--idiopathic--

At Column 346, Line 63: replace:
"Comopund"

With:
--Compound--

At Column 347, Line 1: replace:
"µM,"

With:
--pM,--

At Column 348, Line 3: replace:
"Broncoalevaolar"

With:
--Bronchoalveolar--

At Column 348, Line 52: replace:
"$\mu v \beta_6$"

With:
--$\alpha v \beta_6$--

At Column 348, Line 54: replace:
"$\alpha v \beta 6$"

With:
--$\alpha v \beta_6$--

In the Claims

At Column 349, Claim 1, Line 10-17: replace:

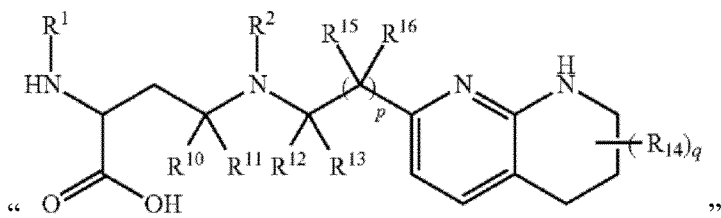
With:
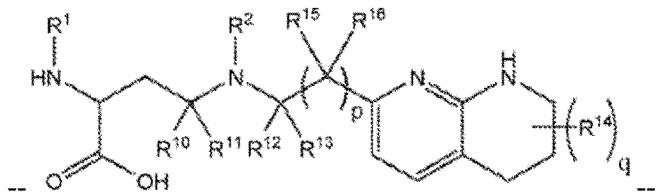
At Column 349, Claim 1, Line 21: replace:
"Ria;"
With:
--$R^{1a}$;--
At Column 349, Claim l, Line 40: replace:
"Ria"
With:
--$R^{1a}$--
At Column 351, Claim 3, Line 14: replace:
"claim 1"
With:
--claim 1,--
At Column 352, Claim 16, Line 34-35: replace:
"methyl sulfonyl,"
With:
--methylsulfonyl,--
At Column 366, Claim 44, Line 15-20: replace:
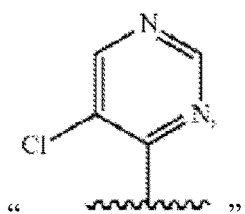

With:
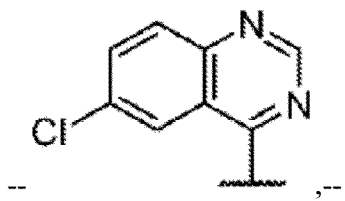
At Column 370, Claim 49, Line 34: replace:
"$OR^6$;"
With:
-—$OR^6$;--
At Column 373, Claim 68, Line 8 replace:
"butylamino)"
With:
--butyl)amino)--